US011208673B2

(12) United States Patent
Burk et al.

(10) Patent No.: US 11,208,673 B2
(45) Date of Patent: Dec. 28, 2021

(54) MICROORGANISMS AND METHODS FOR THE BIOSYNTHESIS OF ADIPATE, HEXAMETHYLENEDIAMINE AND 6-AMINOCAPROIC ACID

(71) Applicant: Genomatica, Inc., San Diego, CA (US)

(72) Inventors: Mark J. Burk, San Diego, CA (US); Anthony P. Burgard, Elizabeth, PA (US); Robin E. Osterhout, San Diego, CA (US); Priti Pharkya, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 16/213,671

(22) Filed: Dec. 7, 2018

(65) Prior Publication Data

US 2019/0330670 A1  Oct. 31, 2019

Related U.S. Application Data

(60) Division of application No. 15/263,149, filed on Sep. 12, 2016, now Pat. No. 10,150,977, which is a continuation of application No. 13/730,612, filed on Dec. 28, 2012, now Pat. No. 9,458,480, which is a continuation of application No. 12/776,365, filed on May 7, 2010, now Pat. No. 8,377,680.

(60) Provisional application No. 61/176,196, filed on May 7, 2009, provisional application No. 61/219,365, filed on Jun. 22, 2009, provisional application No. 61/244,844, filed on Sep. 22, 2009, provisional application No. 61/246,973, filed on Sep. 29, 2009, provisional application No. 61/247,533, filed on Sep. 30, 2009.

(51) Int. Cl.
| | |
|---|---|
| *C12P 17/10* | (2006.01) |
| *C12N 1/38* | (2006.01) |
| *C12N 15/52* | (2006.01) |
| *C12P 7/40* | (2006.01) |
| *C12P 7/44* | (2006.01) |
| *C12P 13/00* | (2006.01) |
| *C12P 13/02* | (2006.01) |
| *C12P 17/12* | (2006.01) |

(52) U.S. Cl.
CPC .............. *C12P 17/10* (2013.01); *C12N 1/38* (2013.01); *C12N 15/52* (2013.01); *C12P 7/40* (2013.01); *C12P 7/44* (2013.01); *C12P 13/001* (2013.01); *C12P 13/005* (2013.01); *C12P 13/02* (2013.01); *C12P 17/12* (2013.01)

(58) Field of Classification Search
None
See application file for complete search history.

(56) References Cited

U.S. PATENT DOCUMENTS

| | | | |
|---|---|---|---|
| 3,912,586 A | 10/1975 | Kaneyuki et al. | |
| 4,871,667 A | 10/1989 | Imada et al. | |
| 5,143,833 A | 9/1992 | Datta | |
| 5,143,834 A | 9/1992 | Glassner et al. | |
| 5,168,055 A | 12/1992 | Datta et al. | |
| 5,487,987 A | 1/1996 | Frost et al. | |
| 5,504,004 A | 4/1996 | Guettler et al. | |
| 5,521,075 A | 5/1996 | Guettler et al. | |
| 5,573,931 A | 11/1996 | Guettler et al. | |
| 5,616,496 A | 4/1997 | Frost et al. | |
| 5,700,934 A | 12/1997 | Wolters et al. | |
| 5,770,435 A | 6/1998 | Donnelly et al. | |
| 5,869,301 A | 2/1999 | Nghiem et al. | |
| 5,958,745 A | 9/1999 | Gruys et al. | |
| 6,159,738 A | 12/2000 | Donnelly et al. | |
| 6,194,572 B1 | 2/2001 | Buijs et al. | |

(Continued)

FOREIGN PATENT DOCUMENTS

| | | |
|---|---|---|
| DE | 198 31 889 A1 | 1/2000 |
| EP | 1 473 368 A1 | 11/2004 |

(Continued)

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Abadjieva et al., "The Yeast ARG7 Gene Product is Autoproteolyzed to Two Subunit Peptides, Yielding Active Ornithine Acetyltransferase," *J. Biol. Chem.* 275(15):11361-11367 (2000).

(Continued)

*Primary Examiner* — Iqbal H Chowdhury
(74) *Attorney, Agent, or Firm* — Greenberg Traurig LLP

(57) ABSTRACT

The invention provides a non-naturally occurring microbial organism having a 6-aminocaproic acid, caprolactam, hexametheylenediamine or levulinic acid pathway. The microbial organism contains at least one exogenous nucleic acid encoding an enzyme in the respective 6-aminocaproic acid, caprolactam, hexametheylenediamine or levulinic acid pathway. The invention additionally provides a method for producing 6-aminocaproic acid, caprolactam, hexametheylenediamine or levulinic acid. The method can include culturing a 6-aminocaproic acid, caprolactam or hexametheylenediamine producing microbial organism, where the microbial organism expresses at least one exogenous nucleic acid encoding a 6-aminocaproic acid, caprolactam, hexametheylenediamine or levulinic acid pathway enzyme in a sufficient amount to produce the respective product, under conditions and for a sufficient period of time to produce 6-aminocaproic acid, caprolactam, hexametheylenediamine or levulinic acid.

14 Claims, 37 Drawing Sheets

Specification includes a Sequence Listing.

(56) References Cited

U.S. PATENT DOCUMENTS

| | | | |
|---|---|---|---|
| 6,214,592 | B1 | 4/2001 | Crouzet et al. |
| 6,280,986 | B1 | 8/2001 | Hespell et al. |
| RE37,393 | E | 9/2001 | Donnelly et al. |
| 6,353,100 | B1 | 3/2002 | Guit et al. |
| 6,448,061 | B1 | 9/2002 | Pan et al. |
| 6,455,284 | B1 | 9/2002 | Gokarn et al. |
| 6,660,857 | B2 | 12/2003 | Agterberg et al. |
| 6,743,610 | B2 | 6/2004 | Donnelly et al. |
| 7,127,379 | B2 | 10/2006 | Palsson et al. |
| 7,223,567 | B2 | 5/2007 | Ka-Yiu et al. |
| 7,262,046 | B2 | 8/2007 | Ka-Yiu et al. |
| 7,309,597 | B2 | 12/2007 | Liao et al. |
| 7,491,520 | B2 | 2/2009 | Raemakers-Franken et al. |
| 7,799,545 | B2 | 9/2010 | Burgard et al. |
| 7,947,483 | B2 | 5/2011 | Burgard et al. |
| 8,377,680 | B2 | 2/2013 | Burk et al. |
| 9,458,480 | B2 * | 10/2016 | Burk ............ C12P 7/44 |
| 10,415,042 | B2 * | 9/2019 | Burgard ............ C12P 7/62 |
| 2002/0012939 | A1 | 1/2002 | Palsson |
| 2002/0062388 | A1 | 5/2002 | Ogier et al. |
| 2002/0106358 | A1 | 8/2002 | Hopwood et al. |
| 2002/0168654 | A1 | 11/2002 | Maranas et al. |
| 2003/0028915 | A1 | 2/2003 | Tilton et al. |
| 2003/0059792 | A1 | 3/2003 | Palsson et al. |
| 2003/0087381 | A1 | 5/2003 | Gokarn |
| 2003/0113886 | A1 | 6/2003 | Brzostowicz et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072542 | A1 | 4/2004 | Palsson et al. |
| 2005/0079482 | A1 | 4/2005 | Maranas et al. |
| 2005/0113532 | A1 | 5/2005 | Fish et al. |
| 2005/0221466 | A1 | 10/2005 | Liao et al. |
| 2005/0250135 | A1 | 11/2005 | Klaenhammer et al. |
| 2007/0111294 | A1 | 5/2007 | Burgard et al. |
| 2007/0184539 | A1 | 8/2007 | San et al. |
| 2007/0239987 | A1 | 10/2007 | Hoole et al. |
| 2007/0254341 | A1 | 11/2007 | Raemakers-Franken et al. |
| 2007/0271453 | A1 | 11/2007 | Pohja et al. |
| 2008/0182308 | A1 | 7/2008 | Donaldson et al. |
| 2008/0261230 | A1 | 10/2008 | Liao et al. |
| 2008/0274526 | A1 | 11/2008 | Bramucci et al. |
| 2009/0047718 | A1 | 2/2009 | Blaschek et al. |
| 2009/0047719 | A1 | 2/2009 | Burgard et al. |
| 2009/0068207 | A1 | 3/2009 | Breitbart et al. |
| 2009/0246842 | A1 | 10/2009 | Hawkins et al. |
| 2009/0305364 | A1 | 12/2009 | Burgard et al. |
| 2010/0168481 | A1 | 7/2010 | Farmer et al. |

FOREIGN PATENT DOCUMENTS

| | | |
|---|---|---|
| JP | 50 006776 | 1/1975 |
| JP | 2007 512427 | 5/2007 |
| JP | 2008-061501 | 3/2008 |
| WO | WO 2002/055995 | 7/2002 |
| WO | WO 2003/106998 | 12/2003 |
| WO | WO 2005/068643 | 7/2005 |
| WO | WO 2006/031424 | 3/2006 |
| WO | WO 2006/034156 | 3/2006 |
| WO | WO 2007/030830 | 3/2007 |
| WO | WO 2007/050671 | 5/2007 |
| WO | WO 2007/103687 | 9/2007 |
| WO | WO 2007/141208 | 12/2007 |
| WO | WO 2008/027742 | 3/2008 |
| WO | WO 2008/080124 | 7/2008 |
| WO | WO 2009/113853 | 9/2009 |
| WO | WO 2009/113855 | 9/2009 |

OTHER PUBLICATIONS

Abe et al., "Discovery of amide (peptide) bond synthetic activity in Acyl-CoA synthetase," *J. Biol. Chem.* 283(17):11312-11321 (2008).

Abo-Dalo et al., "A novel member of the GCN5-related N-acetyltransferase superfamily from Caenorhabditis elegans preferentially catalyses the N-acetylation of thialysine [S-(2-aminoethyl)-L-cysteine]," *Biochem. J.* 384:129-137 (2004).

Aevarsson et al., "Crystal structure of 2-oxoisovalerate and dehydrogenase and the architecture of 2-oxo acid dehydrogenase multienzyme complexes," *Nat. Struct. Biol.* 6:785-792 (1999).

Agnihotri and Liu, "Enoyl-CoA Hydratase: Reaction, Mechanism, and Inhibition," *Bioorg. Med. Chem.* 11(1):9-20 (2003).

Alber et al., "Malonyl-Coenzyme A reductase in the modified 3-hydroxypropionate cycle for autotrophic carbon fixation in archaeal *Metallosphaera* and *Sulfolobus* spp.," *J. Bacteriol.* 188(24):8551-8559 (2006).

Alber et al., "Study of an alternate glyoxylate cycle for acetate assimilation by Rhodobacter sphaeroides," *Mol. Microbiol.* 61(2):297-309 (2006).

Alexson et al., "NADH-sensitive propionyl-CoA hydrolase in brown-adipose-tissue mitochondria of the rat," *Biochim. Biophys. Acta* 1005(1):13-19 (1989).

Alhapel et al., "Molecular and functional analysis of nicotinate catabolism in Eubacterium barkeri," *Proc. Natl. Acad. Sci. U.S.A.* 103(33):12341-12346 (2006).

Alper et al., "Engineering yeast transcription machinery for improved ethanol tolerance and production," *Science* 314(5805):1565-1568 (2006).

Andersen and Hansen, "Cloning of the lysA gene from *Mycobacterium tuberculosis*," *Gene.* 124(1):105-109 (1993).

Andersen et al., "A gene duplication led to specialized γ-aminobutyrate and β-alanine aminotransferase in yeast," *FEBS J.* 274:1804-1817 (2007).

Andersson et al., "Effect of different carbon sources on the production of succinic acid using metabolically engineered *Escherichia coli*," *Biotechnol. Prog.* 23(2):381-388 (2007).

Aneja and Charles, "Poly-3-hydroxybutyrate degradation in Rhizobium (Sinorhizobium) meliloti: isolation and characterization of a gene encoding 3-hydroxybutryate dehydrogenase," *J. Bacteriol.* 181(3):849-857 (1999).

Ansorge and Kula, "Production of Recombinant L-Leucine Dehydrogenase from Bacillus cereus in Pilot Scale Using the Runaway Replication System *E. coli*[pIET98]," *Biotechnol. Bioeng.* 68:557-562 (2000).

Aoshima and Igarashi, "A novel biotin protein required for reductive carboxylation of 2-oxoglutarate by isocitrate dehydrogenase in Hydrogenobacter thermophilus TK-6," *Mol. Microbiol.* 51(3):791-798 (2004).

Aoshima and Igarshi, "Nondecarboxylating and decarboxylating isocitrate dehydrogenases: oxalosuccinate reductase as an ancestral form of isocitrate dehydrogenase," *J. Bacteriol.* 190(6):2050-2055 (2008).

Aoshima et al., "A novel oxalosuccinate-forming enzyme involved in the reductive carboxylation of 2-oxoglutarate in Hydrogenobacter thermophilus TK-6," *Mol. Microbiol.* 62(3):748-759 (2006).

Aragon and Lowenstein, "A survey of Enzymes Which Generate or Use Acetoacetyl Thioesters in Rat Liver," *J. Biol. Chem.* 258(8):4725-4733 (1983).

Arps et al., "Genetics of serine pathway enzymes in Methylobacterium extorquens AM1: phosphoenolpyruvate carboxylase and malyl Coenzyme A lyase," *J. Bacteriol.* 175:3776-3783 (1993).

Atsumi et al., "Metabolic engineering of *Escherichia coli* for 1-butanol production," *Metab. Eng.* 10(6):305-311 (2007).

Atteia et al., "Pyruvate formate-lyase and a novel route of eukaryotic ATP synthesis in Chlamydomonas mitochondria," *J. Biol. Chem.* 281:9909-9918 (2006).

Auerbach et al., "Lactate dehydrogenase from the hyperthermophilic bacterium thermotoga maritima: the crystal structure at 2.1 Å resolution reveals strategies for intrinsic protein stabilization," *Structure* 6:769-781 (1998).

Bachmann and Townsend, "β-Lactam synthetase: a new biosynthetic enzyme," *Proc. Natl. Acad. Sci. U.S.A.* 95(16):9082-9086 (1998).

Bachmann and Townsend, "Kinetic Mechanism of the β-Lactam Synthetase of Streptomyces clavuligerus," *Biochemistry* 39:11187-11193 (2000).

Baker and van der Drift, "Purification and properties of L-erythro-3,5-diaminohexanoate dehydrogenase from Clostridium sticklandii," *Biochemistry* 13(2):292-299 (1974).

(56) References Cited

OTHER PUBLICATIONS

Baker et al., "Purification and properties of L-erythro-3,5-diaminohexanoate dehydrogenase from a lysine-fermenting Clostridium," *J. Biol. Chem.* 247:7724-7734 (1972).
Barker et al., "Butyryl-CoA:Acetoacetate CoA-transferase from Lysine-fermenting clostridium," *J. Biol. Chem.* 253(4):1219-1225 (1978).
Barker et al., "Pathway of Lysine Degradation in Fusobacterium nucleatum," *J. Bacteriol.* 152(1):201-207 (1982).
Barrowman et al., "Immunological comparison of microbial TPP-dependent non-oxidative α-keto acid decarboxylase," *FEMS Microbiol. Lett.* 34:57-60 (1986).
Bartsch et al., "Molecular analysis of two genes of the *Escherichia coli* gab cluster: nucleotide sequence of the glutamate:succinic semialdehyde transaminase gene (gabT) and characterization of the succinic semialdehyde dehydrogenase gene (gabD)," *J. Bacteriol.* 172(12):7035-7042 (1990).
Bauer et al., "Improved Expression of Human Interleukin-2 in High-Cell-Density Fermentor Cultures of *Escherichia coli* K-12 by a Phosphotransacetylase Mutant," *Appl. Environ. Microbiol.* 56:1296-1302 (1990).
Benner et al., "Stereospecificity and sterochemical infidelity of acetoacetate decarboxylase (AAD)," *J. Am. Chem. So.* 103:993-994 (1981).
Benning et al., "New reactions in the crotonase superfamily: Structure of methylmalonyl CoA decarboxylase from *Escherichia coli*," *Biochemistry* 39:4630-4639 (2000).
Berg et al., "A 3-Hydroxypropionate/4-Hydroxybutyrate Autotrophic Carbon Dioxide Assimilation Pathway in Archaea," *Science* 318(5857):1782-1786 (2007).
Bergquist and Gibbs, "Degenerate oligonucleotide gene shuffling," *Meth. Mol. Biol.* 352:191-204 (2007).
Bergquist et al., "Degenerate oligonucleotide gene shuffling (DOGS) and random drift mutagenesis (RNDM): Two complementary techniques for enzyme evolution," *Biomol. Eng.* 22:63-72 (2005).
Biellmann et al., "Aspartate-β-semialdehyde dehydrogenase from *Escherichia coli*. Purification and general properties," *Eur. J. Biochem.* 104(1):53-58 (1980).
Binieda et al., "Purification, characterization, DNA sequence and cloning of a pimeloyl-CoA synthetase from Pseudomonas mendocina 35," *Biochem. J.* 340:793-801 (1999).
Binstock and Schulz, "Fatty acid oxidation complex from *Escherichia coli*," *Methods. Enzymol.* 71(Pt C):403-411 (1981).
Bisswanger, "Substrate specificity of the Pyruvate Dehydrogenase Complex from *Escherichia coli*," *J. Biol. Chem.* 256(2):815-822 (1981).
Blanco et al., "Critical catalytic functional groups in the mechanism of aspartate-β-semialdehyde dehydrogenase," *Acta. Crystallogr. D. Biol. Crystallogr.* 60(Pt 10):1808-1815 (2004).
Blanco et al., "The role of substrate-binding groups in the mechanism of aspartate-β-semialdehyde dehydrogenase," *Acta. Crystallogr. D. Biol. Crystallogr.* 60(Pt 8):1388-1395 (2004).
Blaschkowski et al., "Routes of flavodoxin and ferredoxin reduction in *Escherichia coli*. CoA-acylating pyruvate: flavodoxin and NADPH: flavodoxin oxidoreductases participating in the activation of pyruvate formate-lyase," *Eur. J. Biochem.* 123(3):563-569 (1982).
Blazquez et al., "Identification and analysis of a glutaryl-CoA dehydrogenase-encoding gene and its cognate transcriptional regulator from *Azoarcus* sp. CIB," *Environ. Microbiol.* 10(2):474-482 (2008).
Bock et al., "Purification and characterization of two extremely thermostable enzymes, phosphate acetyltransferase and acetate kinase, from the hyperthermophilic eubacterium Thermotoga maritima," *J. Bacteriol.* 181:1861-1867 (1999).
Bonner and Bloch, "Purification and properties of fatty acyl thioesterase I from *Escherichia coli*," *J. Biol. Chem.* 247(10):3123-3133 (1972).
Boronin et al., "Plasmids specifying ε-caprolactam degradation in Pseudomonas strains," *FEMS Microbiol. Lett.* 22(3):167-170 (1984).
Bower et al., "Cloning, sequencing, and characterization of the Bacillus subtilis biotin biosynthetic operon," *J. Bacteriol.* 178(14):4122-4130 (1996).
Boylan and Dekker, "L-Threonine Dehydrogenase of *Escherichia Coli* K-12," *Biochem. Biophys. Res. Commun.* 85(1):190-197 (1978).
Boynton et al., "Cloning, sequencing, and expression of clustered genes encoding β-hydroxybutyryl-Coenzyme A (CoA) dehydrogenase, crotonase, and butyryl-CoA dehydrogenase from Clostridium acetobutylicum ATCC 824," *J. Bacteriol.* 178(11):3015-3024 (1996).
Branlant, "Nucleotide sequence of *Escherichia coli* gap gene. Different evolutionary behavior of the NAD+-binding domain and of the catalytic domain of D-glyceraldehyde-3-phosphate dehydrogenase," *Eur. J. Biochem.* 150:61-66 (1985).
Bräsen and Schönheit, "Unusual ADP-forming acetyl-Coenzyme A synthetases from the mesophilic halophilic euryarchaeon Haloarcula marismortui and from the hyperthermophilic crenarchaeon Pyrobaculum aerophilum," *Arch. Microbiol.* 182(4):277-287 (2004).
Braune et al., "The sodium ion translocating glutaconyl-CoA decarboxylase from Acidaminococcus fermentans: cloning and function on the genes forming a second operon," *Mol. Microbiol.* 31(2):473-487 (1999).
Bremer, "Pyruvate Dehydrogenase, Substrate Specificity and Product Inhibition," *Eur. J. Biochem.* 8:535-540 (1969).
Brooke et al., "GAMS: A User's Guide. GAMS Development Corporation" (1998).
Brown et al., "Comparative structural analysis and kinetic properties of lactate dehydrogenases from the four species of human malarial parasites," *Biochemistry* 43:6219-6229 (2004).
Bu et al., "Two human glutamate decarboxylases, 65-kDa GAD and 67-kDa GAD, are each encoded by a single gene," *Proc. Natl. Acad. Sci. U.S.A.* 89:2115-2119 (1992).
Buchanan et al., "An extremely thermostable aldolase from Sulfolobus solfataricus with specificity for non-phosphorylated substrates," *Biochem. J.* 343:563-570 (1999).
Buck et al., "Primary structure of the succinyl-CoA synthetase of *Escherichia coli*," *Biochem.* 24(22):6245-6252 (1985).
Buckel and Golding, "Radical species in the catalytic pathways of enzymes from anaerobes," *FEMS Microbiol. Rev.* 22(5):523-541 (1999).
Buckel et al., "Glutaconate CoA-Transferase from Acidaminococcus fermentans," *Eur. J. Biochem.* 118:315-321 (1981).
Bühler and Simon, "On the kinetics and mechanism of enoate reductase," *Hoppe Seylers Z. Physiol. Chem.* 363(6):609-625 (1982).
Bunch, et al., "The ldhA gene encoding the fermentative lactate dehydrogenase of *Escherichia coli*," *Microbiol.* 143:187-195 (1997).
Burgard and Maranas, "Probing the performance limits of the *Escherichia coli* metabolic network subject to gene additions or deletions," *Biotechnol. Bioeng.* 74:364-375 (2001).
Burgard et al., "Minimal Reaction Sets for *Escherichia coli* Metabolism under Different Growth Requirements and Uptake Environments," *Biotechnol. Prog.* 17:791-797 (2001).
Burgard et al., "Optknock: a bilevel programming framework for identifying gene knockout strategies for microbial strain optimization," *Biotechnol. Bioeng.* 84(6):647-657 (2003).
Burks et al., "Stereochemical and Isotopic Labeling Studies of 2-Oxo-hept-4-ene-1,7-dioate Hydratase: Evidence for an Enzyme-Catalyzed Ketonization Step in the Hydration Reaction," *J. Am. Chem. Soc.* 120(31):7665-7675 (1998).
Buu et al., "Functional characterization and localization of acetyl-CoA hydrolase, Ach1p, in *Saccharomyces cerevisiae*," *J. Biol. Chem.* 278:17203-17209 (2003).
Buzenet et al., "Purification and properties of 4-Aminobutyrate 2-Ketoglutarate Aminotransferase From Pig Liver," *Biochimica. Biophysica. Acta.* 522:400-411 (1978).
Caldovic and Tuchman, "N-Acetylglutamate and its changing role through evolution," *Biochem. J.* 372:279-290 (2003).
Camara et al., "Characterization of a Gene Cluster Involved in 4-Chlorocatechol Degradation by Pseudomonas reinekei MT1," *J. Bacteriol.* 191(15):4905-4915 (2009).
Campbell and Cronan, Jr., "The enigmatic *Escherichia coli* fadE gene is yafH," *J. Bacteriol.* 184(13):3759-3764 (2002).

(56) References Cited

OTHER PUBLICATIONS

Campbell et al., "A new *Escherichia coli* metabolic competency: growth on fatty acids by a novel anaerobic β-oxidation pathway," *Mol. Microbiol.* 47(3):793-805 (2003).
Canovas et al., "Characterization of the genes for the biosynthesis of the compatible solute ecotine in the moderately haliphilic bacterium Halomonas elongata DSM 3043," *Syst. Appl. Microbiol.* 21:487-497 (1998).
Carpenter et al., "Structure of dehydroquinate synthase reveals an active site capable of multistep catalysis," *Nature* 394:299-302 (1998).
Cary et al., "Cloning and Expression of Clostridium acetobutylicum ATCC 824 Acetoacetyl-Coenzyme A:Acetate/Butyrate:Coenzyme A-Transferase in *Escherichia coli*," *App. Environ. Microbiol.* 56(6):1576-1583 (1990).
Cary et al., "Cloning and expression of Clostridium acetobutylicum phosphotransbutyrylase and butyrate kinase genes in *Escherichia coli*," *J. Bacteriol.* 170(10):4613-4618 (1988).
Casero and Pegg, "Spermidine/spermine N1-acetyltransferase—the turning point in polyamine metabolism," *FASEB J.* 7:653-661 (1993).
Cha and Bruce, "Stereo- and regiospecific cis,cis-muconate cycloisomerization by Rhodococcus rhodochrous N75," *FEMS Microbiol. Lett.* 224:29-34 (2003).
Chandra et al. "Pyruvate decarboxylase: a key enzyme for the oxidative metabolism of lactic acid by Acetobacter pasteurianus," *Arch. Microbiol.* 176:443-451 (2001).
Chang et al., "Effects of deletions at the carboxyl terminus of Zymomonas mobills pyruvate decarboxylase on the kinetic properties and substrate specificity," *Biochemistry* 39(31):9430-9437 (2000).
Chaparro-Riggers et al., "Comparison of Three Enoate Reductases and their Potential Use for Biotransformations," *Adv. Synth. Catal.* 349:1521-1531 (2007).
Chatterjee et al., "Mutation of the ptsG Gene Results in Increased Production of Succinate in Fermentation of Glucose by *Escherichia coli*," *Appl. Env. Microbiol.* 67:148-154 (2001).
Chen et al., "A novel lysine 2,3-aminomutase encoded by the yodO gene of Bacillus subtilis: characterization and the observation of organic radical intermediates," *Biochem. J.* 348:539-549 (2000).
Chen et al., "Cloning, Sequencing, Heterologous Expression, Purification, and Characterization of Adenosylcobalamin-dependent D-Ornithine Aminomutase from Clostridium sticklandii," *J. Biol. Chem.* 276:44744-44750 (2001).
Chicco et al., "Regulation of Gene Expression of Branched-chain Keto Acid Dehydrogenase Complex in Primary Cultured Hepatocytes by Dexamethasone and a cAMP Analog," *J. Biol. Chem.* 269(30):19427-19434 (1994).
Chirpich et al., "Lysine 2,3-Aminomutase. Purification and Properties of Pyridoxal Phosphate and S-Adenosylmethionine-Activated Enzyme," *J. Biol. Chem.* 245(7):1778-1789 (1970).
Choi et al., "Enhanced production of cis,cis-muconate in a cell-recycle bioreactor," *J. Ferment. Bioeng.* 84:70-76 (1997).
Chopra et al., "Expression, purification, and biochemical characterization of *Mycobacterium tuberculosis* aspartate decarboxylase, PanD," *Protein Expr. Purif.* 25:533-540 (2002).
Christenson et al., "Kinetic analysis of the 4-methylideneimidazole-5-one-containing tyrosine aminomutase in enediyne antitumor antibiotic C-1027 biosynthesis," *Biochemistry* 42:12708-12718 (2003).
Coco et al., "DNA shuffling method for generating highly recombined genes and evolved enzymes," *Nat. Biotechnol.* 19:354-359 (2001).
Colby and Chen, "Purification and properties of 3-hydroxybutyryl-Coenzyme A dehydrogenase from Clostridium beijerinckii ("Clostridium butylicum") NRRL B593," *Appl. Environ. Microbiol.* 58:3297-3302 (1992).
Coleman, "Expression of a glutamate decarboxylase homologue is required for normal oxidative stress tolerance in *Saccharomyces cerevisiae*," *J. Biol. Chem.* 276:244-250 (2001).

Conrad et al., "D- and L-Isoleucine Metabolism and Regulation of Their Pathways in Pseudomonas Putida," *J. Bacteriol.* 118(1):103-111 (1974).
Cooper, "Glutamate-γ-aminobutyrate transaminase," *Methods Enzymol.* 113:80-82 (1985).
Corthesy-Theulaz et al., "Cloning and Characterization of Helicobacter pylori Succinyl CoA:Acetoacetate CoA-transferase, a Novel Prokaryotic Member of the CoA-transferase Family," *J. Biol. Chem.* 272(41):25659-25667 (1997).
Cox et al., "Development of a metabolic network design and optimization framework incorporating implementation constraints: A succinate production case study," *Metab. Eng.* 8(1):46-57 (2006).
Cunningham et al., "Transcriptional regulation of the aconitase genes (acnA and acnB) of *Escherichia coli*," *Microbiology* 143(Pt 12):3795-3805 (1997).
Datsenko et al., "One-step inactivation of chromosomal genes in *Escherichia coli* K-12 using PCR products," *Proc. Natl. Acad. Sci. U.S.A.* 97:6640-6645 (2000).
Davids et al, "Characterization of the N-acetyltransferases respectively responsible for arylalkylamine and diamine acetylation in Ascaris suum," *Mol. Biochem. Parasitol.* 64(2):341-344 (1994).
Davie et al., "Expression and assembly of a functional E1 component (α2β2) of mammalian branched-chain α-ketoacid dehydrogenase complex in *Escherichia coli*," *J. Biol. Chem.* 267:16601-16606 (1992).
De Biase et al., "Isolation, overexpression, and biochemical characterization of the two isoforms of glutamic acid decarboxylase from *Escherichia coli*," *Protein Expr. Purif.* 8:430-438 (1996).
De la Torre et al., "Identification and functional analysis of a prokaryotic-type aspartate aminotransferase: implications for plant amino acid metabolism," *Plant. J.* 46(3):414-425 (2006).
De Mendonca et al., "Functional characterization by genetic complementation of aroB-encoded dehydroquinate synthase from *Mycobacterium tuberculosis* H37Rv and its heterologous expression and purification," *J. Bacteriol.* 189:6246-6252 (2007).
De Smidt et al., "The alcohol dehydrogenases of *Saccharomyces cerevisiae*: a comprehensive review," *FEMS Yeast Rev.* 7:967-978 (2008).
Deana, "Substrate specificity of a dicarboxyl-CoA: dicarboxylic acid Coenzyme A transferase from rat liver mitochondria," *Biochem. Int.* 26(4):767-773 (1992).
Di Gennaro, "Styrene lower catabolic pathway in Pseudomonas fluorescens ST: identification and characterization of genes for phenylacetic acid degradation," *Arch. Microbiol.* 188(2):117-125 (2007).
Diao et al., "Crystal structure of butyrate kinase 2 from Thermotoga maritima, a member of the ASKHA superfamily of phosphotransferases," *J. Bacteriol.* 191:2521-2529 (2009).
Diao et al., "Crystallization of the butyrate kinase 2 from Thermotoga maritima mediated by vapor diffusion of acetic acid," *Acta. Crystallogr. D. Biol. Crystallogr.* 59(Pt 6):1100-1102 (2003).
Diaz et al., "Gene cloning, heterologous overexpression and optimized refolding of the NAD-glutamate dehydrogenase from Haloferax mediterranei," *Extremophiles* 10:105-115 (2006).
Dittrich et al., "Redistribution of Metabolic Fluxes in the Central Aerobic Metabolic Pathway of *E. coli* Mutant Strains with Deletion of the ackA-pta and poxB Pathways for the Synthesis of Isoamyl Acetate," *Biotechnol. Prog.* 21(2):627-631 (2005).
Donnelly and Cooper, "Succinic semialdehyde dehydrogenases of *Escherichia coli*: Their role in the degradation of p-hydroxyphenylacetate and γ-aminobutyrate," *Eur. J. Biochem.* 113:555-561 (1981).
Donnelly and Cooper, "Two succinic semialdehyde dehydrogenases are induced when *Escherichia coli* K-12 Is grown on γ-aminobutyrate," *J. Bacteriol.* 145:1425-1427 (1981).
Doten et al., "Cloning and Genetic Organization of the pca Gene cluster from Acinetobacter calcoaceticus," *J. Bacteriol.* 169(7):3168-3174 (1987).
Drake, "Acetogenesis, acetogenic bacteria, and the acetyl-CoA "Wood/Ljungdahl" pathway: past and current perspectives," in *Acetogenesis*, H. L. Drake, (ed.), Chapman & Hall, New York, p. 3-60 (1994).
Draths and Frost, "Environmentally compatible synthesis of adipic acid from D-glucose," *J. Am. Chem. Soc.* 116:399-400 (1994).

(56) References Cited

OTHER PUBLICATIONS

Drevland et al., "Enzymology and Evolution of the Pyruvate Pathway to 2-Oxobutyrate in Methanocaldococcus jannachii," *J. Bacteriol.* 189(12):4391-4400 (2007).
Drewke et al., "4-O-Phosphoryl-L-threonine, a substrate of the pdxC(serC) gene product involved in vitamin B6 biosynthesis," *FEBS Lett.* 390:179-182 (1996).
Duncan et al., "Acetate utilization and butyryl Coenzyme A (CoA):acetate-CoA transferase in butyrate-producing bacteria from the human large intestine," *Appl. Environ. Microbiol.* 68(10):5186-5190 (2002).
Duran et al., "Characterization of cDNA clones for the 2-methyl branched-chain enoyl-CoA reductase. An enzyme involved in branched-chain fatty acid synthesis in anerobic mitochondria of the parasitic nematode *Ascaris suum*," *J. Biol. Chem.* 268(30):22391-22396 (1993).
Dusch et al., "Expression of the Corynebacterium glutamicum panD gene encoding L-aspartate-α-decarboxylase leads to pantothenate overproduction in *Escherichia coli*," *Appl. Environ. Microbiol.* 65(4):1530-1539 (1999).
Dutscho et al., "Cloning and sequencing of the genes of 2-hydoxyglutaryl-CoA dehydratase from Acidaminococcus fermentans," *Eur. J. Biochem.* 181(3):741-746 (1989).
Eden et al., "Involvement of branched-chain amino acid aminotransferases in the production of fusel alcohols during fermentation in yeast," *Appl. Microbiol. Biotechnol.* 55:296-300 (2001).
Edwards and Palsson, "Systems properties of the Haemophilus influenzae Rd metabolic genotype," *J. Biol. Chem.* 274(25):17410-17416 (1999).
Edwards and Palsson, "The *Escherichia coli* MG1655 in silico Metabolic Genotype: Its Definition, Characteristics, and Capabilities," *Proc. Natl. Acad. Sci. U.S.A.* 97(10):5528-5533 (2000).
Edwards et al., "In Silico Predictions of *Escherichia coli* metabolic capabilities are Consistent with Experimental Data," *Nat. Biotechnol.* 19(2):125-130 (2001).
Eikmanns et al., "The phosphoenolpyruvate carboxylase gene of Corynebacterium glutamicum: Molecular cloning, nucleotide sequence, and expression." *Mol. Gen. Genet.* 218:330-339 (1989).
Estévez et al., "X-ray crystallographic and kinetic correlation of a clinically observed human fumarase mutation," *Protein Sci.* 11(6):1552-1557 (2002).
Faehnle et al., "A New Branch in the Family: Structure of Aspartate-β-semialdehyde Dehydrogenase from Methanococcus jannaschii," *J. Mol. Biol.* 353:1055-1068 (2005).
Fell and Small, "Fat Synthesis in Adipose Tissue. An Examination of Stoichiometric Constraints," *Biochem. J.* 238(3):781-786 (1986).
Fish and Blumenthal, "2-Keto-3-deoxy-D-glucarate aldolase," *Methods Enzymol.* 9:529-534 (1966).
Fitzgerald and Flanagan, "Characterization and sequence analysis of the human ornithine decarboxylase gene," *DNA* 8:(9):623-634 (1989).
Fong and Palsson, "Metabolic gene-deletion strains of *Escherichia coli* evolve to computationally predicted growth phenotypes," *Nat. Genet.* 36(10):1056-1058 (2004).
Fong et al., "Description and Interpretation of Adaptive Evolution of *Escherichia coli* K-12 MG1655 by Using a Genome-Scale in Silico Metabolic Model," *J. Bacteriol.* 185(21):6400-6408 (2003).
Fonknechten et al., "A conserved gene cluster rules anaerobic oxidative degradation of L-ornithine," *J. Bacteriol.* 191(9):3162-3167 (2009).
Fontaine et al., "Molecular charcterization and transcriptional analysis of adhE2, the gene encoding the NADH-dependent aldehyde/alcohol dehydrogenase responsible for butanol production in alcohologenic cultures of Clostridium acetobutylicum ATCC 824," *J. Bacteriol.* 184:821-830 (2002).
Ford et al., "Molecular properties of the lyst1+ gene and the regulation of α-aminoadipate reductase in Schizosaccharomyces pombe," *Curr. Genet.* 28:131-137 (1995).

Forouhar et al., "Structural and Functional Evidence for Bacillus subtilis PaiA as a Novel N1-Spermidine/spermine Acetyltransferase," *J. Biol. Chem.* 280(48):40328-40336 (2005).
Fries et al., "Reaction Mechanism of the heterotetrameric (α2β2) E1 Component of 2-Oxo Acid Dehydrogenase Multienzyme Complexes," *Biochemistry* 42:6996-7002 (2003).
Frost and Draths, "Synthesis of adipic acid from biomass-derived carbon sources," *Biotechnol. Adv.* 15(1):294 (1997).
Frost, "Redefining chemical manufacture. Replacing petroleum with plant-derived feedstocks," *Ind. Biotechnol.* 1(1):23-24 (2005).
Fu et al., "Crystal structures of human glutaryl-CoA dehydrogenase with and without an alternate substrate: structural bases of dehydrogenation and decarboxylation reactions," *Biochemistry* 43(30):9674-9684 (2004).
Fujii et al., "Characterization of L-lysine 6-aminotransferase and its structural gene from Flavobacterium lutescens IFO3084," *J. Biochem.* 128:391-397 (2000).
Fujii et al., "Error-prone rolling circle amplification: the simplest random mutagenesis protocol," *Nat. Protoc.* 1:2493-2497 (2006).
Fujii et al., "One-step random mutagenesis by error-prone rolling circle amplification," *Nucleic Acids Res.* 32:e145 (2004).
Fujishiro et al., "Crystallization and Some Properties of Acetylpolyamine Amidohydrolase From Mycoplana Bullata," *Biochem. Biophys. Res. Commun.* 157(3):1169-1174 (1988).
Fukao et al., "Succinyl-CoA:3-ketoacid CoA transferase (SCOT): cloning of the human SCOT gene, tertiary structural modeling of the human SCOT monomer, and characterization of three pathogenic mutations," *Genomics* 68:144-151 (2000).
Fukuda and Wakagi, "Substrate recognition by 2-oxoacid:ferredoxin oxidoreductase from *Sulfolobus* sp. Strain 7," *Biochim. Biophys. Acta* 1597:74-80 (2002).
Fukuda et al., "Role of a highly conserved YPITP motif in 2-oxoacid:ferredoxin oxidoreductase Heterologous expression of the gene from *Sulfolobus* sp. Strain 7, and characterization of the recombinant and variant enzymes," *Eur. J. Biochem.* 268:5639-5646 (2001).
Fukumura et al, "Hydrolysis of cyclic and linear oligomers of 6-aminocaproic acid by a bacterial cell extract," *J. Biochem.* 59(6):531-536 (1966).
Fukumura et al., "Purification and properties of a novel enzyme, L-α-amino-ε-caprolactamase from Cryptococcus laurentii," *FEBS Lett.* 89(2):298-300 (1978).
Garras et al., "Subcellular localisation and induction of NADH-sensitive acetyl-CoA hydrolase and propionyl-CoA hydrolase activities in rat liver under lipogenic conditions after treatment with sulfur-substituted fatty acids," *Biochim. Biophys. Acta.* 1255(2):154-160 (1995).
Garvie, "Bacterial lactate dehydrogenases," *Microbiol. Rev.* 44:106-139 (1980).
Gay et al., "Cloning Structural Gene sacB, Which Codes for Exoenzyme Levansucrase of Bacillus subtilis: Expression of the Gene in *Escherichia coli*," *J. Bacteriol.* 153(3):1424-1431 (1983).
Genda et al., "Purification and characterization of fumarase from Corynebacterium glutamicum," *Biosci. Biotechnol. Biochem.* 70:1102-1109 (2006).
Gesher et al., "Genes Coding for a New Pathway of Aerobic Benzoate Metabolism in Azoarcus evansii," *J. Bacteriol.* 184(22):6301-6315 (2002).
Gibbs et al., "Degenerate olignucleotide gene shuffling (DOGS): a method for enhancing the frequence of recombination with family shuffling," *Gene* 271:13-20 (2001).
Gibson and McAlister-Henn, "Physical and genetic interactions of cytosolic malate dehydrogenase with other gluconeogenic enzymes," *J. Biol. Chem.* 278:25628-25636 (2003).
Giesel and Simon, "On the occurrence of enoate reductase and 2-oxo-carboxylate reductase in clostridia and some observations on the amino acid fermentation by Peptostreptococcus anaerobius," *Arch. Microbiol.* 135(1):51-57 (1983).
Gillyon et al., "Putrescine Breakdown in the Yeast Candida boidinii: Subcellular Location of Some of the Enzymes Involved and Properties of Two Acetamidoaldehyde Dehydrogenases," *J. of Gen. Microbiol.* 133:2477-2485 (1987).

(56) References Cited

OTHER PUBLICATIONS

Glasemacher et al., "Purification and properties of acetyl-CoA synthetase (ADP-forming), an archael enzyme of acetate formation and ATP synthesis, from the hyperthermophile Pyrococcus furiosus," *Eur. J. Biochem.* 244:561-567 (1997).
Göbel et al., "Degradation of Aromatics and Chloroaromatics by *Pseudomonas* sp. Strain B13: Cloning, Characterization, and analysis of Sequences Encoding 3-Oxoadipate:Succinyl-Coenzyme A (CoA) Transferase and 3-oxoaipyl-CoA Thiolase," *J. Bacteriol.* 184(1):216-223 (2002).
Gokarn et al., "Metabolic Analysis of *Escherichia coli* in the Presence and Absence of the Carboxylating Enzymes Phosphoenolpyruvate Carboxylase and Pyruvate Carboxylase," *Appl. Environ. Microbiol.* 66:1844-1850 (2000).
Gong et al., "Specificity Determinants for the Pyruvate Dehydrogenase Component Reaction Mapped with Mutated and Prosthetic Group Modified Lipoyl Domains," *J. Biol. Chem.* 275(18):13645-13653 (2000).
Gordon and Doelle, "Purification, properties and immunological relationship of L(+)-lactate dehydrogenase from Lactobacillus casei," *Eur. J. Biochem.* 67:543-555 (1976).
Green et al., "Catabolism of a-ketoglutarate by a sucA mutant of Bradyrhizobium japonicum: evidence for an alternative tricarboxylic acid cycle," *J. Bacteriol.* 182:2838-2844 (2000).
Guest et al., "The fumarase genes of *Escherichia coli*: location of the fumB gene and discovery of a new gene (fumC)," *J. Gen. Microbiol.* 131(11):2971-2984 (1985).
Guirard and Snell, "Purification and properties of ornithine decarboxylase from *Lactobacillus* sp. 30a," *J. Biol. Chem.* 255:5960-5964 (1980).
Guo and Bhattacharjee, "Posttranslational activation, site-directed mutation and phylogenetic analyses of the lysine biosynthesis enzymes a-aminoadipate reductase Lys1p (AAR) and the phosphopantetheinyl transferase Lys7p (PPTase) from Schizosaccharomyces pombe," *Yeast* 21:1279-1288 (2004).
Guo and Bhattacharjee, "Site-directed mutational analysis of the novel catalytic domains of a-aminoadipate reductase (Lys2p) from candida albicans," *Mol. Gen. Gemonics* 269:271-279 (2003).
Hadfield et al., "Active Site Analysis of the Potential Antimicrobial Target Aspartate Semialdehyde Dehydrogenase," *Biochemistry* 40:14475-14483 (2001).
Hadfield et al., "Structure of Aspartate-β-semialdehyde Dehydrogenase from *Escherichia coli*, A Key Enzyme in the Aspartate Family of Amino Acid Biosynthesis," *J. Mol. Biol.* 289:991-1002 (1999).
Haller et al., "Discovering new enzymes and metabolic pathways: conversion of succinate to propionate by *Escherichia coli*," *Biochem.* 39(16):4622-4629 (2000).
Hambraeus and Nyberg, "Enzymatic Hydrogenation of trans-2-Nonenal in Barley," *J. Agric. Food Chem.* 53:8714-8721 (2005).
Hammer and Bode, "Purification and characterization of an inducible L-lysine:2-oxoglutarate 6-aminotransferase from Candida utilis," *J. Basic Microbiol.* 32:21-27 (1992).
Hanai et al., "Engineered synthetic pathway for isopropanol production in *Escherichia coli*," *Appl. Environ. Microbiol.* 73(24):7814-7818 (2007).
Hansford, "Control of mitochondrial substrate oxidation," *Curr. Top Bioenergy* 10:217-278 (1980).
Harrison and Harwood, "The pimFABCDE operon from Rhodopseudomonas palustris mediates dicarboxylic acid degradation and participates in anaerobic benzoate degradation," *Microbiology* 151:727-736 (2005).
Hartel et al., "Purification of glutaryl-CoA dehydrogenase from *Pseudomonas* sp., an enzyme involved in the anaerobic degradation of benzoate," *Arch. Mirobiol.* 159:174-181 (1993).
Harwood and Parales, "The β-ketoadipate pathway and the biology of self-identity," *Annu. Rev. Microbiol.* 50:553-590 (1996).
Harwood et al., "Identification of the pcaRKF Gene cluster from Pseudomonas putida: Involvement in Chemotaxis, Biodegradation, and Transport of 4-Hydroxybenzoate," *J. Bacteriol.* 176(21):6479-6488 (1994).

Hasegawa et al., "Transcriptional regulation of ketone body-utilizing enzyme, acetoacetyl-CoA synthetase, by C/EBPa during adipocyte differentiatiion," *Biochimica. Biophysica. Acta* 1779:414-419 (2008).
Hashimoto et al., "Activation of L-Lysine ε-Dehydrogenase from Agrobacterium tumefaciens by Several Amino Acids and Monocarboxylates," *J. Biochem.* 106:76-80 (1989).
Hasson et al., "The crystal structure of benzoylfomate decarboxylase at 1.6 Å resolution: diversity of catalytic residues in thiamin diphosphate-dependent enzymes," *Biochemistry* 37:9918-9930 (1998).
Hayden et al., "Glutamate dehydrogenase of Halobacterium salinarum: evidence that the gene sequence currently assigned to the NADP+-dependent enzyme is in fact that of the NAD+-dependent glutamate dehydrogenase," *FEMS Microbiol. Lett.* 211:37-41 (2002).
Hayes et al., "Combining computational and experimental screening for rapid optimization of protein properties," *Proc. Natl. Acad. Sci. U.S.A.* 99(25):15926-15931 (2002).
Hayes et al., "The Biofine Process: Production of Levulinic Acid, Furfural and Formic Acid from Lignocellulosic Feedstocks," In *Biorefineries: Industrial Proceses and Products*, Wiley, Weinheim, Germany, 139-164. (2006).
Haywood and Large, "4-Acetamidobutyrate Deacetylase in the Yeast Candida boidinii Grown on Putrescine or Spermidine as Sole Nitrogen, Source and Its Probable Role in Polyamine Catabolism," *J. Gen. Microbiol.* 132:7-14 (1986).
Haywood et al., "Characterization of two 3-ketothiolases possessing differing substrate specificities in the polyhydroxyalkanoate synthesizing organism Alcaligenes eutrophus," *FEMS Microbiol. Lett.* 52:91-96 (1988).
Hemschemeier et al., "Biochemical and physiological characterization of the pyruvate formate-lyase Pfl1 of Chlamydomonas reinhardtii, a typically bacterial enzyme in eukaryotic alga," *Eukaryot. Cell* 7:518-526 (2008).
Henning et al., "Identification of novel benzoylformate decarboxylases by growth selection," *Appl. Environ. Microbiol.* 72:7510-7517 (2006).
Hesslinger et al., "Novel keto acid formate-lyase and propionate kinase enzymes are components of an anaerobic pathway in *Escherichia coli* that degrades L-threonine to propionate," *Mol. Microbiol.* 27(2):477-492 (1998).
Heydari et al., "Highly Stable L-Lysine 6-Dehydrogenase from the thermophile Geobacillus stearothermophilus Isolated from a Japanese Hot Spring: characterization, Gene Cloning and sequencing, and Expression," *Appl. Environ. Microbiol.* 70(2):937-942 (2004).
Hibbert et al., "Directed evolution of biocatalytic processes," *Biomol. Eng.* 22:11-19 (2005).
Highbarger et al., "Mechanism of the reaction catalyzed by acetoacetate decarboxylase. Importance of lysine 116 in determining the pKa of active-site lysine 115," *Biochemistry* 35(1):41-46 (1996).
Hijarrubia et al., "Domain Structure Characterization of the Multi-functional α-Aminoadipate Reductase from Penicillium chrysogenum by Limited Proteolysis," *J. Biol. Chem.* 278(10):8250-8256 (2003).
Hillmer and Gottschalk, "Particulate Nature of Enzymes Involved in the Fermentation of Ethanol and Acetate by Clostridium Kluyveri," *FEBS Lett.* 21(3):351-354 (1972).
Hiser et al., "ERG10 from *Saccharomyces cerevisiae* encodes acetoacetyl-CoA thiolase," *J. Biol. Chem.* 269:31383-31389 (1994).
Ho et al., "Regulation of serine biosynthesis in *Arabidopsis*. Crucial role of plastidic 3-phosphoglycerate dehydrogenase in non-photosynthetic tissues," *J. Biol. Chem.* 274:397-402 (1999).
Hoffmann and Dimroth, "Sterochemistry of the methylmalonyl-CoA decarboxylation reaction," *FEBS Lett.* 220:121-125 (1987).
Hoffmeister et al., "Mitochondrial trans-2-enoyl-CoA reductase of wax ester fermentation from Euglena gracilis defines a new family of enzymes involved in lipid synthesis," *J. Biol. Chem.* 280(6):4329-4338 (2005).
Hofmeister and Buckel, "(R)-lactyl-CoA dehydratase from Clostridium propionicum. Stereochemistry of the dehydration of (R)-2-hydroxybutyryl-CoA to crotonly-CoA," *Eur. J. Biochem.* 206(2):547-552 (1992).
Hofmeister et al., "Cloning and expression of the two genes coding for L-serine dehydratase from Peptostreptococcus asaccharolyticus:

(56) References Cited

OTHER PUBLICATIONS relationship of the iron-sulfur protein to both L-serine dehydratases from *Escherichia coli,*" *J. Bacteriol.* 179(15):4937-4941 (1997).
Hong and Lee, "Enhanced Production of Succinic Acid by Metabolically Engineered *Escherichia coli* with Amplified Activities of Malic Enzyme and Fumarase," *Biotechnol. Bioprocess. Eng.* 9:4:252-255 (2004).
Hong et al., "Importance of redox balance on the production of succinic acid by metabolically engineered *Escherichia coli,*" *Appl. Microbiol. Biotechnol.* 58:286-290 (2002).
Huang et al., "Genetic characterization of the resorcinol catabolic pathway in Corynebacterium glutamicum," *Appl. Environ. Microbiol.* 72:7238-7245 (2006).
Huang et al., "Identification and characterization of a second butyrate kinase from Clostridium acetobutylicum ATCC 824," *J. Mol. Microbiol. Biotechnol.* 2(1):33-38 (2000).
Hübner et al., "The mechanism of substrate activation of pyruvate decarboxylase: A first approach," *Eur. J. Biochem.* 92:175-181 (1978).
Hughes et al., "Cloning and expression of pca genes from Pseudomonas putida in *Escherichia coli,*" *J. Gen. Microbiol.* 134:2877-2887 (1988).
Hugler et al., "Malonyl-Coenzyme A Reductase from Chloroflexus aurantiacus, a Key Enzyme of the 3-Hydroxypropionate Cycle for Autotrophic CO2 Fixation," *J. Bacteriol.* 184(9):2404-2410 (2002).
Huisman and Lalonde, "Enzyme evolution for chemical process applications," In R.N. Patel (ed.), *Biocatalysis in the pharmaceutical and biotechnology industries,* CRC Press, p. 717-742 (2007).
Husain and Steenkamp, "Partial purification and characterization of glutaryl-Coenzyme A dehydrogenase, electron transfer flavoprotein, and electron transfer flavoprotein-Q oxidoreductase from Paracoccus denitrificans," *J. Bacteriol.* 163:709-715 (1985).
Ibarra et al., "*Escherichia coli* K-12 undergoes adaptive evolution to achieve in silico predicted optimal growth," *Nature* 420(6912):186-189 (2002).
Ikai and Yamamoto, "Identification and analysis of a gene encoding L-2,4-diaminobutyrate:2-ketoglutarate 4-aminotransferase involved in the 1,3-diaminopropane production pathway in Acinetobacter baummanni," *J. Bacteriol.* 179:5118-5125 (1997).
Ingoldsby et al., "The discovery of four distinct glutamate dehydrogenase genes in a strain of Halobacterium salinarum," *Gene* 349:237-244 (2005).
Inui et al., "Occurrence of Oxygen-Sensitive, NADP+-Dependent Pyruvate-Dehydrogenase in Mitochondria of Euglena-Gracilis," *J. Biochem.* 96:931-934 (1984).
Ishida et al., "Efficient production of L-Lactic acid by metabolically engineered Saccharomyces cerevisiae with a genome-integrated L-lactate dehydrogenase gene." *Appl. Envirom. Microbiol.* 71:1964-1970 (2005).
Ishige et al., "Wax ester production from n-alkanes by *Acinetobacter* sp. strain M-1: ultrastructure of cellular inclusions and role of acyl Coenzyme A reductase," *Appl. Environ. Microbiol.* 68(3):1192-1195 (2002).
Ismaiel et al., "Purification and Characterization of a Primary-Secondary Alcohol Dehydrogenase from Two Strains of Clostridium beijerinckii," *J. Bacteriol.* 175(16):5097-5105 (1993).
Ismail et al., "Functional genomics by NMR spectroscopy. Phenylacetate catabolism in *Escherichia coli,*" *Eur. J. Biochem.* 270(14):3047-3054 (2003).
Ito et al., "D-3-hydroxybutyrate dehydrogenase from Pseudomonas fragi: molecular cloning of the enzyme gene and crystal structure of the enzyme," *J. Mol. Biol.* 355(4):722-733 (2006).
Izard and Blackwell, "Crystal structures of the metal-dependent 2-dehydro-3-deoxy-galacarate aldolase suggest a novel reaction mechanism," *EMBO J.* 19:3849-3856 (2000).
Izumi et al., "Structure and Mechanism of HpcG, a Hydratase in the Homoprotocatechuate Degradation Pathway of *Escherichia coli,*" *J. Mol. Biol.* 370:899-911 (2007).

Jantama et al., "Combining metabolic engineering and metabolic evolution to develop nonrecombinant strains of *Escherichia coli* C that produce succinate and malate," *Biotechnol. Bioeng.* 99(5):1140-1153 (2008).
Jantama et al., "Eliminating Side Products and Increasing succinate Yields in Engineered Strains of *Escherichia coli* C," *Biotechnol. Bioeng.* 101(5) 881-893 (2008).
Javid-Majd and Blanchard, "Mechanistic Analysis of the argE-Encoded N-Acetylornithine Deacetylase," *Biochemistry* 39:1285-1293 (2000).
Jeng et al., "Ornithine degradation in Clostridium sticklandii; pyridoxial phosphate and Coenzyme A dependent thiolytic cleavage of 2-amino-4-ketopentanoate to alanine and acetyl Coenzyme A," *Biochemistry* 13(14):2898-2903 (1974).
Kaclikova et al., "Fumaric acid overproduction in yeast mutants deficient in fumarase," *FEMS Microbiol. Lett.* 91(2):101-106 (1992).
Kai et al., "Phosphoenolpyruvate carboxylase: three-dimensional structure and molecular mechanisms," *Arch. Biochem. Biophys.* 414:170-179 (2003).
Kakimoto et al., "β-aminoisobutyrate-α-ketoglutarate transaminase in relation to β-aminoisobutyric aciduria," *Biochim. Biophys. Acta* 156(2):374-380 (1968).
Kanagawa, et al., "Characterization of the 6-aminohexanoate-dimer hydrolase from *Pseudomonas* sp. NK87," *J. Gen. Microbiol.* 139(4):787-795 (1993).
Kanehisa and Goto, "KEGG: Kyoto Encyclopedia of Genes and Genomes database," *Nucleic Acids Res.* 28(1):27-30 (2000).
Karyakin et al., "Kinetic properties of L-lysine-2-monooxygenase from Pseufomonas putida and its application to biosensors for L-lysine," *Prikladnaya Biokhimiya I Mikrobiologiya* 27:825-832 (1991).
Kasberg et al., "Cloning, characterization, and sequence analysis of the clcE gene encoding the maleylacetate reductase of *Pseufomonas* sp. Strain B13," *J. Bacteriol.* 179:3801-3803 (1997).
Kaschabek and Reineke, "Degradation of chloroaromatics: purification and characterization of maleylacetate reductase from *Pseudomonas* sp. Strain B13," *J. Bacteriol.* 175:6075-6081 (1993).
Kaschabek and Reineke, "Maleylacetate reductase of *Pseufomonas* sp. Strain B13: specificity of substrate conversion and halide elimination," *J. Bacteriol.* 177:320-325 (1995).
Kaschabek et al., "Degradation of aromatics and chloroaromatics by *Pseudomonas* sp. strain B13: purification and characterization of 3-oxoadipate:succinyl-Coenzyme A (CoA) transferase and 3-oxoadipyl-CoA thiolase," *J. Bacteriol.* 184(1):207-215 (2002).
Kato and Asano, "3-Methylaspartate ammonia-lyase as a marker enzyme of the mesaconate pathway for (S)-glutamate fermentation in Enterobacteriaceae," *Arch. Microbiol.* 168(6):457-463 (1997).
Kazahaya et al, "Aerobic Dissimilation of Glucose by Heterolactic Bacteria III. Aldehyde dehydrogenase and alcohol dehydrogenase of luconostoc mesenteroids" *J. Gen. Appl. Microbiol.* 18(1):43-55 (1972).
Keng and Viola, "Specificity of Aspartokinase III from *Escherichia coli* and Examination of Important Catalytic Residues," *Arch. Biochem. Biophys.* 335(1):73-81 (1996).
Kenklies et al., "Proline biosynthesis from L-ornithine in Clostridium sticklandii: purification of Δ1-pyrroline-5-carboxylate reductase, and sequence and expression of encoding gene, proC," *Microbiology* 145(Pt 4):819-826 (1999).
Kessler et al., "Pyruvate-formate-lyase-deactivase and acetyl-CoA reductase activities of *Escherichia coli* reside on a polymeric protein particle encoded by adhE," *FEBS Lett.* 281(1-2):59-63 (1991).
Khan et al., "Molecular Properties and Enhancement of Thermostability by Random Mutagenesis of Glutamate Dehydrogenase from Bacillus subtilis," *Biosci. Biotechnol. Biochem.* 69(10):1861-1870 (2005).
Killenberg-Jabs et al., "Active oligomeric states of pyruvate decarboxylase and their functional characterization," *Eur. J. Biochem.* 268:1698-1704 (2001).
Kim et al, "Effect of Overexpression of Actinobacillus succinogenes Phosphoenolpyruvate Carboxykinase on Succinate Production in *Escherichia coli,*" *Appl. Env. Microbiol.* 70(2) 1238-1241 (2004).

(56) References Cited

OTHER PUBLICATIONS

Kim et al., "Construction of an *Escherichia coli* K-12 Mutant for Homoethanologenic Fermentation of Glucose or Xylose without Foreign Genes," *Appl. Environ. Microbiol.* 73(6):1766-1771 (2007).
Kim et al., "Dehydration of (R)-2-hydroxyacyl-CoA to enoyl-CoA in the fermentation of a-amino acids by anaerobic bacteria," *FEMS Microbiol. Rev.* 28:455-468 (2004).
Kim et al., "Dihydrolipoamide dehydrogenase mutation alters the NADH sensitivity of pyruvate dehydrogenase complex of *Escherichia coli* K-12," *J. Bacteriol.* 190:3851-3858 (2008).
Kim, "Purification and Properties of a diamine α-Ketoglutarate Transminase from *Escherichia coli*," *J. Biol. Chem.* 239(3):783-786 (1964).
Kinghorn et al., "The cloning and analysis of the aroD gene of *E. coli* K-12," *Gene* 14(1-2):73-80 (1981).
Kinoshita et al., "Purification and characterization of 6-aminohexanoic-acid-oligomer hydrolase of *Flavobacterium* sp. KI72," *Eur. J. Biochem.* 116(3):547-551 (1981).
Klatt et al., "Comparative genomics provides evidence for the 3-hydroxypropionate autotrophic pathway in filamentous anoxygenic phototrophic bacteria and in hot spring microbial mats," *Environ. Microbiol.* 9:2067-2078 (2007).
Kisselev, "Polypeptide Release Factors in Prokaryotes and Eukaryotes: Same Function, Different Structure," *Structure,* 10:8-9 (2002).
Klyosov, "Kinetics and specificity of human liver aldehyde dehydrogenases toward aliphatic, aromatic, and fused polycyclic aldehydes," *Biochemistry* 35(14):4457-4467 (1996).
Knapp et al., "Crystal Structure of the Truncated Cubic Core component of the *Escherichia coli* 2-Oxoglutarate Dehydrogenase Multienzyme Complex," *J. Mol. Biol.* 280:655-668 (1998).
Knappe and Sawers, "A radical-chemical route to acetyl-CoA: the anaerobically induced pyruvate formate-lyase system of *Escherichia coli*," *FEMS. Microbiol. Rev.* 75:383-398 (1990).
Knappe et al., "Post-translational activation introduces a free radical into pyruvate formate-lyase," *Proc. Natl. Acad. Sci. U.S.A.* 81:1332-1335 (1984).
Kobayashi et al., "Physicochemical, catalytic, and immunochemical properties of fumarases crystallized separately from mitochondrial and cytosolic fractions of rat liver," *J. Biochem.* 89(6):1923-1931 (1981).
Kollmann-Koch et al., "Nicotinic acid metabolism. Dimethylmaleate hydratase," *Hoppe Seylers Z Physiol Chem.* 365:s.847-857 (1984).
Koo et al., "Cloning and characterization of the bifunctional alcohol/acetaldehyde dehydrogenase gene (adhE) in Leuconostoc mesenteroides isolated from kimchi," *Biotechnol. Lett.* 27(7):505-510 (2005).
Korbert et al., "Crystallization of the NADP+-dependent Glutamate Dehydrogenase from *Escherichia coli*," *J. Mol. Biol.* 234:1270-1273 (1993).
Korolev et al., "Autotracing of *Escherichia coli* acetate CoA-transferase a-subunit structure using 3.4 Å MAD and 1.9 Å native data," *Acta. Crystallogr. D. Biol. Crystallogr.* 58(Pt 12):2116-2121 (2002).
Kort et al., "Glutamate dehydrogenase from the hyperthermophilic bacterium Thermotoga maritima: molecular characterization and phylogenetic implications," *Extremophiles* 1:52-60 (1997).
Kosaka et al., "Characterization of the sol operon in butanol-hyperproducing Clostridium saccharoperbutylacetonicum strain N1-4 and its degeneration mechanism," *Biosci. Biotechnol. Biochem.* 71:58-68 (2007).
Kouzarides, "Acetylation: a regulatory modification to rival phosphorylation?" *EMBO J.* 19(6):1176-1179 (2000).
Kowalchuk et al., "Contrasting patterns of evolutionary divergence within the Acinetobacter calcoaceticus pca operon," *Gene* 146:23-30 (1994).
Kreimeyer et al., "Identification of the Last Unknown Genes in the Fermentation Pathway of Lysine," *J. Biol. Chem.* 282(10):7191-7197 (2007).
Kretz et al., "Gene site saturation mutagenesis: a comprehensive mutagenesis approach," *Methods Enzymol.* 388:3-11 (2004).
Krieger et al., "Pyruvate decarboxylase from Kluyveromyces lactis an enzyme with an extraordinary substrate activation behaviour," *Eur. J. Biochem.* 269:3256-3263 (2002).
Kuchta and Abeles, "Lactate Reduction in Clostridium propionicum Purification and properties of lactyl-CoA dehydratase" *J. Biol Chem.* 260(24): 13181-13189 (1985).
Kulkarni and Kanekar, "Bioremediation of ε-caprolactum from nylon-6 waste water by use of Pseudomonas aeruginosa MCM B-407," *Curr. Microbiol.* 37(3):191-194 (1998).
Kurihara et al., "A Novel Putrescine Utilization Pathway Involves γ-Glutamylated Intermediates of *Escherichia coli* K-12," *J. Biol. Chem.* 280(6):4602-4608 (2005).
Kurihara et al., "γ-Glutamyputrescine synthetase in the putrescine utilization pathway of *Escherichia coli* K-12," *J. Biol. Chem.* 283(29)19981-19990 (2008).
Kuznetsova et al., "Enzyme genomics: Application of general enzymatic screens to discover new enzymes," *FEMS Microbiol. Rev.* 29(2):263-279 (2005).
Kwok and Hanson, "GFP-labelled Rubisco and aspartate aminotransferase are present in plastid stromules and traffic between plastids," *J. Exp. Bot.* 55(397):595-604 (2004).
Laivenieks et al., "Cloning sequencing, and overexpression of the Anaerobiospirillum succinicproducens phosphoenolpyruvate carboxykinase (pckA) gene," *Appl. Environ. Microbiol.* 63:2273-2280 (1997).
Lam and Winkler, "Metabolic Relationships between Pyridoxine (Vitamin B6) and Serine Biosynthesis in *Escherichia coli* K-12," *J. Bacteriol.* 171(11):6518-6528 (1990).
Lamas-Maceiras et al., "Amplification and disruption of the phenylacetyl-CoA ligase gene of Penicillium chrysogenum encoding an aryl-capping enzyme that supplies phenylacetic acid to the isopenicillin N-acyltransferase," *Biochem. J.* 395(1):147-155 (2006).
Lamed and Zeikus, "Novel NADP-linked alcohol-aldehyde/ketone oxidoreductase in thermophilic ethanologenic bacteria," *Biochem. J.* 195:183-190 (1981).
Lebbink et al., "Engineering activity and stability of Thermotoga maritima glutamate dehydrogenase I. Introduction of a six-residue ion-pair network in the hinge region," *J. Mol. Biol.* 280:287-296 (1998).
Lebbink et al., "Engineering Activity and Stability of Thermotoga maritima glutamate Dehydrogenase. II: construction of a 16-Residue Ion-pair Network at the Subunit Interface," *J. Mol. Biol.* 289:357-369 (1999).
Leduc et al., "The hotdog thioesterase EntH (YbdB) plays a role in vivo in optimal enterobactin biosynthesis by interacting with the ArCP domain of EntB," *J. Bacteriol.* 189(19):7112-7126 (2007).
Lee and Cho, "Identification of essential active-site residues in ornithine decarboxylase of Nicotiana glutinosa decarboxylating both L-ornithine and L-lysine," *Biochem. J.* 360:657-665 (2001).
Lee et al., "A new approach to directed gene evolution by recombined extension on truncated templates (RETT)," *J. Molec. Catalysis* 26:119-129 (2003).
Lee et al., "Chaperonin GroESL mediates the protein folding of human liver mitochondrial aldehyde dehydrogenase in *Escherichia coli*," *Biochem. Biophys. Res. Commun.* 298(2):216-224 (2002).
Lee et al., "Cloning and Characterization of Mannheimia succiniciproducens MBEL55E Phosphoenolpyruvate Carboxykinase (pckA) Gene," *Biotechnol. Bioprocess Eng.* 7:95-99 (2002).
Lee et al., "Fermentative production of chemicals that can be used for polymer synthesis," *Macromol. Biosci.* 4:157-164 (2004).
Lee et al., "Genome-based metabolic engineering of Mannheimia succiniciproducens for succinic acid productiion," *Appl. Environ. Microbiol.* 72(3):1939-1948 (2006).
Lee et al., "Isolation and characterization of a new succinic acid-producing bacterium, Mannheimia succiniciproducens MBEL55E, from bovine rumen," *Appl. Microbiol. Biotechnol.* 58(5):663-668 (2002).
Lee et al., "Phylogenetic diversity and the structural basis of substrate specificity in the β/α-barrel fold basic amino acid decarboxylases," *J. Biol. Chem.* 282:27115-27125 (2007).

(56) References Cited

OTHER PUBLICATIONS

Lee et al., "Metabolic engineering of *Escherichia coli* for enhanced production of succinic acid, based on genome comparison and in silico gene knockout simulation," *Appl Environ Microbiol.* 71(12):7880-7887 (2005).
Lehtio and Goldman, "The pyruvate format lyase family: sequences, structures and activation," *Protein Eng. Des.Sel.* 17:545-552 (2004).
Lehtio et al., "Crystal structure of glycyl radical enzyme from Archaeoglobus fulgidus," *J. Mol. Biol.* 357(1):221-235 (2006).
Lemonnier and Lane, "Expression of the second lysine decarboxylase gene of *Escherichia coli,*" *Microbiology* 144(Pt 3):751-760 (1998).
Leonardo et al., "Anaerobic Regulation of the adhE gene, Encoding the Fermentative Alcohol Dehydrogenase of *Escherichia coli,*" *J. Bacteriology* 175(3):870-878 (1993).
Li and Jordan, "Effects of substitution of tryptophan 412 in the substrate activation pathway of yeast pyruvate decarboxylase," *Biochemistry* 38:10004-10012 (1999).
Lin et al., "Chemostat culture characterization of *Escherichia coli* mutant strains metabolically engineered for aerobic succinate production: A study of the modified metabolic network based on metabolite profile, enzyme activity, and gene expression profile," *Metab. Eng.* 7(5-6):337-352 (2005).
Lin et al., "Fed-batch culture of a metabolically engineered *Escherichia coli* strain designed for high-level succinate production and yield under aerobic conditions," *Biotechnol. Bioeng.* 90:775-779 (2005).
Lin et al., "Genetic Reconstruction of the Aerobic Central Metabolism in *Escherichia coli* for the Absolute Aerobic Production of Succinate," *Biotechnol. Bioeng.* 89(2):148-156 (2005).
Lin et al., "Increasing the Acetyl-CoA pool in the Presence of Overexpressed Phosphoenolpyruvate Carboxylase or Pyruvate Carboxylase Enhances Succinate Production in *Escherichia coli,*" *Biotechnol Prog.* 20(5):1599-1604 (2004).
Lin et al., "Metabolic engineering of aerobic succinate production systems in *Escherichia coli* to improve process productivity and achieve the maximum theoretical succinate yield," *Metab Eng.* 7(2):116-127 (2005).
Lin, "Metabolic Network Design and Engineering in *Escherichia coli*" Ph.D. Thesis, Rice University, Dept. of Bioengineering (2005).
Lingen et al., "Alteration of the substrate specificity of benzoylformate decarboxylase from Pseudomonas putida by directed evolution," *Chembiochem.* 4:721-726 (2003).
Lingen et al., "Improving the carboligase activity of benzoylformate decarboxylase from Pseudomonas putida by a combination of directed evolution and site-directed mutagenesis," *Protein Eng.* 15:585-593 (2002).
Liu et al., "Microbial production of R-3-hydroxybutyric acid by recombinant *E. coli* harboring genes of phbA, phbB, and tesB," *Appl. Microbiol. Biotechnol.* 76:811-818 (2007).
Liu et al., "Purification and characterization of ornithine acetyltransferase from Saccharomyces cerevisiae," *Eur. J. Biochem.* 228:291-296 (1995).
Liu et al., "Crystal structures of unbound and aminooxyacetate-bound *Escherichia coli* γ-aminobutyrate aminotransferase," *Biochemistry* 43(34):10896-10905 (2004).
Locher et al., "Crystal structure of the Acidaminococcus fermentans 2-hydroxyglutaryl-CoA dehydratase component A" *J. Mol. Biol.* 307(1):297-308 (2001).
Louie and Chan, "Cloning and characterization of the gamma-glutamyl phosphate reductase gene of Campylobacter jejuni," *Mol. Gen. Genet.* 240:29-35 (1993).
Louis et al., "Restricted distribution of the butyrate kinase pathway among butyrate-producing bacteria from the human colon," *J. Bacteriol.* 186:2099-2106 (2004).
Low et al., "Mimicking somatic hypermutation: Affinity maturation of antibodies displayed on baceriophage using a bacterial mutator strain," *J. Mol. Biol.* 260(3):359-368 (1996).
Lu et al., "Functional Analysis and Regulation of the Divergent spuABCDEFGH-spuI Operons for Polyamine Uptake and Utilization in Pseudomonas aeruginosa PAO1," *J. Bacteriol.* 184(14):3765-3773 (2002).

Luersen, "Leishmania major thialsine Nε-acetyltransferase: Identification of amino acid residues crucial for substrate binding," *FEBS Lett.* 579:5347-5352 (2005).
Lütke-Eversloh and Steinbüchel, "Biochemical and molecular characterization of a succinate semialdehyde dehydrogenase involved in the catabolism of 4-hydroxybutyric acid in Ralstonia eutropha," *FEMS Microbiol. Lett.* 181(1):63-71 (1999).
Lutz et al., "Creating multiple-crossover DNA libraries independent of sequence identity," *Proc. Natl. Acad. Sci U.S.A.* 98:11248-11253 (2001).
Lutz et al., "Dissecting the functional program of *Escherichia coli* promoters: the combined mode of action of Lac repressor and AraC activator," *Nucleic Acids Res.* 29(18):3873-3881 (2001).
Lutz et al., "Rapid generation of incremental truncation libraries for protein enginering using α-phosphothioate nucleotides," *Nucleic Acids Res.* 29:E16 (2001).
Mack and Buckel, "Conversion of glutaconate CoA-transferase from Acidaminococcus fermentans into an acyl-CoA hydrolase by site-directed mutagenesis," *FEBS Lett.* 405(2):209-212 (1997).
Mack et al., "Location of the two genes encoding glutaconate Coenzyme A-transferase at the beginning of the hydroxyglutarate operon in Acidaminococcus fermentans," *Eur. J. Biochem.* 226:41-51 (1994).
Maes et al., "Crystallization of ornithine acetyltransferase from yeast by counter-diffusion and preliminary x-ray study," *Acta. Crystallogr. Sect. F. Struct. Biol. Cryst. Commun.* 62(Pt 12):1294-1297 (2006).
Mahadevan and Schilling, "The effects of alternate optimal solutions in constraint-based genome-scale metabolic models," *Metab. Eng.* 5(4):264-276 (2003).
Mahan and Csonka, "Genetic analysis of the proBA genes of *Salmonella typhimurium*: physical and genetic analyses of the cloned proB+A+ genes of *Escherichia coli* and of a mutant allele that confers proline overproduction and enhanced osmotolerance," *J. Bacteriol.* 156:1249-1262 (1983).
Mai and Adams, "Purification and characterization of two reversible and ADP-dependent acetyl Coenzyme A synthetases from the hyperthermophilic archaeon Pyrococcus furiosus," *J. Bacteriol.* 178:5897-5903 (1996.).
Majewski and Domach, "Simple Constrained-Optimization View of Acete Overflow in *E. Coli,*" *Biotechnol. Bioeng.* 35(7):732-738 (1990).
Marco-Marin et al., "Site-directed Mutagenesis of *Escherichia coli* Acetylglutamate Kinase and Aspartokinase III Probes the Catalytic and Substrate-binding Mechanisms of these Amino Acid Kinase Family Enzymes and Allows Three-dimensional Modelling of Aspartokinase," *J. Mol. Biol.* 334:459-476 (2003).
Marks et al., "Molecular cloning and characterization of (R)-3-hydroxybutyrate dehydrogenase from human heart," *J. Biol. Chem.* 267(22):15459-15463 (1992).
Martin et al., "Engineering a mevalonate pathway in *Escherichia coli* for production of terpenoids," *Nat. Biotechnol.* 21:796-802 (2003).
Martínez-Blanco et al, "Purification and biochemical characterization of phenylacetyl-CoA ligase from Pseudomonas putida. A specific enzyme for the catabolism of phenylacetic acid," *J. Biol. Chem.* 265(12):7084-7090 (1990).
Martins et al., "Crystal structure of 4-hydroxybutyryl-CoA dehydratase: radical catalysis involving a [4Fe—4S] cluster and flavin," *Proc. Natl. Acad. Sci. U.S.A.* 101(44):15645-15649 (2004).
Matiasek et al., "Volatile ketone formation in bacteria: release of 3-oxopentanoate by soil pseudomonads during growth on heptanoate," *Curr. Microbiol.* 42:276-281 (2001).
Mat-Jan et al., "Mutants of *Escherichia coli* Deficient in the Fermentative Lactate Dehydrogenase," *J. Bacteriol.* 171(1):342-348 (1989).
Matsushima et al., "An enone reductase from Nicotiana tabacum: cDNA cloning, expression in *Escherichia coli,* and reduction of enones with the recombinant proteins," *Bioorg. Chem.* 36:23-28 (2008).
Mattevi et al., "Atomic structure of the cubic core of the pyruvate dehydrogenase multienzyme complex," *Science* 255(5051):1544-1550 (1992).

(56) References Cited

OTHER PUBLICATIONS

Matthies and Schink, "Reciprocal Isomerization of Butyrate and Isobutyrate by the Strictly Anaerobic Bacterium Strain WoG13 and Methanogenic Isobutyrate Degradation by a Defined Triculture," *Appl. Environ. Microbiol.* 58(5):1435-1439 (1992).

McAlister-Henn and Thompson, "Isolation and expression of the gene encoding yeast mitochondrial malate dehydrogenase," *J. Bacteriol.* 169:5157-5166 (1987).

McGregor et al., "argE-Encoded N-Acetyl-L-Ornithine Deacetylase from *Escherchia coli* Contains a Dinuclear Metalloactive Site," *J. Am. Chem. Soc.* 127:14100-14107 (2005).

McPherson and Wootton, "Complete nucleotide sequence of the *Escherichia coli* gdhA gene," *Nucleic Acids Res.* 11:5257-5266 (1983).

Megraw et al., "Formation of lactyl-Coenzyme A and pyruvyl-Coenzyme A from lactic acid by *Escherichia coli,*" *J. Bacteriol.* 90(4):984-988 (1965).

Meinnel et al., "Structural and Biochemical Characterization of the *Escherichia coli* argE Gene Product," *J. Bacteriol.* 174(7):2323-2331 (1992).

Meng and Chuang, "Site-directed Mutagenesis and Functional Analysis of the Active-Site Residues of the E2 Component of Bovine Branched-Chain α-Keto Acid Dehydrogenase Complex," *Biochemistry* 33:12879-12885 (1994).

Menzel et al., "Enzymatic evidence for an involvement of pyruvate dehydrogenase in the anaerobic glycerol metabolism of Klebsiella pneumoniae," *J. Biotech.* 56:135-142 (1997).

Merkel and Nichols, "Characterization and sequence of the *Escherichia coli* panBCD gene cluster," *FEMS Microbiol. Lett.* 143(2-3):247-252 (1996).

Meynial-Salles, I., et al., "A new process for the continuous production of succinic acid from glucose at high yield, titer and productivity," *Biotechnol. Bioeng.* 99(1):129-135 (2008).

Millard et al., "Enhanced production of succinic acid by overexpression of phosphoenolpyruvate carboxylase in *Escherichia coli,*" *Appl. Environ. Microbiol.* 62(5):1808-1810 (1996).

Miller et al., "The catalytic cycle of β-lactam synthetase observed by x-ray crystallographic snapshots," *Proc. Natl. Acad. Sci. U.S.A.* 99(23):14752-14757 (2002).

Minard and McAlister-Henn, "Isolation, nucleotide sequence analysis, and disruption of the MDH2 gene from *Saccharomyces cerevisiae*: evidence for three isozymes of yeast malate dehydrogenase," *Mol. Cell. Biol.* 11:370-380 (1991).

Misono and Nagasaki, "Occurrence of L-Lysine ε-Dehydrogenase in Agrobacterium tumefaciens," *J. Bacteriol.* 150(1):398-401 (1982).

Misono et al., "Properties of L-lysine epsilon-dehydrogenase from Agrobacterium tumefaciens," *J. Biochem.* 105(6):1002-1008 (1989).

Miyazaki et al., "α-Aminoadipate aminotransferase from an extremely thermophilic bacterium, Thermus thermophilus," *Microbiology* 150:2327-2334 (2004).

Mizobata et al., "Purification and characterization of a thermostable class II fumarase from Thermus thermophilus," *Arch. Biochem. Biophys.* 355(1):49-55 (1998).

Mizugaki et al. "Studies on the metabolism of unsaturated fatty acids. IX. Stereochemical studies of the reaction catalyzed by trans-2-enoyl-Coenzyme A reductase of *Escherichia coli,*" *J. Biochem.* 92(5):1649-1654 (1982).

Momany et al., "Crystallographic Structure of PLP-Dependent Ornithine Decarboxylase from Lactobacillus 30a to 3.0 Å Resolution," *J. Mol. Biol.* 252:643-655 (1995).

Monastiri et al., "β-Ketothiolase (2-methylacetoacetyl-CoA thiolase) deficiency: A frequent disease in Tunisia?" *J. Inher. Metab. Dis.* 22:932-933 (1999).

Moore et al., "Expression and Purification of Aspartate β-Semialdehyde Dehydrogenase from Infectious Microorganisms," *Protein Expr. Purif.* 25:189-194 (2002).

Morris and Jinks-Robertson, "Nucleotide sequence of the LYS2 gene of *Saccharomyces cerevisiae*: homology to Bacillus brevis tyrocidine synthetase 1," *Gene* 98:141-145 (1991).

Morton et al., "Cloning, sequencing, and expressions of genes encoding enzymes of the autotrophic acetyl-CoA pathway in the acetogen Clostridium thermoaceticum," in M. Sebald (ed.), *Genetics and molecular biology of anaerobic bacteria,* Springer Verlag, New York, 389-406 (1992).

Mouttaki et al., "Cyclohexane Carboxylate and Benzoate Formation from Crotonate in Syntrophus aciditrophicus," *Appl. Environl. Microbiol.* 73(3):930-938 (2007).

Müh et al., "4-Hydroxybutyryl-CoA dehydratase from Clostridium aminobutyricum: characterization of FAD and iron-sulfur clusters involved in an overall non-redox reaction," *Biochemistry* 35:11710-11718 (1996).

Muller and Buckel, "Activation of (R)-2-hydroxyglutaryl-CoA dehydratase from Acidaminococcus fermentans" *Eur. J. Biochem.* 230(2):698-704 (1995).

Muller et al., "Nucleotide exchange and excisiion technology (NExT) DNA shuffling; a robust method for DNA fragmentation and directed evolution," *Nucleic Acids Res.* 33:e117 (2005).

Musfeldt and Schönheit, "Novel type of ADP-forming acetyl Coenzyme A synthetase in hyperthermophilic archaea: heterologous expression and characterization of isoenzymes from the sulfate reducer Archaeoglobus fulgidus and the methanogen Methanococcus jannaschii," *J. Bacteriol.* 184(3):636-644 (2002).

Nagata et al., "Gene cloning, purification, and characterization of thermostable and halophilic leucine dehydrogenase from a halophilic thermophile, Bacillus licheniformis TSN9," *Appl. Microbiol. Biotechnol.* 44:432-438 (1995).

Naggert et al., "Cloning, sequencing, and characterization of *Escherichia coli* thioesterase II," *J. Biol. Chem.* 266(17):11044-11050 (1991).

Nakahigashi and Inokuchi, "Nucleotide sequence of the fadA and fadB genes from *Escherichia coli,*" *Nucleic Acids Res.* 18(16):4937 (1990).

Nakano et al., "Characterization of Anaerobic Fermentative Growth of Bacillus subtilis: Identification of Fermentation End Products and Genes Required for Growth," *J. Bacteriol.* 179(21):6749-6755 (1997).

Nakazawa et al., "Studies on monooxygenases. V. Manifestation of amino acid oxidase activity by L-lysine monooxygenase," *J. Biol. Chem.* 247:3439-3444 (1972).

Namba et al., "Coenzyme A- and Nicotinamide Adenine Dinucleotide-dependent Branched Chain α-Keto Acid Dehydrogenase," *J. Biol. Chem.* 244(16):4437-4447 (1969).

Ness et al., "Synthetic shuffling expands functional protein diversity by allowing amino acids to recombine independently," *Nat. Biotechnol.* 20:1251-1255 (2002).

Nishimaki et al., "Studies on the Metabolism of Unsaturated Fatty Acids. XIV. Purification and Properties of NADPH-Dependent trans-2-Enoyl-CoA Reductase of *Escherichia coli* K-12," *J. Biochem.* 95(5):1315-1321 (1984).

Nishizawa et al., "Gene expression and characterization of two 2-oxoacid:ferredoxin oxidoreductases from Aeropyrum pernix K1," *FEBS Lett.* 579:2319-2322 (2005).

Nissen et al., "Expression of a cytoplasmic transhydrogenase in *Saccharomyces cerevisiae* results in formation of 2-oxoglutarate due to depletion of the NADPH pool." *Yeast* 18:19-32 (2001).

Niu et al., "Benzene-free synthesis of adipic acid," *Biotechnol. Prog.* 18:201-211 (2002).

Njau et al., "Novel β-hydroxyacid dehydrogenases in *Escherichia coli* and Haemophilus influenza," *J. Biol. Chem.* 275(49):38780-38786 (2000).

Nogales et al., "Characterization of the last step of the aerobic phenylacetic acid degradation pathway," *Microbiology* 153(Pt 2):357-365 (2007).

Ohgami et al., "Expression of acetoacetyl-CoA synthetase, a novel cytosolic ketone body-utilizing enzyme, in human brain," *Biochem. Pharmacol.* 65:989-994 (2003).

Ohsugi et al., "Metabolism of L-β-Lysine by Pseudomonas. Purification and Properties of a Deacetylase-Thiolestrerase Utilizing 4-Acetamidobutyryl CoA and Related Compounds," *J. Biol. Chem.* 256(14):7642-7651 (1981).

Okino et al., "An effeicient succinic acid production process in a metabolically engineered Corynebacterium glutamicum strain," *Appl. Microbiol. Biotechnol.* 81(3):459-464 (2008).

(56) References Cited

OTHER PUBLICATIONS

Oku and Kaneda, "Biosynthesis of branched-chain fatty acids in bacillus subtilis. A decarboxylase is essental for branched-chain fatty acid synthetase," *J. Biol. Chem.* 263:18386-18396 (1988).

Okuno et al., "2-Aminoadipate-2-oxoglutarate aminotransferase isoenzymes in human liver: a plausible physiological role in lysine and tryptophan metabolism." *Enzyme Protein* 47:136-148 (1993).

Olivera et al., "Molecular characterization of the phenylacetic acid catabolic pathway in Pseudomonas putida U: the phenylacetyl-CoA catabolon," *Proc. Natl. Acad. Sci. U.S.A.* 95(11):6419-6424 (1998).

O'Reilly and Devine, "Sequence and analysis of the citrulline biosynthetic operon argC-F from Bacillus subtilis," *Microbiology* 140:1023-1025 (1994).

Ostermeier et al., "A Combinatorial approach to hybrid enzymes independent of DNA homology," *Nat. Biotechnol.* 17:1205-1209 (1999).

Ostermeier et al., "Combinatorial protein engineering by incremental truncation," *Proc. Natl. Acad. Sci. U.S.A.* 96:3562-3567 (1999).

Otten and Quax, "Directed evolution:selecting today's biocatalysts," *Biomol. Eng.* 22:1-9 (2005).

Paik and Kim, "Enzymic syntehsis of e-N-Acetyl-L-Lysine," *Arch. Biochem. Biophys.* 108:221-229 (1964).

Parales and Harwood, "Characterization of the Genes Encoding β-Ketoadipate: Succinyl-Coenzyme A Transferase in Pseudomonas putida," *J. Bacteriol.* 174(14):4657-4666 (1992).

Park and Lee, "Biosynthesis of poly(3-hydroxybutyrate-co-3-hydroxyalkanoates) by metabolically engineered *Escherichia coli* strains," *Appl. Biochem. Biotechnol.* 113-116:335-346 (2004).

Park and Lee, "Identification and characterization of a new enoyl Coenzyme A hydratase involved in biosynthesis of medium-chain-length polyhydroxyalkanoates in recombinant *Escherichia coli*," *J. Bacteriol.* 185(18):5391-5397 (2003).

Park and Lee, "New FadB homologous enzymes and their use in enhanced biosynthesis of medium-chain-length polyhydroxyalkanoates in FadB mutant *Escherichia coli*," *Biotechnol. Bioeng*, 86(6):681-686 (2004).

Park et al., "Regulation of succinate dehydrogenase (sdhCDAB) operon expression in *Escherichia coli* in response to carbon supply and anaerobiosis: role of ArcA and FNR," *Mol. Microbiol.* 15(3):473-482 (1995).

Parke et al., "Cloning and Genetic Characterization of dca Genes Required for β-Oxidation of Straight-Chain Dicarboxylic Acids in *Acinetobacter* sp. Strain ADP1," *Appl. Environ. Microbiol.* 67(10):4817-4827 (2001).

Parsot et al., "Nucleotide sequence of *Escherichia coli* argB and argC genes: comparison of N-acetylglutamate kinase and N-acetylglutamate-γ-semialdehyde dehydrogenase with homologous and analogous enzymes," *Gene* 68:275-283 (1988).

Pauli and Overath, "ato Operon: a Highly Inducible System for Acetoacetate and Butyrate Degradation in *Escherichia coli*," *Eur. J. Biochem.* 29:553-562 (1972).

Pauwels et al., "The N-acetylglutamate synthase/N-acetylgltamate kinase metabolon of *Saccharomyces cerevisiae* allows co-ordinated feedback regulation of the first two steps in arginine biosynthesis," *Eur. J. Biochem.* 270:1014-1024 (2003).

Paxton et al., "Role of branched-chain 2-oxo acid dehydrogenase and pyruvate dehydrogenase in 2-oxobutyrate metabolism," *Biochem. J.* 234:295-303 (1986).

Peoples and Sinskey, "Fine structural analysis of the Zoogloea ramigera phbA-phbB locus encoding β-ketothiolase and acetoacetyl-CoA reductase: nucleotide sequence of phbB," *Mol. Microbiol.* 3:349-357 (1989).

Peretz and Burstein, "Amino acid sequence of alcohol dehydrogenase from the thermophilic bacterium Thermoanaerobium brockii," *Biochemistry* 28(16):6549-6555 (1989).

Petersen and Bennett, "Purification of acetoacetate decarboxylase from clostridium acetobutylicum ATCC 824 and cloning of the acetoacetate decarboxylase gene in *Escherichia coli*," *Appl. Environ. Microbiol.* 56:3491-3498 (1990).

Petitdemange et al., "Regulation of the NADH and NADPH-ferredoxin oxidoreductases in clostridia of the butyric group," *Biochim. Biophys. Acta* 421(2):334-337(1976).

Pfluger et al., "Lysine-2,3-Aminomutase and β-Lysine Acetyltransferase Genes of Methanogenic Archaea Are Salt Induced and Are Essential for the Biosynthesis of Nε-Acetyl-β-Lysine and Growth at High Salinity," *Appl. Environ. Microbiol.* 69(10):6047-6055 (2003).

Pharkya et al., "OptiStrain: A computational Framework for redesign of microbial production systems," *Genome Res.* 14(11):2367-2376 (2004).

Pharkya et al., "Exploring the overproduction of amino acids using the bilevel optimization framework OptKnock," *Biotechnol. Bioeng.* 84(7):887-899 (2003).

Ploux et al., "Investigation of the first step of biotin biosynthesis in Bacillus sphericus," *Biochem. J.* 287:685-690 (1992).

Ploux et al., "The NADPH-linked acetoacetyl-CoA reductase from Zoogloea ramigera, Characterization and mechanistic studies of the cloned enzyme over-produced in *Escherichia coli*," *Eur. J. Biochem.* 174:177-182 (1988).

Pollard et al., "Substrate Selectivity and biochemical Properties of 4-Hydroxy-2-Keto-Pentanoic Acid Aldolase from *Escherichia coli*," *Appl. Environ. Microbiol.* 64(10):4093-4094 (1998).

Polovnikova et al., "Structural and kinetic analysis of catalysis by a thiamine diphosphate-deptendent enzyme, benzoylformate decarboxylase," *Biochemistry* 42:1820-1830 (2003).

Postma et al., "Phosphoenolpyruvate Carbohydrate Phosphotransferase Systems of Bacteria," *Microbiol Rev.* 57(3):543-594 (1993).

Poston, "Assay of leucine 2,3-aminomutase," *Methods Enzymol.* 166:130-135 (1988).

Powlowski et al., "Purification and properties of the physically associated meta-cleavage pathway enzymes 4-hydroxy-2-ketovalerate aldolase and aldehyde dehydrogenase (acylating) from *Pseudomonas* sp. strain CF600," *J. Bacteriol.* 175(2):377-385 (1993).

Price et al., "Genome-scale microbial in silico models: the constraints-based approach," *Trends Biotechnol.* 21(4):162-169 (2003).

Price et al., "Genome-scale models of microbial cells: evaluating the consequences of constraints," *Nat. Rev. Microbiol.* 2(11):886-897 (2004).

Prieto et al., "Molecular Characterization of the 4-Hydroxyphenylacetate Catabolic Pathway of *Escherichia coli* W: Engineering a Mobile Aromatic Degradative Cluster," *J. Bacteriol.* 178(1):111-120 (1996).

Pritchard et al., "A general model of error-prone PCR," *J. Theor. Biol.* 234:497-509 (2005).

Pucci et al., "*Staphylococcus haemolyticus* contains two D-glutamic acid biosynthetic activities, a glutamate racemase and a D-amino acid transminase," *J. Bacteriol.* 177(2):336-342 (1995).

Rado and Hoch, "Phosphotransacetylase from Bacillus subtilis: purification and physiological studies," *Biochim. Biophys. Acta* 321:114-125 (1973).

Rajpal et al., "A general method for greatly improving the affinity of antibodies by using combinatorial libraries," *Proc. Natl. Acad. Sci. U.S.A.* 102:8466-8471 (2005).

Ramjee et al., "*Escherichia coli* L-aspartate-α-decarboxylase: preprotein processing and observation of reaction intermediates by electrospray mass spectrometry," *Biochem. J.* 323(Pt 3):661-669 (1997).

Ramon-Maiques et al., "Structure of Acetylglutamate Kinase, a Key Enzyme for Arginine Biosynthesis and Prototype for the Amino Acid Kinase Enzyme Family, during Catalysis," *Structure* 10:329-342 (2002).

Ramos et al., "Mutations affecting the enzymes involved in the utilization of 4-aminobutyric acid as nitrogen source by the yeast *Saccharomyces cerevisiae*," *Eur.J Biochem.* 149:401-404 (1985).

Rasmussen, L.J., et al. "Carbon Metabolism Regulates Expression of the pfl (Pyruvate-Formate-Lyase) Gene in *Escherichia coli*," *J. Bacteriol.* 173(20):6390-6397 (1991).

Ravagnani et al., "Spo0A directly controls the switch from acid to solvent production in solvent-forming clostridia," *Mol. Microbiol.* 37(5):1172-1185 (2000).

Rea et al., "Structure and Mechanism of HpcH: A Metal Ion Dependent Class II Aldolase from the Homoprotocatechuate Degradation Pathway of *Escherichia coli*," *J. Mol. Biol.* 373:866-876 (2007).

(56) References Cited

OTHER PUBLICATIONS

Recasens et al., "Cystein Sulfinate Aminotransferase and Aspartate Aminotransferase Isoenzymes of Rat Brain. Purification, Characterization, and Further Evidence of Identity," *Biochemistry* 19:4583-4589 (1980).
Reed et al., "An expanded genome-scale model of *Escherichia coli* K-12 (iJR904 GSM/GPR)," *Genome. Biol.* 4(9):R54 (2003).
Reetz and Carballeira, "Iterative saturation mutagenesis (ISM) for rapid directed evolution of functional enzymes," *Nat. Protoc.* 2:891-903 (2007).
Reetz et al., "Directed Evolution of an Enantioselective Enzyme through Combinatorial Multiple-Cassette Mutagenesis, " *Angew. Chem. Int. Ed. Engl.* 40:3589-3591 (2001).
Reetz et al., "Iterative saturation mutagenesis on the basis of B factors as a strategy for incresing protein thermostability," *Angew. Chem. Int. Ed.* 45:7745-7751 (2006).
Reidhaar-Olson and Sauer, "Combinatorial cassette mutagenesis as a probe of the informational content of protein sequences," *Science* 241:53-57 (1988).
Reidhaar-Olson et al., "Random mutagenesis of protein sequences using oligonucleotide cassettes," *Methods Enzymmol.* 208:564-586 (1991).
Reiser and Somerville, "Isolation of mutants of Acinetobacter calcoaceticus deficient in wax ester synthesis and complementation of one mutation with a gene encoding a fatty acyl Coenzyme A reductase," *J. Bacteriol.* 179(9):2969-2975 (1997).
Repetto and Tzagoloff, "Structure and Regulation of KGD1, the Structural Gene for Yeast α-Ketoglutarate Dehydrogenase," *Mol. Cell. Biol.* 9(6):2695-2705 (1989).
Reshetnikov, et al., "Characterization of the ectoine biosynthesis genes of haloalkalotolerant obligate methanotroph 'Methylomicrobium alcaliphilum 20Z'," *Arch. Microbiol.* 184:286-297 (2006).
Resnekov et al., "Organization and regulation of the Bacillus subtilis odhAB operon, which encodes two of the subenzymes of the 2-oxoglutarate dehydrogenase complex," *Mol. Gen. Genet.* 234:285-296 (1992).
Riviere et al., "Acetyl: succinate CoA-transferase in procyclic Trypanosoma brucei. Gene identification and role in carbohydrate metabolism." *J. Biol. Chem.* 279:45337-45346 (2004).
Roberts et al, "The Role of Enoyl-CoA Hydratase in the Metabolism of Isoleucine by Pseudomonas putida," *Arch. Microbiol.* 117:99-108 (1978).
Robinson et al., "Studies on Rat Brain Acyl-Coenzyme A Hydrolase (Short Chain)," *Biochem. Biophys. Res. Commun.* 71(4):959-965 (1976).
Rohdich et al., "Enoate reductases of Clostridia. Cloning, sequencing, and expression," *J. Biol. Chem.* 276(8):5779-5787 (2001).
Romero et al., "Partial purification and characterization and nitrogen regulation of the lysine e-aminotransferase of Streptomyces clavuligers," *J. Ind. Microbiol. Biotechnol.* 18:241-246 (1997).
Roper et al., "Sequence of the hpcC and hpcG genes of the meta-fission homoprotocatechuic acid pathway of *Escherichia coli* C: nearly 40% amino-acid identity with the analogues enzymes of the catechol pathway," *Gene* 156:47-51 (1995).
Rose and Weaver, "The role of the allosteric B site in the fumarase reaction," *Proc. Natl. Acad. Sci. U.S.A.* 101(10):3393-3397 (2004).
Roy and Dawes, "Cloning and Characterization of the gene Encoding Lipoamide Dehydrogenase in *Saccharomyces cerevisiae*, " *J. Gen. Microbiol.* 133:925-933 (1987).
Rozell and Benner, "Stereochemical Imperative in Enzymic Decarboxylations. Stereochemical Course of Decarboxylation Catalyzed by Acetoacetate Decarboxylase," *J. Am. Chem. Soc.* 106:4937-4941 (1984).
Rudman and Meister, "Transamination in *Escherichia coli*, " *J. Biol. Chem.* 200(2):591-604 (1953).
Ruldeekulthamrong et al., "Molecular characterization of lysine 6-dehydrogenase from Achromobacter denitrificans," *BMB Reports* 790-795 (2008).

Sabo et al., "Purification and physical properties of inducible *Escherichia coli* lysine decarboxylase," *Biochemistry* 13:662-670 (1974).
Sakanyan et al., "A re-examination of the pathway for ornithine biosynthesis in a thermophilic and two mesophilic *Bacillus* species," *J. Gen. Microbiol.* 138:125-130 (1992).
Sakurada et al., "Acetylpolyamine Amidohydrolase from Mycoplana ramosa: Gene Cloning and Characterization of the Metal-Substituted Enzyme," *J. Bacteriol.* 178(19):5781-5786 (1996).
Samsonova et al., "Molecular cloning and characterization of *Escherichia coli* K12 ygjG gene," *BMC Microbiol.* 3:2 (2003).
Sanchez et al., "Efficient succinic acid production from glucose through overexpression of pyruvate carboxylase in an *Escherichia coli* alcohol dehydrogenase and lactate dehydrogenase mutant," *Biotechnol. Prog.* 21(2):358-365 (2005).
Sanchez et al., "Novel pathway engineering design of the anaerobic central metabolic pathway in *Escherichia coli* to increase succinate yield and productivity," *Metab. Eng.* 7(3): 229-239 (2005).
Sanchez, et al., "Batch culture characterization and metabolic flux analysis of succinate-producing *Escherichia coli* strains," *Metab Eng.* 8(3):209-226 (2006).
Sankaranarayanan et al., "Preliminary x-ray crystallographic analysis of ornithine acetyltransferase (Rv1653) from *Mycobacterium tuberculosis,*" *Acta. Crystallogr. Sect. F. Struct. Biol. Cryst. Commun.* 65(Pt 2):173-176 (2009).
Sato et al., "Poly[(R)-3-hydroxybutyrate] formation in *Escherichia coli* from glucose through an enoyl-CoA hydratase-mediated pathway," *J. Biosci. Bioeng.* 103(1):38-44 (2007).
Schilling et al., "Combining Pathway Analysis with Flux Balance Analysis for the Comprehensive Study of Metabolic Systems," *Biotechnol. Bioeng.* 71(4):286-306 (2000/2001).
Schilling et al., "Theory for the Systematic Definition of Metabolic Pathways and Their Use in Interpreting Metabolic Function from a Pathway-Oriented Perspective," *J. Theor. Biol.* 203(3):229-248 (2000).
Schilling et al., "Toward Metabolic Phenomics: Analysis of Genomic Data Using Flux Balances," *Biotechnol. Prog.* 15(3):288-295 (1999).
Schmitzberger et al., "Structural constraints on protein self-processing in L-aspartate-α-decarboxylase," *EMBO J.* 22:6193-6204 (2003).
Schulz et al., "Stereospecific production of the herbicide phosphinothricin (glufosinate) by transamination: isolation and characterization of a phosphinothricin-specific transaminase from *Escherichia coli*, " *Appl. Environ. Microbiol.* 56(1):1-6 (1990).
Schwarzer et al., "Nonribosomal peptides: from genes to products," *Nat. Prod. Rep.* 20:275-287 (2003).
Schweiger et al., "Purification of 2-hydroxyglutaryl-CoA dehydratase from Acidaminococcus fermentans. An iron-sulfur protein," *Eur. J. Biochem.* 169(2):441-448 (1987).
Scott and Jakoby, "Soluble γ-aminobutyric-glutamic transaminase from Pseudomonas fluorescens," *J. Biol. Chem.* 234(4):932-936 (1959).
Seedorf et al., "The genome of Clostridium kluyveri, a strict anaerobe with unique metabolic features," *Proc. Natl. Acad. Sci. U.S.A.* 105(6):2128-2133 (2008).
Seibert et al., "Characterization of a gene cluster encoding the maleylacetate reductase from Ralstonia eutropha 335T, and enzyme recruited for growth with 4-fluorobenzoate," *Microbiology* 150:463-472 (2004).
Seibert et al., "Characterization of the maleylacteate reductase MacA of Rhodococcus opacus 1CP and evidence for the presence of an isofunctional enzyme," *J. Bacteriol.* 180:3503-3508 (1998).
Seibert et al., "Purification and characterization of maleylacetate reductase from Alcaligenes eutrophys JMP134(pJP4)," *J. Bacteriol.* 175:6745-6754 (1993).
Selifonova et al., "Rapid evolution of novel traits in microorganisms," *Appl. Environ. Microbiol.* 67:3645-3649 (2001).
Sen et al., "Developments in directed evolution for improving enzyme functins," *Appl. Biochem. Biotechnol.* 143:212-223 (2007).
Shafiani et al., "Cloning and characterization of aspartate-β-semialdehyde dehydrogenase from *Mycobacterium tuberculosis* H37 Rv," *J. Appl. Microbiol.* 98:832-838 (2005).

(56) References Cited

OTHER PUBLICATIONS

Shames et al., "Interaction of Aspartate and Aspartate-derived Antimetabolites with the Enzymes of the Threonine Biosynthetic Pathway of *Escherichia coli,*" *J. Biol. Chem.* 258(24):15331-15339 (1984).
Shao et al., "Random-priming in vitro recombination: an effective tool for directed evolution," *Nucleic Acids Res.* 26:681-683 (1998).
Shibata et al., "Purification, characterization, and immunological properties of fumarase from *Euglena gracilis* var. *bacillaris,"* *J. Bacteriol.* 164(2):762-768 (1985).
Shigeoka and Nakano, "Characterization and molecular properties of 2-oxoglutarate decarboxylase from Euglena gracilis," *Arch. Biochem. Biophys.* 288:22-28 (1991).
Shigeoka et al., "Effect of L-glutamate on 2-oxoglutarate decarboxylase in Euglena gracilis," *Biochem. J.* 282 ( Pt 2):319-323 (1992).
Shimoda et al., "Asymmetric Transformation of Enones with *Synechococcus* sp. PCC 7943," *Bulletin of the Chemical Society of Japan* 77(12):2269-2272 (2004).
Shimomura et al., "3-hydroxyisobutyryl-CoA hydrolase," *Methods Enzymol.* 324:229-240 (2000).
Shimomura et al., "Purification and partial characterization of 3-hydroxyisobutyryl-Coenzyme A hydrolase of rat liver," *J. Biol. Chem.* 269(19):14248-14253 (1994).
Shimoyama et al., "MmcBC in Pelotomaculum thermopropionicum represents a novel group of prokaryotic fumarases," *FEMS Microbiol Lett.* 270(2):207-213 (2007).
Sieber et al., "Libraries of hybrid proteins from distantly related sequences," *Nat. Biotechnol.* 19:456-460 (2001).
Siegert et al., "Exchanging the substrate specificities of pyruvate decarboxylase from Zymomonas mobilis and benzoylformate decarboxylase from Pseudomonas putida," *Protein. Eng. Des. Sel.* 18:345-357 (2005).
Siew et al., "Localization and characteristics of rat liver mitochondrial aldehyde dehydrogenases," *Arch. Biochem. Biophys.* 176(2):638-649 (1976).
Simanshu et al., "Structure and function of enzymes involved in the anaerobic degradation of L-threonine to propionate," *J. Biosci.* 32(6):1195-1206 (2007).
Sinclair et al., Purification and characterization of the branched chain α-ketoacid dehydrogenase complex from *Saccharomyces cerevisiae*, *Biochem. Mol. Biol. Int.* 31(5):911-922 (1993).
Skarstedt and Silverstein, "*Escherichia coli* acetate kinase mechanism studied by net initial rate, equilibrium, and independent isotopic exchange kinetics," *J. Biol. Chem.* 251:6775-6783 (1976).
Slater et al., "Multiple β-ketothiolases mediate poly(β-hydroxyalkanoate) copolymer synthesis in Ralstonia eutropha," *J. Bacteriol.* 180(8):1979-1987 (1998).
Smit et al., "Identification, cloning and characterization of Lactococcus lactis branched-chain α-keto acid decarboxylase involved in flavor formation," *Appl. Environ. Microbiol.* 71:303-311 (2005).
Smith and Kaplan, "Purification, properties and kinetic mechanism of Coenzyme A-linked aldehyde dehydrogenase from Clostridium kluyveri," Arch. Biochem. Biophys. 203:663-675 (1980).
Smith et al., "Purification and characteristics of a γ-glutamyl kinase involved in *Escherichia coli* proline biosynthesis," *J. Bacteriol.* 157:545-551 (1984).
Smith et al., "Fumarate metabolism and the microaerophily of *Campylobacter* species," *Int. J. Biochem. Cell Biol.* 31(9):961-975 (1999).
Soda and Misono,"L-Lysine:α-ketoglutarate aminotransferase. II. Purification, crystallization, and properties," *J. Bacteriol.* 7:4110-4119 (1968).
Söhling and Gottschalk, "Molecular analysis of the anaerobic succinate degradation pathway in Clostridium kluyveri," *J. Bacteriol.* 178:871-880 (1996).
Söhling and Gottschalk, "Purification and characterization of a Coenzyme-A-dependent succinate-semialdehyde dehydrogenase from Clostridium kluyveri," *Eur. J. Biochem.* 212:121-127 (1993).
Sokatch et al., "Purification of a Branched-Chain Keto Acid Dehydrogenase from Pseudomonas putida," *J. Bacteriol.* 148(2):647-652 (1981).
Song et al., "Structure, function, and mechanism of the phenylacetate pathway hot dog-fold thioesterase PaaI," *J. Biol. Chem.* 281(16):11028-11038 (2006).
Sovik, "Mitochondrial 2-methylacetoacetyl-CoA thiolase deficiency: an inborn error of isoleucine and ketone body metabolism," *J. Inherit. Metab. Dis.* 16:46-54 (1993).
Sramek and Frerman, "Purification and properties of *Escherichia coli* Coenzyme A-transferase," *Arch. Biochem. Biophys.* 171(1):14-26 (1975).
Steffan and McAlister-Henn, "Isolation and characterization of the yeast gene encoding the MDH3 isozyme of malate dehydrogenase," *J. Biol. Chem.* 267:24708-24715 (1992).
Steinbacher et al., "Enoate reductase family," in Flavins and Flavoproteins, Proceedings of the Fourteenth International Symposium, St. John's College, University of Cambridge, UK, Jul. 14-18 2002, Chapman et al., pp. 941-949, Rudolf Weber, Agency for Scientific Publications Berlin.
Steinbüchel and Schlegel, "NAD-linked L(+)-lactate dehydrogenase from the strict aerobe alcaligenes eutrophus. 2. Kinetic properties and inhibition by oxaloacetate," *Eur. J. Biochem.* 130(2):329-334 (1983).
Stemmer, "DNA shuffling by random fragmentation and reassembly: in vitro recombination for molecular evolution," *Proc. Natl. Acad. Sci. U.S.A.* 91:10747-10751 (1994).
Stemmer, "Rapid evolution of a protein in vitro by DNA shuffling," *Nature* 370:389-391 (1994).
Stim-Herndon et al., "Characterization of an acetyl-CoA C-acetyltransferase (thiolase) gene from Clostridium acetobutylicum ATCC 824," *Gene* 154(1):81-85 (1995).
Stols and Donnelly, "Production of succinic acid through overexpression of NAD(+)-dependent malic enzyme in an *Escherichia coli* mutant," *Appl. Environ. Microbiol.* 63(7):2695-2701 (1997).
Stols et al., "Expression of Ascaris suum malic enzyme in a mutant *Escherichia coli* allows production of succinic acid from glucose," *Appl. Biochem. Biotechnol.* 63-65: 153-158 (1997).
Stols et al., "New vectors for co-expression of proteins: Structure of Bacillus subtilis ScoAB obtained by High-throughput protocols," *Protein Expr. Purif.* 53:396-403 (2007).
Stoyan et al., "Cloning, sequencing and overexpression of the leucine dehydrogenase gene from Bacillus cereus," *J. Biotechnol.* 54:77-80 (1997).
Stringfellow et al., "Sequence of the *Escherichia coli* C homoprotocatechuic acid degradative operon completed with that of the 2,4-dihydroxyhept-2-ene-1,7-dioicic acide aldolase-encoding gene (hpdH)," *Gene* 166:73-76 (1995).
Suarez de Mata et al., "Propionyl-CoA condensing enzyme from Ascaris muscle mitochondria. I. Isolation and characterization of multiple forms," *Arch. Biochem. Biophys.* 285(1):158-165 (1991).
Suarez de Mata et al., "Propionyl-CoA condensing enzyme from Ascaris muscle mitochondria. II. Coenzyme A modulation," *Arch. Biochem. Biophys.* 285:166-171 (1991).
Suda et al., "Purification and properties of α-ketoadipate reductase, a newly discovered enzyme from human placenta," *Arch. Biochem. Biophys.* 176(2):610-620 (1976).
Suda et al., "Subcellular localization and tissue distribution of α-ketoadipate reduction and oxidation in the rat," *Biochem. Biophys. Res. Commun.* 77(2):586-591 (1977).
Suematsu et al., "Molecular cloning and functional expression of rat liver cytosolic acetyl-CoA hydrolase," *Eur. J. Biochem.* 268(9):2700-2709 (2001).
Suzuki et al., "Acetylputrescine deacetylase from Micrococcus luteus K-11," *Biochim. Biophys. Acta* 882:140-142 (1986).
Suzuki, "Phospotransacetylase of *Escherichia coli* B., activation by pyruvate and inhibition by NADH and certain nucleotides," *Biochem. Biophys. Acta* 191:559-569 (1969).
Svetlitchnyi et al., "A functional Ni—Ni-[4Fe—4S] cluster in the monomeric acetyl-CoA synthase from Carboxydothermus hydrogenoformans," *Proc. Natl. Acad. Sci. U.S.A.* 101(2):446-451 (2004).

(56) References Cited

OTHER PUBLICATIONS

Takahashi and Yamada, "Metabolic pathways for cytoxic and end product formation from glutamate- and aspartate-containing peptides by Porphyromonas gingivalis," *J. Bacteriol.* 182:4704-4710 (2000).
Takahashi-Abbe et al., "Biochemical and functional properties of a pyruvate formate-lyase (PFL)-activating system in *Streptococcus mutans*," *Oral Microbiol. Immunol.* 18:293-297 (2003).
Takatsuka et al., "Gene cloning and molecular characterization of lysine decarboxylase from Selenomonas ruminantium delineate its evolutionary relationship to ornithine decarboxylases from eukaryotes," *J. Bacteriol.* 182:6732-6741 (2000).
Takatsuka et al., "Identification of the amino acid residues conferring substrate specificity upon Selenomonas ruminantium lysine decarboxylase," *Biosci. Biotechnol. Biochem.* 63:1843-1846 (1999).
Tamaki et al., "Purification and properties of aldehyde dehydrogenase from *Saccharomyces cerevisiae*," *J. Biochem.* 82(1):73-79 (1977).
Tamaki et al., "Purification, properties, and sequencing of aminoisobutyrate aminotransferases from rat liver," *Methods Enzymol.* 324:376-389 (2000).
Tanaka et al., "Lysine decarboxylase of Vibrio parahaemolyticus: kinetics of transcription and role in acid resistance," *J. Appl. Microbiol.* 104:1283-1293 (2008).
Tanous et al., "Glutamate dehydrogenase activity can be transmitted naturally to Lactococcus lactis strains to stimulate amino acid conversion to aroma compounds," *Appl. Environ. Microbiol.* 72(2):1402-1409 (2006).
Teipel et al., "The substrate specificity of fumarase," *J. Biol. Chem.* 243:5684-5694 (1968).
Ter Schure et al., "Pyruvate decarboxylase catalyzes decarboxylation of branched-chain 2-oxo acids but is not essential for fusel alcohol production by *Saccharomyces cerevisiae*," *Appl. Environ. Microbiol.* 64:1303-1307 (1998).
Thauer, "Microbiology. A Fifth Pathway of Carbon Fixation," *Science* 318:1732-1733 (2007).
Thykaer et al., "Metabolic network analysis of an adipoyl-7-ADCA-producing strain of Penicillium chrysogenum: elucidation of adipate degradation," *Metab. Eng.* 4(2):151-158 (2002).
Tian et al., "Variant tricarboxylic acid cycle in *Mycobacterium tuberculosis*: identification of α-ketoglutarate decarboxylase," *Proc. Natl. Acad. Sci. U.S.A.* 102:10670-10675 (2005).
Tobin et al., "Localization of the Lysine ε-Aminotransferase (lat) and δ-Aminoadipyl)-L-Cysteinyl-D-Valine Synthetase (pcbAB) Genes from Streptomyces clavuligerus and Production of Lysine ε-Aminotransferase Activity in *Escherichia coli*," *J. Bacteriol.* 173(19):6223-6229 (1991).
Toth et al., "The ald Gene, Encoding a Coenzyme A-Acylating Aldehyde Dehydrogenase, Distinguishes Clostridium beijerinckii and Two Other Solvent-Producing Clostridia from Clostridium acetobutylicum," *App. Environ. Microbiol.* 65(11):4973-4980 (1999).
Tretter and Adam-Vizi, "Alpha-ketoglutarate dehydrogenase: a target and generator of oxidative stress," *Philos. Trans. R. Soc. B* 360:2335-2345 (2005).
Tseng et al., "Oxygen- and growth rate-dependent regulation of *Escherichia coli* fumarase (FumA, FumB, and BumC) activity," *J. Bacteriol.* 183(2):461-467 (2001).
Tucci and Martin, "A novel prokaryotic trans-2-enoyl-CoA reductase from the spirochete Treponema denticola," *FEBS Lett.* 581(8):1561-1566 (2007).
Twarog and Wolfe, "Role of butyryl phosphate in the energy metabolism of Clostridium tetanomorphum," *J. Bacteriol.* 86:112-117 (1963).
Urbance et al., "Evaluation of succinic acid continuous and repeat-batch biofilm fermentation by Actinobacillus succinogenes using plastic composite support bioreactors," *Appl. Microbiol. Biotechnol.* 65(6):664-670 (2004).
Vadali, et al., "Cofactor engineering of intercellular CoA/acetyl-CoA and its effect on metabolic flux redistribution in *Escherichia coli*," *Metab Eng.* 6(2): 133-139 (2004).

Valdes-Hevia and Gancedo, "Isolation and characterization of the gene encoding phosphoenolpyruvate carboxykinase from *Saccharomyces cerevisiae*," *FEBS Lett.* 258:313-316 (1989).
Vamecq et al., "The microsomal dicarboxylyl-CoA synthetase," *Biochem. J.* 230(3):683-693 (1985).
Van Grinsven et al., "Acetate:succinate CoA-transferase in the hydrogenosomes of Trichomonas vaginalis: identification and characterization," *J. Biol. Chem.* 283:1411-1418 (2008).
Vandecasteele et al., "Aldehyde dehydrogenases from Pseudomonas aeruginosa," *Methods Enzymol.* 89 Pt D:484-490 (1982).
Vanderwinkel et al., "Growth of *Escherichia coli* on fatty acids: requirement for Coenzyme A transferase activity," *Biochem. Biophys. Res. Commun.* 33(6):902-908 (1968).
Vanrolleghem et al., "Validation of a Metabolic Network for *Saccharomyces cerevisiae* Using Mixed Substrate Studies," *Biotechnol. Prog.* 12(4):434-448 (1996).
Varma and Palsson, "Stoichiometric Flux Balance Models Quantitatively Predice Growth and Metabolic By-Product Secretion in Wild-Type *Escherichia coli* W3110," *Appl. Env. Microbiol.* 60(10):3724-3731 (1994).
Varma and Palsson, "Metabolic Flux Balancing: Basic Concepts, Scientific and Practical Use," *Biotechnology* 12:994-998 (1994).
Varma et al., "Biochemical Production Capabilities of *Escherichia coli*," *Biotechnol. Bioeng.* 42:59-73 (1993).
Varma et al., "Stoichiometric Interpretation of *Escherichia coli* Glucose Catabolism under Various Oxygenation Rates," *Appl. Environ. Microbiol.* 59:2465-2473 (1993).
Venkitasubramanian et al. in Biocatalysis in the Pharmaceutical and Biotechnology Industires, ed. R.N. Patel, Chapter 15, pp. 425-440, CRC Press LLC, Boca Raton, FL. 2007.
Venkitasubramanian et al., "Reduction of Carboxylic Acids by Nocardia Aldehyde Oxidoreductase Requires a Phosphopantetheinylated Enzyme," *J. Biol. Chem.* 282(1):478-485 (2007).
Vernal et al., "Cloning and heterologous expression of a broad specificity aminotransferase of Leishmania mexicana promastigotes," *FEMS Microbiol. Lett.* 229:217-222 (2003).
Vernal et al., "Isolation partial characterization of a broad specificity aminotransferase from leishmania mexicana promastigotes," *Mol. Biochem. Parasitol.* 96:83-92 (1998).
Voellmy and Leisinger, "Role of 4-Aminobutyrate Aminotransferase in the Arginine Metabolism of Pseudomonas aeruginosa," *J. Bacteriol.* 128(3):722-729 (1976).
Volkov et al., "Random chimeragenesis by heteroduplex recombination," *Methods Enzymol.* 328:456-463 (2000).
Volkov et al., "Recombination and chimeragenesis by in vitro heteroduplex formation and in vivo repair," *Nucleic Acids Res.* 27:e18 (1999).
Wakil et al., "Studies on the fatty acid oxidizing system of animal tissues. VI. β-Hydroxyacyl Coenzyme A dehydrogenase," *J. Biol. Chem.* 207(2):631-638 (1954).
Walter et al., "Sequence and arrangement of two genes of the butyrate-synthesis pathway of Clostridium acetobutylicum ATCC 824," *Gene* 134(1):107-111 (1993).
Wang and Barker, "Purification and Properties of L-citramalate hydrolase," *J. Biol. Chem.* 244(10):2516-2526 (1969).
Wang et al, "Molecular cloning and functional identification of a novel phenylacetyl-CoA ligase gene from Penicillium chrysogenum," *Biochem. Biopyhs. Res. Commun.* 360(2):453-458 (2007).
Wang et al., "The primary structure of branched-chain α-oxo acid dehydrogenase from Bacillus subtilis and its similarity to other α-oxo acid dehydrogenases," *Eur. J. Biochem.* 213:1091-1099 (1993).
Wang et al., "Genome-scale in silico aided metabolic analysis and flux comparisons of *Escherichia coli* to improve succinate production," *Appl. Microbiol. Biotechnol.* 73(4):887-894 (2006).
Wanner and Tressl, "Purification and characterization of two enone reductases from *Saccharomyces cerevisia*," *Eur. J. Biochem.* 255(1):271-278 (1998).
Watanabe et al., "A novel α-ketoglutaric semialdehyde dehydrogenase: evolutionary insight into an alternative pathway of bacterial l-arabinose metabolism," *J. Biol. Chem.* 281(39):28876-28888 (2006).
Weaver, "Structure of free fumarase C from *Escherichia coli*," *Acta. Crystallogr. D. Biol. Crystallogr.* 61(Pt 10):1395-1401 (2005).

(56) References Cited

OTHER PUBLICATIONS

Weidner and Sawers, "Molecular characterization of the Genes Encoding Pyruvate Formate-Lyase and Its Activating enzyme of clostridium pasteruianum," *J. Bacteriol.* 178(8):2440-2444 (1996).
Westin et al., "The identification of a succinyl-CoA thioesterase suggests a novel pathway for succinate production in peroxisomes," *J. Biol. Chem.* 280(46):38125-38132 (2005).
Whalen and Berg, "Analysis of an avtA::Mu d1(Ap lac) Mutant: Metabolic Role of Transaminase C," *J. Bacteriol.* 150(2):739-746 (1982).
Whalen and Berg, "Gratuitous repression of avtA in *Escherichia coli* and *Salmonella typhimurium*," *J. Bacteriol.* 158(2):571-574 (1984).
Whisstock et al., "Prediction of protein function from protein sequence and structure," *Quarterly Rev. Biophys.*, 36(3):307-340 (2003).
Wiesenborn et al., "Coenzyme A Transferase from clostridium acetobutylicum ATCC 824 and Its Role in the Uptake of Acids," *Appl. Environ. Microbiol.* 55(2):323-329 (1989).
Wiesenborn et al., "Phosphotransbutyrylase from clostridium acetobutylicum ATCC 824 and its role in acidogenesis," *Appl. Environ. Microbiol.* 55:317-322 (1989).
Wilkie and Warren, "Recombinant expression, purification, and characterization of three isoenzymes of aspartate aminotransferase from *Arabidopsis thaliana*," *Protein Expr. Purif.* 12:381-389 (1998).
Wilks et al., "Designs for a Broad Substrate Specificity Keto Acid Dehydrogenase," *Biochemistry* 29:8587-8591 (1990).
Willke and Vorlop, "Industrial bioconversion of renewable resources as an alternative to conventional chemistry," *Appl. Microbiol. Biotechnol.* 66(2):131-142 (2004).
Winzer et al., "Differential regulation of two thiolase genes from Clostridium acetobutylicum DSM 792," *J. Mol. Microbiol. Biotechnol.* 2(4):531-541 (2000).
Witkowski et al., "Conversion of a β-Ketoacyl Synthase to a Malonyl Decarboxylase by Replacement of the Active-Site Cysteine with Glutamine," *Biochem.*, 38:11643-11650 (1999).
Wittich and Walter, "Putrescine N-acetyltransferase in Onchocerca volvulus and Ascaris suum, an enzyme which is involved in polyamine degradation and release of N-acetylputrescine," *Mol. Biochem. Parasitol.* 38:13-17 (1990).
Wong et al., "Molecular Properties of Pyruvate Formate-Lyase Activating Enzyme," *Biochemistry* 32:14102-14110 (1993).
Wong et al., "Sequence saturation mutagenesis (SeSaM): a novel method for directed evolution," *Nucleic Acids Res.* 32:e26 (2004).
Wong et al., "Sequence saturation mutagenesis with tunable mutation frequencies," *Anal. Biochem.* 341:187-189 (2005).
Wong et al., "Transversion-enriched sequence saturation mutagenesis (SeSaM-Tv+): a random mutagenesis method with consecutive nucleotide exchanges that complements the bias of error-prone PCR," *Biotechnol. J.* 3:74-82 (2008).
Woods et al., "Two biochemically distinct classes of fumarase in *Escherichia coli*," *Biochim. Biophys. Acta* 954(1):14-26 (1988).
Wu et al., "Microbial synthesis of cis-cis-muconic acid by *Sphingobacterium* sp. GcG generated from effluent of a styrene monomer (SM) production plant," *Enzyme Microbial. Tech.* 35:598-604 (2004).
Wynn et al., "Chaperonins groEL and groES promote assembly of heterotetramers (α2β2) of mammalian mitochondrial branched-chain a-keto acid decarboxylase in *Escherichia coli*," *J. Biol. Chem.* 267:12400-12403 (1992).
Wynn et al., "Cloning and expression in *Escherichia coli* of mature E1 βsubunit of bovine mitochondrial branched-chain α-keto acid dehydrogenase complex. Mapping of the E1 β-binding region on E2," *J. Biol. Chem.* 267:1881-1887 (1992).
Yabutani et al., "Analysis of β-ketothiolase and acetoacetyl-CoA reductase genes of a methylotrophic bacterium, Paracoccus denitrificans, and their expression in *Escherichia coli*," *FEMS Microbiol. Lett.* 133:85-90 (1995).

Yagi et al., "Aspartate: 2-oxoglutarate aminotransferase from bakers' yeast: crystallization and characterization," *J. Biochem.* 92(1):35-43 (1982).
Yagi et al., "Crystallization and properties of aspartate aminotransferase from *Escherichia coli* B," *FEBS Lett.* 100(1):81-84 (1979).
Yagi et al., "Glutamate-aspartate transaminase from microorganisms," *Methods Enzymol.* 113:83-89 (1985).
Yan and Chen, "Coenzyme A-acylating aldehyde dehydrogenase from Clostridium beijennckii NRRL B692," *Appl. Environ. Microbiol.* 56:2591-2599 (1990).
Yang et al., "Aspartate Dehydrogenase, a Novel Enzyme Identified from Structural and Functional Studies of TM1643," *J. Biol. Chem.* 278(10):8804-8808 (2003).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 265(18):10424-10429 (1990).
Yang et al., "Nucleotide sequence of the fadA gene. Primary structure of 3-ketoacyl-Coenzyme A thiolase from *Escherichia coli* and the structural organization of the fadAB operon," *J. Biol. Chem.* 266(24):16255 (1991).
Yang et al., "Nucleotide sequence of the promoter and fadB gene of the fadBA operon and primary structure of the multifunctional fatty acid oxidation protein from *Escherichia coli*," *Biochem.* 30(27):6788-6795 (1991).
Yang et al., "The effects of feed and intracellular pyruvate levels on the redistribution of metabolic fluxes in *Escherichia coli*," *Metab Eng.* 3(2):115-123 (2001).
Yang, "Location of the fadBA operon on the physical map of *Escherichia coli*," *J. Bacteriol.* 173(23):7405-7406 (1991).
Yang, et al., "Effect of inactivation of nuo and ackA-pta on redistribution of metabolic fluxes in *Escherichia coli*," *Biotechnol Bioeng.* 65(3):291-297 (1999).
Yang, et al., "Redistribution of Metabolic Fluxes in *Escherichia coli* with Fermentative Lactate Dehydrogenase Overexpression and Deletion," *Metab. Eng.* 1:141-152 (1999).
Yarlett et al., "Trichomonas vaginalis: characterization of ornithine decarboxylase," *Biochem. J.* 293(Pt2):487-493 (1993).
Yeh and Ornston, Evolutionarily Homologous α2β2 Oligomeric Structures in β-Ketoadipate Succinyl-CoA Transferases from Acinetobacter calcoaceticus and Pseudomonas putida, *J. Biol. Chem.* 256(4):1565-1569 (1981).
Youngleson et al., "Homology between hydroxybutyryl and hydroxyacyl Coenzyme A dehydrogenase enzymes from Clostridium acetobutylicum fermentation and vertebrate fatty acid β-oxidation pathways," *J. Bacteriol.* 171(12):6800-6807 (1989).
Yun et al., "The genes for anabolic 2-oxoglutarate: ferredoxin oxidoreductse from hydrogenobacter thermophilus TK-6," *Biochem. Biophys. Res. Commun.* 282(2):589-594 (2001).
Yun et al., "Enhancement of lactate and succinate formation in adhE or pta-ackA mutants of NADH dehydrogenase-deficient *Escherichia coli*," *J. Appl. Microbiol.* 99(6):1404-1412 (2005).
Zeiher and Randall, "Identification and characterization of Mitochondrial Acetyl-Coenzyme A Hydrolase from Pisum sativum L. Seedlings," *Plant. Physiol.* 94:20-27 (1990).
Zeikus et al., "Biotechnology of succinic acid production and markets for derived industrial products," *Appl. Microbiol. Biotechnol.* 51: 545-552 (1999).
Zhang et al., "2-Oxoacid:Ferredoxin Oxidoreductase from the thermoacidophilic Archaeon, *Sulfolobus* sp Strain 7," *J. Biochem.* 120:587-599 (1996).
Zhang et al., "Genes encoding acyl-CoA dehydrogenase (AcdH) homologues from Streptomyces coelicolor and Streptomyces avermitilis provide insights into the metabolism of small branched-chain fayy acids and marcrolide antibiotic production, " *Microbiol.* 145 (Pt 9):2323-2334 (1999).
Zhao and Winkler, "A novel α-ketoglutarate reductase activity of the serA-encoded 3-phosphoglycerate dehydrogenase of *Escherichia coli* K-12 and its possible implications for human 2-hydroxyglutaric aciduria," *J. Bacteriol.* 178(1):232-239 (1996).
Zhao et al., "Molecular evolution by staggered extension process (StEP) in vitro recombination," *Nat. Biotechnol.* 16:258-261 (1998).

(56) References Cited

OTHER PUBLICATIONS

Zhou et al., "Engineering a native homoethanol pathway in *Escherichia coli* B for ethanol production," *Biotechnol. Lett.* 30:335-342 (2008).
Zhou et al., "The remarkable structural and functional organization of the eukaryotic pyruvate dehydrogenase complexes," *Proc. Natl. Acad. Sci. U.S.A.* 98:14802-14807 (2001).
Zhuang, et al., "The YbgC protein encoded by the ybgC gene of the tol-pal gene cluster of Haemophilus influenzae catalyzes acyl-Coenzyme A thioester hydrolysis," *FEBS Lett.* 516(1-3):161-163 (2002).

* cited by examiner

MICROORGANISMS AND METHODS FOR THE BIOSYNTHESIS OF ADIPATE, HEXAMETHYLENEDIAMINE AND 6-AMINOCAPROIC ACID

This application is a divisional of U.S. application Ser. No. 15/263,149, filed Sep. 12, 2016, which is a continuation of U.S. application Ser. No. 13/730,612, filed Dec. 28, 2012, now issued U.S. Pat. No. 9,458,480, which is a continuation of U.S. application Ser. No. 12/776,365, filed May 7, 2010, now issued U.S. Pat. No. 8,377,680, which claims the benefit of priority of U.S. Provisional Application Ser. No. 61/176,196, filed May 7, 2009, U.S. Provisional Application Ser. No. 61/219,365, filed Jun. 22, 2009, U.S. Provisional Application Ser. No. 61/244,844, filed Sep. 22, 2009, U.S. Provisional Application Ser. No. 61/246,973, filed Sep. 29, 2009, and U.S. Provisional Application Ser. No. 61/247,533, filed Sep. 30, 2009, each of which the entire contents of are incorporated herein by reference.

The instant application contains a Sequence Listing which has been submitted via EFS-Web and is hereby incorporated by reference in its entirety. Said ASCII copy, created on Dec. 7, 2018, is named 12956-469-999_SeqList.txt and is 33,776 bytes in size.

BACKGROUND OF THE INVENTION

The present invention relates generally to biosynthetic processes, and more specifically to organisms having adipate, hexamethylenediamine, 6-aminocaproic acid and caprolactam biosynthetic capability.

Adipic acid, a dicarboxylic acid, has a molecular weight of 146.14. It can be used is to produce nylon 6,6, a linear polyamide made by condensing adipic acid with hexamethylenediamine. This is employed for manufacturing different kinds of fibers. Other uses of adipic acid include its use in plasticizers, unsaturated polyesters, and polyester polyols. Additional uses include for production of polyurethane, lubricant components, and as a food ingredient as a flavorant and gelling aid.

Historically, adipic acid was prepared from various fats using oxidation. Some current processes for adipic acid synthesis rely on the oxidation of KA oil, a mixture of cyclohexanone, the ketone or K component, and cyclohexanol, the alcohol or A component, or of pure cyclohexanol using an excess of strong nitric acid. There are several variations of this theme which differ in the routes for production of KA or cyclohexanol. For example, phenol is an alternative raw material in KA oil production, and the process for the synthesis of adipic acid from phenol has been described. The other versions of this process tend to use oxidizing agents other than nitric acid, such as hydrogen peroxide, air or oxygen.

In addition to hexamethylenediamine (HMDA) being used in the production of nylon-6,6 as described above, it is also utilized to make hexamethylene diisocyanate, a monomer feedstock used in the production of polyurethane. The diamine also serves as a cross-linking agent in epoxy resins. HMDA is presently produced by the hydrogenation of adiponitrile.

Caprolactam is an organic compound which is a lactam of 6-aminohexanoic acid (ε-aminohexanoic acid, 6-aminocaproic acid). It can alternatively be considered cyclic amide of caproic acid. One use of caprolactam is as a monomer in the production of nylon-6. Caprolactam can be synthesized from cyclohexanone via an oximation process using hydroxylammonium sulfate followed by catalytic rearrangement using the Beckmann rearrangement process step.

Methods for effectively producing commercial quantities of compounds such as hexamethylenediamine, 6-aminocaproic acid, levulinic acid and carpolactam are described herein and include related advantages.

SUMMARY OF INVENTION

The invention provides a non-naturally occurring microbial organism having a 6-aminocaproic acid, caprolactam or hexametheylenediamine pathway. The microbial organism contains at least one exogenous nucleic acid encoding an enzyme in the respective 6-aminocaproic acid, caprolactam, hexametheylenediamine or levulinic acid pathway. The invention additionally provides a method for producing 6-aminocaproic acid, caprolactam or hexametheylenediamine. The method can include culturing a 6-aminocaproic acid, caprolactam, hexametheylenediamine or levulinic acid producing microbial organism, where the microbial organism expresses at least one exogenous nucleic acid encoding a 6-aminocaproic acid, caprolactam, hexametheylenediamine or levulinic acid pathway enzyme in a sufficient amount to produce the respective product, under conditions and for a sufficient period of time to produce 6-aminocaproic acid, caprolactam, hexametheylenediamine or levulinic acid.

DETAILED DESCRIPTION OF THE INVENTION

Figure 1:
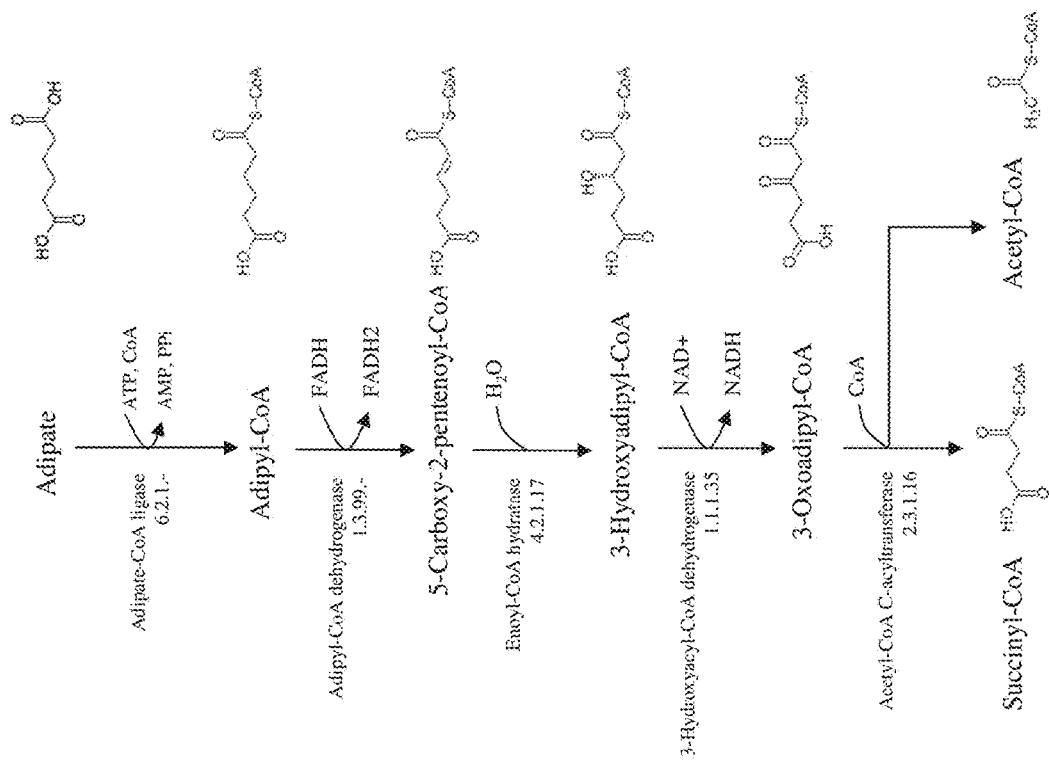
FIG. 1 shows an exemplary pathway for adipate degradation in the peroxisome of *Penicillium chrysogenum*.

The present invention is directed to the design and production of cells and organisms having biosynthetic production capabilities for 6-aminocaproic acid, caprolactam, hexamethylenediamine or levulinic acid. The results described herein indicate that metabolic pathways can be designed and recombinantly engineered to achieve the biosynthesis of 6-aminocaproic acid, caprolactam, hexamethylenediamine or levulinic acid in *Escherichia coli* and other cells or organisms. Biosynthetic production of 6-aminocaproic acid, caprolactam, hexamethylenediamine or levulinic acid can be confirmed by construction of strains having the designed metabolic genotype. These metabolically engineered cells or organisms also can be subjected to adaptive evolution to further augment 6-aminocaproic acid, caprolactam, hexamethylenediamine or levulinic acid biosynthesis, including under conditions approaching theoretical maximum growth.

As disclosed herein, a number of metabolic pathways for the production of 6-aminocaproic acid, caprolactam, hexamethylenediamine or levulinic acid are described. Two routes, the reverse adipate degradation pathway and the 3-oxoadipate pathway, were found to be beneficial with respect to: (i) the adipate yields (92% molar yield on glucose), (ii) the lack of oxygen requirement for adipate synthesis, (iii) the associated energetics, and (iv) the theoretical capability to produce adipate as the sole fermentation product. Metabolic pathways for adipate production that pass through α-ketoadipate or lysine are also described but are lower yielding and require aeration for maximum production. A pathway for producing either or both of 6-aminocaproate and caprolactam from adipyl-CoA, a precursor in the reverse degradation pathway, is also disclosed herein.

As disclosed herein, a number of exemplary pathways for biosynthesis of adipate are described. One exemplary pathway involves adipate synthesis via a route that relies on the reversibility of adipate degradation as described in organisms such as *P. chrysogenum* (see Examples I and II). A second exemplary pathway entails the formation of 3-oxoadipate followed by its reduction, dehydration and again reduction to form adipate (see Examples III and IV). The adipate yield using either of these two pathways is 0.92 moles per mole glucose consumed. The uptake of oxygen is not required for attaining these theoretical maximum yields, and the energetics under anaerobic conditions are favorable for growth and product secretion. A method for producing adipate from glucose-derived cis,cis-muconic acid was described previously (Frost et al., U.S. Pat. No. 5,487,987, issued Jan. 30, 1996)(see Example V). Advantages of the embodiments disclosed herein over this previously described method are discussed. Metabolic pathways for adipate production that pass through α-ketoadipate (Example VI) or lysine (Example VII) precursors are lower yielding and require aeration for maximum production. A pathway for producing either or both of 6-aminocaproate and caprolactam from adipyl-CoA, a precursor in the reverse degradation pathway, is described (see Example VIII and IX). Additional pathways for producing adipate are described in Examples X and XI. Pathways for producing any one, two, three or all four of 6-aminocaproate, caprolactam, hexamethylenediamine and levulinic acid from succinyl-CoA and acetyl-CoA are described in Examples XII, XXVIII. Several pathways for the production of 6-aminocaproate from succinic semialdehyde and pyruvate are described in Example XIX. Several pathways for the production of hexamethylenediamine from 6-aminocaproate are described in Examples XX and XXVII. A pathway for producing either or both 6-aminocaproate and hexamethylenediamine from glutamate is described in Examples XXIV and XXV. Several pathways for the production of hexamethylenediamine from glutaryl-CoA and at least one pathway for production of 6-aminocaproate from glutaryl-CoA are described in Examples XXIV and XXV. A pathway for producing 6-aminocaproate from homolysine is described in Example XXV. Pathways for producing hexamethylenediamine from 2-amino-7-oxosubarate are described in Example XXIV. Several pathways for producing 6-aminocaproate are described in Example XXV. Exemplary genes and enzymes required for constructing microbes with these capabilities are described as well as methods for cloning and transformation, monitoring product formation, and using the engineered microorganisms for production.

As disclosed herein, six different pathways for adipic acid synthesis using glucose/sucrose as a carbon substrate are described. For all maximum yield calculations, the missing reactions in a given pathway were added to the *E. coli* stoichiometric network in SimPheny that is similar to the one described previously (Reed et al., Genome Biol. 4:R54 (2003)). Adipate is a charged molecule under physiological conditions and was assumed to require energy in the form of a proton-based symport system to be secreted out of the network. Such a transport system is thermodynamically feasible if the fermentations are carried out at neutral or near-neutral pH. Low pH adipic acid formation would require an ATP-dependent export mechanism, for example, the ABC system as opposed to proton symport. The reactions in the pathways and methods of implementation of these pathways are described in Examples I-XI.

As used herein, the term "non-naturally occurring" when used in reference to a microbial organism or microorganism of the invention is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes within a 6-aminocaproic acid, caprolactam, hexamethylenediamine or levulinic acid biosynthetic pathway.

A metabolic modification refers to a biochemical reaction that is altered from its naturally occurring state. Therefore, non-naturally occurring microorganisms can have genetic modifications to nucleic acids encoding metabolic polypeptides or, functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" is intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, "adipate," having the chemical formula —OOC—(CH2)4-COO— (see FIG. 2) (IUPAC name hexanedioate), is the ionized form of adipic acid (IUPAC name hexanedioic acid), and it is understood that adipate and adipic acid can be used interchangeably throughout to refer to the compound in any of its neutral or ionized forms, including any salt forms thereof. It is understood by those skilled understand that the specific form will depend on the pH.

As used herein, "6-aminocaproate," having the chemical formula —OOC—(CH2)5-NH2 (see FIGS. 8 and 12), is the ionized form of 6-aminocaproic acid (IUPAC name 6-aminohexanoic acid), and it is understood that 6-aminocaproate and 6-aminocaproic acid can be used interchangeably throughout to refer to the compound in any of its neutral or ionized forms, including any salt forms thereof. It is understood by those skilled understand that the specific form will depend on the pH.

Figure 8:
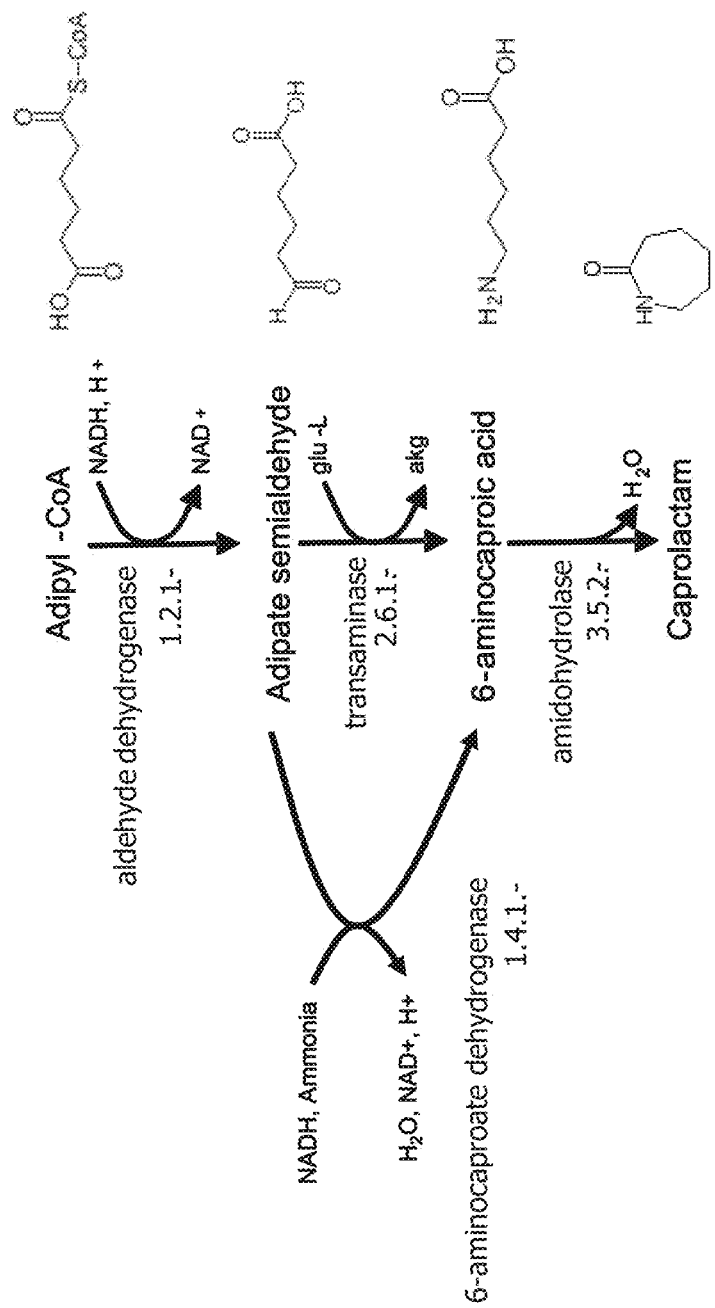
FIG. 8 shows an exemplary caprolactam synthesis pathway using adipyl-CoA as a starting point.

As used herein, "caprolactam" (IUPAC name azepan-2-one) is a lactam of 6-aminohexanoic acid (see FIG. 8).

Figure 10:
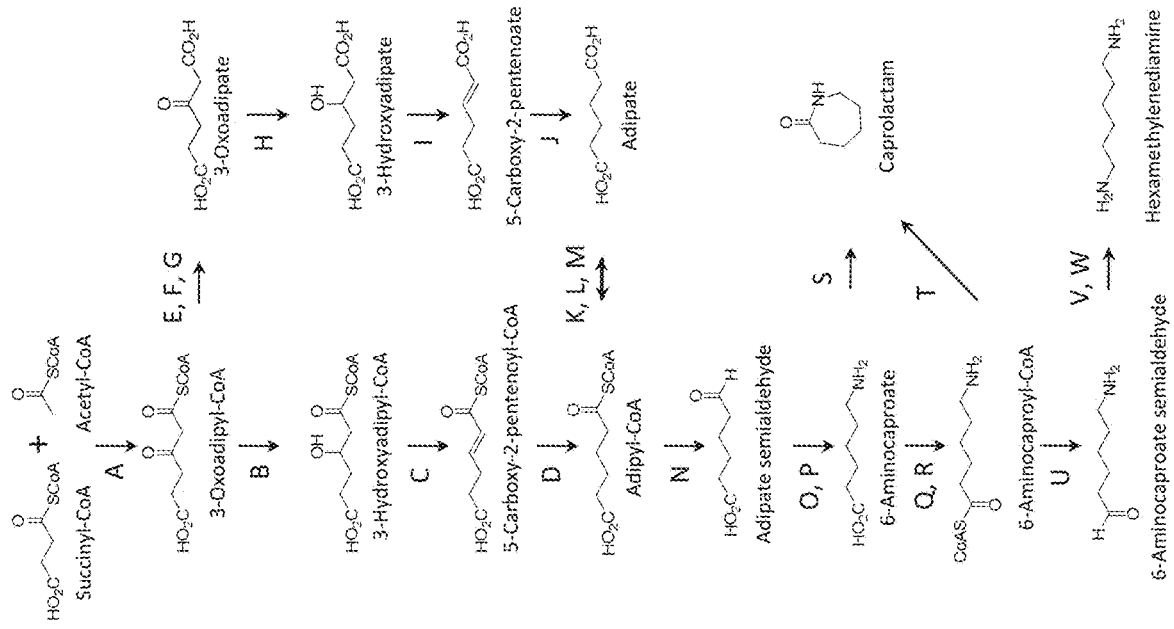
FIG. 10 shows exemplary pathways from succinyl-CoA and acetyl-CoA to hexamethylenediamine (HMDA) and caprolactam. Pathways for the production of adipate, 6-aminocaproate, caprolactam, and hexamethylenediamine from succinyl-CoA and acetyl-CoA are depicted. Abbreviations: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) 3-oxoadipyl-CoA/acyl-CoA transferase, F) 3-oxoadipyl-CoA synthase, G) 3-oxoadipyl-CoA hydrolase, H) 3-oxoadipate reductase, I) 3-hydroxyadipate dehydratase, J) 5-carboxy-2-pentenoate reductase, K) adipyl-CoA/acyl-CoA transferase, L) adipyl-CoA synthase, M) adipyl-CoA hydrolase, N) adipyl-CoA reductase (aldehyde forming), 0) 6-aminocaproate transaminase, P) 6-aminocaproate dehydrogenase, Q) 6-aminocaproyl-CoA/acyl-CoA transferase, R) 6-aminocaproyl-CoA synthase, S) amidohydrolase, T) spontaneous cyclization, U) 6-aminocaproyl-CoA reductase (aldehyde forming), V) HMDA transaminase, W) HMDA dehydrogenase.
Figure 11:
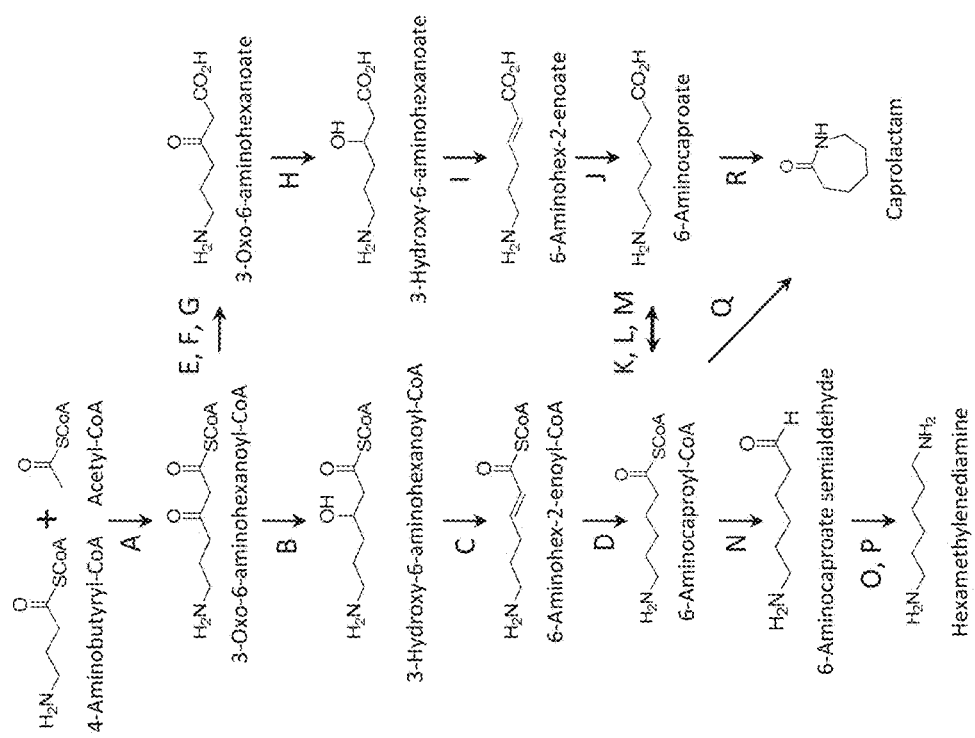
FIG. 11 shows exemplary pathways from 4-aminobutyryl-CoA and acetyl-CoA to hexamethylenediamine and caprolactam. Pathways for the production of 6-aminocaproate, caprolactam, and hexamethylenediamine from 4-aminobutyryl-CoA and acetyl-CoA are depicted. Abbreviations: A) 3-oxo-6-aminohexanoyl-CoA thiolase, B) 3-oxo-6-aminohexanoyl-CoA reductase, C) 3-hydroxy-6-aminohexanoyl-CoA dehydratase, D) 6-aminohex-2-enoyl-CoA reductase, E) 3-oxo-6-aminohexanoyl-CoA/acyl-CoA transferase, F) 3-oxo-6-aminohexanoyl-CoA synthase, G) 3-oxo-6-aminohexanoyl-CoA hydrolase, H) 3-oxo-6-aminohexanoate reductase, I) 3-hydroxy-6-aminohexanoate dehydratase, J) 6-aminohex-2-enoate reductase, K) 6-aminocaproyl-CoA/acyl-CoA transferase, L) 6-aminocaproyl-CoA synthase, M) 6-aminocaproyl-CoA hydrolase, N) 6-aminocaproyl-CoA reductase (aldehyde forming), 0) HMDA transaminase, P) HMDA dehydrogenase, Q) spontaneous cyclization, R) amidohydrolase.
Figure 13:
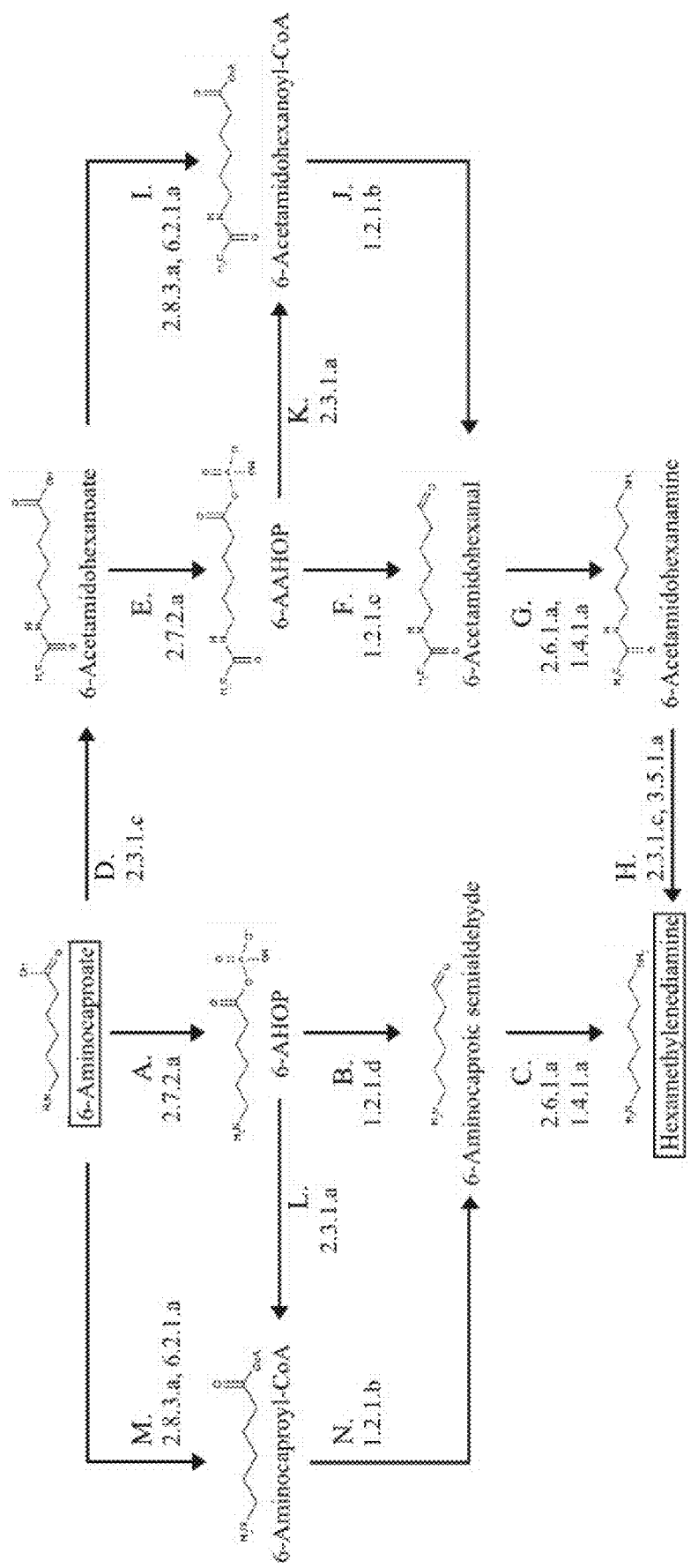
FIG. 13 shows pathways to hexamethylenediamine from 6-aminocapropate. Enzymes are A) 6-aminocaproate kinase, B) 6-AHOP oxidoreductase, C) 6-aminocaproic semialdehyde aminotransferase and/or 6-aminocaproic semialdehyde oxidoreductase (aminating), D) 6-aminocaproate N-acetyltransferase, E) 6-acetamidohexanoate kinase, F) 6-AAHOP oxidoreductase, G) 6-acetamidohexanal aminotransferase and/or 6-acetamidohexanal oxidoreductase (aminating), H) 6-acetamidohexanamine N-acetyltransferase and/or 6-acetamidohexanamine hydrolase (amide), I) 6-acetamidohexanoate CoA transferase and/or 6-acetamidohexanoate CoA ligase, J) 6-acetamidohexanoyl-CoA oxidoreductase, K) 6-AAHOP acyltransferase, L) 6-AHOP acyltransferase, M) 6-aminocaproate CoA transferase and/or 6-aminocaproate CoA ligase, N) 6-aminocaproyl-CoA oxidoreductase. Abbreviations are: 6-AAHOP=[(6-acetamidohexanoyl)oxy]phosphonate and 6-AHOP=[(6-aminohexanoyl)oxy]phosphonate.

As used herein, "hexamethylenediamine," also referred to as 1,6-diaminohexane or 1,6-hexanediamine, has the chemical formula H2N(CH2)6NH2 (see FIGS. 10, 11 and 13).

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "osmoprotectant" when used in reference to a culture or growth condition is intended to mean a compound that acts as an osmolyte and helps a microbial organism as described herein survive osmotic stress. Osmoprotectants include, for example, betaines, amino acids, and the sugar trehalose. Non-limiting examples of such are glycine betaine, praline betaine, dimethylthetin, dimethylslfoniopropionate, 3-dimethyl sulfonio-2-methylproprionate, pipecolic acid, dimethyl sulfonioacetate, choline, L-carnitine and ectoine.

As used herein, the term "growth-coupled" when used in reference to the production of a biochemical is intended to mean that the biosynthesis of the referenced biochemical is produced during the growth phase of a microorganism. In a particular embodiment, the growth-coupled production can be obligatory, meaning that the biosynthesis of the referenced biochemical is an obligatory product produced during the growth phase of a microorganism.

As used herein, "metabolic modification" is intended to refer to a biochemical reaction that is altered from its naturally occurring state. Metabolic modifications can include, for example, elimination of a biochemical reaction activity by functional disruptions of one or more genes encoding an enzyme participating in the reaction. Sets of exemplary metabolic modifications are described herein (see Example XXX).

As used herein, the term "gene disruption," or grammatical equivalents thereof, is intended to mean a genetic alteration that renders the encoded gene product inactive. The genetic alteration can be, for example, deletion of the entire gene, deletion of a regulatory sequence required for transcription or translation, deletion of a portion of the gene which results in a truncated gene product, or by any of various mutation strategies that inactivate the encoded gene product. One particularly useful method of gene disruption is complete gene deletion because it reduces or eliminates the occurrence of genetic reversions in the non-naturally occurring microorganisms of the invention.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid of the invention can utilize either or both a heterologous or homologous encoding nucleic acid.

It is understood that when more than one exogenous nucleic acid is included in a microbial organism that the more than one exogenous nucleic acids refers to the referenced encoding nucleic acid or biosynthetic activity, as discussed above. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The non-naturally occurring microbial organisms of the invention can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

In the case of gene disruptions, a particularly useful stable genetic alteration is a gene deletion. The use of a gene deletion to introduce a stable genetic alteration is particularly useful to reduce the likelihood of a reversion to a phenotype prior to the genetic alteration. For example, stable growth-coupled production of a biochemical can be achieved, for example, by deletion of a gene encoding an enzyme catalyzing one or more reactions within a set of metabolic modifications. The stability of growth-coupled production of a biochemical can be further enhanced through multiple deletions, significantly reducing the likelihood of multiple compensatory reversions occurring for each disrupted activity.

Those skilled in the art will understand that the genetic alterations, including metabolic modifications exemplified herein, are described with reference to a suitable host organism such as E. coli and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the E. coli metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the non-naturally occurring microorganism. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the non-naturally occurring microbial organisms of the invention having 6-aminocaproic acid, caprolactam, hexamethylenediamine or levulinic acid biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes. In gene disruption strategies, evolutionarily related genes can also be disrupted or deleted in a host microbial organism, paralogs or orthologs, to reduce or eliminate activities to ensure that any functional redundancy in enzymatic activities targeted for disruption do not short circuit the designed metabolic modifications.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Disclosed herein are non-naturally occurring microbial organisms capable of producing adipate, 6-aminocaproic acid, caprolactam, hexamethylenediamine or levulinic acid. For example, an adipate pathway can be a reverse adipate degradation pathway (see Examples I and II). For example, a non-naturally occurring microbial organism can have an adipate pathway including at least one exogenous nucleic acid encoding an adipate pathway enzyme expressed in a sufficient amount to produce adipate, the adipate pathway including succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In addition, an adipate pathway can be through a 3-oxoadipate pathway (see Examples III and IV). A non-naturally occurring microbial organism can have an adipate pathway including at least one exogenous nucleic acid encoding an adipate pathway enzyme expressed in a sufficient amount to produce adipate, the adipate pathway including succinyl-CoA:acetyl-CoA acyl transferase, 3-oxoadipyl-CoA transferase, 3-oxoadipate reductase, 3-hydroxyadipate dehydratase, and 2-enoate reductase.

Additionally, a non-naturally occurring microbial organism can have a 6-aminocaproic acid pathway including at least one exogenous nucleic acid encoding a 6-aminocaproic acid pathway enzyme expressed in a sufficient amount to produce 6-aminocaproic acid, the 6-aminocaproic acid pathway including CoA-dependent aldehyde dehydrogenase and transaminase (see Examples VIII and IX). Alternatively, 6-aminocaproate dehydrogenase can be used to convert adipate semialdehyde to form 6-aminocaproate (see FIG. 8). A non-naturally occurring microbial organism can also have a caprolactam pathway including at least one exogenous nucleic acid encoding a caprolactam pathway enzyme expressed in a sufficient amount to produce caprolactam, the caprolactam pathway including CoA-dependent aldehyde dehydrogenase, transaminase or 6-aminocaproate dehydrogenase, and amidohydrolase (see Examples VIII and IX).

As disclosed herein, a 6-aminocaproic acid or caprolactam producing microbial organism can produce 6-aminocaproic acid and/or caprolactam from an adipyl-CoA precursor (see FIG. 8 and Examples VIII and IX). Therefore, it is understood that a 6-aminocaproic acid or caprolactam producing microbial organism can further include a pathway to produce adipyl-CoA. For example an adipyl-CoA pathway can include the enzymes of FIG. 2 that utilize succinyl-CoA and acetyl-CoA as precursors through the production of adipyl-CoA, that is, lacking an enzyme for the final step of converting adipyl-CoA to adipate. Thus, one exemplary adipyl-CoA pathway can include succinyl-CoA:acetyl-CoA acyl transferase, 3-hydroxyacyl-CoA dehydrogenase, 3-hydroxyadipyl-CoA dehydratase and 5-carboxy-2-pentenoyl-CoA reductase.

In addition, as shown in FIG. 1, an adipate degradation pathway includes the step of converting adipate to adipyl-CoA by an adipate CoA ligase. Therefore, an adipyl-CoA pathway can be an adipate pathway that further includes an enzyme activity that converts adipate to adipyl-CoA, including, for example, adipate-CoA ligase activity as in the first step of FIG. 1 or any of the enzymes in the final step of FIG. 2 carried out in the reverse direction, for example, any of adipyl-CoA synthetase (also referred to as adipate Co-A ligase), phosphotransadipylase/adipate kinase, adipyl-CoA:acetyl-CoA transferase or adipyl-CoA hydrolase. An enzyme having adipate to adipyl-CoA activity can be an endogenous activity or can be provided as an exogenous nucleic acid encoding the enzyme, as disclosed herein. Thus, it is understood that any adipate pathway can be utilized with an adipate to adipyl-CoA enzymatic activity to generate an adipyl-CoA pathway. Such a pathway can be included in a 6-aminocaproic acid or caprolactam producing microbial organism to provide an adipyl-CoA precursor for 6-aminocaproic acid and/or caprolactam production.

Figure 6:
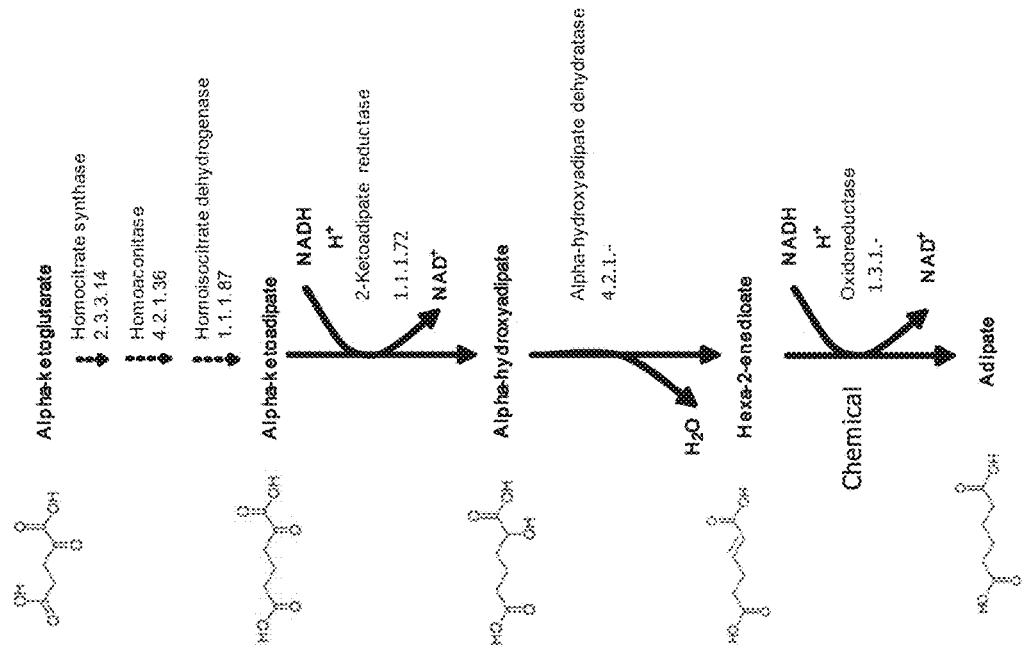
FIG. 6 shows an exemplary pathway for adipate synthesis via alpha-ketoadipate using alpha-ketoglutarate as a starting point.

An additional exemplary adipate pathway utilizes alpha-ketoadipate as a precursor (see FIG. 6 and Example VI). For example, a non-naturally occurring microbial organism can have an adipate pathway including at least one exogenous nucleic acid encoding an adipate pathway enzyme expressed in a sufficient amount to produce adipate, the adipate pathway including homocitrate synthase, homoaconitase, homoisocitrate dehydrogenase, 2-ketoadipate reductase, alpha-hydroxyadipate dehydratase and oxidoreductase. A further exemplary adipate pathway utilizes a lysine dedgradation pathway (see FIG. 7 and Example VII). Another non-naturally occurring microbial organism can have an adipate pathway including at least one exogenous nucleic acid encoding an adipate pathway enzyme expressed in a sufficient amount to produce adipate, the adipate pathway including carbon nitrogen lyase, oxidoreductase, transaminase and oxidoreductase.

Figure 9:
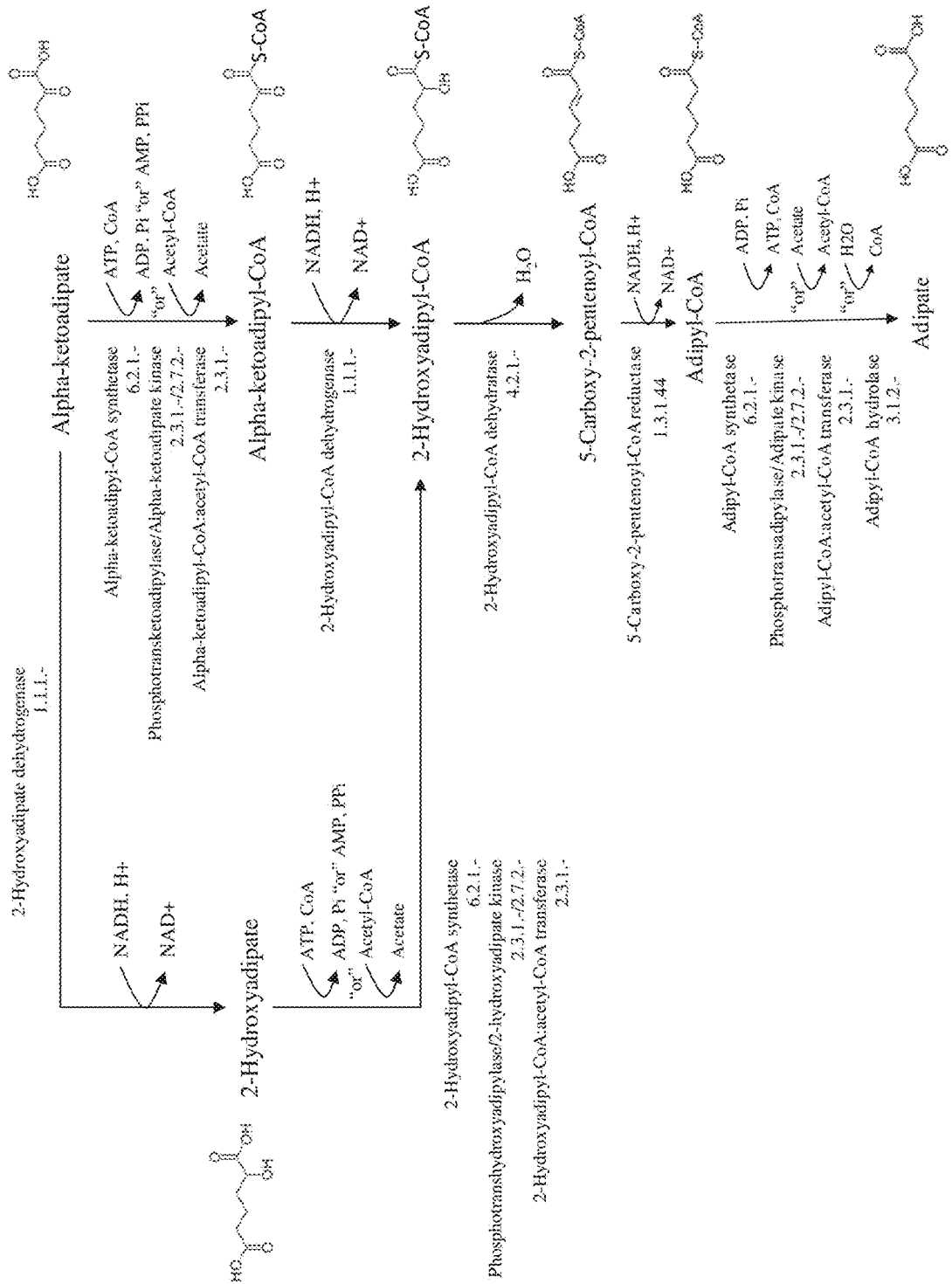
FIG. 9 shows exemplary adipate synthesis pathways using alpha-ketoadipate as a starting point.

Yet another exemplary adipate pathway utilizes alpha-ketoadipate as a precursor (see FIG. 9 and Examples X and XI). Thus, a non-naturally occurring microbial organism can have an adipate pathway including at least one exogenous nucleic acid encoding an adipate pathway enzyme expressed in a sufficient amount to produce adipate, the adipate pathway including alpha-ketoadipyl-CoA synthetase, phosphotransketoadipylase/alpha-ketoadipate kinase or alpha-ketoadipyl-CoA:acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA: acetyl-CoA transferase or adipyl-CoA hydrolase. Additionally, a non-naturally occurring microbial organism can have an adipate pathway including at least one exogenous nucleic acid encoding an adipate pathway enzyme expressed in a sufficient amount to produce adipate, the adipate pathway including 2-hydroxyadipate dehydrogenase; 2-hydroxyadipyl-CoA synthetase, phosphotranshydroxyadipylase/2-hydroxyadipate kinase or 2-hydroxyadipyl-CoA: acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase.

As disclosed herein, the invention provides a non-naturally occurring microbial organism, including a microbial organism having a 6-aminocaproic acid pathway including at least one exogenous nucleic acid encoding a 6-aminocaproic acid pathway enzyme expressed in a sufficient amount to produce 6-aminocaproic acid, the 6-aminocaproic acid pathway including 3-oxo-6-aminohexanoyl-CoA thiolase; 3-oxo-6-aminohexanoyl-CoA reductase; 3-hydroxy-6-aminohexanoyl-CoA dehydratase; 6-aminohex-2-enoyl-CoA reductase; and 6-aminocaproyl-CoA/acyl-CoA transferase, 6-aminocaproyl-CoA synthase, or 6-aminocaproyl-CoA hydrolase (see Examples XII and XIII; steps A/B/C/D/K/L/M of FIG. 11). The invention additionally provides a non-naturally occurring microbial organism, including a microbial organism having a 6-aminocaproic acid pathway including at least one exogenous nucleic acid encoding a 6-aminocaproic acid pathway enzyme expressed in a sufficient amount to produce 6-aminocaproic acid, the 6-aminocaproic acid pathway including 3-oxo-6-aminohexanoyl-CoA thiolase; 3-oxo-6-aminohexanoyl-CoA/acyl-CoA transferase, 3-oxo-6-aminohexanoyl-CoA synthase, or 3-oxo-6-aminohexanoyl-CoA hydrolase; 3-oxo-6-aminohexanoate reductase; 3-hydroxy-6-aminohexanoate dehydratase; and 6-aminohex-2-enoate reductase (see Examples XII and XIV; steps A/E/F/G/H/I/J of FIG. 11).

In another embodiment, the invention provides a non-naturally occurring microbial organism, including a microbial organism having a caprolactam pathway including at least one exogenous nucleic acid encoding a caprolactam pathway enzyme expressed in a sufficient amount to produce caprolactam, the caprolactam pathway including 6-aminocaproyl-CoA/acyl-CoA transferase or 6-aminocaproyl-CoA synthase (see Examples XII and XV; steps K/L of FIG. 11). Such a non-naturally occurring microbial organism containing a caprolactam pathway can further comprise a 6-aminocaproic acid pathway (see FIG. 11). Exemplary 6-aminocaproic acid pathways include the 6-aminocaproic acid pathway including CoA-dependent aldehyde dehydrogenase; and transaminase or 6-aminocaproate dehydrogenase or the 6-aminocaproic acid pathway including 3-oxo-6-aminohexanoyl-CoA thiolase; 3-oxo-6-aminohexanoyl-CoA/acyl-CoA transferase, 3-oxo-6-aminohexanoyl-CoA synthase, or 3-oxo-6-aminohexanoyl-CoA hydrolase; 3-oxo-6-aminohexanoate reductase; 3-hydroxy-6-aminohexanoate dehydratase; and 6-aminohex-2-enoate reductase (steps A/E/F/G/H/I/J of FIG. 11). It is understood that these or other exemplary 6-aminocaproic acid pathways disclosed herein can additionally be included in a microbial organism having a caprolactam pathway, if desired. The invention also provides a non-naturally occurring microbial organism, including a microbial organism having a hexamethylenediamine pathway including at least one exogenous nucleic acid encoding a hexamethylenediamine pathway enzyme expressed in a sufficient amount to produce hexamethylenediamine, the hexamethylenediamine pathway including 6-aminocaproyl-CoA/acyl-CoA transferase or 6-aminocaproyl-CoA synthase; 6-aminocaproyl-CoA reductase (aldehyde forming); and hexamethylenediamine transaminase or hexamethylenediamine dehydrogenase (see Example XII and XVI; steps K/L/N/O/P of FIG. 11). Such a non-naturally occurring microbial organism containing a hexamethylenediamine pathway can further comprise a 6-aminocaproic acid pathway (see FIG. 11). Exemplary 6-aminocaproic acid pathways include the 6-aminocaproic acid pathway including CoA-dependent aldehyde dehydrogenase; and transaminase or 6-aminocaproate dehydrogenase or the 6-aminocaproic acid pathway including 3-oxo-6-aminohexanoyl-CoA thiolase; 3-oxo-6-aminohexanoyl-CoA/acyl-CoA transferase, 3-oxo-6-aminohexanoyl-CoA synthase, or 3-oxo-6-aminohexanoyl-CoA hydrolase; 3-oxo-6-aminohexanoate reductase; 3-hydroxy-6-aminohexanoate dehydratase; and 6-aminohex-2-enoate reductase (steps A/E/F/G/H/I/J of FIG. 11). It is understood that these or other exemplary 6-aminocaproic acid pathways disclosed herein can additionally be included in a microbial organism having a hexamethylenediamine pathway, if desired.

In yet another embodiment, the invention provides a non-naturally occurring microbial organism having a caprolactam pathway including at least one exogenous nucleic acid encoding a caprolactam pathway enzyme expressed in a sufficient amount to produce caprolactam, the caprolactam pathway including 3-oxo-6-aminohexanoyl-CoA thiolase; 3-oxo-6-aminohexanoyl-CoA reductase; 3-hydroxy-6-aminohexanoyl-CoA dehydratase; and 6-aminohex-2-enoyl-CoA reductase (see Examples XII and XVII; steps A/B/C/D of FIG. 11). Also provided is a non-naturally occurring microbial organism having a hexamethylenediamine pathway including at least one exogenous nucleic acid encoding a hexamethylenediamine pathway enzyme expressed in a sufficient amount to produce hexamethylenediamine, the hexamethylenediamine pathway including 3-oxo-6-aminohexanoyl-CoA thiolase; 3-oxo-6-aminohexanoyl-CoA reductase; 3-hydroxy-6-aminohexanoyl-CoA dehydratase; 6-aminohex-2-enoyl-CoA reductase; 6-aminocaproyl-CoA reductase (aldehyde forming); and hexamethylenediamine transaminase or hexamethylenediamine dehydrogenase (see Examples XII and XVIII; steps A/B/C/D/N/O/P of FIG. 11).

Figure 12:
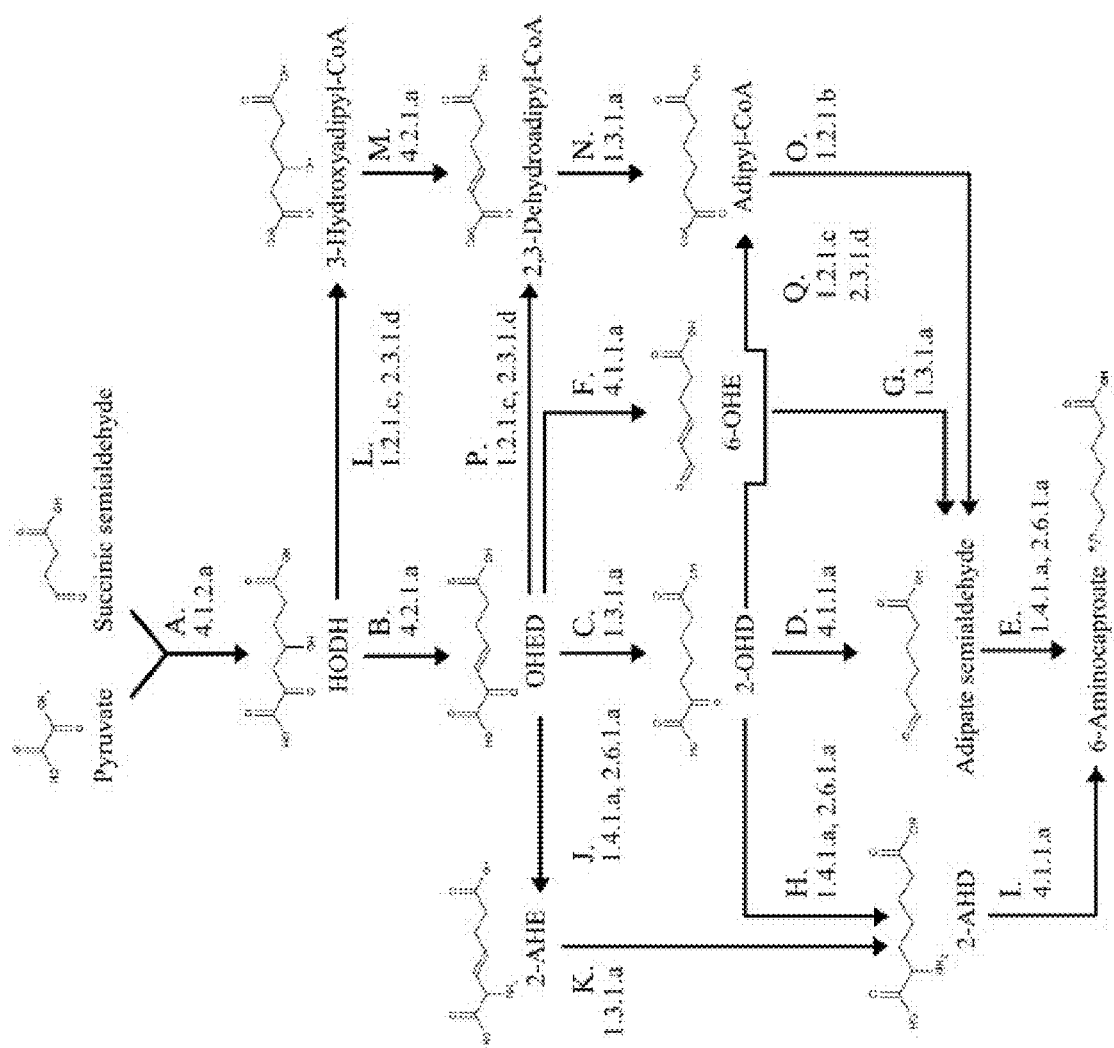
FIG. 12 shows pathways to 6-aminocaproate from pyruvate and succinic semialdehyde. Enzymes are A) HODH aldolase, B) OHED hydratase, C) OHED reductase, D) 2-OHD decarboxylase, E) adipate semialdehyde aminotransferase and/or adipate semialdehyde oxidoreductase (aminating), F) OHED decarboxylase, G) 6-OHE reductase, H) 2-OHD aminotransferase and/or 2-OHD oxidoreductase (aminating), I) 2-AHD decarboxylase, J) OHED aminotransferase and/or OHED oxidoreductase (aminating), K) 2-AHE reductase, L) HODH formate-lyase and/or HODH dehydrogenase, M) 3-hydroxyadipyl-CoA dehydratase, N) 2,3-dehydroadipyl-CoA reductase, 0) adipyl-CoA dehydrogenase, P) OHED formate-lyase and/or OHED dehydrogenase, Q) 2-OHD formate-lyase and/or 2-OHD dehydrogenase. Abbreviations are: HODH=4-hydroxy-2-oxoheptane-1,7-dioate, OHED=2-oxohept-4-ene-1,7-dioate, 2-OHD=2-oxoheptane-1,7-dioate, 2-AHE=2-aminohept-4-ene-1,7-dioate, 2-AHD=2-aminoheptane-1,7-dioate, and 6-OHE=6-oxohex-4-enoate.

In yet another embodiment, the invention provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including a 4-hydroxy-2-oxoheptane-1,7-dioate (HODH) aldolase, a 2-oxohept-4-ene-1,7-dioate (OHED) hydratase, a 2-oxohept-4-ene-1,7-dioate (OHED) reductase, a 2-oxoheptane-1,7-dioate (2-OHD) decarboxylase, an adipate semialdehyde aminotransferase, an adipate semialdehyde oxidoreductase (aminating), a 2-oxohept-4-ene-1,7-dioate (OHED) decarboxylase, a 6-oxohex-4-enoate (6-OHE) reductase, a 2-oxoheptane-1,7-dioate (2-OHD) aminotransferase, a 2-oxoheptane-1,7-dioate (2-OHD) oxidoreductase (aminating), a 2-aminoheptane-1,7-dioate (2-AHD) decarboxylase, a 2-oxohept-4-ene-1,7-dioate (OHED) aminotransferase, a 2-oxohept-4-ene-1,7-dioate (OHED) oxidoreductase (aminating), a 2-aminohept-4-ene-1,7-dioate (2-AHE) reductase, a 4-hydroxy-2-oxoheptane-1,7-dioate (HODH) formate-lyase, a 4-hydroxy-2-oxoheptane-1,7-dioate (HODH) dehydrogenase, a 3-hydroxyadipyl-CoA dehydratase, a 2,3-dehydroadipyl-CoA reductase, a adipyl-CoA dehydrogenase, a 2-oxohept-4-ene-1,7-dioate (OHED) formate-lyase, a 2-oxohept-4-ene-1,7-dioate (OHED) dehydrogenase, a 2-oxoheptane-1,7-dioate (2-OHD) formate-lyase, a 2-oxoheptane-1,7-dioate (2-OHD) dehydrogenase, or a pyruvate formate-lyase activating enzyme (see Examples XIX and XXI; steps A-Q of FIG. 12). In a further aspect, the 6-ACA pathway includes a succinic semialdehyde dehydrogenase, an alpha-ketoglutarate decarboxylase or a phosphoenolpyruvate (PEP) carboxykinase.

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an OHED hydratase; an OHED reductase; a 2-OHD decarboxylase; or an adipate semialdehyde aminotransferase or an adipate semialdehyde oxidoreductase (aminating) (see Examples XIX and XXI; steps A/B/C/D/E of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, wherein the set encodes an HODH aldolase; an OHED hydratase; an OHED reductase; a 2-OHD decarboxylase; and an adipate semialdehyde aminotransferase or an adipate semialdehyde oxidoreductase (aminating).

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an OHED hydratase; an OHED decarboxylase; a 6-OHE reductase; or an adipate semialdehyde aminotransferase or an adipate semialdehyde oxidoreductase (aminating) (see Examples XIX and XXI; steps A/B/F/G/E of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, where the set encode an HODH aldolase; an OHED hydratase; an OHED decarboxylase; a 6-OHE reductase; and an adipate semialdehyde aminotransferase or an adipate semialdehyde oxidoreductase (aminating).

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an OHED hydratase; an OHED aminotransferase or an OHED oxidoreductase (aminating); a 2-AHE reductase; or a 2-AHD decarboxylase (see Examples XIX and XXI; steps A/B/J/D/I of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, where the set encode an HODH aldolase; an OHED hydratase; an OHED aminotransferase or an OHED oxidoreductase (aminating); a 2-AHE reductase; and a 2-AHD decarboxylase.

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an OHED hydratase; an OHED reductase; a 2-OHD aminotransferase or a 2-OHD oxidoreductase (aminating); or a 2-AHD decarboxylase (see Examples XIX and XXI; steps A/B/C/H/I of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, where the set encode an HODH aldolase; an OHED hydratase; an OHED reductase; a 2-OHD aminotransferase or a 2-OHD oxidoreductase (aminating); and a 2-AHD decarboxylase.

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an HODH formate-lyase and a pyruvate formate-lyase activating enzyme or an HODH dehydrogenase; a 3-hydroxyadipyl-CoA dehydratase; a 2,3-dehydroadipyl-CoA reductase; an adipyl-CoA dehydrogenase; or an adipate semialdehyde aminotransferase or an adipate semialdehyde oxidoreductase (aminating) (see Examples XIX and XXI; steps A/L/M/N/O/E of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, where the set encode an HODH aldolase; an HODH formate-lyase and a pyruvate formate-lyase activating enzyme or an HODH dehydrogenase; a 3-hydroxyadipyl-CoA dehydratase; a 2,3-dehydroadipyl-CoA reductase; an adipyl-CoA dehydrogenase; and an adipate semialdehyde aminotransferase or an adipate semialdehyde oxidoreductase (aminating).

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an OHED hydratase; an OHED formate-lyase and a pyruvate formate-lyase activating enzyme or OHED dehydrogenase; a 2,3-dehydroadipyl-CoA reductase; an adipyl-CoA dehydrogenase; or an adipate semialdehyde aminotransferase or an adipate semialdehyde oxidoreductase (aminating) (see Examples XIX and XXI; steps A/B/P/N/O/E of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, where the set encode an HODH aldolase; an OHED hydratase; an OHED formate-lyase and a pyruvate formate-lyase activating enzyme or OHED dehydrogenase; a 2,3-dehydroadipyl-CoA reductase; an adipyl-CoA dehydrogenase; and an adipate semialdehyde aminotransferase or an adipate semialdehyde oxidoreductase (aminating).

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an HODH aldolase; an OHED hydratase; an OHED reductase; a 2-OHD formate-lyase and a pyruvate formate-lyase activating enzyme or a 2-OHD dehydrogenase; an adipyl-CoA dehydrogenase; or an adipate semialdehyde aminotransferase or an adipate semialdehyde oxidoreductase (aminating) (see Examples XIX and XXI; steps A/B/C/Q/O/E of FIG. 12). In a further aspect, the 6-ACA pathway includes a succinic semialdehyde dehydrogenase, an alpha-ketoglutarate decarboxylase or a phosphoenolpyruvate (PEP) carboxykinase. In another aspect of the invention, the non-naturally occurring microbial organism includes a set of exogenous nucleic acids encoding 6-ACA pathway enzymes, where the set encode an HODH aldolase; an OHED hydratase; an OHED reductase; a 2-OHD formate-lyase and a pyruvate formate-lyase activating enzyme or a 2-OHD dehydrogenase; an adipyl-CoA dehydrogenase; and an adipate semialdehyde aminotransferase or an adipate semialdehyde oxidoreductase (aminating). The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including a glutamyl-CoA transferase, a glutamyl-CoA ligase, a beta-ketothiolase, an 3-oxo-6-aminopimeloyl-CoA oxidoreductase, a 3-hydroxy-6-aminopimeloyl-CoA dehydratase, a 6-amino-7-carboxyhept-2-enoyl-CoA reductase, a 6-aminopimeloyl-CoA reductase (aldehyde forming), or a 2-aminopimelate decarboxylase (see Examples XXV and XXVI; steps A/B/C/D/E/I/J of FIG. 20). In another aspect of the invention, the non-naturally occurring microbial organism includes a set of exogenous nucleic acids encoding 6-ACA pathway enzymes, where the set encode a glutamyl-CoA transferase or glutamyl-CoA ligase; a beta-ketothiolase; a 3-oxo-6-aminopimeloyl-CoA oxidoreductase; a 3-hydroxy-6-aminopimeloyl-CoA dehydratase; a 6-amino-7-carboxyhept-2-enoyl-CoA reductase; 6-aminopimeloyl-CoA reductase (aldehyde forming); and a 2-aminopimelate decarboxylase.

Figure 21:
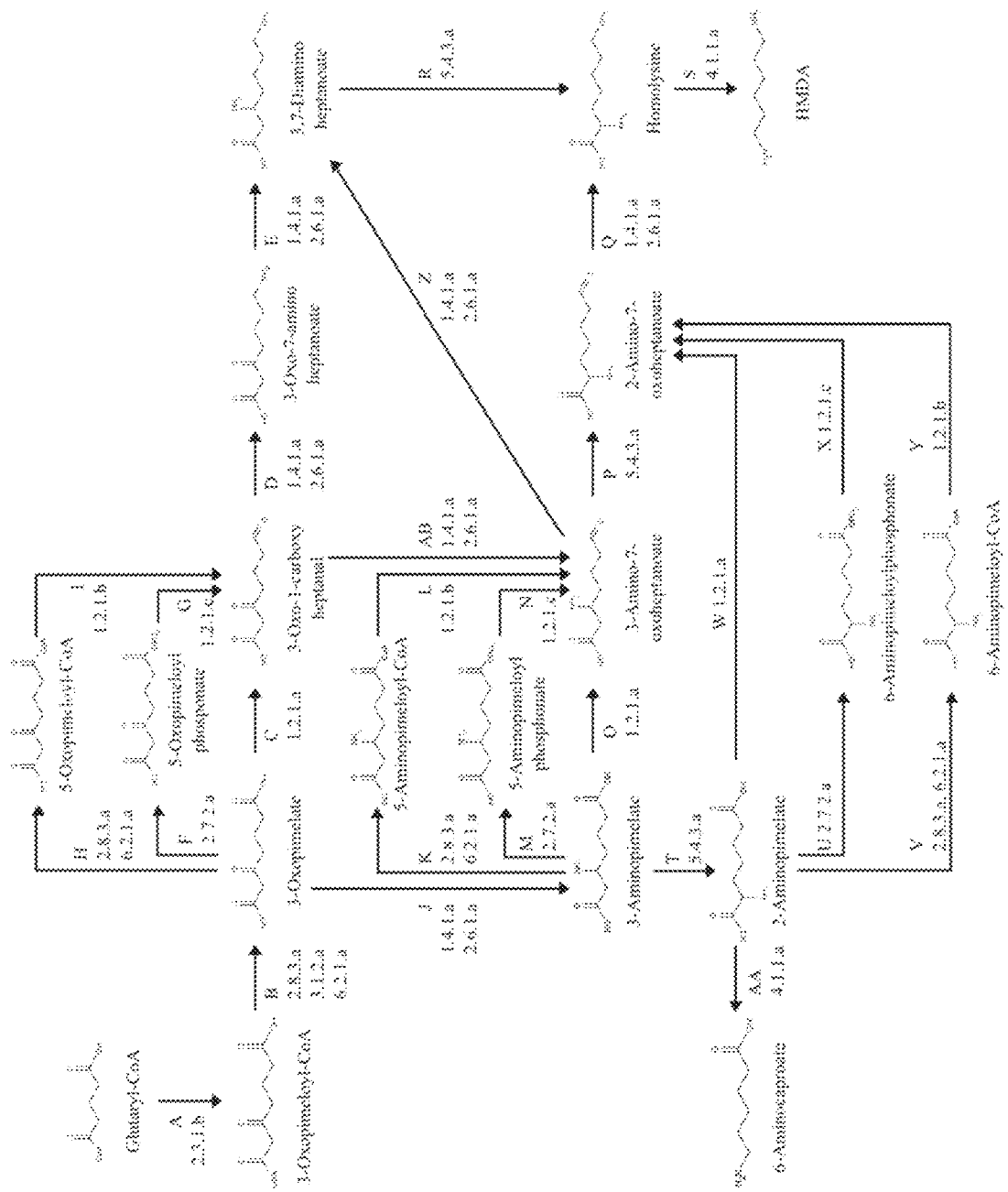
FIG. 21 shows exemplary pathways from glutaryl-CoA to hexamethylenediamine (HMDA) and 6-aminocaproate. The enzymes are designated as follows: A) glutaryl-CoA beta-ketothiolase, B) 3-oxopimeloyl-CoA hydrolase, transferase and/or ligase, C) 3-oxopimelate reductase, D) 3-oxo-1-carboxyheptanal 7-aminotransferase and/or 7-aminating oxidoreductase, E) 3-oxo-7-aminoheptanoate 3-aminotransferase and/or 3-aminating oxidoreductase, F) 3-oxopimelate kinase, G) 5-oxopimeloylphosphonate reductase, H) 3-oxopimelate CoA transferase and/or ligase, I) 5-oxopimeloyl-CoA reductase (aldehyde forming), J) 3-oxopimelate 3-aminotransferase and/or 3-aminating oxidoreductase, K) 3-aminopimelate CoA transferase and/or ligase, L) 5-aminopimeloyl-CoA reductase (aldehyde forming), M) 3-aminopimelate kinase, N) 5-aminopimeloylphosphonate reductase, 0) 3-aminopimelate reductase, P) 3-amino-7-oxoheptanoate 2,3-aminomutase, Q) 2-amino-7-oxoheptanoate 7-aminotransferase and/or aminating oxidoreductase, R) 3,7-diaminoheptanoate 2,3-aminomutase, S) homolysine decarboxylase, T) 3-aminopimelate 2,3-aminomutase, U) 2-aminopimelate kinase, V) 2-aminopimelate CoA transferase and/or ligase, W) 2-aminopimelate reductase, X) 6-aminopimeloylphosphonate reductase, Y) 6-aminopimeloyl-CoA reductase (aldehyde forming), Z) 3-amino-7-oxoheptanoate 7-aminotransferase and/or 7-aminating oxidoreductase, AA) 2-aminopimelate decarboxylase and AB) 3-oxo-1-carboxyheptanal 3-aminotransferase and/or 3-aminating oxidoreductase. The enzyme commission number indicated for each reaction is described in XXVI below.

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, 3-oxopimelate aminating oxidoreductase, a 3-aminopimelate 2,3-aminomutase, or a 2-aminopimelate decarboxylase (see Examples XXV and XXVI; steps A/B/J/T/AA of FIG. 21). In another aspect of the invention, the non-naturally occurring microbial organism includes a set of exogenous nucleic acids encoding 6-ACA pathway enzymes, where the set encode a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate 2,3-aminomutase; and a 2-aminopimelate decarboxylase. The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including a homolysine 2-monooxygenase (see Examples XXV and XXVI; steps A of FIG. 23). In a further aspect, the 6-ACA pathway includes hydrolysis of the 6-aminohexanamide product by a dilute acid or base to convert 6-aminohexanamide to 6-aminocaproate (see Examples XXV and XXVI; step B of FIG. 23).

Figure 25:
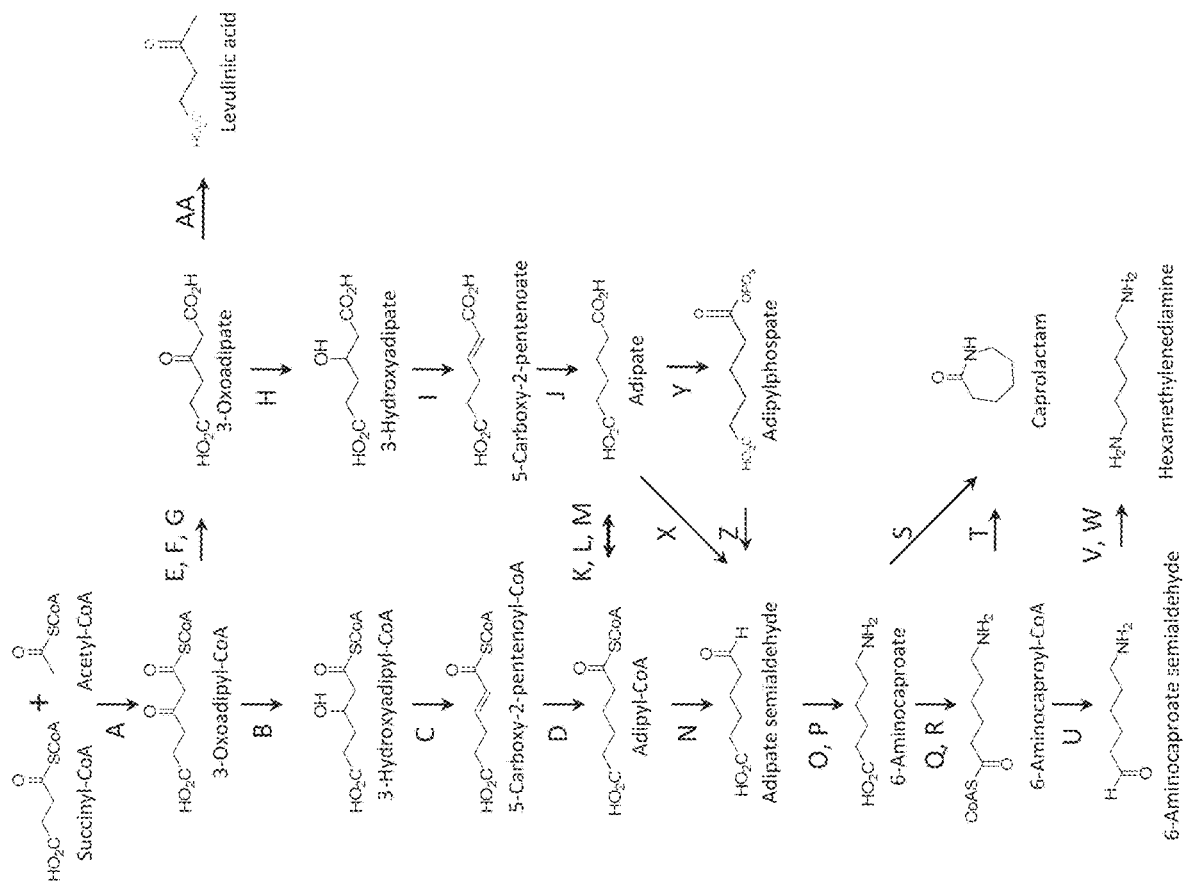
FIG. 25 shows exemplary pathways from succinyl-CoA and acetyl-CoA to hexamethylenediamine (HMDA), caprolactam or levulinic acid. Pathways for the production of adipate, 6-aminocaproate, caprolactam, hexamethylenediamine and levulinic acid from succinyl-CoA and acetyl-CoA are depicted. This figure depicts additional pathways further to those presented in FIG. 10. The enzymes are designated as follows: A) 3-oxoadipyl-CoA thiolase, B) 3-oxoadipyl-CoA reductase, C) 3-hydroxyadipyl-CoA dehydratase, D) 5-carboxy-2-pentenoyl-CoA reductase, E) 3-oxoadipyl-CoA/acyl-CoA transferase, F) 3-oxoadipyl-CoA synthase, G) 3-oxoadipyl-CoA hydrolase, H) 3-oxoadipate reductase, I) 3-hydroxyadipate dehydratase, J) 5-carboxy-2-pentenoate reductase, K) adipyl-CoA/acyl-CoA transferase, L) adipyl-CoA synthase, M) adipyl-CoA hydrolase, N) adipyl-CoA reductase (aldehyde forming), 0) 6-aminocaproate transaminase, P) 6-aminocaproate dehydrogenase, Q) 6-aminocaproyl-CoA/acyl-CoA transferase, R) 6-aminocaproyl-CoA synthase, S) amidohydrolase, T) spontaneous cyclization, U) 6-aminocaproyl-CoA reductase (aldehyde forming), V) HMDA transaminase, W) HMDA dehydrogenase, X) adipate reductase, Y) adipate kinase, Z) adipylphosphate reductase, and AA) 3-oxoadipate decarboxylase.

The invention additionally provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including an adipate reductase, an adipate kinase or an adipylphosphate reductase (see Example XXVIII; steps X/Y/Z of FIG. 25 and Example XXXI). In a further aspect, the 6-ACA pathway includes an adipate reductase. In another further aspect, the 6-ACA pathway includes an adipate kinase and an adipylphosphate reductase. In still another aspect, the microbial organism having the 6-aminocaproic acid (6-ACA) pathway above further comprises an adipate pathway, a caprolactam pathway and/or a hexamethylenediamine pathway described here (see Example XXVIII; steps A-W of FIG. 25).

Figure 26:
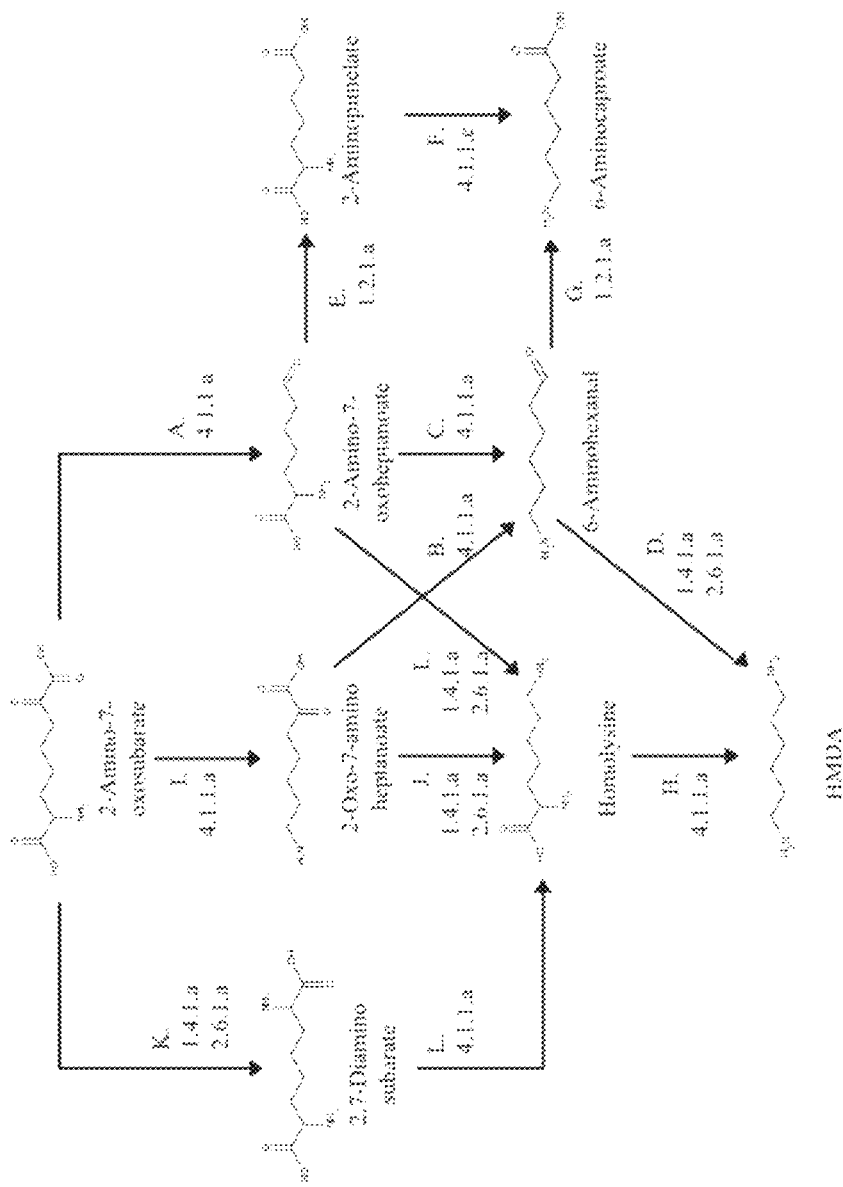
FIG. 26 shows exemplary pathways from 2-amino-7-oxosubarate to hexamethylenediamine (HMDA) and 6-aminocaproate. The enzymes are designated as follows: A) 2-amino-7-oxosubarate keto-acid decarboxylase, B) 2-amino-7-oxoheptanoate decarboxylase, C) 6-aminohexanal aminating oxidoreductase and/or 6-aminohexanal aminotransferase, D) 2-amino-7-oxoheptanoate oxidoreductase, E) 2-aminopimelate decarboxylase, F) 6-aminohexanal oxidoreductase, G) 2-amino-7-oxoheptanoate decarboxylase, H) homolysine decarboxylase, I) 2-amino-7-oxosubarate amino acid decarboxylase, J) 2-oxo-7-aminoheptanoate aminating oxidoreductase and/or 2-oxo-7-aminoheptanoate aminotransferase, K) 2-amino-7-oxosubarate aminating oxidoreductase and/or 2-amino-7-oxosubarate aminotransferase, L) 2,7-diaminosubarate decarboxylase and M) 2-amino-7-oxoheptanoate aminating oxidoreductase and/or 2-amino-7-oxoheptanoate aminotransferase. The enzyme commission number indicated for each reaction is described in Example XXVI below.

In one embodiment, the invention provides a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including a 2-amino-7-oxosubarate keto-acid decarboxylase, a 2-amino-7-oxoheptanoate decarboxylase, a 2-amino-7-oxoheptanoate oxidoreductase, a 2-aminopimelate decarboxylase, a 6-aminohexanal oxidoreductase, a 2-amino-7-oxoheptanoate decarboxylase, or a 2-amino-7- oxosubarate amino acid decarboxylase (see Examples XXV and XXVI; steps A/B/D/E/F/G/I of FIG. 26). In a further aspect, the microbial organism has a 2-amino-7-oxosubarate pathway having at least one exogenous nucleic acid encoding a 2-amino-7-oxosubarate pathway enzyme expressed in a sufficient amount to produce 2-amino-7-oxosubarate, the 2-amino-7-oxosubarate pathway including a 2-amino-5-hydroxy-7-oxosubarate aldolase, a 2-amino-5-hydroxy-7-oxosubarate dehydratase, or a 2-amino-5-ene-7-oxosubarate reductase (see Examples XXV and XXVI; steps A/B/C of FIG. 27).

In another embodiment of the invention, the non-naturally occurring microbial organism includes a set of exogenous nucleic acids encoding 6-ACA pathway enzymes, where the set encodes a 2-amino-7-oxosubarate keto-acid decarboxylase; a 2-amino-7-oxoheptanoate oxidoreductase; and a 2-aminopimelate decarboxylase (see Example XXV; steps A/D/E of FIG. 26). In yet another embodiment of the invention, the non-naturally occurring microbial organism includes a set of exogenous nucleic acids encoding 6-ACA pathway enzymes, where the set encodes a 2-amino-7-oxosubarate keto-acid decarboxylase; a 2-amino-7-oxoheptanoate decarboxylase; and a 6-aminohexanal oxidoreductase (see Example XXV; steps A/B/F of FIG. 26). In still yet another embodiment of the invention, the non-naturally occurring microbial organism includes a set of exogenous nucleic acids encoding 6-ACA pathway enzymes, where the set encodes a 2-amino-7-oxosubarate amino acid decarboxylase; a 2-amino-7-oxoheptanoate decarboxylase; and a 6-aminohexanal oxidoreductase (see Example XXV; steps I/G/F of FIG. 26). In a further aspect of each of the above embodiments, the microbial organism has a 2-amino-7-oxosubarate pathway having a second set of exogenous nucleic acids encoding 2-amino-7-oxosubarate pathway enzymes expressed in a sufficient amount to produce 2-amino-7-oxosubarate, the 2-amino-7-oxosubarate pathway including a 2-amino-5-hydroxy-7-oxosubarate aldolase; a 2-amino-5-hydroxy-7-oxosubarate dehydratase; and a 2-amino-5-ene-7-oxosubarate reductase (see Examples XXV and XXVI; steps A/B/C of FIG. 27).

In yet another embodiment, the invention provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate kinase, an [(6-aminohexanoyl)oxy]phosphonate (6-AHOP) oxidoreductase, a 6-aminocaproic semialdehyde aminotransferase, a 6-aminocaproic semialdehyde oxidoreductase (aminating), a 6-aminocaproate N-acetyltransferase, a 6-acetamidohexanoate kinase, an [(6-acetamidohexanoyl)oxy]phosphonate (6-AAHOP) oxidoreductase, a 6-acetamidohexanal aminotransferase, a 6-acetamidohexanal oxidoreductase (aminating), a 6-acetamidohexanamine N-acetyltransferase, a 6-acetamidohexanamine hydrolase (amide), a 6-acetamidohexanoate CoA transferase, a 6-acetamidohexanoate CoA ligase, a 6-acetamidohexanoyl-CoA oxidoreductase, a [(6-acetamidohexanoyl)oxy]phosphonate (6-AAHOP) acyltransferase, a [(6-aminohexanoyl)oxy]phosphonate (6-AHOP) acyltransferase, a 6-aminocaproate CoA transferase and a 6-aminocaproate CoA ligase (see Examples XX and XXI; steps A-N of FIG. 13).

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate kinase; a 6-AHOP oxidoreductase; or a 6-aminocaproic semialdehyde oxidoreductase (aminating) or a 6-aminocaproic acid semialdehyde aminotransferase (see Examples XX and XXI; steps A/B/C of FIG. 13). In another aspect of the invention, the non-naturally occurring microbial organism includes a set of exogenous nucleic acids encoding HMDA pathway enzymes, wherein the set encodes a 6-aminocaproate kinase; a 6-AHOP oxidoreductase; and a 6-aminocaproic semialdehyde oxidoreductase (aminating) or a 6-aminocaproic acid semialdehyde aminotransferase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate kinase; a 6-AHOP acyltransferase; a 6-aminocaproyl-CoA oxidoreductase; or a 6-aminocaproic semialdehyde oxidoreductase (aminating) or a 6-aminocaproic acid semialdehyde aminotransferase (see Examples XX and XXI; steps A/L/N/C of FIG. 13). In another aspect of the invention, the non-naturally occurring microbial organism includes a set of exogenous nucleic acids encoding HMDA pathway enzymes, wherein the set encodes a 6-aminocaproate kinase; a 6-AHOP acyltransferase; a 6-aminocaproyl-CoA oxidoreductase; and a 6-aminocaproic semialdehyde oxidoreductase (aminating) or a 6-aminocaproic acid semialdehyde aminotransferase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate CoA transferase or a 6-aminocaproate CoA ligase; a 6-aminocaproyl-CoA oxidoreductase; or a 6-aminocaproic semialdehyde oxidoreductase (aminating) or a 6-aminocaproic acid semialdehyde aminotransferase (see Examples XX and XXI; steps M/N/C of FIG. 13). In another aspect of the invention, the non-naturally occurring microbial organism includes a set of exogenous nucleic acids encoding HMDA pathway enzymes, wherein the set encodes a 6-aminocaproate CoA transferase or a 6-aminocaproate CoA ligase; a 6-aminocaproyl-CoA oxidoreductase; and a 6-aminocaproic semialdehyde oxidoreductase (aminating) or a 6-aminocaproic acid semialdehyde aminotransferase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); or a 6-acetamidohexanamine N-acetyltransferase or a 6-acetamidohexanamine hydrolase (amide) (see Examples XX and XXI; steps D/E/F/G/H of FIG. 13). In another aspect of the invention, the non-naturally occurring microbial organism includes a set of exogenous nucleic acids encoding HMDA pathway enzymes, wherein the set encodes a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide).

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate N-acetyltransferase; a 6-acetamidohexanoate CoA transferase or a 6-acetamidohexanoate CoA ligase; a 6-acetamidohexanoyl-CoA oxidoreductase; a 6-acetamidohexanal aminotransferase or a 6-acetamidohexanal oxidoreductase (aminating); or a 6-acetamidohexanamine N-acetyltransferase or a 6-acetamidohexanamine hydrolase (amide) (see Examples XX and XXI; steps D/I/J/G/H of FIG. 13). In another aspect of the invention, the non-naturally occurring microbial organism includes a set of exogenous nucleic acids encoding HMDA pathway enzymes, wherein the set encodes a 6-aminocaproate N-acetyltransferase; a 6-acetamidohexanoate CoA transferase or a 6-acetamidohexanoate CoA ligase; a 6-acetamidohexanoyl-CoA oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide). The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); or a 6-acetamidohexanamine N-acetyltransferase or a 6-acetamidohexanamine hydrolase (amide) (see Examples XX and XXI; steps D/E/K/J/G of FIG. 13). In another aspect of the invention, the non-naturally occurring microbial organism includes a set of exogenous nucleic acids encoding HMDA pathway enzymes, wherein the set encodes a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide). The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutamyl-CoA transferase, a glutamyl-CoA ligase, a beta-ketothiolase, an 3-oxo-6-aminopimeloyl-CoA oxidoreductase, a 3-hydroxy-6-aminopimeloyl-CoA dehydratase, a 6-amino-7-carboxyhept-2-enoyl-CoA reductase, a 6-aminopimeloyl-CoA reductase (aldehyde forming), a 2-amino-7-oxoheptanoate aminotransferase, a 2-amino-7-oxoheptanoate aminating oxidoreductase, or a homolysine decarboxylase (see Examples XXIV and XXVI; steps A-H of FIG. 20). In another aspect of the invention, the non-naturally occurring microbial organism includes a set of exogenous nucleic acids encoding HMDA pathway enzymes, wherein the set encodes a glutamyl-CoA transferase or ligase; a beta-ketothiolase; a 3-oxo-6-aminopimeloyl-CoA oxidoreductase; a 3-hydroxy-6-aminopimeloyl-CoA dehydratase; a 6-amino-7-carboxyhept-2-enoyl-CoA reductase; a 6-aminopimeloyl-CoA reductase (aldehyde forming); a 2-amino-7-oxoheptanoate aminotransferase or aminating oxidoreductase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate reductase, a 3-oxo-1-carboxyheptanal aminotransferase, a 3-oxo-1-carboxyheptanal aminating oxidoreductase, a 3-oxo-7-aminoheptanoate 3-aminotransferase, a 3-oxo-7-aminoheptanoate 3-aminating oxidoreductase, a 3-oxopimelate kinase, a 5-oxopimeloylphosphonate reductase, a 3-oxopimelate CoA transferase, a 3-oxopimelate ligase, a 5-oxopimeloyl-CoA reductase (aldehyde forming), a 3-oxopimelate aminotransferase, a 3-oxopimelate aminating oxidoreductase, a 3-aminopimelate CoA transferase, a 3-aminopimelate ligase, a 5-aminopimeloyl-CoA reductase (aldehyde forming), a 3-aminopimelate kinase, a 5-aminopimeloylphosphonate reductase, a 3-aminopimelate reductase, a 3-amino-7-oxoheptanoate 2,3-aminomutase, a 2-amino-7-oxoheptanoate 7-aminotransferase, a 2-amino-7-oxoheptanoate aminating oxidoreductase, a 3,7-diaminoheptanoate 2,3-aminomutase, a homolysine decarboxylase, a 3-aminopimelate 2,3-aminomutase, a 2-aminopimelate kinase, a 2-aminopimelate CoA transferase, a 2-aminopimelate CoA ligase, a 2-aminopimelate reductase, a 6-aminopimeloylphosphonate reductase, a 6-aminopimeloyl-CoA reductase (aldehyde forming), a 3-amino-7-oxoheptanoate 7-aminotransferase or a 3-amino-7-oxoheptanoate aminating oxidoreductase (see Examples XXIV and XXVI; FIG. 21).

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate reductase, a 3-oxo-1-carboxyheptanal 7-aminotransferase, a 3-oxo-1-carboxyheptanal 7-aminating oxidoreductase, a 3-oxo-7-aminoheptanoate 3-aminotransferase, a 3-oxo-7-aminoheptanoate 3-aminating oxidoreductase, a 3,7-diaminoheptanoate 2,3-aminomutase, or a homolysine decarboxylase (see Examples XXIV and XXVI; steps A/B/C/D/E/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate reductase; a 3-oxo-1-carboxyheptanal 7-aminotransferase or a 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate kinase, a 5-oxopimeloylphosphonate reductase, a 3-oxo-1-carboxyheptanal 7-aminotransferase, a 3-oxo-1-carboxyheptanal 7-aminating oxidoreductase, a 3-oxo-7-aminoheptanoate 3-aminotransferase, a 3-oxo-7-aminoheptanoate 3-aminating oxidoreductase, a 3,7-diaminoheptanoate 2,3-aminomutase, or a homolysine decarboxylase (see Examples XXIV and XXVI; steps A/B/F/G/D/E/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate kinase; a 5-oxopimeloylphosphonate reductase; a 3-oxo-1-carboxyheptanal 7-aminotransferase or a 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate CoA transferase, 3-oxopimelate CoA ligase, a 5-oxopimeloyl-CoA reductase (aldehyde forming), a 3-oxo-1-carboxyheptanal 7-aminotransferase, 3-oxo-1-carboxyheptanal 7-aminating oxidoreductase, a 3-oxo-7-aminoheptanoate 3-aminotransferase, a 3-oxo-7-aminoheptanoate 3-aminating oxidoreductase; a 3,7-diaminoheptanoate 2,3-aminomutase, or a homolysine decarboxylase (see Examples XXIV and XXVI; steps A/B/H/I/D/E/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate CoA transferase or 3-oxopimelate CoA ligase; a 5-oxopimeloyl-CoA reductase (aldehyde forming); a 3-oxo-1-carboxyheptanal 7-aminotransferase or 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate reductase, a 3-oxo-1-carboxyheptanal 3-aminotransferase, a 3-oxo-1-carboxyheptanal 3-aminating oxidoreductase, a 3-amino-7-oxoheptanoate 7-aminotransferase, a 3-amino-7-oxoheptanoate 7-aminating oxidoreductase, a 3,7-diaminoheptanoate 2,3-aminomutase, or a homolysine decarboxylase (see Examples XXIV and XXVI; steps A/B/C/AB/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate reductase; a 3-oxo-1-carboxyheptanal 3-aminotransferase or a 3-oxo-1-carboxyheptanal 3-aminating oxidoreductase; a 3-amino-7-oxoheptanoate 7-aminotransferase or a 3-amino-7-oxoheptanoate 7-aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, 3-oxopimeloyl-CoA ligase, a 3-oxopimelate kinase, a 5-oxopimeloylphosphonate reductase, a 3-oxo-1-carboxyheptanal 3-aminotransferase, a 3-oxo-1-carboxyheptanal 3-aminating oxidoreductase, a 3-amino-7-oxoheptanoate 7-aminotransferase, 3-amino-7-oxoheptanoate 7-aminating oxidoreductase, a 3,7-diaminoheptanoate 2,3-aminomutase, or a homolysine decarboxylase (see Examples XXIV and XXVI; steps A/B/F/G/AB/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate CoA transferase or a 3-oxopimelate CoA ligase; a 5-oxopimeloyl-CoA reductase (aldehyde forming); a 3-oxo-1-carboxyheptanal 3-aminotransferase or a 3-oxo-1-carboxyheptanal 3-aminating oxidoreductase; a 3-amino-7-oxoheptanoate 7-aminotransferase or 3-amino-7-oxoheptanoate 7-aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase or a 3-oxopimelate aminating oxidoreductase, a 3-aminopimelate reductase, a 3-amino-7-oxoheptanoate 2,3-aminomutase, a 2-amino-7-oxoheptanoate 7-aminotransferase, a 2-amino-7-oxoheptanoate aminating oxidoreductase, or a homolysine decarboxylase (see Examples XXIV and XXVI; steps A/B//J/O/P/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate reductase; a 3-amino-7-oxoheptanoate 2,3-aminomutase; a 2-amino-7-oxoheptanoate 7-aminotransferase or a 2-amino-7-oxoheptanoate aminating oxidoreductase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase or a 3-oxopimelate aminating oxidoreductase, a 3-aminopimelate kinase, a 5-aminopimeloylphosphonate reductase, a 3-amino-7-oxoheptanoate 2,3-aminomutase, a 2-amino-7-oxoheptanoate 7-aminotransferase, a 2-amino-7-oxoheptanoate aminating oxidoreductase, or a homolysine decarboxylase (see Examples XXIV and XXVI; steps A/B/J/M/N/P/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate kinase; a 5-aminopimeloylphosphonate reductase; a 3-amino-7-oxoheptanoate 2,3-aminomutase; a 2-amino-7-oxoheptanoate 7-aminotransferase or a 2-amino-7-oxoheptanoate aminating oxidoreductase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate CoA transferase, a 3-aminopimelate CoA ligase, a 5-aminopimeloyl-CoA reductase (aldehyde forming), a 3-amino-7-oxoheptanoate 2,3-aminomutase, a 2-amino-7-oxoheptanoate 7-aminotransferase, 2-amino-7-oxoheptanoate aminating oxidoreductase, or a homolysine decarboxylase (see Examples XXIV and XXVI; steps A/B/J/K/L/P/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate CoA transferase or a 3-aminopimelate CoA ligase; a 5-aminopimeloyl-CoA reductase (aldehyde forming); a 3-amino-7-oxoheptanoate 2,3-aminomutase; a 2-amino-7-oxoheptanoate 7-aminotransferase or 2-amino-7-oxoheptanoate aminating oxidoreductase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate reductase, a 3-amino-7-oxoheptanoate 7-aminotransferase, 3-amino-7-oxoheptanoate 7-aminating oxidoreductase, a 3,7-diaminoheptanoate 2,3-aminomutase, or a homolysine decarboxylase (see Examples XXIV and XXVI; steps A/B/J/O/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate reductase; a 3-amino-7-oxoheptanoate 7-aminotransferase or 3-amino-7-oxoheptanoate 7-aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate CoA transferase, a 3-aminopimelate CoA ligase, a 5-aminopimeloyl-CoA reductase (aldehyde forming), a 3-amino-7-oxoheptanoate 7-aminotransferase, 3-amino-7-oxoheptanoate aminating oxidoreductase, a 3,7-diaminoheptanoate 2,3-aminomutase, or a homolysine decarboxylase (see Examples XXIV and XXVI; steps A/B/J/K/L/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate CoA transferase or a 3-aminopimelate CoA ligase; a 5-aminopimeloyl-CoA reductase (aldehyde forming); a 3-amino-7-oxoheptanoate 7-aminotransferase or 3-amino-7-oxoheptanoate aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate kinase, a 5-aminopimeloylphosphonate reductase, a 3-amino-7-oxoheptanoate 7-aminotransferase, a 3-amino-7-oxoheptanoate aminating oxidoreductase, a 3,7-diaminoheptanoate 2,3-aminomutase, or a homolysine decarboxylase (see Examples XXIV and XXVI; steps A/B/J/M/N/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate kinase; a 5-aminopimeloylphosphonate reductase; a 3-amino-7-oxoheptanoate 7-aminotransferase or a 3-amino-7-oxoheptanoate aminating oxidoreductase; a 3,7-diaminoheptanoate 2,3-aminomutase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, 3-oxopimelate aminating oxidoreductase, a 3-aminopimelate 2,3-aminomutase, a 2-aminopimelate reductase, a 2-amino-7-oxoheptanoate 7-aminotransferase, a 2-amino-7-oxoheptanoate aminating oxidoreductase, or a homolysine decarboxylase (see Examples XXIV and XXVI; steps A/B/J/T/W/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate 2,3-aminomutase; a 2-aminopimelate reductase; a 2-amino-7-oxoheptanoate 7-aminotransferase or a 2-amino-7-oxoheptanoate aminating oxidoreductase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate 2,3-aminomutase, a 2-aminopimelate kinase, a 6-aminopimeloylphosphonate reductase, a 2-amino-7-oxoheptanoate 7-aminotransferase, a 2-amino-7-oxoheptanoate aminating oxidoreductase, or a homolysine decarboxylase (see Examples XXIV and XXVI; steps A/B/J/T/U/X/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate kinase; a 6-aminopimeloylphosphonate reductase; a 2-amino-7-oxoheptanoate 7-aminotransferase or a 2-amino-7-oxoheptanoate aminating oxidoreductase; and a homolysine decarboxylase.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate 2,3-aminomutase, a 2-aminopimelate CoA transferase, 2-aminopimelate CoA ligase, a 6-aminopimeloyl-CoA reductase (aldehyde forming), a 2-amino-7-oxoheptanoate 7-aminotransferase, 2-amino-7-oxoheptanoate aminating oxidoreductase, or a homolysine decarboxylase (see Examples XXIV and XXVI; steps A/B/J/T/V/Y/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate CoA transferase or 2-aminopimelate CoA ligase; a 6-aminopimeloyl-CoA reductase (aldehyde forming); a 2-amino-7-oxoheptanoate 7-aminotransferase or 2-amino-7-oxoheptanoate aminating oxidoreductase; and a homolysine decarboxylase.

Figure 22:
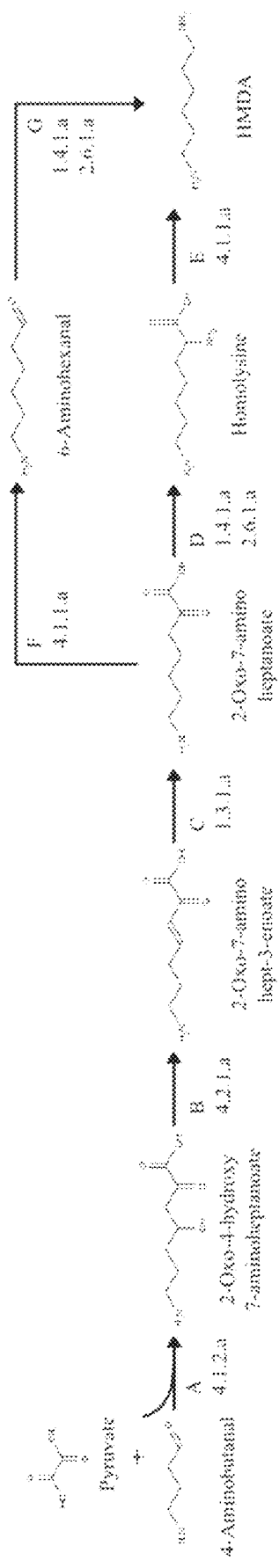
FIG. 22 shows an exemplary pathway from pyruvate and 4-aminobutanal to hexamethylenediamine (HMDA). The enzymes are designated as follows: A) 2-oxo-4-hydroxy-7-aminoheptanoate aldolase, B) 2-oxo-4-hydroxy-7-aminoheptanoate dehydratase, C) 2-oxo-7-aminohept-3-enoate reductase, D) 2-oxo-7-aminoheptanoate aminotransferase and/or aminating oxidoreductase, E) homolysine decarboxylase, F) 2-oxo-7-aminoheptanoate decarboxylase, G) 6-aminohexanal aminotransferase and/or 6-aminohexanal aminating oxidoreductase. The enzyme commission number indicated for each reaction is described in Example XXVI below.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 2-oxo-4-hydroxy-7-aminoheptanoate aldolase, a 2-oxo-4-hydroxy-7-aminoheptanoate dehydratase, a 2-oxo-7-aminohept-3-enoate reductase, a 2-oxo-7-aminoheptanoate aminotransferase, a 2-oxo-7-aminoheptanoate aminotransferase aminating oxidoreductase, a homolysine decarboxylase, a 2-oxo-7-aminoheptanoate decarboxylase, a 6-aminohexanal aminotransferase or a 6-aminohexanal aminating oxidoreductase (see Examples XXIV and XXVI; steps A-G of FIG. 22). In another aspect of the invention, the non-naturally occurring microbial organism includes a set of exogenous nucleic acids encoding HMDA pathway enzymes, wherein the set encodes a 2-oxo-4-hydroxy-7-aminoheptanoate aldolase; a 2-oxo-4-hydroxy-7-aminoheptanoate dehydratase; a 2-oxo-7-aminohept-3-enoate reductase; a 2-oxo-7-aminoheptanoate aminotransferase or a 2-oxo-7-aminoheptanoate aminating oxidoreductase; and a homolysine decarboxylase. In another aspect of the invention, the non-naturally occurring microbial organism includes a set of exogenous nucleic acids encoding HMDA pathway enzymes, wherein the set encodes a 2-oxo-4-hydroxy-7-aminoheptanoate aldolase; a 2-oxo-4-hydroxy-7-aminoheptanoate dehydratase; a 2-oxo-7-aminohept-3-enoate reductase; a 2-oxo-7-aminoheptanoate decarboxylase; and a 6-aminohexanal aminotransferase or a 6-aminohexanal aminating oxidoreductase.

Figure 24:
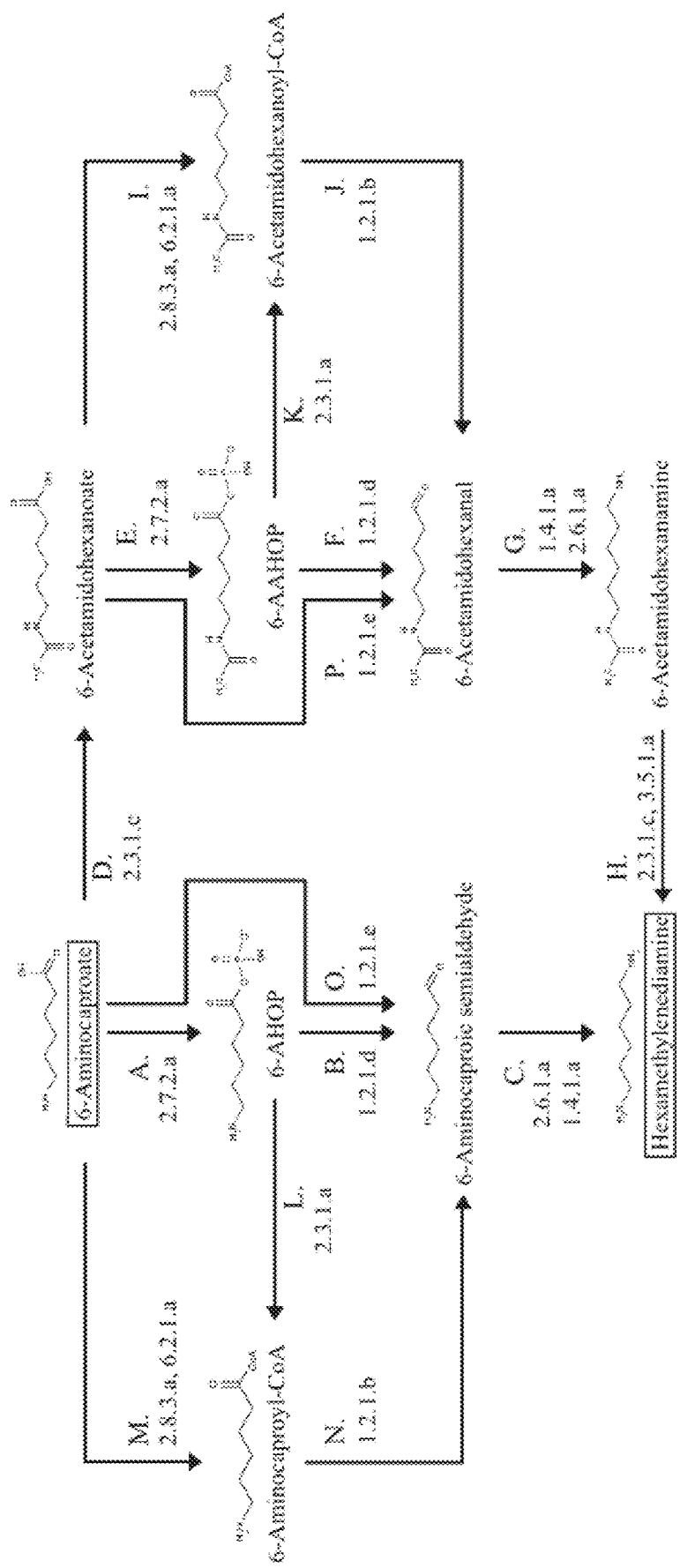
FIG. 24 shows exemplary pathways from 6-aminocaproate to hexamethylenediamine. This figure depicts additional pathways further to those presented in FIG. 13. The enzymes are designated as follows: A) 6-aminocaproate kinase, B) 6-AHOP oxidoreductase, C) 6-aminocaproic semialdehyde aminotransferase and/or 6-aminocaproic semialdehyde oxidoreductase (aminating), D) 6-aminocaproate N-acetyltransferase, E) 6-acetamidohexanoate kinase, F) 6-AAHOP oxidoreductase, G) 6-acetamidohexanal aminotransferase and/or 6-acetamidohexanal oxidoreductase (aminating), H) 6-acetamidohexanamine N-acetyltransferase and/or 6-acetamidohexanamine hydrolase (amide), I) 6-acetamidohexanoate CoA transferase and/or 6-acetamidohexanoate CoA ligase, J) 6-acetamidohexanoyl-CoA oxidoreductase, K) 6-AAHOP acyltransferase, L) 6-AHOP acyltransferase, M) 6-aminocaproate CoA transferase and/or 6-aminocaproate CoA ligase, N) 6-aminocaproyl-CoA oxidoreductase, 0) 6-aminocaproate reductase and P) 6-acetamidohexanoate reductase. Abbreviations are: 6-AAHOP=[(6-acetamidohexanoyl)oxy]phosphonate and 6-AHOP=[(6-aminohexanoyl)oxy]phosphonate. The enzyme commission number indicated for each reaction is described in Example XXVI below.

The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate reductase, a 6-aminocaproic semialdehyde aminotransferase, a 6-aminocaproic semialdehyde oxidoreductase (aminating), 6-aminocaproate N-acetyltransferase, a 6-acetamidohexanoate reductase, 6-acetamidohexanal aminotransferase, 6-acetamidohexanal oxidoreductase (aminating), 6-acetamidohexanamine N-acetyltransferase or acetamidohexanamine hydrolase (amide) (see Example XXVII; steps 0/C or D/P/G/H of FIG. 24 and Example XXXI). In another aspect of the invention, the non-naturally occurring microbial organism includes a set of exogenous nucleic acids encoding HMDA pathway enzymes, wherein the set encodes a 6-aminocaproate reductase; and a 6-aminocaproic semialdehyde aminotransferase or a 6-aminocaproic semialdehyde oxidoreductase (aminating). In another aspect of the invention, the non-naturally occurring microbial organism includes a set of exogenous nucleic acids encoding HMDA pathway enzymes, wherein the set encodes 6-aminocaproate N-acetyltransferase; 6-acetamidohexanoate reductase; 6-acetamidohexanal aminotransferase or 6-acetamidohexanal oxidoreductase (aminating); and 6-acetamidohexanamine N-acetyltransferase or 6-acetamidohexanamine hydrolase (amide). The invention additionally provides a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 2-amino-7-oxosubarate keto-acid decarboxylase, a 2-amino-7-oxoheptanoate decarboxylase, a 6-aminohexanal aminating oxidoreductase, a 6-aminohexanal aminotransferase, a 2-amino-7-oxoheptanoate decarboxylase, a homolysine decarboxylase, a 2-amino-7-oxosubarate amino acid decarboxylase, a 2-oxo-7-aminoheptanoate aminating oxidoreductase, a 2-oxo-7-aminoheptanoate aminotransferase, a 2-amino-7-oxosubarate aminating oxidoreductase, a 2-amino-7-oxosubarate aminotransferase, a 2,7-diaminosubarate decarboxylase, a 2-amino-7-oxoheptanoate aminotransferase or a 2-amino-7-oxoheptanoate aminating oxidoreductase (see Examples XXIV and XXVI; Steps A/B/C/G/H/I/J/K/L/M of FIG. 26). In a further aspect, the microbial organism has a 2-amino-7-oxosubarate pathway having at least one exogenous nucleic acid encoding a 2-amino-7-oxosubarate pathway enzyme expressed in a sufficient amount to produce 2-amino-7-oxosubarate, the 2-amino-7-oxosubarate pathway including a 2-amino-5-hydroxy-7-oxosubarate aldolase, a 2-amino-5-hydroxy-7-oxosubarate dehydratase, or a 2-amino-5-ene-7-oxosubarate reductase (see Examples XXV and XXVI; steps A/B/C of FIG. 27).

In another embodiment of the invention, the non-naturally occurring microbial organism includes a set of exogenous nucleic acids encoding HMDA pathway enzymes, wherein the set encodes a 2-amino-7-oxosubarate aminating oxidoreductase or 2-amino-7-oxosubarate aminotransferase; a 2,7-diaminosubarate decarboxylase; and a homolysine decarboxylase (see Examples XXIV and XXVI; steps K/L/H of FIG. 26). In another embodiment of the invention, the non-naturally occurring microbial organism includes a set of exogenous nucleic acids encoding HMDA pathway enzymes, wherein the set encodes a 2-amino-7-oxosubarate amino acid decarboxylase; a 2-oxo-7-aminoheptanoate aminating oxidoreductase or a 2-oxo-7-aminoheptanoate aminotransferase; and a homolysine decarboxylase (see Examples XXIV and XXVI; steps I/J/H of FIG. 26). In another embodiment of the invention, the non-naturally occurring microbial organism includes a set of exogenous nucleic acids encoding HMDA pathway enzymes, wherein the set encodes a 2-amino-7-oxosubarate keto-acid decarboxylase; a 2-oxo-7-aminoheptanoate decarboxylase; and a 6-aminohexanal aminating oxidoreductase or a 6-aminohexanal aminotransferase (see Examples XXIV and XXVI; steps I/G/C of FIG. 26). In another embodiment of the invention, the non-naturally occurring microbial organism includes a set of exogenous nucleic acids encoding HMDA pathway enzymes, wherein the set encodes a 2-amino-7-oxosubarate keto-acid decarboxylase; a 2-amino-7-oxoheptanoate decarboxylase; and a 6-aminohexanal aminating oxidoreductase or a 6-aminohexanal aminotransferase (see Examples XXIV and XXVI; steps A/B/C of FIG. 26). In another embodiment of the invention, the non-naturally occurring microbial organism includes a set of exogenous nucleic acids encoding HMDA pathway enzymes, wherein the set encodes a 2-amino-7-oxosubarate keto-acid decarboxylase; a 2-amino-7-oxoheptanoate aminating oxidoreductase or a 2-amino-7-oxoheptanoate aminotransferase; and a homolysine decarboxylase (see Examples XXIV and XXVI; steps A/M/H of FIG. 26). In a further aspect of each of the above embodiments, the microbial organism has a 2-amino-7-oxosubarate pathway having a second set of exogenous nucleic acids encoding 2-amino-7-oxosubarate pathway enzymes expressed in a sufficient amount to produce 2-amino-7-oxosubarate, the 2-amino-7-oxosubarate pathway including a 2-amino-5-hydroxy-7-oxosubarate aldolase; a 2-amino-5-hydroxy-7-oxosubarate dehydratase; and a 2-amino-5-ene-7-oxosubarate reductase (see Examples XXV and XXVI; steps A/B/C of FIG. 27). The invention additionally provides a non-naturally occurring microbial organism having a levulinic acid (LA) pathway including at least one exogenous nucleic acid encoding a LA pathway enzyme expressed in a sufficient amount to produce LA, the LA pathway including a 3-oxoadipyl-CoA thiolase, a 3-oxoadipyl-CoA/acyl-CoA transferase, a 3-oxoadipyl-CoA synthase, a 3-oxoadipyl-CoA hydrolase, or a 3-oxoadipate decarboxylase (see Example XXIX; steps A/E/F/G/AA of FIG. 25). In another aspect of the invention, the non-naturally occurring microbial organism includes a set of exogenous nucleic acids encoding LA pathway enzymes, wherein the set encodes a 3-oxoadipyl-CoA thiolase; a 3-oxoadipyl-CoA/acyl-CoA transferase, a 3-oxoadipyl-CoA synthase, or a 3-oxoadipyl-CoA hydrolase; and a 3-oxoadipate decarboxylase.

A non-naturally occurring microbial organism disclosed herein can have, for example, a 6-aminocaproic acid, caprolactam, hexamethylenediamine or levulinic acid pathway, wherein the non-naturally occurring microbial organism includes at least one exogenous nucleic acid encoding a polypeptide that converts a substrate to a product, as disclosed herein. Thus, a non-naturally occurring microbial organism can contain at least one exogenous nucleic acid encoding a polypeptide, where the polypeptide is an enzyme or protein that converts the substrates and products of a 6-aminocaproic acid, caprolactam, hexamethylenediamine or levulinic acid pathway, such as that shown in FIGS. 2, 3, 8, 9, 10, 11, 12, 13 and 20-27.

Figure 2:
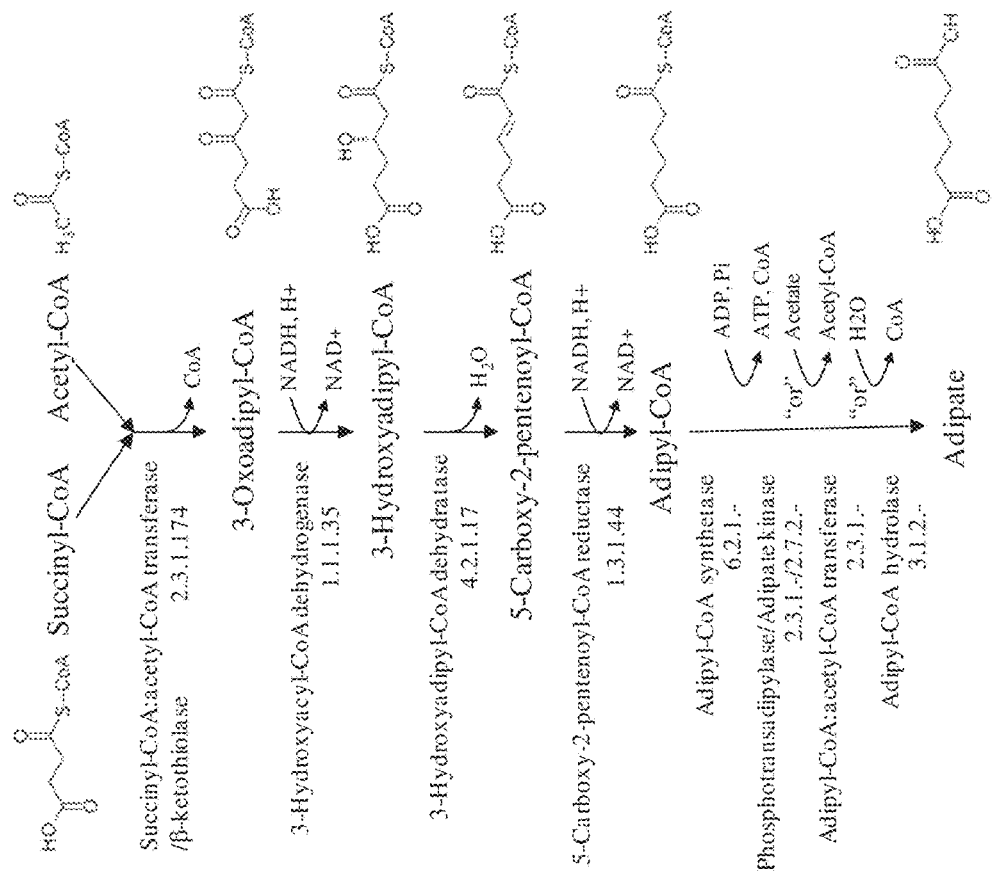
FIG. 2 shows an exemplary pathway for adipate formation via a reverse degradation pathway. Several options are provided for the final conversion of adipyl-CoA to adipate.
Figure 3:
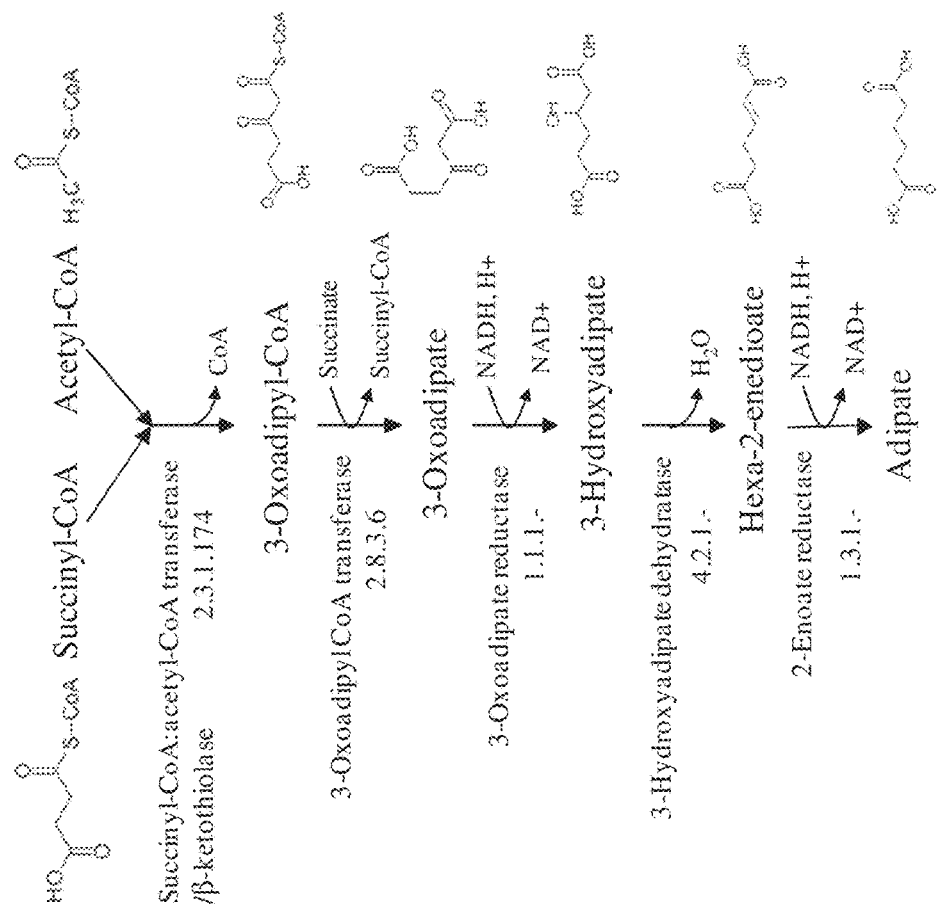
FIG. 3 shows an exemplary pathway for adipate formation via the 3-oxoadipate pathway.
Figure 4:
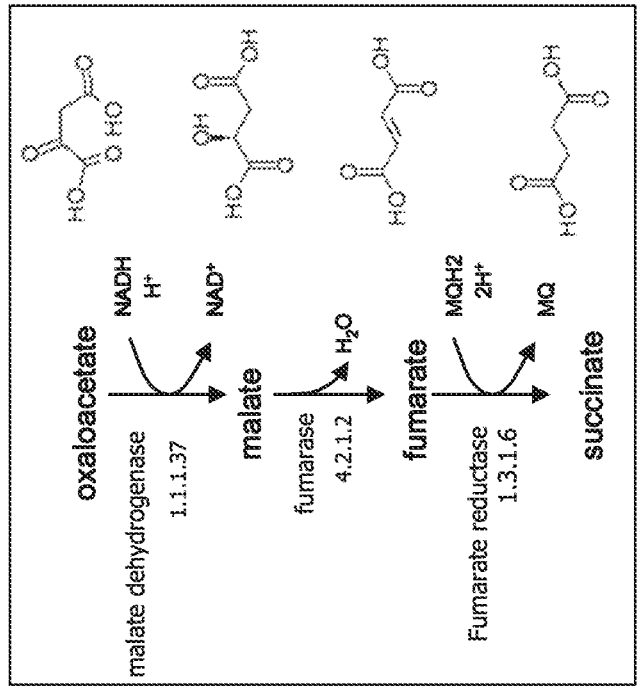
FIG. 4 show the similar enzyme chemistries of the last three steps of the 3-oxoadipate pathway for adipate synthesis and the reductive TCA cycle.
Figure 4:
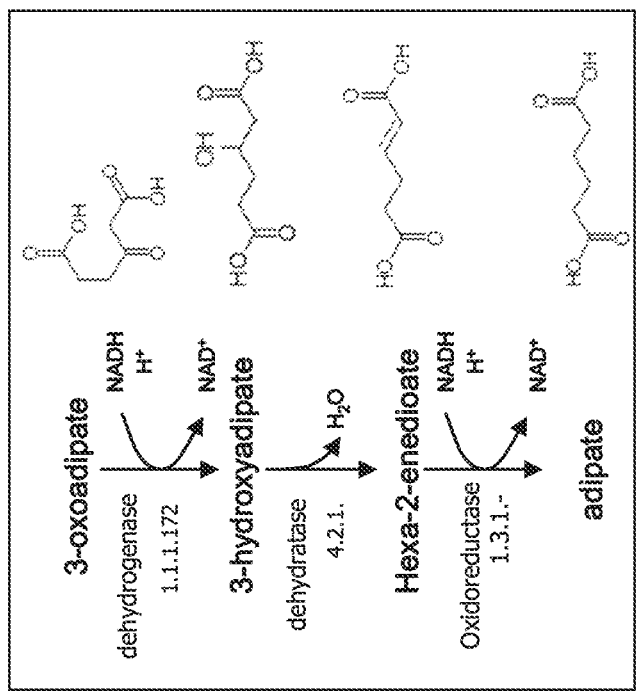

For example, a non-naturally occurring microbial organism can have an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-hydroxyadipyl-CoA; 3-hydroxyadipyl-CoA to 5-carboxy-2-pentenoyl-CoA; 5-carboxy-2-pentenoyl-CoA to adipyl-CoA; adipyl-CoA to adipate (see FIG. 2). Additionally, a non-naturally occurring microbial organism can have an adipate pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-oxoadipate;

3-oxoadipate to 3-hydroxyadipate; 3-hydroxyadipate to hexa-2-enedioate (also referred to herein as 5-carboxy-2-pentenoate); hexa-2-enedioate to adipate (see FIG. 3). Also, a non-naturally occurring microbial organism can have a 6-aminocaproic acid pathway, wherein the microbial organism contains at least one exogenous nucleic acid encoding a polypeptide that converts a substrate to a product selected from adipyl-CoA to adipate semialdehyde; and adipate semialdehyde to 6-aminocaproate (see FIG. 8). Furthermore, a non-naturally occurring microbial organism can have a caprolactam pathway, wherein the microbial organism contains at least one exogenous nucleic acid encoding a polypeptide that converts a substrate to a product selected from adipyl-CoA to adipate semialdehyde; adipate semialdehyde to 6-aminocaproate; and 6-aminocaproate to caprolactam. Additionally, a non-naturally occurring microbial organism can have an adipate pathway, wherein the microbial organism contains at least one exogenous nucleic acid encoding a polypeptide that converts a substrate to a product selected from alpha-ketoadipate to alpha-ketoadipyl-CoA; alpha-ketoadipyl-CoA to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate (see FIG. 9). Also, a non-naturally occurring microbial organism can have an adipate pathway, wherein the microbial organism contains at least one exogenous nucleic acid encoding a polypeptide that converts a substrate to a product selected from alpha-ketoadipate to 2-hydroxyadipate; 2-hydroxyadipate to 2-hydroxyadipyl-CoA; 2-hydroxyadipyl-CoA to 5-carboxy-2-pentenoyl-CoA; 5-carboxy-2-pentenoyl-CoA to adipyl-CoA; and adipyl-CoA to adipate (FIG. 9).

Additionally, a non-naturally occurring microbial organism can have a 6-aminocaproyl-CoA pathway, wherein the microbial organism contains at least one exogenous nucleic acid encoding a polypeptide that converts a substrate to a product selected from 4-aminobutyryl-CoA and acetyl-CoA to 3-oxo-6-aminohexanoyl-CoA; 3-oxo-6-aminohexanoyl-CoA to 3-hydroxy-6-aminohexanoyl-CoA; 3-hydroxy-6-aminohexanoyl-CoA to 6-aminohex-2-enoyl-CoA; 6-aminohex-2-enoyl-CoA to 6-aminocaproyl-CoA (FIG. 11). Additional substrates and products of such a pathway can include 6-aminocaproyl-CoA to 6-aminocaproate; 6-aminocaproyl-CoA to caprolactam; or 6-aminocaproyl-CoA to 6-aminocaproate semialdehyde and 6-aminocaproate semialdehyde to hexamethylenediamine (FIG. 11). A non-naturally occurring microbial organism also can have a 6-aminocaproic acid pathway, wherein the microbial organism contains at least one exogenous nucleic acid encoding a polypeptide that converts a substrate to a product selected from 4-aminobutyryl-CoA and acetyl-CoA to 3-oxo-6-aminohexanoyl-CoA; 3-oxo-6-aminohexanoyl-CoA to 3-oxo-6-aminohexanoate; 3-oxo-6-aminohexanoate to 3-hydroxy-6-aminohexanoate; 3-hydroxy-6-aminohexanoate to 6-aminohex-2-enoate; and 6-aminohex-2-enoate to 6-aminocaproate (FIG. 11). Additional substrates and products of such a pathway can include 6-aminocaproate to caprolactam or 6-aminocaproate to 6-aminocaproyl-CoA, 6-aminocaproyl-CoA to 6-aminocaproate semialdehyde, and 6-aminocaproate semialdehyde to hexamethylenediamine (FIG. 11).

Additionally, a non-naturally occurring microbial organism can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED): 2-oxohept-4-ene-1,7-dioate (OHED) to 2-oxoheptane-1,7-dioate (2-OHD); 2-oxoheptane-1,7-dioate (2-OHD) to adipate semialdehyde; and adipate semialdehyde to 6-aminocaproate (FIG. 12). A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 6-oxohex-4-enoate (6-OHE): 6-oxohex-4-enoate (6-OHE) to adipate semialdehyde; and adipate semialdehyde to 6-aminocaproate (FIG. 12). A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2-aminohept-4-ene-1,7-dioate (2-AHE); 2-aminohept-4-ene-1,7-dioate (2-AHE) to 2-aminoheptane-1,7-dioate (2-AHD); and 2-aminoheptane-1,7-dioate (2-AHD) to 6-aminocaproate (FIG. 12). A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2-oxoheptane-1,7-dioate (2-OHD); 2-oxoheptane-1,7-dioate (2-OHD) to 2-aminoheptane-1,7-dioate (2-AHD); and 2-aminoheptane-1,7-dioate (2-AHD) to 6-aminocaproate (FIG. 12). A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 3-hydroxyadipyl-CoA; 3-hydroxyadipyl-CoA to 2,3-dehydroadipyl-CoA; 2,3-dehydroadipyl-CoA to adipyl-CoA; adipyl-CoA to adipate semialdehyde; and adipate semialdehyde to 6-aminocaproate (FIG. 12). A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2,3-dehydroadipyl-CoA; 2,3-dehydroadipyl-CoA to adipyl-CoA; adipyl-CoA to adipate semialdehyde; and adipate semialdehyde to 6-aminocaproate (FIG. 12). A non-naturally occurring microbial organism alternatively can have a 6-aminocaproic acid pathway, wherein the microbial organism contains at least one exogenous nucleic acid encoding a polypeptide that converts a substrate to a product selected from pyruvate and succinic semialdehyde to 4-hydroxy-2-oxoheptane-1,7-dioate; 4-hydroxy-2-oxoheptane-1,7-dioate (HODH) to 2-oxohept-4-ene-1,7-dioate (OHED); 2-oxohept-4-ene-1,7-dioate (OHED) to 2-oxoheptane-1,7-dioate (2-OHD); 2-oxoheptane-1,7-dioate (2-OHD) to adipyl-CoA; adipyl-CoA to adipate semialdehyde; and adipate semialdehyde to 6-aminocaproate (FIG. 12).

Figure 20:
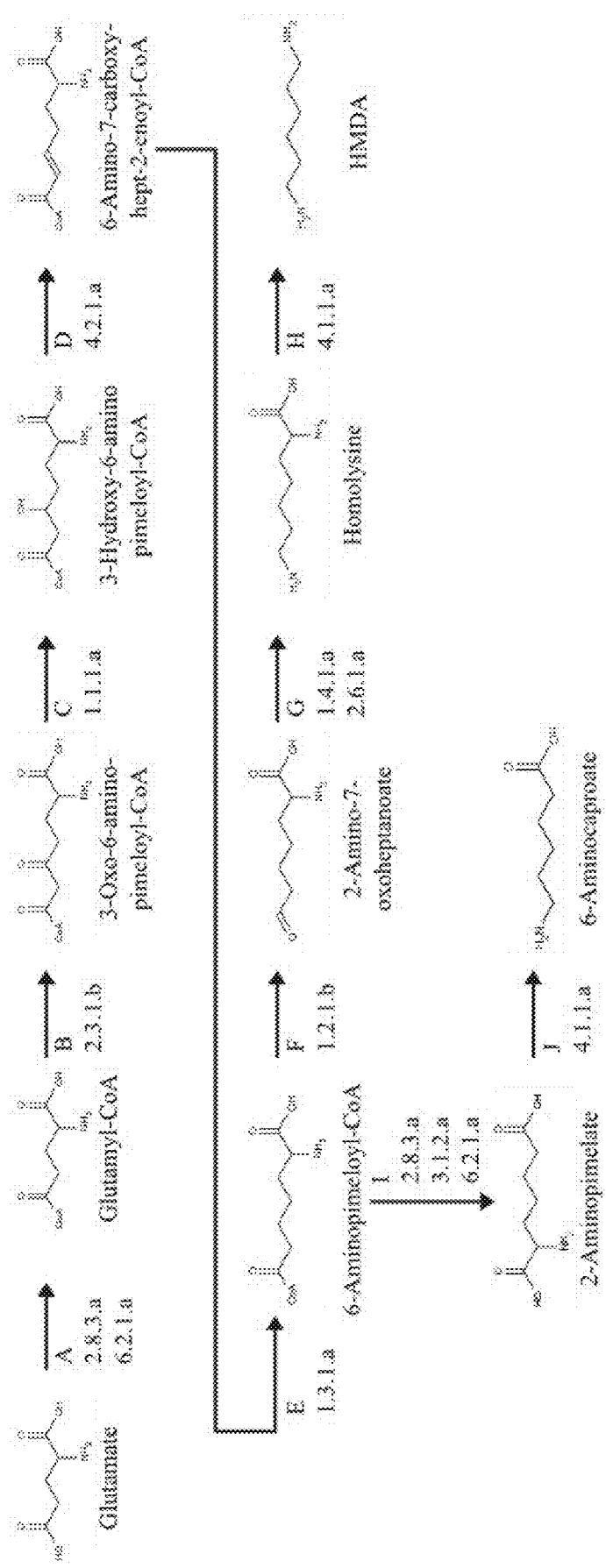
FIG. 20 shows exemplary pathways from glutamate to hexamethylenediamine (HMDA) and 6-aminocaproate. The enzymes are designated as follows: A) glutamyl-CoA transferase and/or ligase, B) beta-ketothiolase, C) 3-oxo-6-aminopimeloyl-CoA oxidoreductase, D) 3-hydroxy-6-aminopimeloyl-CoA dehydratase, E) 6-amino-7-carboxyhept-2-enoyl-CoA reductase, F) 6-aminopimeloyl-CoA reductase (aldehyde forming), G) 2-amino-7-oxoheptanoate aminotransferase and/or aminating oxidoreductase, H) homolysine decarboxylase, I) 6-aminopimeloyl-CoA hydrolase, transferase and/or ligase, J) 2-aminopimelate decarboxylase. The enzyme commission number indicated for each reaction is described in Example XXVI below.
Figure 23:
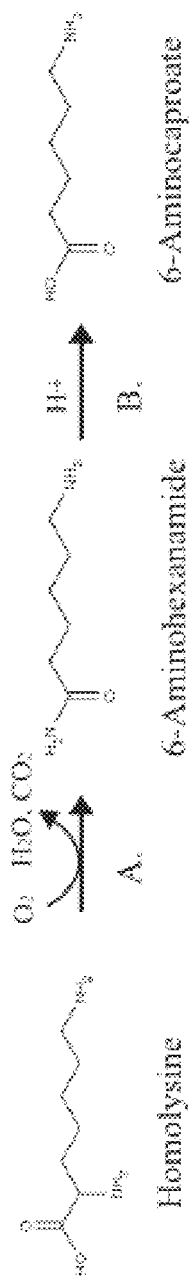
FIG. 23 shows an exemplary pathway from homolysine to 6-aminocaproate. Step A is catalyzed by homolysine 2-monooxygenase. Step B is hydrolysis, catalyzed by dilute acid or base.

Additionally, a non-naturally occurring microbial organism can have a 6-aminocaproic acid pathway, wherein the microbial organism contains at least one exogenous nucleic acid encoding a polypeptide that converts a substrate to a product selected from glutamate to glutamyl-CoA; glutamyl-coA to 3-oxo-6-amino-pimeloyl-CoA; 3-oxo-6-amino-pimeloyl-CoA to 3-hydroxy-6-amino-pimeloyl-CoA; 3-hydroxy-6-amino-pimeloyl-CoA to 6-amino-7-carboxy-hept-2-enoyl-CoA; 6-amino-7-carboxy-hept-2-enoyl-CoA to 6-aminopimeloyl-CoA; 6-aminopimeloyl-CoA to 2-aminopimelate; and 2-aminopimelate to 6-aminocaproate (FIG. 20). A non-naturally occurring microbial organism alternatively can have a 6-aminocaproic acid pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; and 2-aminopimelate to 6-aminocaproate (FIG. 21). A non-naturally occurring microbial organism alternatively can have a 6-aminocaproic acid pathway, wherein the microbial organism contains at least one exogenous nucleic acid encoding a polypeptide that converts a substrate to a product selected from homolysine to 6-aminohexanamide; and 6-aminohexanamide to 6-aminocaproate (FIG. 23). A non-naturally occurring microbial organism alternatively can have a 6-aminocaproic acid pathway, wherein the microbial organism contains at least one exogenous nucleic acid encoding a polypeptide that converts a substrate to a product selected from adipate to adipate semialdehyde; adipate to adipylphospate; and adipylphospate to adipate semialdehyde (FIG. 25).

Figure 27:
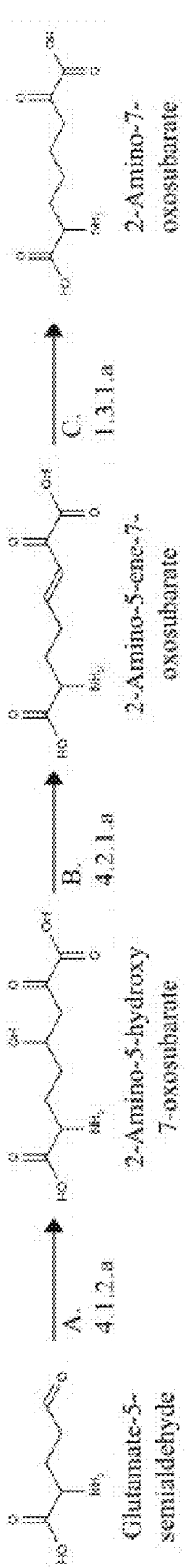
FIG. 27 shows an exemplary pathway from glutamate-5-semialdehyde to 2-amino-7-oxosubarate. The enzymes are designated as follows: A) 2-amino-5-hydroxy-7-oxosubarate aldolase, B) 2-amino-5-hydroxy-7-oxosubarate dehydratase, C) 2-amino-5-ene-7-oxosubarate reductase.

Additionally, a non-naturally occurring microbial organism can have a 6-aminocaproic acid pathway, wherein the microbial organism contains at least one exogenous nucleic acid encoding a polypeptide that converts a substrate to a product selected from 2-amino-7-oxosubarate to 2-amino-7-oxoheptanoate; 2-amino-7-oxoheptanoate to 6-aminohexanal; 6-aminohexanal to 6-aminocaproate; 2-amino-7-oxosubarate to 2-amino-7-oxoheptanoate; 2-amino-7-oxoheptanoate to 6-aminohexanal; 2-amino-7-oxoheptanoate to 2-aminopimelate; and 2-aminopimelate to 6-aminocaproate (FIG. 26). A non-naturally occurring microbial organism can further have a 2-amino-7-oxosubarate pathway, wherein the microbial organism contains at least one exogenous nucleic acid encoding a polypeptide that converts a substrate to a product selected from glutamate-5-semialdehyde to 2-amino-5-hydroxy-7-oxosubarate; 2-amino-5-hydroxy-7-oxosubarate to 2-amino-5-ene-7-oxosubarate; and 2-amino-5-ene-7-oxosubarate to 2-amino-7-oxosubarate (FIG. 27). Additionally, a non-naturally occurring microbial organism can have an hexamethylenediamine (HMDA) pathway, wherein the microbial organism contains at least one exogenous nucleic acid encoding a polypeptide that converts a substrate to a product selected from 6-aminocaproate to [(6-aminohexanoyl)oxy]phosphonate (6-AHOP); [(6-aminohexanoyl)oxy]phosphonate (6-AHOP) to 6-aminocaproaic semialdehyde; and 6-aminocaproaic semialdehyde to hexamethylenediamine (FIG. 13). A non-naturally occurring microbial organism alternatively can have a HMDA pathway, wherein the microbial organism contains at least one exogenous nucleic acid encoding a polypeptide that converts a substrate to a product selected from 6-aminocaproate to [(6-aminohexanoyl)oxy]phosphonate (6-AHOP); [(6-aminohexanoyl)oxy]phosphonate (6-AHOP) to 6-aminocaproyl-CoA; 6-aminocaproyl-CoA to 6-aminocaproaic semialdehyde; and 6-aminocaproaic semialdehyde to hexamethylenediamine (FIG. 13). A non-naturally occurring microbial organism alternatively can have a HMDA pathway, wherein the microbial organism contains at least one exogenous nucleic acid encoding a polypeptide that converts a substrate to a product selected from 6-aminocaproate to 6-aminocaproyl-CoA; 6-aminocaproyl-CoA to 6-aminocaproic semialdehyde; and 6-aminocaproic semialdehyde to hexamethylenediamine (FIG. 13). A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to [(6-acetamidohexanoy)oxy]phosphonate (6-AAHOP); [(6-acetamidohexanoy)oxy]phosphonate (6-AAHOP) to 6-acetamidohexanal; 6-acetamidohexanal to 6-acetamidohexanamine; and 6-acetamidohexanamine to hexamethylenediamine (FIG. 13). A non-naturally occurring microbial organism alternatively can have a HMDA pathway, wherein the microbial organism contains at least one exogenous nucleic acid encoding a polypeptide that converts a substrate selected from 6-aminocaproate to 6-acetamidohexanoate; 6-acetamidohexanoate to 6-acetamidohexanoyl-CoA; 6-acetamidohexanoyl-CoA to 6-acetamidohexanal; 6-acetamidohexanal to 6-acetamidohexanamine; and 6-acetamidohexanamine to hexamethylenediamine (FIG. 13). A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to [(6-acetamidohexanoy)oxy]phosphonate (6-AAHOP); [(6-acetamidohexanoy)oxy]phosphonate (6-AAHOP) to 6-acetamidohexanoyl-CoA; 6-acetamidohexanoyl-CoA to 6-acetamidohexanal; 6-acetamidohexanal to 6-acetamidohexanamine; and 6-acetamidohexanamine to hexamethylenediamine (FIG. 13).

Additionally, a non-naturally occurring microbial organism can have an hexamethylenediamine (HMDA) pathway, wherein the microbial organism contains at least one exogenous nucleic acid encoding a polypeptide that converts a substrate to a product selected from glutamate to glutamyl-CoA; glutamyl-coA to 3-oxo-6-amino-pimeloyl-CoA; 3-oxo-6-amino-pimeloyl-CoA to 3-hydroxy-6-amino-pimeloyl-CoA; 3-hydroxy-6-amino-pimeloyl-CoA to 6-amino-7-carboxy-hept-2-enoyl-CoA; 6-amino-7-carboxy-hept-2-enoyl-CoA to 6-aminopimeloyl-CoA; 6-aminopimeloyl-CoA to 2-amino-7-oxoheptanoate; -amino-7-oxoheptanoate to homolysine; and homolysine to HMDA (FIG. 20). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-oxo-1-carboxy heptanal; 3-oxo-1-carboxy heptanal to 3-oxo-7-amino heptanoate; 3-oxo-7-amino heptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl phosphonate; 5-oxopimeloyl phosphonate to 3-oxo-1-carboxy heptanal; 3-oxo-1-carboxy heptanal to 3-oxo-7-amino heptanoate; 3-oxo-7-amino heptanoate to 3,7-diamino heptanoate; 3,7-diamino heptanoate to homolysine and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl-CoA; 5-oxopimeloyl-CoA to 3-oxo-1-carboxy heptanal; 3-oxo-1-carboxy heptanal to 3-oxo-7-amino heptanoate; 3-oxo-7-amino heptanoate to 3,7-diamino heptanoate; 3,7-diamino heptanoate to homolysine and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-oxo-1-carboxy heptanal; 3-oxo-1-carboxy heptanal to 3-amino-7-oxoheptanoate; 3-amino-7-oxoheptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl-CoA; 5-oxopimeloyl-CoA to 3-oxo-1-carboxy heptanal; 3-oxo-1-carboxy heptanal to 3-amino-7-oxoheptanoate; 3-amino-7-oxoheptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-oxopimeloyl phosphonate; 5-oxopimeloyl phosphonate to 3-oxo-1carboxy heptanal; 3-oxo-1-carboxy heptanal to 3-amino-7-oxoheptanoate; 3-amino-7-oxoheptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 3-amino-7-oxoheptanoate; 3-amino-7-oxoheptanoate to 2-amino-7-oxoheptanoate; 2-amino-7-oxoheptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 5-aminopimeloyl phosphonate; 5-aminopimeloyl phosphonate to 3-amino-7-oxoheptanoate; 3-amino-7-oxoheptanoate to 2-amino-7-oxoheptanoate; 2-amino-7-oxoheptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 5-aminopimeloyl-CoA; 5-aminopimeloyl-CoA to 3-amino-7-oxoheptanoate; 3-amino-7-oxoheptanoate to 2-amino-7-oxoheptanoate; 2-amino-7-oxoheptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 3-amino-7-oxoheptanoate; 3-amino-7-oxoheptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 5-aminopimeloyl-CoA; 5-aminopimeloyl-CoA to 3-amino-7-oxoheptanoate; 3-amino-7-oxoheptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 5-aminopimeloyl phosphonate; 5-aminopimeloyl phosphonate to 3-amino-7-oxoheptanoate; 3-amino-7-oxoheptanoate to 3,7-diamino heptanoate; 3,7-diamino heptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; 2-aminopimelate to 2-amino-7-oxoheptanoate; 2-amino-7-oxoheptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; 2-aminopimelate to 6-aminopimeloylphosphonate; 6-aminopimeloylphosphonate to 2-amino-7-oxoheptanoate; 2-amino-7-oxoheptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from glutaryl-CoA to 3-oxopimeloyl-CoA; 3-oxopimeloyl-CoA to 3-oxopimelate; 3-oxopimelate to 3-aminopimelate; 3-aminopimelate to 2-aminopimelate; 2-aminopimelate to 6-aminopimeloyl-CoA; 6-aminopimeloyl-CoA to 2-amino-7-oxoheptanoate; 2-amino-7-oxoheptanoate to homolysine; and homolysine to HMDA (FIG. 21). A non-naturally occurring microbial organism alternatively can have a HMDA pathway, wherein the microbial organism contains at least one exogenous nucleic acid encoding a polypeptide that converts a substrate to a product selected from pyruvate and 4-aminobutanal to 2-oxo-4-hydroxy 7-aminoheptanoate; 2-oxo-4-hydroxy 7-aminoheptanoate to 2-oxo-7-amino hept-3-enoate; 2-oxo-7-amino hept-3-enoate to 2-oxo-7-amino heptanoate; 2-oxo-7-amino heptanoate to homolysine; and homolysine to HMDA (FIG. 22). A non-naturally occurring microbial organism alternatively can have a HMDA pathway, wherein the microbial organism contains at least one exogenous nucleic acid encoding a polypeptide that converts a substrate to a product selected from pyruvate and 4-aminobutanal to 2-oxo-4-hydroxy 7-aminoheptanoate; 2-oxo-4-hydroxy 7-aminoheptanoate to 2-oxo-7-amino hept-3-enoate; 2-oxo-7-amino hept-3-enoate to 2-oxo-7-amino heptanoate; 2-oxo-7-aminoheptanoate to 6-aminohexanal; and 6-aminohexanal to HMDA (FIG. 22). A non-naturally occurring microbial organism alternatively can have a HMDA pathway, wherein the microbial organism contains at least one exogenous nucleic acid encoding a polypeptide that converts a substrate to a product selected from 6-aminocaproate to 6-aminocaproic semialdehyde; and 6-aminocaproic semialdehyde to HMDA (FIG. 24). A non-naturally occurring microbial organism alternatively can have a HMDA pathway, wherein the microbial organism contains at least one exogenous nucleic acid encoding a polypeptide that converts a substrate to a product selected from 6-aminocaproate to 6-acetamidohexanoate; 6-acetamidohexanoate to 6-acetamidohexanal; 6-acetamidohexanal to 6-acetamidohexanamine; 6-acetamidohexanamine to HMDA (FIG. 24). A non-naturally occurring microbial organism alternatively can have a HMDA pathway, wherein the microbial organism contains at least one exogenous nucleic acid encoding a polypeptide that converts a substrate to a product selected from 2-amino-7-oxosubarate to 2-amino-7-oxoheptanoate; 2-amino-7-oxoheptanoate to 6-aminohexanal; 6-aminohexanal to HMDA; 2-amino-7-oxosubarate to 2-oxo-7-aminoheptanoate; 2-amino-7-oxoheptanoate to homolysine; homolysine to HMDA; 2-oxo-7-aminoheptanoate to homolysine; 2-oxo-7-aminoheptanoate to 6-aminohexanal; 2-amino-7-oxosubarate to 2,7-diaminosubarate; and 2,7-diaminosubarate to homolysine (FIG. 26). A non-naturally occurring microbial organism can further have a 2-amino-7-oxosubarate pathway, wherein the microbial organism contains at least one exogenous nucleic acid encoding a polypeptide that converts a substrate to a product selected from glutamate-5-semialdehyde to 2-amino-5-hydroxy-7-oxosubarate; 2-amino-5-hydroxy-7-oxosubarate to 2-amino-5-ene-7-oxosubarate; and 2-amino-5-ene-7-oxosubarate to 2-amino-7-oxosubarate (FIG. 27).

Additionally, a non-naturally occurring microbial organism can have a levulinic acid pathway, wherein the microbial organism contains at least one exogenous nucleic acid encoding a polypeptide that converts a substrate to a product selected from succinyl-CoA and acetyl-CoA to 3-oxoadipyl-CoA; 3-oxoadipyl-CoA to 3-oxoadipate; and 3-oxoadipate to levulinic acid. It is understood that any of the pathways disclosed herein which produce an intermediate of one pathway can be used to produce that intermediate for another pathway, if desired. For example, as disclosed herein, the alpha-ketoadipate to adipate pathway shown in FIG. 9 produces the intermediate adipyl-CoA, which is also an intermediate in the pathway depicted in FIG. 10. Thus, it is understood that an alternative pathway includes alpha-ketoadipate to adipyl-CoA, which can be converted to adipate, 6-aminocaproate, caprolactam or hexamethylenediamine, as depicted in FIG. 10. It is understood that any of the pathways disclosed herein that produce a desired intermediate can be used in combination with any other pathways disclosed herein so long as a desired product is produced. For example, a non-naturally occurring microbial organism disclosed herein, can have at least one nucleic acid encoding a 6-aminocaproic acid pathway enzyme and at least one nucleic acid encoding a hexamethylenediamine pathway enzyme, such as 2-AHD decarboxylase (Step I of FIG. 12) and 6-acetamidohexanoate kinase (Step E of FIG. 13), or alternatively 2-oxohept-4-ene-1,7-dioate (OHED) decarboxylase (Step F of FIG. 12), adipate semialdehyde aminotransferase (Step E of FIG. 12) and 6-acetamidohexanoyl-CoA oxidoreductase (Step J of FIG. 13), or alternatively 5-carboxy-2pentenoyl-CoA reductase (Step D of FIG. 10), adipyl-CoA dehydrogenase (Step O of FIG. 12) and 6-aminocaproyl-CoA oxidoreductase (Step N of FIG. 13), or alternatively 2-amino-7-oxoheptanoate aminotransferase (Step G of FIG. 20) and 3,7-diaminoheptanoate 2,3-aminomutase (Step R of FIG. 21), or alternatively 6-aminocaproate reductase (Step O of FIG. 24) and 6-aminohex-2-enoate reductase (Step J of FIG. 11), or alternatively adipate reductase (Step X of FIG. 25) and 6-acetamidohexanoate reductase (Step P of FIG. 24).

In an additional embodiment, the invention provides a non-naturally occurring microbial organism having a 6-aminocaproic acid, caprolactam, hexamethylenediamine or levulinic acid pathway, wherein the non-naturally occurring microbial organism comprises at least one exogenous nucleic acid encoding an enzyme or protein that converts a substrate to a product selected from any of the substrates or products disclosed herein or shown in any of FIGS. 1-14 and 20-27. One skilled in the art will understand that any of the substrate-product pairs disclosed herein suitable to produce a desired product and for which an appropriate activity is available for the conversion of the substrate to the product can be readily determined by one skilled in the art based on the teachings herein. Thus, the invention provides a non-naturally occurring microbial organism containing at least one exogenous nucleic acid encoding an enzyme or protein, where the enzyme or protein converts the substrates and products of a 6-aminocaproic acid, caprolactam, hexamethylenediamine or levulinic acid pathway, such as any of those shown in FIGS. 1-14 and 20-27.

While generally described herein as a microbial organism that contains a 6-aminocaproic acid, caprolactam, hexamethylenediamine or levulinic acid pathway, it is understood that the invention additionally provides a non-naturally occurring microbial organism comprising at least one exogenous nucleic acid encoding a 6-aminocaproic acid, caprolactam, hexamethylenediamine or levulinic acid pathway enzyme expressed in a sufficient amount to produce an intermediate of a 6-aminocaproic acid, caprolactam, hexamethylenediamine or levulinic acid pathway. For example, as disclosed herein, 6-aminocaproic acid, caprolactam, hexamethylenediamine or levulinic acid pathway are exemplified in FIGS. 1-14 and 20-27. Therefore, in addition to a microbial organism containing a 6-aminocaproic acid, caprolactam, hexamethylenediamine or levulinic acid pathway that produces 6-aminocaproic acid, caprolactam, hexamethylenediamine or levulinic acid, the invention additionally provides a non-naturally occurring microbial organism comprising at least one exogenous nucleic acid encoding a 6-aminocaproic acid, caprolactam, hexamethylenediamine or levulinic acid pathway enzyme, where the microbial organism produces a 6-aminocaproic acid, caprolactam, hexamethylenediamine or levulinic acid pathway intermediate, for example, any of the intermediates shown in FIGS. 1-14 and 20-27.

It is understood that any of the pathways disclosed herein, including those as described in the Examples and exemplified in the Figures, including the pathways of FIGS. 1-14 and 20-27, can be utilized to generate a non-naturally occurring microbial organism that produces any pathway intermediate or product, as desired. As disclosed herein, such a microbial organism that produces an intermediate can be used in combination with another microbial organism expressing downstream pathway enzymes to produce a desired product. However, it is understood that a non-naturally occurring microbial organism that produces a 6-aminocaproic acid, caprolactam, hexamethylenediamine or levulinic acid pathway intermediate can be utilized to produce the intermediate as a desired product.

The invention is described herein with general reference to the metabolic reaction, reactant or product thereof, or with specific reference to one or more nucleic acids or genes encoding an enzyme associated with or catalyzing the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes as well as the reactants and products of the reaction.

The non-naturally occurring microbial organisms of the invention can be produced by introducing expressible nucleic acids encoding one or more of the enzymes participating in one or more 6-aminocaproic acid, caprolactam, hexamethylenediamine or levulinic acid biosynthetic pathways. Depending on the host microbial organism chosen for biosynthesis, nucleic acids for some or all of a particular 6-aminocaproic acid, caprolactam, hexamethylenediamine or levulinic acid biosynthetic pathway can be expressed. For example, if a chosen host is deficient in one or more enzymes for a desired biosynthetic pathway, then expressible nucleic acids for the deficient enzyme(s) are introduced into the host for subsequent exogenous expression. Alternatively, if the chosen host exhibits endogenous expression of some pathway genes, but is deficient in others, then an encoding nucleic acid is needed for the deficient enzyme(s) to achieve 6-aminocaproic acid, caprolactam, hexamethylenediamine or levulinic acid biosynthesis. Thus, a non-naturally occurring microbial organism of the invention can be produced by introducing exogenous enzyme activities to obtain a desired biosynthetic pathway or a desired biosynthetic pathway can be obtained by introducing one or more exogenous enzyme activities that, together with one or more endogenous enzymes, produces a desired product such as 6-aminocaproic acid, caprolactam, hexamethylenediamine or levulinic acid.

Depending on the 6-aminocaproic acid, caprolactam, hexamethylenediamine or levulinic acid biosynthetic pathway constituents of a selected host microbial organism, the non-naturally occurring microbial organisms of the invention will include at least one exogenously expressed 6-aminocaproic acid, caprolactam, hexamethylenediamine or levulinic acid pathway-encoding nucleic acid and up to all encoding nucleic acids for one or more adipate, 6-aminocaproic acid or caprolactam biosynthetic pathways. For example, 6-aminocaproic acid, caprolactam, hexamethylenediamine or levulinic acid biosynthesis can be established in a host deficient in a pathway enzyme through exogenous expression of the corresponding encoding nucleic acid. In a host deficient in all enzymes of a 6-aminocaproic acid, caprolactam, hexamethylenediamine or levulinic acid pathway, exogenous expression of all enzymes in the pathway can be included, although it is understood that all enzymes of a pathway can be expressed even if the host contains at least one of the pathway enzymes.

For example, exogenous expression of all enzymes in a pathway for production of adipate can be included in a host organism, such as succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. In particular, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase. Alternatively, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and phosphotransadipylase/adipate kinase. In addition, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA:acetyl-CoA transferase. Further, a host organism can contain the adipate pathway enzymes succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA hydrolase.

In the case of a 6-aminocaproic acid producing microbial organism, exogenous expression of all enzymes in a pathway for production of 6-aminocaproic acid can be included in a host organism, such as CoA-dependent aldehyde dehydrogenase and transaminase or CoA-dependent aldehyde dehydrogenase and 6-aminocaproate dehydrogenase. For a caprolactam producing microbial organism, exogenous expression of all enzymes in a pathway for production of caprolactam can be included in a host organism, such as CoA-dependent aldehyde dehydrogenase, transaminase or 6-aminocaproate dehydrogenase, and amidohydrolase. In another example, exogenous expression of all enzymes in a pathway for production of 6-aminocaproic acid (6-ACA) can be included in a host organism, such as an HODH aldolase; an OHED hydratase; an OHED reductase; a 2-OHD decarboxylase; and an adipate semialdehyde aminotransferase or an adipate semialdehyde oxidoreductase (aminating), or alternatively an HODH aldolase; an OHED hydratase; an OHED decarboxylase; a 6-OHE reductase; and an adipate semialdehyde aminotransferase or an adipate semialdehyde oxidoreductase (aminating), or alternatively an HODH aldolase; an OHED hydratase; an OHED aminotransferase or an OHED oxidoreductase (aminating); a 2-AHE reductase; and a 2-AHD decarboxylase, or alternatively an HODH aldolase; an OHED hydratase; an OHED reductase; a 2-OHD aminotransferase or a 2-OHD oxidoreductase (aminating); and a 2-AHD decarboxylase, or alternatively an HODH aldolase; an HODH formate-lyase and a pyruvate formate-lyase activating enzyme or an HODH dehydrogenase; a 3-hydroxyadipyl-CoA dehydratase; a 2,3-dehydroadipyl-CoA reductase; an adipyl-CoA dehydrogenase; and an adipate semialdehyde aminotransferase or an adipate semialdehyde oxidoreductase (aminating), or alternatively an HODH aldolase; an OHED hydratase; an OHED formate-lyase and a pyruvate formate-lyase activating enzyme or OHED dehydrogenase; a 2,3-dehydroadipyl-CoA reductase; an adipyl-CoA dehydrogenase; and an adipate semialdehyde aminotransferase or an adipate semialdehyde oxidoreductase (aminating), or alternatively an HODH aldolase; an OHED hydratase; an OHED reductase; a 2-OHD formate-lyase and a pyruvate formate-lyase activating enzyme or a 2-OHD dehydrogenase; an adipyl-CoA dehydrogenase; and an adipate semialdehyde aminotransferase or an adipate semialdehyde oxidoreductase (aminating). In a further aspect, all of the the 6-ACA pathway described above can include a succinic semialdehyde dehydrogenase, an alpha-ketoglutarate decarboxylase or a phosphoenolpyruvate (PEP) carboxykinase. In another example, exogenous expression of all enzymes in a pathway for production of 6-aminocaproic acid (6-ACA) can be included in a host organism, such as a glutamyl-CoA transferase or glutamyl-CoA ligase; a beta-ketothiolase; a 3-oxo-6-aminopimeloyl-CoA oxidoreductase; a 3-hydroxy-6-aminopimeloyl-CoA dehydratase; a 6-amino-7-carboxyhept-2-enoyl-CoA reductase; a 6-aminopimeloyl-CoA reductase (aldehyde forming); and a 2-aminopimelate decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate 2,3-aminomutase; and a 2-aminopimelate decarboxylase.

In another example, exogenous expression of all enzymes in a pathway for production of hexamethylenediamine can be included in a host organism, such as a 6-aminocaproate kinase; a 6-AHOP oxidoreductase; and a 6-aminocaproic semialdehyde oxidoreductase (aminating) or a 6-aminocaproic acid semialdehyde aminotransferase, or alternatively a 6-aminocaproate kinase; a 6-AHOP acyltransferase; a 6-aminocaproyl-CoA oxidoreductase; and a 6-aminocaproic semialdehyde oxidoreductase (aminating) or a 6-aminocaproic acid semialdehyde aminotransferase, or alternatively a 6-aminocaproate CoA transferase or a 6-aminocaproate CoA ligase; a 6-aminocaproyl-CoA oxidoreductase; and a 6-aminocaproic semialdehyde oxidoreductase (aminating) or a 6-aminocaproic acid semialdehyde aminotransferase, or alternatively a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide), or alternatively a 6-aminocaproate N-acetyltransferase; a 6-acetamidohexanoate CoA transferase or a 6-acetamidohexanoate CoA ligase; a 6-acetamidohexanoyl-CoA oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide), or alternatively a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide). In another example, exogenous expression of all enzymes in a pathway for production of hexamethylenediamine can be included in a host organism, such as a glutamyl-CoA transferase or ligase; a beta-ketothiolase; a 3-oxo-6-aminopimeloyl-CoA oxidoreductase; a 3-hydroxy-6-aminopimeloyl-CoA dehydratase; a 6-amino-7-carboxyhept-2-enoyl-CoA reductase; a 6-aminopimeloyl-CoA reductase (aldehyde forming); a 2-amino-7-oxoheptanoate aminotransferase or aminating oxidoreductase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate reductase; a 3-oxo-1-carboxyheptanal 7-aminotransferase or a 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate kinase; a 5-oxopimeloylphosphonate reductase; a 3-oxo-1-carboxyheptanal 7-aminotransferase or a 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate CoA transferase or 3-oxopimelate CoA ligase; a 5-oxopimeloyl-CoA reductase (aldehyde forming); a 3-oxo-1-carboxyheptanal 7-aminotransferase or 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate reductase; a 3-oxo-1-carboxyheptanal 3-aminotransferase or a 3-oxo-1-carboxyheptanal 3-aminating oxidoreductase; a 3-amino-7-oxoheptanoate 7-aminotransferase or a 3-amino-7-oxoheptanoate 7-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate kinase; a 5-oxopimeloylphosphonate reductase; a 3-oxo-1-carboxyheptanal 3-aminotransferase or a 3-oxo-1-carboxyheptanal 3-aminating oxidoreductase; a 3-amino-7-oxoheptanoate 7-aminotransferase or a 3-amino-7-oxoheptanoate 7-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate CoA transferase or a 3-oxopimelate CoA ligase; a 5-oxopimeloyl-CoA reductase (aldehyde forming), a 5-oxopimeloyl-CoA hydrolase or a 5-oxopimeloyl-CoA ligase; a 3-oxo-1-carboxyheptanal 3-aminotransferase or a 3-oxo-1-carboxyheptanal 3-aminating oxidoreductase; a 3-amino-7-oxoheptanoate 7-aminotransferase or 3-amino-7-oxoheptanoate 7-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate reductase; a 3-amino-7-oxoheptanoate 2,3-aminomutase; a 2-amino-7-oxoheptanoate 7-aminotransferase or a 2-amino-7-oxoheptanoate aminating oxidoreductase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate kinase; a 5-aminopimeloylphosphonate reductase; a 3-amino-7-oxoheptanoate 2,3-aminomutase; a 2-amino-7-oxoheptanoate 7-aminotransferase or a 2-amino-7-oxoheptanoate aminating oxidoreductase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate CoA transferase or a 3-aminopimelate CoA ligase; a 5-aminopimeloyl-CoA reductase (aldehyde forming); a 3-amino-7-oxoheptanoate 2,3-aminomutase; a 2-amino-7-oxoheptanoate 7-aminotransferase or 2-amino-7-oxoheptanoate aminating oxidoreductase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate reductase; a 3-amino-7-oxoheptanoate 7-aminotransferase or 3-amino-7-oxoheptanoate 7-aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate CoA transferase or a 3-aminopimelate CoA ligase; a 5-aminopimeloyl-CoA reductase (aldehyde forming); a 3-amino-7-oxoheptanoate 7-aminotransferase or 3-amino-7-oxoheptanoate aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate kinase; a 5-aminopimeloylphosphonate reductase; a 3-amino-7-oxoheptanoate 7-aminotransferase or a 3-amino-7-oxoheptanoate aminating oxidoreductase; a 3,7-diaminoheptanoate 2,3-aminomutase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate reductase; a 2-amino-7-oxoheptanoate 7-aminotransferase or a 2-amino-7-oxoheptanoate aminating oxidoreductase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate kinase; a 6-aminopimeloylphosphonate reductase; a 2-amino-7-oxoheptanoate 7-aminotransferase or a 2-amino-7-oxoheptanoate aminating oxidoreductase; and a homolysine decarboxylase, or alternatively a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate CoA transferase or 2-aminopimelate CoA ligase; a 6-aminopimeloyl-CoA reductase (aldehyde forming); a 2-amino-7-oxoheptanoate 7-aminotransferase or 2-amino-7-oxoheptanoate aminating oxidoreductase; and a homolysine decarboxylase, or alternatively a 2-oxo-4-hydroxy-7-aminoheptanoate aldolase; a 2-oxo-4-hydroxy-7-aminoheptanoate dehydratase; a 2-oxo-7-aminohept-3-enoate reductase; a 2-oxo-7-aminoheptanoate aminotransferase or a 2-oxo-7-aminoheptanoate aminating oxidoreductase; and a homolysine decarboxylase, or alternatively a 6-aminocaproate reductase; and a 6-aminocaproic semialdehyde aminotransferase or a 6-aminocaproic semialdehyde oxidoreductase (aminating), or alternatively a 6-aminocaproate N-acetyltransferase; a 6-acetamidohexanoate reductase; a 6-acetamidohexanal aminotransferase or 6-acetamidohexanal oxidoreductase (aminating); and a 6-acetamidohexanamine N-acetyltransferase or 6-acetamidohexanamine hydrolase (amide).

Depending on the 6-aminocaproic acid, caprolactam, hexamethylenediamine or levulinic acid biosynthetic pathway constituents of a selected host microbial organism, the non-naturally occurring microbial organisms of the invention will include at least one exogenously expressed 6-aminocaproic acid, caprolactam, hexamethylenediamine or levulinic acid pathway-encoding nucleic acid and up to all encoding nucleic acids for one or more 6-aminocaproic acid, caprolactam, hexamethylenediamine or levulinic acid biosynthetic pathways. For example, 6-aminocaproic acid, caprolactam, hexamethylenediamine or levulinic acid biosynthesis can be established in a host deficient in a pathway enzyme or protein through exogenous expression of the corresponding encoding nucleic acid. In a host deficient in all enzymes or proteins of a 6-aminocaproic acid, caprolactam, hexamethylenediamine or levulinic acid pathway, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of 6-aminocaproic acid, caprolactam, hexamethylenediamine or levulinic acid can be included, as disclosed herein.

Given the teachings and guidance provided herein, those skilled in the art will understand that the number of encoding nucleic acids to introduce in an expressible form will, at least, parallel the adipate, 6-aminocaproic acid, caprolactam, hexamethylenediamine or levulinic acid pathway deficiencies of the selected host microbial organism. Therefore, a non-naturally occurring microbial organism of the invention can have at least one, two, three, four, five, six, seven, eight, nine, ten, eleven or twelve, up to all nucleic acids encoding the above enzymes constituting a 6-aminocaproic acid, caprolactam, hexamethylenediamine or levulinic acid biosynthetic pathway. In some embodiments, the non-naturally occurring microbial organisms also can include other genetic modifications that facilitate or optimize 6-aminocaproic acid, caprolactam, hexamethylenediamine or levulinic acid biosynthesis or that confer other useful functions onto the host microbial organism. One such other functionality can include, for example, augmentation of the synthesis of one or more of the 6-aminocaproic acid, caprolactam, hexamethylenediamine or levulinic acid pathway precursors such as succinyl-CoA and/or acetyl-CoA in the case of adipate synthesis, or adipyl-CoA or adipate in the case of 6-aminocaproic acid or caprolactam synthesis, including the adipate pathway enzymes disclosed herein, or pyruvate and succinic semialdehyde, glutamate, glutaryl-CoA, homolysine or 2-amino-7-oxosubarate in the case of 6-aminocaproate synthesis, or 6-aminocaproate, glutamate, glutaryl-CoA, pyruvate and 4-aminobutanal, or 2-amino-7-oxosubarate in the case of hexamethylenediamine synthesis.

Generally, a host microbial organism is selected such that it produces the precursor of a 6-aminocaproic acid, caprolactam, hexamethylenediamine or levulinic acid pathway, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a 6-aminocaproic acid, caprolactam, hexamethylenediamine or levulinic acid pathway.

In some embodiments, a non-naturally occurring microbial organism of the invention is generated from a host that contains the enzymatic capability to synthesize 6-aminocaproic acid, caprolactam, hexamethylenediamine or levulinic acid. In this specific embodiment it can be useful to increase the synthesis or accumulation of a 6-aminocaproic acid, caprolactam, hexamethylenediamine or levulinic acid pathway product to, for example, drive 6-aminocaproic acid, caprolactam, hexamethylenediamine or levulinic acid pathway reactions toward 6-aminocaproic acid, caprolactam, hexamethylenediamine or levulinic acid production. Increased synthesis or accumulation can be accomplished by, for example, overexpression of nucleic acids encoding one or more of the above-described 6-aminocaproic acid, caprolactam, hexamethylenediamine or levulinic acid pathway enzymes. Over expression of the 6-aminocaproic acid, caprolactam, hexamethylenediamine or levulinic acid pathway enzyme or enzymes can occur, for example, through exogenous expression of the endogenous gene or genes, or through exogenous expression of the heterologous gene or genes. Therefore, naturally occurring organisms can be readily generated to be non-naturally occurring microbial organisms of the invention, for example, producing 6-aminocaproic acid, caprolactam, hexamethylenediamine or levulinic acid, through overexpression of at least one, two, three, four, five, six, seven, eight, nine, ten, eleven, twelve, thirteen, fourteen, that is, up to all nucleic acids encoding 6-aminocaproic acid, caprolactam, hexamethylenediamine or levulinic acid biosynthetic pathway enzymes. In addition, a non-naturally occurring organism can be generated by mutagenesis of an endogenous gene that results in an increase in activity of an enzyme in the 6-aminocaproic acid, caprolactam, hexamethylenediamine or levulinic acid biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a non-naturally occurring microbial organism.

The invention additionally provides a non-naturally occurring microbial organism that includes one or more gene disruptions, such as the gene disruptions disclosed in Example XXX and Tables 14-16, where the organism produces a 6-ACA, adipate and/or HMDA. The disruptions occur in genes encoding an enzyme that couples production of adipate, 6-ACA and/or HMDA to growth of the organism when the gene disruption reduces the activity of the enzyme, such that the gene disruptions confer increased production of adipate, 6-ACA and/or HMDA onto the non-naturally occurring organism. Thus, the invention provides a non-naturally occurring microbial organism, comprising one or more gene disruptions, the one or more gene disruptions occurring in genes encoding proteins or enzymes wherein the one or more gene disruptions confer increased production of adipate, 6-ACA and/or HMDA in the organism. As disclosed herein, such an organism contains a pathway for production of adipate, 6-ACA and/or HMDA, in addition to the gene disruptions, such as those exemplified in Example XXX and Tables 14-16.

It is understood that, in methods of the invention, any of the one or more exogenous nucleic acids can be introduced into a microbial organism to produce a non-naturally occurring microbial organism of the invention. The nucleic acids can be introduced so as to confer, for example, a 6-aminocaproic acid, caprolactam, hexamethylenediamine or levulinic acid biosynthetic pathway onto the microbial organism. Alternatively, encoding nucleic acids can be introduced to produce an intermediate microbial organism having the biosynthetic capability to catalyze some of the required reactions to confer 6-aminocaproic acid, caprolactam, hexamethylenediamine or levulinic acid biosynthetic capability. For example, a non-naturally occurring microbial organism having a 6-aminocaproic acid, caprolactam, hexamethylenediamine or levulinic acid biosynthetic pathway can comprise at least two exogenous nucleic acids encoding desired enzymes. In the case of adipate production, at least two exogenous nucleic acids can encode the enzymes such as the combination of succinyl-CoA:acetyl-CoA acyl transferase and 3-hydroxyacyl-CoA dehydrogenase, or succinyl-CoA:acetyl-CoA acyl transferase and 3-hydroxyadipyl-CoA dehydratase, or 3-hydroxyadipyl-CoA and 5-carboxy-2-pentenoyl-CoA reductase, or 3-hydroxyacyl-CoA and adipyl-CoA synthetase, and the like. In the case of caprolactam production, at least two exogenous nucleic acids can encode the enzymes such as the combination of CoA-dependent aldehyde dehydrogenase and transaminase, or CoA-dependent aldehyde dehydrogenase and amidohydrolase, or transaminase and amidohydrolase. In the case of 6-aminocaproic acid production, at least two exogenous nucleic acids can encode the enzymes such as the combination of an 4-hydroxy-2-oxoheptane-1,7-dioate (HODH) aldolase and a 2-oxohept-4-ene-1,7-dioate (OHED) hydratase, or a 2-oxohept-4-ene-1,7-dioate (OHED) hydratase and a 2-aminoheptane-1,7-dioate (2-AHD) decarboxylase, a 3-hydroxyadipyl-CoA dehydratase and a adipyl-CoA dehydrogenase, a glutamyl-CoA transferase and a 6-aminopimeloyl-CoA hydrolase, or a glutaryl-CoA beta-ketothiolase and a 3-aminopimelate 2,3-aminomutase. In the case of hexamethylenediamine production, at least two exogenous nucleic acids can encode the enzymes such as the combination of 6-aminocaproate kinase and [(6-aminohexanoyl)oxy]phosphonate (6-AHOP) oxidoreductase, or a 6-acetamidohexanoate kinase and an [(6-acetamidohexanoyl)oxy]phosphonate (6-AAHOP) oxidoreductase, 6-aminocaproate N-acetyltransferase and 6-acetamidohexanoyl-CoA oxidoreductase, a 3-hydroxy-6-aminopimeloyl-CoA dehydratase and a 2-amino-7-oxoheptanoate aminotransferase, or a 3-oxopimeloyl-CoA ligase and a homolysine decarboxylase. Thus, it is understood that any combination of two or more enzymes of a biosynthetic pathway can be included in a non-naturally occurring microbial organism of the invention.

Similarly, it is understood that any combination of three or more enzymes of a biosynthetic pathway can be included in a non-naturally occurring microbial organism of the invention, for example, in the case of adipate production, the combination of enzymes succinyl-CoA:acetyl-CoA acyl transferase, 3-hydroxyacyl-CoA dehydrogenase, and 3-hydroxyadipyl-CoA dehydratase; or succinyl-CoA:acetyl-CoA acyl transferase, 3-hydroxyacyl-CoA dehydrogenase and 5-carboxy-2-pentenoyl-CoA reductase; or succinyl-CoA:acetyl-CoA acyl transferase, 3-hydroxyacyl-CoA dehydrogenase and adipyl-CoA synthetase; or 3-hydroxyacyl-CoA dehydrogenase, 3-hydroxyadipyl-CoA dehydratase and adipyl-CoA:acetyl-CoA transferase, and so forth, as desired, so long as the combination of enzymes of the desired biosynthetic pathway results in production of the corresponding desired product. In the case of 6-aminocaproic acid production, the at least three exogenous nucleic acids can encode the enzymes such as the combination of an 4-hydroxy-2-oxoheptane-1,7-dioate (HODH) aldolase, a 2-oxohept-4-ene-1,7-dioate (OHED) hydratase and a 2-oxoheptane-1,7-dioate (2-OHD) decarboxylase, or a 2-oxohept-4-ene-1,7-dioate (OHED) hydratase, a 2-aminohept-4-ene-1,7-dioate (2-AHE) reductase and a 2-aminoheptane-1,7-dioate (2-AHD) decarboxylase, or a 3-hydroxyadipyl-CoA dehydratase, 2,3-dehydroadipyl-CoA reductase and a adipyl-CoA dehydrogenase, or a 6-amino-7-carboxyhept-2-enoyl-CoA reductase, a 6-aminopimeloyl-CoA hydrolase and a 2-aminopimelate decarboxylase, or a glutaryl-CoA beta-ketothiolase, a 3-aminating oxidoreductase and a 2-aminopimelate decarboxylase, or a 3-oxoadipyl-CoA thiolase, a 5-carboxy-2-pentenoate reductase and a adipate reductase. In the case of hexamethylenediamine production, at least three exogenous nucleic acids can encode the enzymes such as the combination of 6-aminocaproate kinase, [(6-aminohexanoyl)oxy]phosphonate (6-AHOP) oxidoreductase and 6-aminocaproic semialdehyde aminotransferase, or a 6-aminocaproate N-acetyltransferase, a 6-acetamidohexanoate kinase and an [(6-acetamidohexanoyl)oxy]phosphonate (6-AAHOP) oxidoreductase, or 6-aminocaproate N-acetyltransferase, a [(6-acetamidohexanoyl)oxy]phosphonate (6-AAHOP) acyltransferase and 6-acetamidohexanoyl-CoA oxidoreductase, or a 3-oxo-6-aminopimeloyl-CoA oxidoreductase, a 3-hydroxy-6-aminopimeloyl-CoA dehydratase and a homolysine decarboxylase, or a 2-oxo-4-hydroxy-7-aminoheptanoate aldolase, a 2-oxo-7-aminohept-3-enoate reductase and a homolysine decarboxylase, or a 6-acetamidohexanoate reductase, a 6-acetamidohexanal aminotransferase and a 6-acetamidohexanamine N-acetyltransferase. Similarly, any combination of four or more enzymes of a biosynthetic pathway as disclosed herein can be included in a non-naturally occurring microbial organism of the invention, as desired, so long as the combination of enzymes of the desired biosynthetic pathway results in production of the corresponding desired product.

In addition to the biosynthesis of 6-aminocaproic acid, caprolactam, hexamethylenediamine or levulinic acid as described herein, the non-naturally occurring microbial organisms and methods of the invention also can be utilized in various combinations with each other and with other microbial organisms and methods well known in the art to achieve product biosynthesis by other routes. For example, one alternative to produce 6-aminocaproic acid, caprolactam, hexamethylenediamine or levulinic acid other than use of the 6-aminocaproic acid, caprolactam, hexamethylenediamine or levulinic acid producers is through addition of another microbial organism capable of converting an adipate, 6-aminocaproic acid or caprolactam pathway intermediate to 6-aminocaproic acid, caprolactam, hexamethylenediamine or levulinic acid. One such procedure includes, for example, the fermentation of a microbial organism that produces a 6-aminocaproic acid, caprolactam, hexamethylenediamine or levulinic acid pathway intermediate. The 6-aminocaproic acid, caprolactam, hexamethylenediamine or levulinic acid pathway intermediate can then be used as a substrate for a second microbial organism that converts the 6-aminocaproic acid, caprolactam, hexamethylenediamine or levulinic acid pathway intermediate to 6-aminocaproic acid, caprolactam, hexamethylenediamine or levulinic acid. The 6-aminocaproic acid, caprolactam, hexamethylenediamine or levulinic acid pathway intermediate can be added directly to another culture of the second organism or the original culture of 6-aminocaproic acid, caprolactam, hexamethylenediamine or levulinic acid pathway intermediate producers can be depleted of these microbial organisms by, for example, cell separation, and then subsequent addition of the second organism to the fermentation broth can be utilized to produce the final product without intermediate purification steps.

In other embodiments, the non-naturally occurring microbial organisms and methods of the invention can be assembled in a wide variety of subpathways to achieve biosynthesis of, for example, 6-aminocaproic acid, caprolactam, hexamethylenediamine or levulinic acid. In these embodiments, biosynthetic pathways for a desired product of the invention can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of 6-aminocaproic acid, caprolactam, hexamethylenediamine or levulinic acid can be accomplished by constructing a microbial organism that contains biosynthetic pathways for conversion of one pathway intermediate to another pathway intermediate or the product. Alternatively, 6-aminocaproic acid, caprolactam, hexamethylenediamine or levulinic acid also can be biosynthetically produced from microbial organisms through co-culture or co-fermentation using two organisms in the same vessel, where the first microbial organism produces a 6-aminocaproic acid, caprolactam, hexamethylenediamine or levulinic acid intermediate and the second microbial organism converts the intermediate to 6-aminocaproic acid, caprolactam, hexamethylenediamine or levulinic acid.

Given the teachings and guidance provided herein, those skilled in the art will understand that a wide variety of combinations and permutations exist for the non-naturally occurring microbial organisms and methods of the invention together with other microbial organisms, with the co-culture of other non-naturally occurring microbial organisms having subpathways and with combinations of other chemical and/or biochemical procedures well known in the art to produce 6-aminocaproic acid, caprolactam, hexamethylenediamine or levulinic acid.

Similarly, it is understood by those skilled in the art that a host organism can be selected based on desired characteristics for introduction of one or more gene disruptions to increase production of 6-aminocaproic acid, caprolactam, hexamethylenediamine or levulinic acid. Thus, it is understood that, if a genetic modification is to be introduced into a host organism to disrupt a gene, any homologs, orthologs or paralogs that catalyze similar, yet non-identical metabolic reactions can similarly be disrupted to ensure that a desired metabolic reaction is sufficiently disrupted. Because certain differences exist among metabolic networks between different organisms, those skilled in the art will understand that the actual genes disrupted in a given organism may differ between organisms. However, given the teachings and guidance provided herein, those skilled in the art also will understand that the methods of the invention can be applied to any suitable host microorganism to identify the cognate metabolic alterations needed to construct an organism in a species of interest that will increase 6-aminocaproic acid, caprolactam, hexamethylenediamine or levulinic acid biosynthesis. In a particular embodiment, the increased production couples biosynthesis of 6-aminocaproic acid, caprolactam, hexamethylenediamine or levulinic acid to growth of the organism, and can obligatorily couple production of 6-aminocaproic acid, caprolactam, hexamethylenediamine or levulinic acid to growth of the organism if desired and as disclosed herein.

Sources of encoding nucleic acids for a 6-aminocaproic acid, caprolactam, hexamethylenediamine or levulinic acid pathway enzyme can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli*, *Escherichia coli* str. K12, *Escherichia coli* C, *Escherichia coli* W, *Pseudomonas* sp, *Pseudomonas knackmussii*, *Pseudomonas* sp. Strain B13, *Pseudomonas putida*, *Pseudomonas fluorescens*, *Pseudomonas stutzeri*, *Pseudomonas mendocina*, *Rhodopseudomonas palustris*, *Mycobacterium tuberculosis*, *Vibrio cholera*, *Heliobacter pylori*, *Klebsiella pneumoniae*, *Serratia proteamaculans*, *Streptomyces* sp. 2065, *Pseudomonas aeruginosa*, *Pseudomonas aeruginosa* PA01, *Ralstonia eutropha*, *Ralstonia eutropha* H16, *Clostridium acetobutylicum*, *Euglena gracilis*, *Treponema denticola*, *Clostridium kluyveri*, *Homo sapiens*, *Rattus norvegicus*, *Acinetobacter* sp. ADP1, *Acinetobacter* sp. Strain M-1, *Streptomyces coelicolor*, *Eubacterium barkeri*, *Peptostreptococcus asaccharolyticus*, *Clostridium botulinum*, *Clostridium botulinum* A3 str, *Clostridium tyrobutyricum*, *Clostridium pasteurianum*, *Clostridium thermoaceticum* (*Moorella thermoaceticum*), *Moorella thermoacetica* *Acinetobacter calcoaceticus*, *Mus musculus*, *Sus scrofa*, *Flavobacterium* sp, *Arthrobacter aurescens*, *Penicillium chrysogenum*, *Aspergillus niger*, *Aspergillus nidulans*, *Bacillus subtilis*, *Saccharomyces cerevisiae*, *Zymomonas mobilis*, *Mannheimia succiniciproducens*, *Clostridium ljungdahlii*, *Clostridium carboxydivorans*, *Geobacillus stearothermophilus*, *Agrobacterium tumefaciens*, *Achromobacter denitrificans*, *Arabidopsis thaliana*, *Haemophilus influenzae*, *Acidaminococcus fermentans*, *Clostridium* sp. M62/1, *Fusobacterium nucleatum*, *Bos taurus*, *Zoogloea ramigera*, *Rhodobacter sphaeroides*, *Clostridium beijerinckii*, *Metallosphaera sedula*, *Thermoanaerobacter species*, *Thermoanaerobacter brockii*, *Acinetobacter baylyi*, *Porphyromonas gingivalis*, *Leuconostoc mesenteroides*, *Sulfolobus tokodaii*, *Sulfolobus tokodaii* 7, *Sulfolobus solfataricus*, *Sulfolobus solfataricus*, *Sulfolobus acidocaldarius*, *Salmonella typhimurium*, *Salmonella enterica*, *Thermotoga maritima*, *Halobacterium salinarum*, *Bacillus cereus*, *Clostridium difficile*, *Alkaliphilus metalliredigenes*, *Thermoanaerobacter tengcongensis*, *Saccharomyces kluyveri*, *Helicobacter pylori*, *Corynebacterium glutamicum*, *Clostridium saccharoperbutylacetonicum*, *Pseudomonas chlororaphis*, *Streptomyces clavuligerus*, *Campylobacter jejuni*, *Thermus thermophilus*, *Pelotomaculum thermopropionicum*, *Bacteroides capillosus*, *Anaerotruncus colihominis*, *Natranaerobius thermophilius*, *Archaeoglobus fulgidus*, *Archaeoglobus fulgidus* DSM 4304, *Haloarcula marismortui*, *Pyrobaculum aerophilum*, *Pyrobaculum aerophilum* str. IM2, *Nicotiana tabacum*, *Menthe piperita*, *Pinus taeda*, *Hordeum vulgare*, *Zea mays*, *Rhodococcus opacus*, *Cupriavidus necator*, *Bradyrhizobium japonicum*, *Bradyrhizobium japonicum* USDA 110, *Ascarius suum*, butyrate-producing bacterium L2-50, *Bacillus megaterium*, *Methanococcus maripaludis*, *Methanosarcina mazei*, *Methanosarcina mazei*, *Methanocarcina barkeri*, *Methanocaldococcus jannaschii*, *Caenorhabditis elegans*, *Leishmania major*, *Methylomicrobium alcaliphilum* 20Z, *Chromohalobacter salexigens*, *Archaeglubus fulgidus*, *Chlamydomonas reinhardtii*, *Trichomonas vaginalis* G3, *Trypanosoma brucei*, *Mycoplana ramose*, *Micrococcus luteas*, *Acetobacter pasteurians*, *Kluyveromyces lactis*, *Mesorhizobium loti*, *Lactococcus lactis*, *Lysinibacillus sphaericus*, *Candida boidinii*, *Candida albicans* SC5314, *Burkholderia ambifaria* AMMD, *Ascaris suum*, *Acinetobacter baumanii*, *Acinetobacter calcoaceticus*, *Burkholderia phymatum*, *Candida albicans*, *Clostridium subterminale*, *Cupriavidus taiwanensis*, *Flavobacterium lutescens*, *Lachancea kluyveri*, *Lactobacillus* sp. 30a, *Leptospira interrogans*, *Moorella thermoacetica*, *Myxococcus xanthus*, *Nicotiana glutinosa*, *Nocardia iowensis* (sp. NRRL 5646), *Pseudomonas reinekei* MT1, *Ralstonia eutropha* JMP 134, *Ralstonia metallidurans*, *Rhodococcus jostii*, *Schizosaccharomyces pombe*, *Selenomonas ruminantium*, *Streptomyces clavuligenus*, *Syntrophus aciditrophicus*, *Vibrio parahaemolyticus*, *Vibrio vulnificus*, as well as other exemplary species disclosed herein or available as source organisms for corresponding genes (see Examples). However, with the complete genome sequence available for now more than 550 species (with more than half of these available on public databases such as the NCBI), including 395 microorganism genomes and a variety of yeast, fungi, plant, and mammalian genomes, the identification of genes encoding the requisite 6-aminocaproic acid, caprolactam, hexamethylenediamine or levulinic acid biosynthetic activity for one or more genes in related or distant species, including for example, homologues, orthologs, paralogs and nonorthologous gene displacements of known genes, and the interchange of genetic alterations between organisms is routine and well known in the art. Accordingly, the metabolic alterations enabling biosynthesis of 6-aminocaproic acid, caprolactam, hexamethylenediamine or levulinic acid described herein with reference to a particular organism such as *E. coli* can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when a 6-aminocaproic acid, caprolactam, hexamethylenediamine or levulinic acid biosynthetic pathway exists in an unrelated species, 6-aminocaproic acid, caprolactam, hexamethylenediamine or levulinic acid biosynthesis can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods of the invention can be applied to all microbial organisms using the cognate metabolic alterations to those exemplified herein to construct a microbial organism in a species of interest that will synthesize 6-aminocaproic acid, caprolactam, hexamethylenediamine or levulinic acid.

Host microbial organisms can be selected from, and the non-naturally occurring microbial organisms generated in, for example, bacteria, yeast, fungus or any of a variety of other microorganisms applicable to fermentation processes. Exemplary bacteria include species selected from *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, and *Pseudomonas putida*. Exemplary yeasts or fungi include species selected from *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae*, and the like. For example, *E. coli* is a particularly useful host organisms since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

Methods for constructing and testing the expression levels of a non-naturally occurring 6-aminocaproic acid, caprolactam, hexamethylenediamine or levulinic acid-producing host can be performed, for example, by recombinant and detection methods well known in the art. Such methods can be found described in, for example, Sambrook et al., Molecular Cloning: A Laboratory Manual, Third Ed., Cold Spring Harbor Laboratory, New York (2001); and Ausubel et al., Current Protocols in Molecular Biology, John Wiley and Sons, Baltimore, Md. (1999).

Exogenous nucleic acid sequences involved in a pathway for production of 6-aminocaproic acid, caprolactam, hexamethylenediamine or levulinic acid can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more 6-aminocaproic acid, caprolactam, hexamethylenediamine or levulinic acid biosynthetic pathway encoding nucleic acids as exemplified herein operably linked to expression control sequences functional in the host organism. Expression vectors applicable for use in the microbial host organisms of the invention include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Directed evolution is one approach that involves the introduction of mutations targeted to a specific gene in order to improve and/or alter the properties of an enzyme. Improved and/or altered enzymes can be identified through implementation screening assays that allow for the identification of useful variants. Particularly useful screening methods include sensitive high-throughput assays that allow the automated screening of many enzyme variants (e.g., $>10^4$). Iterative rounds of mutagenesis and screening typically are performed to identify an enzyme with optimized properties. The greater the number of variants screened, the higher the probability of identifying an ideally suitable variant. Computational algorithms that can help to identify areas of the gene for mutagenesis also have been developed and can significantly reduce the number of enzyme variants that need to be generated and screened.

Numerous directed evolution technologies have been developed (for reviews, see Hibbert et al., *Biomol. Eng*

22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng* 22:1-9 (2005); and Sen et al., *Appl Biochem. Biotechnol* 143:212-223 (2007)) to be effective at creating diverse variant libraries and these methods have been successfully applied to the improvement of a wide range of properties across many enzyme classes.

Enzyme characteristics that have been improved and/or altered by directed evolution technologies include, for example, selectivity/specificity—for conversion of non-natural substrates; temperature stability—for robust high temperature processing; pH stability—for bioprocessing under lower or higher pH conditions; substrate or product tolerance—so that high product titers can be achieved; binding ($K_m$)—broadens substrate binding to include non-natural substrates; inhibition ($K_i$)—to remove inhibition by products, substrates, or key intermediates; activity (kcat)—increases enzymatic reaction rates to achieve desired flux; expression levels—increases protein yields and overall pathway flux; oxygen stability—for operation of air sensitive enzymes under aerobic conditions; and anaerobic activity—for operation of an aerobic enzyme in the absence of oxygen.

The following exemplary methods have been developed for the mutagenesis and diversification of genes to target desired properties of specific enzymes. Any of these can be used to alter/optimize activity of a decarboxylase enzyme.

EpPCR (Pritchard et al., *J Theor. Biol* 234:497-509 (2005)) introduces random point mutations by reducing the fidelity of DNA polymerase in PCR reactions by the addition of $Mn^{2+}$ ions, by biasing dNTP concentrations, or by other conditional variations. The five step cloning process to confine the mutagenesis to the target gene of interest involves: 1) error-prone PCR amplification of the gene of interest; 2) restriction enzyme digestion; 3) gel purification of the desired DNA fragment; 4) ligation into a vector; 5) transformation of the gene variants into a suitable host and screening of the library for improved performance. This method can generate multiple mutations in a single gene simultaneously, which can be useful. A high number of mutants can be generated by EpPCR, so a high-throughput screening assay or a selection method (especially using robotics) is useful to identify those with desirable characteristics.

Error-prone Rolling Circle Amplification (epRCA) (Fujii et al., *Nucleic Acids Res* 32:e145 (2004); and Fujii et al., *Nat. Protoc.* 1:2493-2497 (2006)) has many of the same elements as epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats. Adjusting the $Mn^{2+}$ concentration can vary the mutation rate somewhat. This technique uses a simple error-prone, single-step method to create a full copy of the plasmid with 3-4 mutations/kbp. No restriction enzyme digestion or specific primers are required. Additionally, this method is typically available as a kit.

DNA or Family Shuffling (Stemmer, *Proc Natl Acad Sci U.S.A.* 91:10747-10751 (1994); and Stemmer, *Nature* 370: 389-391 (1994)) typically involves digestion of two or more variant genes with nucleases such as Dnase I or EndoV to generate a pool of random fragments that are reassembled by cycles of annealing and extension in the presence of DNA polymerase to create a library of chimeric genes. Fragments prime each other and recombination occurs when one copy primes another copy (template switch). This method can be used with >1 kbp DNA sequences. In addition to mutational recombinants created by fragment reassembly, this method introduces point mutations in the extension steps at a rate similar to error-prone PCR. The method can be used to remove deleterious, random and neutral mutations that might confer antigenicity.

Staggered Extension (StEP) (Zhao et al., *Nat. Biotechnol* 16:258-261 (1998)) entails template priming followed by repeated cycles of 2 step PCR with denaturation and very short duration of annealing/extension (as short as 5 sec). Growing fragments anneal to different templates and extend further, which is repeated until full-length sequences are made. Template switching means most resulting fragments have multiple parents. Combinations of low-fidelity polymerases (Taq and Mutazyme) reduce error-prone biases because of opposite mutational spectra.

In Random Priming Recombination (RPR) random sequence primers are used to generate many short DNA fragments complementary to different segments of the template. (Shao et al., *Nucleic Acids Res* 26:681-683 (1998)) Base misincorporation and mispriming via epPCR give point mutations. Short DNA fragments prime one another based on homology and are recombined and reassembled into full-length by repeated thermocycling. Removal of templates prior to this step assures low parental recombinants. This method, like most others, can be performed over multiple iterations to evolve distinct properties. This technology avoids sequence bias, is independent of gene length, and requires very little parent DNA for the application.

In Heteroduplex Recombination linearized plasmid DNA is used to form heteroduplexes that are repaired by mismatch repair. (Volkov et al, *Nucleic Acids Res* 27:e18 (1999); and Volkov et al., *Methods Enzymol.* 328:456-463 (2000)) The mismatch repair step is at least somewhat mutagenic. Heteroduplexes transform more efficiently than linear homoduplexes. This method is suitable for large genes and whole operons.

Random Chimeragenesis on Transient Templates (RACHITT) (Coco et al., *Nat. Biotechnol* 19:354-359 (2001)) employs Dnase I fragmentation and size fractionation of ssDNA. Homologous fragments are hybridized in the absence of polymerase to a complementary ssDNA scaffold. Any overlapping unhybridized fragment ends are trimmed down by an exonuclease. Gaps between fragments are filled in, and then ligated to give a pool of full-length diverse strands hybridized to the scaffold (that contains U to preclude amplification). The scaffold then is destroyed and is replaced by a new strand complementary to the diverse strand by PCR amplification. The method involves one strand (scaffold) that is from only one parent while the priming fragments derive from other genes; the parent scaffold is selected against. Thus, no reannealing with parental fragments occurs. Overlapping fragments are trimmed with an exonuclease. Otherwise, this is conceptually similar to DNA shuffling and StEP. Therefore, there should be no siblings, few inactives, and no unshuffled parentals. This technique has advantages in that few or no parental genes are created and many more crossovers can result relative to standard DNA shuffling.

Recombined Extension on Truncated templates (RETT) entails template switching of unidirectionally growing strands from primers in the presence of unidirectional ssDNA fragments used as a pool of templates. (Lee et al., *J. Molec. Catalysis* 26:119-129 (2003)) No DNA endonucleases are used. Unidirectional ssDNA is made by DNA polymerase with random primers or serial deletion with exonuclease. Unidirectional ssDNA are only templates and not primers. Random priming and exonucleases don't introduce sequence bias as true of enzymatic cleavage of DNA shuffling/RACHITT. RETT can be easier to optimize than StEP because it uses normal PCR conditions instead of very short extensions. Recombination occurs as a component of the PCR steps—no direct shuffling. This method can also be more random than StEP due to the absence of pauses.

In Degenerate Oligonucleotide Gene Shuffling (DOGS) degenerate primers are used to control recombination between molecules; (Bergquist and Gibbs, *Methods Mol. Biol* 352:191-204 (2007); Bergquist et al., *Biomol. Eng* 22:63-72 (2005); Gibbs et al., *Gene* 271:13-20 (2001)) this can be used to control the tendency of other methods such as DNA shuffling to regenerate parental genes. This method can be combined with random mutagenesis (epPCR) of selected gene segments. This can be a good method to block the reformation of parental sequences. No endonucleases are needed. By adjusting input concentrations of segments made, one can bias towards a desired backbone. This method allows DNA shuffling from unrelated parents without restriction enzyme digests and allows a choice of random mutagenesis methods.

Incremental Truncation for the Creation of Hybrid Enzymes (ITCHY) creates a combinatorial library with 1 base pair deletions of a gene or gene fragment of interest. (Ostermeier et al., *Proc Natl Acad Sci U.S.A.* 96:3562-3567 (1999); and Ostermeier et al., *Nat. Biotechnol* 17:1205-1209 (1999)) Truncations are introduced in opposite direction on pieces of 2 different genes. These are ligated together and the fusions are cloned. This technique does not require homology between the 2 parental genes. When ITCHY is combined with DNA shuffling, the system is called SCRATCHY (see below). A major advantage of both is no need for homology between parental genes; for example, functional fusions between an *E. coli* and a human gene were created via ITCHY. When ITCHY libraries are made, all possible crossovers are captured.

Thio-Incremental Truncation for the Creation of Hybrid Enzymes (THIO-ITCHY) is similar to ITCHY except that phosphothioate dNTPs are used to generate truncations. (Lutz et al., *Nucleic Acids Res* 29:E16 (2001)) Relative to ITCHY, THIO-ITCHY can be easier to optimize, provide more reproducibility, and adjustability.

SCRATCHY combines two methods for recombining genes, ITCHY and DNA shuffling. (Lutz et al., *Proc Natl Acad Sci U.S.A.* 98:11248-11253 (2001)) SCRATCHY combines the best features of ITCHY and DNA shuffling. First, ITCHY is used to create a comprehensive set of fusions between fragments of genes in a DNA homology-independent fashion. This artificial family is then subjected to a DNA-shuffling step to augment the number of crossovers. Computational predictions can be used in optimization. SCRATCHY is more effective than DNA shuffling when sequence identity is below 80%.

In Random Drift Mutagenesis (RNDM) mutations made via epPCR followed by screening/selection for those retaining usable activity. (Bergquist et al., *Biomol. Eng* 22:63-72 (2005)) Then, these are used in DOGS to generate recombinants with fusions between multiple active mutants or between active mutants and some other desirable parent. Designed to promote isolation of neutral mutations; its purpose is to screen for retained catalytic activity whether or not this activity is higher or lower than in the original gene. RNDM is usable in high throughput assays when screening is capable of detecting activity above background. RNDM has been used as a front end to DOGS in generating diversity. The technique imposes a requirement for activity prior to shuffling or other subsequent steps; neutral drift libraries are indicated to result in higher/quicker improvements in activity from smaller libraries. Though published using epPCR, this could be applied to other large-scale mutagenesis methods.

Sequence Saturation Mutagenesis (SeSaM) is a random mutagenesis method that: 1) generates pool of random length fragments using random incorporation of a phosphothioate nucleotide and cleavage; this pool is used as a template to 2) extend in the presence of "universal" bases such as inosine; 3) replication of a inosine-containing complement gives random base incorporation and, consequently, mutagenesis. (Wong et al., *Biotechnol J* 3:74-82 (2008); Wong et al., *Nucleic Acids Res* 32:e26 (2004); and Wong et al., *Anal. Biochem.* 341:187-189 (2005)) Using this technique it can be possible to generate a large library of mutants within 2-3 days using simple methods. This technique is non-directed in comparison to the mutational bias of DNA polymerases. Differences in this approach makes this technique complementary (or an alternative) to epPCR.

In Synthetic Shuffling, overlapping oligonucleotides are designed to encode "all genetic diversity in targets" and allow a very high diversity for the shuffled progeny. (Ness et al., *Nat. Biotechnol* 20:1251-1255 (2002)) In this technique, one can design the fragments to be shuffled. This aids in increasing the resulting diversity of the progeny. One can design sequence/codon biases to make more distantly related sequences recombine at rates approaching those observed with more closely related sequences. Additionally, the technique does not require physically possessing the template genes.

Nucleotide Exchange and Excision Technology NexT exploits a combination of dUTP incorporation followed by treatment with uracil DNA glycosylase and then piperidine to perform endpoint DNA fragmentation. (Muller et al., *Nucleic Acids Res* 33:e117 (2005)) The gene is reassembled using internal PCR primer extension with proofreading polymerase. The sizes for shuffling are directly controllable using varying dUPT::dTTP ratios. This is an end point reaction using simple methods for uracil incorporation and cleavage. Other nucleotide analogs, such as 8-oxo-guanine, can be used with this method. Additionally, the technique works well with very short fragments (86 bp) and has a low error rate. The chemical cleavage of DNA used in this technique results in very few unshuffled clones.

In Sequence Homology-Independent Protein Recombination (SHIPREC) a linker is used to facilitate fusion between two distantly/unrelated genes. Nuclease treatment is used to generate a range of chimeras between the two genes. These fusions result in libraries of single-crossover hybrids. (Sieber et al., *Nat. Biotechnol* 19:456-460 (2001)) This produces a limited type of shuffling and a separate process is required for mutagenesis. In addition, since no homology is needed this technique can create a library of chimeras with varying fractions of each of the two unrelated parent genes. SHIPREC was tested with a heme-binding domain of a bacterial CP450 fused to N-terminal regions of a mammalian CP450; this produced mammalian activity in a more soluble enzyme.

In Gene Site Saturation Mutagenesis™ (GSSM™) the starting materials are a supercoiled dsDNA plasmid containing an insert and two primers which are degenerate at the desired site of mutations. (Kretz et al., *Methods Enzymol.* 388:3-11 (2004)) Primers carrying the mutation of interest, anneal to the same sequence on opposite strands of DNA. The mutation is typically in the middle of the primer and flanked on each side by ~20 nucleotides of correct sequence.

The sequence in the primer is NNN or NNK (coding) and MNN (noncoding) (N=all 4, K=G, T, M=A, C). After extension, DpnI is used to digest dam-methylated DNA to eliminate the wild-type template. This technique explores all possible amino acid substitutions at a given locus (i.e., one codon). The technique facilitates the generation of all possible replacements at a single-site with no nonsense codons and results in equal to near-equal representation of most possible alleles. This technique does not require prior knowledge of the structure, mechanism, or domains of the target enzyme. If followed by shuffling or Gene Reassembly, this technology creates a diverse library of recombinants containing all possible combinations of single-site up-mutations. The utility of this technology combination has been demonstrated for the successful evolution of over 50 different enzymes, and also for more than one property in a given enzyme.

Combinatorial Cassette Mutagenesis (CCM) involves the use of short oligonucleotide cassettes to replace limited regions with a large number of possible amino acid sequence alterations. (Reidhaar-Olson et al. *Methods Enzymol.* 208: 564-586 (1991); and Reidhaar-Olson et al. *Science* 241:53-57 (1988)) Simultaneous substitutions at two or three sites are possible using this technique. Additionally, the method tests a large multiplicity of possible sequence changes at a limited range of sites. This technique has been used to explore the information content of the lambda repressor DNA-binding domain.

Combinatorial Multiple Cassette Mutagenesis (CMCM) is essentially similar to CCM except it is employed as part of a larger program: 1) Use of epPCR at high mutation rate to 2) ID hot spots and hot regions and then 3) extension by CMCM to cover a defined region of protein sequence space. (Reetz, M. T., S. Wilensek, D. Zha, and K. E. Jaeger, 2001, Directed Evolution of an Enantioselective Enzyme through Combinatorial Multiple-Cassette Mutagenesis. *Angew. Chem. Int. Ed Engl.* 40:3589-3591.) As with CCM, this method can test virtually all possible alterations over a target region. If used along with methods to create random mutations and shuffled genes, it provides an excellent means of generating diverse, shuffled proteins. This approach was successful in increasing, by 51-fold, the enantioselectivity of an enzyme.

In the Mutator Strains technique conditional ts mutator plasmids allow increases of 20- to 4000-X in random and natural mutation frequency during selection and block accumulation of deleterious mutations when selection is not required. (Selifonova et al., *Appl Environ Microbiol* 67:3645-3649 (2001)) This technology is based on a plasmid-derived mutD5 gene, which encodes a mutant subunit of DNA polymerase III. This subunit binds to endogenous DNA polymerase III and compromises the proofreading ability of polymerase III in any strain that harbors the plasmid. A broad-spectrum of base substitutions and frame-shift mutations occur. In order for effective use, the mutator plasmid should be removed once the desired phenotype is achieved; this is accomplished through a temperature sensitive origin of replication, which allows for plasmid curing at 41° C. It should be noted that mutator strains have been explored for quite some time (e.g., see Low et al., *J. Mol. Biol.* 260:359-3680 (1996)). In this technique very high spontaneous mutation rates are observed. The conditional property minimizes non-desired background mutations. This technology could be combined with adaptive evolution to enhance mutagenesis rates and more rapidly achieve desired phenotypes.

"Look-Through Mutagenesis (LTM) is a multidimensional mutagenesis method that assesses and optimizes combinatorial mutations of selected amino acids." (Rajpal et al., *Proc Natl Acad Sci U.S.A.* 102:8466-8471 (2005)) Rather than saturating each site with all possible amino acid changes, a set of nine is chosen to cover the range of amino acid R-group chemistry. Fewer changes per site allows multiple sites to be subjected to this type of mutagenesis. A >800-fold increase in binding affinity for an antibody from low nanomolar to picomolar has been achieved through this method. This method is a rational approach to minimize the number of random combinations and can increase the ability to find improved traits by greatly decreasing the numbers of clones to be screened. This has been applied to antibody engineering, specifically to increase the binding affinity and/or reduce dissociation. The technique can be combined with either screens or selections.

Gene Reassembly is a DNA shuffling method that can be applied to multiple genes at one time or to creating a large library of chimeras (multiple mutations) of a single gene (Tunable GeneReassembly™ (TGR™) Technology supplied by Verenium Corporation). Typically this technology is used in combination with ultra-high-throughput screening to query the represented sequence space for desired improvements. This technique allows multiple gene recombinations independent of homology. The exact number and position of cross-over events can be pre-determined using fragments designed via bioinformatic analysis. This technology leads to a very high level of diversity with virtually no parental gene reformation and a low level of inactive genes. Combined with GSSM™, a large range of mutations can be tested for improved activity. The method allows "blending" and "fine tuning" of DNA shuffling, e.g. codon usage can be optimized.

In Silico Protein Design Automation (PDA) is an optimization algorithm that anchors the structurally defined protein backbone possessing a particular fold, and searches sequence space for amino acid substitutions that can stabilize the fold and overall protein energetics. (Hayes et al., *Proc Natl Acad Sci U.S.A.* 99:15926-15931 (2002)) This technology uses in silico structure-based entropy predictions in order to search for structural tolerance toward protein amino acid variations. Statistical mechanics is applied to calculate coupling interactions at each position. Structural tolerance toward amino acid substitution is a measure of coupling. Ultimately, this technology is designed to yield desired modifications of protein properties while maintaining the integrity of structural characteristics. The method computationally assesses and allows filtering of a very large number of possible sequence variants ($10^{50}$). The choice of sequence variants to test is related to predictions based on the most favorable thermodynamics. Ostensibly only stability or properties that are linked to stability can be effectively addressed with this technology. The method has been successfully used in some therapeutic proteins, especially in engineering immunoglobulins. In silico predictions avoid testing extraordinarily large numbers of potential variants. Predictions based on existing three-dimensional structures are more likely to succeed than predictions based on hypothetical structures. This technology can readily predict and allow targeted screening of multiple simultaneous mutations, something not possible with purely experimental technologies due to exponential increases in numbers.

Iterative Saturation Mutagenesis (ISM) involves: 1) use knowledge of structure/function to choose a likely site for enzyme improvement; 2) saturation mutagenesis at chosen site using Stratagene QuikChange (or other suitable means);

3) screen/select for desired properties; and 4) with improved clone(s), start over at another site and continue repeating. (Reetz et al., *Nat. Protoc.* 2:891-903 (2007); and Reetz et al., *Angew. Chem. Int. Ed Engl.* 45:7745-7751 (2006)) This is a proven methodology, which assures all possible replacements at a given position are made for screening/selection.

Any of the aforementioned methods for mutagenesis can be used alone or in any combination. Additionally, any one or combination of the directed evolution methods can be used in conjunction with adaptive evolution techniques.

The invention additionally provides methods for producing a desired intermediate or product such as adipate, 6-aminocaproic acid, caprolactam, hexamethylenediamine or levulinic acid. For example, a method for producing adipate can involve culturing a non-naturally occurring microbial organism having an adipate pathway, the pathway including at least one exogenous nucleic acid encoding an adipate pathway enzyme expressed in a sufficient amount to produce adipate, under conditions and for a sufficient period of time to produce adipate, the adipate pathway including succinyl-CoA:acetyl-CoA acyl transferase, 3-hydroxyacyl-CoA dehydrogenase, 3-hydroxyadipyl-CoA dehydratase, 5-carboxy-2-pentenoyl-CoA reductase, and adipyl-CoA synthetase or phosphotransadipylase/adipate kinase or adipyl-CoA:acetyl-CoA transferase or adipyl-CoA hydrolase. Additionally, a method for producing adipate can involve culturing a non-naturally occurring microbial organism having an adipate pathway, the pathway including at least one exogenous nucleic acid encoding an adipate pathway enzyme expressed in a sufficient amount to produce adipate, under conditions and for a sufficient period of time to produce adipate, the adipate pathway including succinyl-CoA:acetyl-CoA acyl transferase, 3-oxoadipyl-CoA transferase, 3-oxoadipate reductase, 3-hydroxyadipate dehydratase, and 2-enoate reductase.

Further, a method for producing 6-aminocaproic acid can involve culturing a non-naturally occurring microbial organism having a 6-aminocaproic acid pathway, the pathway including at least one exogenous nucleic acid encoding a 6-aminocaproic acid pathway enzyme expressed in a sufficient amount to produce 6-aminocaproic acid, under conditions and for a sufficient period of time to produce 6-aminocaproic acid, the 6-aminocaproic acid pathway including CoA-dependent aldehyde dehydrogenase and transaminase or 6-aminocaproate dehydrogenase. Additionally, a method for producing caprolactam can involve culturing a non-naturally occurring microbial organism having a caprolactam pathway, the pathway including at least one exogenous nucleic acid encoding a caprolactam pathway enzyme expressed in a sufficient amount to produce caprolactam, under conditions and for a sufficient period of time to produce caprolactam, the caprolactam pathway including CoA-dependent aldehyde dehydrogenase, transaminase or 6-aminocaproate dehydrogenase, and amidohydrolase.

The invention additionally provides methods for producing 6-aminocaproic acid (6-ACA) by culturing a non-naturally occurring microbial organism having a 6-ACA pathway described herein under conditions and for a sufficient period of time to produce 6-ACA. In one aspect the 6-ACA pathway includes an HODH aldolase; an OHED hydratase; an OHED reductase; a 2-OHD decarboxylase; and an adipate semialdehyde aminotransferase or an adipate semialdehyde oxidoreductase (aminating). In another aspect, the 6-ACA pathway includes an HODH aldolase; an OHED hydratase; an OHED decarboxylase; a 6-OHE reductase; and an adipate semialdehyde aminotransferase or an adipate semialdehyde oxidoreductase (aminating). In yet another aspect, the 6-ACA pathway includes an HODH aldolase; an OHED hydratase; an OHED aminotransferase or an OHED oxidoreductase (aminating); a 2-AHE reductase; and a 2-AHD decarboxylase. In still yet another aspect, the 6-ACA pathway includes an HODH aldolase; an OHED hydratase; an OHED reductase; a 2-OHD aminotransferase or a 2-OHD oxidoreductase (aminating); and a 2-AHD decarboxylase. In still yet another aspect, the 6-ACA pathway includes an HODH aldolase; an HODH formate-lyase and a pyruvate formate-lyase activating enzyme or an HODH dehydrogenase; a 3-hydroxyadipyl-CoA dehydratase; a 2,3-dehydroadipyl-CoA reductase; an adipyl-CoA dehydrogenase; and an adipate semialdehyde aminotransferase or an adipate semialdehyde oxidoreductase (aminating). In still yet another aspect, the 6-ACA pathway includes an HODH aldolase; an OHED hydratase; an OHED formate-lyase and a pyruvate formate-lyase activating enzyme or OHED dehydrogenase; a 2,3-dehydroadipyl-CoA reductase; an adipyl-CoA dehydrogenase; and an adipate semialdehyde aminotransferase or an adipate semialdehyde oxidoreductase (aminating). In still yet another aspect, the 6-ACA pathway includes an HODH aldolase; an OHED hydratase; an OHED reductase; a 2-OHD formate-lyase and a pyruvate formate-lyase activating enzyme or a 2-OHD dehydrogenase; an adipyl-CoA dehydrogenase; and an adipate semialdehyde aminotransferase or an adipate semialdehyde oxidoreductase (aminating). In a further aspect, the 6-ACA pathways described above can include a succinic semialdehyde dehydrogenase, an alpha-ketoglutarate decarboxylase or a phosphoenolpyruvate (PEP) carboxykinase.

The invention additionally provides methods for producing hexamethylenediamine (HMDA) by culturing a non-naturally occurring microbial organism having a HMDA pathway described herein under conditions and for a sufficient period of time to produce HMDA. In one aspect the HMDA pathway includes a 6-aminocaproate kinase; a 6-AHOP oxidoreductase; and a 6-aminocaproic semialdehyde oxidoreductase (aminating) or a 6-aminocaproic acid semialdehyde aminotransferase. In another aspect, the HMDA pathway includes a 6-aminocaproate kinase; a 6-AHOP acyltransferase; a 6-aminocaproyl-CoA oxidoreductase; and a 6-aminocaproic semialdehyde oxidoreductase (aminating) or a 6-aminocaproic acid semialdehyde aminotransferase. In yet another aspect, the HMDA pathway includes a 6-aminocaproate CoA transferase or a 6-aminocaproate CoA ligase; a 6-aminocaproyl-CoA oxidoreductase; and a 6-aminocaproic semialdehyde oxidoreductase (aminating) or a 6-aminocaproic acid semialdehyde aminotransferase. In still yet another aspect, the HMDA pathway includes a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide). In still yet another aspect, the HMDA pathway includes a 6-aminocaproate N-acetyltransferase; a 6-acetamidohexanoate CoA transferase or a 6-acetamidohexanoate CoA ligase; a 6-acetamidohexanoyl-CoA oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide). In still yet another aspect, the HMDA pathway includes a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide).

Also, a method for producing adipate can involve culturing a non-naturally occurring microbial organism having an adipate pathway, the pathway including at least one exogenous nucleic acid encoding an adipate pathway enzyme expressed in a sufficient amount to produce adipate, under conditions and for a sufficient period of time to produce adipate, the adipate pathway including alpha-ketoadipyl-CoA synthetase, phosphotransketoadipylase/alpha-ketoadipate kinase or alpha-ketoadipyl-CoA:acetyl-CoA transferase; 2-hydroxyadipyl-CoA dehydrogenase; 2-hydroxyadipyl-CoA dehydratase; 5-carboxy-2-pentenoyl-CoA reductase; and adipyl-CoA synthetase, phosphotransadipylase/adipate kinase, adipyl-CoA:acetyl-CoA transferase or adipyl-CoA hydrolase. Furthermore, a method for producing adipate can involve culturing a non-naturally occurring microbial organism having an adipate pathway, the pathway including at least one exogenous nucleic acid encoding an adipate pathway enzyme expressed in a sufficient amount to produce adipate, under conditions and for a sufficient period of time to produce adipate, the adipate pathway including 2-hydroxyadipate dehydrogenase; 2-hydroxyadipyl-CoA synthetase, phosphotranshydroxyadipylase/2-hydroxyadipate kinase or 2-hydroxyadipyl-CoA: acetyl-CoA transferase; 2-hydroxyadipyl-CoA dehydratase; 5-carboxy-2-pentenoyl-CoA reductase; and adipyl-CoA synthetase, phosphotransadipylase/adipate kinase, adipyl-CoA: acetyl-CoA transferase or adipyl-CoA hydrolase.

As disclosed herein, the invention also provides method for producing 6-aminocaproic acid by culturing a non-naturally occurring microbial organism having a 6-aminocaproic acid pathway including at least one exogenous nucleic acid encoding a 6-aminocaproic acid pathway enzyme expressed in a sufficient amount to produce 6-aminocaproic acid, the 6-aminocaproic acid pathway including 3-oxo-6-aminohexanoyl-CoA thiolase; 3-oxo-6-aminohexanoyl-CoA reductase; 3-hydroxy-6-aminohexanoyl-CoA dehydratase; 6-aminohex-2-enoyl-CoA reductase; and 6-aminocaproyl-CoA/acyl-CoA transferase, 6-aminocaproyl-CoA synthase, or 6-aminocaproyl-CoA hydrolase (see Examples XII and XIII; steps A/B/C/D/K/L/M of FIG. 11). The invention additionally provides a method for producing 6-aminocaproic acid by culturing a non-naturally occurring microbial organism having a 6-aminocaproic acid pathway including at least one exogenous nucleic acid encoding a 6-aminocaproic acid pathway enzyme expressed in a sufficient amount to produce 6-aminocaproic acid, the 6-aminocaproic acid pathway including 3-oxo-6-aminohexanoyl-CoA thiolase; 3-oxo-6-aminohexanoyl-CoA/acyl-CoA transferase, 3-oxo-6-aminohexanoyl-CoA synthase, or 3-oxo-6-aminohexanoyl-CoA hydrolase; 3-oxo-6-aminohexanoate reductase; 3-hydroxy-6-aminohexanoate dehydratase; and 6-aminohex-2-enoate reductase (see Examples XII and XIV; steps A/E/F/G/H/I/J of FIG. 11).

In another embodiment, the invention provides a method for producing caprolactam by culturing a non-naturally occurring microbial organism having a caprolactam pathway including at least one exogenous nucleic acid encoding a caprolactam pathway enzyme expressed in a sufficient amount to produce caprolactam, the caprolactam pathway including 6-aminocaproyl-CoA/acyl-CoA transferase or 6-aminocaproyl-CoA synthase (see Examples XII and XV; steps K/L of FIG. 11). In such a method, the caprolactam can be produced by spontaneous cyclization of 6-aminocaproyl-CoA to caprolactam (see Example XII; step Q of FIG. 11). The invention also provides a non-naturally occurring microbial organism having a hexamethylenediamine pathway including at least one exogenous nucleic acid encoding a hexamethylenediamine pathway enzyme expressed in a sufficient amount to produce hexamethylenediamine, the hexamethylenediamine pathway including 6-aminocaproyl-CoA/acyl-CoA transferase or 6-aminocaproyl-CoA synthase; 6-aminocaproyl-CoA reductase (aldehyde forming); and hexamethylenediamine transaminase or hexamethylenediamine dehydrogenase (see Examples XII and XVI; steps K/L/N/O/P of FIG. 11).

In yet another embodiment, the invention provides a method for producing caprolactam by culturing a non-naturally occurring microbial organism having a caprolactam pathway including at least one exogenous nucleic acid encoding a caprolactam pathway enzyme expressed in a sufficient amount to produce caprolactam, the caprolactam pathway including 3-oxo-6-aminohexanoyl-CoA thiolase; 3-oxo-6-aminohexanoyl-CoA reductase; 3-hydroxy-6-aminohexanoyl-CoA dehydratase; and 6-aminohex-2-enoyl-CoA reductase (see Examples XII and XVII; steps A/B/C/D of FIG. 11). In such a method, the caprolactam can be produced by spontaneous cyclization of 6-aminocaproyl-CoA to caprolactam (see Example XII; step Q of FIG. 11). Also provided is a method for producing hexamethylenediamine by culturing a non-naturally occurring microbial organism having a hexamethylenediamine pathway including at least one exogenous nucleic acid encoding a hexamethylenediamine pathway enzyme expressed in a sufficient amount to produce hexamethylenediamine, the hexamethylenediamine pathway including 3-oxo-6-aminohexanoyl-CoA thiolase; 3-oxo-6-aminohexanoyl-CoA reductase; 3-hydroxy-6-aminohexanoyl-CoA dehydratase; 6-aminohex-2-enoyl-CoA reductase; 6-aminocaproyl-CoA reductase (aldehyde forming); and hexamethylenediamine transaminase or hexamethylenediamine dehydrogenase (see Examples XII and XVIII; steps A/B/C/D/N/O/P of FIG. 11).

In yet another embodiment, the invention provides a method for producing 6-aminocaproic acid (6-ACA) by culturing a non-naturally occurring microbial organism having a 6-ACA pathway, the microbial organism including at least one exogenous nucleic acid encoding a 6-ACA pathway enzyme expressed in a sufficient amount to produce 6-ACA, the 6-ACA pathway including a succinic semialdehyde dehydrogenase, an alpha-ketoglutarate decarboxylase, a phosphoenolpyruvate (PEP) carboxykinase, a 4-hydroxy-2-oxoheptane-1,7-dioate (HODH) aldolase, a 2-oxohept-4-ene-1,7-dioate (OHED) hydratase, a 2-oxohept-4-ene-1,7-dioate (OHED) reductase, a 2-oxoheptane-1,7-dioate (2-OHD) decarboxylase, an adipate semialdehyde aminotransferase, an adipate semialdehyde oxidoreductase (aminating), a 2-oxohept-4-ene-1,7-dioate (OHED) decarboxylase, a 6-oxohex-4-enoate (6-OHE) reductase, a 2-oxoheptane-1,7-dioate (2-OHD) aminotransferase, a 2-oxoheptane-1,7-dioate (2-OHD) oxidoreductase (aminating), a 2-aminoheptane-1,7-dioate (2-AHD) decarboxylase, a 2-oxohept-4-ene-1,7-dioate (OHED) aminotransferase, a 2-oxohept-4-ene-1,7-dioate (OHED) oxidoreductase (aminating), a 2-aminohept-4-ene-1,7-dioate (2-AHE) reductase, a 4-hydroxy-2-oxoheptane-1,7-dioate (HODH) formate-lyase, a 4-hydroxy-2-oxoheptane-1,7-dioate (HODH) dehydrogenase, a 3-hydroxyadipyl-CoA dehydratase, a 2,3-dehydroadipyl-CoA reductase, a adipyl-CoA dehydrogenase, a 2-oxohept-4-ene-1,7-dioate (OHED) formate-lyase, a 2-oxohept-4-ene-1,7-dioate (OHED) dehydrogenase, a 2-oxoheptane-1,7-dioate (2-OHD) formate-lyase, a 2-oxoheptane-1,7-dioate (2-OHD) dehydrogenase, or a pyruvate formate-lyase activating enzyme (see Examples XIX and XXI; steps A-Q of FIG. 12).

In yet another embodiment, the invention provides a method for producing 6-aminocaproic acid (6-ACA) by culturing a non-naturally occurring microbial organism having a 6-ACA pathway, the microbial organism including at least one exogenous nucleic acid encoding a 6-ACA pathway enzyme expressed in a sufficient amount to produce 6-ACA. In one aspect the 6-ACA pathway includes an HODH aldolase; an OHED hydratase; an OHED reductase; a 2-OHD decarboxylase; and an adipate semialdehyde aminotransferase or an adipate semialdehyde oxidoreductase (aminating) (see Examples XIX and XXI; steps A/B/C/D/E of FIG. 12). In another aspect of the invention, the 6-ACA pathway includes an HODH aldolase; an OHED hydratase; an OHED decarboxylase; a 6-OHE reductase; and an adipate semialdehyde aminotransferase or an adipate semialdehyde oxidoreductase (aminating) (see Examples XIX and XXI; steps A/B/F/G/E of FIG. 12). In another aspect of the invention, the 6-ACA pathway includes an HODH aldolase; an OHED hydratase; an OHED aminotransferase or an OHED oxidoreductase (aminating); a 2-AHE reductase; and a 2-AHD decarboxylase (see Examples XIX and XXI; steps A/B/J/D/I of FIG. 12). In another aspect of the invention, the 6-ACA pathway includes an HODH aldolase; an OHED hydratase; an OHED reductase; a 2-OHD aminotransferase or a 2-OHD oxidoreductase (aminating); and a 2-AHD decarboxylase (see Examples XIX and XXI; steps A/B/C/H/I of FIG. 12). In another aspect of the invention, the 6-ACA pathway includes an HODH aldolase; an HODH formate-lyase and a pyruvate formate-lyase activating enzyme or an HODH dehydrogenase; a 3-hydroxyadipyl-CoA dehydratase; a 2,3-dehydroadipyl-CoA reductase; an adipyl-CoA dehydrogenase; and an adipate semialdehyde aminotransferase or an adipate semialdehyde oxidoreductase (aminating) (see Examples XIX and XXI; steps A/L/M/N/O/E of FIG. 12). the 6-ACA pathway includes an HODH aldolase; an OHED hydratase; an OHED formate-lyase and a pyruvate formate-lyase activating enzyme or OHED dehydrogenase; a 2,3-dehydroadipyl-CoA reductase; an adipyl-CoA dehydrogenase; and an adipate semialdehyde aminotransferase or an adipate semialdehyde oxidoreductase (aminating) (see Examples XIX and XXI; steps A/B/P/N/O/E of FIG. 12). In another aspect of the invention, the 6-ACA pathway includes an HODH aldolase; an OHED hydratase; an OHED reductase; a 2-OHD formate-lyase and a pyruvate formate-lyase activating enzyme or a 2-OHD dehydrogenase; an adipyl-CoA dehydrogenase; and an adipate semialdehyde aminotransferase or an adipate semialdehyde oxidoreductase (aminating) (see Examples XIX and XXI; steps A/B/C/Q/O/E of FIG. 12). In a further aspect, the 6-ACA pathways described above can include a succinic semialdehyde dehydrogenase, an alpha-ketoglutarate decarboxylase or a phosphoenolpyruvate (PEP) carboxykinase.

In yet another embodiment, the invention provides a method for producing 6-aminocaproic acid (6-ACA) by culturing a non-naturally occurring microbial organism having a 6-ACA pathway including at least one exogenous nucleic acid encoding a 6-ACA pathway enzyme expressed in a sufficient amount to produce 6-ACA, the 6-ACA pathway including a glutamyl-CoA transferase, a glutamyl-CoA ligase, a beta-ketothiolase, an 3-oxo-6-aminopimeloyl-CoA oxidoreductase, a 3-hydroxy-6-aminopimeloyl-CoA dehydratase, a 6-amino-7-carboxyhept-2-enoyl-CoA reductase, a 6-aminopimeloyl-CoA reductase (aldehyde forming), or a 2-aminopimelate decarboxylase (see Examples XXV and XXVI; steps A/B/C/D/E/I/J of FIG. 20). In another aspect of the invention, the non-naturally occurring microbial organism includes a set of exogenous nucleic acids encoding 6-ACA pathway enzymes, where the set encode a glutamyl-CoA transferase or glutamyl-CoA ligase; a beta-ketothiolase; a 3-oxo-6-aminopimeloyl-CoA oxidoreductase; a 3-hydroxy-6-aminopimeloyl-CoA dehydratase; a 6-amino-7-carboxyhept-2-enoyl-CoA reductase; a 6-aminopimeloyl-CoA reductase (aldehyde forming); and a 2-aminopimelate decarboxylase.

In yet another embodiment, the invention provides a method for producing 6-aminocaproic acid (6-ACA) by culturing a non-naturally occurring microbial organism having a 6-ACA pathway including at least one exogenous nucleic acid encoding a 6-ACA pathway enzyme expressed in a sufficient amount to produce 6-ACA, the 6-ACA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, 3-oxopimelate aminating oxidoreductase, a 3-aminopimelate 2,3-aminomutase, or a 2-aminopimelate decarboxylase (see Examples XXV and XXVI; steps A/B/J/T/AA of FIG. 21). In another aspect of the invention, the non-naturally occurring microbial organism includes a set of exogenous nucleic acids encoding 6-ACA pathway enzymes, where the set encode a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate 2,3-aminomutase; and a 2-aminopimelate decarboxylase.

In yet another embodiment, the invention provides a method for producing 6-aminocaproic acid (6-ACA) by culturing a non-naturally occurring microbial organism having a 6-ACA pathway including at least one exogenous nucleic acid encoding a 6-ACA pathway enzyme expressed in a sufficient amount to produce 6-ACA, the 6-ACA pathway including a homolysine 2-monooxygenase (see Examples XXV and XXVI; steps A of FIG. 23). In a further aspect, the 6-ACA pathway includes hydrolysis of the 6-aminohexanamide product by a dilute acid or base to convert 6-aminohexanamide to 6-aminocaproate (see Example XXV; steps B of FIG. 23).

In yet another embodiment, the invention provides a method for producing 6-aminocaproic acid (6-ACA) by culturing a non-naturally occurring microbial organism having a 6-ACA pathway including at least one exogenous nucleic acid encoding a 6-ACA pathway enzyme expressed in a sufficient amount to produce 6-ACA, the 6-ACA pathway including an adipate reductase, an adipate kinase or an adipylphosphate reductase (see Example XXVIII; steps X/Y/Z of FIG. 25). In a further aspect, the 6-ACA pathway includes an adipate reductase. In another further aspect, the 6-ACA pathway includes an adipate kinase and an adipylphosphate reductase. In still another aspect, the microbial organism having the 6-aminocaproic acid (6-ACA) pathway above further comprises an adipate pathway, a caprolactam pathway and/or a hexamethylenediamine pathway described here (see Example XXVIII; steps A-W of FIG. 25).

In yet another embodiment, the invention provides a method for producing 6-aminocaproic acid (6-ACA) by culturing a non-naturally occurring microbial organism having a 6-aminocaproic acid (6-ACA) pathway including at least one exogenous nucleic acid encoding a 6-ACA pathway enzyme expressed in a sufficient amount to produce 6-ACA, the 6-ACA pathway including a 2-amino-7-oxosubarate keto-acid decarboxylase, a 2-amino-7-oxoheptanoate decarboxylase, a 2-amino-7-oxoheptanoate oxidoreductase, a 2-aminopimelate decarboxylase, a 6-aminohexanal oxidoreductase, a 2-amino-7-oxoheptanoate decarboxylase, or a 2-amino-7-oxosubarate amino acid decarboxylase (see Examples XXV and XXVI; steps A/B/D/E/F/G/I of FIG. 26). In a further aspect, the microbial organism has a 2-amino-7-oxosubarate pathway having at least one exogenous nucleic acid encoding a 2-amino-7-oxosubarate pathway enzyme expressed in a sufficient amount to produce 2-amino-7-oxosubarate, the 2-amino-7-oxosubarate pathway including a 2-amino-5-hydroxy-7-oxosubarate aldolase, a 2-amino-5-hydroxy-7-oxosubarate dehydratase, or a 2-amino-5-ene-7-oxosubarate reductase (see Examples XXV and XXVI; steps A/B/C of FIG. 27).

In another embodiment of the invention, the invention provides a method for producing 6-aminocaproic acid (6-ACA) by culturing a non-naturally occurring microbial organism having a 6-aminocaproic acid (6-ACA) pathway including a set of exogenous nucleic acids encoding 6-ACA pathway enzymes, where the set encodes a 2-amino-7-oxosubarate keto-acid decarboxylase; a 2-amino-7-oxoheptanoate oxidoreductase; and a 2-aminopimelate decarboxylase (see Example XXV; steps A/D/E of FIG. 26). In yet another embodiment of the invention, the non-naturally occurring microbial organism includes a set of exogenous nucleic acids encoding 6-ACA pathway enzymes, where the set encodes a 2-amino-7-oxosubarate keto-acid decarboxylase; a 2-amino-7-oxoheptanoate decarboxylase; and a 6-aminohexanal oxidoreductase (see Example XXV; steps A/B/F of FIG. 26). In still yet another embodiment of the invention, the non-naturally occurring microbial organism includes a set of exogenous nucleic acids encoding 6-ACA pathway enzymes, where the set encodes a 2-amino-7-oxosubarate amino acid decarboxylase; a 2-amino-7-oxoheptanoate decarboxylase; and a 6-aminohexanal oxidoreductase (see Example XXV; steps I/G/F of FIG. 26). In a further aspect of each of the above embodiments, the microbial organism has a 2-amino-7-oxosubarate pathway having a second set of exogenous nucleic acids encoding 2-amino-7-oxosubarate pathway enzymes expressed in a sufficient amount to produce 2-amino-7-oxosubarate, the 2-amino-7-oxosubarate pathway including a 2-amino-5-hydroxy-7-oxosubarate aldolase; a 2-amino-5-hydroxy-7-oxosubarate dehydratase; and a 2-amino-5-ene-7-oxosubarate reductase (see Examples XXV and XXVI; steps A/B/C of FIG. 27).

In yet another embodiment, the invention provides a method for producing hexamethylenediamine (HMDA) by culturing a non-naturally occurring microbial organism having a HMDA pathway, the microbial organism including at least one exogenous nucleic acid encoding a HMDA pathway enzyme expressed in a sufficient amount to produce HMDA, the HMDA pathway including a 6-aminocaproate kinase, an [(6-aminohexanoyl)oxy]phosphonate (6-AHOP) oxidoreductase, a 6-aminocaproic semialdehyde aminotransferase, a 6-aminocaproic semialdehyde oxidoreductase (aminating), a 6-aminocaproate N-acetyltransferase, a 6-acetamidohexanoate kinase, an [(6-acetamidohexanoyl)oxy]phosphonate (6-AAHOP) oxidoreductase, a 6-acetamidohexanal aminotransferase, a 6-acetamidohexanal oxidoreductase (aminating), a 6-acetamidohexanamine N-acetyltransferase, a 6-acetamidohexanamine hydrolase (amide), a 6-acetamidohexanoate CoA transferase, a 6-acetamidohexanoate CoA ligase, a 6-acetamidohexanoyl-CoA oxidoreductase, a [(6-acetamidohexanoyl)oxy]phosphonate (6-AAHOP) acyltransferase, a [(6-aminohexanoyl)oxy]phosphonate (6-AHOP) acyltransferase, a 6-aminocaproate CoA transferase and a 6-aminocaproate CoA ligase (see Examples XX and XXI; steps A-N of FIG. 13).

In yet another embodiment, the invention provides a method for producing hexamethylenediamine (HMDA) by culturing a non-naturally occurring microbial organism having a HMDA pathway, the microbial organism including at least one exogenous nucleic acid encoding a HMDA pathway enzyme expressed in a sufficient amount to produce HMDA. In one aspect the HMDA pathway includes a 6-aminocaproate kinase; a 6-AHOP oxidoreductase; and a 6-aminocaproic semialdehyde oxidoreductase (aminating) or a 6-aminocaproic acid semialdehyde aminotransferase (see Examples XX and XXI; steps A/B/C of FIG. 13). In another aspect of the invention, the HMDA pathway includes a 6-aminocaproate kinase; a 6-AHOP acyltransferase; a 6-aminocaproyl-CoA oxidoreductase; and a 6-aminocaproic semialdehyde oxidoreductase (aminating) or a 6-aminocaproic acid semialdehyde aminotransferase (see Examples XX and XXI; steps A/L/N/C of FIG. 13). In another aspect of the invention, the HMDA pathway includes a 6-aminocaproate CoA transferase or a 6-aminocaproate CoA ligase; a 6-aminocaproyl-CoA oxidoreductase; and a 6-aminocaproic semialdehyde oxidoreductase (aminating) or a 6-aminocaproic acid semialdehyde aminotransferase (see Examples XX and XXI; steps M/N/C of FIG. 13). In another aspect of the invention, the HMDA pathway includes a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide) (see Examples XX and XXI; steps D/E/F/G/H of FIG. 13). In another aspect of the invention, the HMDA pathway includes a 6-aminocaproate N-acetyltransferase; a 6-acetamidohexanoate CoA transferase or a 6-acetamidohexanoate CoA ligase; a 6-acetamidohexanoyl-CoA oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide) (see Examples XX and XXI; steps D/I/J/G/H of FIG. 13). In another aspect of the invention, the HMDA pathway includes a 6-aminocaproate N-acetyltransferase; a 6-acetamidohexanoate kinase; a 6-AAHOP oxidoreductase; a 6-acetamidohexanal aminotransferase or a 6-acetamidohexanal oxidoreductase (aminating); and a 6-acetamidohexanamine N-acetyltransferase or a 6-acetamidohexanamine hydrolase (amide) (see Examples XX and XXI; steps D/E/K/J/G of FIG. 13).

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutamyl-CoA transferase, a glutamyl-CoA ligase, a beta-ketothiolase, an 3-oxo-6-aminopimeloyl-CoA oxidoreductase, a 3-hydroxy-6-aminopimeloyl-CoA dehydratase, a 6-amino-7-carboxyhept-2-enoyl-CoA reductase, a 6-aminopimeloyl-CoA reductase (aldehyde forming), a 2-amino-7-oxoheptanoate aminotransferase, a 2-amino-7-oxoheptanoate aminating oxidoreductase, or a homolysine decarboxylase (see Examples XXIV and XXVI; steps A-H of FIG. 20). In another aspect of the invention, the non-naturally occurring microbial organism includes a set of exogenous nucleic acids encoding HMDA pathway enzymes, wherein the set encodes a glutamyl-CoA transferase or ligase; a beta-ketothiolase; a 3-oxo-6-aminopimeloyl-CoA oxidoreductase; a 3-hydroxy-6-aminopimeloyl-CoA dehydratase; a 6-amino-7-carboxyhept-2-enoyl-CoA reductase; a 6-aminopimeloyl-CoA reductase (aldehyde forming); a 2-amino-7-oxoheptanoate aminotransferase or aminating oxidoreductase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate reductase, a 3-oxo-1-carboxyheptanal aminotransferase, a 3-oxo-1-carboxyheptanal aminating oxidoreductase, a 3-oxo-7-aminoheptanoate 3-aminotransferase, a 3-oxo-7-aminoheptanoate 3-aminating oxidoreductase, a 3-oxopimelate kinase, a 5-oxopimeloylphosphonate reductase, a 3-oxopimelate CoA transferase, a 3-oxopimelate ligase, a 5-oxopimeloyl-CoA reductase (aldehyde forming), a 3-oxopimelate aminotransferase, a 3-oxopimelate aminating oxidoreductase, a 3-aminopimelate CoA transferase, a 3-aminopimelate ligase, a 5-aminopimeloyl-CoA reductase (aldehyde forming), a 3-aminopimelate kinase, a 5-aminopimeloylphosphonate reductase, a 3-aminopimelate reductase, a 3-amino-7-oxoheptanoate 2,3-aminomutase, a 2-amino-7-oxoheptanoate 7-aminotransferase, a 2-amino-7-oxoheptanoate aminating oxidoreductase, a 3,7-diaminoheptanoate 2,3-aminomutase, a homolysine decarboxylase, a 3-aminopimelate 2,3-aminomutase, a 2-aminopimelate kinase, a 2-aminopimelate CoA transferase, a 2-aminopimelate CoA ligase, a 2-aminopimelate reductase, a 6-aminopimeloylphosphonate reductase, a 6-aminopimeloyl-CoA reductase (aldehyde forming), a 3-amino-7-oxoheptanoate 7-aminotransferase or a 3-amino-7-oxoheptanoate aminating oxidoreductase (see Examples XXIV and XXVI; FIG. 21).

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate reductase, a 3-oxo-1-carboxyheptanal 7-aminotransferase, a 3-oxo-1-carboxyheptanal 7-aminating oxidoreductase, a 3-oxo-7-aminoheptanoate 3-aminotransferase, a 3-oxo-7-aminoheptanoate 3-aminating oxidoreductase, a 3,7-diaminoheptanoate 2,3-aminomutase, or a homolysine decarboxylase (see Examples XXIV and XXVI; steps A/B/C/D/E/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate reductase; a 3-oxo-1-carboxyheptanal 7-aminotransferase or a 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate kinase, a 5-oxopimeloylphosphonate reductase, a 3-oxo-1-carboxyheptanal 7-aminotransferase, a 3-oxo-1-carboxyheptanal 7-aminating oxidoreductase, a 3-oxo-7-aminoheptanoate 3-aminotransferase, a 3-oxo-7-aminoheptanoate 3-aminating oxidoreductase, a 3,7-diaminoheptanoate 2,3-aminomutase, or a homolysine decarboxylase (see Examples XXIV and XXVI; steps A/B/F/G/D/E/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate kinase; a 5-oxopimeloylphosphonate reductase; a 3-oxo-1-carboxyheptanal 7-aminotransferase or a 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate CoA transferase, 3-oxopimelate CoA ligase, a 5-oxopimeloyl-CoA reductase (aldehyde forming), a 3-oxo-1-carboxyheptanal 7-aminotransferase, 3-oxo-1-carboxyheptanal 7-aminating oxidoreductase, a 3-oxo-7-aminoheptanoate 3-aminotransferase, a 3-oxo-7-aminoheptanoate 3-aminating oxidoreductase, a 3,7-diaminoheptanoate 2,3-aminomutase, or a homolysine decarboxylase (see Examples XXIV and XXVI; steps A/B/H/I/D/E/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate CoA transferase or 3-oxopimelate CoA ligase; a 5-oxopimeloyl-CoA reductase (aldehyde forming); a 3-oxo-1-carboxyheptanal 7-aminotransferase or 3-oxo-1-carboxyheptanal 7-aminating oxidoreductase; a 3-oxo-7-aminoheptanoate 3-aminotransferase or a 3-oxo-7-aminoheptanoate 3-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate reductase, a 3-oxo-1-carboxyheptanal 3-aminotransferase, a 3-oxo-1-carboxyheptanal 3-aminating oxidoreductase, a 3-amino-7-oxoheptanoate 7-aminotransferase, a 3-amino-7-oxoheptanoate 7-aminating oxidoreductase, a 3,7-diaminoheptanoate 2,3-aminomutase, or a homolysine decarboxylase (see Examples XXIV and XXVI; steps A/B/C/AB/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate reductase; a 3-oxo-1-carboxyheptanal 3-aminotransferase or a 3-oxo-1-carboxyheptanal 3-aminating oxidoreductase; a 3-amino-7-oxoheptanoate 7-aminotransferase or a 3-amino-7-oxoheptanoate 7-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, 3-oxopimeloyl-CoA ligase, a 3-oxopimelate kinase, a 5-oxopimeloylphosphonate reductase, a 3-oxo-1-carboxyheptanal 3-aminotransferase, a 3-oxo-1-carboxyheptanal 3-aminating oxidoreductase, a 3-amino-7-oxoheptanoate 7-aminotransferase, a 3-amino-7-oxoheptanoate 7-aminating oxidoreductase, a 3,7-diaminoheptanoate 2,3-aminomutase, or a homolysine decarboxylase (see Examples XXIV and XXVI; steps A/B/H/I/AB/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate kinase; a 5-oxopimeloylphosphonate reductase; a 3-oxo-1-carboxyheptanal 3-aminotransferase or a 3-oxo-1-carboxyheptanal 3-aminating oxidoreductase; a 3-amino-7-oxoheptanoate 7-aminotransferase or a 3-amino-7-oxoheptanoate 7-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate CoA transferase or a 3-oxopimelate CoA ligase, a 5-oxopimeloyl-CoA reductase (aldehyde forming), a 3-oxo-1-carboxyheptanal 3-aminotransferase, a 3-oxo-1-carboxyheptanal 3-aminating oxidoreductase, a 3-amino-7-oxoheptanoate 7-aminotransferase, 3-amino-7-oxoheptanoate 7-aminating oxidoreductase, a 3,7-diaminoheptanoate 2,3-aminomutase, or a homolysine decarboxylase (see Examples XXIV and XXVI; steps A/B/F/G/AB/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate CoA transferase or a 3-oxopimelate CoA ligase; a 5-oxopimeloyl-CoA reductase (aldehyde forming); a 3-oxo-1-carboxyheptanal 3-aminotransferase or a 3-oxo-1-carboxyheptanal 3-aminating oxidoreductase; a 3-amino-7-oxoheptanoate 7-aminotransferase or 3-amino-7-oxoheptanoate 7-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase or a 3-oxopimelate aminating oxidoreductase, a 3-aminopimelate reductase, a 3-amino-7-oxoheptanoate 2,3-aminomutase, a 2-amino-7-oxoheptanoate 7-aminotransferase, a 2-amino-7-oxoheptanoate aminating oxidoreductase, or a homolysine decarboxylase (see Examples XXIV and XXVI; steps A/B//J/O/P/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate reductase; a 3-amino-7-oxoheptanoate 2,3-aminomutase; a 2-amino-7-oxoheptanoate 7-aminotransferase or a 2-amino-7-oxoheptanoate aminating oxidoreductase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase or a 3-oxopimelate aminating oxidoreductase, a 3-aminopimelate kinase, a 5-aminopimeloylphosphonate reductase, a 3-amino-7-oxoheptanoate 2,3-aminomutase, a 2-amino-7-oxoheptanoate 7-aminotransferase, a 2-amino-7-oxoheptanoate aminating oxidoreductase, or a homolysine decarboxylase (see Examples XXIV and XXVI; steps A/B/J/M/N/P/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate kinase; a 5-aminopimeloylphosphonate reductase; a 3-amino-7-oxoheptanoate 2,3-aminomutase; a 2-amino-7-oxoheptanoate 7-aminotransferase or a 2-amino-7-oxoheptanoate aminating oxidoreductase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate CoA transferase, a 3-aminopimelate CoA ligase, a 5-aminopimeloyl-CoA reductase (aldehyde forming), a 3-amino-7-oxoheptanoate 2,3-aminomutase, a 2-amino-7-oxoheptanoate 7-aminotransferase, 2-amino-7-oxoheptanoate aminating oxidoreductase, or a homolysine decarboxylase (see Examples XXIV and XXVI; steps A/B/J/K/L/P/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate CoA transferase or a 3-aminopimelate CoA ligase; a 5-aminopimeloyl-CoA reductase (aldehyde forming); a 3-amino-7-oxoheptanoate 2,3-aminomutase; a 2-amino-7-oxoheptanoate 7-aminotransferase or 2-amino-7-oxoheptanoate aminating oxidoreductase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, 3-oxopimelate aminating oxidoreductase, a 3-aminopimelate reductase, a 3-amino-7-oxoheptanoate 7-aminotransferase, 3-amino-7-oxoheptanoate 7-aminating oxidoreductase, a 3,7-diaminoheptanoate 2,3-aminomutase, or a homolysine decarboxylase (see Examples XXIV and XXVI; steps A/B/J/O/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate reductase; a 3-amino-7-oxoheptanoate 7-aminotransferase or 3-amino-7-oxoheptanoate 7-aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate CoA transferase, a 3-aminopimelate CoA ligase, a 5-aminopimeloyl-CoA reductase (aldehyde forming), a 3-amino-7-oxoheptanoate 7-aminotransferase, 3-amino-7-oxoheptanoate aminating oxidoreductase, a 3,7-diaminoheptanoate 2,3-aminomutase, or a homolysine decarboxylase (see Examples XXIV and XXVI; steps A/B/J/K/L/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate CoA transferase or a 3-aminopimelate CoA ligase; a 5-aminopimeloyl-CoA reductase (aldehyde forming); a 3-amino-7-oxoheptanoate 7-aminotransferase or 3-amino-7-oxoheptanoate aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate kinase, a 5-aminopimeloylphosphonate reductase, a 3-amino-7-oxoheptanoate 7-aminotransferase, 3-amino-7-oxoheptanoate aminating oxidoreductase, a 3,7-diaminoheptanoate 2,3-aminomutase, or a homolysine decarboxylase (see Examples XXIV and XXVI; steps A/B/J/M/N/Z/R/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate kinase; a 5-aminopimeloylphosphonate reductase; a 3-amino-7-oxoheptanoate 7-aminotransferase or a 3-amino-7-oxoheptanoate aminating oxidoreductase; a 3,7-diaminoheptanoate 2,3-aminomutase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, 3-oxopimelate aminating oxidoreductase, a 3-aminopimelate 2,3-aminomutase, a 2-aminopimelate reductase, a 2-amino-7-oxoheptanoate 7-aminotransferase, a 2-amino-7-oxoheptanoate aminating oxidoreductase, or a homolysine decarboxylase (see Examples XXIV and XXVI; steps A/B/J/T/W/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or 3-oxopimelate aminating oxidoreductase; a 3-aminopimelate 2,3-aminomutase; a 2-aminopimelate reductase; a 2-amino-7-oxoheptanoate 7-aminotransferase or a 2-amino-7-oxoheptanoate aminating oxidoreductase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate 2,3-aminomutase, a 2-aminopimelate kinase, a 6-aminopimeloylphosphonate reductase, a 2-amino-7-oxoheptanoate 7-aminotransferase, a 2-amino-7-oxoheptanoate aminating oxidoreductase, or a homolysine decarboxylase (see Examples XXIV and XXVI; steps A/B/J/T/U/X/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate kinase; a 6-aminopimeloylphosphonate reductase; a 2-amino-7-oxoheptanoate 7-aminotransferase or a 2-amino-7-oxoheptanoate aminating oxidoreductase; and a homolysine decarboxylase.

In yet another embodiment, the invention provides a method for producing hexamethylenediamine (HMDA) by culturing a non-naturally occurring microbial organism having a HMDA pathway including at least one exogenous nucleic acid encoding a HMDA pathway enzyme expressed in a sufficient amount to produce HMDA, the HMDA pathway including a glutaryl-CoA beta-ketothiolase, a 3-oxopimeloyl-CoA hydrolase, a 3-oxopimeloyl-CoA transferase, a 3-oxopimeloyl-CoA ligase, a 3-oxopimelate aminotransferase, a 3-oxopimelate aminating oxidoreductase, a 3-aminopimelate 2,3-aminomutase, a 2-aminopimelate CoA transferase, 2-aminopimelate CoA ligase, a 6-aminopimeloyl-CoA reductase (aldehyde forming), a 2-amino-7-oxoheptanoate 7-aminotransferase, 2-amino-7-oxoheptanoate aminating oxidoreductase, or a homolysine decarboxylase (see Examples XXIV and XXVI; steps A/B/J/T/V/Y/Q/S of FIG. 21). In another aspect of the invention, the non-naturally occurring microbial organism includes a set of exogenous nucleic acids encoding HMDA pathway enzymes, wherein the set encodes a glutaryl-CoA beta-ketothiolase; a 3-oxopimeloyl-CoA hydrolase, a 3-oxopimeloyl-CoA transferase or a 3-oxopimeloyl-CoA ligase; a 3-oxopimelate aminotransferase or a 3-oxopimelate aminating oxidoreductase; a 3-aminopimelate 2,3-aminomutase; a 2-aminopimelate CoA transferase or 2-aminopimelate CoA ligase; a 6-aminopimeloyl-CoA reductase (aldehyde forming); a 2-amino-7-oxoheptanoate 7-aminotransferase or 2-amino-7-oxoheptanoate aminating oxidoreductase; and a homolysine decarboxylase.

The invention additionally provides a method for producing hexamethylenediamine (HMDA) by culturing a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 2-oxo-4-hydroxy-7-aminoheptanoate aldolase, a 2-oxo-4-hydroxy-7-aminoheptanoate dehydratase, a 2-oxo-7-aminohept-3-enoate reductase, a 2-oxo-7-aminoheptanoate aminotransferase, a 2-oxo-7-aminoheptanoate aminating oxidoreductase, a homolysine decarboxylase, a 2-oxo-7-aminoheptanoate decarboxylase, a 6-aminohexanal aminotransferase or 6-aminohexanal aminating oxidoreductase (see Examples XXIV and XXVI; steps A-G of FIG. 22). In another aspect of the invention, the non-naturally occurring microbial organism includes a set of exogenous nucleic acids encoding HMDA pathway enzymes, wherein the set encodes a 2-oxo-4-hydroxy-7-aminoheptanoate aldolase; a 2-oxo-4-hydroxy-7-aminoheptanoate dehydratase; a 2-oxo-7-aminohept-3-enoate reductase; a 2-oxo-7-aminoheptanoate aminotransferase or a 2-oxo-7-aminoheptanoate aminating oxidoreductase; and a homolysine decarboxylase. In another aspect of the invention, the non-naturally occurring microbial organism includes a set of exogenous nucleic acids encoding HMDA pathway enzymes, wherein the set encodes a 2-oxo-4-hydroxy-7-aminoheptanoate aldolase; a 2-oxo-4-hydroxy-7-aminoheptanoate dehydratase; a 2-oxo-7-aminohept-3-enoate reductase; a 2-oxo-7-aminoheptanoate decarboxylase; and a 6-aminohexanal aminotransferase or a 6-aminohexanal aminating oxidoreductase.

The invention additionally provides a method for producing hexamethylenediamine (HMDA) by culturing a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 6-aminocaproate reductase, a 6-aminocaproic semialdehyde aminotransferase, a 6-aminocaproic semialdehyde oxidoreductase (aminating), 6-aminocaproate N-acetyltransferase, a 6-acetamidohexanoate reductase, 6-acetamidohexanal aminotransferase, 6-acetamidohexanal oxidoreductase (aminating), 6-acetamidohexanamine N-acetyltransferase or acetamidohexanamine hydrolase (amide) (see Example XXVII; steps 0/C or D/P/G/H of FIG. 24). In another aspect of the invention, the non-naturally occurring microbial organism includes a set of exogenous nucleic acids encoding HMDA pathway enzymes, wherein the set encodes a 6-aminocaproate reductase; and a 6-aminocaproic semialdehyde aminotransferase or a 6-aminocaproic semialdehyde oxidoreductase (aminating). In another aspect of the invention, the non-naturally occurring microbial organism includes a set of exogenous nucleic acids encoding HMDA pathway enzymes, wherein the set encodes 6-aminocaproate N-acetyltransferase; 6-acetamidohexanoate reductase; 6-acetamidohexanal aminotransferase or 6-acetamidohexanal oxidoreductase (aminating); and 6-acetamidohexanamine N-acetyltransferase or 6-acetamidohexanamine hydrolase (amide).

The invention additionally provides a method for producing hexamethylenediamine (HMDA) by culturing a non-naturally occurring microbial organism having a hexamethylenediamine (HMDA) pathway including at least one exogenous nucleic acid encoding a HMDA pathway enzyme expressed in a sufficient amount to produce HMDA, the HMDA pathway including a 2-amino-7-oxosubarate ketoacid decarboxylase, a 2-amino-7-oxoheptanoate decarboxylase, a 6-aminohexanal aminating oxidoreductase, a 6-aminohexanal aminotransferase, a 2-amino-7-oxoheptanoate aminotransferase, a 2-amino-7-oxoheptanoate aminating oxidoreductase, a 2-oxo-7-aminoheptanoate decarboxylase, a homolysine decarboxylase, a 2-amino-7-oxosubarate amino acid decarboxylase, a 2-oxo-7-aminoheptanoate aminating oxidoreductase, a 2-oxo-7-aminoheptanoate aminotransferase, a 2-amino-7-oxosubarate aminating oxidoreductase, a 2-amino-7-oxosubarate aminotransferase or a 2,7-diaminosubarate decarboxylase (see Examples XXIV and XXVI; Steps A/B/C/G/H/I/J/K/L/M of FIG. 26). In a further aspect, the microbial organism has a 2-amino-7-oxosubarate pathway having at least one nucleic acid encoding a 2-amino-7-oxosubarate pathway enzyme expressed in a sufficient amount to produce 2-amino-7-oxosubarate, the 2-amino-7-oxosubarate pathway including a 2-amino-5-hydroxy-7-oxosubarate aldolase, a 2-amino-5-hydroxy-7-oxosubarate dehydratase, or a 2-amino-5-ene-7-oxosubarate reductase (see Examples XXV and XXVI; steps A/B/C of FIG. 27).

In another embodiment, the invention provides a method for producing hexamethylenediamine (HMDA) by culturing a non-naturally occurring microbial organism having a hexamethylenediamine (HMDA) pathway including a set of exogenous nucleic acids encoding HMDA pathway enzymes, wherein the set encodes a 2-amino-7-oxosubarate aminating oxidoreductase or 2-amino-7-oxosubarate aminotransferase; a 2,7-diaminosubarate decarboxylase; and a homolysine decarboxylase (see Examples XXIV and XXVI; steps K/L/H of FIG. 26). In another embodiment of the invention, the non-naturally occurring microbial organism includes a set of exogenous nucleic acids encoding HMDA pathway enzymes, wherein the set encodes a 2-amino-7-oxosubarate amino acid decarboxylase; a 2-oxo-7-aminoheptanoate aminating oxidoreductase or a 2-oxo-7-aminoheptanoate aminotransferase; and a homolysine decarboxylase (see Examples XXIV and XXVI; steps I/J/H of FIG. 26). In another embodiment of the invention, the non-naturally occurring microbial organism includes a set of exogenous nucleic acids encoding HMDA pathway enzymes, wherein the set encodes a 2-amino-7-oxosubarate amino acid decarboxylase; a 2-oxo-7-aminoheptanoate decarboxylase; and a 6-aminohexanal aminating oxidoreductase or a 6-aminohexanal aminotransferase (see Examples XXIV and XXVI; steps I/G/C of FIG. 26). In another embodiment of the invention, the non-naturally occurring microbial organism includes a set of exogenous nucleic acids encoding HMDA pathway enzymes, wherein the set encodes a 2-amino-7-oxosubarate keto-acid decarboxylase; a 2-amino-7-oxoheptanoate decarboxylase; and a 6-aminohexanal aminating oxidoreductase or a 6-aminohexanal aminotransferase (see Examples XXIV and XXVI; steps A/B/C of FIG. 26). In another embodiment of the invention, the non-naturally occurring microbial organism includes a set of exogenous nucleic acids encoding HMDA pathway enzymes, wherein the set encodes a 2-amino-7-oxosubarate keto-acid decarboxylase; a 2-amino-7-oxoheptanoate aminating oxidoreductase or a 2-amino-7-oxoheptanoate aminotransferase; and a homolysine decarboxylase (see Examples XXIV and XXVI; steps A/M/H of FIG. 26). In a further aspect of each of the above embodiments, the microbial organism has a 2-amino-7-oxosubarate pathway having a second set of exogenous nucleic acids encoding 2-amino-7-oxosubarate pathway enzymes expressed in a sufficient amount to produce 2-amino-7-oxosubarate, the 2-amino-7-oxosubarate pathway including a 2-amino-5-hydroxy-7-oxosubarate aldolase; a 2-amino-5-hydroxy-7-oxosubarate dehydratase; and a 2-amino-5-ene-7-oxosubarate reductase (see Examples XXV and XXVI; steps A/B/C of FIG. 27).

The invention additionally provides a method for producing hexamethylenediamine (HMDA) by culturing a non-naturally occurring microbial organism having a levulinic acid (LA) pathway including at least one exogenous nucleic acid encoding a LA pathway enzyme expressed in a sufficient amount to produce LA, the LA pathway including a 3-oxoadipyl-CoA thiolase, a 3-oxoadipyl-CoA/acyl-CoA transferase, a 3-oxoadipyl-CoA synthase, a 3-oxoadipyl-CoA hydrolase, or a 3-oxoadipate decarboxylase (see Example XXIX; steps A/E/F/G/AA of FIG. 25). In another aspect of the invention, the non-naturally occurring microbial organism includes a set of exogenous nucleic acids encoding LA pathway enzymes, wherein the set encodes a 3-oxoadipyl-CoA thiolase; a 3-oxoadipyl-CoA/acyl-CoA transferase, a 3-oxoadipyl-CoA synthase, or a 3-oxoadipyl-CoA hydrolase; and a 3-oxoadipate decarboxylase.

The invention further provides methods of producing non-naturally microbial organisms having increased production of adipate, 6-ACA and/or HMDA by disruption of one or more genes to confer increased production of adipate, 6-ACA and/or HMDA. Such gene disruptions include those exemplified herein in Example XXX and Tables 14-16.

The invention additionally provides a method for producing adipate, 6-ACA and/or HMDA that includes culturing a non-naturally occurring microbial organism that includes one or more gene disruptions that confer increased production of adipate, 6-ACA and/or HMDA. The disruptions can occur in genes encoding an enzyme obligatory to coupling adipate, 6-ACA and/or HMDA production to growth of the microorganism when the gene disruption reduces an activity of the enzyme, such that the disruptions confer stable growth-coupled production of adipate, 6-ACA and/or HMDA onto the non-naturally microbial organism.

In some embodiments, the gene disruption can include a complete gene deletion. Methods for gene disruption are well known to those skilled in the art and are described herein (see Example XXX). In some embodiments other methods to disrupt a gene include, for example, frameshifting by omission, addition of oligonucleotides or by mutations that render the gene inoperable. One skilled in the art will recognize the advantages of gene deletions, however, because of the stability it can confer to the non-naturally occurring organism from reverting to a phenotype expressing the previously disrupted gene. In particular, the gene disruptions are selected from the gene sets that described in Tables 14-16.

Suitable purification and/or assays to test for the production of 6-aminocaproic acid, caprolactam, hexamethylenediamine or levulinic acid can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., Biotechnol. Bioeng. 90:775-779 (2005)), or other suitable assay and detection methods well known in the art. The individual enzyme activities from the exogenous DNA sequences can also be assayed using methods well known in the art.

The 6-aminocaproic acid, caprolactam, hexamethylenediamine or levulinic acid can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the non-naturally occurring microbial organisms described herein can be cultured to produce and/or secrete the biosynthetic products of the invention. For example, the 6-aminocaproic acid, caprolactam, hexamethylenediamine or levulinic acid producers can be cultured for the biosynthetic production of 6-aminocaproic acid, caprolactam, hexamethylenediamine or levulinic acid.

For the production of 6-aminocaproic acid, caprolactam, hexamethylenediamine or levulinic acid, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in United State publication 2009/0047719 (Ser. No. 11/891,602), filed Aug. 10, 2007. Fermentations can be performed in a batch, fed-batch or continuous manner, as disclosed herein.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the methods of the invention include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms of the invention for the production of 6-aminocaproic acid, caprolactam, hexamethylenediamine or levulinic acid.

In addition to renewable feedstocks such as those exemplified above, the 6-aminocaproic acid, caprolactam, hexamethylenediamine or levulinic acid microbial organisms of the invention also can be modified for growth on syngas as its source of carbon. In this specific embodiment, one or more proteins or enzymes are expressed in the 6-aminocaproic acid, caprolactam, hexamethylenediamine or levulinic acid producing organisms to provide a metabolic pathway for utilization of syngas or other gaseous carbon source.

Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

The Wood-Ljungdahl pathway catalyzes the conversion of CO and $H_2$ to acetyl-CoA and other products such as acetate. Organisms capable of utilizing CO and syngas also generally have the capability of utilizing $CO_2$ and $CO_2/H_2$ mixtures through the same basic set of enzymes and transformations encompassed by the Wood-Ljungdahl pathway. $H_2$-dependent conversion of $CO_2$ to acetate by microorganisms was recognized long before it was revealed that CO also could be used by the same organisms and that the same pathways were involved. Many acetogens have been shown to grow in the presence of $CO_2$ and produce compounds such as acetate as long as hydrogen is present to supply the necessary reducing equivalents (see for example, Drake, *Acetogenesis*, pp. 3-60 Chapman and Hall, New York, (1994)). This can be summarized by the following equation:

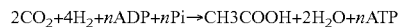

$$2CO_2+4H_2+n\text{ADP}+n\text{Pi} \rightarrow CH3COOH+2H_2O+n\text{ATP}$$

Hence, non-naturally occurring microorganisms possessing the Wood-Ljungdahl pathway can utilize $CO_2$ and $H_2$ mixtures as well for the production of acetyl-CoA and other desired products.

The Wood-Ljungdahl pathway is well known in the art and consists of 12 reactions which can be separated into two branches: (1) methyl branch and (2) carbonyl branch. The methyl branch converts syngas to methyl-tetrahydrofolate (methyl-THF) whereas the carbonyl branch converts methyl-THF to acetyl-CoA. The reactions in the methyl branch are catalyzed in order by the following enzymes: ferredoxin oxidoreductase, formate dehydrogenase, formyltetrahydrofolate synthetase, methenyltetrahydrofolate cyclodehydratase, methylenetetrahydrofolate dehydrogenase and methylenetetrahydrofolate reductase. The reactions in the carbonyl branch are catalyzed in order by the following enzymes or proteins: cobalamine corrinoid/iron-sulfur protein, methyltransferase, carbon monoxide dehydrogenase, acetyl-CoA synthase, acetyl-CoA synthase disulfide reductase and hydrogenase, and these enzymes can also be referred to as methyltetrahydrofolate:corrinoid protein methyltransferase (for example, AcsE), corrinoid iron-sulfur protein, nickel-protein assembly protein (for example, AcsF), ferredoxin, acetyl-CoA synthase, carbon monoxide dehydrogenase and nickel-protein assembly protein (for example, CooC). Following the teachings and guidance provided herein for introducing a sufficient number of encoding nucleic acids to generate a 6-aminocaproic acid, caprolactam, hexamethylenediamine or levulinic acid pathway, those skilled in the art will understand that the same engineering design also can be performed with respect to introducing at least the nucleic acids encoding the Wood-Ljungdahl enzymes or proteins absent in the host organism. Therefore, introduction of one or more encoding nucleic acids into the microbial organisms of the invention such that the modified organism contains the complete Wood-Ljungdahl pathway will confer syngas utilization ability.

Additionally, the reductive (reverse) tricarboxylic acid cycle coupled with carbon monoxide dehydrogenase and/or hydrogenase activities can also be used for the conversion of CO, $CO_2$ and/or $H_2$ to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate:ferredoxin oxidoreductase, succinyl-CoA synthetase, succinyl-CoA transferase, fumarate reductase, fumarase, malate dehydrogenase, NAD(P)H:ferredoxin oxidoreductase, carbon monoxide dehydrogenase, and hydrogenase. Specifically, the reducing equivalents extracted from CO and/or $H_2$ by carbon monoxide dehydrogenase and hydrogenase are utilized to fix $CO_2$ via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the p-toluate, terepathalate, or (2-hydroxy-3-methyl-4-oxobutoxy)phosphonate precursors, glyceraldehyde-3-phosphate, phosphoenolpyruvate, and pyruvate, by pyruvate:ferredoxin oxidoreductase and the enzymes of gluconeogenesis. Following the teachings and guidance provided herein for introducing a sufficient number of encoding nucleic acids to generate a p-toluate, terephthalate or (2-hydroxy-3-methyl-4-oxobutoxy)phosphonate pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms of the invention such that the modified organism contains the complete reductive TCA pathway will confer syngas utilization ability.

Given the teachings and guidance provided herein, those skilled in the art will understand that a non-naturally occurring microbial organism can be produced that secretes the biosynthesized compounds of the invention when grown on a carbon source such as a carbohydrate. Such compounds include, for example, 6-aminocaproic acid, caprolactam, hexamethylenediamine or levulinic acid and any of the intermediate metabolites in the 6-aminocaproic acid, caprolactam, hexamethylenediamine or levulinic acid pathway. All that is required is to engineer in one or more of the required enzyme activities to achieve biosynthesis of the desired compound or intermediate including, for example, inclusion of some or all of the 6-aminocaproic acid, caprolactam, hexamethylenediamine or levulinic acid biosynthetic pathways. Accordingly, the invention provides a non-naturally occurring microbial organism that produces and/or secretes 6-aminocaproic acid, caprolactam, hexamethylenediamine or levulinic acid when grown on a carbohydrate and produces and/or secretes any of the intermediate metabolites shown in the 6-aminocaproic acid, caprolactam, hexamethylenediamine or levulinic acid pathway when grown on a carbohydrate. For example, an adipate producing microbial organisms can initiate synthesis from an intermediate, for example, 3-oxoadipyl-CoA, 3-hydroxyadipyl-CoA, 5-carboxy-2-pentenoyl-CoA, or adipyl-CoA (see FIG. 2), as desired. In addition, an adipate producing microbial organism can initiate synthesis from an intermediate, for example, 3-oxoadipyl-CoA, 3-oxoadipate, 3-hydroxyadipate, or hexa-2-enedioate (see FIG. 3). The 6-aminocaproic acid producing microbial organism of the invention can initiate synthesis from an intermediate, for example, adipate semialdehyde (see FIG. 8). The caprolactam producing microbial organism of the invention can initiate synthesis from an intermediate, for example, adipate semialdehyde or 6-aminocaproic acid (see FIG. 8), as desired.

The non-naturally occurring microbial organisms of the invention are constructed using methods well known in the art as exemplified herein to exogenously express at least one nucleic acid encoding a 6-aminocaproic acid, caprolactam, hexamethylenediamine or levulinic acid pathway enzyme in sufficient amounts to produce 6-aminocaproic acid, caprolactam, hexamethylenediamine or levulinic acid. It is understood that the microbial organisms of the invention are cultured under conditions sufficient to produce 6-aminocaproic acid, caprolactam, hexamethylenediamine or levulinic acid. Following the teachings and guidance provided herein, the non-naturally occurring microbial organisms of the invention can achieve biosynthesis of 6-aminocaproic acid, caprolactam, hexamethylenediamine or levulinic acid resulting in intracellular concentrations between about 0.1-200 mM or more. Generally, the intracellular concentration of 6-aminocaproic acid, caprolactam, hexamethylenediamine or levulinic acid is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the non-naturally occurring microbial organisms of the invention.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. publication 2009/0047719, filed Aug. 10, 2007. Any of these conditions can be employed with the non-naturally occurring microbial organisms as well as other anaerobic conditions well known in the art. Under such anaerobic conditions, the 6-aminocaproic acid, caprolactam, hexamethylenediamine or levulinic acid producers can synthesize 6-aminocaproic acid, caprolactam, hexamethylenediamine or levulinic acid at intracellular concentrations of 5-10 mM or more as well as all other concentrations exemplified herein. It is understood that, even though the above description refers to intracellular concentrations, 6-aminocaproic acid, caprolactam, hexamethylenediamine or levulinic acid producing microbial organisms can produce 6-aminocaproic acid, caprolactam, hexamethylenediamine or levulinic acid intracellularly and/or secrete the product into the culture medium.

The culture conditions can include, for example, liquid culture procedures as well as fermentation and other large scale culture procedures. As described herein, particularly useful yields of the biosynthetic products of the invention can be obtained under anaerobic or substantially anaerobic culture conditions.

As described herein, one exemplary growth condition for achieving biosynthesis of 6-aminocaproic acid, caprolactam, hexamethylenediamine or levulinic acid includes anaerobic culture or fermentation conditions. In certain embodiments, the non-naturally occurring microbial organisms of the invention can be sustained, cultured or fermented under anaerobic or substantially anaerobic conditions. Briefly, anaerobic conditions refers to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of 6-aminocaproic acid, caprolactam, hexamethylenediamine or levulinic acid. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of 6-aminocaproic acid, caprolactam, hexamethylenediamine or levulinic acid. Generally, and as with non-continuous culture procedures, the continuous and/or near-continuous production of 6-aminocaproic acid, caprolactam, hexamethylenediamine or levulinic acid will include culturing a non-naturally occurring 6-aminocaproic acid, caprolactam, hexamethylenediamine or levulinic acid producing organism of the invention in sufficient nutrients and medium to sustain and/or nearly sustain growth in an exponential phase. Continuous culture under such conditions can include, for example, 1 day, 2, 3, 4, 5, 6 or 7 days or more. Additionally, continuous culture can include 1 week, 2, 3, 4 or 5 or more weeks and up to several months. Alternatively, organisms of the invention can be cultured for hours, if suitable for a particular application. It is to be understood that the continuous and/or near-continuous culture conditions also can include all time intervals in between these exemplary periods. It is further understood that the time of culturing the microbial organism of the invention is for a sufficient period of time to produce a sufficient amount of product for a desired purpose.

Fermentation procedures are well known in the art. Briefly, fermentation for the biosynthetic production of 6-aminocaproic acid, caprolactam, hexamethylenediamine or levulinic acid can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the 6-aminocaproic acid, caprolactam, hexamethylenediamine or levulinic acid producers of the invention for continuous production of substantial quantities of 6-aminocaproic acid, caprolactam, hexamethylenediamine or levulinic acid, the 6-aminocaproic acid, caprolactam, hexamethylenediamine or levulinic acid producers also can be, for example, simultaneously subjected to chemical synthesis procedures to convert the product to other compounds or the product can be separated from the fermentation culture and sequentially subjected to chemical conversion to convert the product to other compounds, if desired. As described herein, an intermediate in the adipate pathway utilizing 3-oxoadipate, hexa-2-enedioate, can be converted to adipate, for example, by chemical hydrogenation over a platinum catalyst (see Example III).

As described herein, exemplary growth conditions for achieving biosynthesis of 6-aminocaproic acid, caprolactam, hexamethylenediamine or levulinic acid includes the addition of an osmoprotectant to the culturing conditions. In certain embodiments, the non-naturally occurring microbial organisms of the invention can be sustained, cultured or fermented as described above in the presence of an osmoprotectant. Briefly, an osmoprotectant means a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfoniopro-prionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. For example, as described in Example XXII, *Escherichia coli* in the presence of varying amounts of 6-aminocaproic acid is suitably grown in the presence of 2 mM glycine betaine. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

To generate better producers, metabolic modeling can be utilized to optimize growth conditions. Modeling can also be used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 6-aminocaproic acid, caprolactam, hexamethylenediamine or levulinic acid.

One computational method for identifying and designing metabolic alterations favoring biosynthesis of a desired product is the OptKnock computational framework, Burgard et al., *Biotechnol. Bioeng.* 84:647-657 (2003). OptKnock is a metabolic modeling and simulation program that suggests gene deletion strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by Opt-Knock are to be completely removed from the genome. Therefore, this computational methodology can be used to either identify alternative pathways that lead to biosynthesis of a desired product or used in connection with the non-naturally occurring microbial organisms for further optimization of biosynthesis of a desired product.

The concept of growth-coupled biochemical production can be visualized in the context of the biochemical production envelopes of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. Although exceptions exist, typically the production of a desired biochemical is in direct competition with biomass formation for intracellular resources. Thus, enhanced rates of biochemical production will necessarily result in sub-maximal growth rates. The knockouts suggested by OptKnock are designed to restrict the allowable solution boundaries forcing a change in metabolic behavior from the wild-type strain. Although the actual solution boundaries for a given strain will expand or contract as the substrate uptake rate(s) increase or decrease, each experimental point should lie within its calculated solution boundary. Plots such as these allow one to visualize how close strains are to their performance limits or, in other words, how much room is available for improvement. The OptKnock framework has already been able to identify promising gene deletion strategies for biochemical overproduction, (Burgard et al., *Biotechnol Bioeng*, 84(6):647-657 (2003); Pharkya et al., *Biotechnol Bioeng*, 84(7):887-899 (2003)) and establishes a systematic framework that will naturally encompass future improvements in metabolic and regulatory modeling frameworks.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that enable an effective query of the performance limits of metabolic networks and provides methods for solving the resulting mixed-integer linear programming problems. The metabolic modeling and simulation method referred to herein as OptKnock are described in, for example, U.S. publication 2002/0168654, filed Jan. 10, 2002, in International Patent No. PCT/US02/00660, filed Jan. 10, 2002, and U.S. patent application serial No. 2009/0047719, filed Aug. 10, 2007.

Another computational method for identifying and designing metabolic alterations favoring biosynthetic production of a product is a metabolic modeling and simulation system termed SimPheny®. This computational method and system is described in, for example, U.S. publication 2003/0233218, filed Jun. 14, 2002, and in International Patent Application No. PCT/US03/18838, filed Jun. 13, 2003. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components. Analysis methods such as convex analysis, linear programming and the calculation of extreme pathways as described, for example, in Schilling et al., *J. Theor. Biol.* 203:229-248 (2000); Schilling et al., *Biotech. Bioeng.* 71:286-306 (2000) and Schilling et al., *Biotech. Prog.* 15:288-295 (1999), can be used to determine such phenotypic capabilities.

As described above, one constraints-based method used in the computational programs applicable to the invention is flux balance analysis. Flux balance analysis is based on flux balancing in a steady state condition and can be performed as described in, for example, Varma and Palsson, *Biotech. Bioeng.* 12:994-998 (1994). Flux balance approaches have been applied to reaction networks to simulate or predict systemic properties of, for example, adipocyte metabolism as described in Fell and Small, *J. Biochem.* 138:781-786 (1986), acetate secretion from *E. coli* under ATP maximization conditions as described in Majewski and Domach, *Biotech. Bioeng.* 35:732-738 (1990) or ethanol secretion by yeast as described in Vanrolleghem et al., *Biotech. Prog.* 12:434-448 (1996). Additionally, this approach can be used to predict or simulate the growth of *S. cerevisiae* on a variety of single-carbon sources as well as the metabolism of *H. influenzae* as described in Edwards and Palsson, *Proc. Natl. Acad. Sci.* 97:5528-5533 (2000), Edwards and Palsson, *J. Bio. Chem.* 274:17410-17416 (1999) and Edwards et al., *Nature Biotech.* 19:125-130 (2001).

Once the solution space has been defined, it can be analyzed to determine possible solutions under various conditions. This computational approach is consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration of the invention, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The ability of a cell or organism to obligatory couple growth to the production of a biochemical product can be illustrated in the context of the biochemical production limits of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. The production of a desired biochemical generally is in direct competition with biomass formation for intracellular resources. Under these circumstances, enhanced rates of biochemical production will necessarily result in sub-maximal growth rates. The knockouts suggested by the above metabolic modeling and simulation programs such as OptKnock are designed to restrict the allowable solution boundaries forcing a change in metabolic behavior from the wild-type strain. Although the actual solution boundaries for a given strain will expand or contract as the substrate uptake rate(s) increase or decrease, each experimental point will lie within its calculated solution boundary. Plots such as these allow accurate predictions of how close the designed strains are to their performance limits which also indicates how much room is available for improvement.

The OptKnock mathematical framework is exemplified herein for pinpointing gene deletions leading to growth-coupled biochemical production (see Example XXX). The procedure builds upon constraint-based metabolic modeling which narrows the range of possible phenotypes that a cellular system can display through the successive imposition of governing physico-chemical constraints, Price et al., *Nat Rev Microbiol*, 2: 886-97 (2004). As described above, constraint-based models and simulations are well known in the art and generally invoke the optimization of a particular cellular objective, subject to network stoichiometry, to suggest a likely flux distribution.

Briefly, the maximization of a cellular objective quantified as an aggregate reaction flux for a steady state metabolic network comprising a set $N=\{1, \ldots, N\}$ of metabolites and a set $M=\{1, \ldots, M\}$ of metabolic reactions is expressed mathematically as follows:

$$\text{maximize } v_{cellular\ objective}$$

$$\text{subject to } \sum_{j=1}^{M} S_{ij} v_j = 0, \forall\, i \in N$$

-continued $$v_{substrate} = v_{substrate\_uptake} \text{mmol}/gDW \cdot \text{hr} \ \forall\, i \in \{\text{limiting substrate(s)}\}$$

$$v_{atp} \geq v_{atp\_main} \text{mmol}/gDW \cdot \text{hr}$$

$$v_j \geq 0, \forall\, j \in \{irrev. \text{reactions}\}$$

where $S_{ij}$ is the stoichiometric coefficient of metabolite i in reaction j, $v_j$ is the flux of reaction j, $v_{substrate\_uptake}$ represents the assumed or measured uptake rate(s) of the limiting substrate(s), and $v_{atp\_main}$ is the non-growth associated ATP maintenance requirement. The vector v includes both internal and external fluxes. In this study, the cellular objective is often assumed to be a drain of biosynthetic precursors in the ratios required for biomass formation, Neidhardt, F. C. et al., 2nd ed. 1996, Washington, D.C.: ASM Press. 2 v. (xx, 2822, lxxvi). The fluxes are generally reported per 1 gDW·hr (gram of dry weight times hour) such that biomass formation is expressed as g biomass produced/gDW·hr or 1/hr.

The modeling of gene deletions, and thus reaction elimination, first employs the incorporation of binary variables into the constraint-based approach framework, Burgard et al., *Biotechnol Bioeng*, 74: 364-375 (2001), Burgard et al., *Biotechnol Prog*, 17: 791-797 (2001). These binary variables, $$y_j = \begin{cases} 1, & \text{if reaction flux } v_j \text{ is active} \\ 0, & \text{if reaction flux } v_j \text{ is not active} \end{cases}, \forall\, j \in M$$

assume a value of 1 if reaction j is active and a value of 0 if it is inactive. The following constraint, $$v_j^{min} \cdot y_j \leq v_j \leq v_j^{max} \cdot y_j, \forall j \in M$$

ensures that reaction flux $v_j$ is set to zero only if variable $y_j$ is equal to zero. Alternatively, when $y_j$ is equal to one, $v_j$ is free to assume any value between a lower $v_j^{min}$ and an upper $v_j^{max}$ bound. Here, $v_j^{min}$ and $v_j^{max}$ are identified by minimizing and maximizing, respectively, every reaction flux subject to the network constraints described above, Mahadevan et al., *Metab Eng*, 5: 264-76 (2003).

Optimal gene/reaction knockouts are identified by solving a bilevel optimization problem that chooses the set of active reactions ($y_j=1$) such that an optimal growth solution for the resulting network overproduces the chemical of interest. Schematically, this bilevel optimization problem is illustrated in FIG. 2. Mathematically, this bilevel optimization problem is expressed as the following bilevel mixed-integer optimization problem:

$$\underset{y_j}{\text{maximize}} \ v_{chemical} \quad (OptKnock)$$

$$\begin{cases} \text{subject to} & \underset{y_j}{\text{maximize}} & v_{biomass} \\ & \text{subject to} & \sum_{j=1}^{M} S_{ij} v_j = 0 & \forall\, i \in N \\ & & v_{substrate} = v_{substrate\_uptake} & \forall\, i \in \{\text{limiting substrate(s)}\} \\ & & v_{atp} \geq v_{atp\_main} \\ & & v_{biomass} \geq v_{biomass}^{target} \end{cases}$$

-continued $$v_j^{min} \cdot y_j \leq v_j \leq v_j^{max} \cdot y_j, \forall j \in M$$

$$\sum_{j=M^{forward}} (1 - y_j) = K$$

$$y_j \in \{0, 1\}, \forall j \in M$$

where $v_{chemical}$ is the production of the desired target product, for example adipate, 6-ACA and/or HMDA, or other biochemical product, and K is the number of allowable knockouts. Note that setting K equal to zero returns the maximum biomass solution of the complete network, while setting K equal to one identifies the single gene/reaction knockout ($y_j$=0) such that the resulting network involves the maximum overproduction given its maximum biomass yield. The final constraint ensures that the resulting network meets a minimum biomass yield. Burgard et al., Biotechnol Bioeng, 84: 647-57 (2003), provide a more detailed description of the model formulation and solution procedure. Problems containing hundreds of binary variables can be solved in the order of minutes to hours using CPLEX 8.0, GAMS: The Solver Manuals. 2003: GAMS Development Corporation, accessed via the GAMS, Brooke et al., GAMS Development Corporation (1998), modeling environment on an IBM RS6000-270 workstation. The OptKnock framework has already been able to identify promising gene deletion strategies for biochemical overproduction, Burgard et al., Biotechnol Bioeng, 84: 647-57 (2003), Pharkya et al., Biotechnol Bioeng, 84: 887-899 (2003), and establishes a systematic framework that will naturally encompass future improvements in metabolic and regulatory modeling frameworks.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., Biotechnol. Prog. 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., Biotechnol. Bioeng. 84:647-657 (2003)).

An in silico stoichiometric model of E. coli metabolism can be employed to identify essential genes for metabolic pathways as exemplified previously and described in, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

Given the teachings and guidance provided herein, those skilled in the art will understand that to disrupt an enzymatic reaction the catalytic activity of the one or more enzymes involved in the reaction is to be disrupted. Disruption can occur by a variety of means including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity disruption can occur by a genetic alteration that reduces or destroys the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits in order to form an active complex, by destruction of the catalytic subunit of the multimeric complex or by both. Other functions of multimeric protein association and activity also can be targeted in order to disrupt a metabolic reaction of the invention. Such other functions are well known to those skilled in the art. Further, some or all of the functions of a single polypeptide or multimeric complex can be disrupted according to the invention in order to reduce or abolish the catalytic activity of one or more enzymes involved in a reaction or metabolic modification of the invention. Similarly, some or all of enzymes involved in a reaction or metabolic modification of the invention can be disrupted so long as the targeted reaction is reduced or eliminated.

Given the teachings and guidance provided herein, those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods of the invention and incorporated into the non-naturally occurring microbial organisms of the invention in order to achieve the growth-coupled product production. Exemplary disruptions to confer increased production of adipate, 6-ACA and/or HMDA are described in Example XXX and Tables 14-16.

Employing the methods exemplified above, the methods of the invention allow the construction of cells and organisms that increase production of a desired product, for example, by coupling the production of a desired product to growth of the cell or organism engineered to harbor the identified genetic alterations. As disclosed herein, metabolic alterations have been identified that couple the production of 6-aminocaproic acid, caprolactam, hexamethylenediamine or levulinic acid to growth of the organism. Microbial organism strains constructed with the identified metabolic alterations produce elevated levels, relative to the absence of the metabolic alterations, of 6-aminocaproic acid, caprolactam, hexamethylenediamine or levulinic acid during the exponential growth phase. These strains can be beneficially used for the commercial production of 6-aminocaproic acid, caprolactam, hexamethylenediamine or levulinic acid in continuous fermentation process without being subjected to the negative selective pressures described previously. Although exemplified herein as metabolic alterations, in particular one or more gene disruptions, that confer growth coupled production of 6-aminocaproic acid, caprolactam, hexamethylenediamine or levulinic acid, it is understood that any gene disruption that increases the production of 6-aminocaproic acid, caprolactam, hexamethylenediamine or levulinic acid can be introduced into a host microbial organism, as desired.

Therefore, the methods of the invention provide a set of metabolic modifications that are identified by an in silico method such as OptKnock. The set of metabolic modifications can include functional disruption of one or more metabolic reactions including, for example, disruption by gene deletion. For 6-aminocaproic acid, caprolactam, hexamethylenediamine or levulinic acid production, metabolic modifications can be selected from the set of metabolic modifications listed in Tables 14-16 (see Example XXX).

Also provided is a method of producing a non-naturally occurring microbial organisms having stable growth-coupled production of 6-aminocaproic acid, caprolactam, hexamethylenediamine or levulinic acid. The method can include identifying in silico a set of metabolic modifications that increase production of 6-aminocaproic acid, caprolactam, hexamethylenediamine or levulinic acid, for example, increase production during exponential growth; genetically modifying an organism to contain the set of metabolic modifications that increase production of 6-aminocaproic acid, caprolactam, hexamethylenediamine or levulinic acid, and culturing the genetically modified organism. If desired, culturing can include adaptively evolving the genetically modified organism under conditions requiring production of 6-aminocaproic acid, caprolactam, hexamethylenediamine or levulinic acid. The methods of the invention are applicable to bacterium, yeast and fungus as well as a variety of other cells and microorganism, as disclosed herein.

Thus, the invention provides a non-naturally occurring microbial organism comprising one or more gene disruptions that confer increased production of 6-aminocaproic acid, caprolactam, hexamethylenediamine or levulinic acid. In one embodiment, the one or more gene disruptions confer growth-coupled production of 6-aminocaproic acid, caprolactam, hexamethylenediamine or levulinic acid, and can, for example, confer stable growth-coupled production of 6-aminocaproic acid, caprolactam, hexamethylenediamine or levulinic acid. In another embodiment, the one or more gene disruptions can confer obligatory coupling of 6-aminocaproic acid, caprolactam, hexamethylenediamine or levulinic acid production to growth of the microbial organism. Such one or more gene disruptions reduce the activity of the respective one or more encoded enzymes.

The non-naturally occurring microbial organism can have one or more gene disruptions included in a metabolic modification listed in Tables 14-16. As disclosed herein, the one or more gene disruptions can be a deletion. Such non-naturally occurring microbial organisms of the invention include bacteria, yeast, fungus, or any of a variety of other microorganisms applicable to fermentation processes, as disclosed herein.

Thus, the invention provides a non-naturally occurring microbial organism, comprising one or more gene disruptions, where the one or more gene disruptions occur in genes encoding proteins or enzymes where the one or more gene disruptions confer increased production of 6-aminocaproic acid, caprolactam, hexamethylenediamine or levulinic acid in the organism. The production of 6-aminocaproic acid, caprolactam, hexamethylenediamine or levulinic acid can be growth-coupled or not growth-coupled. In a particular embodiment, the production of 6-aminocaproic acid, caprolactam, hexamethylenediamine or levulinic acid can be obligatorily coupled to growth of the organism, as disclosed herein.

The invention provides non naturally occurring microbial organisms having genetic alterations such as gene disruptions that increase production of 6-aminocaproic acid, caprolactam, hexamethylenediamine or levulinic acid, for example, growth-coupled production of 6-aminocaproic acid, caprolactam, hexamethylenediamine or levulinic acid. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Sets of metabolic alterations or transformations that result in increased production and elevated levels of 6-aminocaproic acid, caprolactam, hexamethylenediamine or levulinic acid biosynthesis are exemplified in Tables 14-16 (see Example XXX). Each alteration within a set corresponds to the requisite metabolic reaction that should be functionally disrupted. Functional disruption of all reactions within each set can result in the increased production of 6-aminocaproic acid, caprolactam, hexamethylenediamine or levulinic acid by the engineered strain during the growth phase. The corresponding reactions to the referenced alterations can be found in Tables 14-16 (see Example XXX), and the gene or genes that encode enzymes or proteins that carry out the reactions are set forth in Tables 14-16.

For example, for each strain exemplified in Tables 14-16, the metabolic alterations that can be generated for 6-aminocaproic acid, caprolactam, hexamethylenediamine or levulinic acid production are shown in each row. These alterations include the functional disruption of the reactions shown in Tables 14-16. Each of these non-naturally occurring alterations result in increased production and an enhanced level of 6-aminocaproic acid, caprolactam, hexamethylenediamine or levulinic acid production, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

It is understood that modifications which do not substantially affect the activity of the various embodiments of this invention are also provided within the definition of the invention provided herein. Accordingly, the following examples are intended to illustrate but not limit the present invention.

Example I

Reverse Adipate Degradation Pathway

This example describes an exemplary adipate synthesis pathway via a reverse adipate degradation pathway.

Organisms such as *Penicillium chrysogenum* have the ability to naturally degrade adipate (Thykaer et al., *Metab. Eng.* 4:151-158. (2002)). The mechanism is similar to the oxidation of fatty acids (see FIG. 1). The first step in adipate degradation is an ATP-dependent reaction that activates adipate with CoA. The second reaction is catalyzed by a dehydrogenase that forms 5-carboxy-2-pentenoyl-CoA from adipyl-CoA. During peroxisomal adipate degradation, the dehydrogenase enzyme contains FAD, which accepts the electrons and then transfers them directly to oxygen. A catalase enzyme dissipates the $H_2O_2$ formed by the reduction of oxygen. In mitochondrial fatty acid oxidation, the FAD from the dehydrogenase transfers electrons directly to the electron transport chain. A multi-functional fatty acid oxidation protein in eukaryotes such as *S. cerevisiae* and *P. chrysogenum* carries out the following hydratase and dehydrogenase steps. The final step is an acyl transferase that splits 3-oxoadipyl CoA into acetyl-CoA and succinyl-CoA.

A highly efficient pathway for the production of adipate is achieved through genetically altering a microorganism such that similar enzymatic reactions are employed for adipate synthesis from succinyl-CoA and acetyl-CoA (see FIG. 2). Successful implementation of this entails expressing the appropriate genes, tailoring their expression, and altering culture conditions so that high acetyl-CoA, succinyl-CoA, and/or redox (for example, NADH/NAD+) ratios will drive the metabolic flux through this pathway in the direction of adipate synthesis rather than degradation. Strong parallels to butyrate formation in *Clostridia* (Kanehisa and Goto, *Nucl. Acids Res.* 28:27-30 (2000)) support that each step in the adipate synthesis pathway is thermodynamically feasible with reaction directionality governed by the concentrations of the participating metabolites. The final step, which forms adipate from adipyl-CoA, can take place either via a synthetase, phosphotransadipylase/kinase, transferase, or hydrolase mechanism.

The maximum theoretical yields of adipate using this pathway were calculated both in the presence and absence of an external electron acceptor such as oxygen. These calculations show that the pathway can efficiently transform glucose into adipate and $CO_2$ under anaerobic conditions with a 92% molar yield (Table 1). The production of adipate using this pathway does not require the uptake of oxygen as NAD+ can be regenerated in the two hydrogenase steps that form 3-hydroxyadipyl-CoA and adipyl-CoA (see FIG. 2). Further, the pathway is favorable energetically as up to 1.55 moles of ATP are formed per mole of glucose consumed at the maximum theoretical yield of adipate assuming either a synthetase, phosphotransadipylase/kinase, or transferase mechanism for the final conversion step. The ATP yield can be further improved to 2.47 moles of ATP produced per mole of glucose if phosphoenolpyruvate carboxykinase (PPCK) is assumed to function in the ATP-generating direction towards oxaloacetate formation. Maximum ATP yield calculations were then performed assuming that the adipyl-CoA to adipate transformation is a hydrolysis step. This reduces the maximum ATP yields at maximum adipate production to 0.85 and 1.77 mole ATP per mole glucose consumed if PPCK is assumed irreversible and reversible, respectively. Nevertheless, these ATP yields are sufficient for cell growth, maintenance, and production.

TABLE 1

The maximum theoretical yields of adipate and the associated ATP yields per mole of glucose using the reverse degradation pathway assuming the final step in the pathway is a synthetase, phosphotransadipylase/kinase, or transferase.

|  | Aerobic | Anaerobic |
| --- | --- | --- |
| Adipate Yield | 0.92 | 0.92 |
| Max ATP yield @ max adipate yield | 1.55 | 1.55 |
| Max ATP yield @ max adipate yield PPCK assumed | 2.47 | 2.47 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of adipate, one or more exogenous DNA sequence(s) are expressed in a suitable host microorganism. In addition, the microorganisms can have endogenous gene(s) functionally deleted. These modifications allow the production of adipate using renewable feedstock.

Below is described a number of biochemically characterized candidate genes that encode enzymes that catalyze each step of the reverse adipate degradation pathway in a production host. Although described using *E. coli* as a host organism to engineer the pathway, essentially any suitable host organism can be used. Specifically listed are genes that are native to *E. coli* as well as genes in other organisms that can be applied to catalyze the appropriate transformations when properly cloned and expressed.

Referring to FIG. 2, step 1 involves succinyl CoA:acetyl CoA acyl transferase ((3-ketothiolase). The first step in the pathway combines acetyl-CoA and succinyl-CoA to form 3-oxoadipyl-CoA. The gene products encoded by pcaF in *Pseudomonas* strain B13 (Kaschabek et al., *J. Bacteriol.* 184:207-215 (2002)), phaD in *Pseudomonas putida* U (Olivera et al., *Proc. Natl. Acad. Sci. USA* 95:6419-6424 (1998)), paaE in *Pseudomonas fluorescens* ST (Di Gennaro et al., *Arch. Microbiol.* 188:117-125 (2007)), and paaJ from *E. coli* (Nogales et al., *Microbiol.* 153:357-365 (2007)) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the first step in adipate synthesis shown in FIG. 2. For example, the ketothiolase phaA from *R. eutropha* combines two molecules of acetyl-CoA to form acetoacetyl-CoA (Sato et al., *J. Biosci. Bioengineer.* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180: 1979-1987 (1998)) in *R. eutropha*. Additional candidates are found in *Burkholderia ambifaria* AMMD. The protein sequences for the above-mentioned gene products are well known in the art and can be accessed in the public databases such as GenBank using the following GI numbers and/or GenBank identifiers:

| Gene name | GI# | GenBank Accession # | Organism |
| --- | --- | --- | --- |
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| paaE | 106636097 | ABF82237.1 | *Pseudomonas fluorescens* |
| Bamb_0447 | 115350501 | YP_772340 | *Burkholderia ambifaria* AMMD |

These exemplary sequences can be used to identify homologue proteins in GenBank or other databases through sequence similarity searches (for example, BLASTp). The resulting homologue proteins and their corresponding gene sequences provide additional exogenous DNA sequences for transformation into *E. coli* or other suitable host microorganisms to generate production hosts.

For example, orthologs of paaJ from *Escherichia coli* K12 can be found using the following GI numbers and/or GenBank identifiers:

| GI# | GenBank Accession # | Organism |
| --- | --- | --- |
| 152970031 | YP_001335140.1 | *Klebsiella pneumoniae* |
| 157371321 | YP_001479310.1 | *Serratia proteamaculans* |
| 3253200 | AAC24332.1 | *Pseudomonas putida* |

Example orthologs of pcaF from *Pseudomonas knackmussii* can be found using the following GI numbers and/or GenBank identifiers:

| GI# | GenBank Accession # | Organism |
| --- | --- | --- |
| 4530443 | AAD22035.1 | *Streptomyces* sp. 2065 |
| 24982839 | AAN67000.1 | *Pseudomonas putida* |
| 115589162 | ABJ15177.1 | *Pseudomonas aeruginosa* |

Additional native candidate genes for the ketothiolase step include atoB, which can catalyze the reversible condensation of 2 acetyl-CoA molecules (Sato et al., *J. Biosci. Bioengineer.* 103:38-44 (2007)), and its homolog yqeF. Non-native gene candidates include phaA (Sato et al., supra, 2007) and bktB (Slater et al., *J. Bacteriol.* 180:1979-1987 (1998)) from *R. eutropha*, and the two ketothiolases, thiA and thiB, from *Clostridium acetobutylicum* (Winzer et al., *J. Mol. Microbiol. Biotechnol.* 2:531-541 (2000)). The protein sequences for each of these exemplary gene products can be found using the following GI numbers and/or GenBank identifiers:

| Gene name | GI# | GenBank Accession # | Organism |
| --- | --- | --- | --- |
| atoB | 16130161 | NP_416728.1 | *Escherichia coli* |
| yqeF | 90111494 | NP_417321.2 | *Escherichia coli* |
| phaA | 113867452 | YP_725941 | *Ralstonia eutropha* |
| bktB | 3046397 | AAC38322.1 | *Ralstonia eutropha* |
| thiA | 15896127 | NP_349476.1 | *Clostridium acetobutylicum* |
| thiB | 15004782 | NP_149242.1 | *Clostridium acetobutylicum* |

It is less desirable to use the thiolase-encoding genes fadA and fadB, genes in fatty acid degradation pathway in *E. coli*, in this exemplary pathway. These genes form a complex that encodes for multiple activities, most of which are not desired in this pathway.

Referring to FIG. 2, step 2 involves 3-hydroxyacyl-CoA dehydrogenase. The second step in the pathway involves the reduction of 3-oxoadipyl-CoA to 3-hydroxyadipyl-CoA. The gene products encoded by phaC in *Pseudomonas putida* U (Olivera et al., *Proc. Natl. Acad. Sci. USA* 95:6419-6424 (1998)) and paaC in *Pseudomonas fluorescens* ST (Di Gennaro et al., *Arch. Microbiol.* 188:117-125 (2007)) catalyze the reverse reaction, that is, the oxidation of 3-hydroxyadipyl-CoA to form 3-oxoadipyl-CoA, during the catabolism of phenylacetate or styrene. The reactions catalyzed by such dehydrogenases are reversible and accordingly these genes represent candidates to carry out the second step of adipate synthesis as shown in FIG. 2. A similar transformation is also carried out by the gene product of hbd in *Clostridium acetobutylicum* (Atsumi et al., *Metab. Eng.* (epub Sep. 14, 2007); Boynton et al., *J. Bacteriol.* 178:3015-3024 (1996)). This enzyme converts acetoacetyl-CoA to 3-hydroxybutyryl-CoA. Lastly, given the proximity in *E. coli* of paaH to other genes in the phenylacetate degradation operon (Nogales et al., *Microbiol.* 153:357-365 (2007)) and the fact that paaH mutants cannot grow on phenylacetate (Ismail et al., *Eur. J. Biochem.* 270:3047-3054 (2003)), it is expected that the *E. coli* paaH gene encodes a 3-hydroxyacyl-CoA dehydrogenase. The protein sequences for each of these exemplary gene products can be found using the following GI numbers and/or GenBank identifiers:

| Gene name | GI# | GenBank Accession # | Organism |
|---|---|---|---|
| paaH | 16129356 | NP_415913.1 | *Escherichia coli* |
| phaC | 26990000 | NP_745425.1 | *Pseudomonas putida* |
| paaC | 106636095 | ABF82235.1 | *Pseudomonas fluorescens* |
| hbd | 15895965 | NP_349314.1 | *Clostridium acetobutylicum* |

Referring to FIG. 2, step 3 involves 3-hydroxyadipyl-CoA dehydratase. The gene product of crt from *C. acetobutylicum* catalyzes the dehydration of 3-hydroxybutyryl-CoA to crotonyl-CoA (see FIG. 2) (Atsumi et al., supra, 2007; Boynton et al., *J. Bacteriol.* 178:3015-3024 (1996)). Homologs of this gene are strong candidates for carrying out the third step in the adipate synthesis pathway exemplified in FIG. 2. In addition, genes known to catalyze the hydroxylation of double bonds in enoyl-CoA compounds represent additional candidates given the reversibility of such enzymatic transformations. For example, the enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)) and thus represent additional candidates for incorporation into *E. coli*. The deletion of these genes precludes phenylacetate degradation in *P. putida*. The paaA and paaB from *P. fluorescens* catalyze analogous transformations (Olivera et al., supra, 1998). Lastly, a number of *Escherichia coli* genes have been shown to demonstrate enoyl-CoA hydratase functionality including maoC (Park and Lee, *J. Bacteriol.* 185:5391-5397 (2003)), paaF (Ismail et al., *Eur. J. Biochem.* 270:3047-3054 (2003); Park and Lee, *Biotechnol. Bioeng.* 86:681-686 (2004); Park and Lee, *Appl. Biochem. Biotechnol.* 113-116:335-346 (2004)), and paaG (Ismail et al., supra, 2003; Park and Lee, supra, 2004; Park and Lee, supra, 2004). The protein sequences for each of these exemplary gene products can be found using the following GI numbers and/or GenBank identifiers:

| Gene name | GI# | GenBank Accession # | Organism |
|---|---|---|---|
| maoC | 16129348 | NP_415905.1 | *Escherichia coli* |
| paaF | 16129354 | NP_415911.1 | *Escherichia coli* |
| paaG | 16129355 | NP_415912.1 | *Escherichia coli* |
| cr | 15895969 | NP_349318.1 | *Clostridium acetobutylicum* |
| paaA | 26990002 | NP_745427.1 | *Pseudomonas putida* |
| paaB | 26990001 | NP_745426.1 | *Pseudomonas putida* |
| phaA | 106636093 | ABF82233.1 | *Pseudomonas fluorescens* |
| phaB | 106636094 | ABF82234.1 | *Pseudomonas fluorescens* |

Alternatively, beta-oxidation genes are candidates for the first three steps in adipate synthesis. Candidate genes for the proposed adipate synthesis pathway also include the native fatty acid oxidation genes of *E. coli* and their homologs in other organisms. The *E. coli* genes fadA and fadB encode a multienzyme complex that exhibits ketoacyl-CoA thiolase, 3-hydroxyacyl-CoA dehydrogenase, and enoyl-CoA hydratase activities (Yang et al., *Biochem.* 30:6788-6795 (1991); Yang et al., *J. Biol. Chem.* 265:10424-10429 (1990); Yang et al., *J. Biol. Chem.* 266:16255 (1991); Nakahigashi and Inokuchi, *Nucl. Acids Res.* 18: 4937 (1990)). These activities are mechanistically similar to the first three transformations shown in FIG. 2. The fadA and fadB genes encode similar functions and are naturally expressed only anaerobically (Campbell et al., *Mol. Microbiol.* 47:793-805 (2003)). These gene products naturally operate to degrade short, medium, and long chain fatty-acyl-CoA compounds to acetyl-CoA, rather than to convert succinyl-CoA and acetyl-CoA into 5-carboxy-2-pentenoyl-CoA as proposed in FIG. 2. However, it is well known that the ketoacyl-CoA thiolase, 3-hydroxyacyl-CoA dehydrogenase, and enoyl-CoA hydratase enzymes catalyze reversible transformations. Furthermore, directed evolution and related approaches can be applied to tailor the substrate specificities of the native beta-oxidation machinery of *E. coli*. Thus these enzymes or homologues thereof can be applied for adipate production. If the native genes operate to degrade adipate or its precursors in vivo, the appropriate genetic modifications are made to attenuate or eliminate these functions. However, it may not be necessary since a method for producing poly[(R)-3-hydroxybutyrate] in *E. coli* that involves activating fadB, by knocking out a negative regulator, fadR, and co-expressing a non-native ketothiolase, phaA from *Ralstonia eutropha*, has been described (Sato et al., *J. Biosci. Bioeng.* 103:38-44 (2007)). This work clearly demonstrated that a beta-oxidation enzyme, in particular the gene product of fadB which encodes both 3-hydroxyacyl-CoA dehydrogenase and enoyl-CoA hydratase activities, can function as part of a pathway to produce longer chain molecules from acetyl-CoA precursors. The protein sequences for each of these exemplary gene products can be found using the following GI numbers and/or GenBank identifiers:

| Gene name | GI# | GenBank Accession # | Organism |
|---|---|---|---|
| fadA | 49176430 | YP_026272.1 | *Escherichia coli* |
| fadB | 16131692 | NP_418288.1 | *Escherichia coli* |
| fadI | 16130275 | NP_416844.1 | *Escherichia coli* |
| fadJ | 16130274 | NP_416843.1 | *Escherichia coli* |
| fadR | 16129150 | NP_415705.1 | *Escherichia coli* |

Referring to FIG. 2, step 4 involves 5-carboxy-2-pentenoyl-CoA reductase. Whereas the ketothiolase, dehydrogenase, and enoyl-CoA hydratase steps are generally reversible, the enoyl-CoA reductase step is almost always oxidative and irreversible under physiological conditions (Hoffmeister et al., *J. Biol. Chem.* 280:4329-4338 (2005)). FadE catalyzes this likely irreversible transformation in *E. coli* (Campbell and Cronan, *J. Bacteriol.* 184:3759-3764 (2002)). The pathway requires an enzyme that can reduce a 2-enoyl-CoA intermediate, not one such as FadE that will only oxidize an acyl-CoA to a 2-enoyl-CoA compound. Furthermore, although it has been suggested that *E. coli* naturally possesses enzymes for enoyl-CoA reduction (Mizugaki et al., *J. Biochem.* 92:1649-1654 (1982); Nishimaki et al., *J. Biochem.* 95:1315-1321 (1984)), no *E. coli* gene possessing this function has been biochemically characterized.

One candidate gene for the enoyl-CoA reductase step is the gene product of bcd from *C. acetobutylicum* (Atsumi et al., supra, 2007; Boynton et al., *J. Bacteriol.* 178:3015-3024 (1996)), which naturally catalyzes the reduction of crotonyl-CoA to butyryl-CoA, a reaction similar in mechanism to the desired reduction of 5-carboxy-2-pentenoyl-CoA to adipyl-CoA in the adipate synthesis pathway. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J. Biol. Chem.* 280:4329-4338 (2005)). A construct derived from this sequence following the removal of its mitochondrial targeting leader sequence was cloned in *E. coli*, resulting in an active enzyme (Hoffmeister et al., supra, 2005). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin, *FEBS Lett.* 581:1561-1566 (2007)). The protein sequences for each of these exemplary gene products can be found using the following GI numbers and/or GenBank identifiers:

| Gene name | GI# | GenBank Accession # | Organism |
|---|---|---|---|
| bcd | 15895968 | NP_349317.1 | *Clostridium acetobutylicum* |
| etfA | 15895966 | NP_349315.1 | *Clostridium acetobutylicum* |
| etfB | 15895967 | NP_349316.1 | *Clostridium acetobutylicum* |
| TER | 62287512 | Q5EU90.1 | *Euglena gracilis* |
| TDE0597 | 42526113 | NP_971211.1 | *Treponema denticola* |

Referring to FIG. 2, step 5 involves adipyl-CoA synthetase (also referred to as adipate-CoA ligase), phosphotransadipylase/adipate kinase, adipyl-CoA:acetyl-CoA transferase, or adipyl-CoA hydrolase. From an energetic standpoint, it is desirable for the final step in the adipate synthesis pathway to be catalyzed by an enzyme or enzyme pair that can conserve the ATP equivalent stored in the thioester bond of adipyl-CoA. The product of the sucC and sucD genes of *E. coli*, or homologs thereof, can potentially catalyze the final transformation shown in FIG. 2 should they exhibit activity on adipyl-CoA. The sucCD genes naturally form a succinyl-CoA synthetase complex that catalyzes the formation of succinyl-CoA from succinate with the contaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA. An enzyme exhibiting adipyl-CoA ligase activity can equivalently carry out the ATP-generating production of adipate from adipyl-CoA, here using AMP and PPi as cofactors, when operating in the opposite physiological direction as depicted in FIG. 1. Exemplary CoA-ligases include the rat dicarboxylate-CoA ligase for which the sequence is yet uncharacterized (Vamecq et al., *Biochem. J.* 230:683-693 (1985)), either of the two characterized phenylacetate-CoA ligases from *P. chrysogenum* (Lamas-Maceiras et al., *Biochem. J.* 395, 147-155 (2005); Wang et al., *Biochem. Biophy. Res. Commun.* 360:453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178:4122-4130 (1996)). The protein sequences for each of these exemplary gene products can be found using the following GI numbers and/or GenBank identifiers:

| Gene name | GI# | GenBank Accession # | Organism |
|---|---|---|---|
| sucC | 16128703 | NP_415256.1 | *Escherichia coli* |
| sucD | 1786949 | AAC73823.1 | *Escherichia coli* |

Another option, using phosphotransadipylase/adipate kinase, is catalyzed by the gene products of buk1, buk2, and ptb from *C. acetobutylicum* (Walter et al., *Gene* 134:107-111 (1993); Huang et al., *J. Mol. Microbiol. Biotechnol.* 2:33-38 (2000)), or homologs thereof. The ptb gene encodes an enzyme that can convert butyryl-CoA into butyryl-phosphate, which is then converted to butyrate via either of the buk gene products with the concomitant generation of ATP. The analogous set of transformations, that is, conversion of adipyl-CoA to adipyl-phosphate followed by conversion of adipyl-phosphate to adipate, can be carried out by the buk1, buk2, and ptb gene products. The protein sequences for each of these exemplary gene products can be found using the following GI numbers and/or GenBank identifiers:

| Gene name | GI# | GenBank Accession # | Organism |
|---|---|---|---|
| ptb | 15896327 | NP_349676 | *Clostridium acetobutylicum* |
| buk1 | 15896326 | NP_349675 | *Clostridium acetobutylicum* |
| buk2 | 20137415 | Q97II1 | *Clostridium acetobutylicum* |

Alternatively, an acetyltransferase capable of transferring the CoA group from adipyl-CoA to acetate can be applied. Similar transformations are catalyzed by the gene products of cat1, cat2, and cat3 of *Clostridium kluyveri* which have been shown to exhibit succinyl-CoA, 4-hydroxybutyryl-CoA, and butyryl-CoA acetyltransferase activity, respectively (Sohling and Gottschalk, *J. Bacteriol.* 178:871-880 (1996); Seedorf et al., *Proc. Natl. Acad. Sci. USA* 105:2128-2133 (2008)). The protein sequences for each of these exemplary gene products can be found using the following GI numbers and/or GenBank identifiers:

| Gene name | GI# | GenBank Accession # | Organism |
|---|---|---|---|
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |

Finally, though not as desirable from an energetic standpoint, the conversion of adipyl-CoA to adipate can also be carried out by an acyl-CoA hydrolase or equivalently a thioesterase. The top *E. coli* gene candidate is tesB (Naggert et al., *J. Biol. Chem.* 266:11044-11050 (1991)), which shows high similarity to the human acot8, which is a dicarboxylic acid acetyltransferase with activity on adipyl-CoA (Westin et al., *J. Biol. Chem.* 280:38125-38132 (2005)). This activity has also been characterized in the rat liver (Deana, *Biochem. Int.* 26:767-773 (1992)). The protein sequences for each of these exemplary gene products can be found using the following GI numbers and/or GenBank identifiers:

| Gene name | GI# | GenBank Accession # | Organism |
|---|---|---|---|
| tesB | 16128437 | NP_414986 | *Escherichia coli* |
| acot8 | 3191970 | CAA15502 | *Homo sapiens* |
| acot8 | 51036669 | NP_570112 | *Rattus norvegicus* |

Other native candidate genes include tesA (Bonner and Bloch, *J. Biol. Chem.* 247:3123-3133 (1972)), ybgC (Kuznetsova et al., *FEMS Microbiol. Rev.* 29:263-279 (2005); Zhuang et al., *FEBS Lett.* 516:161-163 (2002)), paaI (Song et al., *J. Biol. Chem.* 281:11028-11038 (2006)), and ybdB (Leduc et al., *J. Bacteriol.* 189:7112-7126 (2007)). The protein sequences for each of these exemplary gene products can be found using the following GI numbers and/or GenBank identifiers:

| Gene name | GI# | GenBank Accession # | Organism |
|---|---|---|---|
| tesA | 16128478 | NP_415027 | *Escherichia coli* |
| ybgC | 16128711 | NP_415264 | *Escherichia coli* |
| paaI | 16129357 | NP_415914 | *Escherichia coli* |
| ybdB | 16128580 | NP_415129 | *Escherichia coli* |

The above description provides an exemplary adipate synthesis pathway by way of a reverse adipate degradation pathway.

Example II

Preparation of an Adipate Producing Microbial Organism Having a Reverse Degradation Pathway This example describes the generation of a microbial organism capable of producing adipate using the reverse degradation pathway.

*Escherichia coli* is used as a target organism to engineer a reverse adipate degradation pathway as shown in FIG. 2. *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in the reverse degradation pathway are expressed in *E. coli* using well known molecular biology techniques (see, for example, Sambrook, supra, 2001; Ausubel supra, 1999). In particular, the paaI (NP 415915.1), paaH (NP 415913.1), and maoC (NP 415905.1) genes encoding the succinyl-CoA:acetyl-CoA acyl transferase, 3-hydroxyacyl-CoA dehydrogenase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities, respectively, are cloned into the pZA33 vector (Expressys, Ruelzheim, Germany) under the PA1/lacO promoter. The two sets of plasmids are transformed into *E. coli* strain MG1655 to express the proteins and enzymes required for adipate synthesis via the reverse degradation pathway.

The resulting genetically engineered organism is cultured in glucose-containing medium following procedures well known in the art (see, for example, Sambrook et al., supra, 2001). The expression of reverse degradation pathway genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., *Biotechnol. Bioengineer.* 84:647-657 (2003)), which is applied to select gene knockouts that collectively result in better production of adipate. Adaptive evolution also can be used to generate better producers of, for example, the acetyl-CoA and succinyl-CoA intermediates or the adipate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the adipate producer to further increase production.

For large-scale production of adipate, the above reverse degradation pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

This example describes the preparation of an adipate producing microbial organism using a reverse degradation pathway.

Example III

Adipate Synthesis Through 3-Oxoadipate

This example describes an exemplary adipate synthesis pathway through 3-oxoadipate.

An additional pathway from that described in Examples I and II that uses acetyl-CoA and succinyl-CoA as precursors for adipate formation and passes through the metabolic intermediate, 3-oxoadipate, is shown in FIG. 3. The initial two transformations in this pathway are the two terminal steps of the degradation pathway for aromatic and choloroaromatic compounds operating in the reverse direction (Kaschabek et al., *J. Bacteriol.* 184:207-215 (2002); Nogales et al., *Microbiol.* 153:357-365 (2007); Ismail et al., *Eur. J. Biochem.* 270:3047-3054 (2003)). Specifically, the first step forms 3-oxoadipyl CoA by the condensation of succinyl- and acetyl-CoA. The second step forms 3-oxoadipate and is reported to be reversible in *Pseudomonas* sp. Strain B13 (Kaschabek et al., *J. Bacteriol.* 184:207-215 (2002)).

The subsequent steps involve reduction of 3-oxoadipate to 3-hydroxyadipate (conversion of a keto group to hydroxyl group), dehydration of 3-hydroxyadipate to yield hexa-2-enedioate, and reduction of hexa-2-enedioate to form adipate. These steps of the pathway are analogous to the conversion of oxaloacetate into succinate via the reductive TCA cycle (see FIG. 4). This supports the steps in the pathway being thermodynamically favorable subject to the presence of appropriate metabolite concentrations. The final reduction step can be carried out either biochemically or by employing a chemical catalyst to convert hexa-2-enedioate into adipate. Chemical hydrogenation can be performed using Pt catalyst on activated carbon as has been described in (Niu et al., *Biotechnol. Prog.* 18:201-211 (2002)).

The maximum theoretical yield of adipate using this pathway is 0.92 mole per mole glucose consumed, and oxygen is not required for attaining these yields (see Table 2). The associated energetics are identical to those of the reverse adipate pathway. Theoretically, ATP formation of up to 1.55 moles is observed per mole of glucose utilized through this pathway. The ATP yield improves to approximately 2.47 moles if phosphoenolpyruvate kinase (PPCK) is assumed to operate in the direction of ATP generation. Interestingly, the product yield can be increased further to 1 mole adipate per mole of glucose consumed if chemical hydrogenation is used for the last step and a 100% efficiency of catalysis is assumed. In this scenario, up to 1.95 moles of ATP are formed theoretically without assuming the reverse functionality of PPCK.

TABLE 2

The maximum theoretical yields of adipate and the associated ATP yields per mole of glucose using the 3-oxoadipate pathway.

| | Final step enzymatic | | Final step chemical hydrogenation | |
|---|---|---|---|---|
| | Aerobic | Anaerobic | Aerobic | Anaerobic |
| Adipate Yield | 0.92 | 0.92 | 1.00 | 1.00 |
| Max ATP yield @ max adipate yield | 1.55 | 1.55 | 1.95 | 1.95 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of adipate, one or more exogenous DNA sequence(s) can be expressed in a host microorganism. In addition, the host microorganism can have endogenous gene(s) functionally deleted. These modifications allow the production of adipate using renewable feedstock.

Described below are a number of biochemically characterized candidate genes capable of encoding enzymes that catalyze each step of the 3-oxoadipate pathway for adipate synthesis. Although this method is described for *E. coli*, one skilled in the art can apply these teachings to any other suitable host organism. Specifically, listed below are genes that are native to *E. coli* as well as genes in other organisms that can be applied to catalyze the appropriate transformations when properly cloned and expressed.

Referring to FIG. 3, step 1 involves succinyl CoA:acetyl CoA acyl transferase (β-ketothiolase). Gene candidates for this enzyme are listed above (FIG. 2, step 1).

Referring to FIG. 3, step 2 involves 3-oxoadipyl-CoA transferase. In this step, 3-oxoadipate is formed by the transfer of the CoA group from 3-oxoadipyl-CoA to succinate. This activity is reported in a two-unit enzyme encoded by pcaI and pcaJ in *Pseudomonas* (Kaschabek et al., *J. Bacteriol.* 184:207-215 (2002)). This enzyme catalyzes a reversible transformation. The protein sequences of exemplary gene products for subunit A of this complex can be found using the following GI numbers and/or GenBank identifiers:

| Gene name | GI# | GenBank Accession # | Organism |
|---|---|---|---|
| pcaI | 24985644 | AAN69545.1 | *Pseudomonas putida* |
| pcaI | 50084858 | YP_046368.1 | *Acinetobacter* sp. ADP1 |
| pcaI | 21224997 | NP_630776.1 | *Streptomyces coelicolor* |

The protein sequences of exemplary gene products for subunit B of this complex can be found using the following GI numbers and/or GenBank identifiers:

| Gene name | GI# | GenBank Accession # | Organism |
|---|---|---|---|
| pcaJ | 26990657 | NP_746082.1 | *Pseudomonas putida* |
| pcaJ | 21224996 | NP_630775.1 | *Streptomyces coelicolor* |
| pcaJ | 141776 | AAC37147.1 | *Acinetobacter* sp. ADP1 |

Referring to FIG. 3, step 3 involves 3-oxoadipate reductase. E. coli has several candidate alcohol dehydrogenases; two that have analogous functions are malate dehydrogenase (mdh) and lactate dehydrogenase (ldhA). While it has not been shown that these two enzymes have broad substrate specificities in E. coli, lactate dehydrogenase from Ralstonia eutropha has been shown to demonstrate high activities on substrates of various chain lengths such as lactate, 2-oxobutyrate, 2-oxopentanoate and 2-oxoglutarate (Steinbuchel and Schlegel, Eur. J. Biochem. 130:329-334 (1983)). An additional non-native enzyme candidate for this step is the mitochondrial 3-hydroxybutyrate dehydrogenase (bdh) from the human heart which has been cloned and characterized (Marks et al., J. Biol. Chem. 267:15459-15463 (1992)). This enzyme is particularly interesting in that it is a dehydrogenase that operates on a 3-hydroxyacid. Given that dehydrogenases are typically reversible, it is expected that this gene product, or a homlog thereof, will be capable of reducing a 3-oxoacid, for example, 3-oxoadipate, to the corresponding 3-hydroxyacid, for example, 3-hydroxyadipate. The protein sequences for each of these exemplary gene products can be found using the following GI numbers and/or GenBank identifiers:

| Gene name | GI# | GenBank Accession # | Organism |
|---|---|---|---|
| mdh | 1789632 | AAC76268.1 | Escherichia coli |
| ldhA | 16129341 | NP_415898.1 | Escherichia coli |
| ldh | 113866693 | YP_725182.1 | Ralstonia eutropha |
| bdh | 177198 | AAA58352.1 | Homo sapiens |

Referring to FIG. 3, step 4 involves 3-hydroxyadipate dehydratase. In this reaction, 3-hydroxyadipate is dehydrated to hexa-2-enedioate. Although no direct evidence for this enzymatic transformation has been identified, most dehydratases catalyze the α, β-elimination of water. This involves activation of the α-hydrogen by an electron-withdrawing carbonyl, carboxylate, or CoA-thiol ester group and removal of the hydroxyl group from the β-position (Martins et al., Proc. Natl. Acad. Sci. USA 101:15645-15649 (2004); Buckel and Golding, FEMS Microbiol. Rev. 22:523-541 (1998)). The protein sequences for exemplary gene products can be found using the following GI numbers and/or GenBank identifiers:

| Gene name | GI# | GenBank Accession # | Organism |
|---|---|---|---|
| acnA | 166215073 | P25516.3 | Escherichia coli |
| fumB | 33112655 | P14407.2 | Escherichia coli |
| ilvD | 146451 | AAA24013.1 | Escherichia coli |

Other good candidates for carrying out this function are the serine dehydratases. These enzymes catalyze a very similar transformation in the removal of ammonia from serine as required in this dehydration step. The protein sequence for exemplary gene product can be found using the following GI number and/or GenBank identifier:

| Gene name | GI# | GenBank Accession # | Organism |
|---|---|---|---|
| dsdA | 2507445 | P00926 | Escherichia coli |

Non-native gene candidates for this transformation have been identified as well. For example, the multi-subunit L-serine dehydratase from Peptostreptococcus asaccharolyticus was shown to complement an E. coli strain deficient in L-serine dehydratase activity (Hofmeister et al., J. Bacteriol. 179:4937-4941 (1997)). Further, a putative 2-(hydroxymethyl)glutarate dehydratase, encoded by the gene hmd in Eubacterium barkeri shows similarity to both α- and β-subunits of [4Fe-4S]-containing bacterial serine dehydratases (Alhapel et al., Proc. Natl. Acad. Sci. USA 103: 12341-12346 (2006)). The protein sequence for exemplary gene product can be found using the following GI number and/or GenBank identifier:

| Gene name | GI# | GenBank Accession # | Organism |
|---|---|---|---|
| Hmd | 86278275 | ABC88407.1 | Eubacterium barkeri |

Referring to FIG. 3, step 5 involves 2-enoate reductase. The final step in the 3-oxoadipate pathway is reduction of the double bond in hexa-3-enedioate to form adipate. Biochemically, this transformation can be catalyzed by 2-enoate reductase (EC 1.3.1.31) known to catalyze the NADH-dependent reduction of a wide variety of α, β-unsaturated carboxylic acids and aldehydes (Rohdich et al., J. Biol. Chem. 276:5779-5787 (2001)). This enzyme is encoded by enr in several species of Clostridia (Giesel and Simon, Arch. Microbiol. 135:51-57 (1983)) including C. tyrobutyricum and C. thermoaceticum (now called Moorella thermoaceticum) (Rohdich, et al., J. Biol. Chem. 276:5779-5787 (2001)). In the recently published genome sequence of C. kluyveri, 9 coding sequences for enoate reductases have been reported, out of which one has been characterized (Seedorf et al., Proc. Natl. Acad. Sci. USA 105:2128-2133 (2008)). The enr genes from both C. tyrobutyricum and C. thermoaceticum have been cloned and sequenced and show 59% identity to each other. The former gene is also found to have approximately 75% similarity to the characterized gene in C. kluyveri (Giesel and Simon, Arch. Microbiol. 135:51-57 (1983)). It has been reported based on these sequence results that enr is very similar to the dienoyl CoA reductase in E. coli (fadH) (Rohdich et al., J. Biol. Chem. 276:5779-5787 (2001)). Several gene candidates thus exist for catalyzing this last step in the 3-oxoadipate pathway and have been listed below. The C. thermoaceticum enr gene has also been expressed in an enzymatically active form in E. coli (Rohdich et al., supra, 2001). The protein sequences for exemplary gene products can be found using the following GI numbers and/or GenBank identifiers:

| Gene name | GI# | GenBank Accession # | Organism |
|---|---|---|---|
| fadH | 16130976 | NP_417552.1 | Escherichia coli |
| enr | 169405742 | ACA54153.1 | Clostridium botulinum A3 str |
| enr | 2765041 | CAA71086.1 | Clostridium tyrobutyricum |
| enr | 3402834 | CAA76083.1 | Clostridium kluyveri |

The above description provides an exemplary adipate synthesis pathway by way of an 3-oxoadipate pathway.

Example IV

Preparation of an Adipate Producing Microbial Organism Having a 3-Oxoadipate Pathway This example describes the generation of a microbial organism capable of producing adipate using the 3-oxoadipate pathway.

*Escherichia coli* is used as a target organism to engineer the 3-oxoadipate pathway as shown in FIG. 3. *E. coli* provides a good host for generating a non-naturally occurring microorganism capable of producing adipate. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce adipate, nucleic acids encoding the enzymes utilized in the 3-oxoadipate pathway are expressed in *E. coli* using well known molecular biology techniques (see, for example, Sambrook, supra, 2001; Ausubel supra, 1999). In particular, the paaJ (NP_415915.1), pcaIJ (AAN69545.1 and NP_746082.1), and bdh (AAA58352.1) genes encoding the succinyl-CoA:acetyl-CoA acyl transferase, 3-oxoadipyl-CoA transferase, and 3-oxoadipate reductase activities, respectively, are cloned into the pZE13 vector (Expressys, Ruelzheim, Germany) under the PA1/lacO promoter. In addition, the acnA (P25516.3) and enr (ACA54153.1) genes encoding 3-hydroxyadipate dehydratase and 2-enoate reductase activities, respectively, are cloned into the pZA33 vector (Expressys, Ruelzheim, Germany) under the PA1/lacO promoter. The two sets of plasmids are transformed into *E. coli* strain MG1655 to express the proteins and enzymes required for adipate synthesis via the 3-oxoadipate pathway.

The resulting genetically engineered organism is cultured in glucose containing medium following procedures well known in the art (see, for example, Sambrook et al., supra, 2001). The expression of the 3-oxoadipate pathway genes for adipate synthesis is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., *Biotechnol. Bioengineer.* 84:647-657 (2003)), which is applied to select gene knockouts that collectively result in better production of adipate. Adaptive evolution also can be used to generate better producers of, for example, the acetyl-CoA and succinyl-CoA intermediates or the adipate product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the adipate producer to further increase production.

For large-scale production of adipate, the 3-oxoadipate pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., *Biotechnol. Bioeng.* 775-779 (2005)).

This example describes the preparation of an adipate-producing microbial organism containing a 3-oxidoadipate pathway.

Example V

Adipate Synthesis Via Cis,Cis-Muconic Acid

This example describes an adipate synthesis pathway previously described (see Niu et al., *Biotechnol. Prog.* 18(2): p. 201-11. 2002; Frost et al., U.S. Pat. No. 5,487,987, issued Jan. 30, 1996).

Figure 5:
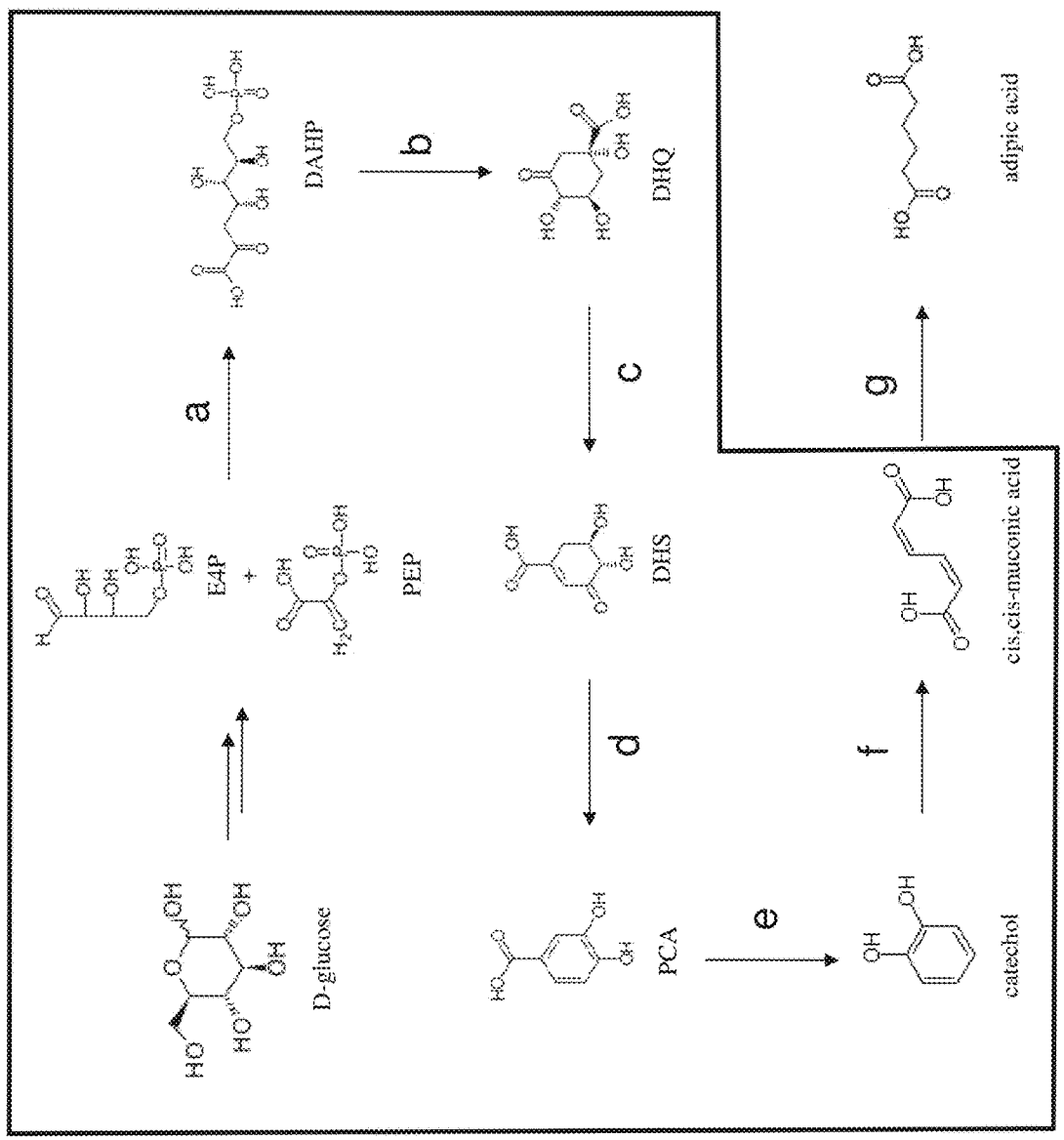
FIG. 5 shows an exemplary pathway for synthesis of adipic acid from glucose via cis,cis-muconic acid. Biosynthetic intermediates (abbreviations): D-erythrose 4-phosphate (E4P), phosphoenolpyruvic acid (PEP), 3-deoxy-D-arabinoheptulosonic acid 7-phosphate (DAHP), 3-dehydroquinic acid (DHQ), 3-dehydroshikimic acid (DHS), protocatechuic acid (PCA). Enzymes (encoding genes) or reaction conditions: (a) DAHP synthase (aroFFBR), (b) 3-dehydroquinate synthase (aroB), (c) 3-dehydroquinate dehydratase (aroD), (d) DHS dehydratase (aroZ), (e) protocatechuate decarboxylase (aroY), (f) catechol 1,2-dioxygenase (catA), (g) 10% Pt/C, H2, 3400 kPa, 25° C. Figure taken from Niu et al., Biotechnol. Prog. 18:201-211 (2002)).

Adipate synthesis via a combined biological and chemical conversion process has been previously described. (Niu et al., *Biotechnol. Prog.* 18:201-211 (2002)) and is shown in FIG. 5. This method is further described in U.S. Pat. No. 5,487,987. Adipate synthesis through this route entails introduction of three heterologous genes into *E. coli* that can convert dehydroshikimate into cis,cis-muconic acid (Niu et al., supra, 2002). A final chemical hydrogenation step leads to the formation of adipic acid. In this step, the pretreated fermentation broth that contained 150 mM cis,cis-muconate was mixed with 10% platinum (Pt) on activated carbon. The hydrogenation reaction was carried out at 3400 KPa of hydrogen pressure for two and a half hour at 250° C. with stirring. The calculated adipate yields are shown in Table 3 assuming either an enzymatic or chemical catalysis step is utilized to convert cis,cis-muconate into adipate. Under aerobic conditions, an 85% molar yield of adipate can be obtained if a chemical reaction is employed for hydrogenation and a 75% molar yield is obtained if an NADH-based hydrogenase is used.

TABLE 3

The maximum theoretical yields of adipate per mole of glucose using the using the cis,cis-muconic acid pathway.

|  | Final step enzymatic | | Final step chemical hydrogenation | |
| --- | --- | --- | --- | --- |
|  | Aerobic | Anaerobic | Aerobic | Anaerobic |
| Adipate Yield | 0.75 | 0.00 | 0.85 | 0.00 |

Although this is an exemplary method, there are disadvantages of this method compared to others, such as those described in Examples I-IV. For example, the first limitation of this method is the lower theoretical yields compared to the reverse adipate degradation and 3-oxoadipate pathways. The second limitation is that the ATP yields of this pathway are negligible. A third limitation of this pathway is that it involves a dioxygenase, necessitating a supply of oxygen to the bioreactor and precluding the option of anaerobic fermentation.

The above description provides an exemplary adipate synthesis pathway by way of a cis,cis-muconic acid pathway Example VI Adipate Synthesis Via Alpha-Ketoadipate This example describes an exemplary adipate synthesis pathway via an alpha-ketoadipate pathway.

Alpha-keto adipate is a known intermediate in lysine biosynthesis in *S. cerevisiae*, and this information was used to identify an additional pathway for adipic acid biosynthesis (see FIG. 6). Conversion of alpha-ketoglutarate to alpha-ketoadipate is catalyzed by homocitrate synthase, homoaconitase, and homoisocitrate dehydrogenase as indicated by dashed arrows in FIG. 6. Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176: 610-620 (1976); Suda et al., *Biochem. Biophys. Res. Commun.* 77:586-591 (1977). Subsequent steps involve a dehydratase for the conversion of alpha-hydroxyadipate into hexa-2-enedioate followed by its reduction to adipic acid. This last step can be catalyzed either by an enzyme or can take place through a chemical reaction as described in Example II. Genes encoding the enzymes for the alpha-ketoadipate pathway are identified as described in Examples I-IV.

The adipate yields associated with this pathway are shown in Table 4. Because of the loss of two $CO_2$ molecules during the conversion of acetyl-CoA to adipate, only 67% of the glucose can be converted into adipate. This is reflected in the molar yields for this pathway under aerobic conditions. The yields are further reduced in the absence of oxygen uptake. Also since the maximum ATP yields under anaerobic conditions are negligible, the engineered organism will have to utilize additional substrate to form energy for cell growth and maintenance under such conditions.

TABLE 4

The maximum theoretical yields of adipate and the associated ATP yields per mole of glucose using the using the alpha-ketoadipate pathway.

|  | Final step enzymatic | | Final step chemical hydrogenation | |
| --- | --- | --- | --- | --- |
|  | Aerobic | Anaerobic | Aerobic | Anaerobic |
| Adipate Yield | 0.67 | 0.45 | 0.67 | 0.40 |
| Max ATP yield @ max adipate yield | 6.17 | 0.00 | 7.50 | 0.00 |

The above description provides an exemplary adipate synthesis pathway by way of an alpha-ketoadipate pathway.

Example VII

Adipate Synthesis Via Lysine Degradation

This example describes an exemplary adipate synthesis pathway via a lysine degradation pathway.

Figure 7:
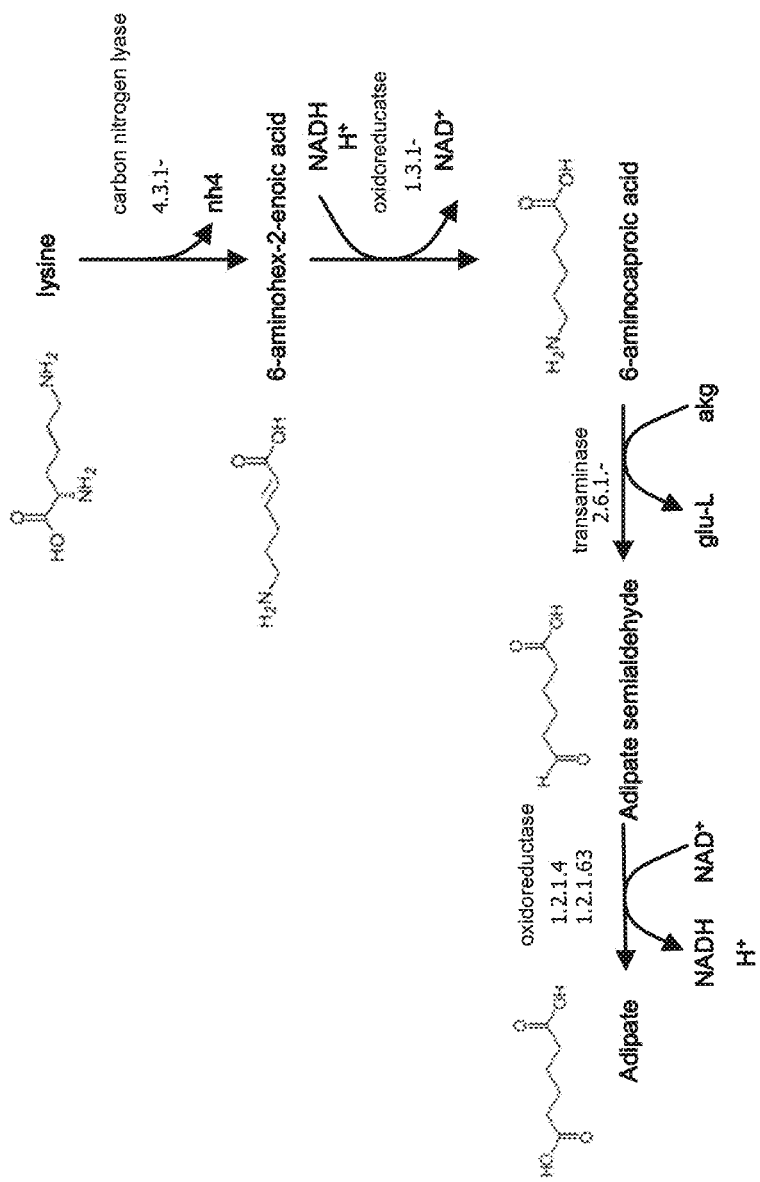
FIG. 7 shows an exemplary pathway for synthesis of adipate using lysine as a starting point.

Two additional pathways for adipate synthesis rely on lysine degradation to form adipate. One pathway starts from alpha-ketoglutarate to form lysine (pathway non-native to *E. coli* and found in *S. cerevisiae*), and the other uses aspartate as a starting point for lysine biosynthesis (pathway native to *E. coli*). FIG. 7 shows adipate formation from lysine. The maximum theoretical yields for adipate, both in the presence and absence of oxygen, using the *E. coli* stoichiometric model are shown in Tables 5 and 6, with alpha-ketoglutarate and aspartate as the respective starting points for lysine. The maximum ATP yields accompanying these theoretical yields were also calculated and are shown in the same tables. These yields are lower in comparison to the other pathways described in Examples I-IV. Genes encoding the enzymes for the alpha-ketoadipate pathway are identified as described in Examples I-IV.

TABLE 5

The maximum theoretical yield of adipate and the accompanying ATP yield per mole of glucose assuming the lysine biosynthesis pathway with alpha-ketoglutarate as a starting point.

|  | Aerobic | Anaerobic |
| --- | --- | --- |
| Adipate Yield | 0.40 | 0.20 |
| Max ATP yield @ max adipate yield | 5.60 | 0.00 |

TABLE 6

The maximum theoretical yield of adipate and the accompanying ATP yield per mole of glucose assuming the lysine biosynthesis pathway with aspartate as a starting point.

|  | Aerobic | Anaerobic |
| --- | --- | --- |
| Adipate Yield | 0.50 | 0.34 |
| Max ATP yield @ max adipate yield | 0.50 | 0.04 |

The above description provides an exemplary adipate synthesis pathway by way of a lysine degradation pathway.

Example VIII

Production of Caprolactam and 6-Aminocaproic Acid Via Adipyl-CoA

This example describes an exemplary caprolactam and/or 6-aminocaproic acid synthesis pathway via an adipyl-CoA pathway.

An exemplary pathway for forming caprolactam and/or 6-aminocaproic acid using adipyl-CoA as the precursor is shown in FIG. 8. The pathway involves a CoA-dependent aldehyde dehydrogenase that can reduce adipyl-CoA to adipate semialdehyde and a transaminase or 6-aminocaproate dehydrogenase that can transform this molecule into 6-aminocaproic acid. The terminal step that converts 6-aminocaproate into caprolactam can be accomplished either via an amidohydrolase or via chemical conversion (Guit and Buijs, U.S. Pat. No. 6,353,100, issued Mar. 7, 2002; Wolters et al., U.S. Pat. No. 5,700,934, issued Dec. 23, 1997; Agterberg et al., U.S. Pat. No. 6,660,857, issued Dec. 9, 2003). The maximum theoretical yield of caprolactam was calculated to be 0.8 mole per mole glucose consumed (see Table 7) assuming that the reverse adipate degradation pathway was complemented with the reaction scheme shown in FIG. 8. The pathway is favorable energetically as up to 0.78 moles of ATP are formed per mole of glucose consumed at the maximum theoretical yield of caprolactam. The ATP yield can be further improved to 1.63 moles of ATP produced per mole of glucose if phosphoenolpyruvate carboxykinase (PPCK) is assumed to function in the ATP-generating direction towards oxaloacetate formation.

The final amidohydrolase step is energetically and redox neutral, and thus the product and ATP molar yields associated with 6-aminocaproic acid production are equivalent to those associated with caprolactam production. Thus one can alternatively envision a microorganism and associated fermentation process that forms 6-aminocaproic acid instead of caprolactam followed by an additional unit operation to dehydrate/cyclize 6-aminocaproic acid to caprolactam.

TABLE 7

The maximum theoretical yield of caprolactam and the accompanying ATP yield per mole of glucose assuming that the reverse fatty acid degradation pathway is complemented with the reaction scheme from FIG. 8.

|  | Aerobic | Anaerobic |
| --- | --- | --- |
| Caprolactam Yield | 0.80 | 0.80 |
| Max ATP yield @ max Caprolactam yield | 0.78 | 0.78 |
| Max ATP yield @ max Caprolactam yield PPCK assumed | 1.63 | 1.63 |

Successfully engineering this pathway involves identifying an appropriate set of enzymes with sufficient activity and specificity. This entails identifying an appropriate set of enzymes, cloning their corresponding genes into a production host, optimizing fermentation conditions, and assaying for product formation following fermentation. To engineer a production host for the production of 6-aminocaproic acid or caprolactam, one or more exogenous DNA sequence(s) can be expressed in a host microorganism. In addition, the microorganism can have endogenous gene(s) functionally deleted. These modifications will allow the production of 6-aminocaproate or caprolactam using renewable feedstock.

Below is described a number of biochemically characterized candidate genes capable of encoding enzymes that catalyze each step of the caprolactam formation pathway described in FIG. 8. Although described for *E. coli*, one skilled in the art can apply these teachings to any other suitable host organism. Specifically, the genes listed are native to *E. coli* or are genes in other organisms that can be applied to catalyze the appropriate transformations when properly cloned and expressed.

Referring to FIG. 8, step 1 involves CoA-dependent aldehyde dehydrogenase. Exemplary genes that encode enzymes for catalyzing the reduction of an acyl-coA to its corresponding aldehyde include the *Acinetobacter calcoaceticus* acr1 encoding a fatty acyl-CoA reductase (Reiser and Somerville, *J. Bacteriol.* 179:2969-2975 (1997)), the *Acinetobacter* sp. M-1 fatty acyl-CoA reductase (Ishige et al., *Appl. Environ. Microbiol.* 68:1192-1195 (2002)) and the sucD gene from *Clostridium kluyveri* (Sohling and Gottschalk, *J. Bacteriol.* 178:871-880 (1996)), which can convert succinyl-CoA to succinate semialdehyde.

| Gene name | GI# | GenBank Accession # | Organism |
| --- | --- | --- | --- |
| acr1 | 50086359 | YP_047869.1 | *Acinetobacter calcoaceticus* |
|  | 18857901 | BAB85476.1 | *Acinetobacter* sp. Strain M-1 |
| sucD | 172046062 | P38947.1 | *Clostridium kluyveri* |

Referring to FIG. 8, step 2 involves transaminase. The second step in the pathway is conversion of the 6-aldehyde to an amine. This transformation can likely be accomplished by gamma-aminobutyrate transaminase (GABA transaminase), a native enzyme encoded by gabT that transfers an amino group from glutamate to the terminal aldehyde of succinyl semialdehyde (Bartsch et al., *J. Bacteriol.* 172:7035-7042 (1990)). The gene product of puuE catalyzes another 4-aminobutyrate transaminase in *E. coli* (Kurihara et al., *J. Biol. Chem.* 280:4602-4608 (2005)). GABA transaminases in *Mus musculus, Pseudomonas fluorescens*, and *Sus scrofa* have been shown to react with 6-aminocaproic acid (Cooper, *Methods Enzymol.* 113:80-82 (1985); Scott and Jakoby, *J. Biol. Chem.* 234:932-936 (1959)). The protein sequences for exemplary gene products can be found using the following GI numbers and/or GenBank identifiers:

| Gene name | GI# | GenBank Accession # | Organism |
| --- | --- | --- | --- |
| gabT | 16130576 | NP_417148.1 | *Escherichia coli* |
| puuE | 16129263 | NP_415818.1 | *Escherichia coli* |
| abat | 37202121 | NP_766549.2 | *Mus musculus* |
| gabT | 70733692 | YP_257332.1 | *Pseudomonas fluorescens* |
| abat | 47523600 | NP_999428.1 | *Sus scrofa* |

Referring to FIG. 8, step 2 can alternatively involve 6-aminocaproate dehydrogenase which comprises the reductive amination of adipate semialdehyde to form 6-aminocaproate. This transformation can be accomplished by lysine-6-dehydrogenase, which naturally converts L-lysine to 2-aminoadipate-6-semialdehyde. Exemplary enzymes can be found in *Geobacillus stearothermophilus* (Heydari et al., *Appl. Environ. Microbiol.* 70(2):937-942 (2004)), *Agrobacterium tumefaciens* (Hashimoto et al., J. Biochem. (Tokyo), 106(1):76-80 (1989); Misono et al., *J. Biochem.* (Tokyo), 105(6):1002-1008 (1989)), and *Achromobacter denitrificans* (Ruldeekulthamrong et al., *BMB Reports* 790-795 (2008)).

| Gene name | GI# | GenBank Accession # | Organism |
| --- | --- | --- | --- |
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

Referring to FIG. 8, step 3 involves amidohydrolase. The final step of caprolactam synthesis is cyclization of 6-aminocaproic acid. This transformation has not been characterized enzymatically but it is very similar to the cyclization of lysine by D-lysine lactamase (EC 3.5.2.11) from *Cryptococcus laurentii* (Fukumura et al., *FEBS Lett.* 89:298-300 (1978)). However, the protein and nucleotide sequences of this enzyme are not currently known and, so far, lysine lactamase activity has not been demonstrated in other organisms.

Plasmids contained in several strains of *Pseudomonas* sp. isolated from soil have been shown to confer ability to grow on caprolactam as a sole carbon source (Boronin et al., *FEMS Microbiol. Lett.* 22:167-170 (1984)); however, associated gene or protein sequences have not been associated with this function to date.

The most closely related candidate enzyme with available sequence information is 6-aminohexanoate-cyclic dimer hydrolase, which has been characterized in *Pseudomonas* sp. and *Flavobacterium* sp. The nylB gene product from *Pseudomonas* sp NK87 was cloned and expressed in *E. coli* (Kanagawa et al., *J. Gen. Microbiol.* 139:787-795 (1993)). The substrate specificity of the enzyme was tested in *Flavobacterium* sp K172 and was shown to react with higher-order oligomers of 6-aminohexanoate but not caprolactam (Kinoshita et al., *Eur. J. Biochem.* 116:547-551 (1981)). The reversibility and ability of 6-aminohexanoate dimer hydrolases in other organisms to react with the desired substrate in the direction of interest can be further tested. The protein sequences for exemplary gene products can be found using the following GI numbers and/or GenBank identifiers:

| Gene name | GI# | GenBank Accession # | Organism |
| --- | --- | --- | --- |
| nylB | 148711 | AAA24929.1 | *Pseudomonas* sp NK87 |
| nylB | 129000 | P13397 | *Flavobacterium* sp K172 |
| nylB | 119961013 | YP_949627.1 | *Arthrobacter aurescens* TC1 |

The above description provides an exemplary pathway to produce caprolactam and/or 6-aminocaproic acid by way of an adipyl-CoA pathway.

Example IX

Preparation of a 6-Aminocaproate or Caprolactam Producing Microbial Organism Having a 3-Oxoadipate Pathway This example describes the generation of a microbial organism capable of producing adipate using the reverse degradation pathway and converting the intracellular adipate to 6-aminocaproate and/or caprolactam.

*Escherichia coli* is used as a target organism to engineer the necessary genes for adipate, 6-aminocaproate, and/or caprolactam synthesis (see FIG. 2 and FIG. 8). *E. coli* provides a good host for generating a non-naturally occurring microorganism capable of producing adipate, 6-aminocaproate, and/or caprolactam. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 6-aminocaproate and/or caprolactam, nucleic acids encoding the enzymes utilized in the reverse adipate degradation pathway and 6-aminocaproate or caprolactam synthesis pathways are expressed in *E. coli* using well known molecular biology techniques (see, for example, Sambrook, supra, 2001; Ausubel, supra, 1999). In particular, the paaJ (NP_415915.1), paaH (NP_415913.1), and maoC (NP_415905.1) genes encoding the succinyl-CoA:acetyl-CoA acyl transferase, 3-hydroxyacyl-CoA dehydrogenase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities, respectively, are cloned into the pZA33 vector (Expressys, Ruelzheim, Germany) under the PA1/lacO promoter. Lastly, the acr1 (YP_047869.1), gabT (NP_417148.1), and nylB (AAA24929.1) genes encoding CoA-dependent aldehyde dehydrogenase, transaminase, and amidohydrolase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for 6-aminocaproate and/or caprolactam synthesis.

The resulting genetically engineered organism is cultured in glucose containing medium following procedures well known in the art (see, for example, Sambrook et al., supra, 2001). The expression of the 6-aminocaproate and caprolactam synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce 6-aminocaproate and/or caprolactam is confirmed using HPLC, gas chromatography-mass spectrometry (GCMS) and/or liquid chromatography-mass spectrometry (LCMS).

Microbial strains engineered to have a functional pathway for the synthesis of 6-aminocaproate and/or caprolactam are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 6-aminocaproate and/or caprolactam. One modeling method is the bilevel optimization approach, OptKnock (Burgard et al., *Biotechnol. Bioengineer.* 84:647-657 (2003)), which is applied to select gene knockouts that collectively result in better production of 6-aminocaproate and/or caprolactam. Adaptive evolution also can be used to generate better producers of, for example, the acetyl-CoA and succinyl-CoA intermediates of the products. Adaptive evolution is performed to improve both growth and production characteristics (Fong and Palsson, *Nat. Genet.* 36:1056-1058 (2004); Alper et al., *Science*

314:1565-1568 (2006)). Based on the results, subsequent rounds of modeling, genetic engineering and adaptive evolution can be applied to the 6-aminocaproate and/or caprolactam producer to further increase production.

For large-scale production of 6-aminocaproate and/or caprolactam, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., Biotechnol. Bioeng. 775-779 (2005)).

Example X

Adipate Synthesis Via 2-Hydroxyadipyl-CoA

This example describes two exemplary adipate synthesis pathways proceeding from alpha-ketoadipate and passing through a 2-hydroxyadipyl-CoA intermediate.

As described in example VI, alpha-ketoadipate is a known intermediate in lysine biosynthesis that can be formed from alpha-ketoglutarate via homocitrate synthase, homoaconitase, and homoisocitrate dehydrogenase. Alpha-ketoadipate can be converted to 2-hydroxyadipyl-CoA by the two routes depicted in FIG. 9. 2-hydroxyadipyl-CoA can be subsequently dehydrated and reduced to adipyl-CoA which can then be converted to adipate as shown in FIG. 9. The maximum yield of adipate from glucose via these pathways is 0.67 mol/mol.

Conversion of alpha-ketoadipate into 2-hydroxyadipate can be catalyzed by 2-ketoadipate reductase, an enzyme reported to be found in rat and in human placenta (Suda et al., Arch. Biochem. Biophys. 176:610-620 (1976); Suda et al., Biochem. Biophys. Res. Commun. 77:586-591 (1977). Alternatively, enzymes capable of reducing alpha-ketoglutarate to 2-hydroxyglutarate may also show activity on alpha-ketoadipate, which is only one carbon atom longer. One such enzyme possessing alpha-ketoglutarate reductase activity is serA of Escherichia coli (Zhao and Winkler, J. Bacteriol. 178(1):232-9 (1996)). Additional exemplary enzymes can be found in Arabidopsis thaliana (Ho, et al., J. Biol. Chem. 274(1):397-402 (1999)) and Haemophilus influenzae.

| Gene name | GI# | GenBank Accession # | Organism |
|---|---|---|---|
| serA | 16130814 | NP_417388.1 | Escherichia coli |
| PGDH | 18394525 | NP_564034 | Arabidopsis thaliana |
| serA | 1173427 | P43885 | Haemophilus influenzae |

Referring to FIG. 9, 2-hydroxyadipate can likely be converted to 2-hydroxyadipyl-CoA by the synthetases, transferases, phosphotransadipylases and kinases described in example I. Alternatively, enzymes with 2-hydroxyglutarate CoA-transferase or glutaconate CoA-transferase activity are likely suitable to transfer a CoA moiety to 2-hydroxyadipate. One example of such an enzyme is encoded by the gctA and gctB genes of Acidaminococcus fermentans (Buckel, et al., Eur. J. Biochem. 118(2):315-321 (1981); Mack, et al., Eur. J. Biochem. 226(1):41-51 (1994)). Similarly, synthetase, transferase, or phosphotransadipylase and kinase activities would be required to convert alpha-ketoadipate into alpha-ketoadipyl-CoA, as depicted in FIG. 9. Conversion of alpha-ketoadipyl-CoA to 2-hydroxyadipyl-CoA can be carried out by an alpha-hydroxyacyl-CoA dehydrogenase enzyme. A similar activity was reported in propionate-adapted E. coli cells whose extracts catalyzed the oxidation of lactyl-CoA to form pyruvyl-CoA (Megraw et al., J. Bacteriol. 90(4): 984-988 (1965)). Additional hydroxyacyl-CoA dehydrogenases were described in example I.

| Gene name | GI# | GenBank Accession # | Organism |
|---|---|---|---|
| gctA | 3122155 | Q59111 | Acidaminococcus fermentans |
| gctB | 3122156 | Q59112 | Acidaminococcus fermentans |

The dehydration of 2-hydroxyadipyl-CoA to form 5-carboxy-2-pentenoyl-CoA can be carried out by a 2-hydroxyacyl-CoA dehydratase. A 2-hydroxyglutaryl-CoA dehydratase system has been characterized in Acidaminococcus fermentans and requires both the hgdA and hgdB subunits and the activator protein, hgdC, for optimal activity (Dutscho et al., Eur. J. Biochem. 181(3):741-746 (1989); Locher et al. J. Mol. Biol. 307(1):297-308; Muller and Buckel, Eur. J. Biochem. 230(2):698-704 (2001); Schweiger et al. Eur. J. Biochem. 169(2):441-448 (1987)). This enzyme system is similar in mechanism to the lactoyl-CoA dehydratase from Clostridium propionicum (Hofmeister and Buckel, Eur. J. Biochem. 206(2):547-552 (1992); Kuchta and Abeles, J. Biol. Chem. 260(24):13181-13189 (1985)). Homologs to hgdA, hgdB, and hgdC exist in several organisms.

| Gene name | GI# | GenBank Accession # | Organism |
|---|---|---|---|
| hgdA | 123112 | P11569 | Acidaminococcus fermentans |
| hgdB | 123113 | P11570 | Acidaminococcus fermentans |
| hgdC | 2506909 | P11568 | Acidaminococcus fermentans |
| hgdA | 225177593 | ZP_03731126.1 | Clostridium sp. M62/1 |
| hgdB | 225177592 | ZP_03731125.1 | Clostridium sp. M62/1 |
| hgdC | 225177594 | ZP_03731127.1 | Clostridium sp. M62/1 |
| hgdA | 19703552 | NP_603114.1 | Fusobacterium nucleatum |
| hgdB | 19703553 | NP_603115.1 | Fusobacterium nucleatum |
| hgdC | 19703551 | NP_603113.1 | Fusobacterium nucleatum |

Conversion of 5-carboxy-2-pentenoyl-CoA to adipate is carried out by the enzymes described in Example I.

The above description provides an exemplary adipate synthesis pathway by way of a 2-hydroxyadipyl-CoA pathway.

Example XI

Preparation of an Adipate Producing Microbial Organism Having a 2-Hydroxyadipyl-CoA Pathway This example describes the generation of a microbial organism capable of producing adipate using a 2-hydroxyadipyl-CoA pathway.

Escherichia coli is used as a target organism to engineer the necessary genes for adipate synthesis (see FIG. 9). E. coli provides a good host for generating a non-naturally occurring microorganism capable of producing adipate. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce adipate, nucleic acids encoding the enzymes utilized in a 2-hydroxyadipyl-CoA to adipate pathway are expressed in E. coli using well known molecular biology techniques (see, for example, Sambrook, supra, 2001; Ausubel, supra, 1999). In particular, the serA (NP_417388.1), gctA (Q59111), and gctB (Q59112)genes encoding the 2-hydroxyadipate dehydrogenase and 2-hydroxyadipyl-CoA:acetyl-CoA transferase activities, respectively, are cloned into the pZE13 vector (Expressys, Ruelzheim, Germany) under the PA1/lacO promoter. In addition, the hgdA (P11569), hgdB (P11570), and hgdC (P11568) genes encoding 2-hydroxyadipyl-CoA dehydratase activity, respectively, are cloned into the pZA33 vector (Expressys, Ruelzheim, Germany) under the PA1/lacO promoter. Further, the bcd (NP_349317.1), etfAB (349315.1 and 349316.1), and sucCD (NP_415256.1 and AAC73823.1) genes encoding 5-carboxy-2-pentenoyl-CoA reductase and adipyl-CoA synthetase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into E. coli strain MG1655 to express the proteins and enzymes required for adipate synthesis.

The resulting genetically engineered organism is cultured in glucose containing medium following procedures well known in the art (see, for example, Sambrook et al., supra, 2001). The expression of the 2-hydroxyadipyl-CoA pathway genes for adipate synthesis is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce adipate is confirmed using HPLC, gas chromatography-mass spectrometry (GCMS) and/or liquid chromatography-mass spectrometry (LCMS).

Microbial strains engineered to have a functional adipate synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of adipate. One modeling method is the bilevel optimization approach, OptKnock (Burgard et al., Biotechnol. Bioengineer. 84:647-657 (2003)), which is applied to select gene knockouts that collectively result in better production of adipate. Adaptive evolution also can be used to generate better producers of, for example, the alpha-ketoadipate intermediate or the adipate product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the adipate producer to further increase production.

For large-scale production of adipate, the 2-hydroxyadipyl-CoA pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at around a pH of 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu), for example, using an Aminex® series of HPLC columns (for example, HPX-87 series) (BioRad), using a refractive index detector for glucose and alcohols, and a UV detector for organic acids (Lin et al., Biotechnol. Bioeng. 775-779 (2005)).

This example describes the preparation of an adipate-producing microbial organism containing a 2-hydroxyadipyl-CoA pathway.

Example XII

Pathways for Production of Hexamethylenediamine, Caprolactam and 6-Aminocaproic Acid This example describes exemplary pathways for production of hexamethylenediamine, caprolactam and 6-aminocaproic acid.

Described below are various pathways leading to the production of caprolactam, hexamethylenediamine (HMDA), or 6-aminocaproate from common central metabolites. The first described pathway entails the activation of 6-aminocaproate to 6-aminocaproyl-CoA by a transferase or synthase enzyme (FIG. 10, Step Q or R) followed by the spontaneous cyclization of 6-aminocaproyl-CoA to form caprolactam (FIG. 10, Step T). The second described pathway entails the activation of 6-aminocaproate to 6-aminocaproyl-CoA (FIG. 10, Step Q or R), followed by a reduction (FIG. 10, Step U) and amination (FIG. 10, Step V or W) to form HMDA. 6-Aminocaproic acid can alternatively be activated to 6-aminocaproyl-phosphate instead of 6-aminocaproyl-CoA. 6-Aminocaproyl-phosphate can spontaneously cyclize to form caprolactam. Alternatively, 6-aminocaproyl-phosphate can be reduced to 6-aminocaproate semialdehyde, which can be then converted to HMDA as depicted in FIGS. 10 and 11. In either this case, the amination reaction must occur relatively quickly to minimize the spontaneous formation of the cyclic imine of 6-aminocaproate semialdehyde. Linking or scaffolding the participating enzymes represents a potentially powerful option for ensuring that the 6-aminocaproate semialdehyde intermediate is efficiently channeled from the reductase enzyme to the amination enzyme.

Another option for minimizing or even eliminating the formation of the cyclic imine or caprolactam during the conversion of 6-aminocaproic acid to HMDA entails adding a functional group (for example, acetyl, succinyl) to the amine group of 6-aminocaproic acid to protect it from cyclization. This is analogous to ornithine formation from L-glutamate in *Escherichia coli*. Specifically, glutamate is first converted to N-acetyl-L-glutamate by N-acetylglutamate synthase. N-Acetyl-L-glutamate is then activated to N-acetylglutamylphosphate, which is reduced and transaminated to form N-acetyl-L-ornithine. The acetyl group is then removed from N-acetyl-L-ornithine by N-acetyl-L-ornithine deacetylase forming L-ornithine. Such a route is necessary because formation of glutamate-5-phosphate from glutamate followed by reduction to glutamate-5-semialdehyde leads to the formation of (S)-1-pyrroline-5-carboxylate, a cyclic imine formed spontaneously from glutamate-5-semialdehyde. In the case of forming HMDA from 6-aminocaproic acid, the steps can involve acetylating 6-aminocaproic acid to acetyl-6-aminocaproic acid, activating the carboxylic acid group with a CoA or phosphate group, reducing, aminating, and deacetylating.

Note that 6-aminocaproate can be formed from various starting molecules. For example, the carbon backbone of 6-aminocaproate can be derived from succinyl-CoA and acetyl-CoA as depicted in FIG. 10 and also described in FIGS. 2, 3 and 8. Alternatively, 6-aminocaproate can be derived from alpha-ketoadipate, where alpha-ketoadipate is converted to adipyl-CoA (see FIG. 9), and adipyl-CoA is converted to 6-aminocaproate as shown in FIG. 10.

FIG. 11 provides two additional metabolic pathways to 6-aminocaproate or 6-aminocaproyl-CoA starting from 4-aminobutyryl-CoA and acetyl-CoA. The first route entails the condensation of 4-aminobutyryl-CoA and acetyl-CoA to form 3-oxo-6-aminohexanoyl-CoA (Step A) followed by a reduction (Step B), dehydration (Step C), and reduction (Step D) to form 6-aminocaproyl-CoA. 6-Aminocaproyl-CoA can be converted to 6-aminocaproate by a transferase (Step K), synthase (Step L), or hydrolase (Step M) enzyme. Alternatively, 6-aminocaproyl-CoA can be converted to caprolactam by spontaneous cyclization (Step Q) or to HMDA following its reduction (Step N) and amination (Step O or P). The second pathway described in FIG. 11 entails the condensation of 4-aminobutyryl-CoA and acetyl-CoA to form 3-oxo-6-aminohexanoyl-CoA (Step A) which is then converted to 3-oxo-6-aminohexanoate by a transferase (Step E), synthase (Step F), or hydrolase (Step G). 3-Oxo-6-aminohexanoate is then reduced (Step H), dehydrated (Step I), and reduced (Step J) to form 6-aminocaproate.

The starting molecule, 4-aminobutyryl-CoA, can be formed from various common central metabolites. For example, glutamate can be decarboxylated to 4-aminobutyrate, which is then activated by a CoA-transferase or synthase to 4-aminobutyryl-CoA. Alternatively, succinate semialdehyde, formed from either the reduction of succinyl-CoA or the decarboxylation of alpha-ketoglutarate, can be transaminated to 4-aminobutyrate prior to activation by a CoA-transferase or synthase to form 4-aminobutyryl-CoA. It is noted that 4-aminobutyryl-CoA and several of the intermediates of the 4-aminobutyryl-CoA to 6-aminocaproyl-CoA pathway may spontaneously cyclize to their corresponding lactams. Thus, adding a protective functional group to the terminal amine group of 4-aminobutyryl-CoA and/or several of the amino-CoA intermediates can be used to minimize the formation of unwanted cyclic byproducts. In this case, the same general set of transformations depicted in FIG. 11 would apply, although two additional steps, for example, an acetylase and deacetylase, can be added to the pathway.

All transformations depicted in FIGS. 10-11 fall into the 12 general categories of transformations shown in Table 8. Below is described a number of biochemically characterized candidate genes in each category. Specifically listed are genes that can be applied to catalyze the appropriate transformations in FIGS. 10-11 when cloned and expressed.

TABLE 8

Enzyme types for conversion of succinyl-CoA, acetyl-CoA, and/or 4-aminobutyryl-CoA to 6-aminocaproate, caprolactam, and/or hexamethylenediamine. The first three digits of each label correspond to the first three Enzyme Commission number digits which denote the general type of transformation independent of substrate specificity.

| Label | Function |
|---|---|
| 1.1.1.a | Oxidoreductase (ketone to hydroxyl or aldehyde to alcohol) |
| 1.2.1.b | Oxidoreductase (acyl-CoA to aldehyde) |
| 1.3.1.a | Oxidoreductase operating on CH—CH donors |
| 1.4.1.a | Oxidoreductase operating on amino acids |
| 2.3.1.b | Acyltransferase |
| 2.6.1.a | Aminotransferase |
| 2.8.3.a | Coenzyme-A transferase |
| 3.1.2.a | Thiolester hydrolase (CoA specific) |
| 4.2.1.a | Hydro-lyase |
| 6.2.1.a | Acid-thiol ligase |
| 6.3.1.a/ 6.3.2.a | Amide synthases/peptide synthases |
| No enzyme required | Spontaneous cyclization |

1.1.1.a Oxidoreductases.

Four transformations depicted in FIGS. 10 and 11 require oxidoreductases that convert a ketone functionality to a hydroxyl group. Step B in both FIGS. 10 and 11 involves converting a 3-oxoacyl-CoA to a 3-hydroxyacyl-CoA. Step H in both FIGS. 1 and 2 involves converting a 3-oxoacid to a 3-hydroxyacid.

Exemplary enzymes that can convert 3-oxoacyl-CoA molecules such as 3-oxoadipyl-CoA and 3-oxo-6-aminohexanoyl-CoA into 3-hydroxyacyl-CoA molecules such as 3-hydroxyadipyl-CoA and 3-hydroxy-6-aminohexanoyl-CoA, respectively, include enzymes whose natural physiological roles are in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71:403-411 (1981)). Furthermore, the gene products encoded by phaC in *Pseudomonas putida* U (Olivera et al., *Proc. Natl. Acad. Sci. USA* 95:6419-6424 (1998)) and paaC in *Pseudomonas fluorescens* ST (Di Gennaro et al., *Arch. Microbiol.* 188:117-125 (2007)) catalyze the reverse reaction of step B in FIG. 10, that is, the oxidation of 3-hydroxyadipyl-CoA to form 3-oxoadipyl-CoA, during the catabolism of phenylacetate or styrene.

Note that the reactions catalyzed by such enzymes are reversible. In addition, given the proximity in E. coli of paaH to other genes in the phenylacetate degradation operon (Nogales et al., Microbiology 153:357-365 (2007)) and the fact that paaH mutants cannot grow on phenylacetate (Ismail et al., Eur. J Biochem. 270:3047-3054 (2003)), it is expected that the E. coli paaH gene encodes a 3-hydroxyacyl-CoA dehydrogenase.

| Gene name | GI# | GenBank Accession # | Organism |
| --- | --- | --- | --- |
| fadB | 119811 | P21177.2 | Escherichia coli |
| fadJ | 3334437 | P77399.1 | Escherichia coli |
| paaH | 16129356 | NP_415913.1 | Escherichia coli |
| phaC | 26990000 | NP_745425.1 | Pseudomonas putida |
| paaC | 106636095 | ABF82235.1 | Pseudomonas fluorescens |

Additional exemplary oxidoreductases capable of converting 3-oxoacyl-CoA molecules to their corresponding 3-hydroxyacyl-CoA molecules include 3-hydroxybutyryl-CoA dehydrogenases. The enzyme from Clostridium acetobutylicum, encoded by hbd, has been cloned and functionally expressed in E. coli (Youngleson et al., J. Bacteriol. 171:6800-6807 (1989)). Additional gene candidates include Hbd1 (C-terminal domain) and Hbd2 (N-terminal domain) in Clostridium kluyveri (Hillmer et al., FEBS Lett. 21:351-354 (1972)) and HSD17B10 in Bos taurus (Wakil et al., J Biol. Chem. 207:631-638 (1954)). Yet other gene candidates demonstrated to reduce acetoacetyl-CoA to 3-hydroxybutyryl-CoA are phbB from Zoogloea ramigera (Ploux et al., Eur. J. Biochem. 174:177-182 (1988)) and phaB from Rhodobacter sphaeroides (Alber et al., Mol. Microbiol 61:297-309 (2006)). The former gene candidate is NADPH-dependent, its nucleotide sequence has been determined (Peoples et al., Mol. Microbiol 3:349-357 (1989)) and the gene has been expressed in E. coli. Substrate specificity studies on the gene led to the conclusion that it could accept 3-oxopropionyl-CoA as a substrate besides acetoacetyl-CoA (Ploux et al., supra).

| Gene name | GI# | GenBank Accession # | Organism |
| --- | --- | --- | --- |
| hbd | 18266893 | P52041.2 | Clostridium acetobutylicum |
| Hbd2 | 146348271 | EDK34807.1 | Clostridium kluyveri |
| Hbd1 | 146345976 | EDK32512.1 | Clostridium kluyveri |
| HSD17B10 | 3183024 | O02691.3 | Bos taurus |
| phbB | 130017 | P23238.1 | Zoogloea ramigera |
| phaB | 146278501 | YP_001168660.1 | Rhodobacter sphaeroides |

A number of similar enzymes have been found in other species of Clostridia and in Metallosphaera sedula (Berg et al., Science 318:1782-1786 (2007)).

| Gene name | GI# | GenBank Accession # | Organism |
| --- | --- | --- | --- |
| hbd | 15895965 | NP_349314.1 | Clostridium acetobutylicum |
| hbd | 20162442 | AAM14586.1 | Clostridium beijerinckii |
| Msed_1423 | 146304189 | YP_001191505 | Metallosphaera sedula |
| Msed_0399 | 146303184 | YP_001190500 | Metallosphaera sedula |
| Msed_0389 | 146303174 | YP_001190490 | Metallosphaera sedula |
| Msed_1993 | 146304741 | YP_001192057 | Metallosphaera sedula |

Various alcohol dehydrogenases represent good candidates for converting 3-oxoadipate to 3-hydroxyadipate (step H, FIG. 10) or 3-oxo-6-aminohexanoate to 3-hydroxy-6-aminohexanoate (step H, FIG. 11). Two such enzymes capable of converting an oxoacid to a hydroxyacid are encoded by the malate dehydrogenase (mdh) and lactate dehydrogenase (ldhA) genes in E. coli. In addition, lactate dehydrogenase from Ralstonia eutropha has been shown to demonstrate high activities on substrates of various chain lengths such as lactate, 2-oxobutyrate, 2-oxopentanoate and 2-oxoglutarate (Steinbuchel et al., Eur. J. Biochem. 130:329-334 (1983)). Conversion of alpha-ketoadipate into alpha-hydroxyadipate can be catalyzed by 2-ketoadipate reductase, an enzyme reported to be found in rat and in human placenta (Suda et al., Arch. Biochem. Biophys. 176:610-620 (1976); Suda et al., Biochem. Biophys. Res. Commun. 77:586-591 (1977)). An additional candidate for these steps is the mitochondrial 3-hydroxybutyrate dehydrogenase (bdh) from the human heart which has been cloned and characterized (Marks et al., J Biol. Chem. 267:15459-15463 (1992)). This enzyme is a dehydrogenase that operates on a 3-hydroxy-acid. Another exemplary alcohol dehydrogenase converts acetone to isopropanol as was shown in C. beijerinckii (Ismaiel et al., J Bacteriol. 175:5097-5105 (1993) and T. brockii (Lamed et al., Biochem. J. 195:183-190 (1981); Peretz et al., Biochemistry 28:6549-6555 (1989)).

| Gene name | GI# | GenBank Accession # | Organism |
| --- | --- | --- | --- |
| mdh | 1789632 | AAC76268.1 | Escherichia coli |
| ldhA | 16129341 | NP_415898.1 | Escherichia coli |
| ldh | 113866693 | YP_725182.1 | Ralstonia eutropha |
| bdh | 177198 | AAA58352.1 | Homo sapiens |
| adh | 60592974 | AAA23199.2 | Clostridium beijerinckii |
| adh | 113443 | P14941.1 | Thermoanaerobacter brockii |

1.2.1.b Oxidoreductase (Acyl-CoA to Aldehyde).

The transformations of adipyl-CoA to adipate semialdehyde (Step N, FIG. 10) and 6-aminocaproyl-CoA to 6-aminocaproate semialdehyde (Step U, FIG. 10; Step N, FIG. 11) require acyl-CoA dehydrogenases capable of reducing an acyl-CoA to its corresponding aldehyde. Exemplary genes that encode such enzymes include the Acinetobacter calcoaceticus acr1 encoding a fatty acyl-CoA reductase (Reiser et al., J. Bacteriology 179:2969-2975 (1997)), the Acinetobacter sp. M-1 fatty acyl-CoA reductase (Ishige et al., Appl. Environ. Microbiol. 68:1192-1195 (2002)), and a CoA- and NADP-dependent succinate semialdehyde dehydrogenase encoded by the sucD gene in Clostridium kluyveri (Sohling et al., J. Bacteriol. 178:871-880 (1996)). SucD of P. gingivalis is another succinate semialdehyde dehydrogenase (Takahashi et al., J. Bacteriol. 182:4704-4710 (2000)). The enzyme acylating acetaldehyde dehydrogenase in Pseudomonas sp, encoded by bphG, is yet another candidate as it has been demonstrated to oxidize and acylate acetaldehyde, propionaldehyde, butyraldehyde, isobutyraldehyde and formaldehyde (Powlowski et al., J Bacteriol. 175:377-385 (1993)). In addition to reducing acetyl-CoA to ethanol, the enzyme encoded by adhE in Leuconostoc mesenteroides has been shown to oxidize the branched chain compound isobutyraldehyde to isobutyryl-CoA (Kazahaya et al., J. Gen. Appl. Microbiol. 18:43-55 (1972); Koo et al., Biotechnol Lett. 27:505-510 (2005)).

| Gene name | GI# | GenBank Accession # | Organism |
|---|---|---|---|
| acr1 | 50086359 | YP_047869.1 | Acinetobacter calcoaceticus |
| acr1 | 1684886 | AAC45217 | Acinetobacter baylyi |
| acr1 | 18857901 | BAB85476.1 | Acinetobacter sp. Strain M-1 |
| sucD | 172046062 | P38947.1 | Clostridium kluyveri |
| sucD | 34540484 | NP_904963.1 | Porphyromonas gingivalis |
| bphG | 425213 | BAA03892.1 | Pseudomonas sp |
| adhE | 55818563 | AAV66076.1 | Leuconostoc mesenteroides |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., supra; Thauer R. K., Science 318:1732-1733 (2007)). The enzyme utilizes NADPH as a cofactor and has been characterized in Metallosphaera and Sulfolobus spp (Alber et al., J. Bacteriol. 188:8551-8559 (2006); Hugler et al., J. Bacteriol. 184:2404-2410 (2002)). The enzyme is encoded by Msed_0709 in Metallosphaera sedula (Alber et al., supra; Berg et al., supra). A gene encoding a malonyl-CoA reductase from Sulfolobus tokodaii was cloned and heterologously expressed in E. coli (Alber et al., supra). This enzyme has also been shown to catalyze the conversion of methylmalonyl-CoA to its corresponding aldehyde (WO/2007/141208). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius and have been listed below. Yet another candidate for CoA-acylating aldehyde dehydrogenase is the ald gene from Clostridium beijerinckii (Toth et al., Appl Environ Microbiol 65:4973-4980 (1999)). This enzyme has been reported to reduce acetyl-CoA and butyryl-CoA to their corresponding aldehydes. This gene is very similar to eutE that encodes acetaldehyde dehydrogenase of Salmonella typhimurium and E. coli (Toth et al., supra).

| Gene name | GI# | GenBank Accession # | Organism |
|---|---|---|---|
| Msed_0709 | 146303492 | YP_001190808.1 | Metallosphaera sedula |
| mcr | 15922498 | NP_378167.1 | Sulfolobus tokodaii |
| asd-2 | 15898958 | NP_343563.1 | Sulfolobus solfataricus |
| Saci_2370 | 70608071 | YP_256941.1 | Sulfolobus acidocaldarius |
| Ald | 49473535 | AAT66436 | Clostridium beijerinckii |
| eutE | 687645 | AAA80209 | Salmonella typhimurium |
| eutE | 2498347 | P77445 | Escherichia coli |

1.3.1.a Oxidoreductase Operating on CH—CH Donors.

Referring to FIG. 10, step D refers to the conversion of 5-carboxy-2-pentenoyl-CoA to adipyl-CoA by 5-carboxy-2-pentenoyl-CoA reductase. Referring to FIG. 11, step D refers to the conversion of 6-aminohex-2-enoyl-CoA to 6-aminocaproyl-CoA. Enoyl-CoA reductase enzymes are suitable enzymes for either transformation. One exemplary enoyl-CoA reductase is the gene product of bcd from C. acetobutylicum (Boynton et al., J Bacteriol. 178:3015-3024 (1996); Atsumi et al., Metab. Eng. 2008 10(6):305-311 (2008)(Epub Sep. 14, 2007), which naturally catalyzes the reduction of crotonyl-CoA to butyryl-CoA. Activity of this enzyme can be enhanced by expressing bcd in conjunction with expression of the C. acetobutylicum etfAB genes, which encode an electron transfer flavoprotein. An additional candidate for the enoyl-CoA reductase step is the mitochondrial enoyl-CoA reductase from E. gracilis (Hoffmeister et al., J. Biol. Chem. 280:4329-4338 (2005)). A construct derived from this sequence following the removal of its mitochondrial targeting leader sequence was cloned in E. coli resulting in an active enzyme (Hoffmeister et al., supra). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote Treponema denticola represents a third enoyl-CoA reductase which has been cloned and expressed in E. coli (Tucci et al., FEBS Letters 581:1561-1566 (2007)).

| Gene name | GI# | GenBank Accession # | Organism |
|---|---|---|---|
| bcd | 15895968 | NP_349317.1 | Clostridium acetobutylicum |
| etfA | 15895966 | NP_349315.1 | Clostridium acetobutylicum |
| etfB | 15895967 | NP_349316.1 | Clostridium acetobutylicum |
| TER | 62287512 | Q5EU90.1 | Euglena gracilis |
| TDE0597 | 42526113 | NP_971211.1 | Treponema denticola |

Step J of both FIGS. 10 and 11 requires a 2-enoate reductase enzyme. 2-Enoate reductases (EC 1.3.1.31) are known to catalyze the NAD(P)H-dependent reduction of a wide variety of α, β-unsaturated carboxylic acids and aldehydes (Rohdich et al., J. Biol. Chem. 276:5779-5787 (2001)). 2-Enoate reductase is encoded by enr in several species of Clostridia (Giesel et al., Arch Microbiol 135:51-57 (1983)) including C. tyrobutyricum, and C. thermoaceticum (now called Moorella thermoaceticum) (Rohdich et al., supra). In the published genome sequence of C. kluyveri, 9 coding sequences for enoate reductases have been reported, out of which one has been characterized (Seedorf et al., Proc. Natl. Acad. Sci. USA, 105:2128-2133 (2008)). The enr genes from both C. tyrobutyricum and C. thermoaceticum have been cloned and sequenced and show 59% identity to each other. The former gene is also found to have approximately 75% similarity to the characterized gene in C. kluyveri (Giesel et al., supra). It has been reported based on these sequence results that enr is very similar to the dienoyl CoA reductase in E. coli (fadH) (Rohdich et al., supra). The C. thermoaceticum enr gene has also been expressed in an enzymatically active form in E. coli (Rohdich et al., supra).

| Gene name | GI# | GenBank Accession # | Organism |
|---|---|---|---|
| fadH | 16130976 | NP_417552.1 | Escherichia coli |
| enr | 169405742 | ACA54153.1 | Clostridium botulinum A3 str |
| enr | 2765041 | CAA71086.1 | Clostridium tyrobutyricum |
| enr | 3402834 | CAA76083.1 | Clostridium kluyveri |
| enr | 83590886 | YP_430895.1 | Moorella thermoacetica |

1.4.1.a Oxidoreductase Operating on Amino Acids.

FIG. 10 depicts two reductive aminations. Specifically, step P of FIG. 10 involves the conversion of adipate semialdehyde to 6-aminocaproate and step W of FIG. 10 entails the conversion of 6-aminocaproate semialdehyde to hexamethylenediamine. The latter transformation is also required in FIG. 11, Step P.

Most oxidoreductases operating on amino acids catalyze the oxidative deamination of alpha-amino acids with NAD+ or NADP+ as acceptor, though the reactions are typically reversible. Exemplary oxidoreductases operating on amino acids include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (McPherson et al., *Nucleic. Acids Res.* 11:5257-5266 (1983); Korber et al., *J. Mol. Biol.* 234:1270-1273 (1993)), gdh from *Thermotoga maritima* (Kort et al., *Extremophiles* 1:52-60 (1997); Lebbink et al., *J. Mol. Biol.* 280:287-296 (1998); Lebbink et al., *J. Mol. Biol.* 289:357-369 (1999)), and gdhA1 from *Halobacterium salinarum* (Ingoldsby et al., *Gene.* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Stoyan et al., *J. Biotechnol* 54:77-80 (1997); Ansorge et al., *Biotechnol Bioeng.* 68:557-562 (2000)). The nadX gene from *Thermotoga maritime* encoding for the aspartate dehydrogenase is involved in the biosynthesis of NAD (Yang et al., *J. Biol. Chem.* 278:8804-8808 (2003)).

| Gene name | GI# | GenBank Accession # | Organism |
| --- | --- | --- | --- |
| gdhA | 118547 | P00370 | *Escherichia coli* |
| gdh | 6226595 | P96110.4 | *Thermotoga maritima* |
| gdhA1 | 15789827 | NP_279651.1 | *Halobacterium salinarum* |
| ldh | 61222614 | P0A393 | *Bacillus cereus* |
| nadX | 15644391 | NP_229443.1 | *Thermotoga maritima* |

The lysine 6-dehydrogenase (deaminating), encoded by the lysDH genes, catalyze the oxidative deamination of the ε-amino group of L-lysine to form 2-aminoadipate-6-semialdehyde, which in turn nonenzymatically cyclizes to form $\Delta^1$-piperideine-6-carboxylate (Misono et al., *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem* 106:76-80 (1989); Misono et al., supra), and *Achromobacter* denitrificans (Ruldeekulthamrong et al., *BMB. Rep.* 41:790-795 (2008)). Such enzymes are particularly good candidates for converting adipate semialdehyde to 6-aminocaproate given the structural similarity between adipate semialdehyde and 2-aminoadipate-6-semialdehyde.

| Gene name | GI# | GenBank Accession # | Organism |
| --- | --- | --- | --- |
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

2.3.1.b Acyl Transferase.

Referring to FIG. 10, step A involves 3-oxoadipyl-CoA thiolase, or equivalently, succinyl CoA:acetyl CoA acyl transferase (β-ketothiolase). The gene products encoded by pcaF in *Pseudomonas* strain B13 (Kaschabek et al., *J. Bacteriol.* 184:207-215 (2002)), phaD in *Pseudomonas putida* U (Olivera et al., supra), paaE in *Pseudomonas fluorescens* ST (Di Gennaro et al., supra), and paaJ from *E. coli* (Nogales et al., supra) catalyze the conversion of 3-oxoadipyl-CoA into succinyl-CoA and acetyl-CoA during the degradation of aromatic compounds such as phenylacetate or styrene. Since β-ketothiolase enzymes catalyze reversible transformations, these enzymes can be employed for the synthesis of 3-oxoadipyl-CoA. For example, the ketothiolase phaA from *R. eutropha* combines two molecules of acetyl-CoA to form acetoacetyl-CoA (Sato et al., *J Biosci Bioeng* 103:38-44 (2007)). Similarly, a β-keto thiolase (bktB) has been reported to catalyze the condensation of acetyl-CoA and propionyl-CoA to form β-ketovaleryl-CoA (Slater et al., *J. Bacteriol.* 180:1979-1987 (1998)) in *R. eutropha*. In addition to the likelihood of possessing 3-oxoadipyl-CoA thiolase activity, all such enzymes represent good candidates for condensing 4-aminobutyryl-CoA and acetyl-CoA to form 3-oxo-6-aminohexanoyl-CoA (step A, FIG. 11) either in their native forms or once they have been appropriately engineered.

| Gene name | GI# | GenBank Accession # | Organism |
| --- | --- | --- | --- |
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| paaE | 106636097 | ABF82237.1 | *Pseudomonas fluorescens* |

2-Amino-4-oxopentanoate (AKP) thiolase or AKP thiolase (AKPT) enzymes present additional candidates for performing step A in FIGS. 10 and 11. AKPT is a pyridoxal phosphate-dependent enzyme participating in ornithine degradation in *Clostridium sticklandii* (Jeng et al., *Biochemistry* 13:2898-2903 (1974); Kenklies et al., *Microbiology* 145: 819-826 (1999)). A gene cluster encoding the alpha and beta subunits of AKPT (or-2 (ortA) and or-3 (ortB)) was recently identified and the biochemical properties of the enzyme were characterized (Fonknechten et al., *J. Bacteriol.* In Press (2009)). The enzyme is capable of operating in both directions and naturally reacts with the D-isomer of alanine. AKPT from *Clostridium sticklandii* has been characterized but its protein sequence has not yet been published. Enzymes with high sequence homology are found in *Clostridium difficile, Alkaliphilus metalliredigenes* QYF, *Thermoanaerobacter* sp. X514, and *Thermoanaerobacter tengcongensis* MB4 (Fonknechten et al., supra).

| Gene name | GI# | GenBank Accession # | Organism |
|---|---|---|---|
| ortA (α) | 126698017 | YP_001086914.1 | Clostridium difficile 630 |
| ortB (β) | 126698018 | YP_001086915.1 | Clostridium difficile 630 |
| Amet_2368 (α) | 150390132 | YP_001320181.1 | Alkaliphilus metalliredigenes QYF |
| Amet_2369 (β) | 150390133 | YP_001320182.1 | Alkaliphilus metalliredigenes QYF |
| Teth514_1478 (α) | 167040116 | YP_001663101.1 | Thermoanaerobacter sp. X514 |
| Teth514_1479 (β) | 167040117 | YP_001663102.1 | Thermoanaerobacter sp. X514 |
| TTE1235 (α) | 20807687 | NP_622858.1 | Thermoanaerobacter tengcongensis MB4 |
| thrC (β) | 20807688 | NP_622859.1 | Thermoanaerobacter tengcongensis MB4 |

2.6.1.a Aminotransferase.

Step O of FIGS. 10 and 11 and Step V of FIG. 10 require transamination of a 6-aldehyde to an amine. These transformations can be catalyzed by gamma-aminobutyrate transaminase (GABA transaminase). One E. coli GABA transaminase is encoded by gabT and transfers an amino group from glutamate to the terminal aldehyde of succinyl semialdehyde (Bartsch et al., J. Bacteriol. 172:7035-7042 (1990)). The gene product of puuE catalyzes another 4-aminobutyrate transaminase in E. coli (Kurihara et al., J. Biol. Chem. 280:4602-4608 (2005)). GABA transaminases in Mus musculus, Pseudomonas fluorescens, and Sus scrofa have been shown to react with 6-aminocaproic acid (Cooper, Methods Enzymol. 113:80-82 (1985); Scott et al., J. Biol. Chem. 234:932-936 (1959)).

| Gene name | GI# | GenBank Accession # | Organism |
|---|---|---|---|
| gabT | 16130576 | NP_417148.1 | Escherichia coli |
| puuE | 16129263 | NP_415818.1 | Escherichia coli |
| abat | 37202121 | NP_766549.2 | Mus musculus |
| gabT | 70733692 | YP_257332.1 | Pseudomonas fluorescens |
| abat | 47523600 | NP_999428.1 | Sus scrofa |

Additional enzyme candidates include putrescine aminotransferases or other diamine aminotransferases. Such enzymes are particularly well suited for carrying out the conversion of 6-aminocaproate semialdehyde to hexamethylenediamine. The E. coli putrescine aminotransferase is encoded by the ygjG gene and the purified enzyme also was able to transaminate cadaverine and spermidine (Samsonova et al., BMC Microbiol 3:2 (2003)). In addition, activity of this enzyme on 1,7-diaminoheptane and with amino acceptors other than 2-oxoglutarate (e.g., pyruvate, 2-oxobutanoate) has been reported (Samsonova et al., supra; Kim, K. H., J Biol Chem 239:783-786 (1964)). A putrescine aminotransferase with higher activity with pyruvate as the amino acceptor than alpha-ketoglutarate is the spuC gene of Pseudomonas aeruginosa (Lu et al., J Bacteriol 184:3765-3773 (2002)).

| Gene name | GI# | GenBank Accession # | Organism |
|---|---|---|---|
| ygjG | 145698310 | NP_417544 | Escherichia coli |
| spuC | 9946143 | AAG03688 | Pseudomonas aeruginosa |

Yet additional candidate enzymes include beta-alanine/alpha-ketoglutarate aminotransferases which produce malonate semialdehyde from beta-alanine (WO08027742). The gene product of SkPYD4 in Saccharomyces kluyveri was also shown to preferentially use beta-alanine as the amino group donor (Andersen et al., FEBS. J. 274:1804-1817 (2007)). SkUGA1 encodes a homologue of Saccharomyces cerevisiae GABA aminotransferase, UGA1 (Ramos et al., Eur. J. Biochem., 149:401-404 (1985)), whereas SkPYD4 encodes an enzyme involved in both β-alanine and GABA transamination (Andersen et al., supra). 3-Amino-2-methylpropionate transaminase catalyzes the transformation from methylmalonate semialdehyde to 3-amino-2-methylpropionate. This enzyme has been characterized in Rattus norvegicus and Sus scrofa and is encoded by Abat (Tamaki et al, Methods Enzymol, 324:376-389 (2000)).

| Gene name | GI# | GenBank Accession # | Organism |
|---|---|---|---|
| SkyPYD4 | 98626772 | ABF58893.1 | Saccharomyces kluyveri |
| SkUGA1 | 98626792 | ABF58894.1 | Saccharomyces kluyveri |
| UGA1 | 6321456 | NP_011533.1 | Saccharomyces cerevisiae |
| Abat | 122065191 | P50554.3 | Rattus norvegicus |
| Abat | 120968 | P80147.2 | Sus scrofa |

2.8.3.a Coenzyme-A Transferase.

CoA transferases catalyze reversible reactions that involve the transfer of a CoA moiety from one molecule to another. For example, step E of FIG. 10 is catalyzed by a 3-oxoadipyl-CoA transferase. In this step, 3-oxoadipate is formed by the transfer of the CoA group from 3-oxoadipyl-CoA to succinate, acetate, or another CoA acceptor. Step E of FIG. 11 entails the transfer of a CoA moiety from another 3-oxoacyl-CoA, 3-oxo-6-aminohexanoyl-CoA. One candidate enzyme for these steps is the two-unit enzyme encoded by pcaI and pcaJ in Pseudomonas, which has been shown to have 3-oxoadipyl-CoA/succinate transferase activity (Kaschabek et al., supra). Similar enzymes based on homology exist in Acinetobacter sp. ADP1 (Kowalchuk et al., Gene 146:23-30 (1994)) and Streptomyces coelicolor. Additional exemplary succinyl-CoA:3:oxoacid-CoA transferases are present in Helicobacter pylori (Corthesy-Theulaz et al., J. Biol. Chem. 272:25659-25667 (1997)) and Bacillus subtilis (Stols et al., Protein. Expr. Purif. 53:396-403 (2007)).

| Gene name | GI# | GenBank Accession # | Organism |
|---|---|---|---|
| pcaI | 24985644 | AAN69545.1 | Pseudomonas putida |
| pcaJ | 26990657 | NP_746082.1 | Pseudomonas putida |
| peaI | 50084858 | YP_046368.1 | Acinetobacter sp. ADP1 |
| pcaJ | 141776 | AAC37147.1 | Acinetobacter sp. ADP1 |
| peaI | 21224997 | NP_630776.1 | Streptomyces coelicolor |
| pcaJ | 21224996 | NP_630775.1 | Streptomyces coelicolor |
| HPAG1_0676 | 108563101 | YP_627417 | Helicobacter pylori |
| HPAG1_0677 | 108563102 | YP_627418 | Helicobacter pylori |
| ScoA | 16080950 | NP_391778 | Bacillus subtilis |
| ScoB | 16080949 | NP_391777 | Bacillus subtilis |

A 3-oxoacyl-CoA transferase that can utilize acetate as the CoA acceptor is acetoacetyl-CoA transferase, encoded by the E. coli atoA (alpha subunit) and atoD (beta subunit) genes (Vanderwinkel et al., Biochem. Biophys. Res Commun. 33:902-908 (1968); Korolev et al., Acta Crystallogr. D Biol Crystallogr. 58:2116-2121 (2002)). This enzyme has also been shown to transfer the CoA moiety to acetate from a variety of branched and linear acyl-CoA substrates, including isobutyrate (Matthies et al., Appl Environ Microbiol 58:1435-1439 (1992)), valerate (Vanderwinkel et al., supra) and butanoate (Vanderwinkel et al., supra). Similar enzymes exist in Corynebacterium glutamicum ATCC 13032 (Duncan et al., Appl Environ Microbiol 68:5186-5190 (2002)), Clostridium acetobutylicum (Cary et al., Appl Environ Microbiol 56:1576-1583 (1990)), and Clostridium saccharoperbutylacetonicum (Kosaka et al., Biosci. Biotechnol Biochem. 71:58-68 (2007)).

| Gene name | GI# | GenBank Accession # | Organism |
|---|---|---|---|
| atoA | 2492994 | P76459.1 | Escherichia coli K12 |
| atoD | 2492990 | P76458.1 | Escherichia coli K12 |
| actA | 62391407 | YP_226809.1 | Corynebacterium glutamicum ATCC 13032 |
| cg0592 | 62389399 | YP_224801.1 | Corynebacterium glutamicum ATCC 13032 |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

The above enzymes may also exhibit the desired activities on adipyl-CoA and adipate (FIG. 10, step K) or 6-aminocaproate and 6-aminocaproyl-CoA (FIG. 10, step Q; FIG. 2, step K). Nevertheless, additional exemplary transferase candidates are catalyzed by the gene products of cat1, cat2, and cat3 of Clostridium kluyveri which have been shown to exhibit succinyl-CoA, 4-hydroxybutyryl-CoA, and butyryl-CoA transferase activity, respectively (Seedorf et al., supra; Sohling et al., Eur. J Biochem. 212:121-127 (1993); Sohling et al., J Bacteriol. 178:871-880 (1996)).

| Gene name | GI# | GenBank Accession # | Organism |
|---|---|---|---|
| cat1 | 729048 | P38946.1 | Clostridium kluyveri |
| cat2 | 172046066 | P38942.2 | Clostridium kluyveri |
| cat3 | 146349050 | EDK35586.1 | Clostridium kluyveri |

The glutaconate-CoA-transferase (EC 2.8.3.12) enzyme from anaerobic bacterium Acidaminococcus fermentans reacts with diacid glutaconyl-CoA and 3-butenoyl-CoA (Mack et al., FEBS Lett. 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., Eur. J. Biochem. 118:315-321 (1981)). The enzyme has been cloned and expressed in E. coli (Mack et al., Eur. J. Biochem. 226:41-51 (1994)).

| Gene name | GI# | GenBank Accession # | Organism |
|---|---|---|---|
| gctA | 559392 | CAA57199.1 | Acidaminococcus fermentans |
| gctB | 559393 | CAA57200.1 | Acidaminococcus fermentans |

3.1.2.a Thiolester Hydrolase (CoA Specific).

Several eukaryotic acetyl-CoA hydrolases have broad substrate specificity and thus represent suitable candidate enzymes for hydrolyzing 3-oxoadipyl-CoA, adipyl-CoA, 3-oxo-6-aminohexanoyl-CoA, or 6-aminocaproyl-CoA (Steps G and M of FIGS. 10 and 11). For example, the enzyme from Rattus norvegicus brain (Robinson et al., Biochem. Biophys. Res. Commun. 71:959-965 (1976)) can react with butyryl-CoA, hexanoyl-CoA and malonyl-CoA.

| Gene name | GI# | GenBank Accession # | Organism |
|---|---|---|---|
| acot12 | 18543355 | NP_570103.1 | Rattus norvegicus |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., J Biol Chem. 269:14248-14253 (1994)). Genes encoding this enzyme include hibch of Rattus norvegicus (Shimomura et al., supra; Shimomura et al., Methods Enzymol. 324:229-240 (2000)) and Homo sapiens (Shimomura et al., supra). Candidate genes by sequence homology include hibch of Saccharomyces cerevisiae and BC 2292 of Bacillus cereus.

| Gene name | GI# | GenBank Accession # | Organism |
|---|---|---|---|
| hibch | 146324906 | Q5XIE6.2 | Rattus norvegicus |
| hibch | 146324905 | Q6NVY1.2 | Homo sapiens |
| hibch | 2506374 | P28817.2 | Saccharomyces cerevisiae |
| BC_2292 | 29895975 | AP09256 | Bacillus cereus |

Yet another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., J. Biol. Chem. 280:38125-38132 (2005)) and the closest E. coli homolog, tesB, which can also hydrolyze a broad range of CoA thiolesters (Naggert et al., J. Biol Chem 266:11044-11050 (1991)). A similar enzyme has also been characterized in the rat liver (Deana R., Biochem Int 26:767-773 (1992)).

| Gene name | GI# | GenBank Accession # | Organism |
|---|---|---|---|
| tesB | 16128437 | NP_414986 | Escherichia coli |
| acot8 | 3191970 | CAA15502 | Homo sapiens |
| acot8 | 51036669 | NP_570112 | Rattus norvegicus |

Other potential E. coli thiolester hydrolases include the gene products of tesA (Bonner et al., J Biol Chem 247:3123-3133 (1972)), ybgC (Kuznetsova et al., FEMS Microbiol Rev 29:263-279 (2005); Zhuang et al., FEBS Lett 516:161-163 (2002)), paaI (Song et al., J Biol Chem 281:11028-11038 (2006)), and ybdB (Leduc et al., J Bacteriol 189:7112-7126 (2007)).

| Gene name | GI# | GenBank Accession # | Organism |
|---|---|---|---|
| tesA | 16128478 | NP_415027 | Escherichia coli |
| ybgC | 16128711 | NP_415264 | Escherichia coli |
| paaI | 16129357 | NP_415914 | Escherichia coli |
| ybdB | 16128580 | NP_415129 | Escherichia coli |

6.3.1.a/6.3.2.a Amide Synthases/Peptide Synthases.

The direct conversion of 6-aminocaproate to caprolactam (Step S, FIG. 10; Step R, FIG. 11) requires the formation of an intramolecular peptide bond. Ribosomes, which assemble amino acids into proteins during translation, are nature's most abundant peptide bond-forming catalysts. Nonribosomal peptide synthetases are peptide bond forming catalysts that do not involve messenger mRNA (Schwarzer et al., Nat Prod. Rep. 20:275-287 (2003)). Additional enzymes capable of forming peptide bonds include acyl-CoA synthetase from Pseudomonas chlororaphis (Abe et al., J Biol Chem 283:11312-11321 (2008)), gamma-Glutamylputrescine synthetase from E. coli (Kurihara et al., J Biol Chem 283:19981-19990 (2008)), and beta-lactam synthetase from Streptomyces clavuligerus (Bachmann et al., Proc Natl Acad Sci USA 95:9082-9086 (1998); Bachmann et al., Biochemistry 39:11187-11193 (2000); Miller et al., Nat Struct. Biol 8:684-689 (2001); Miller et al., Proc Natl Acad Sci USA 99:14752-14757 (2002); Tahlan et al., Antimicrob. Agents. Chemother. 48:930-939 (2004)).

| Gene name | GI# | GenBank Accession # | Organism |
|---|---|---|---|
| acsA | 60650089 | BAD90933 | Pseudomonas chlororaphis |
| puuA | 87081870 | AAC74379 | Escherichia coli |
| bls | 41016784 | Q9R8E3 | Streptomyces clavuligerus |

4.2.1.a Hydrolyase.

Most dehydratases catalyze the α, β-elimination of water. This involves activation of the α-hydrogen by an electron-withdrawing carbonyl, carboxylate, or CoA-thiol ester group and removal of the hydroxyl group from the β-position. Enzymes exhibiting activity on substrates with an electron-withdrawing carboxylate group are excellent candidates for dehydrating 3-hydroxyadipate (FIG. 10, Step I) or 3-hydroxy-6-aminohexanoate (FIG. 11, Step I).

For example, fumarase enzymes naturally catalyze the reversible dehydration of malate to fumarate. E. coli has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Tseng et al., J Bacteriol 183: 461-467 (2001); Woods et al., Biochim Biophys Acta 954: 14-26 (1988); Guest et al., J Gen Microbiol 131:2971-2984 (1985)). Additional enzyme candidates are found in Campylobacter jejuni (Smith et al., Int. J Biochem. Cell Biol 31:961-975 (1999)), Thermus thermophilus (Mizobata et al., Arch. Biochem. Biophys. 355:49-55 (1998)) and Rattus norvegicus (Kobayashi et al., J Biochem. 89:1923-1931 (1981)). Similar enzymes with high sequence homology include fum1 from Arabidopsis thaliana and fumC from Corynebacterium glutamicum. The MmcBC fumarase from Pelotomaculum thermopropionicum is another class of fumarase with two subunits (Shimoyama et al., FEMS Microbiol Lett 270:207-213 (2007)).

| Gene name | GI# | GenBank Accession # | Organism |
|---|---|---|---|
| fumA | 81175318 | P0AC33 | Escherichia coli |
| fumB | 33112655 | P14407 | Escherichia coli |
| fumC | 120601 | P05042 | Escherichia coli |
| fumC | 9789756 | O69294 | Campylobacter jejuni |
| fumC | 3062847 | BAA25700 | Thermus thermophilus |
| fumH | 120605 | P14408 | Rattus norvegicus |
| fum1 | 39931311 | P93033 | Arabidopsis thaliana |
| fumC | 39931596 | Q8NRN8 | Corynebacterium glutamicum |
| MmcB | 147677691 | YP_001211906 | Pelotomaculum thermopropionicum |
| MmcC | 147677692 | YP_001211907 | Pelotomaculum thermopropionicum |

Two additional dehydratase candidates are 2-(hydroxymethyl)glutarate dehydratase and dimethylmaleate hydratase, enzymes studied for their role in nicontinate catabolism in Eubacterium barkeri (formerly Clostridium barkeri) (Alhapel et al., Proc Natl Acad Sci USA 103:12341-6 (2006)). 2-(Hydroxymethyl)glutarate dehydratase is a [4Fe-4S]-containing enzyme that dehydrates 2-(hydroxymethyl)glutarate to 2-methylene-glutarate. This enzyme is encoded by hmd in Eubacterium barkeri (Alhapel et al., supra). Similar enzymes with high sequence homology are found in Bacteroides capillosus, Anaerotruncus colihominis, and Natranaerobius thermophilius. These enzymes are homologous to the alpha and beta subunits of [4Fe-4S]-containing bacterial serine dehydratases (e.g., E. coli enzymes encoded by tdcG, sdhB, and sdaA).

| Gene name | GI# | GenBank Accession # | Organism |
|---|---|---|---|
| hmd | 86278275 | ABC88407.1 | Eubacterium barkeri |
| BACCAP_02294 | 154498305 | ZP_02036683.1 | Bacteroides capillosus |
| ANACOL_02527 | 167771169 | ZP_02443222.1 | Anaerotruncus colihominis DSM 17241 |
| NtherDRAFT_2368 | 169192667 | ZP_02852366.1 | Natranaerobius thermophilus JW/NM-WN-LF |

Dimethylmaleate hydratase (EC 4.2.1.85) is a reversible $Fe^{2+}$-dependent and oxygen-sensitive enzyme in the aconitase family that hydrates dimethylmaeate to form (2R,3S)-2,3-dimethylmalate. This enzyme is encoded by dmdAB in Eubacterium barkeri (Alhapel et al., supra; Kollmann-Koch et al., Hoppe Seylers. Z. Physiol Chem. 365:847-857 (1984)).

| Gene name | GI# | GenBank Accession # | Organism |
|---|---|---|---|
| dmdA | 86278276 | ABC88408 | Eubacterium barkeri |
| dmdB | 86278277 | ABC88409.1 | Eubacterium barkeri |

An additional enzyme candidate is 2-methylmalate dehydratase, also called citramalate hydrolyase, a reversible hydrolyase that catalyzes the alpha, beta elimination of water from citramalate to form mesaconate. This enzyme has been purified and characterized in Clostridium tetanomorphum (Wang et al., J Biol. Chem. 244:2516-2526 (1969)). The activity of this enzyme has also been detected in several bacteria in the genera Citrobacter and Morganella in the context of the glutamate degradation VI pathway (Kato et al., *Arch. Microbiol* 168:457-463 (1997)). Genes encoding this enzyme have not been identified in any organism to date.

Enzymes exhibiting activity on substrates with an electron-withdrawing CoA-thiol ester group adjacent to the α-hydrogen are excellent candidates for dehydrating 3-hydroxyadipyl-CoA (FIG. 10, Step C) or 3-hydroxy-6-aminohexanoyl-CoA (FIG. 11, Step C). The enoyl-CoA hydratases, phaA and phaB, of *P. putida* are believed to carry out the hydroxylation of double bonds during phenylacetate catabolism (Olivera et al., *Proc. Natl. Acad. Sci. USA* 95:6419-6424 (1998)). The paaA and paaB from *P. fluorescens* catalyze analogous transformations (Olivera et al., *Proc. Natl. Acad. Sci. USA* 95:6419-6424 (1998)). Lastly, a number of *Escherichia coli* genes have been shown to demonstrate enoyl-CoA hydratase functionality including maoC (Park et al., *J Bacteriol.* 185:5391-5397 (2003)), paaF (Ismail et al., supra; Park et al., *Appl. Biochem. Biotechnol* 113-116:335-346 (2004); Park et al., *Biotechnol Bioeng* 86:681-686 (2004)) and paaG (Ismail et al., supra; Park et al., *Appl. Biochem. Biotechnol* 113-116:335-346 (2004); Park et al., *Biotechnol Bioeng* 86:681-686 (2004)). Crotonase enzymes are additional candidates for dehydrating the required 3-hydroxyacyl-CoA molecules depicted in FIGS. 10 and 11. These enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus, Acidianus,* and *Metallosphaera*. Exemplary genes encoding crotonase enzymes can be found in *C. acetobutylicum* (Boynton et al., supra), *C. kluyveri* (Hillmer et al., *FEBS Lett.* 21:351-354 (1972)), and *Metallosphaera sedula* (Berg et al., supra) though the sequence of the latter gene is not known. Enoyl-CoA hydratases, which are involved in fatty acid beta-oxidation and/or the metabolism of various amino acids, can also catalyze the hydration of crotonyl-CoA to form 3-hydroxybutyryl-CoA (Roberts et al., *Arch. Microbiol* 117:99-108 (1978); Agnihotri et al., *Bioorg. Med. Chem.* 11:9-20 (2003); Conrad et al., *J Bacteriol.* 118:103-111 (1974)).

| Gene name | GI# | GenBank Accession # | Organism |
|---|---|---|---|
| paaA | 26990002 | NP_745427.1 | *Pseudomonas fluorescens* |
| paaB | 26990001 | NP_745426.1 | *Pseudomonas fluorescens* |
| phaA | 106636093 | ABF82233.1 | *Pseudomonas putida* |
| phaB | 106636094 | ABF82234.1 | *Pseudomonas putida* |
| maoC | 16129348 | NP_415905.1 | *Escherichia coli* |
| paaF | 16129354 | NP_415911.1 | *Escherichia coli* |
| paaG | 16129355 | NP_415912.1 | *Escherichia coli* |
| crt | 15895969 | NP_349318.1 | *Clostridium acetobutylicum* |
| crt1 | 153953091 | YP_001393856 | *Clostridium kluyveri* DSM 555 |

6.2.1.a Acid-Thiol Ligase.

Steps F, L, and R of FIG. 10 and Steps F and L of FIG. 11 require acid-thiol ligase or synthetase functionality (the terms ligase, synthetase, and synthase are used herein interchangeably and refer to the same enzyme class). Exemplary genes encoding enzymes likely to carry out these transformations include the sucCD genes of *E. coli* which naturally form a succinyl-CoA synthetase complex. This enzyme complex naturally catalyzes the formation of succinyl-CoA from succinate with the contaminant consumption of one ATP, a reaction which is reversible in vivo (Buck et al., *Biochem.* 24:6245-6252 (1985)). Given the structural similarity between succinate and adipate, that is, both are straight chain dicarboxylic acids, it is reasonable to expect some activity of the sucCD enzyme on adipyl-CoA.

| Gene name | GI# | GenBank Accession # | Organism |
|---|---|---|---|
| sucC | 16128703 | NP_415256.1 | *Escherichia coli* |
| sucD | 1786949 | AAC73823.1 | *Escherichia coli* |

Additional exemplary CoA-ligases include the rat dicarboxylate-CoA ligase for which the sequence is yet uncharacterized (Vamecq et al., *Biochemical Journal* 230:683-693 (1985)), either of the two characterized phenylacetate-CoA ligases from *P. chrysogenum* (Lamas-Maceiras et al., *Biochem. J.* 395:147-155 (2005); Wang et al., *Biochem Biophy Res Commun* 360(2):453-458 (2007)), the phenylacetate-CoA ligase from *Pseudomonas putida* (Martinez-Blanco et al., *J. Biol. Chem.* 265:7084-7090 (1990)), and the 6-carboxyhexanoate-CoA ligase from *Bacillus subtilis* (Bower et al., *J. Bacteriol.* 178(14):4122-4130 (1996)). Additional candidate enzymes are acetoacetyl-CoA synthetases from *Mus musculus* (Hasegawa et al., *Biochim Biophys Acta* 1779:414-419 (2008)) and *Homo sapiens* (Ohgami et al., *Biochem Pharmacol* 65:989-994 (2003)) which naturally catalyze the ATP-dependent conversion of acetoacetate into acetoacetyl-CoA.

| Gene name | GI# | GenBank Accession # | Organism |
|---|---|---|---|
| phl | 77019264 | CAJ15517.1 | *Penicillium chrysogenum* |
| phlB | 152002983 | ABS19624.1 | *Penicillium chrysogenum* |
| paaF | 22711873 | AAC24333.2 | *Pseudomonas putida* |
| bioW | 50812281 | NP_390902.2 | *Bacillus subtilis* |
| AACS | 21313520 | NP_084486.1 | *Mus musculus* |
| AACS | 31982927 | NP_076417.2 | *Homo sapiens* |

ADP-forming acetyl-CoA synthetase (ACD, EC 6.2.1.13) is another candidate enzyme that couples the conversion of acyl-CoA esters to their corresponding acids with the concurrent synthesis of ATP. Several enzymes with broad substrate specificities have been described in the literature. ACD I from *Archaeoglobus fulgidus*, encoded by AF1211, was shown to operate on a variety of linear and branched-chain substrates including acetyl-CoA, propionyl-CoA, butyryl-CoA, acetate, propionate, butyrate, isobutyrate, isovalerate, succinate, fumarate, phenylacetate, indoleacetate (Musfeldt et al., *J Bacteriol* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., supra). The enzymes from *A. fulgidus, H. marismortui* and *P. aerophilum* have all been cloned, functionally expressed, and characterized in *E. coli* (Musfeldt et al., supra; Brasen et al., supra).

| Gene name | GI# | GenBank Accession # | Organism |
| --- | --- | --- | --- |
| AF1211 | 11498810 | NP_070039.1 | Archaeoglobus fulgidus DSM 4304 |
| scs | 55377722 | YP_135572.1 | Haloarcula marismortui ATCC 43049 |
| PAE3250 | 18313937 | NP_560604.1 | Pyrobaculum aerophilum str. IM2 |

Yet another option is to employ a set of enzymes with net ligase or synthetase activity. For example, phosphotransadipylase and adipate kinase enzymes are catalyzed by the gene products of buk1, buk2, and ptb from C. acetobutylicum (Walter et al., Gene 134:107-111 (1993); Huang et al., J Mol. Microbiol. Biotechnol. 2:33-38 (2000)). The ptb gene encodes an enzyme that can convert butyryl-CoA into butyryl-phosphate, which is then converted to butyrate via either of the buk gene products with the concomitant generation of ATP.

| Gene name | GI# | GenBank Accession # | Organism |
| --- | --- | --- | --- |
| ptb | 15896327 | NP_349676 | Clostridium acetobutylicum |
| buk1 | 15896326 | NP_349675 | Clostridium acetobutylicum |
| buk2 | 20137415 | Q97II1 | Clostridium acetobutylicum |

No enzyme required—Spontaneous cyclization. 6-Aminocaproyl-CoA will cyclize spontaneously to caprolactam, thus eliminating the need for a dedicated enzyme for this step. A similar spontaneous cyclization is observed with 4-aminobutyryl-CoA which forms pyrrolidinone (Ohsugi et al., J Biol Chem 256:7642-7651 (1981)).

Example XIII

Preparation of a 6-Aminocaproic Acid Producing Microbial Organism Having a Pathway for Converting Acetyl-CoA and 4-Aminobutyryl-CoA to 6-Aminocaproic Acid This example describes the generation of a microbial organism capable of producing 6-aminocaproic acid from acetyl-CoA and 4-aminobutyryl-CoA.

Escherichia coli is used as a target organism to engineer the 6-aminocaproic acid pathway shown in FIG. 11 that starts from acetyl-CoA and 4-aminobutyryl-CoA. E. coli provides a good host for generating a non-naturally occurring microorganism capable of producing 6-aminocaproic acid. E. coli is amenable to genetic manipulation and is known to be capable of producing various products, like ethanol, acetic acid, formic acid, lactic acid, and succinic acid, effectively under anaerobic or microaerobic conditions.

To generate an E. coli strain engineered to produce 6-aminocaproic acid, nucleic acids encoding the requisite enzymes are expressed in E. coli using well known molecular biology techniques (see, for example, Sambrook, supra, 2001; Ausubel, supra, 1999). In particular, the paaI (NP_415915.1), paaH (NP_415913.1), and maoC (NP_415905.1) genes encoding the 3-oxo-6-aminohexanoyl-CoA thiolase, 3-oxo-6-aminohexanoyl-CoA reductase, 3-hydroxy-6-aminohexanoyl-CoA dehydratase activities, respectively, are cloned into the pZE13 vector (Expressys, Ruelzheim, Germany) under the PA1/lacO promoter. In addition, the bcd (NP_349317.1), etfAB (NP_349315.1 and NP_349316.1), and acot8 (CAA15502) genes encoding 6-aminohex-2-enoyl-CoA reductase and 6-aminocaproyl-CoA hydrolase activities are cloned into the pZA33 vector (Expressys, Ruelzheim, Germany) under the PA1/lacO promoter. Lastly, the sucD (NP_904963.1), gabT (NP_417148.1), and cat2 (P38942.2) genes encoding succinyl-CoA reductase (aldehyde forming), GABA transaminase, and 4-aminobutyryl-CoA/acyl-CoA transferase activities are cloned into a third compatible plasmid, pZS23, under the PA1/lacO promoter, to increase the availability of 4-aminobutyryl-CoA. pZS23 is obtained by replacing the ampicillin resistance module of the pZS13 vector (Expressys, Ruelzheim, Germany) with a kanamycin resistance module by well-known molecular biology techniques. The three sets of plasmids are transformed into E. coli strain MG1655 to express the proteins and enzymes required for 6-aminocaproic acid synthesis.

The resulting genetically engineered organism is cultured in glucose-containing medium following procedures well known in the art (see, for example, Sambrook et al., supra, 2001). The expression of the 6-aminocaproic acid synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce 6-aminocaproic acid is confirmed using HPLC, gas chromatography-mass spectrometry (GCMS) and/or liquid chromatography-mass spectrometry (LCMS).

Microbial strains engineered to have a functional 6-aminocaproic acid synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 6-aminocaproic acid. One modeling method is the bilevel optimization approach, OptKnock (Burgard et al., Biotechnol. Bioengineer. 84:647-657 (2003)), which is applied to select gene knockouts that collectively result in better production of 6-aminocaproic acid. Adaptive evolution also can be used to generate better producers of, for example, the acetyl-CoA and succinyl-CoA intermediates of the 6-aminocaproic acid product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the 6-aminocaproic acid producer to further increase production.

For large-scale production of 6-aminocaproic acid, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

Example XIV

Preparation of a 6-Aminocaproic Acid Producing Microbial Organism Having a Pathway for Converting Acetyl-CoA and 4-Aminobutyryl-CoA to 6-Aminocaproic Acid This example describes the generation of a microbial organism capable of producing 6-aminocaproic acid from acetyl-CoA and 4-aminobutyryl-CoA.

*Escherichia coli* is used as a target organism to engineer the 6-aminocaproic acid pathway shown in FIG. 11 that starts from acetyl-CoA and 4-aminobutyryl-CoA. *E. coli* provides a good host for generating a non-naturally occurring microorganism capable of producing 6-aminocaproic acid. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce 6-aminocaproic acid, nucleic acids encoding the requisite enzymes are expressed in *E. coli* using well known molecular biology techniques (see, for example, Sambrook, supra, 2001; Ausubel, supra, 1999). In particular, the paaJ (NP_415915.1), pcaIJ (AAN69545.1 and NP_746082.1), and bdh (AAA58352.1) genes encoding the 3-oxo-6-aminohexanoyl-CoA thiolase, 3-oxo-6-aminohexanoyl-CoA/acyl-CoA transferase, 3-oxo-6-aminohexanoate reductase activities, respectively, are cloned into the pZE13 vector (Expressys, Ruelzheim, Germany) under the PA1/lacO promoter. In addition, the enr (CAA76083.1) and hmd (ABC88407.1) genes encoding 6-aminohex-2-enoate reductase and 3-hydroxy-6-aminohexanoate dehydratase activities are cloned into the pZA33 vector (Expressys, Ruelzheim, Germany) under the PA1/lacO promoter. Lastly, the sucD (NP_904963.1), gabT (NP_417148.1), and cat2 (P38942.2) genes encoding succinyl-CoA reductase (aldehyde forming), GABA transaminase, and 4-aminobutyryl-CoA/acyl-CoA transferase activities are cloned into a third compatible plasmid, pZS23, under the PA1/lacO promoter, to increase the availability of 4-aminobutyryl-CoA. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for 6-aminocaproic acid synthesis.

The resulting genetically engineered organism is cultured in glucose-containing medium following procedures well known in the art (see, for example, Sambrook et al., supra, 2001). The expression of the 6-aminocaproic acid synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce 6-aminocaproic acid is confirmed using HPLC, gas chromatography-mass spectrometry (GCMS) and/or liquid chromatography-mass spectrometry (LCMS).

Microbial strains engineered to have a functional 6-aminocaproic acid synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of 6-aminocaproic acid. One modeling method is the bilevel optimization approach, OptKnock (Burgard et al., *Biotechnol. Bioengineer.* 84:647-657 (2003)), which is applied to select gene knockouts that collectively result in better production of 6-aminocaproic acid. Adaptive evolution also can be used to generate better producers of, for example, the acetyl-CoA and succinyl-CoA intermediates of the 6-aminocaproic acid product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the 6-aminocaproic acid producer to further increase production.

For large-scale production of 6-aminocaproic acid, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

Example XV

Preparation of a Caprolactam Producing Microbial Organism Having a Pathway for Converting Acetyl-CoA and Succinyl-CoA to 6-Aminocaproic acid This example describes the generation of a microbial organism capable of producing caprolactam from acetyl-CoA and succinyl-CoA.

*Escherichia coli* is used as a target organism to engineer the caprolactam pathway shown in FIG. 10 that starts from acetyl-CoA and succinyl-CoA. *E. coli* provides a good host for generating a non-naturally occurring microorganism capable of producing caprolactam. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce caprolactam, nucleic acids encoding the requisite enzymes are expressed in *E. coli* using well known molecular biology techniques (see, for example, Sambrook, supra, 2001; Ausubel, supra, 1999). In particular, the paaI (NP_415915.1), paaH (NP_415913.1), and maoC (NP_415905.1) genes encoding the 3-oxoadipyl-CoA thiolase, 3-oxoadipyl-CoA reductase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1) and etfAB (NP_349315.1 and NP_349316.1) genes encoding 5-carboxy-2-pentenoyl-CoA reductase activity are cloned into the pZA33 vector (Expressys, Ruelzheim, Germany) under the PA1/lacO promoter. Lastly, the acr1 (YP_047869.1), gabT (NP_417148.1), and bioW (NP_390902.2) genes encoding adipyl-CoA reductase (aldehyde forming), 6-aminocaproic acid transaminase, and 6-aminocaproyl-CoA synthase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for caprolactam synthesis.

The resulting genetically engineered organism is cultured in glucose-containing medium following procedures well known in the art (see, for example, Sambrook et al., supra, 2001). The expression of the caprolactam synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce caprolactam is confirmed using HPLC, gas chromatography-mass spectrometry (GCMS) and/or liquid chromatography-mass spectrometry (LCMS).

Microbial strains engineered to have a functional caprolactam synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127, 379). Modeling analysis allows reliable predictions of the effects on cell growth of shifting the metabolism towards more efficient production of caprolactam. One modeling method is the bilevel optimization approach, OptKnock (Burgard et al., *Biotechnol. Bioengineer.* 84:647-657 (2003)), which is applied to select gene knockouts that collectively result in better production of caprolactam. Adaptive evolution also can be used to generate better producers of, for example, the acetyl-CoA and succinyl-CoA intermediates of the caprolactam product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the caprolactam producer to further increase production.

For large-scale production of caprolactam, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_{2SO4}$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

Example XVI

Preparation of a Hexamethylenediamine Producing Microbial Organism Having a Pathway for Converting Acetyl-CoA and Succinyl-CoA to 6-Aminocaproic acid This example describes the generation of a microbial organism capable of producing hexamethylenediamine from acetyl-CoA and succinyl-CoA.

*Escherichia coli* is used as a target organism to engineer the hexamethylenediamine pathway shown in FIG. 10 that starts from acetyl-CoA and succinyl-CoA. *E. coli* provides a good host for generating a non-naturally occurring microorganism capable of producing hexamethylenediamine. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce hexamethylenediamine, nucleic acids encoding the requisite enzymes are expressed in *E. coli* using well known molecular biology techniques (see, for example, Sambrook, supra, 2001; Ausubel, supra, 1999). In particular, the paaI (NP_415915.1), paaH (NP_415913.1), and maoC (NP_415905.1) genes encoding the 3-oxoadipyl-CoA thiolase, 3-oxoadipyl-CoA reductase, and 3-hydroxyadipyl-CoA dehydratase activities, respectively, are cloned into the pZE13 vector (Expressys, Ruelzheim, Germany) under the PA1/lacO promoter. In addition, the bcd (NP_349317.1) and etfAB (NP_349315.1 and NP_349316.1) genes encoding 5-carboxy-2-pentenoyl-CoA reductase activity are cloned into the pZA33 vector (Expressys, Ruelzheim, Germany) under the PA1/lacO promoter. Lastly, the acr1 (YP_047869.1), gabT (NP_417148.1), bioW (NP_390902.2), and ygjG (NP_417544) genes encoding adipyl-CoA reductase (aldehyde forming), 6-aminocaproyl-CoA reductase (aldehyde forming), 6-aminocaproic acid transaminase, 6-aminocaproyl-CoA synthase, and hexamethylenediamine transaminase activities are cloned into a third compatible plasmid, pZS23, under the PA1/lacO promoter. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for hexamethylenediamine synthesis.

The resulting genetically engineered organism is cultured in glucose-containing medium following procedures well known in the art (see, for example, Sambrook et al., supra, 2001). The expression of the hexamethylenediamine synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered *E. coli* strain to produce hexamethylenediamine is confirmed using HPLC, gas chromatography-mass spectrometry (GCMS) and/or liquid chromatography-mass spectrometry (LCMS).

Microbial strains engineered to have a functional hexamethylenediamine synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of hexamethylenediamine. One modeling method is the bilevel optimization approach, OptKnock (Burgard et al., *Biotechnol. Bioengineer.* 84:647-657 (2003)), which is applied to select gene knockouts that collectively result in better production of hexamethylenediamine. Adaptive evolution also can be used to generate better producers of, for example, the acetyl-CoA and succinyl-CoA intermediates of the hexamethylenediamine product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the hexamethylenediamine producer to further increase production.

For large-scale production of hexamethylenediamine, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

Example XVII

Preparation of a Caprolactam Producing Microbial Organism Having a Pathway for Converting Acetyl-CoA and 4-aminobutyryl-CoA to 6-Aminocaproyl-CoA This example describes the generation of a microbial organism capable of producing caprolactam from acetyl-CoA and 4-aminobutyryl-CoA.

*Escherichia coli* is used as a target organism to engineer the caprolactam pathway shown in FIG. 11 that starts from acetyl-CoA and 4-aminobutyryl-CoA. *E. coli* provides a good host for generating a non-naturally occurring microorganism capable of producing caprolactam. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce caprolactam, nucleic acids encoding the requisite enzymes are expressed in *E. coli* using well known molecular biology techniques (see, for example, Sambrook, supra, 2001; Ausubel, supra, 1999). In particular, the paaI (NP_415915.1), paaH (NP_415913.1), and maoC (NP_415905.1) genes encoding the 3-oxo-6-aminohexanoyl-CoA thiolase, 3-oxo-6-aminohexanoyl-CoA reductase, 3-hydroxy-6-aminohexanoyl-CoA dehydratase activities, respectively, are cloned into the pZE13 vector (Expressys, Ruelzheim, Germany) under the PA1/lacO promoter. In addition, the bcd (NP_349317.1) and etfAB (NP_349315.1 and NP_349316.1) genes encoding 6-aminohex-2-enoyl-CoA reductase activity are cloned into the pZA33 vector (Expressys, Ruelzheim, Germany) under the PA1/lacO promoter. Lastly, the sucD (NP_904963.1), gabT (NP_417148.1), and cat2 (P38942.2) genes encoding succinyl-CoA reductase (aldehyde forming), GABA transaminase, and 4-aminobutyryl-CoA/acyl-CoA transferase activities are cloned into a third compatible plasmid, pZS23, under the PA1/lacO promoter, to increase the availability of 4-aminobutyryl-CoA. pZS23 is obtained by replacing the ampicillin resistance module of the pZS13 vector (Expressys, Ruelzheim, Germany) with a kanamycin resistance module by well-known molecular biology techniques. The three sets of plasmids are transformed into E. coli strain MG1655 to express the proteins and enzymes required for caprolactam synthesis.

The resulting genetically engineered organism is cultured in glucose-containing medium following procedures well known in the art (see, for example, Sambrook et al., supra, 2001). The expression of the caprolactam synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce caprolactam is confirmed using HPLC, gas chromatography-mass spectrometry (GCMS) and/or liquid chromatography-mass spectrometry (LCMS).

Microbial strains engineered to have a functional caprolactam synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of caprolactam. One modeling method is the bilevel optimization approach, OptKnock (Burgard et al., *Biotechnol. Bioengineer.* 84:647-657 (2003)), which is applied to select gene knockouts that collectively result in better production of caprolactam. Adaptive evolution also can be used to generate better producers of, for example, the acetyl-CoA and succinyl-CoA intermediates of the caprolactam product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the caprolactam producer to further increase production.

For large-scale production of caprolactam, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

Example XVIII

Preparation of a Hexamethylenediamine Producing Microbial Organism Having a Pathway for Converting Acetyl-CoA and 4-aminobutyryl-CoA to 6-Aminocaproyl-CoA This example describes the generation of a microbial organism capable of producing hexamethylenediamine from acetyl-CoA and 4-aminobutyryl-CoA.

*Escherichia coli* is used as a target organism to engineer the hexamethylenediamine pathway shown in Figure XVII that starts from acetyl-CoA and 4-aminobutyryl-CoA. *E. coli* provides a good host for generating a non-naturally occurring microorganism capable of producing hexamethylenediamine. *E. coli* is amenable to genetic manipulation and is known to be capable of producing various products, like ethanol, acetic acid, formic acid, lactic acid, and succinic acid, effectively under anaerobic or microaerobic conditions.

To generate an *E. coli* strain engineered to produce hexamethylenediamine, nucleic acids encoding the requisite enzymes are expressed in *E. coli* using well known molecular biology techniques (see, for example, Sambrook, supra, 2001; Ausubel, supra, 1999). In particular, the paaI (NP_415915.1), paaH (NP_415913.1), and maoC (NP_415905.1) genes encoding the 3-oxo-6-aminohexanoyl-CoA thiolase, 3-oxo-6-aminohexanoyl-CoA reductase, 3-hydroxy-6-aminohexanoyl-CoA dehydratase activities, respectively, are cloned into the pZE13 vector (Expressys, Ruelzheim, Germany) under the PA1/lacO promoter. In addition, the bcd (NP_349317.1), etfAB (NP_349315.1 and NP_349316.1), acr1 (YP_047869.1), and ygjG (NP_417544) genes encoding 6-aminohex-2-enoyl-CoA reductase, 6-aminocaproyl-CoA reductase (aldehyde forming), and hexamethylenediamine transaminase activities are cloned into the pZA33 vector (Expressys, Ruelzheim, Germany) under the PA1/lacO promoter. Lastly, the sucD (NP_904963.1), gabT (NP_417148.1), and cat2 (P38942.2) genes encoding succinyl-CoA reductase (aldehyde forming), GABA transaminase, and 4-aminobutyryl-CoA/acyl-CoA transferase activities are cloned into a third compatible plasmid, pZS23, under the PA1/lacO promoter, to increase the availability of 4-aminobutyryl-CoA. pZS23 is obtained by replacing the ampicillin resistance module of the pZS13 vector (Expressys, Ruelzheim, Germany) with a kanamycin resistance module by well-known molecular biology techniques. The three sets of plasmids are transformed into *E. coli* strain MG1655 to express the proteins and enzymes required for hexamethylenediamine synthesis.

The resulting genetically engineered organism is cultured in glucose-containing medium following procedures well known in the art (see, for example, Sambrook et al., supra, 2001). The expression of the hexamethylenediamine synthesis genes is corroborated using methods well known in the art for determining polypeptide expression or enzymatic activity, including for example, Northern blots, PCR amplification of mRNA, immunoblotting, and the like. Enzymatic activities of the expressed enzymes are confirmed using assays specific for the individual activities. The ability of the engineered E. coli strain to produce hexamethylenediamine is confirmed using HPLC, gas chromatography-mass spectrometry (GCMS) and/or liquid chromatography-mass spectrometry (LCMS).

Microbial strains engineered to have a functional hexamethylenediamine synthesis pathway are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and U.S. Pat. No. 7,127,379). Modeling analysis allows reliable predictions of the effects on cell growth of shifting the metabolism towards more efficient production of hexamethylenediamine. One modeling method is the bilevel optimization approach, OptKnock (Burgard et al., *Biotechnol. Bioengineer.* 84:647-657 (2003)), which is applied to select gene knockouts that collectively result in better production of hexamethylenediamine. Adaptive evolution also can be used to generate better producers of, for example, the acetyl-CoA and succinyl-CoA intermediates of the hexamethylenediamine product. Adaptive evolution is performed to improve both growth and production characteristics (Fong and Palsson, *Nat. Genet.* 36:1056-1058 (2004); Alper et al., *Science* 314:1565-1568 (2006)). Based on the results, subsequent rounds of modeling, genetic engineering and adaptive evolution can be applied to the hexamethylenediamine producer to further increase production.

For large-scale production of hexamethylenediamine, the above organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing the culture vessel, for example, flasks can be sealed with a septum and crimp-cap. Microaerobic conditions also can be utilized by providing a small hole in the septum for limited aeration. The pH of the medium is maintained at a pH of around 7 by addition of an acid, such as $H_2SO_4$. The growth rate is determined by measuring optical density using a spectrophotometer (600 nm) and the glucose uptake rate by monitoring carbon source depletion over time. Byproducts such as undesirable alcohols, organic acids, and residual glucose can be quantified by HPLC (Shimadzu, Columbia Md.), for example, using an Aminex® series of HPLC columns (for example, HPX-87 series) (BioRad, Hercules Calif.), using a refractive index detector for glucose and alcohols, and a UV detector for organic acids (Lin et al., *Biotechnol. Bioeng.* 775-779 (2005)).

Example XIX

Pathways for Production of 6-Aminocaproic Acid from Succinic Semialdehyde and Pyruvate This example describes exemplary pathways for production of 6-aminocaproic acid. Novel pathways for producing 6-aminocaproic acid (6-ACA) and related products are described herein. These pathways synthesize 6-ACA from succinic semialdehyde and pyruvate, utilizing aldolase and hydratase enzymes from the 4-hydroxyphenylacetic acid degradation pathway. The candidate enzymes, and associated risks of implementation are discussed in Example XXI below.

This invention is directed, in part, to non-naturally occurring microorganisms that express genes encoding enzymes that catalyze 6-ACA production. Successfully engineering these pathways entails identifying an appropriate set of enzymes with sufficient activity and specificity, cloning their corresponding genes into a production host, optimizing the expression of these genes in the production host, optimizing fermentation conditions, and assaying for product formation following fermentation.

6-aminocaproic acid and derivatives are produced from succinic semialdehyde and pyruvate in a minimum of five enzymatic steps. In the first step of all pathways, pyruvate and succinic semialdehyde are joined by 4-hydroxy-2-oxoheptane-1,7-dioate (HODH) aldolase. The product of this reaction, HODH, is then dehydrated by 2-oxohept-4-ene-1,7-dioate (OHED) hydratase to form OHED In subsequent steps, OHED is transaminated, decarboxylated or reduced as shown in FIG. 12.

In one route, the alkene of OHED is reduced by OHED reductase, forming 2-oxoheptane-1,7-dioate (2-OHD) (FIG. 12, Step C), a 2-ketoacid. 2-OHD is then converted to adipate semialdehyde by a ketoacid decarboxylase (FIG. 12, Step D). In the final step, the aldehyde of adipate semialdehyde is converted to an amine by an aminotransferase or an aminating oxidoreductase (FIG. 12, Step E).

In a similar route, the 2-keto group of 2-OHD is transaminated by an aminotransferase or an aminating oxidoreductase (FIG. 12, Step H) to form 2-aminoheptane-1,7-dioate (2-AHD). This product is then decarboxylated by 2-AHD decarboxylase to form 6-aminocaproate (FIG. 12, Step I).

In an alternate route, OHED is first decarboxylated by OHED decarboxylase (FIG. 12, Step F), resulting in the formation of 6-oxohex-4-enoate (6-OHE). The alkenal group of 6-OHE is reduced by an oxidoreductase to adipate semialdehyde (FIG. 12, Step G). Adipate semialdehyde is then converted to 6-aminocaproate by an aminotransferase or aminating oxidoreductase (FIG. 12, Step E).

Yet another route calls for an aminotransferase or aminating oxidoreductase to convert OHED to 2-aminohept-4-ene-1,7-dioate (2-AHE) (FIG. 12, Step J). The alkene of 2-AHE is subsequently reduced by an alkene oxidoreductase (FIG. 12, Step K). The product of this reaction, 2-AHD, is then decarboxylated by an amino acid decarboxylase (FIG. 12, Step I) to form 6-aminocaproate.

In yet another route, HODH is converted to 3-hydroxyadipyl-CoA by either an HODH dehydrogenase or and HODH formate-lyase (FIG. 12, Step L). 3-Hydroxyadipyl-CoA is subsequently dehydrated and reduced to form adipyl-CoA (FIG. 12, Steps M, N). Adipyl-CoA is reduced and de-acylated to form adipate semialdehyde (FIG. 12, Step O), which is then converted to 6-aminocaproate by an aminotransferase or an aminating oxidoreductase (FIG. 12, Step E).

In a similar route, HODH is first converted to OHED (FIG. 12, Step B), as described above. OHED is then converted to 2,3-dehydroadipyl-CoA by a dehydrogenase or an OHED formate-lyase (FIG. 12, Step P). 2,3-Dihydroadipyl-CoA is then reduced to adipyl-CoA (FIG. 12, Step N), which is converted to 6-aminocaproate via adipate semialdehyde (FIG. 12, Steps 0, E), as described previously.

In the final route, HODH is converted to 2-OHD via steps B and C, as described previously. A 2-OHD formate-lyase or dehydrogenase converts 2-OHD to adipyl-CoA (FIG. 12, Step Q), which is then reduced by a CoA-dependent aldehyde dehydrogenase (FIG. 12, Step O). The product, adipate semialdehyde, is converted to 6-aminocaproate by an aminotransferase or aminating oxidoreductase (FIG. 12, Step E).

The routes detailed in FIG. 12 are able to achieve the maximum theoretical 6-ACA yield of 0.8 moles 6-ACA per mole glucose utilized. The energetic yield is also favorable, with a maximum of 1.6 moles ATP per mole glucose utilized at the maximum product yield. The following assumptions were used to calculate yield: 1) phosphoenolpyruvate (PEP) carboxykinase is able to operate in the ATP-generating direction, 2) NH4 and 6-ACA are transported into the cell by proton antiport, and 3) succinic semialdehyde is formed from alpha-ketoglutarate and/or succinyl-CoA. Succinic semialdehyde dehydrogenase is a NAD(P)H and CoA-dependent aldehyde dehydrogenase that converts succinyl-CoA to succinic semialdehyde. Succinic semialdehyde is formed from alpha-ketoglutarate by two enzymes: alpha-ketoglutarate decarboxylase and 4-aminobutyrate transaminase.

Example XX

Pathways for Production of Hexamethylenediamine from 6-Aminocaproate

This example describes exemplary pathways for production of hexamethylenediamine.

Novel pathways for producing hexamethylenediamine (HMDA) and related products are described herein. This pathway synthesizes HMDA from 6-Aminocaproate (6-ACA). These pathways involve activation of the acid group by phosphorylation and/or acylation. Acetylation of the terminal amino group provides protection from spontaneous cyclization of pathway intermediates. The candidate enzymes, and associated risks of implementation are discussed in Example XXI below.

This invention is directed, in part, to non-naturally occurring microorganisms that express genes encoding enzymes that catalyze HMDA production. Successfully engineering these pathways entails identifying an appropriate set of enzymes with sufficient activity and specificity, cloning their corresponding genes into a production host, optimizing the expression of these genes in the production host, optimizing fermentation conditions, and assaying for product formation following fermentation.

Several pathways for producing HMDA from 6-aminocaproate are detailed in FIG. 13. All routes entail activation of the carboxylic acid group, followed by reduction and transamination. In three routes, 6-aminocaproate is activated directly while in other routes, the terminal amine group is protected by N-acetylation to prevent spontaneous cyclization.

In one route, 6-aminocaproate is phosphorylated to 6-AHOP by 6-aminocaproate kinase (FIG. 13, Step A). 6-AHOP is then reduced to 6-aminocaproic semialdehyde (FIG. 13, Step B) and subsequently transaminated (FIG. 13, Step C) by an aminotransferase or an aminating oxidoreductase.

Alternately, 6-AHOP is converted to 6-aminocaproyl-CoA by an acyltransferase (FIG. 13, Step L). 6-Aminocaproyl-CoA is then reduced to 6-aminocaproic semialdehyde by a CoA-dependent aldehyde dehydrogenase (FIG. 13, Step N). HMDA is then formed by transamination of 6-aminocaproic semialdehyde by an aminotransferase or aminating oxidoreductase (FIG. 13, Step C).

In yet another route, 6-aminocaproate is first activated to a CoA derivative by a CoA transferase or CoA ligase (FIG. 13, Step M). The product, 6-aminocaproyl-CoA, may spontaneously cyclize, or be converted to 6-aminocaproic semialdehyde by an aldehyde-forming CoA-dependent aldehyde dehydrogenase (FIG. 13, Step N). 6-Aminocaproic semialdehyde is converted to HMDA by an aminotransferase or an aminating oxidoreductase (FIG. 13, Step C).

Additional routes proceed from 6-acetamidohexanoate, the acetylated product of 6-aminocaproate N-acetyltransferase. 6-Acetamidohexanoate is converted to 6-acetamidohexanal by different routes (described below). In the final two steps of these routes, 6-acetamidohexanal is first converted to 6-acetamidohexanamine by an aminotransferase or an aminating oxidoreductase (FIG. 13, Step G). 6-Acetamidohexanamine is subsequently converted to HMDA by an amide hydrolase or an N-acetyltransferase (FIG. 13, Step H).

In one route, 6-acetamidohexanoate is phosphorylated by 6-acetamidohexanoate kinase (FIG. 13, Step E). The product, 6-AAHOP, is reduced to form 6-acetamidohexanal (FIG. 13, Step F), which is then converted to HMDA as described above.

In another route, 6-acetamidohexanoate is activated to 6-acetamidohexanoyl-CoA by a CoA transferase or CoA ligase (FIG. 13, Step I). The CoA derivative is then reduced to 6-acetamidohexanal by an aldehyde-forming CoA-dependent oxidoreductase (FIG. 13, Step J). 6-acetamidohexanal is then converted to HMDA as described above.

Alternately, 6-acetamidohexanoate is phosphorylated to 6-AAHOP (FIG. 13, Step E) and subsequently converted to 6-acetamidohexanoyl-CoA by an acyltransferase (FIG. 13, Step K). 6-Acetamidohexanoyl-CoA is then reduced to HMDA as described previously.

Example XXI

Enzyme Classification System for Production of 6-Aminocaproic Acid and Hexamethylenediamine This example describes the enzyme classification system for the exemplary pathways described in Examples XIX and XX for production of 6-aminocaproate or hexamethylenediamine.

All transformations depicted in FIGS. 12 and 13 fall into the general categories of transformations shown in Table 9. Below is described a number of biochemically characterized genes in each category. Specifically listed are genes that can be applied to catalyze the appropriate transformations in FIGS. 12-13 when properly cloned and expressed.

Table 9 shows the enzyme types useful to convert common central metabolic intermediates into 6-aminocaproate and hexamethylenediamine. The first three digits of each label correspond to the first three Enzyme Commission number digits which denote the general type of transformation independent of substrate specificity.

TABLE 9

| LABEL | FUNCTION |
|---|---|
| 1.2.1.b | Oxidoreductase (acyl-CoA to aldehyde) |
| 1.2.1.c | Oxidoreductase (2-ketoacid to acyl-CoA) |
| 1.2.1.d | Oxidoreductase (phosphonic acid to aldehyde) |
| 1.3.1.a | Oxidoreductase (alkene to alkane) |
| 1.4.1.a | Oxidoreductase (ketone or aldehyde to amino) |
| 2.3.1.a | Acyltransferase (transferring CoA to phospho) |
| 2.3.1.c | Acyltransferase (N-acetyltransferase) |
| 2.3.1.d | Acyltransferase (formate C-acyltransferase) |
| 2.6.1.a | Aminotransferase |
| 2.7.2.a | Phosphotransferase (carboxy acceptor) |
| 2.8.3.a | Coenzyme-A transferase |
| 3.5.1.a | Hydrolase (acting on linear amides) |
| 4.1.1.a | Carboxy-lyase |
| 4.1.2.a | Aldehyde-lyase |
| 4.2.1.a | Hydro-lyase |
| 6.2.1.a | Acid-thiol ligase |

1.2.1.b Oxidoreductase (Acyl-CoA to Aldehyde).

The transformations of 6-acetamidohexanoyl-CoA to 6-acetamidohexanal (FIG. 13, Step J) and 6-aminocaproyl-CoA to 6-aminocaproic semialdehyde (FIG. 13, Step N) are catalyzed by CoA-dependent oxidoreductase enzyme in the EC class 1.2.1. Adipyl-CoA is converted to adipate semialdehyde by adipyl-CoA oxidoreductase, an enzyme with similar functionality (FIG. 12, Step O). Succinic semialdehyde dehydrogenase, an enzyme that forms FIG. 12 precursor succinic semialdehyde from succinyl-CoA, is also a CoA-dependent oxidoreductase. Oxidoreductases in the EC class 1.2.1.- are capable of reducing an acyl-CoA to its corresponding aldehyde. Exemplary genes that encode such enzymes include the *Acinetobacter calcoaceticus* acr1 encoding a fatty acyl-CoA reductase (Reiser and Somerville, *Journal of Bacteriology* 179:2969-2975 (1997)), the *Acinetobacter* sp. M-1 fatty acyl-CoA reductase (Ishige et al., *Appl. Environ. Microbiol.* 68:1192-1195 (2002)), and a CoA- and NADP-dependent succinic semialdehyde dehydrogenase encoded by the sucD gene in *Clostridium kluyveri* (Sohling and Gottschalk, *J. Bacteriol.* 178:871-880 (1996)). SucD of *P. gingivalis* is another succinic semialdehyde dehydrogenase (Takahashi et al., *J. Bacteriol.* 182:4704-4710 (2000)). The acylating acetaldehyde dehydrogenase in *Pseudomonas* sp, encoded by bphG, is yet another candidate as it has been demonstrated to oxidize and acylate acetaldehyde, propionaldehyde, butyraldehyde, isobutyraldehyde and formaldehyde (Powlowski et al., *J. Bacteriol.* 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya et al., *J. Gen. Appl. Microbiol.* 18:43-55 (1972); and Koo et al., *Biotechnol Lett.* 27:505-510 (2005)).

| Gene name | GI# | GenBank Accession # | Organism |
|---|---|---|---|
| acr1 | 50086359 | YP_047869.1 | Acinetobacter calcoaceticus |
| acr1 | 1684886 | AAC45217 | Acinetobacter baylyi |
| acr1 | 18857901 | BAB85476.1 | Acinetobacter sp. Strain M-1 |
| sucD | 172046062 | P38947.1 | Clostridium kluyveri |
| sucD | 34540484 | NP_904963.1 | Porphyromonas gingivalis |
| bphG | 425213 | BAA03892.1 | Pseudomonas sp |
| adhE | 55818563 | AAV66076.1 | Leuconostoc mesenteroides |

An additional enzyme that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg et al., *Science* 318:1782-1786 (2007); and Thauer, R. K., *Science.* 318:1732-1733 (2007)). The enzyme utilizes NADPH as a cofactor and has been characterized in *Metallosphaera* and *Sulfolobus* sp (Alber et al., *J. Bacteriol.* 188:8551-8559 (2006); and Hugler et al., *J. Bacteriol.* 184:2404-2410 (2002)). The enzyme is encoded by Msed_0709 in *Metallosphaera sedula* (Alber et al., *J. Bacteriol.* 188:8551-8559 (2006); and Berg et al., *Science.* 318:1782-1786 (2007)). A gene encoding a malonyl-CoA reductase from *Sulfolobus tokodaii* was cloned and heterologously expressed in *E. coli* (Alber et al., *J. Bacteriol.* 188:8551-8559 (2006)). This enzyme has also been shown to catalyze the conversion of methylmalonyl-CoA to its corresponding aldehyde (WIPO Patent Application WO/2007/141208 Kind Code: A2). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth et al., *Appl Environ Microbiol* 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., *Appl Environ Microbiol* 65:4973-4980 (1999)).

| Gene name | GI# | GenBank Accession # | Organism |
|---|---|---|---|
| Msed_0709 | 146303492 | YP_001190808.1 | Metallosphaera sedula |
| mcr | 15922498 | NP_378167.1 | Sulfolobus tokodaii |
| asd-2 | 15898958 | NP_343563.1 | Sulfolobus solfataricus |
| Saci_2370 | 70608071 | YP_256941.1 | Sulfolobus acidocaldarius |
| Ald | 49473535 | AAT66436 | Clostridium beijerinckii |
| eutE | 687645 | AAA80209 | Salmonella typhimurium |
| eutE | 2498347 | P77445 | Escherichia coli |

1.2.1.c Oxidoreductase (2-Ketoacid to Acyl-CoA).

Several transformations in FIG. 12 require conversion of a 2-ketoacid to an acyl-CoA (Steps L, P and Q) by an enzyme in the EC class 1.2.1. Such reactions are catalyzed by multi-enzyme complexes that catalyze a series of partial reactions which result in acylating oxidative decarboxylation of 2-keto-acids. Exemplary enzymes include 1) branched-chain 2-keto-acid dehydrogenase, 2) alpha-ketoglutarate dehydrogenase, and 3) the pyruvate dehydrogenase multienzyme complex (PDHC). Each of the 2-keto-acid dehydrogenase complexes occupies key positions in intermediary metabolism, and enzyme activity is typically tightly regulated (Fries et al., *Biochemistry* 42:6996-7002 (2003)). The enzymes share a complex but common structure composed of multiple copies of three catalytic components:

alpha-ketoacid decarboxylase (E1), dihydrolipoamide acyltransferase (E2) and dihydrolipoamide dehydrogenase (E3). The E3 component is shared among all 2-keto-acid dehydrogenase complexes in an organism, while the E1 and E2 components are encoded by different genes. The enzyme components are present in numerous copies in the complex and utilize multiple cofactors to catalyze a directed sequence of reactions via substrate channeling. The overall size of these dehydrogenase complexes is very large, with molecular masses between 4 and 10 million Da (i.e. larger than a ribosome).

Activity of enzymes in the 2-keto-acid dehydrogenase family is normally low or limited under anaerobic conditions in *E. coli*. Increased production of NADH (or NADPH) could lead to a redox-imbalance, and NADH itself serves as an inhibitor to enzyme function. Engineering efforts have increased the anaerobic activity of the *E. coli* pyruvate dehydrogenase complex (Kim et al., *Appl. Environ. Microbiol.* 73:1766-1771 (2007); Kim et al., *J. Bacteriol.* 190: 3851-3858 (2008); and Zhou et al., *Biotechnol. Lett.* 30:335-342 (2008)). For example, the inhibitory effect of NADH can be overcome by engineering an $H_{322}Y$ mutation in the E3 component (Kim et al., *J. Bacteriol.* 190:3851-3858 (2008)). Structural studies of individual components and how they work together in complex provide insight into the catalytic mechanisms and architecture of enzymes in this family (Aevarsson et al., *Nat. Struct. Biol.* 6:785-792 (1999); and Zhou et al., *Proc. Natl. Acad. Sci. U.S.A* 98:14802-14807 (2001)). The substrate specificity of the dehydrogenase complexes varies in different organisms, but generally branched-chain keto-acid dehydrogenases have the broadest substrate range.

Alpha-ketoglutarate dehydrogenase (AKGD) converts alpha-ketoglutarate to succinyl-CoA and is the primary site of control of metabolic flux through the TCA cycle (Hansford, *Curr. Top. Bioenerg.* 10:217-278 (1980)). Encoded by genes sucA, sucB and lpd in *E. coli*, AKGD gene expression is downregulated under anaerobic conditions and during growth on glucose (Park et al., *Mol. Microbiol.* 15:473-482 (1995)). Although the substrate range of AKGD is narrow, structural studies of the catalytic core of the E2 component pinpoint specific residues responsible for substrate specificity (Knapp et al., *J. Mol. Biol.* 280:655-668 (1998)). The *Bacillus subtilis* AKGD, encoded by odhAB (E1 and E2) and pdhD (E3, shared domain), is regulated at the transcriptional level and is dependent on the carbon source and growth phase of the organism (Resnekov et al., *Mol. Gen. Genet.* 234:285-296 (1992)). In yeast, the LPD1 gene encoding the E3 component is regulated at the transcriptional level by glucose (Roy and Dawes, *J. Gen. Microbiol.* 133:925-933 (1987)). The E1 component, encoded by KGD1, is also regulated by glucose and activated by the products of HAP2 and HAP3 (Repetto and Tzagoloff, *Mol. Cell Biol.* 9:2695-2705 (1989)). The AKGD enzyme complex, inhibited by products NADH and succinyl-CoA, is well-studied in mammalian systems, as impaired function of has been linked to several neurological diseases (Tretter and dam-Vizi, *Philos. Trans. R. Soc. Lond B Biol. Sci.* 360:2335-2345 (2005)).

| Gene name | GI# | GenBank Accession # | Organism |
|---|---|---|---|
| sucA | 16128701 | NP_415254.1 | Escherichia coli |
| sucB | 16128702 | NP_415255.1 | Escherichia coli |
| lpd | 16128109 | NP_414658.1 | Escherichia coli |
| odhA | 51704265 | P23129.2 | Bacillus subtilis |

| Gene name | GI# | GenBank Accession # | Organism |
|---|---|---|---|
| odhB | 129041 | P16263.1 | Bacillus subtilis |
| pdhD | 118672 | P21880.1 | Bacillus subtilis |
| KGD1 | 6322066 | NP_012141.1 | Saccharomyces cerevisiae |
| KGD2 | 6320352 | NP_010432.1 | Saccharomyces cerevisiae |
| LPD1 | 14318501 | NP_116635.1 | Saccharomyces cerevisiae |

Branched-chain 2-keto-acid dehydrogenase complex (BCKAD), also known as 2-oxoisovalerate dehydrogenase, participates in branched-chain amino acid degradation pathways, converting 2-keto acids derivatives of valine, leucine and isoleucine to their acyl-CoA derivatives and $CO_2$. The complex has been studied in many organisms including *Bacillus subtilis* (Wang et al., *Eur. J. Biochem.* 213:1091-1099 (1993)), *Rattus norvegicus* (Namba et al., *J. Biol. Chem.* 244:4437-4447 (1969)) and *Pseudomonas putida* (Sokatch et al., *J. Bacteriol.* 148:647-652 (1981)). In *Bacillus subtilis* the enzyme is encoded by genes pdhD (E3 component), bfmBB (E2 component), bfmBAA and bfmBAB (E1 component) (Wang et al., *Eur. J. Biochem.* 213:1091-1099 (1993)). In mammals, the complex is regulated by phosphorylation by specific phosphatases and protein kinases. The complex has been studied in rat hepatocites (Chicco et al., *J. Biol. Chem.* 269:19427-19434 (1994)) and is encoded by genes Bckdha (E1 alpha), Bckdhb (E1 beta), Dbt (E2), and Dld (E3). The E1 and E3 components of the *Pseudomonas putida* BCKAD complex have been crystallized (Aevarsson et al., *Nat. Struct. Biol.* 6:785-792 (1999); and Mattevi et al., *Science.* 255:1544-1550 (1992)) and the enzyme complex has been studied (Sokatch et al., *J. Bacteriol.* 148:647-652 (1981)). Transcription of the *P. putida* BCKAD genes is activated by the gene product of bkdR (Hesslinger et al., *Mol. Microbiol* 27:477-492 (1998)). In some organisms including *Rattus norvegicus* (Paxton et al., *Biochem. J.* 234:295-303 (1986)) and *Saccharomyces cerevisiae* (Sinclair et al., *Biochem. Mol. Biol. Int.* 31:911-922 (1993)), this complex has been shown to have a broad substrate range that includes linear oxo-acids such as 2-oxobutanoate and alpha-ketoglutarate, in addition to the branched-chain amino acid precursors. The active site of the bovine BCKAD was engineered to favor alternate substrate acetyl-CoA (Meng and Chuang, *Biochemistry.* 33:12879-12885 (1994)).

| Gene name | GI# | GenBank Accession # | Organism |
|---|---|---|---|
| bfmBB | 16079459 | NP_390283.1 | Bacillus subtilis |
| bfmBAA | 16079461 | NP_390285.1 | Bacillus subtilis |
| bfmBAB | 16079460 | NP_390284.1 | Bacillus subtilis |
| pdhD | 118672 | P21880.1 | Bacillus subtilis |
| lpdV | 118677 | P09063.1 | Pseudomonas putida |
| bkdB | 129044 | P09062.1 | Pseudomonas putida |
| bkdA1 | 26991090 | NP_746515.1 | Pseudomonas putida |
| bkdA2 | 26991091 | NP_746516.1 | Pseudomonas putida |
| Bckdha | 77736548 | NP_036914.1 | Rattus norvegicus |
| Bckdhb | 158749538 | NP_062140.1 | Rattus norvegicus |
| Dbt | 158749632 | NP_445764.1 | Rattus norvegicus |
| Dld | 40786469 | NP_955417.1 | Rattus norvegicus |

The pyruvate dehydrogenase complex, catalyzing the conversion of pyruvate to acetyl-CoA, has also been extensively studied. In the *E. coli* enzyme, specific residues in the E1 component are responsible for substrate specificity (Bisswanger, *J Biol Chem.* 256:815-822 (1981); Bremer, *Eur. J Biochem.* 8:535-540 (1969); and Gong et al., *J Biol Chem.* 275:13645-13653 (2000)). As mentioned previously, enzyme engineering efforts have improved the *E. coli* PDH enzyme activity under anaerobic conditions (Kim et al., *Appl. Environ. Microbiol.* 73:1766-1771 (2007); Kim et al., *J Bacteriol.* 190:3851-3858 (2008)); and Zhou et al., *Biotechnol. Lett.* 30:335-342 (2008)). In contrast to the *E. coli* PDH, the *B. subtilis* complex is active and required for growth under anaerobic conditions (Nakano et al., *J Bacteriol.* 179:6749-6755 (1997)). The *Klebsiella pneumoniae* PDH, characterized during growth on glycerol, is also active under anaerobic conditions (Menzel et al., *J. Biotechnol.* 56:135-142 (1997)). Crystal structures of the enzyme complex from bovine kidney (Zhou et al., *Proc. Natl. Acad. Sci. U.S.A* 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate, although comparative kinetics of *Rattus norvegicus* PDH and BCKAD indicate that BCKAD has higher activity on 2-oxobutanoate as a substrate (Paxton et al., *Biochem. J.* 234:295-303 (1986)).

| Gene name | GI# | GenBank Accession # | Organism |
|---|---|---|---|
| aceE | 16128107 | NP_414656.1 | Escherichia coli |
| aceF | 16128108 | NP_414657.1 | Escherichia coli |
| lpd | 16128109 | NP_414658.1 | Escherichia coli |
| pdhA | 3123238 | P21881.1 | Bacillus subtilis |
| pdhB | 129068 | P21882.1 | Bacillus subtilis |
| pdhC | 129054 | P21883.2 | Bacillus subtilis |
| pdhD | 118672 | P21880.1 | Bacillus subtilis |
| aceE | 152968699 | YP_001333808.1 | Klebsiella pneumonia |
| aceF | 152968700 | YP_001333809.1 | Klebsiella pneumonia |
| lpdA | 152968701 | YP_001333810.1 | Klebsiella pneumonia |
| Pdha1 | 124430510 | NP_001004072.2 | Rattus norvegicus |
| Pdha2 | 16758900 | NP_446446.1 | Rattus norvegicus |
| Dlat | 78365255 | NP_112287.1 | Rattus norvegicus |
| Dld | 40786469 | NP_955417.1 | Rattus norvegicus |

As an alternative to the large multienzyme 2-keto-acid dehydrogenase complexes described above, some anaerobic organisms utilize enzymes in the 2-ketoacid oxidoreductase family (OFOR) to catalyze acylating oxidative decarboxylation of 2-keto-acids. Unlike the dehydrogenase complexes, these enzymes contain iron-sulfur clusters, utilize different cofactors, and use ferredoxin or flavodoxin as electron acceptors in lieu of NAD(P)H. While most enzymes in this family are specific to pyruvate as a substrate (POR) some 2-keto-acid:ferredoxin oxidoreductases have been shown to accept a broad range of 2-ketoacids as substrates including alpha-ketoglutarate and 2-oxobutanoate (Fukuda and Wakagi, *Biochim. Biophys. Acta* 1597:74-80 (2002); and Zhang et al., *J. Biochem.* 120:587-599 (1996)). One such enzyme is the OFOR from the thermoacidophilic archaeon *Sulfolobus tokodaii* 7, which contains an alpha and beta subunit encoded by gene ST2300 (Fukuda and Wakagi, *Biochim. Biophys. Acta* 1597:74-80 (2002); and Zhang et al., *J. Biochem.* 120:587-599 (1996)). A plasmid-based expression system has been developed for efficiently expressing this protein in *E. coli* (Fukuda et al., *Eur. Biochem.* 268: 5639-5646 (2001)) and residues involved in substrate specificity were determined (Fukuda and Wakagi, *Biochim. Biophys. Acta* 1597:74-80 (2002)). Two OFORs from *Aeropyrum pernix* str. K1 have also been recently cloned into *E. coli*, characterized, and found to react with a broad range of 2-oxoacids (Nishizawa et al., *FEBS Lett.* 579:2319-2322 (2005)). The gene sequences of these OFOR candidates are available, although they do not have GenBank identifiers assigned to date. There is bioinformatic evidence that similar enzymes are present in all archaea, some anaerobic bacteria and amitochondrial eukarya (Fukuda and Wakagi, *Biochim. Biophys. Acta* 1597:74-80 (2002)). This class of enzyme is also interesting from an energetic standpoint, as reduced ferredoxin could be used to generate NADH by ferredoxin-NAD reductase (Petitdemange et al., *Biochim. Biophys. Acta* 421:334-337 (1976)). Also, since most of the enzymes are designed to operate under anaerobic conditions, less enzyme engineering may be required relative to enzymes in the 2-keto-acid dehydrogenase complex family for activity in an anaerobic environment.

| Gene name | GI# | GenBank Accession # | Organism |
|---|---|---|---|
| ST2300 | 15922633 | NP_378302.1 | Sulfolobus tokodaii 7 |

1.2.1.d Oxidoreductase (Phosphonic Acid to Aldehyde).

The reduction of a phosphonic acid to its corresponding aldehyde is catalyzed by an oxidoreductase in the EC class 1.2.1. Steps B and F in FIG. 13 require such an enzyme for the reduction of 6-AHOP and 6-AAHOP to their corresponding aldehydes. These reactions are not catalyzed by known enzymes, but a similar reaction is catalyzed by aspartate semialdehyde dehydrogenase (ASD, EC 1.2.1.11): the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J Mol. Biol.* 289:991-1002 (1999)) and the enzyme has been shown to accept the alternate substrate beta-3-methylaspartyl phosphate (Shames et al., *J Biol. Chem.* 259:15331-15339 (1984)). The *Haemophilus influenzae* enzyme has been the subject of enzyme engineering studies to alter substrate binding affinities at the active site (Blanco et al., *Acta Crystallogr. D. Biol. Crystallogr.* 60:1388-1395 (2004); and Blanco et al., *Acta Crystallogr. D. Biol. Crystallogr.* 60:1808-1815 (2004)). Other ASD candidates are found in *Mycobacterium tuberculosis* (Shafiani et al., *J Appl Microbiol* 98:832-838 (2005)), *Methanococcus jannaschii* (Faehnle et al., *J Mol. Biol.* 353:1055-1068 (2005)), and the infectious microorganisms *Vibrio cholera* and *Heliobacter pylori* (Moore et al., *Protein Expr. Purif.* 25:189-194 (2002)). A related enzyme candidate is acetylglutamylphosphate reductase (EC 1.2.1.38), an enzyme that naturally reduces acetylglutamylphosphate to acetylglutamate-5-semialdehyde, found in *S. cerevisiae* (Pauwels et al., *Eur. J Biochem.* 270:1014-1024 (2003)), *B. subtilis* (O'Reilly and Devine, Microbiology 140 (Pt 5):1023-1025 (1994)) and other organisms.

| Gene name | GI# | GenBank Accession # | Organism |
|---|---|---|---|
| Asd | 16131307 | NP_417891.1 | Escherichia coli |
| Asd | 68249223 | YP_248335.1 | Haemophilus influenzae |
| Asd | 1899206 | AAB49996 | Mycobacterium tuberculosis |
| VC2036 | 15642038 | NP_231670 | Vibrio cholera |
| Asd | 210135348 | YP_002301787.1 | Heliobacter pylori |
| ARG5, 6 | 6320913 | NP_010992.1 | Saccharomyces |

| Gene name | GI# | GenBank Accession # | Organism |
|---|---|---|---|
| argC | 16078184 | NP_389001.1 | Bacillus subtilis cerevisiae |

1.3.1.a Oxidoreductase (Alkene to Alkane).

Several transformations fall into the category of oxidoreductases that reduce an alkene to an alkane (EC 1.3.1.-). For example, Steps C, G, K and N in FIG. 12, catalyzed by OHED reductase, 6-OHE reductase, 2-AHE reductase and 2,3-dehydroadipyl-CoA reductase, respectively, fall into this category. Enone reductase, alkenal reductase, and enoate reductase enzymes are suitable enzyme candidates for catalyzing the transformations of Steps C, G and K. Enoyl-CoA reductase enzymes catalyze the conversion of 2,3-dehydroadipyl-CoA to adipyl-CoA (Step N).

Enzymes with enone reductase activity have been identified in prokaryotes, eukaryotes and plants (Shimoda et al., Bulletin of the chemical Society of Japan 77:2269-2 (2004); and Wanner and Tressl, Eur. J. Biochem. 255:271-278 (1998)). Two enone reductases from the cytosolic fraction of Saccharomyces cerevisiae were purified and characterized, and found to accept a variety of alkenals (similar to 6-OHE) and enoyl ketones (similar to OHED) as substrates (Wanner and Tressl, Eur. J. Biochem. 255:271-278 (1998)). Genes encoding these enzymes have not been identified to date. Cell extracts of cyanobacterium Synechococcus sp. PCC7942 reduced a variety enone substrates to their corresponding alkyl ketones (Shimoda et al., Bulletin of the chemical Society of Japan 77:2269-2 (2004)). Genes have not been associated with this activity in this organism. Enone reductases in other organisms can also catalyze this transformation.

A recombinant NADPH-dependent enone reductase from Nicotiana tabacum, encoded by NtRed1, was functionally expressed and characterized in E. coli (Matsushima et al., Bioorganic Chemistry 36:23-28 (2008)). This reductase was functional on the exocyclic enoyl ketone pulegone (Matsushima et al., Bioorganic Chemistry 36:23-28 (2008)). An enzyme candidate in S. cerevisiae at the locus YML131W, bears 30% identity to NtRed1(evalue=1e-26). The amino acid sequence of NtRed1 shares significant homology with 2-alkenal reductase from Arabidopsis thaliana, zeta-crystallin homolog from A. thaliana, pulegone reductase from Menthe piperita and phenylpropenal alkene reductase from Pinus taeda. These enzymes are known to catalyze the reduction of alkenes of α,β-unsaturated ketones and aldehydes.

| Gene name | GI# | GenBank Accession # | Organism |
|---|---|---|---|
| NtRed1 | 6692816 | BAA89423 | Nicotiana tabacum |
| YML131W | 45269874 | AAS56318.1 | Saccharomyces cerevisiae |
| AtDBR1 | 15237888 | NP-197199 | Arabidopsis thaliana |
| P2 | 886430 | CAA89262 | Arabidopsis thaliana |
| PulR | 34559418 | AAQ75423 | Menthe piperita |
| PtPPDBR | 110816011 | ABG91753 | Pinus taeda |

2-Alkenal reductase catalyzes the reduction of α, β-unsaturated double bonds of aldehydes and ketones. A barley alkenal hydrogenase ALH1 was identified with activity for a range of α,β-unsaturated ketones and aldehydes including trans-2-nonenal, 2-hexenal, traumatin and 1-octene-3-one (Hambraeus and Nyberg, J Agric. Food Chem. 53:8714-8721 (2005)). The Hordeum vulgare ALH1 cDNA was cloned expressed in E. coli (Hambraeus and Nyberg, J Agric. Food Chem. 53:8714-8721 (2005)).

| Gene name | GI# | GenBank Accession # | Organism |
|---|---|---|---|
| ALH1 | 62765876 | AAX99161 | Hordeum vulgare |
| ALH1 | 195652571 | ACG45753 | Zea mays |

2-Enoate reductase enzymes are known to catalyze the NAD(P)H-dependent reduction of a wide variety of α, β-unsaturated carboxylic acids and aldehydes (Rohdich et al., J. Biol. Chem. 276:5779-5787 (2001)). In the recently published genome sequence of C. kluyveri, 9 coding sequences for enoate reductases were reported, out of which one has been characterized (Seedorf et al., Proc. Natl. Acad. Sci U.S.A 105:2128-2133 (2008)). The enr genes from both C. tyrobutyricum and M. thermoaceticum have been cloned and sequenced and show 59% identity to each other. The former gene is also found to have approximately 75% similarity to the characterized gene in C. kluyveri (Giesel and Simon, Arch. Microbiol 135:51-57 (1983)). It has been reported based on these sequence results that enr is very similar to the dienoyl CoA reductase in E. coli (fadH) (Rohdich et al., J. Biol. Chem. 276:5779-5787 (2001)). The C. thermoaceticum enr gene has also been expressed in a catalytically active form in E. coli (Rohdich et al., J. Biol. Chem. 276:5779-5787 (2001)).

| Gene name | GI# | GenBank Accession # | Organism |
|---|---|---|---|
| enr | 169405742 | ACA54153.1 | Clostridium botulinum A3 str |
| enr | 2765041 | CAA71086.1 | Clostridium tyrobutyricum |
| enr | 3402834 | CAA76083.1 | Clostridium kluyveri |
| enr | 83590886 | YP_430895.1 | Moorella thermoacetica |
| fadH | 16130976 | NP_417552.1 | Escherichia coli |

Another candidate enoate reductase is 3-oxoadipate oxidoreductase (maleylacetate reductase), an enzyme catalyzing the reduction of 2-maleylacetate (4-oxohex-2-enedioate) to 3-oxoadipate. The enzyme activity was identified and characterized in Pseudomonas sp. strain B13 (Kaschabek and Reineke, J. Bacteriol. 177:320-325 (1995); and Kaschabek. and Reineke, J. Bacteriol. 175:6075-6081 (1993)), and the coding gene was cloned and sequenced (Kasberg et al., J. Bacteriol. 179:3801-3803 (1997)). Candidate genes for 3-oxoadipate oxidoreductase include cicE gene from Pseudomonas sp. strain B13 (Kasberg et al., J. Bacteriol. 179:3801-3803 (1997)), macA gene from Rhodococcus opacus (Seibert et al., J. Bacteriol. 180:3503-3508 (1998)), and macA gene from Ralstonia eutropha (also known as Cupriavidus necator) (Seibert et al., Microbiology 150:463-472 (2004)).

| Gene name | GI# | GenBank Accession # | Organism |
|---|---|---|---|
| clcE | 3913241 | O30847.1 | Pseudomonas sp. strain B13 |
| macA | 7387876 | O84992.1 | Rhodococcus opacus |
| macA | 5916089 | AAD55886 | Cupriavidus necator |

Enoyl-CoA reductase enzymes are suitable enzymes for catalyzing the reduction of 2,3-dehydroadipyl-CoA to adipyl-CoA (FIG. 12, Step N). One exemplary enoyl-CoA reductase is the gene product of bcd from *C. acetobutylicum* (Atsumi et al., *Metab Eng* 10:305-311 (2008); and Boynton et al., *J. Bacteriol.* 178:3015-3024 (1996)), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister et al., *J Biol. Chem.* 280:4329-4338 (2005)). A construct derived from this sequence following the removal of its mitochondrial targeting leader sequence was cloned in *E. coli* resulting in an active enzyme (Hoffmeister et al., *J Biol. Chem.* 280:4329-4338 (2005)). This approach is well known to those skilled in the art of expressing eukaryotic genes, particularly those with leader sequences that may target the gene product to a specific intracellular compartment, in prokaryotic organisms. A close homolog of this gene, TDE0597, from the prokaryote *Treponema denticola* represents a third enoyl-CoA reductase which has been cloned and expressed in *E. coli* (Tucci and Martin, *Febs Letters* 581:1561-1566 (2007)).

| Gene name | GI# | GenBank Accession # | Organism |
|---|---|---|---|
| bcd | 15895968 | NP_349317.1 | Clostridium acetobutylicum |
| etfA | 15895966 | NP_349315.1 | Clostridium acetobutylicum |
| etfB | 15895967 | NP_349316.1 | Clostridium acetobutylicum |
| TER | 62287512 | Q5EU90.1 | Euglena gracilis |
| TDE0597 | 42526113 | NP_971211.1 | Treponema denticola |

Additional enoyl-CoA reductase enzyme candidates are found in organisms that degrade aromatic compounds. *Rhodopseudomonas palustris*, a model organism for benzoate degradation, has the enzymatic capability to degrade pimelate via beta-oxidation of pimeloyl-CoA. Adjacent genes in the pim operon, pimC and pimD, bear sequence homology to *C. acetobutylicum* bcd and are predicted to encode a flavin-containing pimeloyl-CoA dehydrogenase (Harrison and Harwood, Microbiology 151:727-736 (2005)). The genome of nitrogen-fixing soybean symbiont *Bradyrhizobium japonicum* also contains a pim operon composed of genes with high sequence similarity to pimC and pimD of *R. palustris* (Harrison and Harwood, Microbiology 151:727-736 (2005)).

| Gene name | GI# | GenBank Accession # | Organism |
|---|---|---|---|
| pimC | 39650632 | CAE29155 | Rhodopseudomonas palustris |
| pimD | 39650631 | CAE29154 | Rhodopseudomonas palustris |
| pimC | 27356102 | BAC53083 | Bradyrhizobium japonicum |
| pimD | 27356101 | BAC53082 | Bradyrhizobium japonicum |

An additional candidate is 2-methyl-branched chain enoyl-CoA reductase (EC 1.3.1.52), an enzyme catalyzing the reduction of sterically hindered trans-enoyl-CoA substrates. This enzyme participates in branched-chain fatty acid synthesis in the nematode *Ascarius suum* and is capable of reducing a variety of linear and branched chain substrates including 2-methylbutanoyl-CoA, 2-methylpentanoyl-CoA, octanoyl-CoA and pentanoyl-CoA (Duran et al., *J Biol. Chem.* 268:22391-22396 (1993)). Two isoforms of the enzyme, encoded by genes acad1 and acad, have been characterized.

| Gene name | GI# | GenBank Accession # | Organism |
|---|---|---|---|
| acad1 | 2407655 | AAC48316.1 | Ascarius suum |
| acad | 347404 | AAA16096.1 | Ascarius suum |

1.4.1.a Oxidoreductase (Ketone or Aldehyde to Amino).

Oxidoreductases in the EC class 1.4.1 that convert an aldehyde or ketone to its corresponding amine group catalyze several biosynthetic steps in the disclosed pathways. In FIG. 12, the conversions of OHED to 2-AHE (Step J), 2-OHD to 2-AHD (Step H) and adipate semialdehyde to 6-aminocaproate (Step E) are catalyzed by OHED aminating oxidoreductase, 2-OHD aminating oxidoreductase and adipate semialdehyde aminating oxidoreductase. In FIG. 13, conversion of 6-aminocaproate semialdehyde to HMDA (Step H) and 6-acetamidohexanal to 6-acetamidohexanamine (Step G), are also catalyzed by aminating oxidoreductases.

Most aminating oxidoreductases catalyze the reversible oxidative deamination of alpha-amino acids with NAD+ or NADP+ as acceptor, and the reactions are typically reversible. Exemplary enzymes include glutamate dehydrogenase (deaminating), encoded by gdhA, leucine dehydrogenase (deaminating), encoded by ldh, and aspartate dehydrogenase (deaminating), encoded by nadX. The gdhA gene product from *Escherichia coli* (Korber et al., *J Mol. Biol.* 234:1270-1273 (1993); and McPherson et al., *Nucleic Acids Res.* 11:5257-5266 (1983)), gdh from *Thermotoga maritime* (Kort et al., *Extremophiles.* 1:52-60 (1997); Lebbink et al., *J Mol. Biol.* 280:287-296 (1998); and Lebbink et al., *J Mol. Biol.* 289:357-369 (1999)), and gdhA1 from *Halobacterium salinarum* (Ingoldsby et al., *Gene* 349:237-244 (2005)) catalyze the reversible interconversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge and Kula, *Biotechnol Bioeng* 68:557-562 (2000); and Stoyan et al., *J Biotechnol.* 54:77-80 (1997)). The nadX gene from *Thermotoga maritime* encoding for the aspartate dehydrogenase is involved in the biosynthesis of NAD (Yang et al., *J Biol. Chem.* 278:8804-8808 (2003)).

| Gene name | GI# | GenBank Accession # | Organism |
|---|---|---|---|
| gdhA | 118547 | P00370 | Escherichia coli |
| gdh | 6226595 | P96110.4 | Thermotoga maritima |
| gdhA1 | 15789827 | NP_279651.1 | Halobacterium salinarum |
| ldh | 61222614 | P0A393 | Bacillus cereus |
| nadX | 15644391 | NP_229443.1 | Thermotoga maritima |

Lysine 6-dehydrogenase (deaminating), encoded by lysDH, catalyzes the oxidative deamination of the 6-amino group of L-lysine to form 2-aminoadipate-6-semialdehyde, which in turn non-enzymatically cyclizes to form Δ¹-piperideine-6-carboxylate (Misono and Nagasaki, *J. Bacteriol.* 150:398-401 (1982)). Exemplary enzymes can be found in *Geobacillus stearothermophilus* (Heydari et al., *Appl Environ. Microbiol* 70:937-942 (2004)), *Agrobacterium tumefaciens* (Hashimoto et al., *J Biochem.* 106:76-80 (1989); and Misono and Nagasaki, *J. Bacteriol.* 150:398-401 (1982)), and *Achromobacter denitrificans* (Ruldeekulthamrong et al., *BMB. Rep.* 41:790-795 (2008)). Such enzymes are particularly good candidates for converting adipate semialdehyde to 6-aminocaproate given the structural similarity between adipate semialdehyde and 2-aminoadipate-6-semialdehyde.

| Gene name | GI# | GenBank Accession # | Organism |
|---|---|---|---|
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

2.3.1.a Acyltransferase (Transferring CoA to Phospho).

Acyltransferases that exchange a CoA moiety for a phosphate are in the EC class 2.3.1. Transformations in this category include the conversions of 6-AAHOP to 6-acetamidohexanoyl-CoA (FIG. 13, Step K) and 6-AHOP to 6-aminocaproyl-CoA (FIG. 13, Step L). Exemplary phosphate-transferring acyltransferases include phosphotransacetylase (EC 2.3.1.8), encoded by pta, and phosphotransbutyrylase (EC 2.3.1.19), encoded by ptb. The pta gene from *E. coli* encodes an enzyme that reversibly converts acetyl-CoA into acetyl-phosphate (Suzuki, T., *Biochim. Biophys. Acta* 191:559-569 (1969)). This enzyme can also utilize propionyl-CoA as a substrate, forming propionate in the process (Hesslinger et al., *Mol. Microbiol* 27:477-492 (1998)). Similarly, the ptb gene from *C. acetobutylicum* encodes phosphate transbutyrylase, an enzyme that reversibly converts butyryl-CoA into butyryl-phosphate (Walter et al., *Gene* 134:107-111 (1993); and Wiesenborn et al., *Appl Environ. Microbiol* 55:317-322 (1989)). Additional ptb genes are found in butyrate-producing bacterium L2-50 (Louis et al., *J. Bacteriol.* 186:2099-2106 (2004)) and *Bacillus megaterium* (Vazquez et al., *Curr. Microbiol* 42:345-349 (2001)).

| Gene name | GI# | GenBank Accession # | Organism |
|---|---|---|---|
| Pta | 16130232 | NP_416800.1 | *Escherichia coli* |
| Ptb | 15896327 | NP_349676 | *Clostridium acetobutylicum* |
| Ptb | 38425288 | AAR19757.1 | butyrate-producing bacterium L2-50 |
| Ptb | 10046659 | CAC07932.1 | *Bacillus megaterium* |

2.3.1.c Acyltransferase (N-acetyltransferase).

N-Acetyltransferases transfer an acetyl group to an amine, forming an N-acetyl group. N-Acetylation serves diverse functions in biological systems including transcriptional regulation, nuclear import, chromosome assembly and nucleosome remodeling (Kouzarides, *EMBO J* 19:1176-1179 (2000)). N-Acetylation of metabolic intermediates of arginine biosynthetic pathways serves both to protect reactive intermediates from spontaneous cyclization and also to sequester pathway intermediates from competing pathways (Caldovic and Tuchman, *Biochem. J* 372:279-290 (2003)). Acetylation of 6-ACA (FIG. 13, step D) serves a similar role in the proposed HMDA biosynthesis route of FIG. 13, protecting reactive intermediates from spontaneous cyclization.

One candidate enzyme for acetylating 6-ACA is lysine N-acetyltransferase (EC 2.3.1.32), an enzyme which selectively transfers the acetyl moiety from acetyl phosphate to the terminal amino group of L-lysine, beta-L-lysine or L-ornithine. Although this enzyme is not known to acetylate 6-ACA, this substrate is structurally similar to the natural substrate. Lysine N-acetyltransferase has been characterized in *Bos taurus* (Paik. and Kim, *Arch. Biochem. Biophys.* 108:221-229, 1964) and *Methanosarcina mazei* (Pfluger et al., *Appl Environ. Microbiol* 69:6047-6055 (2003)). Methanogenic archaea *M. maripaludis*, *M. acetivorans*, *M. barkeri* and *M. jannaschii* are also predicted to encode enzymes with this functionality (Pfluger et al., *Appl Environ. Microbiol* 69:6047-6055 (2003)).

| Gene name | GI# | GenBank Accession # | Organism |
|---|---|---|---|
| ablB | 21227037 | NP_632959.1 | *Methanosarcina mazei* |
| yodP | 44921183 | CAF30418 | *Methanococcus maripaludis* |
| MA3978 | 20092772 | NP_618847.1 | *Methanosarcina acetivorans* |
| MJ0635 | 15668816 | NP_247619.1 | *Methanocaldococcus jannaschii* |
| Mbar_A0671 | 73668215 | YP_304230.1 | *Methanosarcina barkeri* |

Alternately, 6-ACA acetylation can be catalyzed by an enzyme in the GNAT family of N-acetyltransferases. Such enzymes transfer an acetyl group from acetyl-CoA to a primary amine. The enzyme spermidine N-acetyltransferase (SSAT), also known as diamine N-acetyltransferase (EC 2.3.1.57), is capable of acetylating a variety of small molecule substrates. Purified enzymes from *Ascaris suum* and *Onchocerca volvulus* exhibit a broad substrate range that includes HMDA (Davids et al., *Mol. Biochem. Parasitol.* 64:341-344 (1994); and Wittich and Walter, *Mol. Biochem. Parasitol.* 38:13-17 (1990)), but the associated genes have not been identified to date. Other enzymes with this functionality are found in *Bacillus subtilis* (Forouhar et al., *J Biol. Chem.* 280:40328-40336 (2005)) and *Homo sapiens* (Casero and Pegg, *FASEB J* 7:653-661 (1993)). A closely related enzyme is thialysine N-acetyltransferase in *C. elegans*, an enzyme that accepts a range of substrates including lysine, ornithine, thialysine and others (bo-Dalo et al., *Biochem. J* 384:129-137 (2004)). Amino acid residues involved in substrate binding were identified in the thialysine N-acetyltransferase from *Leishmania major* (Luersen, K., *FEBS Lett.* 579:5347-5352 (2005)). An additional candidate is the diaminobutyrate acetyltransferase (EC 2.3.1.178), an enzyme participating in ectoine biosynthesis in *Methylomicrobium alcaliphilum* (Reshetnikov et al., *Arch. Microbiol* 184:286-297 (2006)) *C. salexigens* (formerly *Halomonas elongata*) (Canovas et al., *Syst. Appl Microbiol* 21:487-497 (1998)).

| Gene name | GI# | GenBank Accession # | Organism |
|---|---|---|---|
| paiA | 16080268 | NP_391095.1 | *Bacillus subtilis* |
| SSAT1 | 114322 | P21673 | *Homo sapiens* |
| D2023.4 | 17559148 | NP_505978.1 | *Caenorhabditis elegans* |
| LmjF36.2750 | 68129928 | CAJ09234.1 | *Leishmania major* |

| Gene name | GI# | GenBank Accession # | Organism |
| --- | --- | --- | --- |
| ectA | 68366269 | AAY96770.1 | Methylomicrobium alcaliphilum 20Z |
| ectA | 6685422 | Q9ZEU8.1 | Chromohalobacter salexigens |

An additional enzyme candidate for acetylating 6-ACA (FIG. 13, Step D) and de-acetylating 6-acetamidehexanamine (FIG. 13, Step H) is ornithine acetyltransferase (OAT, EC 2.3.1.35 and EC 2.3.1.1), a bifunctional enzyme which catalyzes two steps of arginine biosynthesis (FIG. 14A). The first step of arginine biosynthesis (FIG. 14A, step 1) is the N-acetylation of glutamate, catalyzed by OAT with acetyl-CoA as an acetyl donor (O'Reilly and Devine, Microbiology 140 (Pt 5):1023-1025 (1994)). OAT also catalyzes the fifth step of arginine biosynthesis (FIG. 14A, step 2), in which an N-acetyl group is transferred from N-acetyl-L-ornithine to L-glutamate, the first metabolite in the arginine biosynthesis pathway. This transformation serves to recycle the acetyl group and regenerate N-acetylglutamate, conserving energy and thereby making the linear pathway a cyclic route. A similar strategy can be employed in HMDA biosynthesis from 6-aminocaproate, with a single enzyme acetylating 6-aminocaproate and de-acetylating 6-acetamidohexanamine to form HMDA (FIG. 14B). Exemplary OAT enzymes are encoded by argJ in Bacillus subtilis (O'Reilly and Devine, Microbiology 140 (Pt 5):1023-1025 (1994); and Sakanyan et al., Journal of General Microbiology 138:125-130 (1992)) and ECM40 in S. cerevisiae (Abadjieva et al., J Biol. Chem. 275:11361-11367 (2000); and Liu et al., Eur. J Biochem. 228:291-296 (1995)). Crystal structures of the enzymes from yeast (Maes et al., Acta Crystallogr. Sect. F. Struct. Biol. Cryst. Commun. 62:1294-1297 (2006)) and Mycobacterium tuberculosis (Sankaranarayanan et al., Acta Crystallogr. Sect. F. Struct. Biol. Cryst. Commun. 65:173-176 (2009)) are available. Although encoded by a single open reading frame, OAT enzymes have distinct alpha and beta subunit peptides (Liu et al., Eur. J Biochem. 228:291-296 (1995)).

| Gene name | GI# | GenBank Accession # | Organism |
| --- | --- | --- | --- |
| argJ | 16078185 | NP_389002.1 | Bacillus subtilis |
| ECM40 (ARG7) | 6323707 | NP_013778.1 | Saccharomyces cerevisiae |
| Rv1653 | 15608791 | NP_216169.1 | Mycobacterium tuberculosis |

2.3.1.d Acyltransferase (Formate C-Acyltransferase).

The acylation of ketoacids HODH, OHED and 2-OHD to their corresponding CoA derivatives (FIG. 12, Steps L, P and Q) and concurrent release of formate, is catalyzed by formate C-acyltransferase enzymes in the EC class 2.3.1. Enzymes in this class include pyruvate formate-lyase and ketoacid formate-lyase. Pyruvate formate-lyase (PFL, EC 2.3.1.54), encoded by pflB in E. coli, converts pyruvate into acetyl-CoA and formate. The active site of PFL contains a catalytically essential glycyl radical that is posttranslationally activated under anaerobic conditions by PFL-activating enzyme (PFL-AE, EC 1.97.1.4) encoded by pflA (Knappe et al., Proc. Natl. Acad. Sci U.S.A 81:1332-1335 (1984); and Wong et al., Biochemistry 32:14102-14110 (1993)). A pyruvate formate-lyase from Archaeglubus fulgidus encoded by pflD has been cloned, expressed in E. coli and characterized (Lehtio, L. and A. Goldman, Protein Eng Des Sel 17:545-552 (2004)). The crystal structures of the A. fulgidus and E. coli enzymes have been resolved (Lehtio et al., J Mol. Biol. 357:221-235 (2006)). Additional PFL and PFL-AE candidates are found in Clostridium pasteurianum (Weidner and Sawers, J Bacteriol. 178:2440-2444 (1996)) and the eukaryotic alga Chlamydomonas reinhardtii (Cary et al., Appl. Environ. Microbiol 56:1576-1583 (1990)). Keto-acid formate-lyase (EC 2.3.1.-), also known as 2-ketobutyrate formate-lyase (KFL) and pyruvate formate-lyase 4, is the gene product of tdcE in E. coli. This enzyme catalyzes the conversion of 2-ketobutyrate to propionyl-CoA and formate during anaerobic threonine degradation, and can also substitute for pyruvate formate-lyase in anaerobic catabolism (Simanshu et al., J Biosci. 32:1195-1206 (2007)). The enzyme is oxygen-sensitive and, like PflB, requires post-translational modification by PFL-AE to activate a glycyl radical in the active site (Hesslinger et al., Mol. Microbiol 27:477-492 (1998)).

| Gene name | GI# | GenBank Accession # | Organism |
| --- | --- | --- | --- |
| pflB | 16128870 | NP_415423.1 | Escherichia coli |
| pflA | 16128869 | NP_415422.1 | Escherichia coli |
| tdcE | 48994926 | AAT48170.1 | Escherichia coli |
| pflD | 11499044 | NP_070278.1 | Archaeglubus fulgidus |
| pfl | 2500058 | Q46266.1 | Clostridium pasteurianum |
| act | 1072362 | CAA63749.1 | Clostridium pasteurianum |
| pfl1 | 159462978 | XP_001689719.1 | Chlamydomonas reinhardtii |
| pflA1 | 159485246 | XP_001700657.1 | Chlamydomonas reinhardtii |

2.6.1.a Aminotransferase.

Steps E, H and J of FIG. 12 and Steps C and G of FIG. 13 require conversion of an aldehyde or ketone to an amino group. This transformation can be accomplished by an aminotransferase (EC 2.6.1.-). The conversion of an aldehyde to a terminal amine (FIG. 12, Step E; FIG. 13, Steps C and G) can be catalyzed by gamma-aminobutyrate transaminase (GABA transaminase). One E. coli GABA transaminase is encoded by gabT and transfers an amino group from glutamate to the terminal aldehyde of succinic semialdehyde (Bartsch et al., J. Bacteriol. 172:7035-7042 (1990)). This enzyme exhibits a broad substrate range (Liu et al., Biochemistry 43:10896-10905 (2004)). The gene product of puuE encodes the other 4-aminobutyrate transaminase in E. coli (Kurihara et al., J Biol. Chem. 280:4602-4608 (2005)). GABA transaminases in Mus musculus, Pseudomonas fluorescens, and Sus scrofa have been shown to react with 6-aminocaproic acid (Cooper, Methods Enzymol. 113:80-82 (1985); and Scott and Jakoby, J Biol. Chem. 234:932-936 (1959)).

| Gene name | GI# | GenBank Accession # | Organism |
| --- | --- | --- | --- |
| gabT | 16130576 | NP_417148.1 | Escherichia coli |
| puuE | 16129263 | NP_415818.1 | Escherichia coli |
| abat | 37202121 | NP_766549.2 | Mus musculus |
| gabT | 70733692 | YP_257332.1 | Pseudomonas fluorescens |
| abat | 47523600 | NP_999428.1 | Sus scrofa |

Additional enzyme candidates include putrescine aminotransferases or other diamine aminotransferases. Such enzymes are particularly well suited for carrying out the conversion of 6-aminocaproate semialdehyde to HMDA. The E. coli putrescine aminotransferase is encoded by the ygjG gene and the purified enzyme also was able to transaminate cadaverine and spermidine (Samsonova et al., BMC. Microbiol 3:2 (2003)). In addition, activity of this enzyme on 1,7-diaminoheptane and with amino acceptors other than 2-oxoglutarate (e.g., pyruvate, 2-oxobutanoate) has been reported (Kim, J Biol. Chem. 239:783-786 (1964); and Samsonova et al., BMC. Microbiol 3:2 (2003)). A putrescine aminotransferase with higher activity with pyruvate as the amino acceptor than alpha-ketoglutarate is the spuC gene of Pseudomonas aeruginosa (Lu et al., J. Bacteriol. 184:3765-3773 (2002)).

| Gene name | GI# | GenBank Accession # | Organism |
|---|---|---|---|
| ygjG | 145698310 | NP_417544 | Escherichia coli |
| spuC | 9946143 | AAG03688 | Pseudomonas aeruginosa |

Additional candidate enzymes include beta-alanine/alpha-ketoglutarate aminotransferases which produce malonic semialdehyde from beta-alanine (WO08027742). The gene product of SkPYD4 in Saccharomyces kluyveri was shown to preferentially use beta-alanine as the amino group donor (Andersen and Hansen, Gene 124:105-109 (1993)). SkUGA1 encodes a homologue of Saccharomyces cerevisiae GABA aminotransferase, UGA1 (Ramos et al., Eur. J. Biochem. 149:401-404 (1985)), whereas SkPYD4 encodes an enzyme involved in both β-alanine and GABA transamination (Andersen and Hansen, Gene 124:105-109 (1993)). 3-Amino-2-methylpropionate transaminase catalyzes the transformation from methylmalonate semialdehyde to 3-amino-2-methylpropionate. The enzyme has been characterized in Rattus norvegicus and Sus scrofa and is encoded by Abat 1968 (Kakimoto et al., Biochim. Biophys. Acta 156:374-380 (1968); and Tamaki et al., Methods Enzymol. 324:376-389 (2000)).

| Gene name | GI# | GenBank Accession # | Organism |
|---|---|---|---|
| SkyPYD4 | 98626772 | ABF58893.1 | Saccharomyces kluyveri |
| SkUGA1 | 98626792 | ABF58894.1 | Saccharomyces kluyveri |
| UGA1 | 6321456 | NP_011533.1 | Saccharomyces cerevisiae |
| Abat | 122065191 | P50554.3 | Rattus norvegicus |
| Abat | 120968 | P80147.2 | Sus scrofa |

Steps J and H of FIG. 12 are catalyzed by aminotransferases that transform amino acids into oxo-acids. In Step J, OHED is transaminated to form 2-AHE by OHED aminotransferase. The transamination of 2-OHD to 2-AHD by 2-OHD aminotransferase (Step H) is a similar reaction. An exemplary enzyme candidate for catalyzing these reactions is aspartate aminotransferase, an enzyme that naturally transfers an oxo group from oxaloacetate to glutamate, forming alpha-ketoglutarate and aspartate. Aspartate is similar in structure to OHED and 2-AHD. Aspartate aminotransferase activity is catalyzed by, for example, the gene products of aspC from Escherichia coli (Yagi et al., FEBS Lett. 100:81-84, (1979); and Yagi et al., Methods Enzymol. 113: 83-89 (1985)), AAT2 from Saccharomyces cerevisiae (Yagi et al., J Biochem. 92:35-43 (1982)) and ASP5 from Arabidopsis thaliana (de la Torre et al., Plant J 46:414-425 (2006); Kwok and Hanson, J Exp. Bot. 55:595-604 (2004); and Wilkie and Warren, Protein Expr. Purif. 12:381-389 (1998)). The enzyme from Rattus norvegicus has been shown to transaminate alternate substrates such as 2-aminohexanedioic acid and 2,4-diaminobutyric acid (Recasens et al., Biochemistry 19:4583-4589 (1980)). Aminotransferases that work on other amino-acid substrates can catalyze this transformation. Valine aminotransferase catalyzes the conversion of valine and pyruvate to 2-ketoisovalerate and alanine. The E. coli gene, avtA, encodes one such enzyme (Whalen and Berg, C. J. Bacteriol. 150:739-746 (1982)). This gene product also catalyzes the transamination of α-ketobutyrate to generate α-aminobutyrate, although the amine donor in this reaction has not been identified (Whalen and Berg, J Bacteriol. 158:571-574 (1984)). The gene product of the E. coli serC catalyzes two reactions, phosphoserine aminotransferase and phosphohydroxythreonine aminotransferase (Lam and Winkler, J. Bacteriol. 172:6518-6528 (1990)), and activity on non-phosphorylated substrates could not be detected (Drewke et al., FEBS. Lett. 390:179-182 (1996)).

| Gene name | GI# | GenBank Accession # | Organism |
|---|---|---|---|
| aspC | 16128895 | NP_415448.1 | Escherichia coli |
| AAT2 | 1703040 | P23542.3 | Saccharomyces cerevisiae |
| ASP5 | 20532373 | P46248.2 | Arabidopsis thaliana |
| Got2 | 112987 | P00507 | Rattus norvegicus |
| avtA | 49176374 | YP_026231.1 | Escherichia coli |
| serC | 16128874 | NP_415427.1 | Escherichia coli |

2.7.2.a Phosphotransferase (Carboxy Acceptor).

Phosphotransferase enzymes in the EC class 2.7.2 transform carboxylic acids to phosphonic acids with concurrent hydrolysis of one ATP. Steps A and E in FIG. 13 require a phosphotransferase to activate the carboxyl groups of 6-ACA (Step A) and 6-acetamidohexanoate (Step E) to their corresponding phosphonic acids. Butyrate kinase carries out the reversible conversion of butyryl-phosphate to butyrate during acidogenesis in C. acetobutylicum (Cary et al., Appl. Environ. Microbiol 56:1576-1583 (1990)). This enzyme is encoded by either of the two buk gene products (Huang et al., J Mol. Microbiol Biotechnol 2:33-38 (2000)). Related enzyme isobutyrate kinase from Thermotoga maritima has also been expressed in E. coli and crystallized (Diao et al., Acta Crystallogr. D. Biol. Crystallogr. 59:1100-1102 (2003); and Diao and Hasson, J. Bacteriol. 191:2521-2529 (2009)). Aspartokinase catalyzes the ATP-dependent phosphorylation of aspartate and participates in the synthesis of several amino acids. The aspartokinase III enzyme in E. coli, encoded by lysC, has a broad substrate range and the catalytic residues involved in substrate specificity have been elucidated (Keng and Viola, Arch. Biochem. Biophys. 335: 73-81 (1996)). Two additional kinases in E. coli are also good candidates: acetate kinase and gamma-glutamyl kinase. The E. coli acetate kinase, encoded by ackA (Skarstedt and Silverstein, J. Biol. Chem. 251:6775-6783 (1976)), phosphorylates propionate in addition to acetate (Hesslinger et al., Mol. Microbiol 27:477-492 (1998)). The E. coli gamma-glutamyl kinase, encoded by proB (Smith et al., J. Bacteriol. 157:545-551 (1984)), phosphorylates the gamma carbonic acid group of glutamate.

| Gene name | GI# | GenBank Accession # | Organism |
|---|---|---|---|
| buk1 | 15896326 | NP_349675 | Clostridium acetobutylicum |
| buk2 | 20137415 | Q97II1 | Clostridium acetobutylicum |
| buk2 | 6685256 | Q9X278.1 | Thermotoga maritima |
| lysC | 16131850 | NP_418448.1 | Escherichia coli |
| ackA | 16130231 | NP_416799.1 | Escherichia coli |
| proB | 16128228 | NP_414777.1 | Escherichia coli |

Acetylglutamate kinase phosphorylates acetylated glutamate during arginine biosynthesis and is a good candidate for phosphorylating 6-acetamidohexanoate (FIG. 13, Step E). This enzyme is not known to accept alternate substrates; however, several residues of the E. coli enzyme involved in substrate binding and phosphorylation have been elucidated by site-directed mutagenesis (Marco-Martin et al., J Mol. Biol. 334:459-476 (2003); and Ramon-Maiques et al., Structure. 10:329-342 (2002)). The enzyme is encoded by argB in Bacillus subtilis and E. coli (Parsot et al., Gene 68:275-283 (1988)), and ARG5,6 in S. cerevisiae (Pauwels et al., Eur. J Biochem. 270:1014-1024 (2003)). The ARG5,6 gene of S. cerevisiae encodes a polyprotein precursor that is matured in the mitochondrial matrix to become acetylglutamate kinase and acetylglutamylphosphate reductase, an enzyme candidate for the reduction of 6-AAHOP (FIG. 13, Step F).

| Gene name | GI# | GenBank Accession # | Organism |
|---|---|---|---|
| argB | 145698337 | NP_418394.3 | Escherichia coli |
| argB | 16078186 | NP_389003.1 | Bacillus subtilis |
| ARG5, 6 | 6320913 | NP_010992.1 | Saccharomyces cerevisiae |

2.8.3.a Coenzyme-A Transferase.

Coenzyme-A (CoA) transferases catalyze the reversible transfer of a CoA moiety from one molecule to another. In Step M of FIG. 13, 3-aminocaproyl-CoA is formed by the transfer of a CoA group from acetyl-CoA, succinyl-CoA, or another CoA donor. A similar transformation is catalyzed by 6-acetamidohexanoate CoA-transferase, shown in Step I of FIG. 13. Exemplary CoA transferase candidates are catalyzed by the gene products of cat1, cat2, and cat3 of Clostridium kluyveri which have been shown to exhibit succinyl-CoA, 4-hydroxybutyryl-CoA, and butyryl-CoA transferase activity, respectively (Seedorf et al., Proc. Natl. Acad. Sci U.S.A 105:2128-2133 (2008); and Sohling and Gottschalk, J. Bacteriol. 178:871-880 (1996)). Similar CoA transferase activities are also present in Trichomonas vaginalis (van Grinsven et al., J. Biol. Chem. 283:1411-1418 (2008)) and Trypanosoma brucei (Riviere et al., J. Biol. Chem. 279:45337-45346 (2004)).

| Gene name | GI# | GenBank Accession # | Organism |
|---|---|---|---|
| cat1 | 729048 | P38946.1 | Clostridium kluyveri |
| cat2 | 172046066 | P38942.2 | Clostridium kluyveri |
| cat3 | 146349050 | EDK35586.1 | Clostridium kluyveri |
| TVAG_395550 | 123975034 | XP_001330176 | Trichomonas vaginalis G3 |
| Tb11.02.0290 | 71754875 | XP_828352 | Trypanosoma brucei |

A CoA transferase that can utilize acetyl-CoA as the CoA donor is acetoacetyl-CoA transferase, encoded by the E. coli atoA (alpha subunit) and atoD (beta subunit) genes (Korolev et al., Acta Crystallogr. D. Biol. Crystallogr. 58:2116-2121 (2002); and Vanderwinkel et al., Biochem. Biophys. Res. Commun. 33:902-908 (1968)). This enzyme has a broad substrate range (Sramek and Frerman, Arch. Biochem. Biophys. 171:14-26 (1975)) and has been shown to transfer the CoA moiety to acetate from a variety of branched and linear acyl-CoA substrates, including isobutyrate (Matthies and Schink, Appl Environ. Microbiol 58:1435-1439 (1992)), valerate (Vanderwinkel et al., Biochem. Biophys. Res. Commun. 33:902-908 (1968)) and butanoate (Vanderwinkel et al., Biochem. Biophys. Res. Commun. 33:902-908 (1968)). This enzyme is induced at the transcriptional level by acetoacetate, so modification of regulatory control may be necessary for engineering this enzyme into a pathway (Pauli and Overath, Eur. J Biochem. 29:553-562 (1972)). Similar enzymes exist in Corynebacterium glutamicum ATCC 13032 (Duncan et al., Appl. Environ. Microbiol 68:5186-5190 (2002)), Clostridium acetobutylicum (Cary et al., Appl. Environ. Microbiol 56:1576-1583 (1990); and Wiesenborn et al., Appl. Environ. Microbiol 55:323-329 (1989)), and Clostridium saccharoperbutylacetonicum (Kosaka et al., Biosci. Biotechnol Biochem. 71:58-68 (2007)).

| Gene name | GI# | GenBank Accession # | Organism |
|---|---|---|---|
| AtoA | 2492994 | NP_416726 | Escherichia coli K12 |
| AtoD | 2492990 | NP_416725 | Escherichia coli K12 |
| actA | 62391407 | YP_226809.1 | Corynebacterium glutamicum ATCC 13032 |
| cg0592 | 62389399 | YP_224801.1 | Corynebacterium glutamicum ATCC 13032 |
| ctfA | 15004866 | NP_149326.1 | Clostridium acetobutylicum |
| ctfB | 15004867 | NP_149327.1 | Clostridium acetobutylicum |
| ctfA | 31075384 | AAP42564.1 | Clostridium saccharoperbutylacetonicum |
| ctfB | 31075385 | AAP42565.1 | Clostridium saccharoperbutylacetonicum |

The glutaconyl-CoA-transferase (EC 2.8.3.12) enzyme from anaerobic bacterium Acidaminococcus fermentans reacts with glutaconyl-CoA and 3-butenoyl-CoA (Mack et al., Eur. Biochem. 226:41-51 (1994)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., Eur. J Biochem. 118:315-321 (1981)). The enzyme has been cloned and expressed in E. coli (Mack et al., Eur. J. Biochem. 226:41-51 (1994)).

| Gene name | GI# | GenBank Accession # | Organism |
|---|---|---|---|
| gctA | 559392 | CAA57199.1 | Acidaminococcus fermentans |
| gctB | 559393 | CAA57200.1 | Acidaminococcus fermentans |

Yet another CoA transferase is the two-unit succinyl-CoA:3:oxoacid-CoA transferase encoded by pcaI and pcaJ in Pseudomonas putida (Kaschabek et al., J. Bacteriol. 184:207-215 (2002)). Similar enzymes based on homology exist in Acinetobacter sp. ADP1 (Kowalchuk et al., Gene 146:23-30 (1994)). Additional exemplary succinyl-CoA:3:oxoacid-CoA transferases are present in Helicobacter pylori (Corthesy-Theulaz et al., J Biol. Chem. 272:25659-25667 (1997)) and Bacillus subtilis (Stols et al., Protein Expr. Purif. 53:396-403 (2007)).

| Gene name | GI# | GenBank Accession # | Organism |
| --- | --- | --- | --- |
| pcaI | 24985644 | AAN69545.1 | *Pseudomonas putida* |
| pcaI | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |

3.5.1.a Hydrolase (Acting on Linear Amides).

Deacetylation of linear acetamides is catalyzed by an amidohydrolase in the 3.5.1 family of enzymes. Such an enzyme is required for the deacetylation of 6-acetamidohexanamine to HMDA (FIG. 13, Step H). An enzyme catalyzing a similar transformation is 4-acetamidobutyrate deacetylase (EC 3.5.1.63), which naturally deacetylates 4-acetamidobutyrate. The enzyme, studied for its role in putrescine degradation in *Candida boidinii* (Gillyon et al., *Journal of General Microbiology* 133:2477-2485 (1987)), has been shown to deacetylate a variety of substrates including 6-acetamidohexanoate (Haywood and Large, *Journal of General Microbiology* 132:7-14 (1986)). Although 6-Acetamidohexanoate is similar in structure to the desired substrate, deacetylation of this compound (FIG. 13, step D, reverse reaction) may hinder efficient production of HMDA. Protein engineering or directed evolution may be required to improve specificity for 6-acetamidohexanamine. The gene associated with this activity has not been identified to date.

Acetylpolyamine amidohydrolase (EC 3.5.1.62), is another candidate enzyme that forms the diamines putrescine and cadaverine from their acetylated precursors. The acetylpolyamine deacetylase (AphA) from *Mycoplana ramosa* has been cloned in *E. coli* and characterized (Sakurada et al., *J Bacteriol.* 178:5781-5786 (1996)) and a crystal structure is available (Fujishiro et al., *Biochem. Biophys. Res. Commun.* 157:1169-1174 (1988)). This enzyme has also been studied in *Micrococcus luteus*, but the associated gene has not been identified to date (Suzuki et al., *Biochim. Biophys. Acta* 882:140-142 (1986)). A protein the histone deacetylase superfamily with high sequence similarity to AphA was identified in the *M. luteus* genome (evalue=1e-18, 37% identity). The N-acetyl-L-ornithine deacetylase from *E. coli* is another candidate amidohydrolase (EC 3.5.1.16). The *E. coli* enzyme, encoded by the argE gene (McGregor et al., *J Am. Chem. Soc.* 127:14100-14107 (2005); and Meinnel et al., *Bacteriol.* 174:2323-2331 (1992)), removes N-acetyl groups from a variety of substrates including ornithine, lysine, glutamine, and other amino acids (Javid-Majd and Blanchard, Biochemistry 39:1285-1293 (2000)).

| Gene name | GI# | GenBank Accession # | Organism |
| --- | --- | --- | --- |
| aphA | 3023317 | Q48935.1 | *Mycoplana ramose* |
| MlutDRAFT_1143 | 172071524 | EDT57566.1 | *Micrococcus luteus* |
| argE | 16131795 | NP_418392.1 | *Escherichia coli* |

4.1.1.a Carboxy-Lyase.

Steps D and F in FIG. 12 are catalyzed by 2-ketoacid decarboxylase enzymes that generate 6-OHE and adipate semialdehyde from OHED (Step F) and 2-OHD (Step D). In addition, alpha-ketoglutarate is decarboxylated to form pathway precursor succinic semialdehyde by alpha-ketoglutarate decarboxylase, a keto-acid decarboxylase. The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (22). This enzyme has been extensively studied, engineered for altered activity, and functionally expressed in *E. coli* (Killenberg-Jabs et al., *Eur. J. Biochem.* 268:1698-1704 (2001); Li, H. and F. Jordan, *Biochemistry.* 38:10004-10012 (1999); and ter Schure et al., *Appl. Environ. Microbiol.* 64:1303-1307 (1998)). The PDC from *Zymomonas mobilus*, encoded by pdc, also has a broad substrate range and has been a subject of directed engineering studies to alter the affinity for different substrates (Siegert et al., *Protein Eng Des Sel* 18:345-357 (2005)). The crystal structure of this enzyme is available (Killenberg-Jabs et al., *Eur. J. Biochem.* 268:1698-1704 (2001)). Other well-characterized PDC candidates include the enzymes from *Acetobacter pasteurians* (Chandra et al., *Arch. Microbiol.* 176:443-451 (2001)) and *Kluyveromyces lactis* (Krieger et al., *Eur. J. Biochem.* 269: 3256-3263 (2002)).

| Gene name | GI# | GenBank Accession # | Organism |
| --- | --- | --- | --- |
| pdc | 118391 | P06672.1 | *Zymomonas mobilus* |
| pdc1 | 30923172 | P06169 | *Saccharomyces cerevisiae* |
| pdc | 20385191 | Q8L388 | *Acetobacter pasteurians* |
| pdc1 | 52788279 | Q12629 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al., *Biochemistry* 37:9918-9930 (1998); and Polovnikova et al., *Biochemistry* 42:1820-1830 (2003)). Site-directed mutagenesis of two residues in the active site of the *Pseudomonas putida* enzyme altered the affinity (Km) of naturally and non-naturally occurring substrates (Siegert et al., *Protein Eng Des Sel* 18:345-357 (2005)). The properties of this enzyme have been further modified by directed engineering (Lingen et al., *Protein Eng* 15:585-593 (2002); and Lingen et al., *Chembiochem.* 4:721-726 (2003)). The enzyme from *Pseudomonas aeruginosa*, encoded by mdlC, has also been characterized experimentally (Barrowman et al., *FEMS Microbiology Letters* 34:57-60 (1986)). Additional gene candidates from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.* 72:7510-7517 (2006)).

| Gene name | GI# | GenBank Accession # | Organism |
|---|---|---|---|
| mdlC | 3915757 | P20906.2 | Pseudomonas putida |
| mdlC | 81539678 | Q9HUR2.1 | Pseudomonas aeruginosa |
| dpgB | 126202187 | ABN80423.1 | Pseudomonas stutzeri |
| ilvB-1 | 70730840 | YP_260581.1 | Pseudomonas fluorescens |

A third enzyme capable of decarboxylating 2-oxoacids is alpha-ketoglutarate decarboxylase (KGD). The substrate range of this class of enzymes has not been studied to date. The KDC from Mycobacterium tuberculosis (Tian et al., Proc Natl Acad Sci U S. A 102:10670-10675 (2005)) has been cloned and functionally expressed in other internal projects at Genomatica. However, it is not an ideal candidate for strain engineering because it is large (~130 kD) and GC-rich. KDC enzyme activity has been detected in several species of rhizobia including Bradyrhizobium japonicum and Mesorhizobium loti (Green et al., J Bacteriol. 182:2838-2844 (2000)). Although the KDC-encoding gene(s) have not been isolated in these organisms, the genome sequences are available and several genes in each genome are annotated as putative KDCs. A KDC from Euglena gracilis has also been characterized but the gene associated with this activity has not been identified to date (Shigeoka and Nakano, Arch. Biochem. Biophys. 288:22-28 (1991)). The first twenty amino acids starting from the N-terminus were sequenced MTYKAPVKDVKFLLDKVFKV (SEQ ID NO: 1) (Shigeoka and Nakano, Arch. Biochem. Biophys. 288:22-28 (1991)). The gene can be identified by testing candidate genes containing this N-terminal sequence for KDC activity.

| Gene name | GI# | GenBank Accession # | Organism |
|---|---|---|---|
| kgd | 160395583 | O50463.4 | Mycobacterium tuberculosis |
| kgd | 27375563 | NP_767092.1 | Bradyrhizobium japonicum |
| kgd | 13473636 | NP_105204.1 | Mesorhizobium loti |

A fourth candidate enzyme for catalyzing this step is branched chain alpha-ketoacid decarboxylase (BCKA). This class of enzyme has been shown to act on a variety of compounds varying in chain length from 3 to 6 carbons (Oku and Kaneda, J Biol Chem. 263:18386-18396 (1988); and Smit et al., Appl Environ Microbiol. 71:303-311 (2005)). The enzyme in Lactococcus lactis has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate (Smit et al., Appl Environ Microbiol. 71:303-311 (2005)). The enzyme has been structurally characterized (Berg et al., Science. 318:1782-1786 (2007)). Sequence alignments between the Lactococcus lactis enzyme and the pyruvate decarboxylase of Zymomonas mobilus indicate that the catalytic and substrate recognition residues are nearly identical (Siegert et al., Protein Eng Des Sel 18:345-357 (2005)), so this enzyme would be a promising candidate for directed engineering. Decarboxylation of alpha-ketoglutarate by a BCKA was detected in Bacillus subtilis; however, this activity was low (5%) relative to activity on other branched-chain substrates (Oku and Kaneda, J Biol Chem. 263:18386-18396 (1988)) and the gene encoding this enzyme has not been identified to date. Additional BCKA gene candidates can be identified by homology to the Lactococcus lactis protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

| Gene name | GI# | GenBank Accession # | Organism |
|---|---|---|---|
| kdcA | 44921617 | AAS49166.1 | Lactococcus lactis |

Recombinant branched chain alpha-keto acid decarboxylase enzymes derived from the E1 subunits of the mitochondrial branched-chain keto acid dehydrogenase complex from Homo sapiens and Bos taurus have been cloned and functionally expressed in E. coli (Davie et al., J. Biol. Chem. 267:16601-16606 (1992); Wynn et al., J. Biol. Chem. 267: 1881-1887 (1992); and Wynn et al., J. Biol. Chem. 267: 12400-12403 (1992)). In these studies, the authors found that co-expression of chaperonins GroEL and GroES enhanced the specific activity of the decarboxylase by 500-fold (Wynn et al., J. Biol. Chem. 267:12400-12403 (1992)). These enzymes are composed of two alpha and two beta subunits.

| Gene name | GI# | GenBank Accession # | Organism |
|---|---|---|---|
| BCKDHB | 34101272 | NP_898871.1 | Homo sapiens |
| BCKDHA | 11386135 | NP_000700.1 | Homo sapiens |
| BCKDHB | 115502434 | P21839 | Bos taurus |
| BCKDHA | 129030 | P11178 | Bos taurus |

The decarboxylation of 2-AHD to 6-aminocaproate (FIG. 12, Step I) is catalyzed by an amino acid decarboxylase such as aspartate decarboxylase. Aspartate decarboxylase participates in pantothenate biosynthesis and is encoded by gene panD in Escherichia coli (Dusch et al., Appl. Environ. Microbiol 65:1530-1539 (1999); Merke and Nichols, FEMS Microbiol Lett. 143:247-252 (1996); Ramjee et al., Biochem. J 323 (Pt 3):661-669 (1997); and Schmitzberger et al., EMBO J 22:6193-6204 (2003)). Similar enzymes from Mycobacterium tuberculosis (Chopra et al., Protein Expr. Purif. 25:533-540 (2002)) and Corynebacterium glutamicum (Dusch et al., Appl. Environ. Microbiol 65:1530-1539 (1999)) have been expressed and characterized in E. coli.

| Gene name | GI# | GenBank Accession # | Organism |
|---|---|---|---|
| panD | 67470411 | P0A790 | Escherichia coli K12 |
| panD | 18203593 | Q9X4N0 | Corynebacterium glutamicum |
| panD | 54041701 | P65660.1 | Mycobacterium tuberculosis |

4.1.2.a Aldehyde-Lyase.

HOHD aldolase, also known as HHED aldolase, catalyzes the conversion of 4-hydroxy-2-oxo-heptane-1,7-dioate (HOHD) into pyruvate and succinic semialdehyde (FIG. 12, Step A). The enzyme is a divalent metal ion dependent class II aldolase, catalyzing the final step of 4-hydroxyphenylacetic acid degradation in E. coli C, E. coli W, and other organisms. In the native context, the enzyme functions in the degradative direction. The reverse (condensation) reaction is thermodynamically unfavorable; however the equilibrium can be shifted through coupling HOHD aldolase with downstream pathway enzymes that work efficiently on reaction products. Such strategies have been effective for shifting the equilibrium of other aldolases in the condensation direction (Nagata et al., *Appl Microbiol Biotechnol* 44:432-438 (1995); and Pollard et al., *Appl Environ. Microbiol* 64:4093-4094 (1998)). The *E. coli* C enzyme, encoded by hpcH, has been extensively studied and has recently been crystallized (Rea et al., *J Mol. Biol.* 373:866-876 (2007); and Stringfellow et al., *Gene* 166:73-76 (1995)). The *E. coli* W enzyme is encoded by hpaI (Prieto et al., *J Bacteriol.* 178:111-120 (1996)).

| Gene name | GI# | GenBank Accession # | Organism |
|---|---|---|---|
| hpcH | 633197 | CAA87759.1 | *Escherichia coli* C |
| hpaI | 38112625 | AAR11360.1 | *Escherichia coli* W |

4.2.1.a Hydro-Lyase.

The enzyme OHED hydratase participates in 4-hydroxyphenylacetic acid degradation, where it converts 2-oxo-hept-4-ene-1,7-dioate (OHED) to 2-oxo-4-hydroxy-hepta-1,7-dioate (HODH) using magnesium as a cofactor (Burks et al., *Am. Chem. Soc.* 120 (1998)) (FIG. 12, Step B). OHED hydratase enzyme candidates have been identified and characterized in *E. coli* C (Izumi et al., *J Mol. Biol.* 370:899-911 (2007); and Roper et al., *Gene* 156:47-51 (1995)) and *E. coli* W (Prieto et al., *J Bacteriol.* 178:111-120 (1996)). Sequence comparison reveals homologs in a range of bacteria, plants and animals. Enzymes with highly similar sequences are contained in *Klebsiella pneumonia* (91% identity, evalue=2e-138) and *Salmonella enterica* (91% identity, evalue=4e-138), among others.

| Gene name | GI# | GenBank Accession # | Organism |
|---|---|---|---|
| hpcG | 556840 | CAA57202.1 | *Escherichia coli* C |
| hpaH | 757830 | CAA86044.1 | *Escherichia coli* W |
| hpaH | 150958100 | ABR80130.1 | *Klebsiella pneumoniae* |
| Sari_01896 | 160865156 | ABX21779.1 | *Salmonella enterica* |

Figure 14:
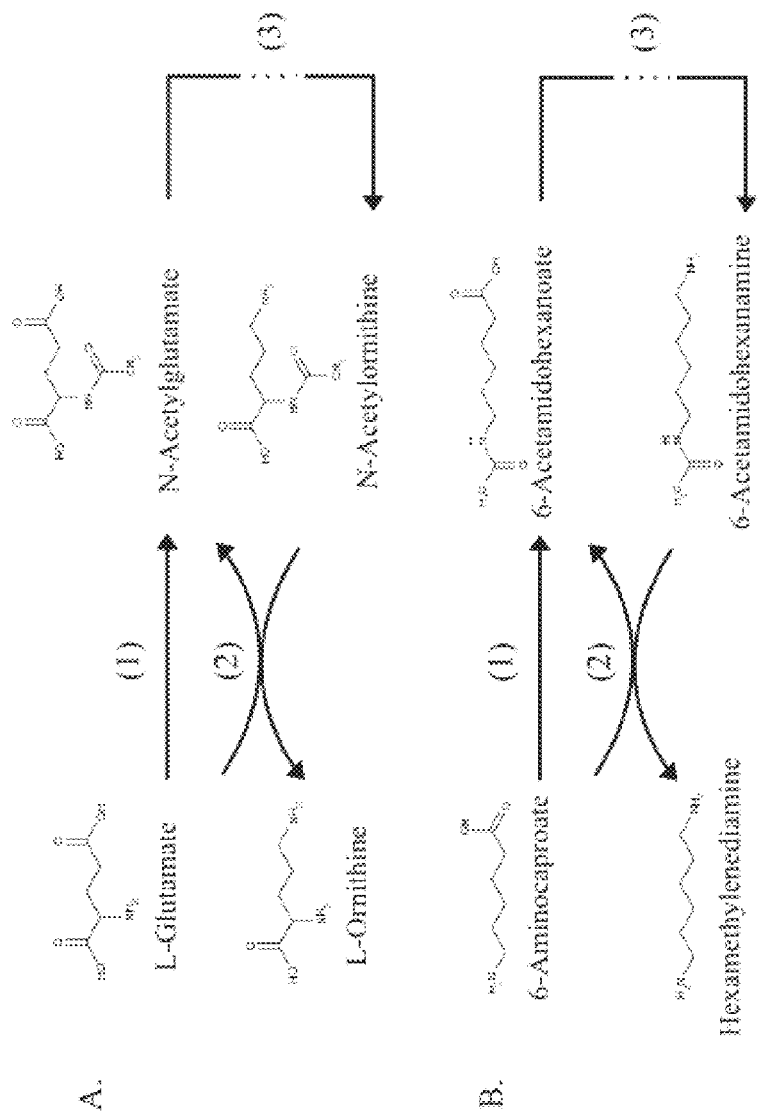
FIG. 14 shows: A) the acetyl-CoA cycle of arginine biosynthesis. Reactions (1) and (2) are catalyzed by ornithine acetyltransferase with acetylglutamate synthase and ornithine acyltransferase functionality. Reaction 3 is a lumped reaction catalyzed by acetylglutamate kinase, N-acetylglutamylphosphate reductase, and acetylornithine aminotransferase; B) the acetyl-CoA cycle of HMDA biosynthesis. Reactions (1) and (2) are catalyzed by HMDA acetyltransferase. Reaction (3) is a lumped reaction that includes all pathways to 6-acetamidohexanamine from 6-acetamidohexanoate shown in FIG. 13.

Dehydration of 3-hydroxyadipyl-CoA to 2,3-dehydroadipyl-CoA (FIG. 12, Step M) is catalyzed by an enzyme with enoyl-CoA hydratase activity. 3-Hydroxybutyryl-CoA dehydratase (EC 4.2.1.55), also called crotonase, dehydrates 3-hydroxyisobutyryl-CoA to form crotonoyl-CoA (FIG. 14, step 2). Crotonase enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Atsumi et al., *Metab Eng* 10:305-311 (2008); and Boynton et al., *J. Bacteriol.* 178:3015-3024 (1996)), *C. kluyveri* (Hillmer and Gottschalk, *FEBS Lett.* 21:351-354 (1972)), and *Metallosphaera sedula* (Berg et al., *Science.* 318:1782-1786 (2007)) though the sequence of the latter gene is not known.

| Gene name | GI# | GenBank Accession # | Organism |
|---|---|---|---|
| crt | 15895969 | NP_349318.1 | *Clostridium acetobutylicum* |
| crt1 | 153953091 | YP_001393856.1 | *Clostridium kluyveri* |

Enoyl-CoA hydratases (EC 4.2.1.17) also catalyze the dehydration of 3-hydroxyacyl-CoA substrates (Agnihotri and Liu., *J. Bacteriol.* 188:8551-8559(2003); Conrad et al., *J. Bacteriol.* 118:103-111 (1974); and Roberts et al., *Arch. Microbiol* 117:99-108 (1978)). The enoyl-CoA hydratase of *Pseudomonas putida*, encoded by ech, catalyzes the conversion of 3-hydroxybutyryl-CoA to crotonoyl-CoA (Roberts et al., *Arch. Microbiol* 117:99-108 (1978)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison and Harwood, *Microbiology* 151:727-736 (2005)). Lastly, a number of *Escherichia coli* genes have been shown to demonstrate enoyl-CoA hydratase functionality including maoC (Park and Lee, *J Bacteriol.* 185:5391-5397 (2003)), paaF (Ismail et al., *J Biochem.* 270:3047-3054 (2003); Park and Lee, *Appl. Biochem. Biotechnol* 113-116:335-346 (2004); and Park and Yup, *Biotechnol Bioeng* 86:681-686 (2004)) and paaG (Ismail et al., *J Biochem.* 270:3047-3054(2003); Park and Lee, *Appl. Biochem. Biotechnol* 113-116:335-346 (2004); and Park and Yup, *Biotechnol Bioeng* 86:681-686 (2004)).

| Gene name | GI# | GenBank Accession # | Organism |
|---|---|---|---|
| ech | 26990073 | NP_745498.1 | *Pseudomonas putida* |
| paaA | 26990002 | NP_745427.1 | *Pseudomonas putida* |
| paaB | 26990001 | NP_745426.1 | *Pseudomonas putida* |
| phaA | 106636093 | ABF82233.1 | *Pseudomonas fluorescens* |
| phaB | 106636094 | ABF82234.1 | *Pseudomonas fluorescens* |
| pimF | 39650635 | CAE29158 | *Rhodopseudomonas palustris* |
| maoC | 16129348 | NP_415905.1 | *Escherichia coli* |
| paaF | 16129354 | NP_415911.1 | *Escherichia coli* |
| paaG | 16129355 | NP_415912.1 | *Escherichia coli* |

Alternatively, the *E. coli* gene products of fadA and fadB encode a multienzyme complex involved in fatty acid oxidation that exhibits enoyl-CoA hydratase activity (Nakahigashi and Inokuchi, *Nucleic Acids Res.* 18:4937 (1990); Yang, *J. Bacteriol.* 173:7405-7406 (1991); and Yang et al., *Biochemistry* 30:6788-6795 (1991)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Gene name | GI# | GenBank Accession # | Organism |
|---|---|---|---|
| fadA | 49176430 | YP_026272.1 | *Escherichia coli* |
| fadB | 16131692 | NP_418288.1 | *Escherichia coli* |
| fadI | 16130275 | NP_416844.1 | *Escherichia coli* |
| fadJ | 16130274 | NP_416843.1 | *Escherichia coli* |
| fadR | 16129150 | NP_415705.1 | *Escherichia coli* |

6.2.1.a Acid-Thiol Ligase (Also Called CoA Synthetase).

Steps I and M of FIG. 13 require acid-thiol ligase or CoA synthetase functionality to transform 6-ACA and 6-acetamidohexanoate into their corresponding CoA derivatives (the terms ligase, synthetase, and synthase are used herein interchangeably and refer to the same enzyme class). Enzymes catalyzing these exact transformations have not been characterized to date; however, several enzymes with broad substrate specificities have been described in the literature. ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt and Schonheit, *J. Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt and Schonheit, *J. Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen and Schonheit, *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen and Schonheit, *Arch. Microbiol* 182:277-287 (2004)). Directed evolution or engineering can be used to modify this enzyme to operate at the physiological temperature of the host organism. The enzymes from *A. fulgidus*, *H. marismortui* and *P. aerophilum* have all been cloned, functionally expressed, and characterized in *E. coli* (Brasen and Schonheit, *Arch. Microbiol* 182:277-287 (2004); and Musfeldt and Schonheit, *J. Bacteriol.* 184:636-644 (2002)). An additional candidate is the enzyme encoded by sucCD in *E. coli*, which naturally catalyzes the formation of succinyl-CoA from succinate with the concomitant consumption of one ATP, a reaction which is reversible in vivo (Buck et al., *Biochemistry* 24:6245-6252 (1985)).

| Gene name | GI# | GenBank Accession # | Organism |
|---|---|---|---|
| AF1211 | 11498810 | NP_070039.1 | *Archaeoglobus fulgidus* DSM 4304 |
| AF1983 | 11499565 | NP_070807.1 | *Archaeoglobus fulgidus* DSM 4304 |
| scs | 55377722 | YP_135572.1 | *Haloarcula marismortui* ATCC 43049 |
| PAE3250 | 18313937 | NP_560604.1 | *Pyrobaculum aerophilum* str. IM2 |
| sucC | 16128703 | NP_415256.1 | *Escherichia coli* |
| sucD | 1786949 | AAC73823.1 | *Escherichia coli* |

Another candidate enzyme for this step is 6-carboxyhexanoate-CoA ligase, also known as pimeloyl-CoA ligase (EC 6.2.1.14), which naturally activates pimelate to pimeloyl-CoA during biotin biosynthesis in gram-positive bacteria. The enzyme from *Pseudomonas mendocina*, cloned into *E. coli*, was shown to accept the alternate substrates hexanedioate and nonanedioate (Binieda et al., *Biochem. J* 340 (Pt 3):793-801 (1999)). Other candidates are found in *Bacillus subtilis* (Bower et al., *J. Bacteriol.* 178: 4122-4130 (1996)) and Lysinibacillus *sphaericus* (formerly *Bacillus sphaericus*) (Ploux et al., *Biochem. J* 287 (Pt 3):685-690 (1992)).

| Gene name | GI# | GenBank Accession # | Organism |
|---|---|---|---|
| pauA | 15596214 | NP_249708.1 | *Pseudomonas mendocina* |
| bioW | 50812281 | NP_390902.2 | *Bacillus subtilis* |
| bioW | 115012 | P22822.1 | *Lysinibacillus sphaericus* |

Additional CoA-ligases include the rat dicarboxylate-CoA ligase for which the sequence is yet uncharacterized (Vamecq et al., *Biochem. J* 230:683-693 (1985)), either of the two characterized phenylacetate-CoA ligases from *P. chrysogenum* (Lamas-Maceiras et al., *Biochem. J* 395:147-155 (2006); and Wang et al., *Biochem. Biophys. Res. Commun.* 360:453-458 (2007)) and the phenylacetate-CoA ligase from *Pseudomonas putida* (Martinez-Blanco et al., *J Biol. Chem.* 265:7084-7090 (1990)). Additional candidate enzymes are acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)) which naturally catalyze the ATP-dependent conversion of acetoacetate into acetoacetyl-CoA.

| Gene name | GI# | GenBank Accession # | Organism |
|---|---|---|---|
| phl | 77019264 | CAJ15517.1 | *Penicillium chrysogenum* |
| phlB | 152002983 | ABS19624.1 | *Penicillium chrysogenum* |
| paaF | 22711873 | AAC24333.2 | *Pseudomonas putida* |
| AACS | 21313520 | NP_084486.1 | *Mus musculus* |
| AACS | 31982927 | NP_076417.2 | *Homo sapiens* |

Example XXII

Demonstration of *Escherichia coli* Tolerance to 6-Aminocaproate

Figure 15:
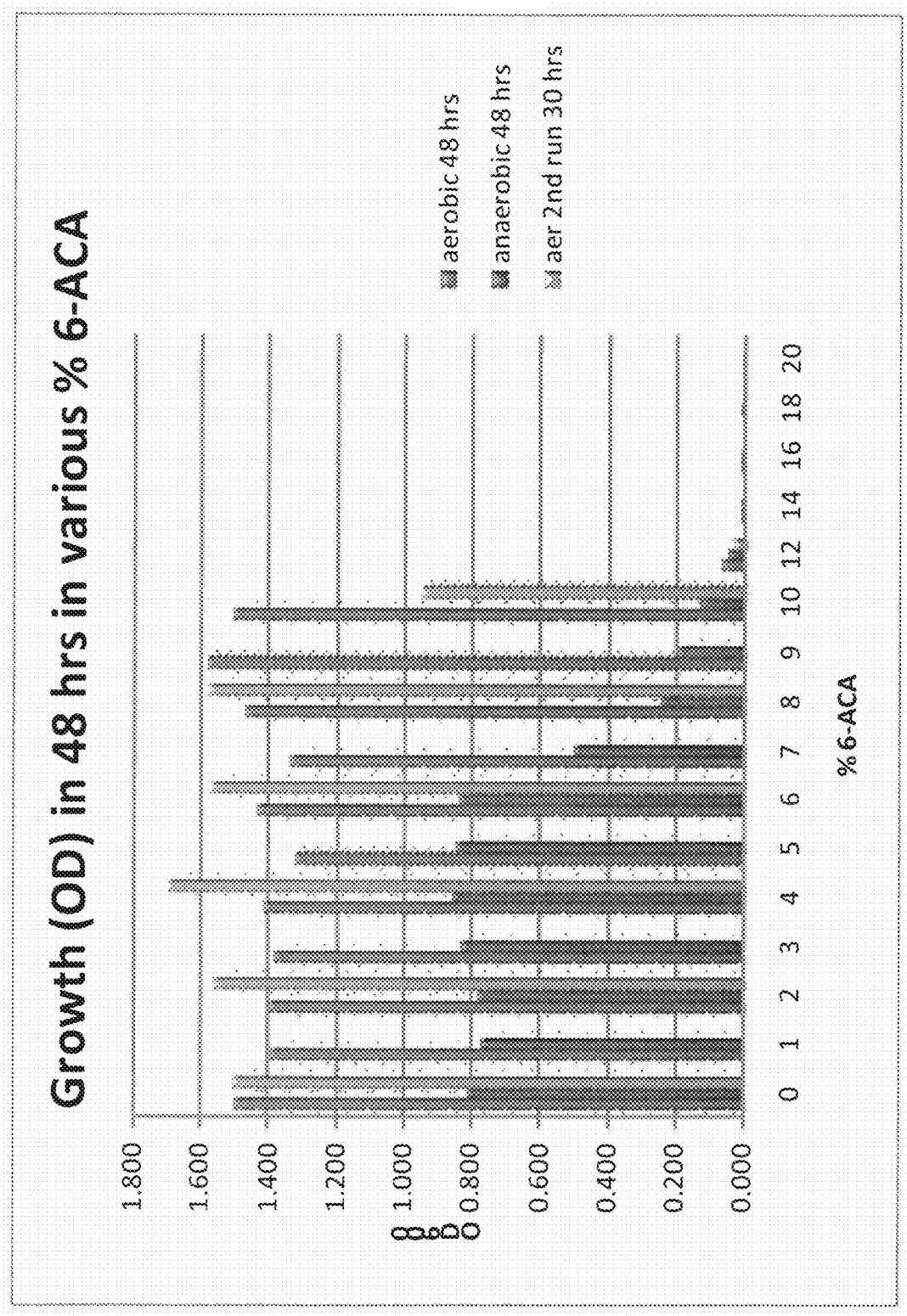
FIG. 15 shows the growth of *E. coli* in media containing various concentrations of 6-ACA. *E. coli* was inoculated into media and grown in either aerobic (left and right bars) or anaerobic (middle bars) conditions. The cultures were grown for 48 hrs during the first trial and 30 hrs for a second trial under aerobic conditions (right bars).
Figure 16:
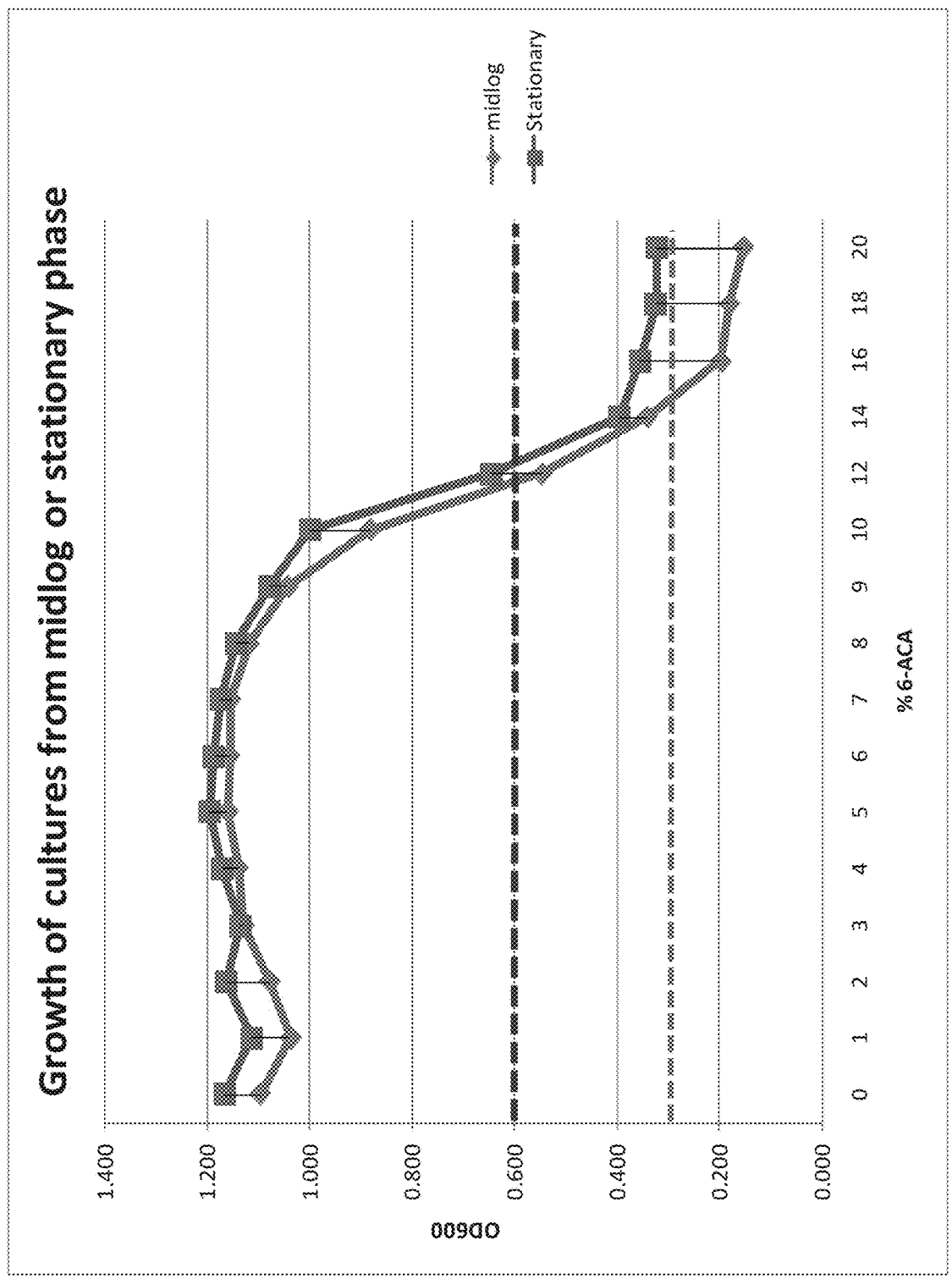
FIG. 16 shows the tolerance of *E. coli* when exposed to 6-ACA. Midlog (OD600=0.3, lower dashed line) or early stationary (OD600=0.6, upper dashed line) cells were spun down and resuspended in fresh M9-Glucose medium with various concentrations of 6-ACA. After overnight growth, cultures were measured for growth by measuring OD600.
Figure 17:
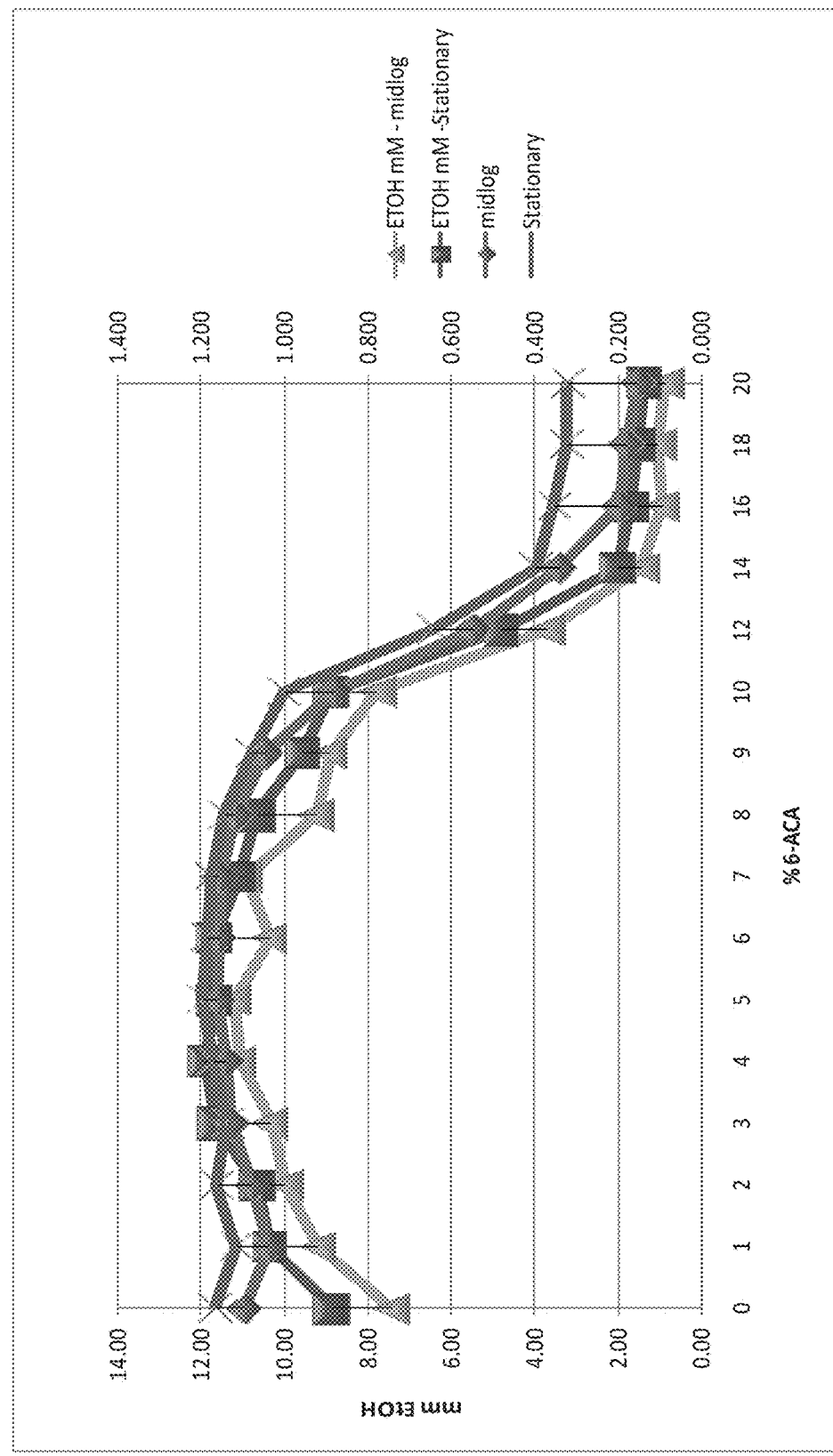
FIG. 17 shows the ethanol production from cultures exposed to various concentrations of 6-ACA. Midlog or early stationary cells were spun down and resuspended in fresh M9-Glucose medium with various concentrations of 6-ACA. After overnight growth, cultures were measured for growth by measuring OD600 and metabolic activity assayed by ethanol production.

*E. coli* was assayed for tolerance, metabolic activity and growth during exposure to various concentrations of 6-aminocaproate (6-ACA). Aerobically, cultures were able to grow media with up to 10% 6-ACA, while anaerobic cultures could grow in media with approximately 6% 6-ACA (FIG. 15). Because the pathway for producing 6-ACA could require anaerobic conditions, all other further testing was performed under anaerobic conditions. To assay tolerance, cultures were grown anaerobically to mid-log (0.3 OD) and early stationary phase (0.6 OD), the cells were spun down and resuspended in medium containing various concentrations of 6-ACA. The cultures were grown in capped microfuge tubes, grown overnight and the ODs of the cultures were assayed (FIG. 16). Under these conditions, cultures were able to grow (double at least 1 time) in up to 10% 6-ACA. The additional tolerance could have been from the additional glucose from resuspending the cultures in fresh M9-glucose medium or from limited oxygen that was present in the capped microfuge tube. To determine if the cells were metabolically active in the presence of 6-ACA, samples were taken and assayed for ethanol production (FIG. 17). Ethanol production (and thus metabolic activity) closely tracked with OD suggesting that if cells are present, they are likely to be metabolically active. This is helpful to understand because it suggests that even though cells may be growth inhibited by the accumulation of a product, they can still continue to produce product.

Figure 18:
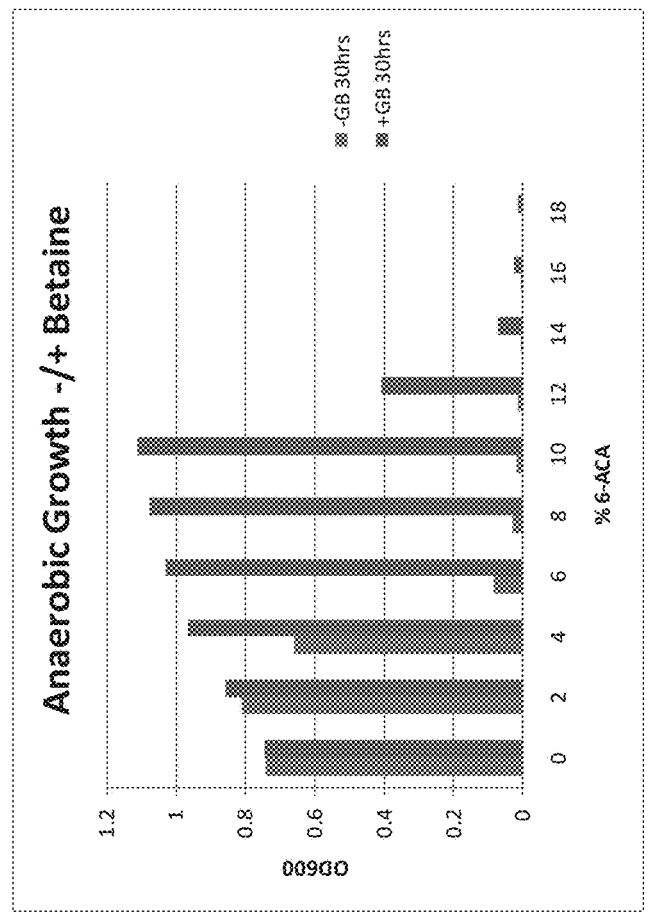
FIG. 18, panels A and B, show the growth in various concentrations of 6-ACA with and without glycine betaine. Panel A. OD600 measurements of medium inoculated with midlog cultures of *E. coli* with various concentrations of 6-ACA with (right bars) and without (left bars) 2 mM glycine betaine. Panel B. Photograph showing the growth of same cultures in the anaerobic bottles.
Figure 18:
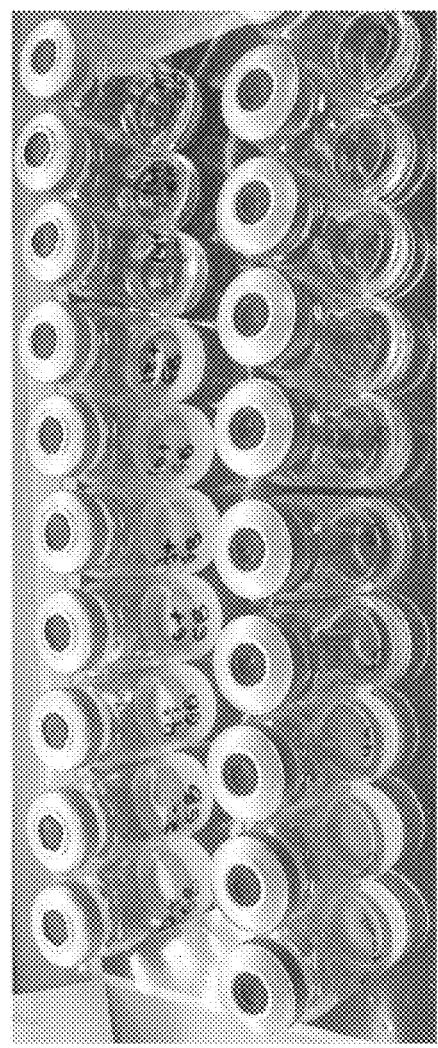

At high concentrations (>65 g/L) the osmolarity of 6-ACA is ~0.5 M which may cause osmotic stress. To determine osmotic stress as the basis for 6-ACA growth inhibition, cultures were grown in various concentrations of 6-ACA with and without the osmoprotectant glycine betaine. As seen in FIG. 18, anaerobic growth in medium with up to 10-12% 6-ACA can be achieved if glycine betaine is present but only 4-6% without glycine betaine. Therefore much of the toxicity of 6-ACA is likely due to the osmotic stress. However, it should be noted that 6-ACA is similar to the amino acid lysine and could have a greater toxic effect in the cell cytoplasm vs. outside the cell.

Example XXIII

Demonstration of Enzyme Activity for Condensing Succinyl-CoA and Acetyl-CoA to Form β-ketoadipyl-CoA Several β-ketothiolase enzymes have been shown to break β-ketoadipyl-CoA into acetyl-CoA and succinyl-CoA. For example, the gene products encoded by pcaF in *Pseudomonas* strain B13 (Kaschabek et al., *J. Bacteriol*, 184(1): 207-15 (2002)), phaD in *Pseudomonas putida* U (Olivera et al., *Proc Natl Acad Sci USA*, 95(11), 6419-24 (1998)), paaE in *Pseudomonas fluorescens* ST (Di Gennaro et al., *Arch Microbiol*, 188(2), 117-25 (2007)), and paaJ from *E. coli* (Nogales et al., Microbiology, 153(Pt 2), 357-65 (2007)) catalyze the conversion of 3-oxoadipyl-CoA into succinyl-CoA and acetyl-CoA during the degradation of aromatic compounds such as phenylacetate or styrene. To confirm that β-ketothiolase enzymes exhibit condensation activity, several thiolases (Table 10; SEQ ID NOS: 3-50, respectively) were cloned into a derivative of pZE13(Lutz et al., *Nucleic Acids Res*, 29(18), 3873-81 (2001)), which results in the clones having a carboxy-terminal 6×His tag (SEQ ID NO: 2).

TABLE 10

Cloned Thiolases

| Enzyme | Species template | Gene | Length | 5' PRIMER | 3' PRIMER | ORF SEQ |
|---|---|---|---|---|---|---|
| beta-ketothiolase | *Ralstonia eutropha* H16 | bktB | 1185 | ATGACGCGTG AAGTGGTAGT GGTAAG (SEQ ID NO: 3) | GATACGCTCGatgacgcgtgaagtggtagtggtaagcggtgtccgta AAGATGGCGGccgcgatcgggacctttggcggcagcctgaaggatgt (SEQ ID ggcaccggcggagctgggcgcactggtggtgcgcgag NO: 4) gcgctggcgcgcgcgcaggtgtcgggcgacgatgtcg | gccacgtggtattcggcaacgtgatccagaccgagcc gcgcgacatgtatctgggccgcgtcgcggccgtcaac ggcggggtgacgatcaacgccccccgcgctgaccgtga accgcctgtgcggctcgggcctgcaggccattgtcag cgccgcgcagaccatcctgctgggcgataccgacgtc gccatcggcggcggcgcggaaagcatgagccgcgcac cgtacctggcgccggcagcgcgctggggcgcacgcat gggcgacgccggcctggtcgacatgatgctgggtgcg ctgcacgatcccttccatcgcatccacatgggcgtga ccgccgagaatgtcgccaaggaatacgacatctcgcg cgcgcagcaggacgaggccgcgctggaatcgcaccgc cgcgcttcggcagcgatcaaggccggctacttcaagg accagatcgtcccggtggtgagcaagggccgcaagg cgacgtgaccttcgacaccgacgagcacgtgcgccat gacgccaccatcgacgacatgaccaagctcaggccgg tcttcgtcaaggaaaacggcacggtcacggccggcaa tgcctcgggcctgaacgacgccgccgccgccggtggtg atgatggagcgcgccgaagccgagcgccgcggcctga agccgctggcccgcctggtgtcgtacggccatgccgg cgtggacccgaaggccatgggcatcggcccggtgccg gcgacgaagatcgcgctggagcgcgccggcctgcagg tgtcggacctggacgtgatcgaagccaacgaagcctt tgccgcacaggcgtgcgccgtgaccaaggcgctcggt ctggacccggccaaggttaacccgaacggctcgggca tctcgctgggccacccgatcggcgccaccggtgccct gatcacggtgaaggcgctgcatgagctgaaccgcgtg cagggccgctacgcgctggtgacgatgtgcatcggcg gcgggcagggcattgccgccatcttcgagcgtatct ga (SEQ ID NO: 5) |
| 2-Methyl-acetoacetyl CoA Thiolase (branched chain?) | *Mus musculus* | ACAT1 | 1215 | ATGGAAGTAA GATGCCTGGA ACGAAG (SEQ ID NO: 6) | CAGCTTCTCAatggaagtaagatgcctggaacgaagttatgcatcc ATCAGCAGGGaaacccactttgaatgaagtggttatagtaagtgct C ataagaactcccattggatccttcctgggcagcctt (SEQ ID gcctctcagccggccactaaacttggtactgctgca NO: 7) attcagggagccattgagaaggcagggattccaaaa | gaagaagtgaaggaagtctacatgggcaatgtcatc caaggggtgaaggacaggcccctaccaggcaagca acactgggcgcaggtttacctatttccactccatgc accacagtaaacaaggtttgtgcttcaggaatgaaa gccatcatgatggcctctcaaagtcttatgtgtgga catcaggatgtgatggtggcaggcgggatggagagc atgtccaatgtcccatacgtaatgagcagaggagca acaccatatggtgggtaaaacttgaagacctgatt gtaaaagacgggctaactgatgtctacaataaaatt catatgggtaactgtgctgagaatactgcaaagaag atgaatatctcacggcaggaacaggatacgtacgct ctcagctcttacaccagaagtaaagaagcgtgggac |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | gcagggaagtttgccagtgagattactcccatcacc atctcagtgaaaggtaaaccagatgtggtggtgaaa gaagatgaagaatacaagcgtgttgactttagtaaa gtgccaaagctcaagaccgtgttccagaaagaaaat ggcacaataacagctgccaatgccagcacactgaac gatggagcagctgctctggttctcatgactgcagag gcagcccagaggctcaatgttaagccattggcacga attgcagcatttgctgatgctgccgtagaccccatt gattttccacttgcgcctgcatatgccgtacctaag gttcttaaatatgcaggactgaaaaaagaagacatt gccatgtgggaagtaaatgaagcattcagtgtggtt gtgctagccaacattaaaatgctggagattgacccc caaaaagtaaatatccacggaggagctgtttctctg ggccatccaattgggatgtctggagcccggattgtt gttcatatggctcatgccctgaagccaggagagttc ggtctggctagtatttgcaacggaggaggaggtgct tccgccctgctgattgagaagctgtag (SEQ ID NO: 8) |
| 2-Methyl-acetoacetyl-CoA Thiolase (branched chain?) | Pseudomonas putida (KT2440) | fadAx | 1194 | ATGACCCTCG CCAATGACCC TGG (SEQ ID NO: 9) | GTACAGGCAT TCAACAGCCA (SEQ ID NO: 10) | atgaccctcgccaatgaccccatcgttatcgtcagc gccgtgcgcacgcccatgggcgggttgcagggcgac ctcaagagcctgactgcgccgcaactgggcagcgcc gccattcgtgctgccgtggaacgggccggcatcgat gccgccggtgtcgagcaggtactgttcggctgcgtg ctgccggccggcaggcaccggcacgccag gccgcgctgggcgccgggctggacaagcacaccacc tgcaccaccctgaacaagatgtgcggctcgggtatg caagccgcgatcatggcccatgacctgctgctggcc ggcaccgcagacgtggtagtggcgggtggcatggaa agcatgaccaacgcgccgtacctgctggacaaagcc cgtggcggctaccgcatgggccacggcaagatcatc gaccacatgttcatggacggtctcgaagacgcctac gacaaaggccgcctgatgggtacctttgccgaggac tgtgcccaggccaatgccttcagccgcgaggcccag gaccagttcgccatcgcctcgctgacccgagcgcga gaagccatcagcagcggccgttttgccgccgagatc gtgccgctggaagtcaccgagggcaaggaaaagcgc gtcatcaaggatgacgagcagccgcccaaggcgcgt ctggacaagattgcgcagctcaaaccggcgtttcgt gaaggcggcaccgtgacggcggccaacgccagttcg atttccgacggcgctgcggcgctggtactgatgcgc cgctccgaggccgacaaacgtggcctcaagccattg gccgtcatccacggccacgccgcctttgccgacacc ccggcgctgttcccgaccgccccgatcggcgcgatc gacaaactgatgaaacgcaccggctggaacctggcc gaagtcgacctgttcgagatcaacgaggccttcgcc gtggtcaccctggcggccatgaaacacctcgacctg ccacacgacaaggtcaatatccacggcggcgcctgc gccctcggtcacccgatcggcgcttctggcgcacgt attctggtcaccctgttgtcggccttgcgccagaac aatctgcgtcggggtgtggcggccatctgcatcggc ggtggcgaggccacggccatggctgttgaatgcctg tactga (SEQ ID NO: 11) |
| beta-ketothiolase | Caenorhabditis elegans | kat-1 | 1167 | ATGAACAAAC ATGCTTTCATC GTCG (SEQ ID NO: 12) | TAATTTCTGG ATAACCATTC CACTTGAGC (SEQ ID NO: 13) | atgaacaaacatgctttcatcgtcggagccgcccgt gtaactgctccagagctcgcctcggttgccatcaaa gcagcattggagcgtggagcagtgaagccgagttca attcaggaggtgttccttggtcaagtctgtcaagca aatgctggtcaagctcccgctcgtcaagcagctctt ggagccggactcgatctttcggttgctgttaccacc gtcaataaagtgtgctcttctgggctgaaagcaatc attcttgctgcccagcaaattcaaaccggtcatcaa gattttgccattggcggaggaatggagagcatgtca caagtaccattttatgttcaaagaggagagatccca tatggtggatttcaagtgattgatggaatcgtcaaa gacggactgaccgatgcttatgataaagttcacatg ggaaactgcgagagaagacttcaaaagaaatggga attacacgtaaagaccaagacgaatatgctatcaac agctacaaaaagtcagctaaagcatgggagaatgga aatatcggaccagaagtggtgccagtgggaacgtcaaa tcaaagagggagtcacgattgttgataaagatgaa gagttcacaaaagtcaatttcgacaagttcacctcg ctgagaactgttttccagaaagacggaactatcact |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | gctgctaatgcttcaacattgaacgacggtgcagct gctgtcattgttgcctcacaggaagcagtttccgag caaagcttaaagcctctggcccgaattttggcttat ggagatgccgccacgcacccactcgatttcgctgta gcaccaactttgatgttcccaaaaattcttgaaaga gcaggagtgaagcaatcagatgttgctcaatgggaa gttaatgaagccttctcatgtgttcccttgctttc atcaaaaaactaggagtcgatcctcccttgtgaac ccacatggaggagctgtttcaattggtcacccatc ggaatgtccggagcccgcctcatcactcatcttgtg cacacactcaaaagtggccaaatcggagttgctgcc atttgcaatggaggtggtggctcaagtggaatggtt atccagaaattataa (SEQ ID NO: 14) |
| beta-ketothiolase NP_415915.1 | Escherichia coli | paaJ | 1206 | ATGCGTGAAG CCTTTATTTGT GACG (SEQ ID NO: 15) | AACACGTCCc atgcgtgaagcctttatttgtgacggaattcgtacg AGAATCATGG ccaattggtcgctacggcggggcattatcaagtgtt CG cgggctgatgatctggctgctatcccctttgcgggaa (SEQ ID ctgctggtgcgaaacccgcgtctcgatgcggagtgt NO: 16) atcgatgatgtgatcctcggctgtgctaatcaggcg ggagaagataaccgtaacgtagccggatggcgact ttactggcggggctgccgcagagtgtttccggcaca accattaaccgcttgtgtggttccgggctggacgca ctgggtttgccgcacgggcgattaaagcgggcgat ggcgatttgctgatcgccggtggcgtggagtcaatg tcacgggcaccgtttgttatgggcaaggcagccagt gcattttctcgtcaggctgagatgttcgataccact attggctggcgatttgtgaacccgctcatggctcag caatttggaactgacagcatgccggaaacggcagag aatgtagctgaactgttaaaaatctcacgagaagat caagatagttttgcgctacgcagtcagcaacgtacg gcaaaagcgcaatcctcaggcattctggctgaggag attgttccggttgtgttgaaaaacaagaaaggtgtt gtaacagaaatacaacatgatgagcatctgcgcccg gaaacgacgctggaacagttacgtgggttaaaagca ccatttcgtgccaatggggtgattaccgcaggcaat gcttccggggtgaatgacggagcgctgcgttgatt attgccagtgaacagatggcagcagcgcaaggactg acaccgcgggcgcgtatcgtagccatgcaaccgcc ggggtggaaccgcgcctgatgggcttggtccggtg cctgcaactcgccgggtgctggaacgcgcagggctg agtattcacgatatggacgtgattgaactgaacgaa gcgttcgcggcccaggcgttgggtgtactacgcgaa ttggggctgcctgatgatgccccacatgttaacccc aacggaggcgctatcgccttaggccatccgttggga atgagtggtgcccgcctggcactggctgccagccat gagctgcatcggcgtaacggtcgttacgcattgtgc accatgtgcatcggtgtcggtcagggcatcgccatg attctggagcgtgtttga (SEQ ID NO: 17) |
| beta-ketothiolase AAN68887.1 | Pseudomonas putida (KT2440) | phaD | 1221 | ATGAATGAAC CGACCCACGC C (SEQ ID NO: 18) | GAGGCGCTCG ATGATCATGG (SEQ ID NO: 19) | gatgaatgaaccgacccacgccgatgccttgatcatc gacgccgtgcgcacgccattggccgctatgccggg gccctgagcagcgtgcgcgccgacgacctggccggcc atcccgctcaaagccttgatccagcgtcaccccgaa ctggactggaaagccattgatgacgttatcttcggc tgtgccaaccaggctggcgaagacaaccgcaacgtg gcccacatggcgagcctgctggccgggctgccactc gaagtaccagggaccacgatcaaccgcctgtgcggt tccggtctggatgccatcggtaatgcggcacgtgcc ctgcgctgcggtgaagcggggctcatgctggccggt ggtgtggagtccatgtcgcgtgcaccgtttgtgatg ggtaagtcggagcaggcattcgggcgtgcggccgag ctgttcgacaccaccatcggctggcgtttcgtcaac ccgctgatgaaggccgcctacggcatcgattcgatg ccggaaacggctgaaaacgtggccgaacagttcggc atctcgcgcgccgaccaggatgcctttgccctgcgc agccagcacaaagccgcagcagctcaggccccgcggc cgcctggcgcggggaaatcgtgccggtcgaaatcccg caacgcaaaggcccagccaaagtggtcgagcatgac gagcacccgcgcggcgacacgaccctggagcagctg gctcggctcgggacgccgtttcgtgaaggcggcagc gtaacggcgggtaatgcctccgcgtgaatgacggc gcttgcgccctgctgctggccagcagcgccgcggcc cgccgccatgggttgaaggcccgcggccgcatcgtc |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | ggcatggcggtggccggggttgagcccaggctgatg<br>ggcattggtccggtgcctgcgacccgcaaggtgctg<br>gcgctcaccggcctggcactggctgacctggatgtc<br>atcgaactcaatgaggcctttgccgcccaagggctg<br>gccgtgttgcgcgagctgggcctggccgacgacgac<br>ccgcgagtcaaccgcaacggcggcgccatcgccctg<br>ggccatcccctgggcatgagcggtgcccggttggtg<br>accactgccttgcacgagcttgaagaaacggccggc<br>cgctacgccctgtgcaccatgtgcatcggcgtaggc<br>caaggcattgccatgatcatcgagcgcctctga<br>(SEQ ID NO: 20) |
| beta-<br>ketothiolase<br>NP_349476.1 | *Clostridium aceto-butylicum* ATCC 824 | thiA | 1179 | ATGAAAGAAG<br>TTGTAATAGCT<br>AGTGCAGTAA<br>GAAC<br>(SEQ ID<br>NO: 21) | GCACTTTTCTatgaaagaagttgtaatagctagtgcagtaagaaca<br>AGCAATATTGgcgattggatcttatggaaagtctcttaaggatgta<br>CTGTTCC<br>(SEQ ID<br>NO: 22) | ccagcagtagatttaggagctacagctataaaggaa<br>gcagttaaaaaagcaggaataaaaaccagaggatgtt<br>aatgaagtcattttaggaaatgttcttcaagcaggt<br>ttaggacagaatccagcaagacaggcatcttttaaa<br>gcaggattaccagttgaaattccagctatgactatt<br>aataaggtttgtggttcaggacttagaacagttagc<br>ttagcagcacaaattataaaagcaggagatgctgac<br>gtaataatagcaggtggtatggaaaatatgtctaga<br>gctccttacttagcgaataacgctagatggggatat<br>agaatgggaaacgctaaatttgttgatgaaatgatc<br>actgacggattgtgggatgcatttaatgattaccac<br>atgggaataacagcagaaaaacatagctgagagatgg<br>aacatttcaagagaagaacaagatgagtttgctctt<br>gcatcacaaaaaaagctgaagaagctataaaatca<br>ggtcaatttaaagatgaaatagttcctgtagtaatt<br>aaaggcagaaagggagaaactgtagttgatacagat<br>gagcaccctagatttggatcaactatagaaggactt<br>gcaaaattaaaacctgccttcaaaaaagatggaaca<br>gttacagctggtaatgcatcaggattaaatgactgt<br>gcagcagtacttgtaatcatgagtgcagaaaaagct<br>aaagagcttggagtaaaaccacttgctaagatagtt<br>tcttatggttcagcaggagttgacccagcaataatg<br>ggatatggacctttctatgcaacaaaagcagctatt<br>gaaaaagcaggttggacagttgatgaattagattta<br>atagaatcaaatgaagcttttgcagctcaaagttta<br>gcagtagcaaaagatttaaaatttgatatgaataaa<br>gtaaatgtaaatggaggagctattgcccttggtcat<br>ccaattggagcatcaggtgcaagaatactcgttact<br>cttgtacacgcaatgcaaaaaagagatgcaaaaaaa<br>ggcttagcaactttatgtataggtggcggacaagga<br>acagcaatattgctagaaaagtgctag<br>(SEQ ID NO: 23) |
| beta-<br>ketothiolase<br>NP_149242.1 | *Clostridium aceto-butylicum* ATCC 824 | thiB | 1179 | ATGAGAGATG<br>TAGTAATAGT<br>AAGTGCTGTA<br>AGAACTG<br>(SEQ ID<br>NO: 24) | GTCTCTTTCAatgagagatgtagtaatagtaagtgctgtaagaact<br>ACTACGAGAGgcaataggagcatatgaaaaacattaaaggatgta<br>CTGTTCCC<br>(SEQ ID<br>NO: 25) | cctgcaacagagttaggagctatagtaataaaggaa<br>gctgtaagaagagctaatatatatccaaatgagatt<br>aatgaagttattttggaaatgtacttcaagctgga<br>ttaggccaaaacccagcaagacaagcagcagtaaaa<br>gcaggattacctttagaaaacacctgcgtttacaatc<br>aataaggtttgtggttcaggtttaagatctataagt<br>ttagcagctcaaattataaaagctggagatgctgat<br>accattgtagtaggtggtatggaaaatatgtctaga<br>tcaccatatttgattaacaatcagagatgggggtcaa<br>agaatgggagatagtgaattagttgatgaaatgata<br>aaggatggttgtgggatgcatttaatggatatcat<br>atgggagtaactgcagaaaatattgcagaacaatgg<br>aatataacaagagaagagcaagatgaatttctcactt<br>atgtcacaacaaaaagctgaaaaagccattaaaaat<br>ggagaatttaaggatgaaatagttcctgtattaata<br>aagactaaaaaaggtgaaatagtctttgatcaagat<br>gaatttcctagattcggaaacactattgaagcatta<br>agaaaacttaaacctatttttcaaggaaaatggtact<br>gttacagcaggtaatgcatccgattaaatgatgga<br>gctgcagcactagtaataatgagcgctgataaagct<br>aacgctctcggaataaaaccacttgctaagattact<br>tcttacggatcatatgggggtagatccatcaataatg<br>ggatatggagcttttatgcaactaaagctgcctta<br>gataaaattaatttaaaacctgaagacttagttta<br>attgaagctaacgaggcatatgcttctcaaagtata<br>gcagtaactagagatttaaatttagatatgagtaaa |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | gttaatgttaatggtggagctatagcacttggacat ccaataggtgcatctggtgcacgtattttagtaaca ttactatacgctatgcaaaaaagagattcaaaaaaa ggtcttgctactctatgtattggtggaggtcaggg aacagctctcgtagttgaaagagactaa (SEQ ID NO: 26) |
| 3-oxoadipyl-CoA thiolase | *Candida albicans* SC5314 | POT9 | 81182 | ATGTTCAAGA AATCAGCTAA TGATATTGTTG (SEQ ID NO: 27) | CTCGTTAGCA AACAAGGCAG CG (SEQ ID NO: 28) | atgttcaagaaatcagctaatgatattgttgttat gtcagcaaagagaactccaatcaccaagtcaatta aaggtgggttgagtagattatttcctgaggaaata ttatatcaagtggttaagggtactgtatcagattc acaagttgatttaaacttgattgatgatgtgttag tcggtacggtcttgcaaactttaggggacagaaa gctagtgccttggccattaaaaagattggattccc aattaagaccacggttaatacggtcaatcgtcaat gtgctagttctgctcaagcgattacttatcaagca ggtagtttgcgtagtggggagaatcaatttgctat tgctgctggagtagaaagtatgactcatgattatt ttcctcatcgtgggattcccacaagaatttctgaa tcatttttagctgatgcatccgatgaagctaaaaa cgtcttgatgccaatggggataaccagtgaaaatg ttgccactaaatatggaatttctcgtaaacaacaa gatgagttgcccttaattctcatttgaaagcaga caaggctacaaaactgggtcattttgcaaaagaaa tcattcctattcaaacaacggatgaaaacaaccaa cacgtttcaataaccaaagatgatggtataagggg aagttcaacaattgaaaagtggggtggcttaaaac ctgtgttcaaggatgatgggactactactgctggt aattcctcgcaaatttcagatggagggtctgctgt gattttaactactcgtcaaaatgctgagaaatcgg gagtaaagccaatagctagatttattggttcgtca gtagctggtgttccttcgggacttatgggaattgg tccatcggctgctattcctcaattgttgtcgagat taaatgttgacacgaaagacattgatattttgaa ttgaacgaggcatttgcatcccaactgatttattg tattgaaaaattgggtcttgattatgataaagtca atccatatggtggagctatagccttgggacatcca ttaggagccactggcgcaagagttacggcaacgtt gcttaatggattaaaagatcagaataaagagttgg gtgtcatctcaatgtgcacatccacaggtcaagga tacgctgccttgtttgctaacgagtag (SEQ ID NO: 29) |
| 3-oxoadipyl-CoA thiolase | *Candida albicans* SC5314 | POT1 | 1227 | ATGGATAGAT TAAATCAATT AAGTGGTCAA TTAAAACC (SEQ ID NO: 30) | TTCCTTAATC AATATGGAGG CAGCAC (SEQ ID NO: 31) | atggatagattaaatcaattaagtggtcaattaaa aatatggaggaccaactcaaaacaatccctactcaaaagaacc cagacgatgttgtcatcgttgcagcatacagaact gccatcggtaaaggtttcaaagggtcttcaaatc tgtgcaatctgaattcatcttgactgaattcttga aagaatttattaaaaagactggagtcgatgcatct ttgattgaagatgttgctattggtaacgttttgaa ccaagctgctggtgccaccgaacacagaggtgcta gtttggctgcaggtattccttacactgcagctttc cttgccatcaacagattgtgttcctcagggttaat ggccatttctgacattgccaacaaaatcaaaaccg gtgaaatcgaatgtggtcttgctggtggtattgaa tccatgtctaaaaactatggtagtccaaaagttat tccaaagattgacccacacttggctgatgacgaac aaatgagtaaatgtttgattccaatgggtatcacc aacgaaaatgttgctaatgaattcaacattccaag agaaaaacaagatgcctttgctgctaaatcttata gtaaagccgaaaagccatctcctctggagctttc aaagatgaaatcttaccaatcagatccattatcag atccccagacggttctgaaaaagaaatcattgtcg ataccgacgaaggtccaagaaagggtgttgacgct gcttccttgagcaaattgaaaccagcatttggtgg tactaccactgccggtaacgcttctcaaatttcag atggtgctgctggtgttttattgatgaagagaagt ttggctgaagccaaaggttacccaattgttgctaa atacattgcttgttcaactgttggtgttccgcag aaatcatgggtgttggtccagcttacgccattcca gaagtgttgaagagaactggattgactgtggatga cgttgatgtgtttgaaatcaacgaagcttttgctg ctcaatgtctttactcagctgaacaatgtaatgtt ccagaagaaaaattgaacataaacggtggtgccat cgctttaggtcatcctcttggttgtactggtgcca |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | gacaatatgccactatcttgagattgttgaaacca ggtgaaattggtttgacttctatgtgtatcggtag tggtatgggtgctgcctccatattgattaaggaat ag (SEQ ID NO: 32) |
| 3-oxoadipyl- CoA thiolase | Candida albicans SC5314 | POT2 | 1233 | ATGTCATCCA ACAACAATA CTTGAAGAAG (SEQ ID NO: 33) | TTCTCTAACCatgtcatccaaacaacaatacttgaagaagaatc AAAACAGAAGctgacgatgtcgttgtcgttgcagcatacagaac CAGCACC (SEQ ID NO: 34) | tgctttaaccaaaggtggaagaggtggattcaaa gatgttggatctgatttcctttttgaaaaaattga ctgaagaatttgttaaaaaaactggtgttgaccc taaaatcattcaagatgctgccattggtaatgtc ttgaacagaagagctggtgatttcgaacatagag gtgcattattatctgctggattaccttattcagt tccatttgttgcccttaacagacaatgttcatct gggttaatggccatttctcaagtggccaacaaga tcaagactggtgaaattgaatgtggtttagctgg tggtgttgaaagtatgacaaaaaactatggtcca gaagcattgattgctattgaccctgcttatgaaa aagacccagaatttgttaaaaacggtattccaat gggtattactaatgaaaatgtttgtgccaaattc aatatttcaagagatgttcaagatcaatttgctg ctgaatcttatcaaaaagctgaaaaggcacaaaa agaaggtaaatttgatgatgaaattttaccaatt gaagttttccaagaagatgaagatgctgaagatg aagacgaagatgaagatgaagatgctgaaccaaa agaaaaattggttgttattagtaaagatgaaggt attagaccaggtgttactaaagaaaaattggcta aaattaaaccagctttcaaatctgatggtatc ttcagctggtaactcttcacaagtttccgatggt gctgccttggtgttattgatgaaacgttcatttg ctgaaaagaatggattcaaaccattggctaaata catttcttgtggtgttgctggtgtcccaccagaa attatgggtattggtccagctgttgccattccaa aagtttttgaaacaaactggattatcagtcagtga tattgatatttatgaaatcaatgaagcatttgcc ggtcaatgtttgtactcaattgaaagttgtaata ttccaagagaaaaagtcaatcttaatgggggtgc tattgccttgggtcaccctcttggttgtactggt gctagacaatacgctactattttaagattgttaa aaccaggtgaatttggtgtgacttctatgtgtat tggtactggtatgggtgctgcttctgttttggtt agagaataa (SEQ ID NO: 35) |
| beta- ketoadipyl CoA thiolase pcaF | Pseudomonas aeruginosa PA01 | pcaF | 1206 | ATGAGCCGCG AGGTATTCAT CTG (SEQ ID NO: 36) | GACCCGCTCGatgagccgcgaggtattcatctgcgatgccgtgc ATGGCCAG gcacgccgatcggccgtttcggcggcagtctttc (SEQ ID cgcggtgcgcgccgacgacctcgcggcggtgccg NO: 37) ctgaaggccctggtcgagcgcaacccggggtcg | actggtcggcgttggacgaggtgttcctcggctg cgccaaccaggccggcgaggacaaccgtaacgtg gcgcgcatggcgctgctgctggccggtttgccgg agagcgtgcccggcgtcaccctcaaccgcctctg cgcctcggggatggacgccatcggcacggcgttc cgcgccatcgcctgcggcgagatggagctggcca tcgccggcggcgtcgagtcgatgtcgcgcgcgcc gtacgtgatgggcaaggccgatagcgccttcggt cgcggccagaagatcgaggacaccaccatcggct ggcgcttcgtcaatccgctgatgaaggagcagta cggcatcgacccgatgccgcagaccgccgacaac gtcgccgacgactatcgcgtgtcgcgtgccgacc aggatgccttcgccctgcgcagccagcagcgcgc cggcagggcgcaggaggccggttttcttcgccgag gaaatcgtcccggtgacgattcgcgggcgcaagg gcgacacctggtcgagcacgacgagcatccgcg tcccgacaccaccctggaggcgctggcccggctc aagccggtcaacgggccggagaagaccgtcaccg ccggcaacgcgtccgggtcaacgacggcgccgc cgcgctggtcctggcctcgccgaggcagtggag aagcacggcctgactccgcgcgcgcgggtgctgg gcatggccagcgccggcgtcgccccacggatcat gggcatcggcccggtgccggcggtgcgcaagctg ctgcggcgcctggacctggcgatcgacgccttcg acgtgatcgaactcaacgaagccttcgccagcca gggcctggcctgcctgcgcgaactgggcgtggcc |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | gacgacagtgagaaggtcaacccgaacggcggtg ccatcgccctcggccacccgctggggatgagcgg tgcgcggctggtcctcaccgcgctccatcaactt gagaagagcggcggccggcgcggcctggcgacca tgtgcgtaggcgtcggccaaggcctggcgctggc catcgagcgggtctga (SEQ ID NO: 38) |
| acyl-CoA thiolase | *Pseudomonas aeruginosa* PA01 | bkt | 1206 | ATGCTCGATG CCTATATCTAC GCC (SEQ ID NO: 39) | TCGGCAGCG TCGATCAC (SEQ ID NO: 40) | atgctcgatgcctatatctacgccggcctgcgta cgcctttcggccggcatgccggtgcactctcgac ggtgcgtccggacgacctggccggcctgctgctg gcgcgtctcgcggaaacctcccgggttcgccgtcg acgacctggaggatgtgatcctcggttgcaccaa ccaggccggcgaagacagccgcaacctggcgcgc aacgcgctgctcgcagccggcctgccggcgcggc tgcccggggcagacggtcaaccgcttgtgtgccag cggactgtcggcggtgatcgacgcggcgcgcgcg atcagttgcggtgagggccggctgtacctggccg gcggcgccgaaagcatgtcccgggcgccgttcgt catgggcaaggcggagagcgccttcagccgcacg ctggaggtcttcgacagcaccatcggcgcgcgct tcgccaaccccaggctggtcgagcgctatggcaa cgacagcatgccggagaccggcgacaacgtggcc cgcgccttcggcatcgcccgcgaagacgccgacc gtttcgccgcttcttcccaggcgcgctaccaggc tgcgctggaggagggcttttttcctcggcgagatc cttccggtggaggtcgctgccggacgcaagggcg agacgcggctggtggagcgcgacgagcatccgcg accgcaggccgacctggcggcccctggcgcgcttg ccggcgttgttcgccggtggggtagtgaccgccg gtaatgcgtctgggatcaacgacggggcggcgt agtgctgctgggcgatcgcgcgatcggcgagcgc gagggcatccggccgttggcgcggatcctcgcca gcgccagcgtcggcgtcgagccccggttgatggg catcggcccgcagcaggcgatcctccgcgcgctg caacgcgccggcatcgacctggacgaggtcggcc tgatcgagatcaacgaagccttcgcgccgcaggt cctggcctgcctgaagttgctcggcctggactac gaggacccgcgggtcaatccccatggcggcgcca ttgccctcggccatccgctcggcgcctccggtgc gcgcctggtgctcaccgccgcccgcgggctgcaa cgcatcgagcggcgctacgcggtggtcagcctgt gcgtcgggctcggccagggcgtggcgatggtgat cgagcgctgccgatga (SEQ ID NO: 41) |
| 3-oxoadipyl-CoA thiolase | *Pseudomonas putida* (KT2440) | pcaF | 1203 | ATGCACGACG TATTCATCTGT GACG (SEQ ID NO: 42) | AACCCGCTCG ATGGCCAAC (SEQ ID NO: 43) | atgcacgacgtattcatctgtgacgccatccgta ccccgatcggccgcttcggcggcgccctggccag cgtgcgggccgacgacctggccgcgtgccgctg aaggcgctgatcgagcgcaaccctggcgtgcagt gggaccaggtagacgaagtgttcttcggctgcgc caaccaggccggtgaagacaaccgcaacgtggcc cgcatggcactgctgctggccggcctgccggaaa gcatcccgggcgtcaccctgaacgtctctgtgcgc gtcgggcatggatgccgtcggcaccgcgttccgc gccatcgccagcggcgagatggagctggtgattg ccggtggcgtcgagtcgatgtcgcgcgcccgtt cgtcatgggcaaggctgaaagcgcctattcgcgc aacatgaagctggaagacaccaccattggctggc gtttcatcaacccgctgatgaagagccagtacgg tgtggattccatgccggaaaccgccgacaacgtg gccgacgactatcaggtttcgcgtgctgatcagg acgctttcgccctgcgcagccagcagaaggctgc cgctcgcgaggctgccggcttctttgccgaagaa atcgtgccggtgcgtatcgctcacaagaagggcg aaatcatcgtcgaacgtgacgaacacctgcgccc ggaaaccacgctggaggcgctgaccaagctcaaa ccggtcaacggcccggacaagacggtcaccgccg gcaacgcctcgggcgtgaacgacggtgctgcggc gatgatcctggcctcggccgcagcggtgaagaaa cacgcctgactccgcgtgcccgcgttctgggca tggccagcggcggcgttgcgccacgtgtcatggg cattggcccggtgccggcggtgcgcaaactgacc gagcgtctggggatagcggtaagtgatttcgacg tgatcgagcttaacgaagcgttgccagccaaggc |

TABLE 10-continued

Cloned Thiolases

| Enzyme | Species template | Gene | Length | 5' PRIMER | 3' PRIMER | ORF SEQ |
|---|---|---|---|---|---|---|
| | | | | | | ctggcggtgctgcgtgagctgggtgtggctgacg atgcgccccaggtaaaccctaatggcggtgccat tgccctgggccaccccctgggcatgagcggtgca cgcctggtactgactgcgttgcaccagctggaga agagtggcggtcgcaagggcctggcgaccatgtg tgtgggtgtcggccaaggtctggcgttggccatc gagcgggtttga (SEQ ID NO: 44) |
| 3-oxoadipyl-CoA thiolase | Burkholderia ambifaria AMMD | bkt | 1203 | ATGACCGACG CCTACATCTGC G (SEQ ID NO: 45) | CACGCGTTCG ATCGCGATC (SEQ ID NO: 46) | atgaccgacgcctacatctgcgatgcgattcgca cacccatcggccgctacggcggcgccctgaaaga cgttcgtgccgacgatctcggcgcggtgccgctc aaggcgctgatcgaacgcaaccggaacgtcgact ggtcggcgatcgacgacgtgatctatggctgcgc gaaccaggccggcgaagacaaccgcaacgtcgcg cgcatgtccgcgctgctcgcgggcttgccgaccg ccgtgccgggcacgacgctgaaccggttatgcgg ctcgggcatggacgccgtcggcacggccgcgcgc gcgatcaaggcgggcgaggcacgcttgatgatcg cgggcggcgtcgaaagcatgacgcgcgcgcgtt cgtgatgggcaaggccgccagcgcattcgcgcgc caggctgcgattttcgacacgacgatcggctggc gtttcattaatccgctgatgaaacagcaatacgg cgtcgattcgatgcccgagacggccgagaacgtc gcggtcgactacaacatcagccgcgcgccgaccagg atctattcgcgctgcgcagccagcagaaggccgc gcgtgcgcagcaggacggcacgctcgccgccgaa atcgtccccgtcacggattgcgcagaaaaaaggcg acgcgctcgtcgtatcgctcgacgagcatccgcg cgaaacatcgctcgaagcgctcgcgaagctgaag ggcgtcgtgcgtcccgacggctcggtcacggccg gcaacgcgtcaggcgtcaacgacggcgcatgcgc actgctgctcgccaacgcggaagccgccgatcaa tatgggctgcgccgccgcgcgcgtgtcgtcggca tggcgagcgccggcgtcgagccgcgcgtgatggg tatcggccgcgccggccacgcagaaactgttg cgccagctcggcatgacgatcgaccagttcgacg tgatcgagctgaacgaagcgttcgcgtcgcaggg tctcgcggtgctgcgcatgctcggtgtcgccgac gacgatccgcgcgtgaaccccaacggcggtgcga tcgcgctcggccatccgctcggcgcatcgggtgc gcggctcgtgaccacggcgcttcaccaactcgag cgtacgggcggccgctttgcgctctgtacgatgt gcatcggcgtcggccagggcatcgcgatcgcgat cgaacgcgtgtaa (SEQ ID NO: 47) |
| beta-ketothiolase | Ascaris suum | bkt | 1242 | ATGGCCACCT CAAGACTTGT CTGC (SEQ ID NO: 48) | CAATTTCTCG ATGACCATTC CACC (SEQ ID NO: 49) | gtgatggccacctcaagacttgtctgcagcaatt taacgaagcaatgctttacgatctcgtcacgtgc tgctagccaatttaccgatgtggtattcgtgggt gccgcacgaacaccggtcggatcgtttcgctctt cgcttttccactgttccagccactgtcctcggagc tgaggctattaagggtgcacttaaacatgccaat ctaaaaccctcacaagtgcaagaggtgttctttg gctgtgtcgttccatccaactgtggacaagttcc tgcccgtcaagcgacacttggagctggatgcgat ccttcgacaatcgttacaactctcaataaattgt gcgcctcgggaatgaagtcgattgcttgtgccgc ctcacttttgcaacttggtcttcaagaggttacc gttggtggcggtatggagagcatgagcttagtgc cgtactatcttgaacgtggtgaaactacttatgg tggaatgaagctcatcgacggtatcccaagagat ggtccgactgatgcatatagtaatcaacttatgg gtgcatgcgctgataatgtggctaaacgattcaa catcacccgtgaggaacaggataaattcgctatt gaaagctataaacgatctgctgctgcatgggaga gtggagcatgcaaagctgaagtagttcctattga agtgacaaagggcaagaaaacatacattgtcaac aaggatgaggaatacatcaaagtcaacttcgaga agcttcccaaactgaaaccgccttcttgaaaga cggaaccatcacggctggcaatgcttcaacactg aacgatggtgctgcggcagttgtgatgacgactg tcgaaggagcgaaaaaatacggtgtgaaaccatt ggcccgattgctctcatatggtgatgcggcaaca aatccagtcgattttgctattgcaccatcaatgg |

TABLE 10-continued

Cloned Thiolases

| Enzyme | Species template | Gene Length | 5' PRIMER | 3' PRIMER | ORF SEQ |
|---|---|---|---|---|---|
| | | | | | ttatcccaaaggtacttaaattggctaatctcga gatcaaggatattgatttgtgggaaatcaacgag gctttcgccgttgttcccttcattcaatgaaga cactcggtatcgatcactcgaaagtgaacattca tggtggtggcgtatctcttggacatcctattgga atgtctggagctcgaattatcgttcatctgattc atgcgttgaaacctggccagaaaggctgcgctgc aatctgcaatggtggcggtggcgctggtggaatg gtcatcgagaaattgtaa (SEQ ID NO: 50) |

Figure 19:
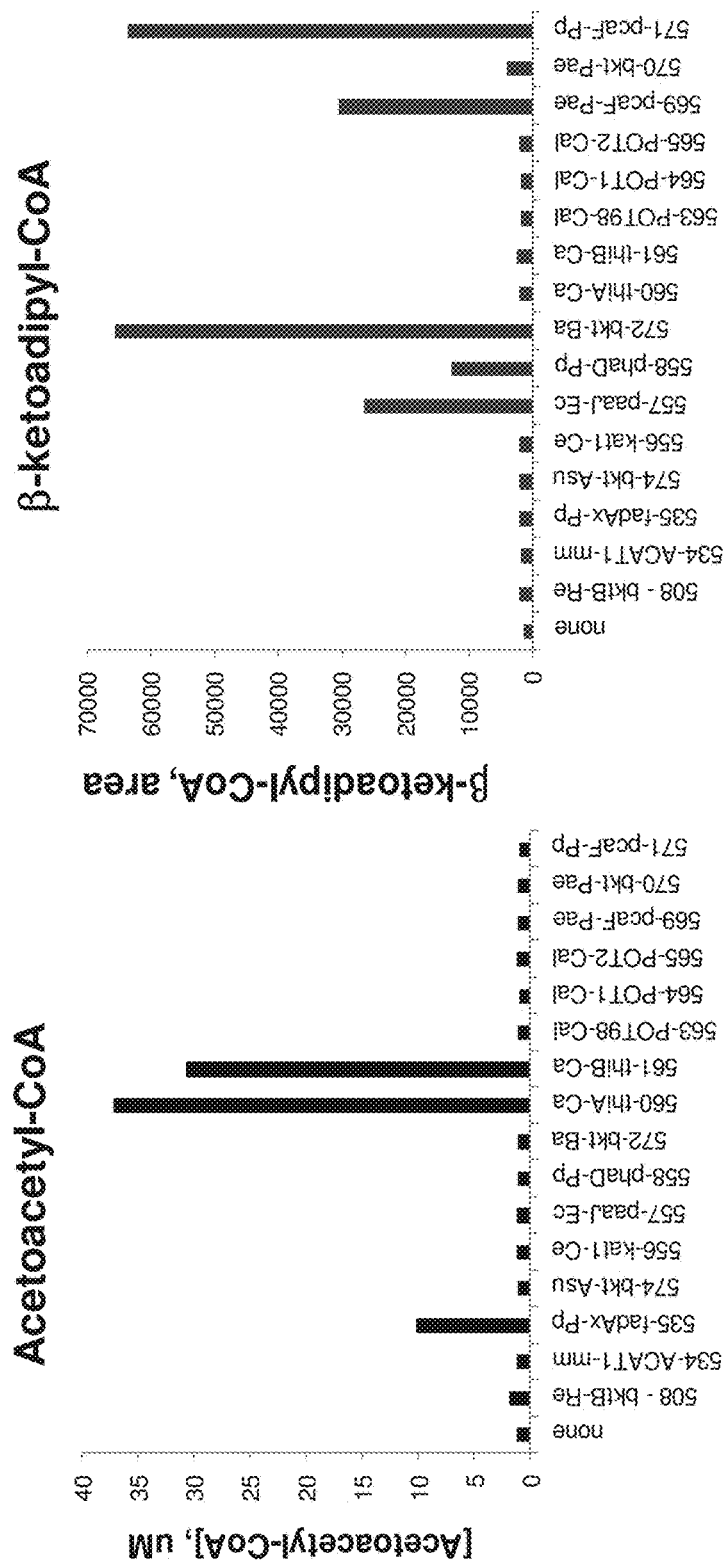
FIG. 19 shows LC/MS analysis of in vitro thiolase reactions. Succinyl-CoA and acetyl-CoA were added to His-tagged, purified thiolases at a ratio of 2:1 (succinyl-CoA: acetyl-CoA). Reactions were analyzed by LC/MS and quantified by comparison to a standard for acetoacetyl-CoA or peak area determined for 3-oxoadipyl-CoA (β-ketoadipyl-CoA).

The genes were expressed in E. coli and the proteins purified using Ni-NTA spin columns and quantified. To assay enzyme activity in vitro, a 5× CoA:DTNB (Ellman's reagent or 5, 5'-dithiobis-(2-nitrobenzoic acid)) mixture was prepared. The mixture consisted of 10 mM succinyl-CoA, 5 mM acetyl-CoA, 30 mM DTNB in 100 mM Tris buffer, pH 7.4. Five µL of the CoA:DTNB mixture was added to 0.5 µM purified thiolase enzyme in 100 mM Tris buffer, pH 7.8 in a final volume of 50 µL. The reaction was incubated at 30° C. for 30 minutes, then quenched with 2.5 µl, 10% formic acid and samples frozen at −20° C. until ready for analysis by LC/MS. Because many thiolases can condense two acetyl-CoA molecules into acetoaceytl-CoA, production of acetoacetyl-CoA was examined. FIG. 19 shows that 3 thiolases demonstrated thiolase activity which resulted in acetoacetyl-CoA formation. These were fadAx from Pseudomonas putida, thiA from Clostridium acetobutylicum and thiB also from Clostridium acetobutylicum. When enzyme assays were examined for condensation of succinyl-CoA and acetyl-CoA into β-ketoadipyl-CoA, several candidates demonstrated the desired activity; paaJ from Escherichia coli (Nogales et al., Microbiol. 153:357-365 (2007)), phaD from Pseudomonas putida (Olivera et al., Proc. Natl. Acad. Sci. USA 95:6419-6424 (1998)), bkt from Burkholderia ambifaria AMMD, pcaF from Pseudomonas putida KT2440 (Harwood et al., J. Bacteriol. 176:6479-6488 (1994)), and pcaF from Pseudomonas aeruginosa PAO1. There was excellent specificity between the thiolases. Those that generated significant amounts of β-ketoadipyl-CoA did not produce significant amounts of acetoacetyl-CoA and likewise those that made acetoacetyl-CoA did not make detectable amounts of β-ketoadipyl-CoA.

Example XXIV

Pathways for Production of Hexamethylenediamine from Glutamate, Glutaryl-CoA or Pyruvate and 4-Aminobutanal This example describes exemplary pathways for production of hexamethylenediamine (HMDA) from glutamate, glutaryl-CoA, pyruvate and 4-aminobutanal, or 2-amino-7-oxosubarate through homolysine, the seven-carbon analog of lysine. Homolysine is an attractive precursor to HMDA. Although homolysine is a potentially valuable precursor, it is not a known metabolic intermediate of any organism. Homolysine can be formed biocatalytically from the central metabolic precursors glutamate, glutaryl-CoA or pyruvate and 4-aminobutanal. Subsequent decarboxylation of homolysine by an enzyme analogous to lysine decarboxylase yields HMDA.

This example describes additional pathways that proceed from 2-amino-7-oxosubarate, or pyruvate and 4-aminobutanal through the intermediate 6-aminohexanal. 6-Aminohexanal can readily be converted to HMDA by an aminotransferase or an aminating oxidoreductase.

The maximum theoretical yield of HMDA is 0.71 moles per mole glucose utilized (0.46 g/g). The pathways disclosed in FIGS. 20-22 and 26 achieve a maximum HMDA yield of 0.67 mol/mol (0.43 g/g).

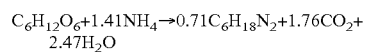

$$C_6H_{12}O_6 + 1.41NH_4 \rightarrow 0.71C_6H_{18}N_2 + 1.76CO_2 + 2.47H_2O$$

Novel pathways for producing hexamethylenediamine (HMDA) and related products are described herein. The candidate enzymes, and associated risks of implementation are discussed in Example XXVI below.

This invention is directed, in part, to non-naturally occurring microorganisms that express genes encoding enzymes that catalyze HMDA production. Successfully engineering these pathways entails identifying an appropriate set of enzymes with sufficient activity and specificity, cloning their corresponding genes into a production host, optimizing the expression of these genes in the production host, optimizing fermentation conditions, and assaying for product formation following fermentation.

HMDA can be produced from glutamate via glutaryl-CoA in eight enzymatic steps, shown in FIG. 20. In this route, glutamate is acylated to glutamyl-CoA by a CoA transferase or ligase (Step A of FIG. 20). Glutamyl-CoA and acetyl-CoA are joined by a beta-ketothiolase to form the C7 compound 3-oxo-6-aminopimeloyl-CoA (Step B of FIG. 20). The 3-oxo group of this product is then reduced and dehydrated, resulting in 6-amino-7-carboxyhept-2-enoyl-CoA (Steps C and D of FIG. 20). An enoyl-CoA reductase reduces the double bond, forming 6-aminopimeloyl-CoA (Step E of FIG. 20). 6-Aminopimeloyl-CoA is then converted to 2-amino-7-oxoheptanoate by a CoA-dependent aldehyde dehydrogenase (Step F). Transamination of the aldehyde to an amine yields homolysine (Step G of FIG. 20). Finally, HMDA is formed as the decarboxylation product of homolysine (Step H of FIG. 20). The maximum theoretical HMDA yield for this pathway is 0.67 moles of HMDA per mole of glucose utilized. Yield calculations assume aerobic conditions and the utilization of a CoA transferase in Step A.

HMDA can also be produced from glutaryl-CoA by several routes. Exemplary routes for HMDA production are shown in FIG. 21. Glutaryl-CoA is a common metabolic intermediate in organisms that metabolize aromatic compounds. In the disclosed pathways to HMDA, glutaryl-CoA is first condensed with acetyl-CoA by a beta-ketothiolase to form 3-oxopimeloyl-CoA (Step A of FIG. 21). The CoA moiety of 3-oxopimeloyl-CoA is removed by a CoA hydrolase, transferase and ligase (Step B of FIG. 21). Several alternate routes for converting 3-oxopimelate to HMDA are outlined in FIG. 21 and described herein. The final step of all routes to HMDA entails decarboxylation of homolysine (Step S of FIG. 21).

One route entails conversion of 3-oxopimelate to 3-oxo-1-carboxyheptanal. This conversion can be catalyzed by an ATP- and NAD(P)H dependent enzyme with 3-oxopimelate reductase activity (Step C of FIG. 21), or alternately can proceed through activated intermediates 5-oxopimeloyl-CoA (Steps H, I of FIG. 21) or 5-oxopimeloyl-phosphonate (Steps F, G of FIG. 21). Once formed, 3-oxo-1-carboxyheptanal is transaminated at the 3-position (Step AB of FIG. 21) or 7-position (Step D of FIG. 21). Subsequent transamination of 3-oxo-7-aminoheptanoate (Step E of FIG. 21) or 3-amino-7-oxoheptanoate (Step Z of FIG. 21) yields 3,7-diaminoheptanoate. An enzyme with 3,7-diaminoheptanoate 2,3-aminomutase activity then forms homolysine (Step R of FIG. 21), which is decarboxylated to HMDA (Step S of FIG. 21).

In an alternate route, 3-oxopimelate is transaminated to 3-aminopimelate (Step J of FIG. 21). 3-Aminopimelate is then converted to 3-amino-7-oxoheptanoate directly (Step O of FIG. 21) or via a CoA (Steps K, L of FIG. 21) or phosphonic acid (Steps M, N of FIG. 21) intermediate. 3-Amino-7-oxoheptanoate is subsequently converted to 2-amino-7-oxoheptanoate by a 2,3-aminomutase (Step P of FIG. 21). 2-Amino-7-oxoheptanoate is converted to homolysine by an aminotransferase or aminating oxidoreductase. Alternately, 3-amino-7-oxoheptanoate is first transaminated (Step Z of FIG. 21) and then converted to homolysine by an aminomutase (Step R of FIG. 21).

3-Aminopimelate can be converted to 2-aminopimelate by a 2,3-aminomutase enzyme (Step T of FIG. 21). An HMDA pathway involving this intermediate requires reduction of the 7-carboxylic acid to an aldehyde. This reduction is catalyzed by a bifunctional reductase (Step W of FIG. 21) or by two enzymes that proceed through a CoA (Steps V, Y of FIG. 21) or phosphonic acid (Steps U, X of FIG. 21) intermediate. The product, 2-amino-7-oxoheptanoate is converted to HMDA as described above.

Two routes for producing HMDA from pyruvate and 4-aminobutanal are shown in FIG. 22. The routes achieve a maximum yield of 0.67 moles of HMDA per mole glucose utilized (0.43 g/g) under anaerobic and aerobic conditions. 4-Aminobutanal is naturally derived from ornithine by decarboxylation to putrescine and subsequent transamination. 4-Aminobutanal can also originate from 4-aminobutanoate. In one pathway, 4-aminobutanal and pyruvate are joined by aldol condensation to form 2-oxo-4-hydroxy-7-aminoheptanoate (Step A of FIG. 22). The condensation product is subsequently dehydrated (Step B of FIG. 22) and reduced (Step C of FIG. 22). Transamination of 2-oxo-7-aminoheptanoate yields homolysine (Step D of FIG. 22). HMDA is the decarboxylation product of homolysine decarboxylase (Step E of FIG. 22). Alternately, pathway intermediate 2-oxo-7-aminoheptanoate is decarboxylated to form 6-aminohexanal (Step F of FIG. 22). 6-Aminohexanal is subsequently converted to HMDA by an aminotransferase or aminating oxidoreductase (Step G of FIG. 22).

Several routes for producing HMDA from 2-amino-7-oxosubarate are shown in FIG. 26. 2-Amino-7-oxosubarate is not known to be a naturally occurring metabolite. An exemplary route for synthesizing 2-amino-7-oxosubarate is shown in FIG. 27. The pathway originates with glutamate-5-semialdehyde, a metabolite naturally formed during ornithine biosynthesis. 2-Amino-7-oxosubarate is then synthesized in three enzymatic steps. In the first step, glutamate-5-semialdehyde is condensed with pyruvate by an aldolase (FIG. 27, Step A). The product, 2-amino-5-hydroxy-7-oxosubarate is subsequently dehydrated and the resulting alkene is reduced to form 2-amino-7-oxosubarate (FIG. 27, Steps B/C). In one proposed pathway to HMDA from 2-amino-7-oxosubarate, the 2-oxo acid is first decarboxylated to form 2-amino-7-oxoheptanoate (Step A of FIG. 26). This product is again decarboxylated, forming 6-aminohexanal (Step B of FIG. 26). Finally, 6-aminohexanal is converted to HMDA by an aminotransferase or aminating oxidoreductase (Step C of FIG. 26).

Alternately, the intermediate 2-amino-7-oxoheptanoate is first converted to homolysine by an aminotransferase or aminating oxidoreductase (Step M of FIG. 26). Homolysine is decarboxylated to HMDA as described previously (Step H of FIG. 26).

In yet another route, the 2-amino acid group of 2-amino-7-oxosubarate is decarboxylated, yielding 2-oxo-7-aminoheptanoate (Step I of FIG. 26). This product can then be further decarboxylated to 6-aminohexanal (Step G of FIG. 26) or transaminated to homolysine (Step J of FIG. 26). Homolysine or 6-aminohexanal is then converted to HMDA as described previously.

In yet another route, the 2-oxo group of 2-amino-7-oxosubarate is converted to an amino group, forming 2,7-diaminosubarate (Step K of FIG. 26). Two subsequent decarboxylations yield HMDA (Steps L, H of FIG. 26).

Described herein is the generation of a microbial organism that has been engineered to produce HMDA from pyruvate and 4-aminobutanal, as shown in FIG. 22 (Steps A-E). This example also teaches a method for engineering a strain that overproduces HMDA.

*Escherichia coli* is used as a target organism to engineer a HMDA-producing pathway as shown in FIG. 22. *E. coli* provides a good host for generating a non-naturally occurring microorganism capable of producing HMDA. *E. coli* is amenable to genetic manipulation and is known to be capable of producing various products, like ethanol, acetic acid, formic acid, lactic acid, and succinic acid, effectively under anaerobic, microaerobic or aerobic conditions.

An *E. coli* strain is engineered to produce HMDA from 4-aminobutanal via the route outlined in FIG. 22. For the first stage of pathway construction, genes encoding enzymes to transform 4-aminobutanal and pyruvate to homolysine (FIG. 3, Steps A-D) are assembled onto vectors. In particular, the genes hpcH (CAA87759), hpcG (CAA57202), enr (YP_430895) and lysN ( ) genes encoding 2-oxo-4-hydroxy-7-aminoheptanoate aldolase, 2-oxo-4-hydroxy-7-aminoheptanoate dehydratase, 2-oxo-7-aminohept-3-enoate reductase and 2-oxo-7-aminoheptanoate aminotransferase, respectively, are cloned into the pZE13 vector (Expressys, Ruelzheim, Germany), under the control of the PA1/lacO promoter. The plasmid is transformed into *E. coli* strain MG1655 to express the proteins and enzymes required for HMDA synthesis from 4-aminobutanal. *E. coli* naturally encodes two lysine decarboxylase enzymes which convert homolysine to HMDA.

The resulting genetically engineered organism is cultured in glucose containing medium following procedures well known in the art (see, for example, Sambrook et al., supra, 2001). The expression of HMDA pathway genes is corroborated using methods well known in the art for determining polypeptide expression or enzymatic activity, including for example, Northern blots, PCR amplification of mRNA and immunoblotting. Enzymatic activities of the expressed enzymes are confirmed using assays specific for the individually activities. The ability of the engineered E. coli strain to produce HMDA through this pathway is confirmed using HPLC, gas chromatography-mass spectrometry (GCMS) or liquid chromatography-mass spectrometry (LCMS).

Microbial strains engineered to have a functional HMDA synthesis pathway from 4-aminobutanal are further augmented by optimization for efficient utilization of the pathway. Briefly, the engineered strain is assessed to determine whether any of the exogenous genes are expressed at a rate limiting level. Expression is increased for any enzymes expressed at low levels that can limit the flux through the pathway by, for example, introduction of additional gene copy numbers.

After successful demonstration of enhanced HMDA production via the activities of the exogenous enzymes, the genes encoding these enzymes are inserted into the chromosome of a wild type E. coli host using methods known in the art. Such methods include, for example, sequential single crossover (Gay et al., J. Bacteriol. 3:153 (1983)). and Red/ET methods from GeneBridges (Zhang et al., European Patent Application No. 01117 (2001))). Chromosomal insertion provides several advantages over a plasmid-based system, including greater stability and the ability to co-localize expression of pathway genes.

To generate better producers, metabolic modeling is utilized to optimize growth conditions. Modeling is also used to design gene knockouts that additionally optimize utilization of the pathway (see, for example, U.S. patent publications US 2002/0012939, US 2003/0224363, US 2004/0029149, US 2004/0072723, US 2003/0059792, US 2002/0168654 and US 2004/0009466, and in U.S. Pat. No. 7,127,379). Modeling analysis allows reliable predictions of the effects on cell growth of shifting the metabolism towards more efficient production of HMDA. One modeling method is the bilevel optimization approach, OptKnock (Burgard et al., Biotechnol. Bioengineer. 84:647-657 (2003)), which is applied to select gene knockouts that collectively result in better production of HMDA. Adaptive evolution also can be used to generate better producers of, for example, the 2-oxo-4-hydroxy-7-aminoheptanoate intermediate or the HMDA product. Adaptive evolution is performed to improve both growth and production characteristics (Fong and Palsson, Nat. Genet. 36:1056-1058 (2004); Alper et al., Science 314:1565-1568 (2006)). Based on the results, subsequent rounds of modeling, genetic engineering and adaptive evolution can be applied to the HMDA producer to further increase production.

For large-scale production of HMDA, the above HMDA pathway-containing organism is cultured in a fermenter using a medium known in the art to support growth of the organism under anaerobic conditions. Fermentations are performed in either a batch, fed-batch or continuous manner. Anaerobic conditions are maintained by first sparging the medium with nitrogen and then sealing culture vessel (e.g., flasks can be sealed with a septum and crimp-cap). Microaerobic conditions also can be utilized by providing a small hole for limited aeration. The pH of the medium is maintained at a pH of 7 by addition of an acid, such as $H_2SO_4$. The growth rate is determined by measuring optical density using a spectrophotometer (600 nm), and the glucose uptake rate by monitoring carbon source depletion over time. Byproducts such as undesirable alcohols, organic acids, and residual glucose can be quantified by HPLC (Shimadzu) with an HPX-087 column (BioRad), using a refractive index detector for glucose and alcohols, and a UV detector for organic acids, Lin et al., Biotechnol. Bioeng., 775-779 (2005).

Example XXV

Pathways for Production of 6-Aminocaproate from Glutamate, Glutaryl-CoA, Homolysine, or 2-Amino-7-oxosubarate Novel pathways for producing 6-aminocaproate (6-ACA) and related products are described herein. The candidate enzymes, and associated risks of implementation are discussed in Example XXVI below.

This invention is directed, in part, to non-naturally occurring microorganisms that express genes encoding enzymes that catalyze 6-ACA production. Successfully engineering these pathways entails identifying an appropriate set of enzymes with sufficient activity and specificity, cloning their corresponding genes into a production host, optimizing the expression of these genes in the production host, optimizing fermentation conditions, and assaying for product formation following fermentation.

6-ACA can be produced from glutamate as a starting molecule. Glutamate is transformed to 6-aminopimeloyl-CoA as described previously (FIG. 20, Steps A-E). Removal of the CoA moiety of 6-Aminopimeloyl-CoA by a CoA hydrolase, transferase or ligase yields 2-aminopimelate (Step I of FIG. 20). Decarboxylation of this product yields 6-ACA (Step J of FIG. 20).

6-ACA can also be produced from glutaryl-CoA as a starting molecule. In the disclosed pathway to 6-ACA, similar to the HMDA pathway described above, glutaryl-CoA is first condensed with acetyl-CoA by a beta-ketothiolase to form 3-oxopimeloyl-CoA (Step A of FIG. 21). The CoA moiety of 3-oxopimeloyl-CoA is removed by a CoA hydrolase, transferase and ligase (Step B of FIG. 21). Then 3-oxopimelate is transaminated to 3-aminopimelate (Step J of FIG. 21). 3-Aminopimelate can be converted to 2-aminopimelate by a 2,3-aminomutase enzyme (Step T of FIG. 21). Aminopimelate can then be decarboxylated to form 6-aminocaproic acid (Step AA of FIG. 21).

Homolysine is also an attractive precursor to 6-aminocaproate (6-ACA) production. Although homolysine is a potentially valuable precursor, it is not a known metabolic intermediate of any organism. Under aerobic conditions, oxidation of homolysine by a lysine 2-monooxygenase yields 6-aminohexanamide, which is readily hydrolyzed to 6-ACA in dilute acid or basic solution (FIG. 23).

6-ACA can also be produced from 2-amino-7-oxosubarate as a starting molecule (FIG. 26). 2-Amino-7-oxosubarate is not known to be a naturally occurring metabolite. An exemplary route for synthesizing 2-amino-7-oxosubarate is shown in FIG. 27. The pathway originates with glutamate-5-semialdehyde, a metabolite naturally formed during ornithine biosynthesis. 2-Amino-7-oxosubarate is then synthesized in three enzymatic steps. In the first step, glutamate-5-semialdehyde is condensed with pyruvate by an aldolase (FIG. 27, Step A). The product, 2-amino-5-hydroxy-7-oxosubarate is subsequently dehydrated and the resulting alkene is reduced to form 2-amino-7-oxosubarate (FIG. 27, Steps B/C). In one proposed route, 2-amino-7-oxosubarate is decarboxylated to form 2-amino-7-oxoheptanoate (Step A of FIG. 26). The aldehyde of 2-amino-7-oxoheptanoate is oxidized by an oxidoreductase to form 2-aminopimelate (Step D of FIG. 26). 6-ACA is the decarboxylation product of 2-aminopimelate (Step E of FIG. 26). Alternately, the 2-amino-7-oxoheptanoate intermediate is decarboxylated to form 6-aminohexanal (Step B of FIG. 26), which is transaminated to 6-ACA (Step F of FIG. 26). In a third proposed route, the 2-amino acid group of 2-amino-7-oxosubarate is decarboxylated, yielding 2-oxo-7-aminoheptanoate (Step I of FIG. 26). This product can then be further decarboxylated to 6-aminohexanal (Step G of FIG. 26). Finally, 6-aminohexanal is transaminated to 6-ACA (Step F of FIG. 26).

Example XXVI

Enzyme Classification System for Production of Hexamethylenediamine and 6-Aminocaproic acid This example describes the enzyme classification system for the exemplary pathways described in Examples XXIV and XXV for production of hexamethylenediamine or 6-aminocaproate.

All transformations depicted in FIGS. 20-23 and 26 fall into the general categories of transformations shown in Table 11. Below is described a number of biochemically characterized genes in each category. Specifically listed are genes that can be applied to catalyze the appropriate transformations in FIGS. 20-23 and 26 when properly cloned and expressed.

Table 11 shows the enzyme types useful to convert common central metabolic intermediates into 6-aminocaproate and hexamethylenediamine. The first three digits of each label correspond to the first three Enzyme Commission number digits which denote the general type of transformation independent of substrate specificity.

TABLE 11

| LABEL | FUNCTION |
| --- | --- |
| 1.1.1.a | Oxidoreductase (oxo to alcohol) |
| 1.13.12.a | Monooxygenase ($O_2$ incorporating) |
| 1.2.1.a | Oxidoreductase (aldehyde to acid) |
| 1.2.1.b | Oxidoreductase (acyl-CoA to aldehyde) |
| 1.2.1.d | Oxidoreductase (phosphonate reductase) |
| 1.2.1.e | Acid reductase |
| 1.3.1.a | Oxidoreductase (alkene to alkane) |
| 1.4.1.a | Oxidoreductase (aminating) |
| 2.3.1.b | Acyltransferase (beta-ketothiolase) |
| 2.6.1.a | Aminotransferase |
| 2.7.2.a | Phosphotransferase (carboxy acceptor) |
| 2.8.3.a | Coenzyme-A transferase |
| 3.1.2.a | CoA hydrolase |
| 4.1.1.a | Carboxy-lyase |
| 4.1.2.a | Aldehyde-lyase |
| 4.2.1.a | Hydro-lyase |
| 5.4.3.a | Aminomutase |
| 6.2.1.a | Acid-thiol ligase |

1.1.1.a Oxidoreductase (Oxo to Alcohol)—

The reduction of 3-oxo-6-aminopimeloyl-CoA to 3-hydroxy-6-aminopimeloyl-CoA is catalyzed by a 3-oxoacyl-CoA dehydrogenase (FIG. 20, Step C). Such enzymes convert 3-oxoacyl-CoA molecules into 3-hydroxyacyl-CoA molecules and are often involved in fatty acid beta-oxidation or phenylacetate catabolism. For example, subunits of two fatty acid oxidation complexes in *E. coli*, encoded by fadB and fadJ, function as 3-hydroxyacyl-CoA dehydrogenases (Binstock et al., *Methods Enzymol.* 71 Pt C:403-411 (1981)). Furthermore, the gene products encoded by phaC in *Pseudomonas putida* U (Olivera et al., *Proc. Natl. Acad. Sci U.S.A* 95:6419-6424 (1998)) and paaC in *Pseudomonas fluorescens* ST (Di Arch et al., *Microbiol* 188:117-125 (2007)) catalyze the reverse reaction of step B in FIG. 10, that is, the oxidation of 3-hydroxyadipyl-CoA to form 3-oxoadipyl-CoA, during the catabolism of phenylacetate or styrene. Note that the reactions catalyzed by such enzymes are reversible. In addition, given the proximity in *E. coli* of paaH to other genes in the phenylacetate degradation operon (Nogales et al., *Microbiology* 153:357-365 (2007)) and the fact that paaH mutants cannot grow on phenylacetate (Ismail et al., *Eur. J Biochem.* 270:3047-3054 (2003)), it is expected that the *E. coli* paaH gene encodes a 3-hydroxyacyl-CoA dehydrogenase.

| Gene name | GI# | GenBank Accession # | Organism |
| --- | --- | --- | --- |
| fadB | 119811 | P21177.2 | Escherichia coli |
| fadJ | 3334437 | P77399.1 | Escherichia coli |
| paaH | 16129356 | NP_415913.1 | Escherichia coli |
| phaC | 26990000 | NP_745425.1 | Pseudomonas putida |
| paaC | 106636095 | ABF82235.1 | Pseudomonas fluorescens |

Additional exemplary oxidoreductases capable of converting 3-oxoacyl-CoA molecules to their corresponding 3-hydroxyacyl-CoA molecules include 3-hydroxybutyryl-CoA dehydrogenases. The enzyme from *Clostridium acetobutylicum*, encoded by hbd, has been cloned and functionally expressed in *E. coli* (Youngleson et al., *J Bacteriol.* 171:6800-6807 (1989)). Additional gene candidates include Hbd1 (C-terminal domain) and Hbd2 (N-terminal domain) in *Clostridium kluyveri* (Hillmer et al., *FEBS Lett.* 21:351-354 (1972)) and HSD17B10 in *Bos taurus* (Wakil et al., *J Biol. Chem.* 207:631-638 (1954)). Yet other gene candidates demonstrated to reduce acetoacetyl-CoA to 3-hydroxybutyryl-CoA are phbB from *Zoogloea ramigera* (Ploux et al., *Eur. J Biochem.* 174:177-182 (1988)) and phaB from *Rhodobacter sphaeroides* (Alber et al., *Mol. Microbiol.* 61:297-309 (2006)).) The former gene candidate is NADPH-dependent, its nucleotide sequence has been determined (Peoples et al., *Mol. Microbiol* 3:349-357 (1989)) and the gene has been expressed in *E. coli*. Substrate specificity studies on the gene led to the conclusion that it could accept 3-oxopropionyl-CoA as an alternate substrate (Peoples et al., *Mol. Microbiol* 3:349-357 (1989)).

| Gene name | GI# | GenBank Accession # | Organism |
| --- | --- | --- | --- |
| hbd | 18266893 | P52041.2 | Clostridium acetobutylicum |
| Hbd2 | 146348271 | EDK34807.1 | Clostridium kluyveri |
| Hbd1 | 146345976 | EDK32512.1 | Clostridium kluyveri |
| HSD17B10 | 3183024 | O02691.3 | Bos taurus |
| phaB | 77464321 | YP_353825.1 | Rhodobacter sphaeroides |
| phbB | 130017 | P23238.1 | Zoogloea ramigera |

A number of similar enzymes have been found in other species of *Clostridia* and in *Metallosphaera sedula* (Berg et al., *Science.* 318:1782-1786 (2007).

| Gene name | GI# | GenBank Accession # | Organism |
| --- | --- | --- | --- |
| hbd | 15895965 | NP_349314.1 | Clostridium acetobutylicum |
| hbd | 20162442 | AAM14586.1 | Clostridium beijerinckii |
| Msed_1423 | 146304189 | YP_001191505 | Metallosphaera sedula |

| Gene name | GI# | GenBank Accession # | Organism |
|---|---|---|---|
| Msed_0399 | 146303184 | YP_001190500 | Metallosphaera sedula |
| Msed_0389 | 146303174 | YP_001190490 | Metallosphaera sedula |
| Msed_1993 | 146304741 | YP_001192057 | Metallosphaera sedula |

1.13.12.a Monooxygenase (O₂ Incorporating)—

An 02-incorporating monooxygenase is required to convert homolysine to 6-aminohexanamide (Step A of FIG. 23). The lysine 2-monooxygenase (EC 1.13.12.2) from Pseudomonas fluorescens reacts with homolysine as a substrate (Nakazawa et al., J Biol. Chem. 247:3439-3444 (1972)). The enzyme from P. putida has been characterized biochemically and the gene has been identified (Karyakin et al., Prikladnaya Biokhimiya i Mikrobiologiya 27:825-832 (1991)). Genes encoding lysine 2-monooxygenase enzymes in P. fluorescens (eval=0.0, 90% identity), Streptomyces coelicolor (eval=0.0, 58% identity), Rhodococcus jostii (eval=0.0, 56% identity) and others were identified by protein sequence homology to the P. putida enzyme.

| Gene name | GI# | GenBank Accession # | Organism |
|---|---|---|---|
| davB | 193805882 | BAG54787.1 | Pseudomonas putida |
| pfl_5670 | 68347255 | AAY94861.1 | Pseudomonas fluorescens |
| SCO1454 | 7209214 | CAB76876.1 | Streptomyces coelicolor |
| RHA1_ro03531 | 110820050 | ABG95334.1 | Rhodococcus jostii |

1.2.1.a Oxidoreductase (Aldehyde to Acid)

Two transformations in FIG. 26 require conversion of an aldehyde to an acid: conversion of 2-amino-7-oxoheptanoate to 2-aminopimelate (Step D) and 6-aminohexanal to 6-aminocaproate (Step F). Such reactions are catalyzed by NAD(P)+-dependent oxidoreductases that convert aldehydes to acids in the EC class 1.2.1. A candidate enzyme is the NAD+-dependent aldehyde dehydrogenase (EC 1.2.1.3). Two aldehyde dehydrogenases found in human liver, ALDH-1 and ALDH-2, have broad substrate ranges for a variety of aliphatic, aromatic and polycyclic aldehydes (Klyosov et al., Biochemistry 35:4457-4467 (1996)). Active ALDH-2 has been efficiently expressed in E. coli using the GroEL proteins as chaperonins (Lee et al., Biochem. Biophys. Res. Commun. 298:216-224 (2002)). The rat mitochondrial aldehyde dehydrogenase also has a broad substrate range that includes the enoyl-aldehyde crotonaldehyde (Siew et al., Arch. Biochem. Biophys. 176:638-649 (1976)). The E. coli gene astD also encodes an NAD+-dependent aldehyde dehydrogenase that converts succinic semialdehyde to succinate (Kuznetsova et al., FEMS Microbiol Rev 29:263-279 (2005)).

| Gene name | GI# | GenBank Accession # | Organism |
|---|---|---|---|
| ALDH-2 | 118504 | P05091.2 | Homo sapiens |
| ALDH-2 | 14192933 | NP_115792.1 | Rattus norvegicus |
| astD | 3913108 | P76217.1 | Escherichia coli |

1.2.1.b Oxidoreductase (Acyl-CoA to Aldehyde)—

Reductive de-acylation of 3-oxopimeloyl-CoA (FIG. 21, Step I), 5-aminopimeloyl-CoA (FIG. 21, Step L) and 6-aminopimeloyl-CoA (FIG. 21, Step Y) to their corresponding aldehydes is catalyzed by enzymes in the EC class 1.2.1. Exemplary acyl-CoA dehydrogenases that reduce an acyl-CoA to its corresponding aldehyde include the fatty acid acyl-CoA reductase enzymes of Acinetobacter calcoaceticus (Reiser et al., Journal of Bacteriology 179:2969-2975 (1997)) and Acinetobacter sp. M-1 (Ishige et al., Appl. Environ. Microbiol. 68:1192-1195 (2002)), and a CoA- and NADP-dependent succinate semialdehyde dehydrogenase encoded by the sucD gene in Clostridium kluyveri (Sohling et al., J Bacteriol. 178:871-880 (1996); and Sohling et al., J Bacteriol 178:871-80 (1996)). SucD of P. gingivalis is another succinate semialdehyde dehydrogenase (Takahashi et al., J. Bacteriol. 182:4704-4710 (2000)). The enzyme acylating acetaldehyde dehydrogenase in Pseudomonas sp, encoded by bphG, is yet another as it has been demonstrated to oxidize and acylate acetaldehyde, propionaldehyde, butyraldehyde, isobutyraldehyde and formaldehyde (Powlowski et al., J Bacteriol. 175:377-385 (1993)). In addition to reducing acetyl-CoA to ethanol, the enzyme encoded by adhE in Leuconostoc mesenteroides has been shown to oxidize the branched chain compound isobutyraldehyde to isobutyryl-CoA (Koo et al., Biotechnol Lett. 27:505-510 (2005)).

| Gene name | GI# | GenBank Accession # | Organism |
|---|---|---|---|
| acr1 | 50086359 | YP_047869.1 | Acinetobacter calcoaceticus |
| acr1 | 1684886 | AAC45217 | Acinetobacter baylyi |
| acr1 | 18857901 | BAB85476.1 | Acinetobacter sp. Strain M-1 |
| sucD | 172046062 | P38947.1 | Clostridium kluyveri |
| sucD | 34540484 | NP_904963.1 | Porphyromonas gingivalis |
| bphG | 425213 | BAA03892.1 | Pseudomonas sp |

An additional enzyme type that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archael bacteria (Berg et al., Science. 318:1782-1786 (2007); and Thauer et al., Science. 318:1732-1733 (2007)). The enzyme utilizes NADPH as a cofactor and has been characterized in Metallosphaera and Sulfolobus spp (Alber et al., J. Bacteriol. 188:8551-8559 (2006); and Hugler et al., J. Bacteriol. 184:2404-2410 (2002)). The enzyme is encoded by Msed_0709 in Metallosphaera sedula (Alber et al., J. Bacteriol. 188:8551-8559 (2006) and Berg et al., Science. 318:1782-1786 (2007)). A gene encoding a malonyl-CoA reductase from Sulfolobus tokodaii was cloned and heterologously expressed in E. coli (Alber et al., J. Bacteriol. 188:8551-8559 (2006)). This enzyme has also been shown to catalyze the conversion of methylmalonyl-CoA to its corresponding aldehyde (WO/2007/141208). Although the aldehyde dehydrogenase functionality of these enzymes is similar to the bifunctional dehydrogenase from Chloroflexus aurantiacus, there is little sequence similarity. Both malonyl-CoA reductase enzyme candidates have high sequence similarity to aspartate-semialdehyde dehydrogenase, an enzyme catalyzing the reduction and concurrent dephosphorylation of aspartyl-4-phosphate to aspartate semialdehyde. Additional gene candidates can be found by sequence homology to proteins in other organisms including Sulfolobus solfataricus and Sulfolobus acidocaldarius. Yet another candidate for CoA-acylating aldehyde dehydrogenase is the ald gene from Clostridium beijerinckii (Toth et al., Appl Environ. Microbiol 65:4973-4980 (1999)). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth et al., *Appl Environ. Microbiol* 65:4973-4980 (1999)).

| Gene name | GI# | GenBank Accession # | Organism |
|---|---|---|---|
| Msed_0709 | 146303492 | YP_001190808.1 | *Metallosphaera sedula* |
| mcr | 15922498 | NP_378167.1 | *Sulfolobus tokodaii* |
| asd-2 | 15898958 | NP_343563.1 | *Sulfolobus solfataricus* |
| Saci_2370 | 70608071 | YP_256941.1 | *Sulfolobus acidocaldarius* |
| Ald | 49473535 | AAT66436 | *Clostridium beijerinckii* |
| eutE | 687645 | AAA80209 | *Salmonella typhimurium* |
| eutE | 2498347 | P77445 | *Escherichia coli* |

1.2.1.d Oxidoreductase (Phosphonate Reductase)—

The reduction of a phosphonic acid to its corresponding aldehyde is catalyzed by an oxidoreductase in the EC class 1.2.1. Steps G, N and X in FIG. 21 require such an enzyme for the reduction of 5-oxopimeloyl-phosphonate, 5-aminopimeloylphosphonate and 6-aminopimeloylphosphonate to their corresponding aldehydes. These reactions are not catalyzed by known enzymes. A similar reaction is catalyzed by aspartate semialdehyde dehydrogenase (ASD, EC 1.2.1.11): the NADPH-dependent reduction of 4-aspartyl phosphate to aspartate-4-semialdehyde. ASD participates in amino acid biosynthesis and recently has been studied as an antimicrobial target (Hadfield et al., *Biochemistry* 40:14475-14483 (2001)). The *E. coli* ASD structure has been solved (Hadfield et al., *J Mol. Biol.* 289:991-1002 (1999)) and the enzyme has been shown to accept the alternate substrate beta-3-methylaspartyl phosphate (Shames, et al., *J Biol. Chem.* 259:15331-15339 (1984)). The *Haemophilus influenzae* enzyme has been the subject of enzyme engineering studies to alter substrate binding affinities at the active site (Blanco et al., *Crystallogr.* 60:1388-1395 (2004)). Other ASD candidates are found in *Mycobacterium tuberculosis* (Shafiani et al., *J Appl Microbiol* 98:832-838 (2005)), *Methanococcus jannaschii* Faehnle et al. *J Mol.* 353:1055-1068 (2005)) and the infectious microorganisms *Vibrio cholera* and *Heliobacter pylori* (Moore et al., *Protein Expr. Purif.* 25:189-194 (2002)). Acetylglutamylphosphate reductase (EC 1.2.1.38) is a related enzyme that naturally reduces acetylglutamylphosphate to acetylglutamate-5-semialdehyde. Genes encoding this enzyme are found in *S. cerevisiae* (Pauwels et al., *Eur. J Biochem.* 270:1014-1024 (2003)), *B. subtilis* (O'Reilly et al., Microbiology 140 (Pt 5):1023-1025 (1994)) and other organisms.

| Gene name | GI# | GenBank Accession # | Organism |
|---|---|---|---|
| asd | 16131307 | NP_417891.1 | *Escherichia coli* |
| asd | 68249223 | YP_248335.1 | *Haemophilus influenzae* |
| asd | 1899206 | AAB49996 | *Mycobacterium tuberculosis* |
| VC2036 | 15642038 | NP_231670 | *Vibrio cholera* |
| asd | 210135348 | YP_002301787.1 | *Heliobacter pylori* |
| ARG5,6 | 6320913 | NP_010992.1 | *Saccharomyces cerevisiae* |
| argC | 16078184 | NP_389001.1 | *Bacillus subtilis* |

Other exemplary phosphonate reductase enzymes include glyceraldehyde 3-phosphate dehydrogenase which converts glyceraldehyde-3-phosphate into D-glycerate 1,3-bisphosphate (e.g., *E. coli* gapA (Branlant et al., *Eur. J. Biochem.* 150:61-66 (1985)).23)), N-acetyl-gamma-glutamyl-phosphate reductase which converts N-acetyl-L-glutamate-5-semialdehyde into N-acetyl-L-glutamyl-5-phosphate (e.g., *E. coli* argC (Parsot et al., *Gene.* 68:275-283 (1988)), and glutamate-5-semialdehyde dehydrogenase which converts L-glutamate-5-semialdehyde into L-glutamyl-5-phospate (e.g., *E. coli* proA (Smith et al., *J. Bacteriol.* 157:545-551 (1984))). Genes encoding glutamate-5-semialdehyde dehydrogenase enzymes from *Salmonella typhimurium* (Mahan et al., *J Bacteriol.* 156:1249-1262 (1983)) and *Campylobacter jejuni* (Louie et al., *Mol. Gen. Genet.* 240:29-35 (1993)) were cloned and expressed in *E. coli*.

| Gene name | GI# | GenBank Accession # | Organism |
|---|---|---|---|
| gapA | 71159358 | P0A9B2.2 | *Escherichia coli* |
| argC | 16131796 | NP_418393.1 | *Escherichia coli* |
| proA | 16128229 | NP_414778.1 | *Escherichia coli* |
| proA | 16763704 | NP_459319.1 | *Salmonella typhimurium* |
| proA | 9087222 | P53000.2 | *Campylobacter jejuni* |

1.2.1.e Acid Reductase—

Several transformations in FIG. 21 require the conversion of an acid to an aldehyde (FIG. 21, Steps C, O, W). Such a transformation is thermodynamically unfavorable and typically requires energy-rich cofactors and multiple enzymatic steps. For example, in butanol biosynthesis conversion of butyrate to butyraldehyde is catalyzed by activation of butyrate to its corresponding acyl-CoA by a CoA transferase or ligase, followed by reduction to butyraldehyde by a CoA-dependent aldehyde dehydrogenase. Alternately, an acid can be activated to an acyl-phosphate and subsequently reduced by a phosphate reductase. Direct conversion of the acid to aldehyde by a single enzyme is catalyzed by an enzyme in the 1.2.1 family. Exemplary enzymes that catalyze these transformations include carboxylic acid reductase, alpha-aminoadipate reductase and retinoic acid reductase.

Carboxylic acid reductase, found in *Nocardia iowensis*, catalyzes the magnesium, ATP and NADPH-dependent reduction of carboxylic acids to their corresponding aldehydes (Venkitasubramanian et al., *J Biol. Chem.* 282:478-485 (2007)). This enzyme, encoded by car, was cloned and functionally expressed in *E. coli* (Venkitasubramanian et al., *J Biol. Chem.* 282:478-485 (2007)). Expression of the npt gene product improved activity of the enzyme via post-transcriptional modification. The npt gene encodes a specific phosphopantetheine transferase (PPTase) that converts the inactive apo-enzyme to the active holo-enzyme. The natural substrate of this enzyme is vanillic acid and the enzyme exhibits broad acceptance of aromatic and aliphatic substrates (Venkitasubramanian et al. "Biocatalytic Reduction of Carboxylic Acids: Mechanism and Applications" Chapter 15 in Biocatalysis in the Pharmaceutical and Biotechnology Industries, ed. R. N. Patel, CRC Press LLC, Boca Raton, Fla. (2006)).

| Gene name | GI# | GenBank Accession # | Organism |
|---|---|---|---|
| car | 40796035 | AAR91681.1 | *Nocardia iowensis* (sp. NRRL 5646) |
| npt | 114848891 | ABI83656.1 | *Nocardia iowensis* (sp. NRRL 5646) |

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem* 278:8250-8256 (2003)). The gene encoding the *P. chrysogenum* PPTase has not been identified to date and no high-confidence hits were identified by sequence comparison homology searching. Directed evolution or other enzyme engineering methods may be required to enhance reactivity with the substrates in FIG. 21.

| Gene name | GI# | GenBank Accession # | Organism |
|---|---|---|---|
| LYS2 | 171867 | AAA34747.1 | Saccharomyces cerevisiae |
| LYS5 | 1708896 | P50113.1 | Saccharomyces cerevisiae |
| LYS2 | 2853226 | AAC02241.1 | Candida albicans |
| LYS5 | 28136195 | AAO26020.1 | Candida albicans |
| Lys1p | 13124791 | P40976.3 | Schizosaccharomyces pombe |
| Lys7p | 1723561 | Q10474.1 | Schizosaccharomyces pombe |
| Lys2 | 3282044 | CAA74300.1 | Penicillium chrysogenum |

1.3.1.a Oxidoreductase (Alkene to Alkane)—

Three transformations fall into the category of oxidoreductases that reduce an alkene to an alkane (EC 1.3.1.-). The conversion of 6-amino-7-carboxy-hept-2-enoyl-CoA to 6-aminopimeloyl-CoA (FIG. 20, Step E), 2-oxo-7-amino-hept-3-onoate to 2-oxo-7-aminoheptanoate (FIG. 22, Step C) and 2-amino-5-ene-7-oxosubarate to 2-amino-7-oxosubarate (FIG. 27, Step C) are catalyzed by a 2-enoate reductase. 2-Enoate reductase enzymes are known to catalyze the NAD(P)H-dependent reduction of a wide variety of α, β-unsaturated carboxylic acids and aldehydes (Rohdich, et al., *J Biol. Chem.* 276:5779-5787 (2001)). In the recently published genome sequence of *C. kluyveri*, 9 coding sequences for enoate reductases were reported, out of which one has been characterized (Seedorf et al., *Proc. Natl. Acad. Sci U.S.A* 105:2128-2133 (2008)). The enr genes from both *C. tyrobutyricum* and *M. thermoaceticum* have been cloned and sequenced and show 59% identity to each other. The former gene is also found to have approximately 75% similarity to the characterized gene in *C. kluyveri* (Giesel et al., *Arch. Microbiol* 135:51-57 (1983)). It has been reported based on these sequence results that enr is very similar to the dienoyl CoA reductase in *E. coli* (fadH) (Rohdich, et al., *J Biol. Chem.* 276:5779-5787 (2001)). The *Moorella thermoacetica* (formerly *C. thermoaceticum*) enr gene has also been expressed in a catalytically active form in *E. coli* (Ohdich, et al., *J Biol. Chem.* 276:5779-5787 (2001)).

| Gene name | GI# | GenBank Accession # | Organism |
|---|---|---|---|
| enr | 169405742 | ACA54153.1 | Clostridium botulinum A3 str |
| enr | 2765041 | CAA71086.1 | Clostridium tyrobutyricum |
| enr | 3402834 | CAA76083.1 | Clostridium kluyveri |
| enr | 83590886 | YP_430895.1 | Moorella thermoacetica |
| fadH | 16130976 | NP_417552.1 | Escherichia coli |

Another candidate 2-enoate reductase is maleylacetate reductase (MAR), an enzyme catalyzing the reduction of 2-maleylacetate (4-oxohex-2-enedioate) to 3-oxoadipate. MAR enzymes naturally participate in aromatic degradation pathways (Camara et al., *J Bacteriol.* (2009); Huang et al., *Appl Environ. Microbiol* 72:7238-7245 (2006)); Kaschabek et al., *J Bacteriol.* 177:320-325 (1995) and Kaschabek et al., *J Bacteriol.* 175:6075-6081 (1993)). The enzyme activity was identified and characterized in *Pseudomonas* sp. strain B13 (Kaschabek et al., *J Bacteriol* 177:320-325 (1995); and Kaschabek et al., *J Bacteriol* 175:6075-6081 (1993)), and the coding gene was cloned and sequenced (Kasberg et al., *J Bacteriol.* 179:3801-3803 (1997)). Additional MAR gene candidates include cicE gene from *Pseudomonas* sp. strain B13 (Kasberg et al., *J Bacteriol.* 179:3801-3803 (1997)), macA gene from *Rhodococcus opacus* (Seibert et al., *J Bacteriol* 180:3503-3508 (1998)), the macA gene from *Ralstonia eutropha* (also known as *Cupriavidus* necator) (Seibert et al., *Microbiology* 150:463-472 (2004)), tfdFII from *Ralstonia eutropha* (Seibert et al., *J Bacteriol.* 175: 6745-6754 (1993)) and NCgl1112 in *Corynebacterium glutamicum* (Huang et al., *Appl Environ. Microbiol* 72:7238-7245 (2006)). A MAR in *Pseudomonas reinekei* MT1, encoded by ccaD, was recently identified and the nucleotide sequence is available under the DBJ/EMBL GenBank accession number EF159980 (Camara et al., *J Bacteriol.* (2009)).

| Gene name | GI# | GenBank Accession # | Organism |
|---|---|---|---|
| clcE | 3913241 | O30847.1 | Pseudomonas sp. strain B13 |
| macA | 7387876 | O84992.1 | Rhodococcus opacus |
| macA | 5916089 | AAD55886 | Cupriavidus necator |
| tfdFII | 1747424 | AAC44727.1 | Ralstonia eutropha JMP134 |
| NCgl1112 | 19552383 | NP_600385 | Corynebacterium glutamicum |
| ccaD | 134133940 | ABO61029.1 | Pseudomonas reinekei MT1 |

Enoyl-CoA reductase enzymes are suitable enzymes for catalyzing the reduction of 6-amino-7-carboxyhept-2-enoyl-CoA to 6-aminopimeloyl-CoA (FIG. 20, Step E). One exemplary enoyl-CoA reductase is the gene product of bcd from *C. acetobutylicum* (Atsumi et al., *Metab Eng.* 10:305-311 (2008)); and Boynton et al., *J Bacteria* 178:3015-3024 (1996)), which naturally catalyzes the reduction of crotonyl-CoA to butyryl-CoA. Activity of this enzyme can be enhanced by expressing bcd in conjunction with expression of the *C. acetobutylicum* etfAB genes, which encode an electron transfer flavoprotein. An additional candidate for the enoyl-CoA reductase step is the mitochondrial enoyl-CoA reductase from *E. gracilis* (Hoffmeister, et al., *J Biol. Chem.* 280:4329-4338 (2005)). A construct derived from this sequence following the removal of its mitochondrial targeting leader sequence was cloned in *E. coli* resulting in an active enzyme (Hoffmeister, et al., *J Biol. Chem.* 280: 4329-4338 (2005)). This approach is well known to those skilled in the art of expressing eukaryotic genes, particularly those with leader sequences that may target the gene product to a specific intracellular compartment, in prokaryotic organisms. A close homolog of this gene, TDE0597 from the prokaryote *Treponema denticola*, represents a third enoyl-CoA reductase which has been cloned and expressed in *E. coli* (Tucci et al., *Febs Letters* 581:1561-1566 (2007)).

| Gene name | GI# | GenBank Accession # | Organism |
|---|---|---|---|
| bcd | 15895968 | NP_349317.1 | *Clostridium acetobutylicum* |
| etfA | 15895966 | NP_349315.1 | *Clostridium acetobutylicum* |
| etfB | 15895967 | NP_349316.1 | *Clostridium acetobutylicum* |
| TER | 62287512 | Q5EU90.1 | *Euglena gracilis* |
| TDE0597 | 42526113 | NP_971211.1 | *Treponema denticola* |

Additional enoyl-CoA reductase enzyme candidates are found in organisms that degrade aromatic compounds. *Rhodopseudomonas palustris*, a model organism for benzoate degradation, has the enzymatic capability to degrade pimelate via beta-oxidation of pimeloyl-CoA. Adjacent genes in the pim operon, pimC and pimD, bear sequence homology to *C. acetobutylicum* bcd and are predicted to encode a flavin-containing pimeloyl-CoA dehydrogenase (Harrison et al., *Microbiology* 151:727-736 (2005)). The genome of nitrogen-fixing soybean symbiont *Bradyrhizobium japonicum* also contains a pim operon composed of genes with high sequence similarity to pimC and pimD of *R. palustris* (Harrison et al., *Microbiology* 151:727-736 (2005)).

| Gene name | GI# | GenBank Accession # | Organism |
|---|---|---|---|
| pimC | 39650632 | CAE29155 | *Rhodopseudomonas palustris* |
| pimD | 39650631 | CAE29154 | *Rhodopseudomonas palustris* |
| pimC | 27356102 | BAC53083 | *Bradyrhizobium japonicum* |
| pimD | 27356101 | BAC53082 | *Bradyrhizobium japonicum* |

An additional candidate is 2-methyl-branched chain enoyl-CoA reductase (EC 1.3.1.52), an enzyme catalyzing the reduction of sterically hindered trans-enoyl-CoA substrates. This enzyme participates in branched-chain fatty acid synthesis in the nematode *Ascarius suum* and is capable of reducing a variety of linear and branched chain substrates including 2-methylbutanoyl-CoA, 2-methylpentanoyl-CoA, octanoyl-CoA and pentanoyl-CoA (Duran et al., *J Biol. Chem.* 268:22391-22396 (1993))). Two isoforms of the enzyme, encoded by genes acad1 and acad, have been characterized.

| Gene name | GI# | GenBank Accession # | Organism |
|---|---|---|---|
| acad1 | 2407655 | AAC48316.1 | *Ascarius suum* |
| acad | 347404 | AAA16096.1 | *Ascarius suum* |

1.4.1.a Oxidoreductase (Aminating)—

Several reactions in FIGS. 20-23 require the conversion of ketones or aldehydes to amine groups. Such a transformation can be accomplished by aminating oxidoreductases in the EC class 1.4.1. Enzymes in this EC class catalyze the oxidative deamination of amino groups with NAD+ or NADP+ as acceptor, and the reactions are typically reversible.

In Step D of FIG. 22 the 2-oxoacid 2-oxo-7-aminoheptanoate is converted to homolysine, a molecule resembling an amino acid (FIG. 22, Step D; FIG. 26, Step J). The conversion of 2-amino-7-oxosubarate to 2,7-diaminosubarate (Step K of FIG. 26) is a similar transformation. Exemplary enzymes for catalyzing these reactions include glutamate dehydrogenase (EC 1.4.1.2), leucine dehydrogenase (EC 1.4.1.9), and aspartate dehydrogenase (EC 1.4.1.21). The gdhA gene product from *Escherichia coli* (Korber, et al., *J Mol. Biol.* 234:1270-1273. (1993)), gdh from *Thermotoga maritime* (Kort et al., *Extremophiles* 1:52-60. 1997); Lebbink et al., *J Mol. Biol.* 280:287-296 (1998) and Lebbink et al., *J Mol. Biol.* 289:357-369 (1999))), and gdhA1 from *Halobacterium salinarum* (Ingoldsby et al., *Gene* 349:237-244 (2005)) catalyze the reversible conversion of glutamate to 2-oxoglutarate and ammonia, while favoring NADP(H), NAD(H), or both, respectively. The ldh gene of *Bacillus cereus* encodes the LeuDH protein that has a wide of range of substrates including leucine, isoleucine, valine, and 2-aminobutanoate (Ansorge et al., *Biotechnol Bioeng.* 68:557-562 (2000)); and Stoyan et al., *J Biotechnol* 54:77-80 (1997)). The nadX gene from *Thermotoga maritima* encoding for the aspartate dehydrogenase is involved in the biosynthesis of NAD (Yang et al., *J Biol. Chem.* 278:8804-8808 (2003)).

| Gene name | GI# | GenBank Accession # | Organism |
|---|---|---|---|
| gdhA | 118547 | P00370 | *Escherichia coli* |
| gdh | 6226595 | P96110.4 | *Thermotoga maritima* |
| gdhA1 | 15789827 | NP_279651.1 | *Halobacterium salinarum* |
| ldh | 61222614 | P0A393 | *Bacillus cereus* |
| nadX | 15644391 | NP_229443.1 | *Thermotoga maritima* |

Two reactions entail conversion of 3-oxoacids to 3-amino acids: 3-oxo-7-aminoheptanoate to 3,7-diaminoheptanoate (FIG. 21, Step E), 3-oxopimelate to 3-aminopimelate (FIG. 21, Step J) and 3-oxo-1-carboxyheptanal to 3-amino-7-oxoheptanoate (FIG. 21, Step AB). An enzyme that reacts with 3-oxoacids is 3,5-diaminohexanoate dehydrogenase (EC 1.4.1.11), an enzyme found in organisms that ferment lysine. The gene encoding this enzyme, kdd, was recently identified in *Fusobacterium nucleatum* (Kreimeyer et al., *J Biol. Chem.* 282:7191-7197 (2007)). The enzyme has been purified and characterized in other organisms (Baker et al., *Chem.* 247:7724-7734 (1972)); and Baker et al., *Biochemistr.* 13:292-299 (1974)) but the genes associated with these enzymes are not known. Candidates in *Myxococcus xanthus*, *Porphyromonas gingivalis* W83 and other sequenced organisms can be inferred by sequence homology.

| Gene name | GI# | GenBank Accession # | Organism |
|---|---|---|---|
| kdd | 19713113 | AAL93966.1 | *Fusobacterium nucleatum* |
| mxan_4391 | 108462082 | ABF87267.1 | *Myxococcus xanthus* |
| pg_1069 | 34397119 | AAQ66183.1 | *Porphyromonas gingivalis* |

The conversions of 2-amino-7-oxoheptanoate to homolysine (FIG. 20, Step G; FIG. 21, Step Q; FIG. 26, Step M), 3-oxo-1-carboxyheptanal to 3-oxo-7-aminoheptanoate (FIG. 21, Step D) 3-amino-7-oxoheptanoate to 3,7-diaminoheptanoate (FIG. 21, Step Z) and 6-aminohexanal to HMDA (FIG. 26, Step C; FIG. 22, Step G) are catalyzed by aminating oxidoreductases that transform aldehydes to their corresponding primary amines. An enzyme that catalyzes a similar reaction is lysine 6-dehydrogenase (EC 1.4.1.18), encoded by the lysDH genes. This enzyme catalyzes the reversible oxidative deamination of the 6-amino group of L-lysine to form 2-aminoadipate-6-semialdehyde (Misono et al., *J Bacteriol.* 150:398-401 (1982)). Exemplary enzyme candidates are found in *Geobacillus stearothermophilus* (Heydari et al., *Appl Environ. Microbiol* 70:937-942 (2004)), *Agrobacterium tumefaciens* (Hashimoto et al., *J Biochem* 106:76-80 (1989); and Misono et al., *J Bacteriol.* 150:398-401 (1982)), and *Achromobacter denitrificans* (Ruldeekulthamrong et al., *BMP Rep.* 41:790-795 (2008)).

| Gene name | GI# | GenBank Accession # | Organism |
|---|---|---|---|
| lysDH | 13429872 | BAB39707 | *Geobacillus stearothermophilus* |
| lysDH | 15888285 | NP_353966 | *Agrobacterium tumefaciens* |
| lysDH | 74026644 | AAZ94428 | *Achromobacter denitrificans* |

2.3.1.b Acyltransferase (Beta-Ketothiolase)—

In Step A of FIG. 21, Glutaryl-CoA and acetyl-CoA are condensed to form 3-oxopimeloyl-CoA by oxopimeloyl-CoA:glutaryl-CoA acyltransferase, a beta-ketothiolase (EC 2.3.1.16). An enzyme catalyzing this transformation is found in *Ralstonia eutropha* (formerly known as *Alcaligenes eutrophus*), encoded by genes bktB and bktC (Haywood et al., *FEMS Microbiology Letters* 52:91-96 (1988); and Slater et al., *Bacteriol.* 180:1979-1987 (1998)). The sequence of the BktB protein is known; however, the sequence of the BktC protein has not been reported. The pim operon of *Rhodopseudomonas palustris* also encodes a beta-ketothiolase, encoded by pimB, predicted to catalyze this transformation in the degradative direction during benzoyl-CoA degradation (Harrison et al., *Microbiology* 151:727-736 (2005)). A beta-ketothiolase enzyme candidate in *S. aciditrophicus* was identified by sequence homology to bktB (43% identity, evalue=1e-93).

| Gene name | GI# | GenBank Accession # | Organism |
|---|---|---|---|
| bktB | 11386745 | YP_725948 | *Ralstonia eutropha* |
| pimB | 39650633 | CAE29156 | *Rhodopseudomonas palustris* |
| syn_02642 | 85860483 | YP_462685.1 | *Syntrophus aciditrophicus* |

Beta-ketothiolase enzymes catalyzing the formation of beta-ketovalerate from acetyl-CoA and propionyl-CoA may also be able to catalyze the formation of 3-oxopimeloyl-CoA. *Zoogloea ramigera* possesses two ketothiolases that can form β-ketovaleryl-CoA from propionyl-CoA and acetyl-CoA and *R. eutropha* has a β-oxidation ketothiolase that is also capable of catalyzing this transformation (Gruys et al., U.S. Pat. No. 5,958,745 (1999)). The sequences of these genes or their translated proteins have not been reported, but several candidates in *R. eutropha*, *Z. ramigera*, or other organisms can be identified based on sequence homology to bktB from *R. eutropha*. These include:

| Gene name | GI# | GenBank Accession # | Organism |
|---|---|---|---|
| phaA | 113867452 | YP_725941.1 | *Ralstonia eutropha* |
| h16_A1713 | 113867716 | YP_726205.1 | *Ralstonia eutropha* |
| pcaF | 116694155 | YP_728366.1 | *Ralstonia eutropha* |
| h16_B1369 | 116695312 | YP_840888.1 | *Ralstonia eutropha* |
| h16_A0170 | 113866201 | YP_724690.1 | *Ralstonia eutropha* |
| h16_A0462 | 113866491 | YP_724980.1 | *Ralstonia eutropha* |
| h16_A1528 | 113867539 | YP_726028.1 | *Ralstonia eutropha* |
| h16_B0381 | 116694334 | YP_728545.1 | *Ralstonia eutropha* |
| h16_B0662 | 116694613 | YP_728824.1 | *Ralstonia eutropha* |
| h16_B0759 | 116694710 | YP_728921.1 | *Ralstonia eutropha* |
| h16_B0668 | 116694619 | YP_728830.1 | *Ralstonia eutropha* |
| h16_A1720 | 113867723 | YP_726212.1 | *Ralstonia eutropha* |
| h16_A1887 | 113867867 | YP_726356.1 | *Ralstonia eutropha* |
| phbA | 135759 | P07097.4 | *Zoogloea ramigera* |
| bktB | 194289475 | YP_002005382.1 | *Cupriavidus taiwanensis* |
| Rmet_1362 | 94310304 | YP_583514.1 | *Ralstonia metallidurans* |
| Bphy_0975 | 186475740 | YP_001857210.1 | *Burkholderia phymatum* |

Additional candidates include beta-ketothiolases that are known to convert two molecules of acetyl-CoA into acetoacetyl-CoA (EC 2.1.3.9). Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007)); and Winzer et al., *J Mol. Microbiol Biotechnol* 2:531-541 (2000)), and ERG10 from *S. cerevisiae* (Hiser, et al., *J. Biol. Chem.* 269:31383-31389 (1994)).

| Gene name | GI# | GenBank Accession # | Organism |
|---|---|---|---|
| atoB | 16130161 | NP_416728 | *Escherichia coli* |
| thlA | 15896127 | NP_349476.1 | *Clostridium acetobutylicum* |
| thlB | 15004782 | NP_149242.1 | *Clostridium acetobutylicum* |
| ERG10 | 6325229 | NP_015297 | *Saccharomyces cerevisiae* |

Beta-ketoadipyl-CoA thiolase (EC 2.3.1.174), also called 3-oxoadipyl-CoA thiolase, converts beta-ketoadipyl-CoA to succinyl-CoA and acetyl-CoA, and is a key enzyme of the beta-ketoadipate pathway for aromatic compound degradation. The enzyme is widespread in soil bacteria and fungi including *Pseudomonas putida* (Harwood et al., *J Bacteriol* 176:6479-6488 (1994)) and *Acinetobacter calcoaceticus* (Doten et al., *J Bacteriol.* 169:3168-3174 (1987)). The gene products encoded by pcaF in *Pseudomonas* strain B13 (Kaschabek et al., *J Bacteriol.* 184:207-215 (2002)), phaD in *Pseudomonas putida* U (Olivera et al., *Proc. Natl. Acad. Sci U S. A* 95:6419-6424 (1998)), paaE in *Pseudomonas fluorescens* ST (Di Arch et al., *Microbiol* 188:117-125 (2007)), and paaJ from *E. coli* (Nogales et al., *Microbiology* 153: 357-365 (2007)) also catalyze this transformation. Several beta-ketothiolases exhibit significant and selective activities in the oxoadipyl-CoA forming direction including bkt from *Pseudomonas putida*, pcaF and bkt from *Pseudomonas aeruginosa* PAO1, bkt from *Burkholderia ambifaria* AMMD, paaJ from *E. coli*, and phaD from *P. putida*. These enzymes can also be employed for the synthesis of 3-oxopimeloyl-CoA, a compound structurally similar to 3-oxoadipyl-CoA.

| Gene name | GI# | GenBank Accession # | Organism |
|---|---|---|---|
| paaJ | 16129358 | NP_415915.1 | *Escherichia coli* |
| pcaF | 17736947 | AAL02407 | *Pseudomonas knackmussii* (B13) |
| phaD | 3253200 | AAC24332.1 | *Pseudomonas putida* |
| pcaF | 506695 | AAA85138.1 | *Pseudomonas putida* |
| pcaF | 141777 | AAC37148.1 | *Acinetobacter calcoaceticus* |
| paaE | 106636097 | ABF82237.1 | *Pseudomonas fluorescens* |
| bkt | 115360515 | YP_777652.1 | *Burkholderia ambifaria* AMMD |
| bkt | 9949744 | AAG06977.1 | *Pseudomonas aeruginosa* PAO1 |
| pcaF | 9946065 | AAG03617.1 | *Pseudomonas aeruginosa* PAO1 |

A beta-ketothiolase is also required to condense glutamyl-CoA and acetyl-CoA (FIG. 20, Step B). This transformation is not known to occur naturally. The beta-ketothiolase candidates described above are also exemplary candidates for catalyzing this transformation.

2.6.1.a Aminotransferase—

Several reactions in FIGS. 20-26 are catalyzed by aminotransferases in the EC class 2.6.1. Such enzymes reversibly transfer amino groups from aminated donors to acceptors such as pyruvate and alpha-ketoglutarate.

Aminotransferases selective for aldehydes are required for transaminating 2-amino-7-oxoheptanoate (FIG. 20, Step G; FIG. 21, Step Q; FIG. 26, Step M), 3-oxo-1-carboxyheptanal (FIG. 21, Step D) 3-amino-7-oxoheptanoate (FIG. 21, Step Z) and 6-aminohexanal (FIG. 26, Step C; FIG. 22, Step G). An exemplary enzyme for converting aldehydes to primary amines is lysine-6-aminotransferase (EC 2.6.1.36). This enzyme function, converting lysine to alpha-aminoadipate semialdehyde, has been demonstrated in yeast and bacteria. Candidates from *Candida utilis* (Hammer et al., *J Basic Microbiol* 32:21-27 (1992)), *Flavobacterium lutescens* (Fujii et al., *J Biochem.* 128:391-397 (2000)) and *Streptomyces* clavuligenus (Romero et al., *Microbiol Biotechnol* 18:241-246 (1997)) have been characterized. A recombinant lysine-6-aminotransferase from *S. clavuligenus* was functionally expressed in *E. coli* (Tobin et al., *J Bacteriol.* 173:6223-6229 (1991)). The *F. lutescens* enzyme is specific to alpha-ketoglutarate as the amino acceptor (Soda et al., *Biochemistry* 7:4110-4119 (1968)). Other enzymes which convert aldehydes to terminal amines include the dat gene product in *Acinetobacter baumanii* encoding 2,4-diaminobutanoate:2-ketoglutarate 4-transaminase (Ikai et al., *J Bacteriol.* 179:5118-5125 (1997)). In addition to its natural substrate, 2,4-diaminobutyrate, DAT transaminases the terminal amines of lysine, 4-aminobutyrate and ornithine.

| Gene name | GI# | GenBank Accession # | Organism |
|---|---|---|---|
| lat | 10336502 | BAB13756.1 | *Flavobacterium lutescens* |
| lat | 153343 | AAA26777.1 | *Streptomyces clavuligenus* |
| dat | 6685373 | P56744.1 | *Acinetobacter baumanii* |

Additional enzyme candidates include putrescine aminotransferases or other diamine aminotransferases. The *E. coli* putrescine aminotransferase is encoded by the ygjG gene and the purified enzyme was also able to transaminate cadaverine and spermidine (Samsonova et al., *Microbiol* 3:2 (2003)). In addition, activity of this enzyme on 1,7-diaminoheptane and with amino acceptors other than 2-oxoglutarate (e.g., pyruvate, 2-oxobutanoate) has been reported (Kim et al., *J Biol. Chem.* 239:783-786 (1964); and Samsonova et al., *Microbiol* 3:2 (2003)). The spuC gene of *Pseudomonas aeruginosa* encodes a putrescine aminotransferase with higher activity with pyruvate as the amino acceptor than alpha-ketoglutarate (Lu et al., *J Bacteriol.* 184:3765-3773 (2002)).

| Gene name | GI# | GenBank Accession # | Organism |
|---|---|---|---|
| ygjG | 145698310 | NP_417544 | *Escherichia coli* |
| spuC | 9946143 | AAG03688 | *Pseudomonas aeruginosa* |

The conversion of an aldehyde to a terminal amine can also be catalyzed by gamma-aminobutyrate transaminase (GABA transaminase). This enzyme naturally interconverts succinic semialdehyde and glutamate to 4-aminobutyrate and alpha-ketoglutarate and is known to have a broad substrate range (Liu et al., *Biochemistry* 43:10896-10905 (2004); and Schulz et al., *Appl Environ Microbiol* 56:1-6 (1990)). The two GABA transaminases in *E. coli* are encoded by gabT (Bartsch et al., *J Bacteriol.* 172:7035-7042 (1990)) and puuE (Kurihara et al., *J Biol. Chem.* 280:4602-4608 (2005)). GABA transaminases in *Mus musculus, Pseudomonas fluorescens,* and *Sus scrofa* have been shown to react with a range of alternate substrates including 6-aminocaproic acid (Cooper, *Methods Enzymol.* 113:80-82 (1985)); and Scott et al., *J Biol. Chem.* 234:932-936 (1959)).

| Gene name | GI# | GenBank Accession # | Organism |
|---|---|---|---|
| gabT | 16130576 | NP_417148.1 | *Escherichia coli* |
| puuE | 16129263 | NP_415818.1 | *Escherichia coli* |
| abat | 37202121 | NP_766549.2 | *Mus musculus* |
| gabT | 70733692 | YP_257332.1 | *Pseudomonas fluorescens* |
| abat | 47523600 | NP_999428.1 | *Sus scrofa* |

Enzymes that transaminate 3-oxoacids are required to convert 3-oxo-7-aminoheptanoate to 3,7-diaminoheptanoate (FIG. 21, Step E), 3-oxopimelate to 3-aminopimelate (FIG. 21, Step J) and 3-oxo-1-carboxyheptanal to 3-amino-7-oxoheptanoate (FIG. 21, Step AB). Enzymes catalyzing these exact transformations have not been identified to date. Beta-alanine/alpha-ketoglutarate aminotransferase (WO08027742) reacts with beta-alanine to form malonic semialdehyde, a 3-oxoacid. The gene product of SkPYD4 in *Saccharomyces kluyveri* was shown to preferentially use beta-alanine as the amino group donor (Andersen et al., *Gene.* 124:105-109 (1993)). SkUGA1 encodes a homologue of *Saccharomyces cerevisiae* GABA aminotransferase, UGA1 (Ramos et al., *Eur. J. Biochem.* 149:401-404 (1985)), whereas SkPYD4 encodes an enzyme involved in both beta-alanine and GABA transamination (Andersen et al., *Gene.* 124:105-109 (1993)). 3-Amino-2-methylpropionate transaminase catalyzes the transformation from methylmalonate semialdehyde to 3-amino-2-methylpropionate. The enzyme has been characterized in *Rattus norvegicus* and *Sus scrofa* and is encoded by Abat (Kakimoto et al., *Biochim. Biophys. Acta* 156:374-380 (1968); and Tamaki et al., *Methods Enzymol.* 324:376-389 (2000)).

| Gene name | GI# | GenBank Accession # | Organism |
|---|---|---|---|
| SkyPYD4 | 98626772 | ABF58893.1 | *Lachancea kluyveri* |
| SkUGA1 | 98626792 | ABF58894.1 | *Lachancea kluyveri* |
| UGA1 | 6321456 | NP_011533.1 | *Saccharomyces cerevisiae* |
| Abat | 122065191 | P50554.3 | *Rattus norvegicus* |
| Abat | 120968 | P80147.2 | *Sus scrofa* |

Several aminotransferases transaminate the amino groups of 2-oxo acids to form amino acids. Such an enzyme is required for the transamination of 2-oxo-7-aminoheptanoate to homolysine (FIG. 22, Step D; FIG. 26, Step M) and 2-amino-7-oxosubarate to 2,7-diaminosubarate (FIG. 26, Step K). A promising enzyme candidate is alpha-aminoadipate aminotransferase (EC 2.6.1.39), an enzyme that participates in lysine biosynthesis and degradation in some organisms. This enzyme interconverts 2-aminoadipate and 2-oxoadipate, using alpha-ketoglutarate as the amino acceptor. Gene candidates are found in *Homo sapiens* (Okuno et al., *Enzyme Protein* 47:136-148 (1993)) and *Thermus thermophilus* (Miyazaki et al., *Microbiology* 150:2327-2334 (2004)). The *Thermus thermophilus* enzyme, encoded by lysN, is active with several alternate substrates including oxaloacetate, 2-oxoisocaproate, 2-oxoisovalerate, and 2-oxo-3-methylvalerate.

| Gene name | GI# | GenBank Accession # | Organism |
|---|---|---|---|
| lysN | 31096548 | BAC76939.1 | *Thermus thermophilus* |
| AadAT-II | 46395904 | Q8N5Z0.2 | *Homo sapiens* |

Another candidate is aspartate aminotransferase, an enzyme that naturally transfers an oxo group from oxaloacetate to glutamate, forming alpha-ketoglutarate and aspartate. Aspartate aminotransferase activity is catalyzed by, for example, the gene products of aspC from *Escherichia coli* (Yagi et al., *FEBS Lett.* 100:81-84 (1979); and Yagi et al., *Methods Enzymol.* 113:83-89 (1985)), AAT2 from *Saccharomyces cerevisiae* (Yagi et al., *J Biochem.* 92:35-43 (1982)) and ASP5 from *Arabidopsis thaliana* (de la et al., *Plant J* 46:414-425 (2006); Kwok et al., *J Exp. Bot.* 55:595-604 (2004) and Wilkie et al., *Protein Expr. Purif.* 12:381-389 (1998)). The enzyme from *Rattus norvegicus* has been shown to transaminate alternate substrates such as 2-aminohexanedioic acid and 2,4-diaminobutyric acid (Recasens et al., *Biochemistry* 19:4583-4589 (1980)). Aminotransferases that work on other amino-acid substrates may also be able to catalyze this transformation. Valine aminotransferase catalyzes the conversion of valine and pyruvate to 2-ketoisovalerate and alanine. The *E. coli* gene, avtA, encodes one such enzyme (Whalen et al., *J. Bacteriol.* 150:739-746 (1982)). This gene product also catalyzes the transamination of α-ketobutyrate to generate α-aminobutyrate, although the amine donor in this reaction has not been identified (Whalen et al., *J. Bacteriol.* 158:571-574 (1984)). The gene product of the *E. coli* serC catalyzes two reactions, phosphoserine aminotransferase and phosphohydroxythreonine aminotransferase (Lam, J. et al., *Bacteriol.* 172:6518-6528 (1990)), and activity on non-phosphorylated substrates could not be detected (Drewke et al., *FEBS. Lett.* 390:179-182 (1996)).

| Gene name | GI# | GenBank Accession # | Organism |
|---|---|---|---|
| aspC | 16128895 | NP_415448.1 | *Escherichia coli* |
| AAT2 | 1703040 | P23542.3 | *Saccharomyces cerevisiae* |
| ASP5 | 20532373 | P46248.2 | *Arabidopsis thaliana* |
| Got2 | 112987 | P00507 | *Rattus norvegicus* |
| avtA | 49176374 | YP_026231.1 | *Escherichia coli* |
| serC | 16128874 | NP_415427.1 | *Escherichia coli* |

2.7.2.a Phosphotransferase (Carboxy Acceptor)—

Phosphotransferase enzymes in the EC class 2.7.2 transform carboxylic acids to phosphonic acids with concurrent hydrolysis of one ATP. Steps F, M and U in FIG. 21 require a phosphotransferase to activate the carboxyl groups of 3-oxopimelate (Step F), 3-aminopimelate (Step M) and 2-aminopimelate (Step U) to their corresponding phosphonic acids. Butyrate kinase (EC 2.7.2.7) carries out the reversible conversion of butyryl-phosphate to butyrate during acidogenesis in *C. acetobutylicum* (Cary et al., *Appl. Environ. Microbiol* 56:1576-1583 (1990)). This enzyme is encoded by either of the two buk gene products (Huang et al., *J Mol. Microbiol Biotechnol* 2:33-38 (2000)). Other butyrate kinase enzymes are found in *C. butyricum* and *C. tetanomorphum* (Twarog et al., *J Bacteriol.* 86:112-117 (1963)). Related enzyme isobutyrate kinase from *Thermotoga maritima* has also been expressed in *E. coli* and crystallized (Diao et al., *E. Biol. Crystallogr.* 59:1100-1102 (2003); and Diao et al., *J Bacteriol.* 191:2521-2529 (2009)). Aspartokinase catalyzes the ATP-dependent phosphorylation of aspartate and participates in the synthesis of several amino acids. The aspartokinase III enzyme in *E. coli*, encoded by lysC, has a broad substrate range and the catalytic residues involved in substrate specificity have been elucidated (Keng et al., *Arch. Biochem. Biophys.* 335:73-81 (1996)). Two additional kinases in *E. coli* are also good candidates: acetate kinase and gamma-glutamyl kinase. The *E. coli* acetate kinase, encoded by ackA (Skarstedt et al., *J. Biol. Chem.* 251:6775-6783 (1976)), phosphorylates propionate in addition to acetate (Hesslinger et al., *Mol. Microbiol* 27:477-492 (1998)). The *E. coli* gamma-glutamyl kinase, encoded by proB (Smith et al., *J. Bacteriol.* 157:545-551 (1984)), phosphorylates the gamma carbonic acid group of glutamate.

| Gene name | GI# | GenBank Accession # | Organism |
|---|---|---|---|
| buk1 | 15896326 | NP_349675 | *Clostridium acetobutylicum* |
| buk2 | 20137415 | Q97II1 | *Clostridium acetobutylicum* |
| buk2 | 6685256 | Q9X278.1 | *Thermotoga maritima* |
| lysC | 16131850 | NP_418448.1 | *Escherichia coli* |
| ackA | 16130231 | NP_416799.1 | *Escherichia coli* |
| proB | 16128228 | NP_414777.1 | *Escherichia coli* |

2.8.3.a Coenzyme-A Transferase—

CoA transferases catalyze the reversible transfer of a CoA moiety from one molecule to another. Several transformations in FIGS. 20 and 21 require a CoA transferase to activate carboxylic acids to their corresponding acyl-CoA derivatives (FIG. 20, Steps A and I; FIG. 21, Steps H, J, V). Candidate enzymes for catalyzing these transformations include the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., *Proc. Natl. Acad. Sci U.S.A* 105:2128-2133 (2008); and Sohling et al., *J Bacteriol.* 178:871-880 (1996)). Similar CoA transferase activities are also present in *Trichomonas vaginalis* (van Grinsven et al., *J Biol. Chem.* 283:1411-1418 (2008)) and *Trypanosoma brucei* (Riviere et al., *J. Biol. Chem.* 279: 45337-45346 (2004)).

| Gene name | GI# | GenBank Accession # | Organism |
|---|---|---|---|
| cat1 | 729048 | P38946.1 | *Clostridium kluyveri* |
| cat2 | 172046066 | P38942.2 | *Clostridium kluyveri* |
| cat3 | 146349050 | EDK35586.1 | *Clostridium kluyveri* |
| TVAG_395550 | 123975034 | XP_001330176 | *Trichomonas vaginalis* G3 |
| Tb11.02.0290 | 71754875 | XP_828352 | *Trypanosoma brucei* |

The glutaconyl-CoA-transferase (EC 2.8.3.12) enzyme from anaerobic bacterium *Acidaminococcus fermentans* reacts with glutaconyl-CoA and 3-butenoyl-CoA (Mack et al., *Eur. Biochem.* 226:41-51 (1994)), substrates similar in structure to 2,3-dehydroadipyl-CoA. The genes encoding this enzyme are gctA and gctB. This enzyme has reduced but detectable activity with other CoA derivatives including glutaryl-CoA, 2-hydroxyglutaryl-CoA, adipyl-CoA, crotonyl-CoA and acrylyl-CoA (Buckel et al., *Eur. J Biochem.* 118:315-321 (1981)). The enzyme has been cloned and expressed in *E. coli* (Mack et al., *Eur. J Biochem.* 226:41-51 (1994)).

| Gene name | GI# | GenBank Accession # | Organism |
|---|---|---|---|
| gctA | 559392 | CAA57199.1 | *Acidaminococcus fermentans* |
| gctB | 559393 | CAA57200.1 | *Acidaminococcus fermentans* |

A CoA transferase that can utilize acetyl-CoA as the CoA donor is acetoacetyl-CoA transferase, encoded by the *E. coli* atoA (alpha subunit) and atoD (beta subunit) genes (Korolev et al., *Biol. Crystallogr.* 58:2116-2121 (2002); and Vanderwinkel et al., *Biophys. Res. Commun.* 33:902-908 (1968)). This enzyme has a broad substrate range (Sramek et al., *Arch. Biochem. Biophys.* 171:14-26 (1975)) and has been shown to transfer the CoA moiety to acetate from a variety of branched and linear acyl-CoA substrates, including isobutyrate (Matthies et al., *Appl Environ. Microbiol* 58:1435-1439 (1992)), valerate (Vanderwinkel et al., *Biophys. Res. Commun.* 33:902-908 (1968)) and butanoate (Vanderwinkel et al., *Biophys. Res. Commun.* 33:902-908 (1968)). This enzyme is induced at the transcriptional level by acetoacetate, so modification of regulatory control may be necessary for engineering this enzyme into a pathway (Pauli et al., *Eur. J Biochem.* 29:553-562 (1972)). Similar enzymes exist in *Corynebacterium glutamicum* ATCC 13032 (Duncan et al., *Appl. Environ. Microbiol* 68:5186-5190 (2002)), *Clostridium acetobutylicum* (Cary et al., *Appl. Environ. Microbiol* 56:1576-1583 (1990); and Wiesenborn et al., *Appl. Environ. Microbiol* 55:323-329 (1989)), and *Clostridium saccharoperbutylacetonicum* (Kosaka et al., *Biosci. Biotechnol Biochem* 71:58-68 (2007)).

| Gene name | GI# | GenBank Accession # | Organism |
|---|---|---|---|
| atoA | 2492994 | P76459.1 | *Escherichia coli* |
| atoD | 2492990 | P76458.1 | *Escherichia coli* |
| actA | 62391407 | YP_226809.1 | *Corynebacterium glutamicum* |
| cg0592 | 62389399 | YP_224801.1 | *Corynebacterium glutamicum* |
| ctfA | 15004866 | NP_149326.1 | *Clostridium acetobutylicum* |
| ctfB | 15004867 | NP_149327.1 | *Clostridium acetobutylicum* |
| ctfA | 31075384 | AAP42564.1 | *Clostridium saccharoperbutylacetonicum* |
| ctfB | 31075385 | AAP42565.1 | *Clostridium saccharoperbutylacetonicum* |

The de-acylation 3-oxopimeloyl-CoA to 3-oxopimelate (FIG. 21, Step B) is catalyzed by a 3-oxoacid-CoA transferase (EC 2.8.3.6). Succcinyl-CoA:3-oxoacid-CoA transferase, also known as beta-ketoadipyl-CoA transferase, is encoded by pcaI and pcaJ in *Pseudomonas putida* (Kaschabek et al., *J Bacteriol.* 184:207-215 (2002)). Similar enzymes based on protein sequence homology exist in *Acinetobacter* sp. ADP1 (Kowalchuk et al., *Gene* 146:23-30 (1994)). Additional exemplary succinyl-CoA:3:oxoacid-CoA transferases are present in *Helicobacter pylori* (Corthesy-Theulaz et al., *J Biol. Chem.* 272:25659-25667 (1997)) and *Bacillus subtilis* (Stols et al., *Protein Expr. Purif.* 53:396-403 (2007)).

| Gene name | GI# | GenBank Accession # | Organism |
|---|---|---|---|
| pcaI | 24985644 | AAN69545.1 | *Pseudomonas putida* |
| pcaJ | 26990657 | NP_746082.1 | *Pseudomonas putida* |
| pcaI | 50084858 | YP_046368.1 | *Acinetobacter* sp. ADP1 |
| pcaJ | 141776 | AAC37147.1 | *Acinetobacter* sp. ADP1 |
| pcaI | 21224997 | NP_630776.1 | *Streptomyces coelicolor* |
| pcaJ | 21224996 | NP_630775.1 | *Streptomyces coelicolor* |
| HPAG1_0676 | 108563101 | YP_627417 | *Helicobacter pylori* |
| HPAG1_0677 | 108563102 | YP_627418 | *Helicobacter pylori* |
| ScoA | 16080950 | NP_391778 | *Bacillus subtilis* |
| ScoB | 16080949 | NP_391777 | *Bacillus subtilis* |

3.1.2.a Coa Hydrolase—

The hydrolysis of 6-aminopimeloyl-CoA to 6-aminopimelate (FIG. 20, Step I) is carried out by an acyl CoA hydrolase enzyme in the 3.1.2 family. An enzyme catalyzing this transformation has not been demonstrated to date. Several eukaryotic acetyl-CoA hydrolases (EC 3.1.2.1) have broad substrate specificity and thus represent suitable candidate enzymes for hydrolyzing 6-aminopimelate. For example, the enzyme from *Rattus norvegicus* brain (Robinson et al., *Res. Commun.* 71:959-965 (1976)) can react with butyryl-CoA, hexanoyl-CoA and malonyl-CoA. Though its sequence has not been reported, the enzyme from the mitochondrion of the pea leaf also has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)). The acetyl-CoA hydrolase, ACH1, from *S. cerevisiae* represents another candidate hydrolase (Buu et al., *J. Biol. Chem.* 278:17203-17209 (2003)).

| Gene name | GI# | GenBank Accession # | Organism |
|---|---|---|---|
| acot12 | 18543355 | NP_570103.1 | *Rattus norvegicus* |
| ACH1 | 6319456 | NP_009538 | *Saccharomyces cerevisiae* |

Another candidate hydrolase is the human dicarboxylic acid thioesterase, acot8, which exhibits activity on glutaryl-CoA, adipyl-CoA, suberyl-CoA, sebacyl-CoA, and dodecanedioyl-CoA (Westin et al., *J Biol. Chem.* 280:38125-38132 (2005)) and the closest *E. coli* homolog, tesB, which can also hydrolyze a broad range of CoA thioesters (Naggert et al., *J Biol. Chem.* 266:11044-11050 (1991)). A similar enzyme has also been characterized in the rat liver (Deana et al., *Biochem. Int.* 26:767-773 (1992)). Other potential *E. coli* thioester hydrolases include the gene products of tesA (Bonner et al., Chem. 247:3123-3133 (1972)), ybgC (Kuznetsova et al., *FEMS Microbiol Rev* 29:263-279 (2005); and (Zhuang et al., *FEBS Lett.* 516:161-163 (2002)), paaI (Song et al., *J Biol. Chem.* 281:11028-11038 (2006)), and ybdB (Leduc et al., *J Bacteriol.* 189:7112-7126 (2007)).

| Gene name | GI# | GenBank Accession # | Organism |
|---|---|---|---|
| tesB | 16128437 | NP_414986 | *Escherichia coli* |
| acot8 | 3191970 | CAA15502 | *Homo sapiens* |
| acot8 | 51036669 | NP_570112 | *Rattus norvegicus* |
| tesA | 16128478 | NP_415027 | *Escherichia coli* |
| ybgC | 16128711 | NP_415264 | *Escherichia coli* |
| paaI | 16129357 | NP_415914 | *Escherichia coli* |
| ybdB | 16128580 | NP_415129 | *Escherichia coli* |

Yet another candidate hydrolase is the glutaconate CoA-transferase from *Acidaminococcus fermentans*. This enzyme was transformed by site-directed mutagenesis into an acyl-CoA hydrolase with activity on glutaryl-CoA, acetyl-CoA and 3-butenoyl-CoA (Mack et al., *FEBS. Lett.* 405:209-212 (1997)). This suggests that the enzymes encoding succinyl-CoA:3-ketoacid-CoA transferases and acetoacetyl-CoA: acetyl-CoA transferases may also serve as candidates for this reaction step but would require certain mutations to change their function.

| Gene name | GI# | GenBank Accession # | Organism |
|---|---|---|---|
| gctA | 559392 | CAA57199 | *Acidaminococcus fermentans* |
| gctB | 559393 | CAA57200 | *Acidaminococcus fermentans* |

4.1.1.a Carboxy-Lyase—

The decarboxylation reactions of homolysine to HMDA (FIG. 20, Step H; FIG. 21, Step S; FIG. 22, Step E; FIG. 26, Step H), 2-aminopimelate to 6-ACA (FIG. 20, Step J, FIG. 21, Step AA and FIG. 26, Step E), 2,7-diaminosubarate to homolysine (FIG. 26, Step L), 2-amino-7-oxoheptanoate to 6-aminohexanal (FIG. 26, Step B; FIG. 22, Step F) and 2-amino-7-oxosubarate to 2-oxo-7-aminoheptanoate (FIG. 26, Step I) are catalyzed by amino acid decarboxylase enzymes. Lysine decarboxylase (EC 4.1.1.18) catalyzes a similar transformation: the decarboxylation of lysine to form cadaverine. Two isozymes of this enzyme are encoded in the *E. coli* genome by genes cadA and ldcC. CadA is involved in acid resistance and is subject to positive regulation by the cadC gene product (Lemonnier et al., Microbiology 144 (Pt 3):751-760 (1998)). CadC accepts hydroxylysine and S-aminoethylcysteine as alternate substrates, but 2-Aminopimelate and 6-ACA act as competitive inhibitors to this enzyme (Sabo et al., *Biochemistry* 13:662-670 (1974)). Directed evolution or other enzyme engineering methods may be required for this enzyme to decarboxylate 2-aminopimelate. The constitutively expressed ldc gene product is less active than CadA (Lemonnier et al., *Microbiology* 144 (Pt 3):751-760 (1998)). A lysine decarboxylase analogous to CadA was recently identified in *Vibrio parahaemolyticus* (Tanaka, et al., *J Appl Microbiol* 104:1283-1293 (2008)). The lysine decarboxylase from *Selenomonas ruminantium*, encoded by ldc, bears sequence similarity to eukaryotic ornithine decarboxylases, and accepts both L-lysine and L-ornithine as substrates (Takatsuka et al., *Biosci. Biotechnol Biochem.* 63:1843-1846 (1999)). Active site residues were identified and engineered to alter the substrate specificity of the enzyme (Takatsuka et al., *J Bacteriol.* 182:6732-6741 (2000)).

| Gene name | GI# | GenBank Accession # | Organism |
|---|---|---|---|
| cadA | 145458 | AAA23536.1 | *Escherichia coli* |
| ldcC | 1786384 | AAC73297.1 | *Escherichia coli* |
| ldc | 13124043 | O50657.1 | *Selenomonas ruminantium* |
| cadA | 44886078 | AB124819.1 | *Vibrio parahaemolyticus* |

Several ornithine decarboxylase enzymes (EC 4.1.1.17) exhibit activity on lysine and other similar compounds. Such enzymes are found in *Nicotiana glutinosa* (Lee et al., *Biochem. J* 360:657-665 (2001)), *Lactobacillus* sp. 30a (Guirard et al., *J Biol. Chem.* 255:5960-5964 (1980)) and *Vibrio vulnificus* (Lee et al., *J Biol. Chem.* 282:27115-27125 (2007)). The enzymes from *Lactobacillus* sp. 30a (Momany et al., *J Mol. Biol.* 252:643-655 (1995)) and *V. vulnificus* have been crystallized. The *V. vulnificus* enzyme efficiently catalyzes lysine decarboxylation and the residues involved in substrate specificity have been elucidated (Lee et al., *J Biol. Chem.* 282:27115-27125 (2007)). A similar enzyme has been characterized in *Trichomonas vaginalis* but the gene encoding this enzyme is not known (Yarlett et al., *Biochem. J* 293 (Pt 2):487-493 (1993)).

| Gene name | GI# | GenBank Accession # | Organism |
|---|---|---|---|
| AF323910.1: 1 . . . 1299 | 12007488 | AAG45222.1 | *Nicotiana glutinosa* |
| odc1 | 1169251 | P43099.2 | *Lactobacillus* sp. 30a |
| VV2_1235 | 27367615 | NP_763142.1 | *Vibrio vulnificus* |

Keto-acid decarboxylase enzymes are required to convert 2-oxo-7-aminoheptanoate to 6-aminohexanal (Step F of FIG. 22; Step G of FIG. 26) and 2-amino-7-oxosubarate to 2-amino-7-oxoheptanoate (Step A of FIG. 26). The decarboxylation of keto-acids is catalyzed by a variety of enzymes with varied substrate specificities, including pyruvate decarboxylase (EC 4.1.1.1), benzoylformate decarboxylase (EC 4.1.1.7), alpha-ketoglutarate decarboxylase and branched-chain alpha-ketoacid decarboxylase. Pyruvate decarboxylase (PDC), also termed keto-acid decarboxylase, is a key enzyme in alcoholic fermentation, catalyzing the decarboxylation of pyruvate to acetaldehyde. The enzyme from *Saccharomyces cerevisiae* has a broad substrate range for aliphatic 2-keto acids including 2-ketobutyrate, 2-ketovalerate, 3-hydroxypyruvate and 2-phenylpyruvate (Henning et al., *Appl. Environ. Microbiol.* 72:7510-7517 (2006)). This enzyme has been extensively studied, engineered for altered activity, and functionally expressed in *E. coli* (Killenberg-Jabs et al., *Eur. J. Biochem.* 268:1698-1704 (2001); Li, H. and F. Jordan, *Biochemistry*. 38:10004-10012 (1999); and ter Schure et al., *Appl. Environ. Microbiol.* 64:1303-1307 (1998)). The PDC from *Zymomonas mobilus*, encoded by pdc, also has a broad substrate range and has been a subject of directed engineering studies to alter the affinity for different substrates (Siegert et al., *Protein Eng Des Sel* 18:345-357 (2005)). The crystal structure of this enzyme is available (Killenberg-Jabs et al., *Eur. J. Biochem.* 268:1698-1704 (2001)). Other well-characterized PDC candidates include the enzymes from *Acetobacter pasteurians* (Chandra et al., *Arch. Microbiol.* 176:443-451 (2001)) and *Kluyveromyces lactis* (Krieger et al., *Eur. J. Biochem.* 269: 3256-3263 (2002)).

| Gene name | GI# | GenBank Accession # | Organism |
|---|---|---|---|
| pdc | 118391 | P06672.1 | *Zymomonas mobilus* |
| pdc1 | 30923172 | P06169 | *Saccharomyces cerevisiae* |
| pdc | 20385191 | AM21208 | *Acetobacter pasteurians* |
| pdc1 | 52788279 | Q12629 | *Kluyveromyces lactis* |

Like PDC, benzoylformate decarboxylase (EC 4.1.1.7) has a broad substrate range and has been the target of enzyme engineering studies. The enzyme from *Pseudomonas putida* has been extensively studied and crystal structures of this enzyme are available (Hasson et al., *Biochemistry* 37:9918-9930 (1998); and Polovnikova et al., *Biochemistry* 42:1820-1830 (2003)). Site-directed mutagenesis of two residues in the active site of the *Pseudomonas putida* enzyme altered the affinity ($K_m$) of naturally and non-naturally occurring substrates (Siegert et al., *Protein Eng Des Sel* 18:345-357 (2005)). The properties of this enzyme have been further modified by directed engineering (Lingen et al., *Protein Eng* 15:585-593 (2002); and Lingen et al., *Chembiochem.* 4:721-726 (2003)). The enzyme from *Pseudomonas aeruginosa*, encoded by mdlC, has also been characterized experimentally (Barrowman et al., *FEMS Microbiology Letters* 34:57-60 (1986)). Additional gene candidates from *Pseudomonas stutzeri*, *Pseudomonas fluorescens* and other organisms can be inferred by sequence homology or identified using a growth selection system developed in *Pseudomonas putida* (Henning et al., *Appl. Environ. Microbiol.* 72:7510-7517 (2006)).

| Gene name | GI# | GenBank Accession # | Organism |
| --- | --- | --- | --- |
| mdlC | 3915757 | P20906.2 | *Pseudomonas putida* |
| mdlC | 81539678 | Q9HUR2.1 | *Pseudomonas aeruginosa* |
| dpgB | 126202187 | ABN80423.1 | *Pseudomonas stutzeri* |
| ilvB-1 | 70730840 | YP_260581.1 | *Pseudomonas fluorescens* |

A third enzyme capable of decarboxylating 2-oxoacids is alpha-ketoglutarate decarboxylase (KGD). The substrate range of this class of enzymes has not been studied to date. The KDC from *Mycobacterium tuberculosis* (Tian et al., *Proc Natl Acad Sci US.A* 102:10670-10675 (2005)) has been cloned and functionally expressed in other internal projects at Genomatica. However, it is not an ideal candidate for strain engineering because it is large (~130 kD) and GC-rich. KDC enzyme activity has been detected in several species of *rhizobia* including *Bradyrhizobium japonicum* and *Mesorhizobium loti* (Green et al., *J Bacteriol.* 182:2838-2844 (2000)). Although the KDC-encoding gene(s) have not been isolated in these organisms, the genome sequences are available and several genes in each genome are annotated as putative KDCs. A KDC from *Euglena gracilis* has also been characterized but the gene associated with this activity has not been identified to date (Shigeoka and Nakano, *Arch. Biochem. Biophys.* 288:22-28 (1991)). The first twenty amino acids starting from the N-terminus were sequenced MTYKAPVKDVKFLLDKVFKV (SEQ ID NO: 1) (Shigeoka and Nakano, *Arch. Biochem. Biophys.* 288:22-28 (1991)). The gene could be identified by testing candidate genes containing this N-terminal sequence for KDC activity.

| Gene name | GI# | GenBank Accession # | Organism |
| --- | --- | --- | --- |
| kgd | 160395583 | O50463.4 | *Mycobacterium tuberculosis* |
| kgd | 27375563 | NP_767092.1 | *Bradyrhizobium japonicum* |
| kgd | 13473636 | NP_105204.1 | *Mesorhizobium loti* |

A fourth candidate enzyme for catalyzing this reaction is branched chain alpha-ketoacid decarboxylase (BCKA). This class of enzyme has been shown to act on a variety of compounds varying in chain length from 3 to 6 carbons (Oku and Kaneda, *J Biol Chem.* 263:18386-18396 (1988); and Smit et al., *Appl Environ Microbiol.* 71:303-311 (2005)). The enzyme in *Lactococcus lactis* has been characterized on a variety of branched and linear substrates including 2-oxobutanoate, 2-oxohexanoate, 2-oxopentanoate, 3-methyl-2-oxobutanoate, 4-methyl-2-oxobutanoate and isocaproate isocaproate (Smit et al., *Appl Environ Microbiol.* 71:303-311 (2005)). The enzyme has been structurally characterized (Berg et al., *Science.* 318:1782-1786 (2007)). Sequence alignments between the *Lactococcus lactis* enzyme and the pyruvate decarboxylase of *Zymomonas mobilus* indicate that the catalytic and substrate recognition residues are nearly identical (Siegert et al., *Protein Eng Des Sel* 18:345-357 (2005)), so this enzyme would be a promising candidate for directed engineering. Decarboxylation of alpha-ketoglutarate by a BCKA was detected in *Bacillus subtilis*; however, this activity was low (5%) relative to activity on other branched-chain substrates (Oku and Kaneda, *J Biol Chem.* 263:18386-18396 (1988)) and the gene encoding this enzyme has not been identified to date. Additional BCKA gene candidates can be identified by homology to the *Lactococcus lactis* protein sequence. Many of the high-scoring BLASTp hits to this enzyme are annotated as indolepyruvate decarboxylases (EC 4.1.1.74). Indolepyruvate decarboxylase (IPDA) is an enzyme that catalyzes the decarboxylation of indolepyruvate to indoleacetaldehyde in plants and plant bacteria.

| Gene name | GI# | GenBank Accession # | Organism |
| --- | --- | --- | --- |
| kdcA | 44921617 | AAS49166.1 | *Lactococcus lactis* |

Recombinant branched chain alpha-keto acid decarboxylase enzymes derived from the E1 subunits of the mitochondrial branched-chain keto acid dehydrogenase complex from *Homo sapiens* and *Bos taurus* have been cloned and functionally expressed in *E. coli* (Davie et al., *J. Biol. Chem.* 267:16601-16606 (1992); Wynn et al., *J. Biol. Chem.* 267: 1881-1887 (1992); and Wynn et al., *J. Biol. Chem.* 267: 12400-12403 (1992)). In these studies, the authors found that co-expression of chaperonins GroEL and GroES enhanced the specific activity of the decarboxylase by 500-fold (Wynn et al., *J. Biol. Chem.* 267:12400-12403 (1992)). These enzymes are composed of two alpha and two beta subunits.

| Gene name | GI# | GenBank Accession # | Organism |
| --- | --- | --- | --- |
| BCKDHB | 34101272 | NP_898871.1 | *Homo sapiens* |
| BCKDHA | 11386135 | NP_000700.1 | *Homo sapiens* |
| BCKDHB | 115502434 | P21839 | *Bos taurus* |
| BCKDHA | 129030 | P11178 | *Bos taurus* |

4.1.2.a

The condensation of pyruvate with 4-aminobutanal (FIG. 22, Step A) or glutamate-5-semialdehyde (FIG. 27, Step A) is catalyzed by an aldehyde lyase in the EC class 4.1.2. A variety of aldehyde lyase enzymes utilize pyruvate as an acceptor; however, none have been demonstrated to utilize 4-aminobutanal or glutamate-5-semialdehyde as a donor. The enzyme 4-hydroxy-2-oxopimelate (HODH) aldolase (EC 4.1.2.-), condenses succinic semialdehyde and pyruvate to catalyze the formation of 4-hydroxy-2-oxopimelate. This enzyme is a divalent metal ion-dependent class II aldolase, catalyzing the final step of 4-hydroxyphenylacetic acid degradation in *E. coli* C, *E. coli* W, and other organisms. In the native context, the enzyme functions in the degradative direction. The reverse (condensation) reaction is thermodynamically unfavorable; however the equilibrium can be shifted through coupling HODH aldolase with downstream pathway enzymes that work efficiently on reaction products.

Such strategies have been effective for shifting the equilibrium of other aldolases in the condensation direction (Nagata et al., *Appl Microbiol Biotechnol* 44:432-438 (1995); and Pollard et al., *Appl Environ. Microbiol* 64:4093-4094 (1998)). The *E. coli* C enzyme, encoded by hpcH, is able to condense a range of aldehyde acceptors with pyruvate and has recently been crystallized (Rea et al., *J. Mol. Biol.* 373:866-876 (2007); and Stringfellow et al., *Gene* 166:73-76 (1995)). The *E. coli* W enzyme is encoded by hpaI (Prieto et al., *J Bacteriol.* 178:111-120 (1996)).

| Gene name | GI# | GenBank Accession # | Organism |
|---|---|---|---|
| hpcH | 633197 | CAA87759.1 | *Escherichia coli* C |
| hpaI | 38112625 | AAR11360.1 | *Escherichia coli* W |

Another pyruvate-utilizing aldehyde lyase is 2-dehydro-3-deoxyglucarate aldolase (DDGA, EC 4.1.2.20), a type II aldolase that participates in the catabolic pathway for D-glucarate/galactarate utilization in *E. coli*. The natural donor of this enzyme is tartronate semialdehyde, but this enzyme has a broad substrate specificity and has been shown to reversibly condense a wide range of aldehydes with pyruvate (Fish et al., *Methods Enzymol.* 9:529-534 (1966)). The crystal structure of this enzyme has been determined and a catalytic mechanism proposed (Izard et al., *EMBO J* 19:3849-3856 (2000)). Additional candidate DDGA enzymes are found in *Leptospira interrogans* (118) and *Sulfolobus solfataricus* (Buchanan et al., *Biochem. J* 343 Pt 3:563-570 (1999)). The *S. solfataricus* enzyme is highly thermostable and was cloned and expressed in *E. coli* (Buchanan et al., *Biochem. J* 343 Pt 3:563-570 (1999)).

| Gene name | GI# | GenBank Accession # | Organism |
|---|---|---|---|
| garL | 1176153 | P23522.2 | *Escherichia coli* |
| LA_1624 | 24195249 | AAN48823.1 | *Leptospira interrogans* |
| AJ224174.1:1..885 | 2879782 | CAA11866.1 | *Sulfolobus solfataricus* |

4.2.1.a Hydro-Lyase—

Two reactions in FIGS. 20 and 22 employ enzymes in the dehydratase class (EC 4.1.2). The dehydration of 3-hydroxy-6-aminopimeloyl-CoA (FIG. 20, Step D) is catalyzed by an enoyl-CoA hydratase. This reaction is not known to occur naturally; however the ability to dehydrate 3-hydroxyacyl-CoA derivatives is widespread. Enoyl-CoA hydratases (EC 4.2.1.17) catalyze the dehydration of a range of 3-hydroxyacyl-CoA substrates (Agnihotri et al., *Bioorg. Med. Chem.* 11:9-20 (2003; Conrad et al., *J Bacteriol.* 118:103-111 (1974) and Roberts et al., *Arch. Microbiol* 117:99-108 (1978)). The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). Additional enoyl-CoA hydratase candidates are phaA and phaB, of *P. putida*, and paaA and paaB from *P. fluorescens* (Olivera et al., *Proc. Natl. Acad. Sci U.S.A* 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol.* 185:5391-5397. 2003), paaF (Ismail et al., *Eur. J Biochem.* 270:3047-3054 (2003); Park et al., *Appl. Biochem. Biotechnol* 113-116:335-346 (2004) and (Park et al., *Biotechnol Bioeng* 86:681-686 (2004)) and paaG (Park et al., *J Bacteriol.* 185:5391-5397. 2003), paaF (Ismail et al., *Eur. J Biochem.* 270:3047-3054 (2003); Park et al., *Appl. Biochem. Biotechnol* 113-116:335-346 (2004) and (Park et al., *Biotechnol Bioeng* 86:681-686 (2004)).

| Gene name | GI# | GenBank Accession # | Organism |
|---|---|---|---|
| ech | 26990073 | NP_745498.1 | *Pseudomonas putida* |
| paaA | 26990002 | NP_745427.1 | *Pseudomonas putida* |
| paaB | 26990001 | NP_745426.1 | *Pseudomonas putida* |
| phaA | 106636093 | ABF82233.1 | *Pseudomonas fluorescens* |
| phaB | 106636094 | ABF82234.1 | *Pseudomonas fluorescens* |
| pimF | 39650635 | CAE29158 | *Rhodopseudomonas palustris* |
| maoC | 16129348 | NP_415905.1 | *Escherichia coli* |
| paaF | 16129354 | NP_415911.1 | *Escherichia coli* |
| paaG | 16129355 | NP_415912.1 | *Escherichia coli* |

3-Hydroxybutyryl-CoA dehydratase (EC 4.2.1.55), also called crotonase, is an enoyl-CoA hydratase that dehydrates 3-hydroxyisobutyryl-CoA to form crotonyl-CoA. Crotonase enzymes are required for n-butanol formation in some organisms, particularly Clostridial species, and also comprise one step of the 3-hydroxypropionate/4-hydroxybutyrate cycle in thermoacidophilic Archaea of the genera *Sulfolobus*, *Acidianus*, and *Metallosphaera*. Exemplary genes encoding crotonase enzymes can be found in *C. acetobutylicum* (Atsumi et al., *Metab Eng.* 10:305-311 (2008); and Boynton et al., *J Bacteriol.* 178:3015-3024 (1996)), *C. kluyveri* (Hillmer et al., *FEBS Lett.* 21:351-354. 1972)), and *Metallosphaera sedula* (Berg et al., *Science.* 318:1782-1786 (2007)) though the sequence of the latter gene is not known.

| Gene name | GI# | GenBank Accession # | Organism |
|---|---|---|---|
| crt | 15895969 | NP_349318.1 | *Clostridium acetobutylicum* |
| crt1 | 153953091 | YP_001393856.1 | *Clostridium kluyveri* |

Alternatively, the *E. coli* gene products of fadA and fadB encode a multienzyme complex involved in fatty acid oxidation that exhibits enoyl-CoA hydratase activity (Nakahigashi et al., *Nucleic Acids Res.* 18:4937 (1990); Yang et al., *J Bacteriol.* 173:7405-7406 (1991) and Yang et al., *Biochemistry* 30:6788-6795 (1991)). Knocking out a negative regulator encoded by fadR can be utilized to activate the fadB gene product (Sato et al., *J Biosci. Bioeng* 103:38-44 (2007)). The fadI and fadJ genes encode similar functions and are naturally expressed under anaerobic conditions (Campbell et al., *Mol. Microbiol* 47:793-805 (2003)).

| Gene name | GI# | GenBank Accession # | Organism |
|---|---|---|---|
| fadA | 49176430 | YP_026272.1 | *Escherichia coli* |
| fadB | 16131692 | NP_418288.1 | *Escherichia coli* |
| fadI | 16130275 | NP_416844.1 | *Escherichia coli* |
| fadJ | 16130274 | NP_416843.1 | *Escherichia coli* |
| fadR | 16129150 | NP_415705.1 | *Escherichia coli* |

2-Oxo-7-aminohept-3-enoate is formed from the dehydration of 2-oxo-4-hydroxy-7-aminoheptanoate (FIG. 22, Step B). The dehydration of 2-amino-5-hydroxy-7-oxosubarate to 2-amino-5-ene-7-oxosubarate (FIG. 27, Step B) is a similar transformation. Enzymes catalyzing these exact reactions are not known to occur naturally. A candidate enzyme that catalyzes a similar reaction is OHED hydratase, which naturally dehydrates 2-oxo-4-hydroxy-hepta-1,7-dioate (HODH) to 2-oxo-hept-4-ene-1,7-dioate (OHED) HODH is similar in structure to the desired substrates. This enzyme requires magnesium as a cofactor (Burks et al., *J. Am. Chem. Soc.* 120 (1998)). OHED hydratase enzyme candidates have been identified and characterized in *E. coli* C (Izumi et al., *J Mol. Biol.* 370:899-911 (2007; and Roper et al., *Gene* 156:47-51 (1995)) and *E. coli* W (Prieto et al., *J Bacteriol.* 178:111-120 (1996)). Sequence comparison reveals homologs in a range of bacteria, plants and animals. Enzymes with highly similar sequences are contained in *Klebsiella pneumonia* (91% identity, evalue=2e-138) and *Salmonella enterica* (91% identity, evalue=4e-138), among others.

| Gene name | GI# | GenBank Accession # | Organism |
|---|---|---|---|
| hpcG | 556840 | CAA57202.1 | *Escherichia coli* C |
| hpaH | 757830 | CAA86044.1 | *Escherichia coli* W |
| hpaH | 150958100 | ABR80130.1 | *Klebsiella pneumoniae* |
| Sari_01896 | 160865156 | ABX21779.1 | *Salmonella enterica* |

An alternate enzyme candidate for catalyzing this reaction is fumarase, also known as fumarate hydratase (EC 4.2.1.2). *E. coli* has three fumarases: FumA, FumB, and FumC that are regulated by growth conditions. FumB is oxygen sensitive and only active under anaerobic conditions. FumA is active under microanaerobic conditions, and FumC is the only active enzyme in aerobic growth (Guest et al., *J Gen Microbiol.* 131:2971-2984 (1985); Tseng et al., *J Bacteriol* 183:461-467 (2001) and Woods et al., *Biochim Biophys Acta* 954:14-26 (1988)). FumC has been shown to dehydrate alternate substrates including tartrate and threo-hydroxyaspartate (Teipel et al., *J Biol. Chem.* 243:5684-5694 (1968)). A wealth of structural information is available for FumC and researchers have successfully engineered the enzyme to alter activity, inhibition and localization (Weaver et al., *D Biol Crystallogr.* 61:1395-1401 (2005)). Additional fumarate hydratase enzymes are found in *Escherichia coli* (Estevez et al., *Protein Sci* 11:1552-1557 (2002); Hong, et al., *Biotechnol. Bioprocess Eng.* 9:252-255 (2005)) and Rose et al., *Proc Natl Acad Sci US. A* 101:3393-3397 (2004)), *Corynebacterium glutamicum* (Genda et al., *Biotechnol Biochem.* 70:1102-1109 (2006)), *Campylobacter jejuni* (Smith et al., *Cell Biol* 31:961-975 (1999)), *Thermus thermophilus* (Mizobata et al., *Arch. Biochem. Biophys.* 355:49-55 (1998)), and *Rattus norvegicus* (Kobayashi et al., *J Biochem.* 89:1923-1931 (1981)). The MmcBC fumarase from *Pelotomaculum thermopropionicum* is another class of fumarase with two subunits (Shimoyama et al., *FEMS Microbiol Lett* 270:207-213 (2007)).

| Gene name | GI# | GenBank Accession # | Organism |
|---|---|---|---|
| fumA | 81175318 | P0AC33 | *Escherichia coli* K12 |
| fumB | 33112655 | P14407 | *Escherichia coli* K12 |
| fumC | 120601 | P05042.1 | *Escherichia coli* K12 |
| fumC | 39931596 | Q8NRN8.1 | *Corynebacterium glutamicum* |
| fumC | 9789756 | O69294.1 | *Campylobacter jejuni* |
| fumC | 75427690 | P84127 | *Thermus thermophilus* |
| fumH | 120605 | P14408.1 | *Rattus norvegicus* |
| MmcB | 147677691 | YP_001211906 | *Pelotomaculum thermopropionicum* |
| MmcC | 147677692 | YP_001211907 | *Pelotomaculum thermopropionicum* |

Another enzyme candidate is citramalate hydrolyase (EC 4.2.1.34), an enzyme that naturally dehydrates 2-methylmalate to mesaconate. This enzyme has been studied in *Methanocaldococcus jannaschii* in the context of the pyruvate pathway to 2-oxobutanoate, where it has been shown to have a broad substrate specificity (Drevland et al., *J Bacteriol.* 189:4391-4400 (2007)). This enzyme activity was also detected in *Clostridium tetanomorphum, Morganella morganii, Citrobacter amalonaticus* where it is thought to participate in glutamate degradation (Kato et al., *Arch. Microbiol* 168:457-463 1997)). The *M. jannaschii* protein sequence does not bear significant homology to genes in these organisms.

| Gene name | GI# | GenBank Accession # | Organism |
|---|---|---|---|
| leuD | 3122345 | Q58673.1 | *Methanocaldococcus jannaschii* |

5.4.3.a Aminomutase—Several reactions in FIG. 21 involve shifting a secondary amine from the 3- to the 2-position (FIG. 21, Steps P, R, T). A promising enzyme candidate for catalyzing these transformations is lysine 2,3-aminomutase (EC 5.4.3.2), an enzyme that naturally converts lysine to (3S)-3,6-diaminohexanoate, reversibly shifting an amine group from the 2- to the 3-position. The enzyme is found in bacteria that ferment lysine to acetate and butyrate, including *Fusobacterium nucleatum* (kamA) (Barker et al., *J Bacteriol.* 152:201-207 (1982)) and *Clostridium subterminale* (kamA) (Chirpich et al., *J Biol. Chem.* 245:1778-1789 (1970)). The enzyme from *Clostridium subterminale* has been crystallized (117). An enzyme encoding this function is also encoded by yodO in *Bacillus subtilis* (Chen et al., *Biochem. J.* 348 Pt 3:539-549 (2000)). The enzyme utilizes pyridoxal 5'-phosphate as a cofactor, requires activation by S-adenosylmethoionine, and is stereoselective for L-lysine. The enzyme has not been shown to react with alternate substrates, so directed evolution or other engineering methods may be required for this enzyme to react with the non-natural substrates 3-amino-7-oxohexanoate, 3,7-diaminoheptanoate and 3-aminopimelate. For example, Cargill has developed a novel 2,3-aminomutase enzyme derived from lysine-2,3-aminomutase that converts L-alanine to β-alanine (Liao et al., United States Patent 20050221466 (2005)).

| Gene name | GI# | GenBank Accession # | Organism |
|---|---|---|---|
| kamA | 75423266 | Q9XBQ8.1 | *Clostridium subterminale* |
| kamA | 81485301 | Q8RHX4 | *Fusobacterium nucleatum* |
| yodO | 4033499 | O34676.1 | *Bacillus subtilis* |

Other enzymes with 2,3-aminomutase activity include tyrosine 2,3-aminomutase (EC 5.4.3.6) and leucine 2,3-aminomutase (EC 5.4.3.7). Tyrosine 2,3-aminomutase participates in tyrosine biosynthesis, reversibly converting tyrosine to 3-amino-3-(4-hydroxyphenyl)-propionoate by shifting an amine from the 2- to the 3-position. In *Streptomyces globisporus* the enzyme has also been shown to react with tyrosine derivatives (Christenson et al., *Biochemistry* 42:12708-12718 (2003)); however, the sequence of this enzyme is not yet available. Leucine 2,3-aminomutase converts L-leucine to beta-leucine during leucine biosynthesis and degradation. A leucine 2,3-aminomutase-specific assay detected enzyme activity in many organisms (Poston et al., *Methods Enzymol.* 166:130-135 (1988)) but genes encoding the enzyme have not been identified to date.

6.2.1.a Acid-Thiol Ligase—

The activation of carboxylic acids to acyl-CoA derivatives is catalyzed by CoA acid-thiol ligases or CoA synthetases in the EC class 6.2.1 (the terms ligase, synthetase, and synthase are used herein interchangeably and refer to the same enzyme class). Such enzymes couple the energetic cost of thioester bond formation to the hydrolysis of ATP into ADP or AMP. Several ADP-forming CoA ligases have been demonstrated to react in the reverse direction, removing the CoA moiety from acyl-CoA molecules and concomitantly forming ATP. Reversible CoA ligases are required to de-acylate 6-aminopimeloyl-CoA (FIG. 20, Step I) and 3-oxopimeloyl-CoA (FIG. 21, Step B), whereas AMP or ADP forming ligases can acylate 3-oxopimelate (FIG. 21, Step H), 3-aminopimelate (FIG. 21, Step K) and 2-aminopimelate (FIG. 21, Step V). Enzymes catalyzing these exact transformations have not been characterized to date; however, several enzymes with broad substrate specificities have been described in the literature.

ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., *J Bacteriol.* 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt et al., *J Bacteriol.* 184:636-644 (2002)). The enzyme from *Haloarcula marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch. Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al., *Arch. Microbiol* 182:277-287 (2004)). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen et al., *Arch. Microbiol* 182:277-287 (2004); and Musfeldt et al., *J Bacteriol.* 184: 636-644 (2002)). An additional candidate is the enzyme encoded by sucCD in *E. coli*, which naturally catalyzes the formation of succinyl-CoA from succinate with the concomitant consumption of one ATP, a reaction which is reversible in vivo (Buck et al., *Biochemistry* 24:6245-6252 (1985)).

| Gene name | GI# | GenBank Accession # | Organism |
|---|---|---|---|
| AF1211 | 11498810 | NP_070039.1 | *Archaeoglobus fulgidus* DSM 4304 |
| AF1983 | 11499565 | NP_070807.1 | *Archaeoglobus fulgidus* DSM 4304 |
| scs | 55377722 | YP_135572.1 | *Haloarcula marismortui* |
| PAE3250 | 18313937 | NP_560604.1 | *Pyrobaculum aerophilum* str. IM2 |
| sucC | 16128703 | NP_415256.1 | *Escherichia coli* |
| sucD | 1786949 | AAC73823.1 | *Escherichia coli* |

Another candidate enzyme is the AMP-forming pimeloyl-CoA ligase (EC 6.2.1.14) which naturally activates pimelate to pimeloyl-CoA during biotin biosynthesis in gram-positive bacteria. The enzyme from *Pseudomonas mendocina*, cloned into *E. coli*, was shown to accept the alternate substrates hexanedioate and nonanedioate (Binieda et al., *Biochem. J* 340 (Pt 3):793-801 (1999)). Other pimeloyl-CoA ligase candidates are found in *Bacillus subtilis* (Bower et al., *J Bacteriol.* 178:4122-4130 (1996)) and *Lysinibacillus sphaericus* (formerly *Bacillus sphaericus*) (Ploux et al., *Biochem. J* 287 (Pt 3):685-690 (1992)).

| Gene name | GI# | GenBank Accession # | Organism |
|---|---|---|---|
| pauA | 15596214 | NP_249708.1 | *Pseudomonas mendocina* |
| bioW | 50812281 | NP_390902.2 | *Bacillus subtilis* |
| bioW | 115012 | P22822.1 | *Lysinibacillus sphaericus* |

Additional CoA-ligases include the rat dicarboxylate-CoA ligase for which the sequence is yet uncharacterized (Vamecq et al., *Biochem J* 230:683-693 (1985)), either of the two characterized phenylacetate-CoA ligases from *P. chrysogenum* (Lamas-et al., Maceiras, J 395:147-155 (2006); and Wang et al., *Biophys. Res. Commun.* 360:453-458 (2007)) and the phenylacetate-CoA ligase from *Pseudomonas putida* (Martinez-Blanco et al., *J Biol. Chem.* 265:7084-7090 (1990)). Acetoacetyl-CoA synthetases from *Mus musculus* (Hasegawa et al., *Biochim. Biophys. Acta* 1779:414-419 (2008)) and *Homo sapiens* (Ohgami et al., *Biochem. Pharmacol.* 65:989-994 (2003)) naturally catalyze the ATP-dependent conversion of acetoacetate into acetoacetyl-CoA.

| Gene name | GI# | GenBank Accession # | Organism |
|---|---|---|---|
| phl | 77019264 | CAJ15517.1 | *Penicillium chrysogenum* |
| phlB | 152002983 | ABS19624.1 | *Penicillium chrysogenum* |
| paaF | 22711873 | AAC24333.2 | *Pseudomonas putida* |
| AACS | 21313520 | NP_084486.1 | *Mus musculus* |
| AACS | 31982927 | NP_076417.2 | *Homo sapiens* |

Example XXVII

Additional Pathways for Production of Hexamethylenediamine from 6-Aminocaproate

FIG. 24 provides additional pathways for HMDA production and is further to FIG. 13 and Example XX above. Arrows for Steps 0 and P indicate the direct conversion of 6-aminocaproate and 6-acetamidohexanoate to 6-aminocaproic semialdehyde and 6-acetamidohexanal, respectively.

These reactions are catalyzed by a reductase in EC class 1.2.1.e. For a description of enzyme candidates, see Example XXVI (EC 1.2.1.e).

Example XXVIII

Pathways for Production of 6-Aminocaproate from Adipate

FIG. 25 provides additional pathways for 6-ACA production and is further to FIG. 10 and Example XVI above. The conversion of adipate to adipate semialdehyde (FIG. 25, Step X) is catalyzed by an enzyme with adipate reductase functionality. Adipate kinase catalyzes the formation of adipylphosphate from adipate (FIG. 25, Step Y). Adipate semialdehyde is formed from adipylphosphate by adipylphosphate reductase (FIG. 25, Step Z). Enzyme candidates for catalyzing these transformations are described in Example XXVI.

Example XXIX

Pathway for Production of Levulinic Acid

Levulinic acid (LA), also known as 4-oxopentanoic acid and 4-ketovaleric acid, is a precursor to nylon-like polymers, synthetic rubbers and plastics. It is also a precursor of other commodity chemicals such as methyltetrahydrofuran, valerolactone and ethyl levulinate. Other potential applications include use as a fuel extender and a biodegradable herbicide/pesticide. It is traditionally prepared by treating cellulosic biomass with strong acids such as hydrochloric and sulfuric acids. This process has the disadvantages of low LA yield and numerous byproducts. More recently, the Biofine Process was developed which converts cellulosic biomass into LA, formic acid and furfural at a yield of 70% the theoretical maximum (Hayes et al., "The biofine process—production of levulinic acid, furfural and formic acid from lignocellulosic feedstock" p. 139-164. In Biorefineries: Industrial Processes and Products. Wiley, Weinheim, Germany (2006)). Described herein is a process for selectively producing LA from sugar or syngas feedstocks using a microbial organism.

The maximum theoretical yield of LA from glucose is 1.45 moles of LA per mole glucose utilized (0.938 g/g), according to the following equation:

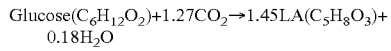

LA is produced from the central metabolites succinyl-CoA and acetyl-CoA in three enzymatic steps. In the first step, acetyl-CoA and succinyl-CoA are condensed by a beta-ketothiolase to form 3-oxoadipyl-CoA (Step A of FIG. 25). The CoA moiety is subsequently removed by a CoA hydrolase, transferase or ligase (Steps E/F/G of FIG. 25). In the final step of the pathway, 3-oxoadipate is decarboxylated to LA (Step AA of FIG. 25).

The decarboxylation of 3-oxoadipate to LA can occur enzymatically or spontaneously. In *E. coli*, several 3-oxoacids produced during amino acid biosynthesis have been shown to undergo spontaneous decarboxylation (Boylan et al., *Biochem. Biophys. Res Commun.* 85:190-197 (1978)). An enzyme catalyzing the decarboxylation of 3-oxoadipate to LA has not been demonstrated to our knowledge. An exemplary enzyme candidate catalyzing a similar reaction is acetoacetate decarboxylase (EC 4.1.1.4). The acetoacetate decarboxylase from *Clostridium acetobutylicum*, encoded by adc, has a broad substrate specificity and has been shown to decarboxylate 3-oxopentanoate, 2-oxo-3-phenylpropionic acid and 2-methyl-3-oxobutyrate (Benner et al., *J. Am. Chem. Soc.* 103:993-994 (1981) and Rozzel et al., *J. Am. Chem. Soc.* 106:4937-4941 (1984)). An acetoacetate decarboylase has also been characterized in *Clostridium beijerinckii* (Ravagnani et al., *Mol. Microbiol* 37:1172-1185 (2000)). The acetoacetate decarboxylase from *Bacillus polymyxa*, characterized in cell-free extracts, also has a broad substrate specificity for 3-keto acids and can decarboxylate 3-oxopentanoate (Matiasek et al., *Curr. Microbiol* 42:276-281 (2001)). The gene encoding this enzyme has not been identified to date and the genome sequence of *B. polymyxa* is not yet available. Another adc is found in *Clostridium saccharoperbutylacetonicum* (Kosaka, et al., *Biosci. Biotechnol Biochem.* 71:58-68 (2007)).

| Gene name | GI# | GenBank Accession # | Organism |
|---|---|---|---|
| adc | 15004868 | NP_149328.1 | *Clostridium acetobutylicum* |
| adc | 31075386 | AAP42566.1 | *Clostridium saccharoperbutylacetonicum* |
| cbei_3835 | 150018652 | YP_001310906.1 | *Clostridium beijerinckii* |

Example XXX

In Silico Knockout Strategies for Production of Adipate, 6-ACA and HMDA

This example describes gene disruption strategies for production of adipate 6-aminocaproic acid (6-ACA) and hexamethylenediamine (HMDA).

Described below in more detail are sets of enzymatic activities that can be reduced by appropriate gene disruptions or deletions in a production host engineered to contain the adipate, 6-aminocaproic acid (6-ACA) and hexamethylenediamine (HMDA) production pathways, for example, pathways using succinyl CoA and acetyl CoA as precursors.

OptKnock is a bilevel computational framework formulated with the overall objective of developing genetically stable overproducing microorganisms. Specifically, the framework examines the complete network of a microorganism in order to suggest genetic manipulations that force the desired biochemical to become an obligatory byproduct of cell growth. By coupling biochemical production with cell growth through strategically placed gene disruptions or deletions, the growth selection pressures imposed on the engineered strains after long periods of time in a bioreactor lead to improvements in performance as a result of the compulsory growth-coupled biochemical production. Lastly, in the case of a gene deletion, there is negligible possibility of the designed strains reverting to their wild-type states because the genes selected by OptKnock are completely removed from the genome.

Growth-coupled biochemical production can be visualized in the context of the biochemical production envelopes of a typical metabolic network calculated using an in silico model. These limits are obtained by fixing the uptake rate(s) of the limiting substrate(s) to their experimentally measured value(s) and calculating the maximum and minimum rates of biochemical production at each attainable level of growth. Although exceptions exist, typically the production of a desired biochemical is in direct competition with biomass formation for intracellular resources. Thus, enhanced rates of biochemical production will generally result in submaximal growth rates. The knockouts suggested by OptKnock are designed to restrict the allowable solution boundaries forcing a change in metabolic behavior from the wild-type strain. Although the actual solution boundaries for a given strain will expand or contract as the substrate uptake rate(s) increase or decrease, each experimental point should lie within its calculated solution boundary. Plots such as these allow visualization of how close strains are to their performance limits or, in other words, how much room is available for improvement. The OptKnock framework has been used to identify promising gene deletion strategies for biochemical overproduction and establishes a systematic framework that will naturally encompass future improvements in metabolic and regulatory modeling frameworks.

Described below are sets of enzyme activities that should be absent, attenuated, or eliminated for creating host organisms that achieve growth-coupled adipate, 6-ACA or HMDA production upon the addition of the biosynthetic pathway that proceeds through succinyl-CoA and acetyl-CoA. To enumerate all potential strategies, an optimization technique, termed integer cuts, has been implemented which entails iteratively solving the OptKnock problem with the incorporation of an additional constraint referred to as an integer cut at each iteration.

The OptKnock algorithm was used to identify designs based on a stoichiometric model of *Escherichia coli* metabolism. Assumptions include (i) a glucose uptake rate of 10 mmol/gdw/hr; (ii) anaerobic or microaerobic conditions; and (iii) a minimum non-growth associated maintenance requirement of 4 mmol/gdw/hr. Table 12 provides a list of all the reaction stoichiometries and the associated genes known to be associated with the reactions identified for deletion in the strategies. Table 13 provides a list of the metabolite abbreviations, the corresponding names and locations of all the metabolites that participate in the reactions listed in Table 12. The growth-coupled productions designs for adipic acid, GACA and HMDA are provided in Tables 14-16. The product formation rates shown in Tables 14-16 are in mmol/gDCW·hr. The basis glucose uptake rate is 10 mmol/gDCW·hr and the biomass formation rate is shown in units of 1/hr. These tables list the reactions that are knocked out in a particular strategy, the anticipated product and biomass yields. Although the designs were identified using a metabolic model of *E. coli* metabolism, and the gene names listed are specific to *E. coli*, the method of choosing the metabolic engineering strategies and also the designs themselves are applicable to any HMDA, 6-ACA or adipate-producing organism. Thus the designs are essentially lists of enzymatic transformations whose activity is to be either eliminated, attenuated, or initially absent from a microorganism to provide the growth coupled production of adipate, GACA and HMDA.

The key criterion for prioritizing the final selection of designs was the growth-coupled yield of each of the products. To examine this, production cones were constructed for each strategy by first maximizing and, subsequently minimizing the product yields at different rates of biomass formation, as described above. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs were given a lower priority.

The metabolic engineering strategies described below assume that the organism can produce adipate, 6-ACA or HMDA via the succinyl CoA and acetyl-CoA utilizing pathway. The construction of a recombinant host organism capable of producing these products via the pathway is described herein.

Strain Construction:

In order to validate the computational predictions proposed in this report, the strains are constructed, evolved, and tested. *Escherichia coli* K-12 MG1655 housing the succinyl-CoA-acetyl-CoA pathway serves as the strain into which the deletions are introduced. The strains are constructed by incorporating in-frame deletions using homologous recombination via the λ Red recombinase system of Datsenko and Wanner (*Proc. Natl. Acad. Sci. USA* 97(12):6640-6645 2000)). The approach involves replacing a chromosomal sequence, that is, the gene targeted for removal, with a selectable antibiotic resistance gene, which itself is later removed. The knockouts are integrated one by one into the recipient strain. No antibiotic resistance markers remain after each deletion, allowing accumulation of multiple mutations in each target strain. The deletion technology completely removes the gene targeted for removal so as to substantially reduce the possibility of the constructed mutants reverting back to the wild-type.

Shake Flask Characterization:

As intermediate strains are being constructed, strain performance is quantified by performing shake flask fermentations. Anaerobic conditions are obtained by sealing the flasks with a rubber septum and then sparging the medium with nitrogen. For strains where growth is not observed under strict anaerobic conditions, microaerobic conditions can be applied by covering the flask with foil and poking a small hole for limited aeration. All experiments are performed using M9 minimal medium supplemented with glucose unless otherwise stated. Pre-cultures are grown overnight and used as inoculum for a fresh batch culture for which measurements are taken during exponential growth. The growth rate is determined by measuring optical density using a spectrophotometer (600 nm), and the glucose uptake rate by monitoring carbon source depletion over time. The products, ethanol, and organic acids are analyzed by GC-MS or HPLC using routine procedures. Triplicate cultures are grown for each strain.

Batch Fermenter Testing:

The performance of select strains is tested in anaerobic, pH-controlled batch fermentations. This allows reliable quantification of the growth, glucose uptake, and formation rates of all products, as well as ensure that the accumulation of acidic fermentation products will not limit cell growth. In addition, it allows accurate determination of volumetric productivity and yield of product formation, two of the most important parameters in benchmarking strain performance. Fermentations are carried out in 1-L bioreactors with 600 mL working volume, equipped with temperature and pH control. The reactor is continuously sparged with $N_2$ at approximately 0.5 L/min to ensure that dissolved oxygen (DO) levels remain below detection levels. The culture medium is the same as described above, except that the glucose concentration is increased in accordance with the higher cell density achievable in a fermentation vessel.

Chemostat Testing:

Chemostat experiments are conducted to obtain a direct measure of how the switch in fermentation mode from batch to continuous affects product yield and volumetric productivity. The bioreactors described above using batch mode are operated in chemostat mode through continuous supply of medium and removal of spent culture. The inlet flow rate is set to maintain a constant dilution rate of 80% of the maximum growth rate observed for each strain in batch, and the outlet flow is controlled to maintain level. Glucose is the limiting nutrient in the medium, and set to achieve the desired optical density in the vessel.

Adaptive Evolution:

The knockout strains are initially expected to exhibit suboptimal growth rates until their metabolic networks have adjusted to their missing functionalities. To allow this adjustment, the strains is adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36(10):1056-1058 (2004). The OptKnock-generated strains are adaptively evolved in triplicate (running in parallel) due to differences in the evolutionary patterns witnessed previously in *E. coli* (Fong and Palsson, *Nat Genet.* 36(10):1056-1058 (2004); Fong et al., *J. Bacteriol.* 185(21):6400-6408 (2003); Ibarra et al., *Nature* 420(6912):186-189 (2002)) that could potentially result in one strain having superior production qualities over the others. Evolutions are run for a period of 2-6 weeks, depending upon the rate of growth improvement attained. In general, evolutions are stopped once a stable phenotype is obtained. The growth-coupled biochemical production concept behind the OptKnock approach results in the generation of genetically stable overproducers.

Although described as deletion sets, it is understood, as disclosed herein, that gene sets can be deleted or disrupted so that encoded gene product activities are reduced or eliminated. Thus, the gene deletion sets of Tables 14-16 can be used to delete or disrupt a gene set in a host organism in which an increased production of 6-ACA, adipate and/or HMDA is desired. It is understood that any of the disclosed gene deletion sets can be used to generate knockout strains with disrupted or deleted genes that confer increased production of 6-ACA, adipate and/or HMDA.

TABLE 12

A list of all the reaction stoichiometries and the associated genes known to be associated with the reactions identified for deletion in the strategies listed in Tables 1 and 2.

| Reaction Abbreviation | Reaction Name | Reaction Stoichiometry | Associated genes |
|---|---|---|---|
| ACKr | Acetate kinase | [c]: ac + atp <==> actp + adp | (b3115 or b2296 or b1849) |
| ADHEr | Alcohol dehydrogenase | [c]: accoa + (2) h + (2) nadh <==> coa + etoh + (2) nad | (b0356 or b1478 or b1241) |
| AKGD | Alpha-ketoglutarate dehydrogenase | [c]: akg + coa + nad --> co2 + nadh + succoa | (b0116 and b0726 and b0727) |
| ALAR | Alanine racemase | [c]: ala-L <==> ala-D | b4053 |
| ASNS2 | Asparagine synthetase | [c]: asp-L + atp + nh4 --> amp + asn-L + h + ppi | b3744 |
| ASPT | L-aspartase | [c]: asp-L --> fum + nh4 | b4139 |
| ATPS4r | ATP synthase | adp[c] + (4) h[p] + pi[c] <==> atp[c] + (3) h[c] + h2o[c] | (((b3736 and b3737 and b3738) and (b3731 and b3732 and b3733 and b3734 and b3735)) or ((b3736 and b3737 and b3738) and (b3731 and b3732 and b3733 and b3734 and b3735) and b3739)) |
| CBMK2 | Carbamate kinase | [c]: atp + co2 + nh4 --> adp + cbp + (2) h | (b0521 or b0323 or b2874) |
| DAAD | D-amino acid dehydrogenase | [c]: ala-D + fad + h2o --> fadh2 + nh4 + pyr | b1189 |
| EDA | 2-dehydro-3-deoxy-phosphogluconate aldolase | [c]: 2ddg6p --> g3p + pyr | b1850 |
| ENO | Enolase | [c]: 2pg <==> h2o + pep | b2779 |
| FBA | Fructose-bis-phosphate aldolase | [c]: fdp <==> dhap + g3p | (b2097 or b2925 or b1773) |
| FRD | Fumarate reductase | [c]: fum + mql8 --> mqn8 + succ | (b4151 and b4152 and b4153 and b4154) |
| FUM | Fumarase | [c]: fum + h2o <==> mal-L | (b1612 or b4122 or b1611) |
| G5SD | Glutamate-5-semialdehyde dehydrogenase | [c]: glu5p + h + nadph --> glu5sa + nadp + pi | b0243 |
| G6PDHy | Glucose-6-phosphate dehydrogenase | [c]: g6p + nadp <==> 6pgl + h + nadph | b1852 |
| GLCpts | D-glucose transport via PTS mechanism | glc-D[e] + pep[c] --> g6p[c] + pyr[c] | ((b2417 and b1101 and b2415 and b2416) or (b1817 and b1818 and b1819 and b2415 and b2416) or (b2417 and b1621 and b2415 and b2416)) |
| GLU5K | Gluatmate-5-kinase | [c]: atp + glu-L --> adp + glu5p | b0242 |
| GLUDy | Glutamate dehydrogenase | [c]: glu-L + h2o + nadp <==> akg + h + nadph + nh4 | b1761 |
| HEX1 | Hexokinase | [c]: atp + glc-D --> adp + g6p + h | b2388 |
| LDH_D | Lactate dehydrogenase | [c]: lac-D + nad <==> h + nadh + pyr | b1380 or b2133 |
| MDH | Malate dehydrogenase | [c]: mal-L + nad <==> h + nadh + oaa | b3236 |

TABLE 12-continued

A list of all the reaction stoichiometries and the associated genes known to be associated with the reactions identified for deletion in the strategies listed in Tables 1 and 2.

| Reaction Abbreviation | Reaction Name | Reaction Stoichiometry | Associated genes |
|---|---|---|---|
| ME1x | Malic enzyme (NAD) | [c]: mal-L + nad --> co2 + nadh + pyr | b1479 |
| ME2 | Malic enzyme (NADP) | [c]: mal-L + nadp --> co2 + nadph + pyr | b2463 |
| NADH12 | NADH dehydrogenase (ubiquinone-8) | [c]: h + nadh + ubq8 --> nad + ubq8h2 | b1109 |
| NADH6 | NADH dehydrogenase (ubiquinone-8 and 3.5 protons) | (4.5) h[c] + nadh[c] + ubq8[c] --> (3.5) h[e] + nad[c] + ubq8h2[c] | (b2276 and b2277 and b2278 and b2279 and b2280 and b2281 and b2282 and b2283 and b2284 and b2285 and b2286 and b2287 and b2288) |
| PDH | Pyruvate dehydrogenase | [c]: coa + nad + pyr --> accoa + co2 + nadh | ((b0114 and b0115 and b0116) or (b0116 and b0726 and b0727) or (b0116 and b2903 and b2904 and b2905)) |
| PFK | Phosphofructokinase | [c]: atp + f6p --> adp + fdp + h | (b3916 or b1723) |
| PFLi | Pyruvate formate lyase | [c]: coa + pyr --> accoa + for | (((b0902 and b0903) and b2579) or (b0902 and b0903) or (b0902 and b3114) or (b3951 and b3952)) |
| PGDH | Phosphogluconate dehyrogenase | [c]: 6pgc + nadp --> co2 + nadph + ru5p-D | b2029 |
| PGDHY | Phosphogluconate dehydratase | [c]: 6pgc --> 2ddg6p + h2o | b1851 |
| PGI | Glucose-6-phosphate isomerase | [c]: g6p <==> f6p | b4025 |
| PGL | 6-Phosphogluconolactonase | [c]: 6pgl + h2o --> 6pgc + h | b0767 |
| PGM | Phosphoglycerate mutase | [c]: 3pg <==> 2pg | b3612 |
| PPC | Phosphoenolpyruvate carboxylase | [c]: co2 + h2o + pep --> h + oaa + pi | b3956 |
| PPCK | Phosphoenolpyruvate carboxykinase | [c]: atp + oaa --> adp + co2 + pep | b3403 |
| PRO1z | Proline oxidase | [c]: fad + pro-L --> 1pyr5c + fadh2 + h | b1014 |
| PTAr | Phosphotransacetylase | [c]: accoa + pi <==> actp + coa | b2297 |
| PYK | Pyruvate kinase | [c]: adp + h + pep --> atp + pyr | (b1854 or b1676) |
| RPE | Ribulose-5-phosphate-5-epimerase | [c]: ru5p-D <==> xu5p-D | (b4301 or b3386) |
| SUCD4 | Succinate dehydrogenase | [c]: fadh2 + ubq8 <==> fad + ubq8h2 | (b0721 and b0722 and b0723 and b0724) |
| SUCOAS | Succinyl-CoA synthetase | [c]: atp + coa + succ <==> adp + pi + succoa | (b0728 and b0729) |
| TAL | Transaldoalse | [c]: g3p + s7p <==> e4p + f6p | (b2464 or b0008) |
| THD2 | NADP transhydrogenase | (2) h[e] + nadh[c] + nadp[c] --> (2) h[c] + nad[c] + nadph[c] | (b1602 and b1603) |
| THD5 | NAD transhydrogenase | [c]: nad + nadph --> nadh + nadp | (b3962 or (b1602 and b1603)) |
| TKT1 | Transketolase | [c]: r5p + xu5p-D <==> g3p + s7p | (b2935 or b2465) |
| TKT2 | Transketolase | [c]: e4p + xu5p-D <==> f6p + g3p | (b2935 or b2465) |
| TPI | Triosephosphate isomerase | [c]: dhap <==> g3p | b3919 |
| VALTA | Valine transaminase | [c]: akg + val-L <==> 3mob + glu-L | b3770 |

TABLE 13

List of the metabolite abbreviations, the corresponding names and locations of all the metabolites that participate in the reactions listed in Table 12.

| Metabolite Abbreviation | Compartment | Metabolite Name |
|---|---|---|
| 13dpg | Cytosol | 3-Phospho-D-glyceroyl phosphate |
| 1pyr5c | Cytosol | 1-Pyrroline-5-carboxylate |
| 2ddg6p | Cytosol | 2-Dehydro-3-deoxy-D-gluconate 6-phosphate |
| 2pg | Cytosol | D-Glycerate 2-phosphate |
| 3mob | Cytosol | 3-Methyl-2-oxobutanoate |
| 3pg | Cytosol | 3-Phospho-D-glycerate |
| 6pgc | Cytosol | 6-Phospho-D-gluconate |
| 6pgl | Cytosol | 6-phospho-D-glucono-1,5-lactone |

TABLE 13-continued

List of the metabolite abbreviations, the corresponding names and locations of all the metabolites that participate in the reactions listed in Table 12.

| Metabolite Abbreviation | Compartment | Metabolite Name |
|---|---|---|
| ac | Cytosol | Acetate |
| accoa | Cytosol | Acetyl-CoA |
| actp | Cytosol | Acetyl phosphate |
| adp | Cytosol | Adenosine diphosphate |
| akg | Cytosol | 2-Oxoglutarate |
| ala-D | Cytosol | D-alanine |
| ala-L | Cytosol | L-alanine |
| amp | Cytosol | Adenosine monophosphate |
| asn-L | Cytosol | L-asparagine |
| asp-L | Cytosol | L-aspartate |
| atp | Cytosol | Adenosine triphosphate |
| cbp | Cytosol | Carbamoyl phosphate |
| co2 | Cytosol | Carbon dioxide |
| coa | Cytosol | Coenzyme A |
| dha | Cytosol | Dihydroxyacetone |
| dhap | Cytosol | Dihydroxyacetone phosphate |
| e4p | Cytosol | D-Erythrose 4-phosphate |
| etoh | Cytosol | Ethanol |
| f6p | Cytosol | D-Fructose 6-phosphate |
| fad | Cytosol | Flavin adenine dinucleotide |
| fadh2 | Cytosol | Flavin adenine dinucleotide-reduced |
| fdp | Cytosol | D-Fructose 1,6-bisphosphate |
| for | Cytosol | Formate |
| fum | Cytosol | Fumarate |
| g3p | Cytosol | Glyceraldehyde 3-phosphate |
| g6p | Cytosol | D-Glucose 6-phosphate |
| glc-D[e] | Extra-organism | D-Glucose |
| glu5p | Cytosol | L-glutamate 5-phosphate |
| glu5sa | Cytosol | L-glutamate 5-semialdehyde |
| glu-L | Cytosol | L-Glutamate |
| h | Cytosol | H$^+$ |
| h[e] | Extra-organism | H$^+$ |
| h2o | Cytosol | Water |
| lac-D | Cytosol | D-Lactate |
| mal-L | Cytosol | L-Malate |
| mql-8 | Cytosol | Menaquinol-8 |
| mqn-8 | Cytosol | Menaquinone-8 |
| nad | Cytosol | Nicotinamide adenine dinucleotide |
| nadh | Cytosol | Nicotinamide adenine dinucleotide - reduced |
| nadp | Cytosol | Nicotinamide adenine dinucleotide phosphate |
| nadph | Cytosol | Nicotinamide adenine dinucleotide phosphate - reduced |
| nh4 | Cytosol | Ammonium |
| o2 | Cytosol | Oxygen |
| oaa | Cytosol | Oxaloacetate |
| pep | Cytosol | Phosphoenolpyruvate |
| pi | Cytosol | Phosphate |
| ppi | Cytosol | Diphosphate |
| pyr | Cytosol | Pyruvate |
| r5p | Cytosol | alpha-D-Ribose 5-phosphate |
| ru5p-D | Cytosol | D-Ribulose 5-phosphate |
| s7p | Cytosol | Sedoheptulose 7-phosphate |
| succ | Cytosol | Succinate |
| succoa | Cytosol | Succinyl-CoA |
| ubq8 | Cytosol | Ubiquinone-8 |
| ubq8h2 | Cytosol | Ubiquinol-8 |
| val-L | Cytosol | L-valine |
| xu5p-D | Cytosol | D-Xylulose 5-phosphate |

TABLE 14

Knockout strain designs for increased production of 6-ACA, showing yields of 6-ACA and biomass.

| New Design ID | Num KO | 6ACA. Yield | Biomass | Rxnlist |
|---|---|---|---|---|
| 1 | 1 | 1.72604 | 0.38773 | ATPS4r |
| 2 | 1 | 0.83466 | 0.26712 | PGI |
| 3 | 2 | 5.04234 | 0.22255 | HEX1, PGI |
| 4 | 2 | 4.11897 | 0.24338 | EDA and/or PGDHY, PGI |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 5 | 2 | 3.26272 | 0.35236 | ADHEr, NADH6 |
| 6 | 2 | 2.8403 | 0.28275 | ADHEr, PPCK |
| 7 | 2 | 2.05537 | 0.33531 | GLCpts, NADH6 |
| 8 | 2 | 2.0373 | 0.38161 | ATPS4r, RPE |
| 9 | 2 | 1.89007 | 0.3845 | ATPS4r, TAL |
| 10 | 2 | 1.49147 | 0.26024 | PFLi, PGI |
| 11 | 2 | 1.11406 | 0.32382 | NADH6, PFLi |
| 12 | 2 | 0.95551 | 0.27773 | PFLi, PPCK |
| 13 | 2 | 0.89333 | 0.37885 | ADHEr, FUM |
| 14 | 2 | 0.41621 | 0.38953 | ADHEr, HEX1 |
| 15 | 2 | 0.31773 | 0.36065 | ASPT, FUM |
| 16 | 3 | 6.93034 | 0.18126 | EDA and/or PGDHY, NADH6, PGI |
| 17 | 3 | 6.91845 | 0.19552 | HEX1, PFLi, PGI |
| 18 | 3 | 6.14899 | 0.1758 | EDA and/or PGDHY, PFLi, PGI |
| 19 | 3 | 5.81422 | 0.16481 | ATPS4r, EDA and/or PGDHY, PGI |
| 20 | 3 | 5.71646 | 0.21908 | ADHEr, HEX1, PGI |
| 21 | 3 | 4.83364 | 0.29669 | ADHEr, NADH6, PFLi |
| 22 | 3 | 4.23803 | 0.24209 | ACKr and/or PTAr, EDA and/or PGDHY, PGI |
| 23 | 3 | 4.02855 | 0.29483 | ADHEr, MDH, THD2 and/or GLUDy |
| 24 | 3 | 3.77533 | 0.25553 | ADHEr, ASPT, MDH |
| 25 | 3 | 3.65248 | 0.19372 | ADHEr, NADH6, PGI |
| 26 | 3 | 3.47283 | 0.25194 | ADHEr, NADH6, PPCK |
| 27 | 3 | 3.39319 | 0.29001 | ADHEr, MDH, NADH6 |
| 28 | 3 | 3.35305 | 0.34906 | ADHEr, NADH6, RPE |
| 29 | 3 | 3.23462 | 0.28717 | ACKr and/or PTAr, ATPS4r, SUCOAS |
| 30 | 3 | 3.0877 | 0.16431 | ADHEr, PGI, PPCK |
| 31 | 3 | 2.90019 | 0.24841 | ADHEr, GLCpts, PPCK |
| 32 | 3 | 2.89855 | 0.2815 | ADHEr, PPCK, RPE |
| 33 | 3 | 2.88617 | 0.25645 | ADHEr, FUM, THD2 and/or GLUDy |
| 34 | 3 | 2.72186 | 0.35068 | ADHEr, FUM, HEX1 |
| 35 | 3 | 2.60615 | 0.3202 | ATPS4r, HEX1, PFLi |
| 36 | 3 | 2.54001 | 0.22798 | PFLi, PGDH, PGI |
| 37 | 3 | 2.5259 | 0.22921 | PFLi, PGI, TAL |
| 38 | 3 | 2.5129 | 0.23034 | PFLi, PGI, RPE |
| 39 | 3 | 2.50442 | 0.16853 | ATPS4r, PFLi, PGI |
| 40 | 3 | 2.38919 | 0.18418 | GLCpts, NADH6, PGI |
| 41 | 3 | 2.30741 | 0.33343 | ATPS4r, GLCpts, NADH6 |
| 42 | 3 | 2.16995 | 0.33092 | GLCpts, NADH6, RPE |
| 43 | 3 | 2.11568 | 0.333 | GLCpts, NADH6, TAL |
| 44 | 3 | 2.10576 | 0.25488 | ATPS4r, PPCK, PYK |
| 45 | 3 | 1.5933 | 0.25891 | FUM, PFLi, PGI |
| 46 | 3 | 1.25154 | 0.3194 | NADH6, PFLi, RPE |
| 47 | 3 | 1.23093 | 0.32359 | ACKr and/or PTAr, NADH6, PFLi |
| 48 | 3 | 1.18643 | 0.32149 | NADH6, PFLi, TAL |
| 49 | 3 | 1.08143 | 0.27599 | PFLi, PPCK, RPE |
| 50 | 3 | 1.0527 | 0.27673 | ACKr and/or PTAr, PFLi, PPCK |
| 51 | 3 | 1.03356 | 0.34314 | FUM, HEX1, PFLi |
| 52 | 3 | 1.02156 | 0.27682 | PFLi, PPCK, TAL |
| 53 | 3 | 0.8538 | 0.24817 | MDH, PFLi, THD2 and/or GLUDy |
| 54 | 3 | 0.5753 | 0.38695 | ADHEr, HEX1, RPE |
| 55 | 3 | 0.49968 | 0.38818 | ADHEr, HEX1, TAL |
| 56 | 3 | 0.31402 | 0.35643 | FDH2, FUM, NADH6 |
| 57 | 3 | 0.23944 | 0.28074 | FUM, PFLi, THD2 and/or GLUDy |
| 58 | 3 | 0.23418 | 0.26581 | ASPT, MDH, PFLi |
| 59 | 3 | 0.20901 | 0.23724 | ASPT, MDH, PYK |
| 60 | 4 | 7.08404 | 0.12641 | EDA and/or PGDHY, NADH6, PFLi, PGI |
| 61 | 4 | 7.0245 | 0.10838 | EDA and/or PGDHY, PFLi, PGI, PPCK |
| 62 | 4 | 6.92332 | 0.16482 | ADHEr, HEX1, NADH6, PGI |
| 63 | 4 | 6.89839 | 0.18171 | ACKr and/or PTAr, ADHEr, NADH6, PGI |
| 64 | 4 | 6.58534 | 0.16513 | EDA and/or PGDHY, GLCpts, PFLi, PGI |
| 65 | 4 | 6.36357 | 0.11937 | EDA and/or PGDHY, PFLi, PGI, THD2 and/or GLUDy |
| 66 | 4 | 6.22082 | 0.11375 | ATPS4r, EDA and/or PGDHY, PFLi, PGI |
| 67 | 4 | 5.8701 | 0.13379 | ADHEr, EDA and/or PGDHY, PGI, PPCK |
| 68 | 4 | 5.85757 | 0.23874 | ADHEr, MDH, NADH6, THD2 and/or GLUDy |
| 69 | 4 | 5.85411 | 0.19685 | ADHEr, HEX1, PGI, PPS |
| 70 | 4 | 5.67774 | 0.13549 | EDA and/or PGDHY, PGI, PPCK, PYK |
| 71 | 4 | 5.46506 | 0.26673 | EDA and/or PGDHY, MDH, PFLi, THD2 and/or GLUDy |
| 72 | 4 | 5.40131 | 0.26362 | ADHEr, MDH, PFLi, THD2 and/or GLUDy |
| 73 | 4 | 5.08219 | 0.13778 | ATPS4r, NADH6, PFLi, PGI |
| 74 | 4 | 4.88764 | 0.27849 | ADHEr, NADH12, NADH6, PFLi |
| 75 | 4 | 4.88489 | 0.27942 | ADHEr, FUM, NADH6, PFLi |
| 76 | 4 | 4.81778 | 0.26037 | ADHEr, ATPS4r, MDH, NADH6 |
| 77 | 4 | 4.73419 | 0.21859 | ADHEr, NADH6, PPCK, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 78 | 4 | 4.63783 | 0.29595 | ADHEr, ATPS4r, FDH2, NADH6 |
| 79 | 4 | 4.51525 | 0.21818 | ADHEr, FUM, PPCK, THD2 and/or GLUDy |
| 80 | 4 | 4.51525 | 0.21818 | ADHEr, MDH, PPCK, THD2 and/or GLUDy |
| 81 | 4 | 4.30547 | 0.19131 | ADHEr, ATPS4r, NADH6, PGI |
| 82 | 4 | 4.2733 | 0.23078 | ADHEr, ATPS4r, NADH6, PPCK |
| 83 | 4 | 4.16417 | 0.18771 | ATPS4r, NADH6, PGI, RPE |
| 84 | 4 | 4.16053 | 0.18697 | ATPS4r, NADH6, PGI, TAL |
| 85 | 4 | 4.15658 | 0.18617 | ATPS4r, NADH6, PGDH, PGI |
| 86 | 4 | 4.12032 | 0.32701 | ADHEr, ATPS4r, FUM, NADH6 |
| 87 | 4 | 3.9718 | 0.23354 | ADHEr, ATPS4r, MDH, PPCK |
| 88 | 4 | 3.9718 | 0.23354 | ADHEr, ATPS4r, FUM, PPCK |
| 89 | 4 | 3.8747 | 0.21758 | ADHEr, ASPT, GLCpts, MDH |
| 90 | 4 | 3.84814 | 0.25342 | ADHEr, ASPT, MDH, RPE |
| 91 | 4 | 3.83986 | 0.2047 | ADHEr, ASPT, MDH, PYK |
| 92 | 4 | 3.75472 | 0.32987 | ADHEr, ATPS4r, HEX1, NADH6 |
| 93 | 4 | 3.54965 | 0.29114 | ADHEr, ATPS4r, MDH, PGDH |
| 94 | 4 | 3.54605 | 0.21695 | ADHEr, GLCpts, NADH6, PPCK |
| 95 | 4 | 3.54385 | 0.218 | ADHEr, NADH6, PPCK, PYK |
| 96 | 4 | 3.53615 | 0.25027 | ADHEr, NADH6, PPCK, RPE |
| 97 | 4 | 3.5018 | 0.32809 | ADHEr, ATPS4r, FUM, HEX1 |
| 98 | 4 | 3.46904 | 0.25375 | ADHEr, GLCpts, MDH, NADH6 |
| 99 | 4 | 3.46528 | 0.28851 | ADHEr, MDH, NADH6, RPE |
| 100 | 4 | 3.44916 | 0.13425 | ADHEr, PFLi, PGI, PPCK |
| 101 | 4 | 3.44555 | 0.26498 | ADHEr, HEX1, NADH6, THD2 and/or GLUDy |
| 102 | 4 | 3.43776 | 0.29402 | ADHEr, ATPS4r, MDH, TAL |
| 103 | 4 | 3.36596 | 0.19156 | FUM, NADH6, PGI, THD5 |
| 104 | 4 | 3.36596 | 0.19156 | MDH, NADH6, PGI, THD5 |
| 105 | 4 | 3.33377 | 0.2967 | ADHEr, ATPS4r, MDH, RPE |
| 106 | 4 | 3.33152 | 0.33978 | ADHEr, FUM, NADH6, TAL |
| 107 | 4 | 3.32935 | 0.34088 | ADHEr, HEX1, NADH6, TAL |
| 108 | 4 | 3.32788 | 0.32122 | ADHEr, FUM, HEX1, NADH6 |
| 109 | 4 | 3.31278 | 0.3493 | ADHEr, GLU5K, NADH6, TAL |
| 110 | 4 | 3.31278 | 0.3493 | ADHEr, G5SD, NADH6, TAL |
| 111 | 4 | 3.17484 | 0.10602 | ADHEr, PGI, PPCK, THD2 and/or GLUDy |
| 112 | 4 | 3.16614 | 0.11184 | ADHEr, MDH, PGI, THD2 and/or GLUDy |
| 113 | 4 | 3.16614 | 0.11184 | ADHEr, FUM, PGI, THD2 and/or GLUDy |
| 114 | 4 | 3.11125 | 0.24826 | ADHEr, ATPS4r, PPCK, THD2 and/or GLUDy |
| 115 | 4 | 2.96628 | 0.21051 | ADHEr, LDH_D, MDH, THD2 and/or GLUDy |
| 116 | 4 | 2.95529 | 0.24477 | ADHEr, PPCK, RPE, THD2 and/or GLUDy |
| 117 | 4 | 2.95136 | 0.24731 | ADHEr, GLCpts, PPCK, RPE |
| 118 | 4 | 2.94249 | 0.25305 | ADHEr, FUM, RPE, THD2 and/or GLUDy |
| 119 | 4 | 2.93765 | 0.22693 | ADHEr, MDH, PPCK, PYK |
| 120 | 4 | 2.93765 | 0.22693 | ADHEr, FUM, PPCK, PYK |
| 121 | 4 | 2.9332 | 0.24406 | ADHEr, PPCK, TAL, THD2 and/or GLUDy |
| 122 | 4 | 2.90913 | 0.24328 | ADHEr, PGDH, PPCK, THD2 and/or GLUDy |
| 123 | 4 | 2.90913 | 0.24328 | ADHEr, PGL and/or G6PDHy, PPCK, THD2 and/or GLUDy |
| 124 | 4 | 2.90081 | 0.26381 | ADHEr, FUM, PPCK, TAL |
| 125 | 4 | 2.90081 | 0.26381 | ADHEr, MDH, PPCK, TAL |
| 126 | 4 | 2.86334 | 0.28161 | ATPS4r, GLCpts, NADH6, PFLi |
| 127 | 4 | 2.79498 | 0.34856 | ADHEr, FUM, HEX1, RPE |
| 128 | 4 | 2.7362 | 0.31504 | ATPS4r, HEX1, PFLi, RPE |
| 129 | 4 | 2.70922 | 0.18179 | ATPS4r, GLCpts, NADH6, PGI |
| 130 | 4 | 2.67469 | 0.31748 | ATPS4r, HEX1, PFLi, TAL |
| 131 | 4 | 2.61943 | 0.36027 | ADHEr, HEX1, PFLi, PPS |
| 132 | 4 | 2.60629 | 0.2178 | PFLi, PGDH, PGI, TAL |
| 133 | 4 | 2.60314 | 0.31113 | ADHEr, HEX1, MDH, PFLi |
| 134 | 4 | 2.56456 | 0.18551 | ASPT, NADH6, PGI, THD5 |
| 135 | 4 | 2.55949 | 0.17944 | ATPS4r, PFLi, PPCK, PYK |
| 136 | 4 | 2.45433 | 0.3546 | ADHEr, ATPS4r, HEX1, THD2 and/or GLUDy |
| 137 | 4 | 2.45166 | 0.03625 | GLCpts, NADH6, PPCK, PYK |
| 138 | 4 | 2.44258 | 0.32891 | ATPS4r, GLCpts, NADH6, RPE |
| 139 | 4 | 2.43939 | 0.25153 | ATPS4r, PPCK, PYK, RPE |
| 140 | 4 | 2.37857 | 0.33105 | ATPS4r, GLCpts, NADH6, TAL |
| 141 | 4 | 2.30961 | 0.22691 | ATPS4r, NADH6, PPCK, PYK |
| 142 | 4 | 2.28135 | 0.25311 | ATPS4r, PPCK, PYK, TAL |
| 143 | 4 | 2.18633 | 0.3609 | ADHEr, HEX1, PPS, THD2 and/or GLUDy |
| 144 | 4 | 2.11347 | 0.31979 | ADHEr, ATPS4r, HEX1, MDH |
| 145 | 4 | 2.05497 | 0.19746 | ASPT, ATPS4r, PGI, THD5 |
| 146 | 4 | 1.83108 | 0.25754 | MDH, PFLi, PGI, THD2 and/or GLUDy |
| 147 | 4 | 1.65594 | 0.25767 | ACKr and/or PTAr, FUM, PFLi, PGI |
| 148 | 4 | 1.36673 | 0.31918 | ACKr and/or PTAr, NADH6, PFLi, RPE |
| 149 | 4 | 1.30242 | 0.32127 | ACKr and/or PTAr, NADH6, PFLi, TAL |
| 150 | 4 | 1.28243 | 0.32216 | ACKr and/or PTAr, GLU5K, NADH6, PFLi |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 151 | 4 | 1.28243 | 0.32216 | ACKr and/or PTAr, G5SD, NADH6, PFLi |
| 152 | 4 | 1.26654 | 0.34191 | ACKr and/or PTAr, FUM, HEX1, PFLi |
| 153 | 4 | 1.18926 | 0.34046 | FUM, HEX1, PFLi, RPE |
| 154 | 4 | 1.17756 | 0.275 | ACKr and/or PTAr, PFLi, PPCK, RPE |
| 155 | 4 | 1.1182 | 0.27583 | ACKr and/or PTAr, PFLi, PPCK, TAL |
| 156 | 4 | 1.1153 | 0.34173 | FUM, HEX1, PFLi, TAL |
| 157 | 4 | 0.95889 | 0.24471 | MDH, PFLi, RPE, THD2 and/or GLUDy |
| 158 | 4 | 0.9475 | 0.3633 | ADHEr, FUM, PGL and/or G6PDHy, TAL |
| 159 | 4 | 0.9475 | 0.3633 | ADHEr, FUM, PGDH, TAL |
| 160 | 4 | 0.90913 | 0.24635 | MDH, PFLi, TAL, THD2 and/or GLUDy |
| 161 | 4 | 0.36773 | 0.36076 | HEX1, PFLi, PPS, THD2 and/or GLUDy |
| 162 | 4 | 0.3476 | 0.2132 | ADHEr, MDH, RPE, THD2 and/or GLUDy |
| 163 | 4 | 0.32915 | 0.27571 | FUM, PFLi, RPE, THD2 and/or GLUDy |
| 164 | 5 | 6.98742 | 0.06748 | ADHEr, EDA and/or PGDHY, NADH6, PGI, THD2 and/or GLUDy |
| 165 | 5 | 6.97749 | 0.0848 | ACKr and/or PTAr, ATPS4r, HEX1, PFLi, PGI |
| 166 | 5 | 6.70882 | 0.01277 | EDA and/or PGDHY, FUM, PFLi, PGI, THD2 and/or GLUDy |
| 167 | 5 | 6.70882 | 0.01277 | EDA and/or PGDHY, MDH, PFLi, PGI, THD2 and/or GLUDy |
| 168 | 5 | 6.69134 | 0.13239 | ADHEr, ASPT, ATPS4r, GLCpts, MDH |
| 169 | 5 | 6.55123 | 0.09841 | ADHEr, ASPT, MDH, PGL and/or G6PDHy, PYK |
| 170 | 5 | 6.55123 | 0.09841 | ADHEr, ASPT, EDA and/or PGDHY, MDH, PYK |
| 171 | 5 | 6.3052 | 0.17034 | ADHEr, ASPT, ATPS4r, MDH, PGL and/or G6PDHy |
| 172 | 5 | 6.20871 | 0.17434 | EDA and/or PGDHY, MDH, PFLi, PGI, THD5 |
| 173 | 5 | 6.12639 | 0.08557 | ADHEr, FRD and/or SUCD4, LDH_D, MDH, THD2 and/or GLUDy |
| 174 | 5 | 6.03386 | 0.19348 | ACKr and/or PTAr, ADHEr, ASPT, LDH_D, MDH |
| 175 | 5 | 5.98628 | 0.0693 | ATPS4r, EDA and/or PGDHY, PGI, PPCK, PYK |
| 176 | 5 | 5.98165 | 0.07186 | ADHEr, ATPS4r, EDA and/or PGDHY, PGI, PPCK |
| 177 | 5 | 5.93527 | 0.09761 | ADHEr, EDA and/or PGDHY, GLCpts, PGI, PPCK |
| 178 | 5 | 5.87444 | 0.0434 | ADHEr, EDA and/or PGDHY, MDH, PGI, THD2 and/or GLUDy |
| 179 | 5 | 5.87444 | 0.0434 | ADHEr, EDA and/or PGDHY, FUM, PGI, THD2 and/or GLUDy |
| 180 | 5 | 5.82336 | 0.16439 | ACKr and/or PTAr, ADHEr, ASPT, MDH, PYK |
| 181 | 5 | 5.75418 | 0.21654 | ACKr and/or PTAr, ADHEr, LDH_D, MDH, NADH6 |
| 182 | 5 | 5.65488 | 0.26204 | ACKr and/or PTAr, ADHEr, MDH, PFLi, THD2 and/or GLUDy |
| 183 | 5 | 5.59555 | 0.20952 | ADHEr, ASPT4r, GLCpts, MDH, NADH6 |
| 184 | 5 | 5.30614 | 0.21123 | ADHEr, ASPT, LDH_D, MDH, THD2 and/or GLUDy |
| 185 | 5 | 5.21058 | 0.214 | ADHEr, ASPT, ATPS4r, LDH_D, MDH |
| 186 | 5 | 5.20451 | 0.17174 | ADHEr, LDH_D, NADH6, PFLi, PPCK |
| 187 | 5 | 5.1776 | 0.13724 | ADHEr, NADH12, NADH6, PFLi, PGI |
| 188 | 5 | 5.11744 | 0.13758 | ADHEr, MDH, NADH6, PFLi, PGI |
| 189 | 5 | 5.11744 | 0.13758 | ADHEr, FUM, NADH6, PFLi, PGI |
| 190 | 5 | 5.11714 | 0.20117 | ADHEr, LDH_D, MDH, PFLi, PPCK |
| 191 | 5 | 5.11714 | 0.20117 | ADHEr, FUM, LDH_D, PFLi, PPCK |
| 192 | 5 | 5.10437 | 0.12227 | ADHEr, FUM, PFLi, PGI, PPCK |
| 193 | 5 | 5.10437 | 0.12227 | ADHEr, MDH, PFLi, PGI, PPCK |
| 194 | 5 | 5.09877 | 0.17589 | ADHEr, ATPS4r, GLCpts, NADH6, PPCK |
| 195 | 5 | 5.0606 | 0.22022 | ADHEr, LDH_D, MDH, NADH6, PFLi |
| 196 | 5 | 5.02693 | 0.21085 | ADHEr, ATPS4r, NADH6, PGDH, PPCK |
| 197 | 5 | 5.02693 | 0.21085 | ADHEr, ATPS4r, NADH6, PGL and/or G6PDHy, PPCK |
| 198 | 5 | 5.00057 | 0.21154 | ADHEr, ATPS4r, NADH6, PPCK, TAL |
| 199 | 5 | 4.97638 | 0.21218 | ADHEr, ATPS4r, NADH6, PPCK, RPE |
| 200 | 5 | 4.88781 | 0.27844 | ADHEr, HEX1, LDH_D, NADH6, PFLi |
| 201 | 5 | 4.88512 | 0.29281 | ADHEr, GLU5K, NADH6, PFLi, RPE |
| 202 | 5 | 4.88512 | 0.29281 | ADHEr, G5SD, NADH6, PFLi, RPE |
| 203 | 5 | 4.885 | 0.29286 | ADHEr, ASNS2, NADH6, PFLi, RPE |
| 204 | 5 | 4.85776 | 0.29446 | ADHEr, ATPS4r, FDH2, NADH6, RPE |
| 205 | 5 | 4.83644 | 0.29517 | ADHEr, ATPS4r, FDH2, NADH6, TAL |
| 206 | 5 | 4.7175 | 0.34071 | ADHEr, FUM, LDH_D, PFLi, THD2 and/or GLUDy |
| 207 | 5 | 4.66386 | 0.18074 | ADHEr, ATPS4r, GLCpts, MDH, PPCK |
| 208 | 5 | 4.66386 | 0.18074 | ADHEr, ATPS4r, FUM, GLCpts, PPCK |
| 209 | 5 | 4.63095 | 0.20189 | ADHEr, ATPS4r, GLCpts, PFLi, PPCK |
| 210 | 5 | 4.49707 | 0.25782 | ADHEr, ATPS4r, EDA and/or PGDHY, MDH, THD2 and/or GLUDy |
| 211 | 5 | 4.4958 | 0.1778 | ADHEr, ASPT, MDH, NADH6, PYK |
| 212 | 5 | 4.41977 | 0.25646 | ADHEr, ATPS4r, GLCpts, MDH, THD2 and/or GLUDy |
| 213 | 5 | 4.29965 | 0.18828 | ADHEr, ASPT, ATPS4r, MDH, PYK |
| 214 | 5 | 4.29026 | 0.24034 | ACKr and/or PTAr, EDA and/or PGDHY, GLU5K, GLYCL, PGI |
| 215 | 5 | 4.29026 | 0.24034 | ACKr and/or PTAr, EDA and/or PGDHY, G5SD, GLYCL, PGI |
| 216 | 5 | 4.28287 | 0.11665 | ACKr and/or PTAr, ATPS4r, PPCK, PYK, SUCOAS |
| 217 | 5 | 4.24299 | 0.26303 | ACKr and/or PTAr, ADHEr, HEX1, LDH_D, NADH6 |
| 218 | 5 | 4.18509 | 0.32432 | ADHEr, ATPS4r, HEX1, NADH6, PGL and/or G6PDHy |
| 219 | 5 | 4.18509 | 0.32432 | ADHEr, ATPS4r, HEX1, NADH6, PGDH |
| 220 | 5 | 4.15013 | 0.1124 | ADHEr, ASPT, MDH, PYK, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 221 | 5 | 4.14582 | 0.32483 | ADHEr, ATPS4r, HEX1, NADH6, TAL |
| 222 | 5 | 4.1099 | 0.32529 | ADHEr, ATPS4r, HEX1, NADH6, RPE |
| 223 | 5 | 4.04473 | 0.12883 | ADHEr, PFLi, PGDH, PGI, PPCK |
| 224 | 5 | 4.03844 | 0.12934 | ADHEr, PFLi, PGI, PPCK, TAL |
| 225 | 5 | 4.03266 | 0.12981 | ADHEr, PFLi, PGI, PPCK, RPE |
| 226 | 5 | 4.02531 | 0.1111 | ADHEr, GLCpts, PFLi, PGI, PPCK |
| 227 | 5 | 3.95205 | 0.10694 | ACKr and/or PTAr, ATPS4r, PGDH, PGI, SUCOAS |
| 228 | 5 | 3.94203 | 0.1079 | ACKr and/or PTAr, ATPS4r, PGI, SUCOAS, TAL |
| 229 | 5 | 3.9367 | 0.21579 | ADHEr, ASPT, GLCpts, MDH, RPE |
| 230 | 5 | 3.93273 | 0.1088 | ACKr and/or PTAr, ATPS4r, PGI, RPE, SUCOAS |
| 231 | 5 | 3.88257 | 0.21457 | ADHEr, ASPT, LDH_D, MDH, PPCK |
| 232 | 5 | 3.84571 | 0.22865 | ADHEr, ASPT, LDH_D, MDH, NADH6 |
| 233 | 5 | 3.76049 | 0.30843 | ADHEr, ATPS4r, FUM, HEX1, PFLi |
| 234 | 5 | 3.74674 | 0.21738 | ADHEr, ATPS4r, LDH_D, PFLi, PPCK |
| 235 | 5 | 3.71345 | 0.27754 | ADHEr, ATPS4r, MDH, PGDH, TAL |
| 236 | 5 | 3.69299 | 0.14673 | ADHEr, NADH6, PPCK, PYK, THD2 and/or GLUDy |
| 237 | 5 | 3.64625 | 0.1409 | ACKr and/or PTAr, ADHEr, FUM, PGI, PPCK |
| 238 | 5 | 3.64625 | 0.1409 | ACKr and/or PTAr, ADHEr, MDH, PGI, PPCK |
| 239 | 5 | 3.60057 | 0.21551 | ADHEr, GLCpts, NADH6, PPCK, RPE |
| 240 | 5 | 3.59735 | 0.21725 | ADHEr, NADH6, PPCK, PYK, RPE |
| 241 | 5 | 3.59622 | 0.19297 | ADHEr, GLCpts, MDH, NADH6, PPCK |
| 242 | 5 | 3.59622 | 0.19297 | ADHEr, FUM, GLCpts, NADH6, PPCK |
| 243 | 5 | 3.59594 | 0.19311 | ADHEr, MDH, NADH6, PPCK, PYK |
| 244 | 5 | 3.59594 | 0.19311 | ADHEr, FUM, NADH6, PPCK, PYK |
| 245 | 5 | 3.59157 | 0.1952 | ADHEr, FUM, GLCpts, NADH6, THD2 and/or GLUDy |
| 246 | 5 | 3.57086 | 0.18962 | ATPS4r, FUM, NADH6, PGI, THD5 |
| 247 | 5 | 3.57086 | 0.18962 | ATPS4r, MDH, NADH6, PGI, THD5 |
| 248 | 5 | 3.55204 | 0.22769 | ADHEr, FUM, NADH6, PPCK, TAL |
| 249 | 5 | 3.55204 | 0.22769 | ADHEr, MDH, NADH6, PPCK, TAL |
| 250 | 5 | 3.53212 | 0.25244 | ADHEr, GLCpts, MDH, NADH6, RPE |
| 251 | 5 | 3.52326 | 0.22785 | ADHEr, FUM, GLU5K, NADH6, PPCK |
| 252 | 5 | 3.52326 | 0.22785 | ADHEr, G5SD, MDH, NADH6, PPCK |
| 253 | 5 | 3.52326 | 0.22785 | ADHEr, GLU5K, MDH, NADH6, PPCK |
| 254 | 5 | 3.52326 | 0.22785 | ADHEr, FUM, G5SD, NADH6, PPCK |
| 255 | 5 | 3.52319 | 0.22788 | ADHEr, ASNS2, FUM, NADH6, PPCK |
| 256 | 5 | 3.52319 | 0.22788 | ADHEr, ASNS2, MDH, NADH6, PPCK |
| 257 | 5 | 3.51328 | 0.26261 | ADHEr, HEX1, NADH6, RPE, THD2 and/or GLUDy |
| 258 | 5 | 3.40958 | 0.31856 | ADHEr, FUM, HEX1, NADH6, RPE |
| 259 | 5 | 3.19551 | 0.34972 | ADHEr, ATPS4r, HEX1, PPS, THD2 and/or GLUDy |
| 260 | 5 | 3.04993 | 0.16253 | ADHEr, FUM, LDH_D, PPCK, THD2 and/or GLUDy |
| 261 | 5 | 3.04993 | 0.16253 | ADHEr, LDH_D, MDH, PPCK, THD2 and/or GLUDy |
| 262 | 5 | 3.02516 | 0.17674 | ADHEr, GLCpts, LDH_D, MDH, THD2 and/or GLUDy |
| 263 | 5 | 2.95797 | 0.22895 | ADHEr, GLCpts, MDH, PPCK, TAL |
| 264 | 5 | 2.95797 | 0.22895 | ADHEr, FUM, GLCpts, PPCK, TAL |
| 265 | 5 | 2.94768 | 0.30664 | ADHEr, ATPS4r, HEX1, MDH, PFLi |
| 266 | 5 | 2.93267 | 0.03242 | ATPS4r, GLCpts, NADH6, PPCK, PYK |
| 267 | 5 | 2.93156 | 0.27787 | ATPS4r, GLCpts, NADH6, PFLi, RPE |
| 268 | 5 | 2.92149 | 0.26881 | ADHEr, ATPS4r, MDH, PGL and/or G6PDHy, PPS |
| 269 | 5 | 2.76831 | 0.35787 | ADHEr, HEX1, PFLi, PPS, RPE |
| 270 | 5 | 2.73201 | 0.30945 | ADHEr, HEX1, MDH, PFLi, RPE |
| 271 | 5 | 2.69754 | 0.35901 | ADHEr, HEX1, PFLi, PPS, TAL |
| 272 | 5 | 2.69256 | 0.22448 | ATPS4r, NADH6, PPCK, PYK, RPE |
| 273 | 5 | 2.67071 | 0.31025 | ADHEr, HEX1, MDH, PFLi, TAL |
| 274 | 5 | 2.63273 | 0.17703 | ATPS4r, PFLi, PPCK, PYK, RPE |
| 275 | 5 | 2.61965 | 0.35455 | ADHEr, ATPS4r, HEX1, RPE, THD2 and/or GLUDy |
| 276 | 5 | 2.5479 | 0.2938 | ADHEr, ATPS4r, GLUDy, HEX1, THD2 and/or GLUDy |
| 277 | 5 | 2.5408 | 0.35457 | ADHEr, ATPS4r, HEX1, TAL, THD2 and/or GLUDy |
| 278 | 5 | 2.51093 | 0.22563 | ATPS4r, NADH6, PPCK, PYK, TAL |
| 279 | 5 | 2.50239 | 0.09117 | GLCpts, PFLi, PGI, PPCK, PYK |
| 280 | 5 | 1.97671 | 0.25583 | ACKr and/or PTAr, MDH, PFLi, PGI, THD2 and/or GLUDy |
| 281 | 5 | 1.41987 | 0.33925 | ACKr and/or PTAr, FUM, HEX1, PFLi, RPE |
| 282 | 5 | 1.41694 | 0.31779 | ACKr and/or PTAr, GLU5K, NADH6, PFLi, RPE |
| 283 | 5 | 1.41694 | 0.31779 | ACKr and/or PTAr, G5SD, NADH6, PFLi, RPE |
| 284 | 5 | 1.35397 | 0.34014 | ACKr and/or PTAr, FUM, GLU5K, HEX1, PFLi |
| 285 | 5 | 1.35397 | 0.34014 | ACKr and/or PTAr, FUM, G5SD, HEX1, PFLi |
| 286 | 5 | 1.35324 | 0.31986 | ACKr and/or PTAr, GLU5K, NADH6, PFLi, TAL |
| 287 | 5 | 1.35324 | 0.31986 | ACKr and/or PTAr, G5SD, NADH6, PFLi, TAL |
| 288 | 5 | 1.34703 | 0.34051 | ACKr and/or PTAr, FUM, HEX1, PFLi, TAL |
| 289 | 5 | 1.16644 | 0.24173 | ADHEr, FRD and/or SUCD4, LDH_D, PPS, THD2 and/or GLUDy |
| 290 | 5 | 0.935 | 0.24579 | ACKr and/or PTAr, ACS, MDH, PFLi, THD2 and/or GLUDy |
| 291 | 5 | 0.5376 | 0.11141 | ADHEr, FRD and/or SUCD4, GLUDy, LDH_D, THD2 and/or GLUDy |
| 292 | 5 | 0.44145 | 0.36033 | HEX1, PFLi, PPS, RPE, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 293 | 5 | 0.41407 | 0.27855 | ACKr and/or PTAr, ACS, FUM, PFLi, THD2 and/or GLUDy |
| 294 | 5 | 0.34153 | 0.21403 | ACKr and/or PTAr, ADHEr, MDH, TAL, THD2 and/or GLUDy |
| 295 | 5 | 0.29506 | 0.27092 | FUM, PFLi, PGDH, TAL, THD2 and/or GLUDy |
| 296 | 5 | 0.29506 | 0.27092 | FUM, PFLi, PGL and/or G6PDHy, TAL, THD2 and/or GLUDy |
| 297 | 5 | 0.29233 | 0.27766 | FUM, GLYCL, PFLi, TAL, THD2 and/or GLUDy |
| 298 | 2 | 1.72604 | 0.38773 | ADHEr, ATPS4r |
| 299 | 2 | 0.83466 | 0.26712 | ADHEr, PGI |
| 300 | 3 | 4.11897 | 0.24338 | ADHEr, EDA and/or PGDHY, PGI |
| 301 | 3 | 2.0373 | 0.38161 | ADHEr, ATPS4r, RPE |
| 302 | 3 | 1.89007 | 0.3845 | ADHEr, ATPS4r, TAL |
| 303 | 3 | 1.49147 | 0.26024 | ADHEr, PFLi, PGI |
| 304 | 4 | 6.93034 | 0.18126 | ADHEr, EDA and/or PGDHY, NADH6, PGI |
| 305 | 4 | 6.91845 | 0.19552 | ADHEr, HEX1, PFLi, PGI |
| 306 | 4 | 6.14899 | 0.1758 | ADHEr, EDA and/or PGDHY, PFLi, PGI |
| 307 | 4 | 5.81422 | 0.16481 | ADHEr, ATPS4r, EDA and/or PGDHY, PGI |
| 308 | 4 | 4.23803 | 0.24209 | ACKr and/or PTAr, ADHEr, EDA and/or PGDHY, PGI |
| 309 | 4 | 3.23462 | 0.28717 | ACKr and/or PTAr, ADHEr, ATPS4r, SUCOAS |
| 310 | 4 | 2.60615 | 0.3202 | ADHEr, ATPS4r, HEX1, PFLi |
| 311 | 4 | 2.54001 | 0.22798 | ADHEr, PFLi, PGDH, PGI |
| 312 | 4 | 2.5259 | 0.22921 | ADHEr, PFLi, PGI, TAL |
| 313 | 4 | 2.5129 | 0.23034 | ADHEr, PFLi, PGI, RPE |
| 314 | 4 | 2.50442 | 0.16853 | ADHEr, ATPS4r, PFLi, PGI |
| 315 | 4 | 1.5933 | 0.25891 | ADHEr, FUM, PFLi, PGI |
| 316 | 5 | 7.08404 | 0.12641 | ADHEr, EDA and/or PGDHY, NADH6, PFLi, PGI |
| 317 | 5 | 7.0245 | 0.10838 | ADHEr, EDA and/or PGDHY, PFLi, PGI, PPCK |
| 318 | 5 | 6.58534 | 0.16513 | ADHEr, EDA and/or PGDHY, GLCpts, PFLi, PGI |
| 319 | 5 | 6.36357 | 0.11937 | ADHEr, EDA and/or PGDHY, PFLi, PGI, THD2 and/or GLUDy |
| 320 | 5 | 6.22082 | 0.11375 | ADHEr, ATPS4r, EDA and/or PGDHY, PFLi, PGI |
| 321 | 5 | 5.08219 | 0.13778 | ADHEr, ATPS4r, NADH6, PFLi, PGI |
| 322 | 5 | 2.7362 | 0.31504 | ADHEr, ATPS4r, HEX1, PFLi, RPE |
| 323 | 5 | 2.67469 | 0.31748 | ADHEr, ATPS4r, HEX1, PFLi, TAL |
| 324 | 5 | 2.60629 | 0.2178 | ADHEr, PFLi, PGDH, PGI, TAL |
| 325 | 5 | 2.05497 | 0.19746 | ADHEr, ASPT, ATPS4r, PGI, THD5 |
| 326 | 5 | 1.65594 | 0.25767 | ACKr and/or PTAr, ADHEr, FUM, PFLi, PGI |
| 327 | 6 | 7.82999 | 0.02101 | ADHEr, ASPT, LDH_D, MDH, PFLi, THD2 and/or GLUDy |
| 328 | 6 | 7.21161 | 0.05631 | ADHEr, EDA and/or PGDHY, HEX1, NADH6, PGI, THD2 and/or GLUDy |
| 329 | 6 | 7.16447 | 0.10326 | ADHEr, ASPT, LDH_D, MDH, PFLi, PYK |
| 330 | 6 | 6.97749 | 0.0848 | ACKr and/or PTAr, ADHEr, ATPS4r, HEX1, PFLi, PGI |
| 331 | 6 | 6.89088 | 0.16538 | ADHEr, ASPT, ATPS4r, LDH_D, MDH, PGL and/or G6PDHy |
| 332 | 6 | 6.86543 | 0.14022 | ADHEr, ASPT, ATPS4r, LDH_D, MDH, PFLi |
| 333 | 6 | 6.72704 | 0.08076 | ADHEr, ASPT, EDA and/or PGDHY, MDH, NADH6, PYK |
| 334 | 6 | 6.72704 | 0.08076 | ADHEr, ASPT, MDH, NADH6, PGL and/or G6PDHY, PYK |
| 335 | 6 | 6.67303 | 0.15616 | ADHEr, LDH_D, MDH, PFLi, PPCK, THD2 and/or GLUDy |
| 336 | 6 | 6.67303 | 0.15616 | ADHEr, FUM, LDH_D, PFLi, PPCK, THD2 and/or GLUDy |
| 337 | 6 | 6.62564 | 0.17535 | ADHEr, LDH_D, MDH, NADH6, PFLi, THD2 and/or GLUDy |
| 338 | 6 | 6.44535 | 0.24832 | ADHEr, FUM, HEX1, LDH_D, PFLi, THD2 and/or GLUDy |
| 339 | 6 | 6.44535 | 0.24832 | ADHEr, HEX1, LDH_D, MDH, PFLi, THD2 and/or GLUDy |
| 340 | 6 | 6.3515 | 0.04992 | ADHEr, FRD and/or SUCD4, GLCpts, LDH_D, MDH, THD2 and/or GLUDy |
| 341 | 6 | 6.3052 | 0.17034 | ADHEr, ASPT, ATPS4r, EDA and/or PGDHY, MDH, PGDH |
| 342 | 6 | 6.25221 | 0.15227 | ACKr and/or PTAr, ADHEr, ASPT, GLCpts, LDH_D, MDH |
| 343 | 6 | 6.22508 | 0.18792 | ADHEr, ATPS4r, LDH_D, MDH, NADH6, PFLi |
| 344 | 6 | 6.20871 | 0.17434 | ADHEr, EDA and/or PGDHY, MDH, PFLi, PGI, THD5 |
| 345 | 6 | 6.19852 | 0.09326 | ADHEr, ASPT, FUM, LDH_D, MDH, THD2 and/or GLUDy |
| 346 | 6 | 6.19408 | 0.16324 | ACKr and/or PTAr, ADHEr, ASPT, LDH_D, MDH, PYK |
| 347 | 6 | 6.19255 | 0.17194 | ADHEr, ASPT, ATPS4r, EDA and/or PGDHY, MDH, TAL |
| 348 | 6 | 6.18674 | 0.18098 | ACKr and/or PTAr, ADHEr, ASPT, LDH_D, MDH, NADH6 |
| 349 | 6 | 6.18358 | 0.11862 | ADHEr, ATPS4r, GLCpts, MDH, NADH6, PFLi |
| 350 | 6 | 6.12313 | 0.19075 | ACKr and/or PTAr, ADHEr, FDH_D, LDH_D, MDH, NADH6 |
| 351 | 6 | 6.09846 | 0.03275 | ADHEr, ASPT, LDH_D, MALS, MDH, THD2 and/or GLUDy |
| 352 | 6 | 6.09846 | 0.03275 | ADHEr, ASPT, ICL, LDH_D, MDH, THD2 and/or GLUDy |
| 353 | 6 | 6.08794 | 0.17343 | ADHEr, ASPT, ATPS4r, EDA and/or PGDHY, MDH, RPE |
| 354 | 6 | 6.01307 | 0.17456 | ADHEr, ASPT, ATPS4r, LDH_D, MDH, NADH6 |
| 355 | 6 | 6.00837 | 0.14517 | ADHEr, LDH_D, NADH6, PFLi, PPCK, THD2 and/or GLUDy |
| 356 | 6 | 5.99004 | 0.18339 | ACKr and/or PTAr, ADHEr, GLCpts, LDH_D, MDH, NADH6 |
| 357 | 6 | 5.9797 | 0.19373 | ACKr and/or PTAr, ACS, ADHEr, HEX1, PGI, PPS |
| 358 | 6 | 5.97334 | 0.11266 | ADHEr, GLCpts, MDH, NADH6, PFLi, PGI |
| 359 | 6 | 5.96643 | 0.16387 | ACKr and/or PTAr, ADHEr, ASPT, MDH, PYK, RPE |
| 360 | 6 | 5.8983 | 0.16412 | ACKr and/or PTAr, ADHEr, ASPT, MDH, PYK, TAL |
| 361 | 6 | 5.89777 | 0.06803 | ADHEr, ATPS4r, EDA and/or PGDHY, HEX1, PGI, THD2 and/or GLUDy |
| 362 | 6 | 5.81808 | 0.13048 | ADHEr, ATPS4r, MDH, NADH6, PFLi, PGI |

TABLE 14-continued

Knockout strain designs for increased production of 6-ACA, showing yields of 6-ACA and biomass.

| New Design ID | Num KO | 6ACA. Yield | Biomass | Rxnlist |
| --- | --- | --- | --- | --- |
| 363 | 6 | 5.77313 | 0.13132 | ADHEr, ATPS4r, NADH12, NADH6, PFLi, PGI |
| 364 | 6 | 5.75832 | 0.26044 | ACKr and/or PTAr, ADHEr, GLU5K, MDH, PFLi, THD2 and/or GLUDy |
| 365 | 6 | 5.75832 | 0.26044 | ACKr and/or PTAr, ADHEr, G5SD, MDH, PFLi, THD2 and/or GLUDy |
| 366 | 6 | 5.75556 | 0.13165 | ADHEr, ATPS4r, FUM, NADH6, PFLi, PGI |
| 367 | 6 | 5.68405 | 0.15589 | ADHEr, ATPS4r, LDH_D, NADH6, PFLi, PPCK |
| 368 | 6 | 5.64518 | 0.25081 | ADHEr, HEX1, LDH_D, NADH6, PFLi, THD2 and/or GLUDy |
| 369 | 6 | 5.61474 | 0.1274 | ADHEr, FRD and/or SUCD4, HEX1, LDH_D, PPS, THD2 and/or GLUDy |
| 370 | 6 | 5.57706 | 0.11542 | ADHEr, ATPS4r, GLCpts, NADH6, PFLi, THD2 and/or GLUDy |
| 371 | 6 | 5.55724 | 0.20645 | ADHEr, ATPS4r, FDH2, LDH_D, MDH, NADH6 |
| 372 | 6 | 5.39028 | 0.01098 | ADHEr, ASPT, LDH_D, MDH, SUCOAS, THD2 and/or GLUDy |
| 373 | 6 | 5.36336 | 0.12039 | ADHEr, ASPT, ATPS4r, LDH_D, MDH, THD2 and/or GLUDy |
| 374 | 6 | 5.35114 | 0.12824 | ADHEr, NADH12, NADH6, PFLi, PGI, RPE |
| 375 | 6 | 5.34992 | 0.12867 | ADHEr, FUM, NADH6, PFLi, PGI, RPE |
| 376 | 6 | 5.34421 | 0.12775 | ADHEr, NADH12, NADH6, PFLi, PGI, TAL |
| 377 | 6 | 5.34298 | 0.12817 | ADHEr, FUM, NADH6, PFLi, PGI, TAL |
| 378 | 6 | 5.33668 | 0.12721 | ADHEr, NADH12, NADH6, PFLi, PGDH, PGI |
| 379 | 6 | 5.33544 | 0.12763 | ADHEr, FUM, NADH6, PFLi, PGDH, PGI |
| 380 | 6 | 5.3133 | 0.13509 | ADHEr, GLCpts, LDH_D, NADH6, PFLi, PPCK |
| 381 | 6 | 5.30121 | 0.14588 | ADHEr, ATPS4r, GLCpts, NADH6, PPCK, RPE |
| 382 | 6 | 5.29298 | 0.14544 | ADHEr, ATPS4r, GLCpts, NADH6, PPCK, TAL |
| 383 | 6 | 5.28823 | 0.16642 | ADHEr, ASPT, ATPS4r, LDH_D, MDH, PPCK |
| 384 | 6 | 5.28401 | 0.14496 | ADHEr, ATPS4r, GLCpts, NADH6, PGL and/or G6PDHy, PPCK |
| 385 | 6 | 5.28401 | 0.14496 | ADHEr, ATPS4r, GLCpts, NADH6, PGDH, PPCK |
| 386 | 6 | 5.28388 | 0.145 | ADHEr, LDH_D, NADH6, PFLi, PPCK, PYK |
| 387 | 6 | 5.23479 | 0.26578 | ADHEr, ATPS4r, HEX1, LDH_D, NADH6, PFLi |
| 388 | 6 | 5.22487 | 0.16488 | ADHEr, GLCpts, LDH_D, MDH, PFLi, PPCK |
| 389 | 6 | 5.22487 | 0.16488 | ADHEr, FUM, GLCpts, LDH_D, PFLi, PPCK |
| 390 | 6 | 5.18966 | 0.19912 | ADHEr, ATPS4r, FUM, LDH_D, PFLi, PPCK |
| 391 | 6 | 5.18966 | 0.19912 | ADHEr, ATPS4r, LDH_D, MDH, PFLi, PPCK |
| 392 | 6 | 5.17671 | 0.18111 | ADHEr, LDH_D, MDH, NADH12, NADH6, PFLi |
| 393 | 6 | 5.17275 | 0.18244 | ADHEr, GLCpts, LDH_D, MDH, NADH6, PFLi |
| 394 | 6 | 5.16547 | 0.14992 | ADHEr, ASPT, ATPS4r, EDA and/or PGDHY, MDH, PFLi |
| 395 | 6 | 5.14231 | 0.02949 | ADHEr, FRD and/or SUCD4, GLUDy, HEX1, LDH_D, THD2 and/or GLUDy |
| 396 | 6 | 5.1335 | 0.31969 | ADHEr, HEX1, LDH_D, PFLi, PPS, THD2 and/or GLUDy |
| 397 | 6 | 5.12241 | 0.20902 | ADHEr, ATPS4r, LDH_D, MDH, NADH6, RPE |
| 398 | 6 | 5.11384 | 0.20727 | ADHEr, ATPS4r, LDH_D, MDH, NADH6, TAL |
| 399 | 6 | 5.1046 | 0.2054 | ADHEr, ATPS4r, LDH_D, MDH, NADH6, PGDH |
| 400 | 6 | 5.00987 | 0.10652 | ADHEr, ATPS4r, LDH_D, MDH, NADH6, THD2 and/or GLUDy |
| 401 | 6 | 4.99324 | 0.24292 | ADHEr, HEX1, LDH_D, NADH12, NADH6, PFLi |
| 402 | 6 | 4.98859 | 0.24448 | ADHEr, FUM, HEX1, LDH_D, NADH6, PFLi |
| 403 | 6 | 4.91516 | 0.18237 | ADHEr, ATPS4r, FUM, LDH_D, NADH6, PPCK |
| 404 | 6 | 4.91516 | 0.18237 | ADHEr, ATPS4r, LDH_D, MDH, NADH6, PPCK |
| 405 | 6 | 4.90997 | 0.20313 | ADHEr, ATPS4r, FDH2, LDH_D, NADH6, THD2 and/or GLUDy |
| 406 | 6 | 4.86469 | 0.20078 | ADHEr, ATPS4r, GLCpts, PFLi, PPCK, RPE |
| 407 | 6 | 4.79988 | 0.22937 | ACKr and/or PTAr, ADHEr, FUM, MDH, NADH6, PYK |
| 408 | 6 | 4.75998 | 0.22327 | ADHEr, HEX1, LDH_D, PGDH, PPS, THD2 and/or GLUDy |
| 409 | 6 | 4.75998 | 0.22327 | ADHEr, HEX1, LDH_D, PGL and/or G6PDHy, PPS, THD2 and/or GLUDy |
| 410 | 6 | 4.75352 | 0.20131 | ADHEr, ATPS4r, GLCpts, PFLi, PPCK, TAL |
| 411 | 6 | 4.72575 | 0.27672 | ADHEr, ATPS4r, FDH2, HEX1, LDH_D, NADH6 |
| 412 | 6 | 4.68468 | 0.22968 | ADHEr, HEX1, LDH_D, PPS, TAL, THD2 and/or GLUDy |
| 413 | 6 | 4.67203 | 0.24577 | ACKr and/or PTAr, ADHEr, ATPS4r, HEX1, LDH_D, THD2 and/or GLUDy |
| 414 | 6 | 4.6646 | 0.15914 | ADHEr, ATPS4r, FUM, GLCpts, NADH6, THD2 and/or GLUDy |
| 415 | 6 | 4.6568 | 0.25634 | ADHEr, ATPS4r, ICL, MDH, PGL and/or G6PDHy, PPS |
| 416 | 6 | 4.6568 | 0.25634 | ADHEr, ATPS4r, FUM, MDH, PGL and/or G6PDHy, PPS |
| 417 | 6 | 4.6568 | 0.25634 | ADHEr, ATPS4r, MALS, MDH, PGL and/or G6PDHy, PPS |
| 418 | 6 | 4.64861 | 0.22305 | ADHEr, HEX1, LDH_D, PFLi, PPCK, THD2 and/or GLUDy |
| 419 | 6 | 4.61213 | 0.23585 | ADHEr, HEX1, LDH_D, PPS, RPE, THD2 and/or GLUDy |
| 420 | 6 | 4.54731 | 0.14834 | ADHEr, EDA and/or PGDHY, GLUDy, LDH_D, MDH, THD2 and/or GLUDy |
| 421 | 6 | 4.45035 | 0.18822 | ADHEr, ASPT, ATPS4r, MDH, PYK, RPE |
| 422 | 6 | 4.44107 | 0.285 | ADHEr, ATPS4r, FUM, HEX1, LDH_D, NADH6 |
| 423 | 6 | 4.37848 | 0.18825 | ADHEr, ASPT, ATPS4r, MDH, PYK, TAL |
| 424 | 6 | 4.35711 | 0.22671 | ADHEr, ASPT, LDH_D, MDH, NADH12, NADH6 |
| 425 | 6 | 4.30745 | 0.05232 | ACKr and/or PTAr, ADHEr, LDH_D, MDH, PPCK, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 426 | 6 | 4.29111 | 0.05856 | ADHEr, ASPT, LDH_D, MDH, PGI, THD2 and/or GLUDy |
| 427 | 6 | 4.29026 | 0.24034 | ACKr and/or PTAr, ADHEr, EDA and/or PGDHY, G5SD, GLYCL, PGI |
| 428 | 6 | 4.29026 | 0.24034 | ACKr and/or PTAr, ADHEr, EDA and/or PGDHY, GLU5K, GLYCL, PGI |
| 429 | 6 | 4.19017 | 0.18892 | ADHEr, ATPS4r, FUM, LDH_D, NADH6, THD2 and/or GLUDy |
| 430 | 6 | 4.14405 | 0.19951 | ADHEr, ATPS4r, FUM, LDH_D, PGDH, PPCK |
| 431 | 6 | 4.14405 | 0.19951 | ADHEr, ATPS4r, FUM, LDH_D, PGL and/or G6PDHy, PPCK |
| 432 | 6 | 4.14405 | 0.19951 | ADHEr, ATPS4r, LDH_D, MDH, PGDH, PPCK |
| 433 | 6 | 4.13843 | 0.19251 | ADHEr, EDA and/or PGDHY, MDH, PPCK, RPE |
| 434 | 6 | 4.11865 | 0.20026 | ADHEr, ATPS4r, LDH_D, MDH, PPCK, TAL |
| 435 | 6 | 4.11865 | 0.20026 | ADHEr, ATPS4r, FUM, LDH_D, PPCK, TAL |
| 436 | 6 | 4.10258 | 0.11665 | ACKr and/or PTAr, ADHEr, ATPS4r, PPCK, PYK, SUCOAS |
| 437 | 6 | 4.09791 | 0.11017 | ADHEr, ATPS4r, LDH_D, MDH, PPCK, THD2 and/or GLUDy |
| 438 | 6 | 4.09791 | 0.11017 | ADHEr, ATPS4r, FUM, LDH_D, PPCK, THD2 and/or GLUDy |
| 439 | 6 | 4.09533 | 0.20095 | ADHEr, ATPS4r, LDH_D, MDH, PPCK, RPE |
| 440 | 6 | 4.09533 | 0.20095 | ADHEr, ATPS4r, FUM, LDH_D, PPCK, RPE |
| 441 | 6 | 4.08336 | 0.13789 | ADHEr, ASPT, LDH_D, MDH, PPCK, THD2 and/or GLUDy |
| 442 | 6 | 4.08234 | 0.13828 | ADHEr, ASPT, GLCpts, LDH_D, MDH, THD2 and/or GLUDy |
| 443 | 6 | 4.0683 | 0.31169 | ADHEr, FUM, HEX1, LDH_D, PPS, THD2 and/or GLUDy |
| 444 | 6 | 4.05789 | 0.14762 | ADHEr, ASPT, LDH_D, MDH, NADH6, THD2 and/or GLUDy |
| 445 | 6 | 4.04139 | 0.17129 | ADHEr, ASPT, LDH_D, MDH, RPE, THD2 and/or GLUDy |
| 446 | 6 | 3.97871 | 0.17786 | ADHEr, ASPT, GLCpts, LDH_D, MDH, PPCK |
| 447 | 6 | 3.95205 | 0.10694 | ACKr and/or PTAr, ADHEr, ATPS4r, PGDH, PGI, SUCOAS |
| 448 | 6 | 3.95184 | 0.18812 | ADHEr, ASPT, LDH_D, MDH, NADH6, PPCK |
| 449 | 6 | 3.94624 | 0.19026 | ADHEr, ASPT, GLCpts, LDH_D, MDH, NADH6 |
| 450 | 6 | 3.94455 | 0.21245 | ADHEr, ASPT, LDH_D, MDH, PPCK, RPE |
| 451 | 6 | 3.94203 | 0.1079 | ACKr and/or PTAr, ADHEr, ATPS4r, PGI, SUCOAS, TAL |
| 452 | 6 | 3.93874 | 0.25675 | ACKr and/or PTAr, ADHEr, FUM, HEX1, LDH_D, THD2 and/or GLUDy |
| 453 | 6 | 3.93273 | 0.1088 | ACKr and/or PTAr, ADHEr, ATPS4r, PGI, RPE, SUCOAS |
| 454 | 6 | 3.91186 | 0.22634 | ADHEr, ASPT, LDH_D, MDH, NADH6, RPE |
| 455 | 6 | 3.90038 | 0.04761 | ADHEr, GLCpts, NADH6, PGI, PPCK, THD2 and/or GLUDy |
| 456 | 6 | 3.8947 | 0.05032 | ADHEr, FUM, GLCpts, NADH6, PGI, THD2 and/or GLUDy |
| 457 | 6 | 3.8947 | 0.05032 | ADHEr, GLCpts, MDH, NADH6, PGI, THD2 and/or GLUDy |
| 458 | 6 | 3.84046 | 0.12564 | ACKr and/or PTAr, ADHEr, ATPS4r, LDH_D, PPCK, THD2 and/or GLUDy |
| 459 | 6 | 3.81228 | 0.08972 | ADHEr, EDA and/or PGDHY, MDH, NADH6, PYK, THD2 and/or GLUDy |
| 460 | 6 | 3.81228 | 0.08972 | ADHEr, MDH, NADH6, PGL and/or G6PDHy, PYK, THD2 and/or GLUDy |
| 461 | 6 | 3.76251 | 0.07312 | ACKr and/or PTAr, ADHEr, LDH_D, NADH6, PPCK, THD2 and/or GLUDy |
| 462 | 6 | 3.70324 | 0.1395 | ACKr and/or PTAr, ADHEr, LDH_D, NADH6, PPCK, PYK |
| 463 | 6 | 3.70023 | 0.1556 | ACKr and/or PTAr, ADHEr, LDH_D, MDH, PPCK, PYK |
| 464 | 6 | 3.70023 | 0.1556 | ACKr and/or PTAr, ADHEr, FUM, LDH_D, PPCK, PYK |
| 465 | 6 | 3.67651 | 0.1546 | ADHEr, MDH, NADH6, PGL and/or G6PDHy, PPCK, PYK |
| 466 | 6 | 3.67651 | 0.1546 | ADHEr, EDA and/or PGDHY, MDH, NADH6, PPCK, PYK |
| 467 | 6 | 3.652 | 0.16631 | ADHEr, LDH_D, MDH, NADH12, NADH6, THD2 and/or GLUDy |
| 468 | 6 | 3.64497 | 0.19156 | ADHEr, FUM, GLCpts, NADH6, RPE, THD2 and/or GLUDy |
| 469 | 6 | 3.62254 | 0.1804 | ADHEr, LDH_D, NADH12, NADH6, PPCK, THD2 and/or GLUDy |
| 470 | 6 | 3.5494 | 0.21535 | ADHEr, FUM, LDH_D, NADH12, NADH6, THD2 and/or GLUDy |
| 471 | 6 | 3.41696 | 0.27865 | ADHEr, DAAD, FDH2, NADH12, NADH6, PRO1z |
| 472 | 6 | 3.41696 | 0.27865 | ADHEr, ALAR, FDH2, NADH12, NADH6, PRO1z |
| 473 | 6 | 3.40228 | 0.13474 | ADHEr, ATPS4r, FRD and/or SUCD4, HEX1, LDH_D, THD2 and/or GLUDy |
| 474 | 6 | 3.27381 | 0.03414 | ACKr and/or PTAr, ADHEr, FUM, LDH_D, PPCK, THD2 and/or GLUDy |
| 475 | 6 | 3.22868 | 0.19148 | ADHEr, FRD and/or SUCD4, LDH_D, PPS, SUCOAS, THD2 and/or GLUDy |
| 476 | 6 | 3.11905 | 0.12289 | ADHEr, FUM, LDH_D, PPCK, PYK, THD2 and/or GLUDy |
| 477 | 6 | 3.11905 | 0.12289 | ADHEr, LDH_D, MDH, PPCK, PYK, THD2 and/or GLUDy |
| 478 | 6 | 3.10777 | 0.12936 | ADHEr, FUM, GLCpts, LDH_D, PPCK, THD2 and/or GLUDy |
| 479 | 6 | 3.10777 | 0.12936 | ADHEr, GLCpts, LDH_D, MDH, PPCK, THD2 and/or GLUDy |
| 480 | 6 | 2.9427 | 0.20328 | ADHEr, FRD and/or SUCD4, LDH_D, MALS, PPS, THD2 and/or GLUDy |
| 481 | 6 | 2.9427 | 0.20328 | ADHEr, FRD and/or SUCD4, ICL, LDH_D, PPS, THD2 and/or GLUDy |
| 482 | 6 | 2.80361 | 0.3231 | ADHEr, FUM, HEX1, LDH_D, TAL, THD2 and/or GLUDy |
| 483 | 6 | 2.79375 | 0.29126 | ACKr and/or PTAr, ADHEr, ATPS4r, FUM, LDH_D, THD2 and/or GLUDy |
| 484 | 6 | 2.68652 | 0.29222 | ADHEr, ATPS4r, GLUDy, HEX1, RPE, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 485 | 6 | 2.62059 | 0.29297 | ADHEr, ATPS4r, GLUDy, HEX1, TAL, THD2 and/or GLUDy |
| 486 | 6 | 2.46956 | 0.30762 | ADHEr, FUM, LDH_D, PPS, SUCOAS, THD2 and/or GLUDy |
| 487 | 6 | 0.97386 | 0.28207 | ACKr and/or PTAr, ADHEr, FUM, MDH, PGL and/or G6PDHy, SUCOAS |
| 488 | 6 | 0.97386 | 0.28207 | ACKr and/or PTAr, ADHEr, ICL, MDH, PGL and/or G6PDHy, SUCOAS |
| 489 | 6 | 0.97386 | 0.28207 | ACKr and/or PTAr, ADHEr, FUM, MDH, PGDH, SUCOAS |
| 490 | 6 | 0.97386 | 0.28207 | ACKr and/or PTAr, ADHEr, MALS, MDH, PGL and/or G6PDHy, SUCOAS |
| 491 | 6 | 0.97386 | 0.28207 | ACKr and/or PTAr, ADHEr, ICL, MDH, PGDH, SUCOAS |
| 492 | 6 | 0.97386 | 0.28207 | ACKr and/or PTAr, ADHEr, MALS, MDH, PGDH, SUCOAS |
| 493 | 6 | 0.90686 | 0.28301 | ACKr and/or PTAr, ADHEr, MALS, MDH, SUCOAS, TAL |
| 494 | 6 | 0.90686 | 0.28301 | ACKr and/or PTAr, ADHEr, ICL, MDH, SUCOAS, TAL |
| 495 | 6 | 0.84537 | 0.28387 | ACKr and/or PTAr, ADHEr, ICL, MDH, RPE, SUCOAS |
| 496 | 6 | 0.84537 | 0.28387 | ACKr and/or PTAr, ADHEr, MALS, MDH, RPE, SUCOAS |
| 497 | 3 | 3.26272 | 0.35236 | ADHEr, LDH_D, NADH6 |
| 498 | 3 | 2.8403 | 0.28275 | ADHEr, LDH_D, PPCK |
| 499 | 3 | 1.72604 | 0.38773 | ADHEr, ATPS4r, LDH_D |
| 500 | 3 | 0.89333 | 0.37885 | ADHEr, FUM, LDH_D |
| 501 | 3 | 0.83466 | 0.26712 | ADHEr, LDH_D, PGI |
| 502 | 3 | 0.41621 | 0.38953 | ADHEr, HEX1, LDH_D |
| 503 | 4 | 5.71646 | 0.21908 | ADHEr, HEX1, LDH_D, PGI |
| 504 | 4 | 4.83364 | 0.29669 | ADHEr, LDH_D, NADH6, PFLi |
| 505 | 4 | 4.11897 | 0.24338 | ADHEr, EDA and/or PGDHY, LDH_D, PGI |
| 506 | 4 | 3.77533 | 0.25553 | ADHEr, ASPT, LDH_D, MDH |
| 507 | 4 | 3.65248 | 0.19372 | ADHEr, LDH_D, NADH6, PGI |
| 508 | 4 | 3.47283 | 0.25194 | ADHEr, LDH_D, NADH6, PPCK |
| 509 | 4 | 3.39319 | 0.29001 | ADHEr, LDH_D, MDH, NADH6 |
| 510 | 4 | 3.35305 | 0.34906 | ADHEr, LDH_D, NADH6, RPE |
| 511 | 4 | 3.0877 | 0.16431 | ADHEr, LDH_D, PGI, PPCK |
| 512 | 4 | 2.90019 | 0.24841 | ADHEr, GLCpts, LDH_D, PPCK |
| 513 | 4 | 2.89855 | 0.2815 | ADHEr, LDH_D, PPCK, RPE |
| 514 | 4 | 2.88617 | 0.25645 | ADHEr, FUM, LDH_D, THD2 and/or GLUDy |
| 515 | 4 | 2.72186 | 0.35068 | ADHEr, FUM, HEX1, LDH_D |
| 516 | 4 | 2.0373 | 0.38161 | ADHEr, ATPS4r, LDH_D, RPE |
| 517 | 4 | 1.89007 | 0.3845 | ADHEr, ATPS4r, LDH_D, TAL |
| 518 | 4 | 1.49147 | 0.26024 | ADHEr, LDH_D, PFLi, PGI |
| 519 | 4 | 0.5753 | 0.38695 | ADHEr, HEX1, LDH_D, RPE |
| 520 | 4 | 0.49968 | 0.38818 | ADHEr, HEX1, LDH_D, TAL |
| 521 | 5 | 6.93034 | 0.18126 | ADHEr, EDA and/or PGDHY, LDH_D, NADH6, PGI |
| 522 | 5 | 6.92332 | 0.16482 | ADHEr, HEX1, LDH_D, NADH6, PGI |
| 523 | 5 | 6.91845 | 0.19552 | ADHEr, HEX1, LDH_D, PFLi, PGI |
| 524 | 5 | 6.89839 | 0.18171 | ACKr and/or PTAr, ADHEr, LDH_D, NADH6, PGI |
| 525 | 5 | 6.14899 | 0.1758 | ADHEr, EDA and/or PGDHY, LDH_D, PFLi, PGI |
| 526 | 5 | 5.8701 | 0.13379 | ADHEr, EDA and/or PGDHY, LDH_D, PGI, PPCK |
| 527 | 5 | 5.85757 | 0.23874 | ADHEr, LDH_D, MDH, NADH6, THD2 and/or GLUDy |
| 528 | 5 | 5.85411 | 0.19685 | ADHEr, HEX1, LDH_D, PGI, PPS |
| 529 | 5 | 5.81422 | 0.16481 | ADHEr, ATPS4r, EDA and/or PGDHY, LDH_D, PGI |
| 530 | 5 | 5.40131 | 0.26362 | ADHEr, LDH_D, MDH, PFLi, THD2 and/or GLUDy |
| 531 | 5 | 4.88764 | 0.27849 | ADHEr, LDH_D, NADH12, NADH6, PFLi |
| 532 | 5 | 4.88489 | 0.27942 | ADHEr, FUM, LDH_D, NADH6, PFLi |
| 533 | 5 | 4.81778 | 0.26037 | ADHEr, ATPS4r, LDH_D, MDH, NADH6 |
| 534 | 5 | 4.73419 | 0.21859 | ADHEr, LDH_D, NADH6, PPCK, THD2 and/or GLUDy |
| 535 | 5 | 4.63783 | 0.29595 | ADHEr, ATPS4r, FDH2, LDH_D, NADH6 |
| 536 | 5 | 4.30547 | 0.19131 | ADHEr, ATPS4r, LDH_D, NADH6, PGI |
| 537 | 5 | 4.2733 | 0.23078 | ADHEr, ATPS4r, LDH_D, NADH6, PPCK |
| 538 | 5 | 4.23803 | 0.24209 | ACKr and/or PTAr, ADHEr, EDA and/or PGDHY, LDH_D, PGI |
| 539 | 5 | 4.12032 | 0.32701 | ADHEr, ATPS4r, FUM, LDH_D, NADH6 |
| 540 | 5 | 3.9718 | 0.23354 | ADHEr, ATPS4r, LDH_D, MDH, PPCK |
| 541 | 5 | 3.9718 | 0.23354 | ADHEr, ATPS4r, FUM, LDH_D, PPCK |
| 542 | 5 | 3.8747 | 0.21758 | ADHEr, ASPT, GLCpts, LDH_D, MDH |
| 543 | 5 | 3.84814 | 0.25342 | ADHEr, ASPT, LDH_D, MDH, RPE |
| 544 | 5 | 3.83986 | 0.2047 | ADHEr, ASPT, LDH_D, MDH, PYK |
| 545 | 5 | 3.75472 | 0.32987 | ADHEr, ATPS4r, HEX1, LDH_D, NADH6 |
| 546 | 5 | 3.54965 | 0.29114 | ADHEr, ATPS4r, LDH_D, MDH, PGDH |
| 547 | 5 | 3.54605 | 0.21695 | ADHEr, GLCpts, LDH_D, NADH6, PPCK |
| 548 | 5 | 3.54385 | 0.218 | ADHEr, LDH_D, NADH6, PPCK, PYK |
| 549 | 5 | 3.53615 | 0.25027 | ADHEr, LDH_D, NADH6, PPCK, RPE |
| 550 | 5 | 3.5018 | 0.32809 | ADHEr, ATPS4r, FUM, HEX1, LDH_D |
| 551 | 5 | 3.46904 | 0.25375 | ADHEr, GLCpts, LDH_D, MDH, NADH6 |
| 552 | 5 | 3.46528 | 0.28851 | ADHEr, LDH_D, MDH, NADH6, RPE |
| 553 | 5 | 3.44916 | 0.13425 | ADHEr, LDH_D, PFLi, PGI, PPCK |
| 554 | 5 | 3.44555 | 0.26498 | ADHEr, HEX1, LDH_D, NADH6, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 555 | 5 | 3.43776 | 0.29402 | ADHEr, ATPS4r, LDH_D, MDH, TAL |
| 556 | 5 | 3.33377 | 0.2967 | ADHEr, ATPS4r, LDH_D, MDH, RPE |
| 557 | 5 | 3.33152 | 0.33978 | ADHEr, FUM, LDH_D, NADH6, TAL |
| 558 | 5 | 3.32935 | 0.34088 | ADHEr, HEX1, LDH_D, NADH6, TAL |
| 559 | 5 | 3.32788 | 0.32122 | ADHEr, FUM, HEX1, LDH_D, NADH6 |
| 560 | 5 | 3.31278 | 0.3493 | ADHEr, G5SD, LDH_D, NADH6, TAL |
| 561 | 5 | 3.31278 | 0.3493 | ADHEr, GLU5K, LDH_D, NADH6, TAL |
| 562 | 5 | 3.23462 | 0.28717 | ACKr and/or PTAr, ADHEr, ATPS4r, LDH_D, SUCOAS |
| 563 | 5 | 3.17484 | 0.10602 | ADHEr, LDH_D, PGI, PPCK, THD2 and/or GLUDy |
| 564 | 5 | 3.16614 | 0.11184 | ADHEr, LDH_D, MDH, PGI, THD2 and/or GLUDy |
| 565 | 5 | 3.16614 | 0.11184 | ADHEr, FUM, LDH_D, PGI, THD2 and/or GLUDy |
| 566 | 5 | 3.11125 | 0.24826 | ADHEr, ATPS4r, LDH_D, PPCK, THD2 and/or GLUDy |
| 567 | 5 | 2.95529 | 0.24477 | ADHEr, LDH_D, PPCK, RPE, THD2 and/or GLUDy |
| 568 | 5 | 2.95136 | 0.24731 | ADHEr, GLCpts, LDH_D, PPCK, RPE |
| 569 | 5 | 2.94249 | 0.25305 | ADHEr, FUM, LDH_D, RPE, THD2 and/or GLUDy |
| 570 | 5 | 2.93765 | 0.22693 | ADHEr, FUM, LDH_D, PPCK, PYK |
| 571 | 5 | 2.93765 | 0.22693 | ADHEr, LDH_D, MDH, PPCK, PYK |
| 572 | 5 | 2.9332 | 0.24406 | ADHEr, LDH_D, PPCK, TAL, THD2 and/or GLUDy |
| 573 | 5 | 2.90913 | 0.24328 | ADHEr, LDH_D, PGDH, PPCK, THD2 and/or GLUDy |
| 574 | 5 | 2.90913 | 0.24328 | ADHEr, LDH_D, PGL and/or G6PDHy, PPCK, THD2 and/or GLUDy |
| 575 | 5 | 2.90081 | 0.26381 | ADHEr, LDH_D, MDH, PPCK, TAL |
| 576 | 5 | 2.90081 | 0.26381 | ADHEr, FUM, LDH_D, PPCK, TAL |
| 577 | 5 | 2.79498 | 0.34856 | ADHEr, FUM, HEX1, LDH_D, RPE |
| 578 | 5 | 2.61943 | 0.36027 | ADHEr, HEX1, LDH_D, PFLi, PPS |
| 579 | 5 | 2.60615 | 0.3202 | ADHEr, ATPS4r, HEX1, LDH_D, PFLi |
| 580 | 5 | 2.60314 | 0.31113 | ADHEr, HEX1, LDH_D, MDH, PFLi |
| 581 | 5 | 2.54001 | 0.22798 | ADHEr, LDH_D, PFLi, PGDH, PGI |
| 582 | 5 | 2.5259 | 0.22921 | ADHEr, LDH_D, PFLi, PGI, TAL |
| 583 | 5 | 2.5129 | 0.23034 | ADHEr, LDH_D, PFLi, PGI, RPE |
| 584 | 5 | 2.50442 | 0.16853 | ADHEr, ATPS4r, LDH_D, PFLi, PGI |
| 585 | 5 | 2.45433 | 0.3546 | ADHEr, ATPS4r, HEX1, LDH_D, THD2 and/or GLUDy |
| 586 | 5 | 2.18633 | 0.3609 | ADHEr, HEX1, LDH_D, PPS, THD2 and/or GLUDy |
| 587 | 5 | 2.11347 | 0.31979 | ADHEr, ATPS4r, HEX1, LDH_D, MDH |
| 588 | 5 | 1.5933 | 0.25891 | ADHEr, FUM, LDH_D, PFLi, PGI |
| 589 | 5 | 0.9475 | 0.3633 | ADHEr, FUM, LDH_D, PGDH, TAL |
| 590 | 5 | 0.9475 | 0.3633 | ADHEr, FUM, LDH_D, PGL and/or G6PDHy, TAL |
| 591 | 6 | 7.08404 | 0.12641 | ADHEr, EDA and/or PGDHY, LDH_D, NADH6, PFLi, PGI |
| 592 | 6 | 7.0245 | 0.10838 | ADHEr, EDA and/or PGDHY, LDH_D, PFLi, PGI, PPCK |
| 593 | 6 | 6.98742 | 0.06748 | ADHEr, EDA and/or PGDHY, LDH_D, NADH6, PGI, THD2 and/or GLUDy |
| 594 | 6 | 6.69134 | 0.13239 | ADHEr, ASPT, ATPS4r, GLCpts, LDH_D, MDH |
| 595 | 6 | 6.58534 | 0.16513 | ADHEr, EDA and/or PGDHY, GLCpts, LDH_D, PFLi, PGI |
| 596 | 6 | 6.55123 | 0.09841 | ADHEr, ASPT, LDH_D, MDH, PGL and/or G6PDHy, PYK |
| 597 | 6 | 6.55123 | 0.09841 | ADHEr, ASPT, EDA and/or PGDHY, LDH_D, MDH, PYK |
| 598 | 6 | 6.36357 | 0.11937 | ADHEr, EDA and/or PGDHY, LDH_D, PFLi, PGI, THD2 and/or GLUDy |
| 599 | 6 | 6.22082 | 0.11375 | ADHEr, ATPS4r, EDA and/or PGDHY, LDH_D, PFLi, PGI |
| 600 | 6 | 5.98165 | 0.07186 | ADHEr, ATPS4r, EDA and/or PGDHY, LDH_D, PGI, PPCK |
| 601 | 6 | 5.93527 | 0.09761 | ADHEr, EDA and/or PGDHY, GLCpts, LDH_D, PGI, PPCK |
| 602 | 6 | 5.87444 | 0.0434 | ADHEr, EDA and/or PGDHY, FUM, LDH_D, PGI, THD2 and/or GLUDy |
| 603 | 6 | 5.87444 | 0.0434 | ADHEr, EDA and/or PGDHY, LDH_D, MDH, PGI, THD2 and/or GLUDy |
| 604 | 6 | 5.65488 | 0.26204 | ACKr and/or PTAr, ADHEr, LDH_D, MDH, PFLi, THD2 and/or GLUDy |
| 605 | 6 | 5.59555 | 0.20952 | ADHEr, ATPS4r, GLCpts, LDH_D, MDH, NADH6 |
| 606 | 6 | 5.1776 | 0.13724 | ADHEr, LDH_D, NADH12, NADH6, PFLi, PGI |
| 607 | 6 | 5.11744 | 0.13758 | ADHEr, FUM, LDH_D, NADH6, PFLi, PGI |
| 608 | 6 | 5.11744 | 0.13758 | ADHEr, LDH_D, MDH, NADH6, PFLi, PGI |
| 609 | 6 | 5.09877 | 0.17589 | ADHEr, ATPS4r, GLCpts, LDH_D, NADH6, PPCK |
| 610 | 6 | 5.08219 | 0.13778 | ADHEr, ATPS4r, LDH_D, NADH6, PFLi, PGI |
| 611 | 6 | 5.02693 | 0.21085 | ADHEr, ATPS4r, LDH_D, NADH6, PGDH, PPCK |
| 612 | 6 | 5.02693 | 0.21085 | ADHEr, ATPS4r, LDH_D, NADH6, PGL and/or G6PDHy, PPCK |
| 613 | 6 | 5.00057 | 0.21154 | ADHEr, ATPS4r, LDH_D, NADH6, PPCK, TAL |
| 614 | 6 | 4.97638 | 0.21218 | ADHEr, ATPS4r, LDH_D, NADH6, PPCK, RPE |
| 615 | 6 | 4.88512 | 0.29281 | ADHEr, GLU5K, LDH_D, NADH6, PFLi, RPE |
| 616 | 6 | 4.88512 | 0.29281 | ADHEr, G5SD, LDH_D, NADH6, PFLi, RPE |
| 617 | 6 | 4.885 | 0.29286 | ADHEr, ASNS2, LDH_D, NADH6, PFLi, RPE |
| 618 | 6 | 4.85776 | 0.29446 | ADHEr, ATPS4r, FDH2, LDH_D, NADH6, RPE |
| 619 | 6 | 4.83644 | 0.29517 | ADHEr, ATPS4r, FDH2, LDH_D, NADH6, TAL |
| 620 | 6 | 4.66386 | 0.18074 | ADHEr, ATPS4r, FUM, GLCpts, LDH_D, PPCK |
| 621 | 6 | 4.66386 | 0.18074 | ADHEr, ATPS4r, GLCpts, LDH_D, MDH, PPCK |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 622 | 6 | 4.63095 | 0.20189 | ADHEr, ATPS4r, GLCpts, LDH_D, PFLi, PPCK |
| 623 | 6 | 4.49707 | 0.25782 | ADHEr, ATPS4r, EDA and/or PGDHY, LDH_D, MDH, THD2 and/or GLUDy |
| 624 | 6 | 4.4958 | 0.1778 | ADHEr, ASPT, LDH_D, MDH, NADH6, PYK |
| 625 | 6 | 4.41977 | 0.25646 | ADHEr, ATPS4r, GLCpts, LDH_D, MDH, THD2 and/or GLUDy |
| 626 | 6 | 4.18509 | 0.32432 | ADHEr, ATPS4r, HEX1, LDH_D, NADH6, PGL and/or G6PDHy |
| 627 | 6 | 4.18509 | 0.32432 | ADHEr, ATPS4r, HEX1, LDH_D, NADH6, PGDH |
| 628 | 6 | 4.15013 | 0.1124 | ADHEr, ASPT, LDH_D, MDH, PYK, THD2 and/or GLUDy |
| 629 | 6 | 4.14582 | 0.32483 | ADHEr, ATPS4r, HEX1, LDH_D, NADH6, TAL |
| 630 | 6 | 4.1099 | 0.32529 | ADHEr, ATPS4r, HEX1, LDH_D, NADH6, RPE |
| 631 | 6 | 4.04473 | 0.12883 | ADHEr, LDH_D, PFLi, PGDH, PGI, PPCK |
| 632 | 6 | 4.03844 | 0.12934 | ADHEr, LDH_D, PFLi, PGI, PPCK, TAL |
| 633 | 6 | 4.03266 | 0.12981 | ADHEr, LDH_D, PFLi, PGI, PPCK, RPE |
| 634 | 6 | 4.02531 | 0.1111 | ADHEr, GLCpts, LDH_D, PFLi, PGI, PPCK |
| 635 | 6 | 3.9367 | 0.21579 | ADHEr, ASPT, GLCpts, LDH_D, MDH, RPE |
| 636 | 6 | 3.76049 | 0.30843 | ADHEr, ATPS4r, FUM, HEX1, LDH_D, PFLi |
| 637 | 6 | 3.71345 | 0.27754 | ADHEr, ATPS4r, LDH_D, MDH, PGDH, TAL |
| 638 | 6 | 3.69299 | 0.14673 | ADHEr, LDH_D, NADH6, PPCK, PYK, THD2 and/or GLUDy |
| 639 | 6 | 3.64625 | 0.1409 | ACKr and/or PTAr, ADHEr, LDH_D, MDH, PGI, PPCK |
| 640 | 6 | 3.64625 | 0.1409 | ACKr and/or PTAr, ADHEr, FUM, LDH_D, PGI, PPCK |
| 641 | 6 | 3.60057 | 0.21551 | ADHEr, GLCpts, LDH_D, NADH6, PPCK, RPE |
| 642 | 6 | 3.59735 | 0.21725 | ADHEr, LDH_D, NADH6, PPCK, PYK, RPE |
| 643 | 6 | 3.59622 | 0.19297 | ADHEr, FUM, GLCpts, LDH_D, NADH6, PPCK |
| 644 | 6 | 3.59622 | 0.19297 | ADHEr, GLCpts, LDH_D, MDH, NADH6, PPCK |
| 645 | 6 | 3.59594 | 0.19311 | ADHEr, FUM, LDH_D, NADH6, PPCK, PYK |
| 646 | 6 | 3.59594 | 0.19311 | ADHEr, LDH_D, MDH, NADH6, PPCK, PYK |
| 647 | 6 | 3.59157 | 0.1952 | ADHEr, FUM, GLCpts, LDH_D, NADH6, THD2 and/or GLUDy |
| 648 | 6 | 3.55204 | 0.22769 | ADHEr, LDH_D, MDH, NADH6, PPCK, TAL |
| 649 | 6 | 3.55204 | 0.22769 | ADHEr, FUM, LDH_D, NADH6, PPCK, TAL |
| 650 | 6 | 3.53212 | 0.25244 | ADHEr, GLCpts, LDH_D, MDH, NADH6, RPE |
| 651 | 6 | 3.52326 | 0.22785 | ADHEr, GLU5K, LDH_D, MDH, NADH6, PPCK |
| 652 | 6 | 3.52326 | 0.22785 | ADHEr, G5SD, LDH_D, MDH, NADH6, PPCK |
| 653 | 6 | 3.52326 | 0.22785 | ADHEr, FUM, GLU5K, LDH_D, NADH6, PPCK |
| 654 | 6 | 3.52326 | 0.22785 | ADHEr, FUM, G5SD, LDH_D, NADH6, PPCK |
| 655 | 6 | 3.52319 | 0.22788 | ADHEr, ASNS2, FUM, LDH_D, NADH6, PPCK |
| 656 | 6 | 3.52319 | 0.22788 | ADHEr, ASNS2, LDH_D, MDH, NADH6, PPCK |
| 657 | 6 | 3.51328 | 0.26261 | ADHEr, HEX1, LDH_D, NADH6, RPE, THD2 and/or GLUDy |
| 658 | 6 | 3.40958 | 0.31856 | ADHEr, FUM, HEX1, LDH_D, NADH6, RPE |
| 659 | 6 | 3.19551 | 0.34972 | ADHEr, ATPS4r, HEX1, LDH_D, PPS, THD2 and/or GLUDy |
| 660 | 6 | 2.95797 | 0.22895 | ADHEr, FUM, GLCpts, LDH_D, PPCK, TAL |
| 661 | 6 | 2.95797 | 0.22895 | ADHEr, GLCpts, LDH_D, MDH, PPCK, TAL |
| 662 | 6 | 2.94768 | 0.30664 | ADHEr, ATPS4r, HEX1, LDH_D, MDH, PFLi |
| 663 | 6 | 2.92149 | 0.26881 | ADHEr, ATPS4r, LDH_D, MDH, PGL and/or G6PDHy, PPS |
| 664 | 6 | 2.76831 | 0.35787 | ADHEr, HEX1, LDH_D, PFLi, PPS, RPE |
| 665 | 6 | 2.7362 | 0.31504 | ADHEr, ATPS4r, HEX1, LDH_D, PFLi, RPE |
| 666 | 6 | 2.73201 | 0.30945 | ADHEr, HEX1, LDH_D, MDH, PFLi, RPE |
| 667 | 6 | 2.69754 | 0.35901 | ADHEr, HEX1, LDH_D, PFLi, PPS, TAL |
| 668 | 6 | 2.67469 | 0.31748 | ADHEr, ATPS4r, HEX1, LDH_D, PFLi, TAL |
| 669 | 6 | 2.67071 | 0.31025 | ADHEr, HEX1, LDH_D, MDH, PFLi, TAL |
| 670 | 6 | 2.61965 | 0.35455 | ADHEr, ATPS4r, HEX1, LDH_D, RPE, THD2 and/or GLUDy |
| 671 | 6 | 2.60629 | 0.2178 | ADHEr, LDH_D, PFLi, PGDH, PGI, TAL |
| 672 | 6 | 2.5479 | 0.2938 | ADHEr, ATPS4r, GLUDy, HEX1, LDH_D, THD2 and/or GLUDy |
| 673 | 6 | 2.5408 | 0.35457 | ADHEr, ATPS4r, HEX1, LDH_D, TAL, THD2 and/or GLUDy |
| 674 | 6 | 2.05497 | 0.19746 | ADHEr, ASPT, ATPS4r, LDH_D, PGI, THD5 |
| 675 | 6 | 1.65594 | 0.25767 | ACKr and/or PTAr, ADHEr, FUM, LDH_D, PFLi, PGI |
| 676 | 7 | 7.90077 | 0.01226 | ADHEr, ASPT, LDH_D, MDH, PPCK, PFLi, THD2 and/or GLUDy |
| 677 | 7 | 7.84104 | 0.01965 | ADHEr, ASPT, LDH_D, MDH, NADH6, PFLi, THD2 and/or GLUDy |
| 678 | 7 | 7.7052 | 0.03644 | ADHEr, ASPT, HEX1, LDH_D, MDH, PFLi, THD2 and/or GLUDy |
| 679 | 7 | 7.67191 | 0.04055 | ADHEr, ASPT, GLCpts, LDH_D, MDH, PFLi, THD2 and/or GLUDy |
| 680 | 7 | 7.61518 | 0.06956 | ADHEr, ATPS4r, LDH_D, MDH, NADH12, PFLi, THD2 and/or GLUDy |
| 681 | 7 | 7.57942 | 0.07603 | ADHEr, ATPS4r, FDH2, LDH_D, MDH, NADH6, PGDH |
| 682 | 7 | 7.57942 | 0.07603 | ADHEr, ATPS4r, LDH_D, MDH, NADH6, PFLi, PGDH |
| 683 | 7 | 7.57606 | 0.07664 | ADHEr, ATPS4r, FDH2, LDH_D, MDH, NADH6, TAL |
| 684 | 7 | 7.57606 | 0.07664 | ADHEr, ATPS4r, LDH_D, MDH, NADH6, PFLi, TAL |
| 685 | 7 | 7.57295 | 0.0772 | ADHEr, ATPS4r, FDH2, LDH_D, MDH, NADH6, RPE |
| 686 | 7 | 7.57295 | 0.0772 | ADHEr, ATPS4r, LDH_D, MDH, NADH6, PFLi, RPE |
| 687 | 7 | 7.55163 | 0.08105 | ADHEr, LDH_D, MDH, NADH12, NADH6, PFLi, THD2 and/or GLUDy |
| 688 | 7 | 7.38115 | 0.07649 | ADHEr, ASPT, ATPS4r, GLCpts, LDH_D, MDH, PFLi |
| 689 | 7 | 7.293 | 0.07152 | ADHEr, ASPT, ATPS4r, GLCpts, LDH_D, MDH, NADH6 |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 690 | 7 | 7.21161 | 0.05631 | ADHEr, EDA and/or PGDHY, HEX1, LDH_D, NADH6, PGI, THD2 and/or GLUDy |
| 691 | 7 | 7.10953 | 0.03056 | ACKr and/or PTAr, ADHEr, LDH_D, MDH, NADH6, PYK, THD2 and/or GLUDy |
| 692 | 7 | 7.04629 | 0.01861 | ADHEr, ARGt4, ASPT, LDH_D, MALS, MDH, THD2 and/or GLUDy |
| 693 | 7 | 7.04629 | 0.01861 | ADHEr, ARGt4, ASPT, ICL, LDH_D, MDH, THD2 and/or GLUDy |
| 694 | 7 | 7.01619 | 0.17329 | ACKr and/or PTAr, ADHEr, ATPS4r, LDH_D, MDH, NADH6, PGDH |
| 695 | 7 | 7.00623 | 0.10284 | ADHEr, LDH_D, MDH, NADH12, NADH6, PFLi, PGI |
| 696 | 7 | 7.00542 | 0.17519 | ACKr and/or PTAr, ADHEr, ATPS4r, LDH_D, MDH, NADH6, TAL |
| 697 | 7 | 6.99744 | 0.05155 | ACKr and/or PTAr, ADHEr, ICL, LDH_D, MDH, NADH6, THD2 and/or GLUDy |
| 698 | 7 | 6.99744 | 0.05155 | ACKr and/or PTAr, ADHEr, FUM, LDH_D, MDH, NADH6, THD2 and/or GLUDy |
| 699 | 7 | 6.99744 | 0.05155 | ACKr and/or PTAr, ADHEr, LDH_D, MALS, MDH, NADH6, THD2 and/or GLUDy |
| 700 | 7 | 6.99618 | 0.02608 | ADHEr, ASPT, ATPS4r, GLCpts, LDH_D, MDH, THD2 and/or GLUDy |
| 701 | 7 | 6.99539 | 0.17696 | ACKr and/or PTAr, ADHEr, ATPS4r, LDH_D, MDH, NADH6, RPE |
| 702 | 7 | 6.99098 | 0.13845 | ADHEr, ASPT, ATPS4r, LDH_D, MDH, PFLi, PGL and/or G6PDHy |
| 703 | 7 | 6.99098 | 0.13845 | ADHEr, ASPT, ATPS4r, EDA and/or PGDHY, LDH_D, MDH, PFLi |
| 704 | 7 | 6.97749 | 0.0848 | ACKr and/or PTAr, ADHEr, ATPS4r, HEX1, LDH_D, PFLi, PGI |
| 705 | 7 | 6.95495 | 0.04834 | ACKr and/or PTAr, ADHEr, GLUDy, LDH_D, MDH, NADH6, THD2 and/or GLUDy |
| 706 | 7 | 6.94643 | 0.04549 | ADHEr, ATPS4r, LDH_D, MDH, PFLi, PPCK, THD2 and/or GLUDy |
| 707 | 7 | 6.94643 | 0.04549 | ADHEr, ATPS4r, FUM, LDH_D, PFLi, PPCK, THD2 and/or GLUDy |
| 708 | 7 | 6.94035 | 0.16409 | ACKr and/or PTAr, ADHEr, ASPT, ATPS4r, LDH_D, MDH, PGDH |
| 709 | 7 | 6.93216 | 0.19304 | ADHEr, HEX1, LDH_D, MDH, PFLi, PPS, THD2 and/or GLUDy |
| 710 | 7 | 6.9218 | 0.16465 | ACKr and/or PTAr, ADHEr, ASPT, ATPS4r, LDH_D, MDH, TAL |
| 711 | 7 | 6.90477 | 0.16517 | ACKr and/or PTAr, ADHEr, ASPT, ATPS4r, LDH_D, MDH, RPE |
| 712 | 7 | 6.89223 | 0.07039 | ADHEr, LDH_D, NADH12, NADH6, PFLi, PPCK, THD2 and/or GLUDy |
| 713 | 7 | 6.89088 | 0.16538 | ADHEr, ASPT, ATPS4r, EDA and/or PGDHY, LDH_D, MDH, PGDH |
| 714 | 7 | 6.88301 | 0.07117 | ADHEr, LDH_D, MDH, NADH6, PFLi, PPCK, THD2 and/or GLUDy |
| 715 | 7 | 6.88301 | 0.07117 | ADHEr, FUM, LDH_D, NADH6, PFLi, PPCK, THD2 and/or GLUDy |
| 716 | 7 | 6.86164 | 0.16622 | ADHEr, ASPT, ATPS4r, EDA and/or PGDHY, LDH_D, MDH, TAL |
| 717 | 7 | 6.83471 | 0.167 | ADHEr, ASPT, ATPS4r, EDA and/or PGDHY, LDH_D, MDH, RPE |
| 718 | 7 | 6.81823 | 0.05671 | ADHEr, ATPS4r, LDH_D, NADH12, PFLi, PPCK, THD2 and/or GLUDy |
| 719 | 7 | 6.75858 | 0.12153 | ADHEr, GLCpts, LDH_D, MDH, PFLi, PPCK, THD2 and/or GLUDy |
| 720 | 7 | 6.75858 | 0.12153 | ADHEr, FUM, GLCpts, LDH_D, PFLi, PPCK, THD2 and/or GLUDy |
| 721 | 7 | 6.74354 | 0.0559 | ADHEr, GLUDy, HEX1, LDH_D, MDH, PFLi, THD2 and/or GLUDy |
| 722 | 7 | 6.72704 | 0.08076 | ADHEr, ASPT, EDA and/or PGDHY, LDH_D, MDH, NADH6, PYK |
| 723 | 7 | 6.72704 | 0.08076 | ADHEr, ASPT, LDH_D, MDH, NADH6, PGL and/or G6PDHy, PYK |
| 724 | 7 | 6.72478 | 0.09245 | ACKr and/or PTAr, ADHEr, ATPS4r, FUM, LDH_D, PPCK, THD2 and/or GLUDy |
| 725 | 7 | 6.71779 | 0.1313 | ADHEr, FBP, LDH_D, MDH, PFLi, PGDH, THD2 and/or GLUDy |
| 726 | 7 | 6.71371 | 0.1397 | ADHEr, GLCpts, LDH_D, MDH, NADH6, PFLi, THD2 and/or GLUDy |
| 727 | 7 | 6.69882 | 0.08259 | ADHEr, ATPS4r, LDH_D, MDH, PFLi, PGDH, THD2 and/or GLUDy |
| 728 | 7 | 6.69814 | 0.08084 | ADHEr, LDH_D, MDH, NADH6, PFLi, PGDH, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 729 | 7 | 6.68517 | 0.13281 | ADHEr, FBP, LDH_D, MDH, PFLi, TAL, THD2 and/or GLUDy |
| 730 | 7 | 6.67827 | 0.0833 | ADHEr, ATPS4r, LDH_D, MDH, PFLi, TAL, THD2 and/or GLUDy |
| 731 | 7 | 6.67803 | 0.08153 | ADHEr, LDH_D, MDH, NADH6, PFLi, TAL, THD2 and/or GLUDy |
| 732 | 7 | 6.66553 | 0.13149 | ADHEr, LDH_D, MDH, PFLi, PGDH, PGI, THD2 and/or GLUDy |
| 733 | 7 | 6.65922 | 0.08397 | ADHEr, ATPS4r, LDH_D, MDH, PFLi, RPE, THD2 and/or GLUDy |
| 734 | 7 | 6.65477 | 0.13422 | ADHEr, FBP, LDH_D, MDH, PFLi, RPE, THD2 and/or GLUDy |
| 735 | 7 | 6.65444 | 0.13292 | ADHEr, LDH_D, MDH, PFLi, PGI, TAL, THD2 and/or GLUDy |
| 736 | 7 | 6.64411 | 0.13426 | ADHEr, LDH_D, MDH, PFLi, PGI, RPE, THD2 and/or GLUDy |
| 737 | 7 | 6.54706 | 0.05865 | ADHEr, ATPS4r, EDA and/or PGDHY, LDH_D, MDH, NADH6, RPE |
| 738 | 7 | 6.50546 | 0.0488 | ADHEr, ASPT, EDA and/or PGDHY, FUM, LDH_D, MDH, THD2 and/or GLUDy |
| 739 | 7 | 6.4951 | 0.09302 | ACKr and/or PTAr, ADHEr, ATPS4r, LDH_D, PPCK, RPE, THD2 and/or GLUDy |
| 740 | 7 | 6.48152 | 0.09261 | ACKr and/or PTAr, ADHEr, ATPS4r, LDH_D, PPCK, TAL, THD2 and/or GLUDy |
| 741 | 7 | 6.4815 | 0.14937 | ACKr and/or PTAr, ADHEr, LDH_D, MDH, NADH6, RPE, THD2 and/or GLUDy |
| 742 | 7 | 6.4814 | 0.1488 | ACKr and/or PTAr, ADHEr, LDH_D, MDH, NADH6, TAL, THD2 and/or GLUDy |
| 743 | 7 | 6.48129 | 0.14819 | ACKr and/or PTAr, ADHEr, LDH_D, MDH, NADH6, PGDH, THD2 and/or GLUDy |
| 744 | 7 | 6.46677 | 0.09217 | ACKr and/or PTAr, ADHEr, ATPS4r, LDH_D, PGDH, PPCK, THD2 and/or GLUDy |
| 745 | 7 | 6.46677 | 0.09217 | ACKr and/or PTAr, ADHEr, ATPS4r, LDH_D, PGL and/or G6PDHy, PPCK, THD2 and/or GLUDy |
| 746 | 7 | 6.40404 | 0.13985 | ACKr and/or PTAr, ADHEr, ASPT, GLCpts, LDH_D, MDH, NADH6 |
| 747 | 7 | 6.39358 | 0.0544 | ADHEr, ASPT, FUM, GLCpts, LDH_D, MDH, THD2 and/or GLUDy |
| 748 | 7 | 6.36333 | 0.16503 | ACKr and/or PTAr, ADHEr, ASPT, LDH_D, MDH, NADH6, THD2 and/or GLUDy |
| 749 | 7 | 6.35537 | 0.14906 | ACKr and/or PTAr, ADHEr, ASPT, LDH_D, MDH, NADH6, PYK |
| 750 | 7 | 6.34075 | 0.15004 | ACKr and/or PTAr, ADHEr, FDH2, GLCpts, LDH_D, MDH, NADH6 |
| 751 | 7 | 6.33847 | 0.16728 | ACKr and/or PTAr, ADHEr, ASPT, ATPS4r, LDH_D, MDH, NADH6 |
| 752 | 7 | 6.30136 | 0.19463 | ACKr and/or PTAr, ADHEr, ATPS4r, LDH_D, MDH, NADH6, THD2 and/or GLUDy |
| 753 | 7 | 6.30082 | 0.1583 | ACKr and/or PTAr, ADHEr, ASPT, ATPS4r, LDH_D, MDH, PYK |
| 754 | 7 | 6.23552 | 0.18763 | ACKr and/or PTAr, ADHEr, FDH2, LDH_D, MDH, NADH6, THD2 and/or GLUDy |
| 755 | 7 | 6.23519 | 0.15548 | ACKr and/or PTAr, ADHEr, HEX1, LDH_D, MDH, PGDH, THD2 and/or GLUDy |
| 756 | 7 | 6.22748 | 0.15693 | ACKr and/or PTAr, ADHEr, HEX1, LDH_D, MDH, TAL, THD2 and/or GLUDy |
| 757 | 7 | 6.22033 | 0.15828 | ACKr and/or PTAr, ADHEr, HEX1, LDH_D, MDH, RPE, THD2 and/or GLUDy |
| 758 | 7 | 6.2176 | 0.1588 | ACKr and/or PTAr, ADHEr, ASPT, LDH_D, MDH, PGDH, THD2 and/or GLUDy |
| 759 | 7 | 6.21321 | 0.15963 | ACKr and/or PTAr, ADHEr, ASPT, LDH_D, MDH, TAL, THD2 and/or GLUDy |
| 760 | 7 | 6.20917 | 0.16039 | ACKr and/or PTAr, ADHEr, ASPT, LDH_D, MDH, RPE, THD2 and/or GLUDy |
| 761 | 7 | 6.20871 | 0.17434 | ADHEr, EDA and/or PGDHY, LDH_D, MDH, PFLi, PGI, THD5 |
| 762 | 7 | 6.18575 | 0.17904 | ACKr and/or PTAr, ADHEr, FDH2, LDH_D, MDH, NADH12, NADH6 |
| 763 | 7 | 6.17771 | 0.01562 | ADHEr, ASPT, ICL, LDH_D, MDH, NADH6, THD2 and/or GLUDy |
| 764 | 7 | 6.17771 | 0.01562 | ADHEr, ASPT, LDH_D, MALS, MDH, NADH6, THD2 and/or GLUDy |
| 765 | 7 | 6.10255 | 0.12296 | ADHEr, ASPT, ATPS4r, LDH_D, MDH, NADH6, PPCK |
| 766 | 7 | 6.08364 | 0.10963 | ADHEr, GLCpts, LDH_D, NADH6, PFLi, PPCK, THD2 and/or GLUDy |
| 767 | 7 | 6.05909 | 0.217 | ACKr and/or PTAr, ADHEr, ATPS4r, FUM, HEX1, LDH_D, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 768 | 7 | 5.99909 | 0.09659 | ADHEr, FUM, GLCpts, LDH_D, PFLi, PGI, PPCK |
| 769 | 7 | 5.99909 | 0.09659 | ADHEr, GLCpts, LDH_D, MDH, PFLi, PGI, PPCK |
| 770 | 7 | 5.9797 | 0.19373 | ACKr and/or PTAr, ACS, ADHEr, HEX1, LDH_D, PGI, PPS |
| 771 | 7 | 5.97334 | 0.11266 | ADHEr, GLCpts, LDH_D, MDH, NADH6, PFLi, PGI |
| 772 | 7 | 5.94122 | 0.14646 | ACKr and/or PTAr, ADHEr, LDH_D, MDH, PFLi, PPCK, PYK |
| 773 | 7 | 5.94122 | 0.14646 | ACKr and/or PTAr, ADHEr, FUM, LDH_D, PFLi, PPCK, PYK |
| 774 | 7 | 5.9395 | 0.02821 | ADHEr, ATPS4r, FDH2, LDH_D, MDH, NADH6, THD2 and/or GLUDy |
| 775 | 7 | 5.89777 | 0.06803 | ADHEr, ATPS4r, EDA and/or PGDHY, HEX1, LDH_D, PGI, THD2 and/or GLUDy |
| 776 | 7 | 5.86803 | 0.06511 | ADHEr, ATPS4r, LDH_D, NADH6, PFLi, PPCK, THD2 and/or GLUDy |
| 777 | 7 | 5.84763 | 0.01509 | ACKr and/or PTAr, ADHEr, ATPS4r, HEX1, LDH_D, PGI, THD2 and/or GLUDy |
| 778 | 7 | 5.80727 | 0.03994 | ADHEr, ATPS4r, GLCpts, LDH_D, MDH, NADH6, THD2 and/or GLUDy |
| 779 | 7 | 5.80665 | 0.23182 | ACKr and/or PTAr, ADHEr, ATPS4r, HEX1, LDH_D, RPE, THD2 and/or GLUDy |
| 780 | 7 | 5.77313 | 0.13132 | ADHEr, ATPS4r, LDH_D, NADH12, NADH6, PFLi, PGI |
| 781 | 7 | 5.77052 | 0.23124 | ACKr and/or PTAr, ADHEr, ATPS4r, HEX1, LDH_D, TAL, THD2 and/or GLUDy |
| 782 | 7 | 5.75832 | 0.26044 | ACKr and/or PTAr, ADHEr, G5SD, LDH_D, MDH, PFLi, THD2 and/or GLUDy |
| 783 | 7 | 5.75832 | 0.26044 | ACKr and/or PTAr, ADHEr, GLU5K, LDH_D, MDH, PFLi, THD2 and/or GLUDy |
| 784 | 7 | 5.75556 | 0.13165 | ADHEr, ATPS4r, FUM, LDH_D, NADH6, PFLi, PGI |
| 785 | 7 | 5.75413 | 0.21628 | ACKr and/or PTAr, ADHEr, FUM, HEX1, LDH_D, NADH6, THD2 and/or GLUDy |
| 786 | 7 | 5.75142 | 0.15 | ADHEr, ATPS4r, GLCpts, LDH_D, MDH, PFLi, PPCK |
| 787 | 7 | 5.75142 | 0.15 | ADHEr, ATPS4r, FUM, GLCpts, LDH_D, PFLi, PPCK |
| 788 | 7 | 5.73569 | 0.11619 | ACKr and/or PTAr, ADHEr, FUM, LDH_D, NADH6, PPCK, THD2 and/or GLUDy |
| 789 | 7 | 5.73112 | 0.23062 | ACKr and/or PTAr, ADHEr, ATPS4r, HEX1, LDH_D, PGDH, THD2 and/or GLUDy |
| 790 | 7 | 5.73112 | 0.23062 | ACKr and/or PTAr, ADHEr, ATPS4r, HEX1, LDH_D, PGL and/or G6PDHy, THD2 and/or GLUDy |
| 791 | 7 | 5.7037 | 0.1229 | ADHEr, ATPS4r, GLCpts, LDH_D, MDH, NADH6, PPCK |
| 792 | 7 | 5.7037 | 0.1229 | ADHEr, ATPS4r, FUM, GLCpts, LDH_D, NADH6, PPCK |
| 793 | 7 | 5.67082 | 0.04313 | ADHEr, ATPS4r, LDH_D, NADH6, PFLi, PGI, THD2 and/or GLUDy |
| 794 | 7 | 5.67082 | 0.04313 | ADHEr, ATPS4r, FDH2, LDH_D, NADH6, PGI, THD2 and/or GLUDy |
| 795 | 7 | 5.6689 | 0.01529 | ADHEr, LDH_D, MDH, NADH6, PFLi, PYK, THD2 and/or GLUDy |
| 796 | 7 | 5.57706 | 0.11542 | ADHEr, ATPS4r, GLCpts, LDH_D, NADH6, PFLi, THD2 and/or GLUDy |
| 797 | 7 | 5.57479 | 0.20482 | ACKr and/or PTAr, ADHEr, ATPS4r, HEX1, LDH_D, MDH, THD2 and/or GLUDy |
| 798 | 7 | 5.56128 | 0.20483 | ACKr and/or PTAr, ADHEr, ATPS4r, LDH_D, MDH, NADH12, THD2 and/or GLUDy |
| 799 | 7 | 5.53687 | 0.15179 | ADHEr, FUM, LDH_D, NADH12, NADH6, PPCK, THD2 and/or GLUDy |
| 800 | 7 | 5.48032 | 0.07882 | ADHEr, ATPS4r, FUM, LDH_D, NADH6, PFLi, THD2 and/or GLUDy |
| 801 | 7 | 5.48032 | 0.07882 | ADHEr, ATPS4r, FDH2, FUM, LDH_D, NADH6, THD2 and/or GLUDy |
| 802 | 7 | 5.4574 | 0.07896 | ADHEr, ASPT, ATPS4r, LDH_D, MDH, PPCK, THD2 and/or GLUDy |
| 803 | 7 | 5.43688 | 0.14109 | ADHEr, ASPT, FUM, HEX1, LDH_D, PPS, THD2 and/or GLUDy |
| 804 | 7 | 5.42926 | 0.03599 | ACKr and/or PTAr, ADHEr, GLUDy, LDH_D, MDH, PPCK, THD2 and/or GLUDy |
| 805 | 7 | 5.41288 | 0.10644 | ADHEr, FUM, LDH_D, PFLi, PGI, PPCK, RPE |
| 806 | 7 | 5.41288 | 0.10644 | ADHEr, LDH_D, MDH, PFLi, PGI, PPCK, RPE |
| 807 | 7 | 5.40727 | 0.10598 | ADHEr, FUM, LDH_D, PFLi, PGI, PPCK, TAL |
| 808 | 7 | 5.40727 | 0.10598 | ADHEr, LDH_D, MDH, PFLi, PGI, PPCK, TAL |
| 809 | 7 | 5.40541 | 0.10406 | ADHEr, LDH_D, NADH12, NADH6, PFLi, PPCK, PYK |
| 810 | 7 | 5.40329 | 0.10477 | ADHEr, LDH_D, MDH, NADH6, PFLi, PPCK, PYK |
| 811 | 7 | 5.40329 | 0.10477 | ADHEr, FUM, LDH_D, NADH6, PFLi, PPCK, PYK |
| 812 | 7 | 5.40117 | 0.10549 | ADHEr, LDH_D, MDH, PFLi, PGDH, PGI, PPCK |
| 813 | 7 | 5.40117 | 0.10549 | ADHEr, FUM, LDH_D, PFLi, PGDH, PGI, PPCK |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 814 | 7 | 5.38947 | 0.11011 | ACKr and/or PTAr, ADHEr, FUM, LDH_D, NADH6, PPCK, PYK |
| 815 | 7 | 5.37417 | 0.11441 | ACKr and/or PTAr, ADHEr, ATPS4r, LDH_D, MDH, PPCK, THD2 and/or GLUDy |
| 816 | 7 | 5.37043 | 0.12143 | ADHEr, LDH_D, MDH, NADH6, PFLi, PGI, RPE |
| 817 | 7 | 5.37015 | 0.12013 | ADHEr, ASPT, EDA and/or PGDHY, GLUDy, LDH_D, MDH, THD2 and/or GLUDy |
| 818 | 7 | 5.36414 | 0.12087 | ADHEr, LDH_D, MDH, NADH6, PFLi, PGI, TAL |
| 819 | 7 | 5.3573 | 0.12027 | ADHEr, LDH_D, MDH, NADH6, PFLi, PGDH, PGI |
| 820 | 7 | 5.3512 | 0.12232 | ADHEr, LDH_D, NADH12, NADH6, PFLi, PRO1z, THD2 and/or GLUDy |
| 821 | 7 | 5.35114 | 0.12824 | ADHEr, LDH_D, NADH12, NADH6, PFLi, PGI, RPE |
| 822 | 7 | 5.34992 | 0.12867 | ADHEr, FUM, LDH_D, NADH6, PFLi, PGI, RPE |
| 823 | 7 | 5.34421 | 0.12775 | ADHEr, LDH_D, NADH12, NADH6, PFLi, PGI, TAL |
| 824 | 7 | 5.34298 | 0.12817 | ADHEr, FUM, LDH_D, NADH6, PFLi, PGI, TAL |
| 825 | 7 | 5.33668 | 0.12721 | ADHEr, LDH_D, NADH12, NADH6, PFLi, PGDH, PGI |
| 826 | 7 | 5.33544 | 0.12763 | ADHEr, FUM, LDH_D, NADH6, PFLi, PGDH, PGI |
| 827 | 7 | 5.32853 | 0.04869 | ADHEr, ATPS4r, LDH_D, MDH, PGL and/or G6PDHy, PPCK, THD2 and/or GLUDy |
| 828 | 7 | 5.32586 | 0.13717 | ADHEr, ATPS4r, FDH2, LDH_D, NADH6, PPCK, RPE |
| 829 | 7 | 5.31986 | 0.13616 | ADHEr, ATPS4r, FDH2, LDH_D, NADH6, PPCK, TAL |
| 830 | 7 | 5.31768 | 0.14006 | ADHEr, ATPS4r, LDH_D, MDH, NADH6, PPCK, RPE |
| 831 | 7 | 5.31768 | 0.14006 | ADHEr, ATPS4r, FUM, LDH_D, NADH6, PPCK, RPE |
| 832 | 7 | 5.31338 | 0.13506 | ADHEr, ATPS4r, FDH2, LDH_D, NADH6, PGL and/or G6PDHy, PPCK |
| 833 | 7 | 5.31338 | 0.13506 | ADHEr, ATPS4r, FDH2, LDH_D, NADH6, PGDH, PPCK |
| 834 | 7 | 5.31161 | 0.139 | ADHEr, ATPS4r, FUM, LDH_D, NADH6, PPCK, TAL |
| 835 | 7 | 5.31161 | 0.139 | ADHEr, ATPS4r, LDH_D, MDH, NADH6, PPCK, TAL |
| 836 | 7 | 5.30507 | 0.13786 | ADHEr, ATPS4r, FUM, LDH_D, NADH6, PGL and/or G6PDHy, PPCK |
| 837 | 7 | 5.30507 | 0.13786 | ADHEr, ATPS4r, LDH_D, MDH, NADH6, PGDH, PPCK |
| 838 | 7 | 5.30507 | 0.13786 | ADHEr, ATPS4r, FUM, LDH_D, NADH6, PGDH, PPCK |
| 839 | 7 | 5.30121 | 0.14588 | ADHEr, ATPS4r, GLCpts, LDH_D, NADH6, PPCK, RPE |
| 840 | 7 | 5.29298 | 0.14544 | ADHEr, ATPS4r, GLCpts, LDH_D, NADH6, PPCK, TAL |
| 841 | 7 | 5.29144 | 0.14245 | ADHEr, GLCpts, LDH_D, MDH, NADH12, NADH6, PFLi |
| 842 | 7 | 5.28753 | 0.08933 | ADHEr, ATPS4r, FDH2, LDH_D, NADH6, PPCK, THD2 and/or GLUDy |
| 843 | 7 | 5.28422 | 0.14489 | ADHEr, ATPS4r, FDH2, LDH_D, NADH12, NADH6, THD2 and/or GLUDy |
| 844 | 7 | 5.28422 | 0.14489 | ADHEr, ATPS4r, LDH_D, NADH12, NADH6, PFLi, THD2 and/or GLUDy |
| 845 | 7 | 5.28401 | 0.14496 | ADHEr, ATPS4r, GLCpts, LDH_D, NADH6, PGDH, PPCK |
| 846 | 7 | 5.28401 | 0.14496 | ADHEr, ATPS4r, GLCpts, LDH_D, NADH6, PGL and/or G6PDHy, PPCK |
| 847 | 7 | 5.27588 | 0.18393 | ADHEr, FUM, HEX1, LDH_D, PGDH, PPS, THD2 and/or GLUDy |
| 848 | 7 | 5.27588 | 0.18393 | ADHEr, FUM, HEX1, LDH_D, PGL and/or G6PDHy, PPS, THD2 and/or GLUDy |
| 849 | 7 | 5.2736 | 0.14846 | ADHEr, HEX1, LDH_D, NADH12, NADH6, PFLi, THD2 and/or GLUDy |
| 850 | 7 | 5.25759 | 0.18586 | ADHEr, FUM, HEX1, LDH_D, PPS, TAL, THD2 and/or GLUDy |
| 851 | 7 | 5.24329 | 0.06953 | ADHEr, ATPS4r, LDH_D, MDH, NADH6, PGDH, THD2 and/or GLUDy |
| 852 | 7 | 5.24057 | 0.18767 | ADHEr, FUM, HEX1, LDH_D, PPS, RPE, THD2 and/or GLUDy |
| 853 | 7 | 5.23194 | 0.07004 | ADHEr, ATPS4r, LDH_D, MDH, NADH6, TAL, THD2 and/or GLUDy |
| 854 | 7 | 5.22143 | 0.07051 | ADHEr, ATPS4r, LDH_D, MDH, NADH6, RPE, THD2 and/or GLUDy |
| 855 | 7 | 5.1096 | 0.03265 | ADHEr, ASPT, FUM, GLUDy, HEX1, LDH_D, THD2 and/or GLUDy |
| 856 | 7 | 5.07833 | 0.23187 | ACKr and/or PTAr, ADHEr, ATPS4r, HEX1, LDH_D, NADH6, THD2 and/or GLUDy |
| 857 | 7 | 4.9126 | 0.20186 | ADHEr, HEX1, LDH_D, PGDH, PPS, TAL, THD2 and/or GLUDy |
| 858 | 7 | 4.9126 | 0.20186 | ADHEr, HEX1, LDH_D, PGL and/or G6PDHy, PPS, TAL, THD2 and/or GLUDy |
| 859 | 7 | 4.89537 | 0.08136 | ACKr and/or PTAr, ADHEr, ATPS4r, GLUDy, LDH_D, MDH, THD2 and/or GLUDy |
| 860 | 7 | 4.86469 | 0.20078 | ADHEr, ATPS4r, GLCpts, LDH_D, PFLi, PPCK, RPE |
| 861 | 7 | 4.86188 | 0.1035 | ACKr and/or PTAr, ADHEr, ATPS4r, LDH_D, PPCK, PYK, THD2 and/or GLUDy |
| 862 | 7 | 4.85917 | 0.04186 | ADHEr, ATPS4r, GLCpts, LDH_D, MDH, PPCK, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 863 | 7 | 4.85917 | 0.04186 | ADHEr, ATPS4r, FUM, GLCpts, LDH_D, PPCK, THD2 and/or GLUDy |
| 864 | 7 | 4.84043 | 0.16101 | ADHEr, ATPS4r, FDH2, LDH_D, NADH6, PPCK, PYK |
| 865 | 7 | 4.75352 | 0.20131 | ADHEr, ATPS4r, GLCpts, LDH_D, PFLi, PPCK, TAL |
| 866 | 7 | 4.6646 | 0.15914 | ADHEr, ATPS4r, FUM, GLCpts, LDH_D, NADH6, THD2 and/or GLUDy |
| 867 | 7 | 4.6568 | 0.25634 | ADHEr, ATPS4r, LDH_D, MALS, MDH, PGL and/or G6PDHy, PPS |
| 868 | 7 | 4.6568 | 0.25634 | ADHEr, ATPS4r, ICL, LDH_D, MDH, PGL and/or G6PDHy, PPS |
| 869 | 7 | 4.6568 | 0.25634 | ADHEr, ATPS4r, FUM, LDH_D, MDH, PGL and/or G6PDHy, PPS |
| 870 | 7 | 4.60984 | 0.1687 | ACKr and/or PTAr, ADHEr, ATPS4r, LDH_D, MDH, RPE, THD2 and/or GLUDy |
| 871 | 7 | 4.60771 | 0.13834 | ADHEr, ASPT, LDH_D, MDH, NADH12, NADH6, THD2 and/or GLUDy |
| 872 | 7 | 4.5647 | 0.0741 | ADHEr, ATPS4r, HEX1, LDH_D, MDH, SUCOAS, THD2 and/or GLUDy |
| 873 | 7 | 4.51839 | 0.16783 | ACKr and/or PTAr, ADHEr, ATPS4r, LDH_D, MDH, TAL, THD2 and/or GLUDy |
| 874 | 7 | 4.48284 | 0.18237 | ADHEr, ASPT, LDH_D, MDH, NADH12, NADH6, PPCK |
| 875 | 7 | 4.46608 | 0.18828 | ADHEr, ASPT, GLCpts, LDH_D, MDH, NADH12, NADH6 |
| 876 | 7 | 4.43524 | 0.31394 | ADHEr, ATPS4r, FUM, HEX1, LDH_D, PGDH, PPS |
| 877 | 7 | 4.43524 | 0.31394 | ADHEr, ATPS4r, FUM, HEX1, LDH_D, PGL and/or G6PDHy, PPS |
| 878 | 7 | 4.43072 | 0.22439 | ADHEr, ASPT, LDH_D, MDH, NADH12, NADH6, RPE |
| 879 | 7 | 4.41919 | 0.16689 | ACKr and/or PTAr, ADHEr, ATPS4r, LDH_D, MDH, PGDH, THD2 and/or GLUDy |
| 880 | 7 | 4.4053 | 0.01495 | ACKr and/or PTAr, ADHEr, GLCpts, LDH_D, MDH, PPCK, THD2 and/or GLUDy |
| 881 | 7 | 4.39394 | 0.31457 | ADHEr, ATPS4r, FUM, HEX1, LDH_D, PPS, TAL |
| 882 | 7 | 4.37728 | 0.02565 | ADHEr, ASPT, LDH_D, MDH, PGI, PPCK, THD2 and/or GLUDy |
| 883 | 7 | 4.37061 | 0.04989 | ADHEr, ATPS4r, LDH_D, NADH6, PGI, PPCK, THD2 and/or GLUDy |
| 884 | 7 | 4.36653 | 0.05265 | ADHEr, ATPS4r, FUM, LDH_D, NADH6, PGI, THD2 and/or GLUDy |
| 885 | 7 | 4.36374 | 0.03082 | ADHEr, ASPT, LDH_D, MDH, NADH6, PGI, THD2 and/or GLUDy |
| 886 | 7 | 4.36277 | 0.03119 | ADHEr, ASPT, GLCpts, LDH_D, MDH, PGI, THD2 and/or GLUDy |
| 887 | 7 | 4.35613 | 0.31514 | ADHEr, ATPS4r, FUM, HEX1, LDH_D, PPS, RPE |
| 888 | 7 | 4.29026 | 0.24034 | ACKr and/or PTAr, ADHEr, EDA and/or PGDHY, GLU5K, GLYCL, LDH_D, PGI |
| 889 | 7 | 4.29026 | 0.24034 | ACKr and/or PTAr, ADHEr, EDA and/or PGDHY, G5SD, GLYCL, LDH_D, PGI |
| 890 | 7 | 4.25283 | 0.07318 | ADHEr, ASPT, LDH_D, MDH, PPCK, PYK, THD2 and/or GLUDy |
| 891 | 7 | 4.17894 | 0.31889 | ADHEr, HEX1, LDH_D, NADH12, NADH6, PPS, THD2 and/or GLUDy |
| 892 | 7 | 4.17527 | 0.08598 | ADHEr, ATPS4r, FRD and/or SUCD4, HEX1, LDH_D, MALS, THD2 and/or GLUDy |
| 893 | 7 | 4.17527 | 0.08598 | ADHEr, ATPS4r, FRD and/or SUCD4, HEX1, ICL, LDH_D, THD2 and/or GLUDy |
| 894 | 7 | 4.17215 | 0.10398 | ADHEr, ASPT, GLCpts, LDH_D, MDH, PPCK, THD2 and/or GLUDy |
| 895 | 7 | 4.15042 | 0.11229 | ADHEr, ASPT, GLCpts, LDH_D, MDH, NADH6, THD2 and/or GLUDy |
| 896 | 7 | 4.14938 | 0.11268 | ADHEr, ASPT, LDH_D, MDH, NADH6, PPCK, THD2 and/or GLUDy |
| 897 | 7 | 4.141 | 0.08314 | ADHEr, ATPS4r, FRD and/or SUCD4, HEX1, LDH_D, SUCOAS, THD2 and/or GLUDy |
| 898 | 7 | 4.10258 | 0.11665 | ACKr and/or PTAr, ADHEr, ATPS4r, LDH_D, PPCK, PYK, SUCOAS |
| 899 | 7 | 4.08743 | 0.09886 | ACKr and/or PTAr, ADHEr, ATPS4r, LDH_D, PPCK, SUCOAS, THD2 and/or GLUDy |
| 900 | 7 | 4.04907 | 0.15099 | ADHEr, ASPT, GLCpts, LDH_D, MDH, NADH6, PPCK |
| 901 | 7 | 4.03008 | 0.1761 | ADHEr, ASPT, GLCpts, LDH_D, MDH, PPCK, RPE |
| 902 | 7 | 4.01398 | 0.06136 | ADHEr, ATPS4r, LDH_D, PFLi, PGI, PPCK, THD2 and/or GLUDy |
| 903 | 7 | 4.00698 | 0.18592 | ADHEr, ASPT, LDH_D, MDH, NADH6, PPCK, RPE |
| 904 | 7 | 4.00128 | 0.18834 | ADHEr, ASPT, GLCpts, LDH_D, MDH, NADH6, RPE |
| 905 | 7 | 3.95205 | 0.10694 | ACKr and/or PTAr, ADHEr, ATPS4r, LDH_D, PGDH, PGI, SUCOAS |
| 906 | 7 | 3.94203 | 0.1079 | ACKr and/or PTAr, ADHEr, ATPS4r, LDH_D, PGI, SUCOAS, TAL |
| 907 | 7 | 3.93273 | 0.1088 | ACKr and/or PTAr, ADHEr, ATPS4r, LDH_D, PGI, RPE, SUCOAS |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 908 | 7 | 3.90038 | 0.04761 | ADHEr, GLCpts, LDH_D, NADH6, PGI, PPCK, THD2 and/or GLUDy |
| 909 | 7 | 3.8947 | 0.05032 | ADHEr, FUM, GLCpts, LDH_D, NADH6, PGI, THD2 and/or GLUDy |
| 910 | 7 | 3.8947 | 0.05032 | ADHEr, GLCpts, LDH_D, MDH, NADH6, PGI, THD2 and/or GLUDy |
| 911 | 7 | 3.88125 | 0.03656 | ACKr and/or PTAr, ADHEr, GLCpts, LDH_D, NADH6, PPCK, THD2 and/or GLUDy |
| 912 | 7 | 3.86624 | 0.19846 | ACKr and/or PTAr, ADHEr, CITL, LDH_D, NADH12, NADH6, THD2 and/or GLUDy |
| 913 | 7 | 3.82356 | 0.31976 | ADHEr, ATPS4r, HEX1, LDH_D, NADH6, PPS, THD2 and/or GLUDy |
| 914 | 7 | 3.81228 | 0.08972 | ADHEr, EDA and/or PGDHY, LDH_D, MDH, NADH6, PYK, THD2 and/or GLUDy |
| 915 | 7 | 3.81228 | 0.08972 | ADHEr, LDH_D, MDH, NADH6, PGL and/or G6PDHy, PYK, THD2 and/or GLUDy |
| 916 | 7 | 3.77115 | 0.10937 | ADHEr, LDH_D, MDH, NADH12, NADH6, PPCK, THD2 and/or GLUDy |
| 917 | 7 | 3.7291 | 0.12947 | ADHEr, LDH_D, MDH, NADH12, NADH6, PYK, THD2 and/or GLUDy |
| 918 | 7 | 3.7245 | 0.13167 | ADHEr, GLCpts, LDH_D, MDH, NADH12, NADH6, THD2 and/or GLUDy |
| 919 | 7 | 3.68994 | 0.14818 | ADHEr, GLCpts, LDH_D, NADH12, NADH6, PPCK, THD2 and/or GLUDy |
| 920 | 7 | 3.67651 | 0.1546 | ADHEr, LDH_D, MDH, NADH6, PGL and/or G6PDHy, PPCK, PYK |
| 921 | 7 | 3.67651 | 0.1546 | ADHEr, EDA and/or PGDHY, LDH_D, MDH, NADH6, PPCK, PYK |
| 922 | 7 | 3.64497 | 0.19156 | ADHEr, FUM, GLCpts, LDH_D, NADH6, RPE, THD2 and/or GLUDy |
| 923 | 7 | 3.60739 | 0.21183 | ADHEr, FUM, LDH_D, NADH12, NADH6, RPE, THD2 and/or GLUDy |
| 924 | 7 | 3.41696 | 0.27865 | ADHEr, ALAR, FDH2, LDH_D, NADH12, NADH6, PRO1z |
| 925 | 7 | 3.41696 | 0.27865 | ADHEr, DAAD, FDH2, LDH_D, NADH12, NADH6, PRO1z |
| 926 | 7 | 3.40396 | 0.28486 | ADHEr, FUM, HEX1, LDH_D, NADH12, NADH6, THD2 and/or GLUDy |
| 927 | 7 | 3.25909 | 0.04258 | ADHEr, GLCpts, LDH_D, MDH, PGI, PPCK, THD2 and/or GLUDy |
| 928 | 7 | 3.25909 | 0.04258 | ADHEr, FUM, GLCpts, LDH_D, PGI, PPCK, THD2 and/or GLUDy |
| 929 | 7 | 3.2372 | 0.06431 | ADHEr, FBP, LDH_D, MDH, PGI, PPCK, THD2 and/or GLUDy |
| 930 | 7 | 3.2372 | 0.06431 | ADHEr, FBP, FUM, LDH_D, PGI, PPCK, THD2 and/or GLUDy |
| 931 | 7 | 3.23399 | 0.06432 | ADHEr, FUM, LDH_D, PGI, PPCK, RPE, THD2 and/or GLUDy |
| 932 | 7 | 3.23399 | 0.06432 | ADHEr, LDH_D, MDH, PGI, PPCK, RPE, THD2 and/or GLUDy |
| 933 | 7 | 3.22783 | 0.06435 | ADHEr, FUM, LDH_D, PGI, PPCK, TAL, THD2 and/or GLUDy |
| 934 | 7 | 3.22783 | 0.06435 | ADHEr, LDH_D, MDH, PGI, PPCK, TAL, THD2 and/or GLUDy |
| 935 | 7 | 3.01859 | 0.19992 | ADHEr, ASPT, FUM, LDH_D, PPS, SUCOAS, THD2 and/or GLUDy |
| 936 | 7 | 3.00174 | 0.19757 | ADHEr, FRD and/or SUCD4, LDH_D, MALS, PPS, RPE, THD2 and/or GLUDy |
| 937 | 7 | 3.00174 | 0.19757 | ADHEr, FRD and/or SUCD4, ICL, LDH_D, PPS, RPE, THD2 and/or GLUDy |
| 938 | 7 | 2.96091 | 0.22716 | ADHEr, FUM, GLUDy, HEX1, LDH_D, TAL, THD2 and/or GLUDy |
| 939 | 7 | 2.93716 | 0.22721 | ADHEr, FUM, GLU5K, GLUDy, HEX1, LDH_D, THD2 and/or GLUDy |
| 940 | 7 | 2.93716 | 0.22721 | ADHEr, FUM, G5SD, GLUDy, HEX1, LDH_D, THD2 and/or GLUDy |
| 941 | 7 | 2.93711 | 0.22724 | ADHEr, ASNS2, FUM, GLUDy, HEX1, LDH_D, THD2 and/or GLUDy |
| 942 | 7 | 2.7731 | 0.32129 | ADHEr, ASNS2, FUM, GLU5K, HEX1, LDH_D, THD2 and/or GLUDy |
| 943 | 7 | 2.7731 | 0.32129 | ADHEr, ASNS2, FUM, G5SD, HEX1, LDH_D, THD2 and/or GLUDy |
| 944 | 7 | 2.68652 | 0.29222 | ADHEr, ATPS4r, GLUDy, HEX1, LDH_D, RPE, THD2 and/or GLUDy |
| 945 | 7 | 2.62059 | 0.29297 | ADHEr, ATPS4r, GLUDy, HEX1, LDH_D, TAL, THD2 and/or GLUDy |
| 946 | 7 | 2.35991 | 0.29396 | ACKr and/or PTAr, ADHEr, FUM, LDH_D, RPE, SUCOAS, THD2 and/or GLUDy |
| 947 | 7 | 2.35766 | 0.29368 | ACKr and/or PTAr, ADHEr, FUM, LDH_D, SUCOAS, TAL, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 948 | 7 | 2.3552 | 0.29337 | ACKr and/or PTAr, ADHEr, FUM, LDH_D, PGL and/or G6PDHy, SUCOAS, THD2 and/or GLUDy |
| 949 | 7 | 2.3552 | 0.29337 | ACKr and/or PTAr, ADHEr, FUM, LDH_D, PGDH, SUCOAS, THD2 and/or GLUDy |
| 950 | 7 | 1.91133 | 0.2766 | ACKr and/or PTAr, ADHEr, FUM, LDH_D, MDH, PGL and/or G6PDHy, SUCOAS |
| 951 | 7 | 1.91133 | 0.2766 | ACKr and/or PTAr, ADHEr, FUM, LDH_D, MDH, PGDH, SUCOAS |
| 952 | 7 | 1.91133 | 0.2766 | ACKr and/or PTAr, ADHEr, ICL, LDH_D, MDH, PGDH, SUCOAS |
| 953 | 7 | 1.91133 | 0.2766 | ACKr and/or PTAr, ADHEr, LDH_D, MALS, MDH, PGL and/or G6PDHy, SUCOAS |
| 954 | 7 | 1.91133 | 0.2766 | ACKr and/or PTAr, ADHEr, ICL, LDH_D, MDH, PGL and/or G6PDHy, SUCOAS |
| 955 | 7 | 1.91133 | 0.2766 | ACKr and/or PTAr, ADHEr, LDH_D, MALS, MDH, PGDH, SUCOAS |
| 956 | 7 | 1.86676 | 0.2774 | ACKr and/or PTAr, ADHEr, FUM, LDH_D, MDH, SUCOAS, TAL |
| 957 | 7 | 1.86676 | 0.2774 | ACKr and/or PTAr, ADHEr, LDH_D, MALS, MDH, SUCOAS, TAL |
| 958 | 7 | 1.86676 | 0.2774 | ACKr and/or PTAr, ADHEr, ICL, LDH_D, MDH, SUCOAS, TAL |
| 959 | 7 | 1.8259 | 0.27813 | ACKr and/or PTAr, ADHEr, LDH_D, MALS, MDH, RPE, SUCOAS |
| 960 | 7 | 1.8259 | 0.27813 | ACKr and/or PTAr, ADHEr, FUM, LDH_D, MDH, RPE, SUCOAS |
| 961 | 7 | 1.8259 | 0.27813 | ACKr and/or PTAr, ADHEr, ICL, LDH_D, MDH, RPE, SUCOAS |
| 962 | 7 | 1.11652 | 0.25888 | ADHEr, ASPT, FUM, LDH_D, MALS, PPS, THD2 and/or GLUDy |
| 963 | 7 | 1.11652 | 0.25888 | ADHEr, ASPT, FUM, ICL, LDH_D, PPS, THD2 and/or GLUDy |
| 964 | 5 | 7.09275 | 0.11213 | ADHEr, ASPT, LDH_D, MDH, PFLi |
| 965 | 5 | 6.00696 | 0.20464 | ADHEr, ATPS4r, LDH_D, NADH6, PFLi |
| 966 | 5 | 5.40138 | 0.11184 | ADHEr, LDH_D, NADH6, PFLi, PGI |
| 967 | 5 | 2.59719 | 0.29318 | ADHEr, FUM, HEX1, LDH_D, PFLi |
| 968 | 5 | 2.57488 | 0.22587 | ADHEr, HEX1, LDH_D, PFLi, PPCK |
| 969 | 5 | 0.16844 | 0.19119 | ADHEr, ASPT, FUM, LDH_D, PFLi |
| 970 | 6 | 7.39516 | 0.07475 | ADHEr, ASPT, GLCpts, LDH_D, MDH, PFLi |
| 971 | 6 | 7.007 | 0.09285 | ACKr and/or PTAr, ADHEr, LDH_D, NADH6, PFLi, PGI |
| 972 | 6 | 6.90414 | 0.13454 | ADHEr, ATPS4r, GLCpts, LDH_D, NADH6, PFLi |
| 973 | 6 | 6.57261 | 0.1606 | ADHEr, ATPS4r, LDH_D, NADH12, NADH6, PFLi |
| 974 | 6 | 6.00781 | 0.09114 | ADHEr, LDH_D, MDH, PFLi, PGI, PPCK |
| 975 | 6 | 6.00781 | 0.09114 | ADHEr, FUM, LDH_D, PFLi, PGI, PPCK |
| 976 | 6 | 5.39072 | 0.10901 | ADHEr, LDH_D, NADH12, NADH6, PFLi, PPCK |
| 977 | 6 | 5.38861 | 0.10972 | ADHEr, FUM, LDH_D, NADH6, PFLi, PPCK |
| 978 | 6 | 5.38861 | 0.10972 | ADHEr, LDH_D, MDH, NADH6, PFLi, PPCK |
| 979 | 6 | 5.06553 | 0.21856 | ADHEr, FUM, LDH_D, NADH12, NADH6, PFLi |
| 980 | 6 | 5.00212 | 0.2515 | ADHEr, HEX1, LDH_D, NADH6, PFLi, RPE |
| 981 | 6 | 4.98367 | 0.25221 | ADHEr, HEX1, LDH_D, NADH6, PFLi, TAL |
| 982 | 6 | 4.96609 | 0.25206 | ADHEr, GLU5K, HEX1, LDH_D, NADH6, PFLi |
| 983 | 6 | 4.96609 | 0.25206 | ADHEr, G5SD, HEX1, LDH_D, NADH6, PFLi |
| 984 | 6 | 4.96599 | 0.2521 | ADHEr, ASNS2, HEX1, LDH_D, NADH6, PFLi |
| 985 | 6 | 4.95562 | 0.24186 | ADHEr, EDA and/or PGDHY, LDH_D, MDH, PFLi, THD2 and/or GLUDy |
| 986 | 6 | 2.71835 | 0.29123 | ADHEr, FUM, HEX1, LDH_D, PFLi, RPE |
| 987 | 6 | 2.66849 | 0.22473 | ADHEr, HEX1, LDH_D, PFLi, PPCK, RPE |
| 988 | 6 | 2.66076 | 0.29216 | ADHEr, FUM, HEX1, LDH_D, PFLi, TAL |
| 989 | 6 | 1.85699 | 0.28717 | ACKr and/or PTAr, ADHEr, ATPS4r, LDH_D, PFLi, SUCOAS |
| 990 | 6 | 1.63724 | 0.03081 | ADHEr, FUM, LDH_D, PFLi, PGI, THD2 and/or GLUDy |
| 991 | 6 | 1.63724 | 0.03081 | ADHEr, LDH_D, MDH, PFLi, PGI, THD2 and/or GLUDy |
| 992 | 6 | 1.38263 | 0.33268 | ADHEr, ATPS4r, LDH_D, NADH12, PFLi, THD2 and/or GLUDy |
| 993 | 6 | 0.25855 | 0.07515 | ADHEr, ASPT, ATPS4r, FUM, LDH_D, PFLi |
| 994 | 7 | 7.86642 | 0.01651 | ADHEr, ASPT, LDH_D, MDH, NADH6, PFLi, PYK |
| 995 | 7 | 7.71509 | 0.0515 | ADHEr, ATPS4r, LDH_D, NADH6, PFLi, PGI, PPS |
| 996 | 7 | 7.70416 | 0.03656 | ADHEr, ASPT, ATPS4r, LDH_D, MDH, PFLi, PPCK |
| 997 | 7 | 7.48515 | 0.04452 | ADHEr, EDA and/or PGDHY, GLCpts, LDH_D, PFLi, PGI, PPCK |
| 998 | 7 | 7.44181 | 0.09832 | ACKr and/or PTAr, ADHEr, LDH_D, MDH, NADH12, NADH6, PFLi |
| 999 | 7 | 7.06656 | 0.04513 | ADHEr, ATPS4r, LDH_D, MDH, NADH12, NADH6, PFLi |
| 1000 | 7 | 7.00811 | 0.04002 | ADHEr, ATPS4r, FUM, LDH_D, NADH6, PFLi, PPCK |
| 1001 | 7 | 7.00811 | 0.04002 | ADHEr, ATPS4r, LDH_D, MDH, NADH6, PFLi, PPCK |
| 1002 | 7 | 7.00532 | 0.07752 | ADHEr, ATPS4r, FUM, LDH_D, NADH12, NADH6, PFLi |
| 1003 | 7 | 6.99105 | 0.04159 | ADHEr, ATPS4r, LDH_D, NADH12, NADH6, PFLi, PPCK |
| 1004 | 7 | 6.96695 | 0.09776 | ADHEr, ATPS4r, FUM, GLCpts, LDH_D, NADH6, PFLi |
| 1005 | 7 | 6.69345 | 0.1479 | ADHEr, ATPS4r, HEX1, LDH_D, MDH, PFLi, THD2 and/or GLUDy |
| 1006 | 7 | 6.49322 | 0.12467 | ADHEr, ATPS4r, FUM, LDH_D, NADH6, PFLi, PPS |
| 1007 | 7 | 6.43565 | 0.1244 | ACKr and/or |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| | | | | PTAr, ADHEr, ATPS4r, FUM, LDH_D, NADH6, PFLi |
| 1008 | 7 | 6.21891 | 0.18801 | ADHEr, ATPS4r, LDH_D, NADH6, PFLi, PGDH, PPS |
| 1009 | 7 | 6.21891 | 0.18801 | ADHEr, ATPS4r, LDH_D, NADH6, PFLi, PGL and/or G6PDHy, PPS |
| 1010 | 7 | 6.21459 | 0.18835 | ADHEr, ATPS4r, LDH_D, NADH6, PFLi, PPS, TAL |
| 1011 | 7 | 6.21064 | 0.18866 | ADHEr, ATPS4r, LDH_D, NADH6, PFLi, PPS, RPE |
| 1012 | 7 | 6.16665 | 0.08397 | ADHEr, FUM, LDH_D, NADH12, NADH6, PFLi, PGI |
| 1013 | 7 | 6.13458 | 0.01447 | ADHEr, LDH_D, NADH12, NADH6, PFLi, PGI, PPCK |
| 1014 | 7 | 6.13051 | 0.01457 | ADHEr, LDH_D, MDH, NADH6, PFLi, PGI, PPCK |
| 1015 | 7 | 6.13051 | 0.01457 | ADHEr, FUM, LDH_D, NADH6, PFLi, PGI, PPCK |
| 1016 | 7 | 5.49961 | 0.07232 | ADHEr, GLCpts, LDH_D, NADH12, NADH6, PFLi, PPCK |
| 1017 | 7 | 5.49821 | 0.07279 | ADHEr, FUM, GLCpts, LDH_D, NADH6, PFLi, PPCK |
| 1018 | 7 | 5.49821 | 0.07279 | ADHEr, GLCpts, LDH_D, MDH, NADH6, PFLi, PPCK |
| 1019 | 7 | 5.22113 | 0.16614 | ADHEr, ATPS4r, HEX1, LDH_D, NADH12, PFLi, THD2 and/or GLUDy |
| 1020 | 7 | 5.17418 | 0.18196 | ADHEr, FUM, HEX1, LDH_D, NADH12, NADH6, PFLi |
| 1021 | 7 | 5.15097 | 0.18978 | ADHEr, FUM, LDH_D, NADH12, NADH6, PFLi, THD2 and/or GLUDy |
| 1022 | 7 | 4.01417 | 0.12149 | ADHEr, ATPS4r, FUM, HEX1, LDH_D, PFLi, THD2 and/or GLUDy |
| 1023 | 7 | 3.75439 | 0.27459 | ADHEr, ATPS4r, FUM, HEX1, LDH_D, PFLi, PPS |
| 1024 | 7 | 3.75439 | 0.27459 | ADHEr, ATPS4r, HEX1, LDH_D, MDH, PFLi, PPS |
| 1025 | 7 | 2.64048 | 0.21814 | ADHEr, HEX1, LDH_D, PFLi, PGL and/or G6PDHy, PPCK, TAL |
| 1026 | 7 | 2.64048 | 0.21814 | ADHEr, HEX1, LDH_D, PFLi, PGDH, PPCK, TAL |
| 1027 | 7 | 2.62716 | 0.22497 | ADHEr, GLYCL, HEX1, LDH_D, PFLi, PPCK, TAL |
| 1028 | 7 | 1.5697 | 0.24425 | ACKr and/or PTAr, ACS, ADHEr, LDH_D, MDH, PFLi, THD2 and/or GLUDy |
| 1029 | 7 | 1.09053 | 0.33566 | ADHEr, ATPS4r, FUM, LDH_D, PFLi, PGDH, PPS |
| 1030 | 7 | 1.09053 | 0.33566 | ADHEr, ATPS4r, FUM, LDH_D, PFLi, PGL and/or G6PDHy, PPS |
| 1031 | 7 | 0.78572 | 0.33663 | ADHEr, ATPS4r, FUM, LDH_D, PFLi, PPS, TAL |
| 1032 | 7 | 0.50621 | 0.33751 | ADHEr, ATPS4r, FUM, LDH_D, PFLi, PPS, RPE |
| 1033 | 8 | 7.88716 | 0.0204 | ACKr and/or PTAr, ADHEr, ATPS4r, LDH_D, MDH, NADH12, NADH6, PFLi |
| 1034 | 8 | 7.88653 | 0.02051 | ADHEr, ATPS4r, LDH_D, MDH, NADH12, NADH6, PFLi, POX |
| 1035 | 8 | 7.88026 | 0.02165 | ADHEr, GLCpts, LDH_D, MDH, NADH12, NADH6, PFLi, THD2 and/or GLUDy |
| 1036 | 8 | 7.84104 | 0.02874 | ADHEr, ATPS4r, EDA and/or PGDHY, LDH_D, NADH6, PFLi, PGI, PPS |
| 1037 | 8 | 7.80925 | 0.03448 | ADHEr, ATPS4r, FUM, LDH_D, NADH12, NADH6, PFLi, PGI |
| 1038 | 8 | 7.80925 | 0.03448 | ADHEr, ATPS4r, LDH_D, MDH, NADH12, NADH6, PFLi, PGI |
| 1039 | 8 | 7.67439 | 0.05735 | ACKr and/or PTAr, ADHEr, GLCpts, LDH_D, MDH, NADH12, NADH6, PFLi |
| 1040 | 8 | 7.42051 | 0.09374 | ADHEr, ATPS4r, FUM, GLCpts, LDH_D, NADH6, PFLi, PPS |
| 1041 | 8 | 7.32674 | 0.0933 | ACKr and/or PTAr, ADHEr, ATPS4r, FUM, GLCpts, LDH_D, NADH6, PFLi |
| 1042 | 8 | 6.93593 | 0.04641 | ADHEr, ATPS4r, HEX1, LDH_D, NADH12, PFLi, PPCK, THD2 and/or GLUDy |
| 1043 | 8 | 6.58791 | 0.09796 | ADHEr, ATPS4r, HEX1, LDH_D, NADH6, PFLi, PGL and/or G6PDHy, PPS |
| 1044 | 8 | 6.58791 | 0.09796 | ADHEr, ATPS4r, HEX1, LDH_D, NADH6, PFLi, PGDH, PPS |
| 1045 | 8 | 6.5802 | 0.09979 | ADHEr, ATPS4r, HEX1, LDH_D, NADH6, PFLi, PPS, TAL |
| 1046 | 8 | 6.57291 | 0.10152 | ADHEr, ATPS4r, HEX1, LDH_D, NADH6, PFLi, PPS, RPE |
| 1047 | 8 | 5.75656 | 0.15131 | ADHEr, HEX1, LDH_D, NADH12, NADH6, PFLi, PPS, THD2 and/or GLUDy |
| 1048 | 8 | 5.74602 | 0.16073 | ADHEr, ATPS4r, HEX1, LDH_D, NADH12, PFLi, PPS, THD2 and/or GLUDy |
| 1049 | 8 | 5.67321 | 0.16148 | ACKr and/or PTAr, ADHEr, ATPS4r, HEX1, LDH_D, NADH12, PFLi, THD2 and/or GLUDy |
| 1050 | 8 | 5.60169 | 0.03793 | ADHEr, FUM, LDH_D, NADH12, NADH6, PFLi, PPCK, PYK |
| 1051 | 8 | 5.60169 | 0.03793 | ADHEr, LDH_D, MDH, NADH12, NADH6, PFLi, PPCK, PYK |
| 1052 | 8 | 5.56692 | 0.04965 | ADHEr, EDA and/or PGDHY, LDH_D, MDH, NADH6, PFLi, PPCK, PYK |
| 1053 | 8 | 5.56692 | 0.04965 | ADHEr, LDH_D, MDH, NADH6, PFLi, PGL and/or G6PDHy, PPCK, PYK |
| 1054 | 8 | 5.50925 | 0.07241 | ADHEr, ATPS4r, HEX1, LDH_D, PFLi, PPCK, RPE, THD2 and/or GLUDy |
| 1055 | 8 | 5.50597 | 0.07191 | ADHEr, ATPS4r, HEX1, LDH_D, PFLi, PPCK, TAL, THD2 and/or GLUDy |
| 1056 | 8 | 5.50242 | 0.07138 | ADHEr, ATPS4r, HEX1, LDH_D, PFLi, PGL and/or G6PDHy, PPCK, THD2 and/or GLUDy |
| 1057 | 8 | 5.50242 | 0.07138 | ADHEr, ATPS4r, HEX1, LDH_D, PFLi, PGDH, PPCK, THD2 and/or GLUDy |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 1058 | 8 | 5.44507 | 0.0907 | ADHEr, HEX1, LDH_D, NADH12, NADH6, PFLi, PRO1z, THD2 and/or GLUDy |
| 1059 | 8 | 5.37306 | 0.11496 | ADHEr, DAAD, LDH_D, MDH, NADH12, NADH6, PFLi, PRO1z |
| 1060 | 8 | 5.37306 | 0.11496 | ADHEr, ALAR, LDH_D, MDH, NADH12, NADH6, PFLi, PRO1z |
| 1061 | 8 | 5.33606 | 0.12742 | ADHEr, FUM, LDH_D, MDH, NADH12, NADH6, PFLi, PYK |
| 1062 | 8 | 5.17764 | 0.18079 | ADHEr, DAAD, HEX1, LDH_D, NADH12, NADH6, PFLi, PRO1z |
| 1063 | 8 | 5.17764 | 0.18079 | ADHEr, ALAR, HEX1, LDH_D, NADH12, NADH6, PFLi, PRO1z |
| 1064 | 8 | 5.17492 | 0.2398 | ACKr and/or PTAr, ACS, ADHEr, EDA and/or PGDHY, LDH_D, MDH, PFLi, THD2 and/or GLUDy |
| 1065 | 8 | 4.65995 | 0.20434 | ADHEr, ATPS4r, HEX1, LDH_D, MDH, PFLi, PPS, RPE |
| 1066 | 8 | 4.6123 | 0.20163 | ADHEr, ATPS4r, HEX1, LDH_D, MDH, PFLi, PPS, TAL |
| 1067 | 8 | 4.56149 | 0.19874 | ADHEr, ATPS4r, HEX1, LDH_D, MDH, PFLi, PGDH, PPS |
| 1068 | 8 | 4.13777 | 0.23628 | ADHEr, ATPS4r, FUM, HEX1, LDH_D, PFLi, PPS, RPE |
| 1069 | 8 | 4.06785 | 0.23403 | ADHEr, ATPS4r, FUM, HEX1, LDH_D, PFLi, PPS, TAL |
| 1070 | 8 | 4.04062 | 0.10178 | ADHEr, ATPS4r, FUM, HEX1, LDH_D, PDH, PFLi, PPS |
| 1071 | 8 | 4.04062 | 0.10178 | ADHEr, ATPS4r, HEX1, LDH_D, MDH, PDH, PFLi, PPS |
| 1072 | 8 | 3.9927 | 0.23161 | ADHEr, ATPS4r, FUM, HEX1, LDH_D, PFLi, PGL and/or G6PDHy, PPS |
| 1073 | 8 | 3.9927 | 0.23161 | ADHEr, ATPS4r, FUM, HEX1, LDH_D, PFLi, PGDH, PPS |
| 1074 | 8 | 2.03637 | 0.11796 | ACKr and/or PTAr, ADHEr, FBP, LDH_D, MDH, PFLi, PGDH, THD2 and/or GLUDy |
| 1075 | 8 | 1.98516 | 0.11932 | ACKr and/or PTAr, ADHEr, FBP, LDH_D, MDH, PFLi, TAL, THD2 and/or GLUDy |
| 1076 | 8 | 1.93743 | 0.12058 | ACKr and/or PTAr, ADHEr, FBP, LDH_D, MDH, PFLi, RPE, THD2 and/or GLUDy |
| 1077 | 8 | 1.76983 | 0.24401 | ACKr and/or PTAr, ACS, ADHEr, LDH_D, MDH, PFLi, PGI, THD2 and/or GLUDy |
| 1078 | 8 | 1.5107 | 0.31956 | ADHEr, ATPS4r, LDH_D, NADH12, PFLi, PGL and/or G6PDHy, TAL, THD2 and/or GLUDy |
| 1079 | 8 | 1.5107 | 0.31956 | ADHEr, ATPS4r, LDH_D, NADH12, PFLi, PGDH, TAL, THD2 and/or GLUDy |
| 1080 | 8 | 1.45644 | 0.3201 | ADHEr, ATPS4r, FUM, LDH_D, PFLi, PGDH, PPS, TAL |
| 1081 | 8 | 1.45644 | 0.3201 | ADHEr, ATPS4r, FUM, LDH_D, PFLi, PGL and/or G6PDHy, PPS, TAL |
| 1082 | 3 | 0.165681142 | 0.248770484 | ADHEr, LDH_D, PFK and/or FBA and/or TPI |
| 1083 | 3 | 2.792461067 | 0.310192487 | ADHEr, FRD and/or SUCD4, LDH_D |
| 1084 | 4 | 0.245091981 | 0.278197481 | ADHEr, ASPT, FUM, LDH_D |
| 1085 | 4 | 1.163607813 | 0.384018912 | ADHEr, ATPS4r, CBMK2, LDH_D |
| 1086 | 4 | 2.27265597 | 0.332308612 | ADHEr, ATPS4r, LDH_D, NADH6 |
| 1087 | 4 | 1.260046787 | 0.384504476 | ADHEr, ATPS4r, LDH_D, TKT1 |
| 1088 | 4 | 1.454891201 | 0.378757536 | ADHEr, ATPS4r, LDH_D, TKT2 |
| 1089 | 4 | 2.042634808 | 0.153142196 | ADHEr, HEX1, LDH_D, PFK and/or FBA and/or TPI |
| 1090 | 4 | 2.041701304 | 0.149789093 | ADHEr, LDH_D, PFK and/or FBA and/or TPI, PPCK |
| 1091 | 4 | 0.270967943 | 0.244721556 | ADHEr, LDH_D, PFK and/or FBA and/or TPI, TKT2 |
| 1092 | 4 | 2.907366868 | 0.244293538 | ADHEr, FUM, LDH_D, PPCK |
| 1093 | 4 | 0.363337262 | 0.340044232 | ADHEr, HEX1, LDH_D, MDH |
| 1094 | 4 | 2.907366868 | 0.244293538 | ADHEr, LDH_D, MDH, PPCK |
| 1095 | 4 | 2.085082479 | 0.31290916 | ADHEr, LDH_D, ME2, NADH6 |
| 1096 | 4 | 2.881545955 | 0.259101938 | ADHEr, FRD and/or SUCD4, LDH_D, ME2 |
| 1097 | 4 | 3.647199605 | 0.168610416 | ADHEr, LDH_D, NADH6, PFK and/or FBA and/or TPI |
| 1098 | 4 | 2.774595569 | 0.320438424 | ADHEr, FDH2, LDH_D, NADH6 |
| 1099 | 4 | 3.335904914 | 0.317384404 | ADHEr, FUM, LDH_D, NADH6 |
| 1100 | 4 | 3.331989713 | 0.319255557 | ADHEr, HEX1, LDH_D, NADH6 |
| 1101 | 4 | 2.224731454 | 0.327457036 | ADHEr, LDH_D, NADH6, TKT2 |
| 1102 | 4 | 0.23734264 | 0.246014656 | ADHEr, LDH_D, PFK and/or FBA and/or TPI, RPE |
| 1103 | 4 | 0.454138927 | 0.26931886 | ADHEr, LDH_D, PPCK, TKT2 |
| 1104 | 4 | 0.413317212 | 0.38682004 | ADHEr, HEX1, LDH_D, PPS |
| 1105 | 4 | 2.860294682 | 0.306273023 | ADHEr, FRD and/or SUCD4, LDH_D, RPE |
| 1106 | 4 | 2.808840722 | 0.300798688 | ADHEr, FRD and/or SUCD4, FUM, LDH_D |
| 1107 | 4 | 2.817574813 | 0.295789651 | ADHEr, FRD and/or SUCD4, HEX1, LDH_D |
| 1108 | 4 | 2.916137696 | 0.239263432 | ADHEr, FRD and/or SUCD4, LDH_D, MDH |
| 1109 | 4 | 2.973865652 | 0.206156212 | ADHEr, FRD and/or SUCD4, LDH_D, PPCK |
| 1110 | 4 | 2.892050239 | 0.30443817 | ADHEr, FRD and/or SUCD4, LDH_D, TKT2 |
| 1111 | 4 | 0.203360099 | 0.247321495 | ADHEr, LDH_D, PFK and/or FBA and/or TPI, TAL |
| 1112 | 4 | 2.117903686 | 0.331070152 | ADHEr, LDH_D, NADH6, TAL |
| 1113 | 4 | 0.34884992 | 0.271004016 | ADHEr, LDH_D, PPCK, TAL |
| 1114 | 4 | 2.828154021 | 0.308130129 | ADHEr, FRD and/or SUCD4, LDH_D, TAL |
| 1115 | 4 | 0.203360099 | 0.247321495 | ADHEr, LDH_D, PFK and/or FBA and/or TPI, TKT1 |
| 1116 | 4 | 2.117903686 | 0.331070152 | ADHEr, LDH_D, NADH6, TKT1 |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 1117 | 4 | 0.34884992 | 0.271004016 | ADHEr, LDH_D, PPCK, TKT1 |
| 1118 | 4 | 2.828154021 | 0.308130129 | ADHEr, FRD and/or SUCD4, LDH_D, TKT1 |
| 1119 | 5 | 3.948360602 | 0.222825522 | ADHEr, ASPT, LDH_D, MDH, TKT2 |
| 1120 | 5 | 3.966967048 | 0.182343827 | ADHEr, ASPT, FRD and/or SUCD4, LDH_D, MDH |
| 1121 | 5 | 3.752898719 | 0.126622688 | ADHEr, ATPS4r, FRD and/or SUCD4, LDH_D, ME2 |
| 1122 | 5 | 4.408716092 | 0.258053531 | ADHEr, ATPS4r, LDH_D, MDH, THD2 and/or GLUDy |
| 1123 | 5 | 6.415221004 | 0.039824926 | ADHEr, FADH4, LDH_D, MDH, THD2 and/or GLUDy |
| 1124 | 5 | 2.983060356 | 0.241650921 | ADHEr, FUM, LDH_D, PPCK, TKT2 |
| 1125 | 5 | 2.997718029 | 0.231538695 | ADHEr, FUM, LDH_D, THD2 and/or GLUDy, TKT2 |
| 1126 | 5 | 2.937396425 | 0.227071464 | ADHEr, FUM, HEX1, LDH_D, THD2 and/or GLUDy |
| 1127 | 5 | 3.001461104 | 0.190330107 | ADHEr, FRD and/or SUCD4, FUM, LDH_D, THD2 and/or GLUDy |
| 1128 | 5 | 2.935886887 | 0.22793719 | ADHEr, FRD and/or SUCD4, HEX1, LDH_D, THD2 and/or GLUDy |
| 1129 | 5 | 3.081083028 | 0.144666606 | ADHEr, FRD and/or SUCD4, LDH_D, PPCK, THD2 and/or GLUDy |
| 1130 | 5 | 2.988449413 | 0.197792365 | ADHEr, FRD and/or SUCD4, LDH_D, PRO1z, THD2 and/or GLUDy |
| 1131 | 5 | 2.948350239 | 0.234817401 | ADHEr, FUM, LDH_D, TAL, THD2 and/or GLUDy |
| 1132 | 5 | 3.101419157 | 0.133003752 | ADHEr, GLUDy, LDH_D, MDH, THD2 and/or GLUDy |
| 1133 | 5 | 2.948350239 | 0.234817401 | ADHEr, FUM, LDH_D, THD2 and/or GLUDy, TKT1 |
| 1134 | 5 | 2.983060356 | 0.241650921 | ADHEr, LDH_D, MDH, PPCK, TKT2 |
| 1135 | 5 | 2.916137696 | 0.239263432 | ADHEr, FRD and/or SUCD4, FUM, LDH_D, ME2 |
| 1136 | 5 | 3.711787388 | 0.165696592 | ADHEr, LDH_D, NADH6, PFK and/or FBA and/or TPI, TKT2 |
| 1137 | 5 | 3.457829994 | 0.311699463 | ADHEr, FUM, LDH_D, NADH6, TKT2 |
| 1138 | 5 | 3.451407023 | 0.315392099 | ADHEr, HEX1, LDH_D, NADH6, TKT2 |
| 1139 | 5 | 3.543757983 | 0.262298527 | ADHEr, LDH_D, MDH, NADH6, TKT2 |
| 1140 | 5 | 3.445461549 | 0.265025086 | ADHEr, FUM, LDH_D, ME2, NADH6 |
| 1141 | 5 | 3.609567252 | 0.224464061 | ADHEr, LDH_D, NADH6, PPCK, TKT2 |
| 1142 | 5 | 3.691174432 | 0.166626529 | ADHEr, LDH_D, NADH6, PFK and/or FBA and/or TPI, RPE |
| 1143 | 5 | 3.065706296 | 0.153485225 | ADHEr, FRD and/or SUCD4, FUM, LDH_D, PFK and/or FBA and/or TPI |
| 1144 | 5 | 3.071383178 | 0.15022951 | ADHEr, FRD and/or SUCD4, LDH_D, MDH, PFK and/or FBA and/or TPI |
| 1145 | 5 | 5.367175665 | 0.178044995 | ADHEr, CBMK2, HEX1, LDH_D, PGI |
| 1146 | 5 | 5.888703714 | 0.106589745 | ADHEr, EDA and/or PGDHY, FRD and/or SUCD4, LDH_D, PGI |
| 1147 | 5 | 3.110919215 | 0.148780301 | ADHEr, FRD and/or SUCD4, LDH_D, MDH, PGI |
| 1148 | 5 | 2.958795095 | 0.242498072 | ADHEr, FUM, LDH_D, PPCK, RPE |
| 1149 | 5 | 2.958795095 | 0.242498072 | ADHEr, LDH_D, MDH, PPCK, RPE |
| 1150 | 5 | 2.936051582 | 0.257223558 | ADHEr, FRD and/or SUCD4, LDH_D, ME2, RPE |
| 1151 | 5 | 3.418935049 | 0.313512999 | ADHEr, FUM, LDH_D, NADH6, RPE |
| 1152 | 5 | 3.413158878 | 0.316629525 | ADHEr, HEX1, LDH_D, NADH6, RPE |
| 1153 | 5 | 2.967063614 | 0.237144547 | ADHEr, FRD and/or SUCD4, LDH_D, MDH, RPE |
| 1154 | 5 | 3.018085814 | 0.204109778 | ADHEr, FRD and/or SUCD4, LDH_D, PPCK, RPE |
| 1155 | 5 | 3.009552774 | 0.185689501 | ADHEr, FRD and/or SUCD4, FUM, LDH_D, PPCK |
| 1156 | 5 | 3.009552774 | 0.185689501 | ADHEr, FRD and/or SUCD4, LDH_D, MDH, PPCK |
| 1157 | 5 | 2.991038247 | 0.23614703 | ADHEr, FRD and/or SUCD4, LDH_D, MDH, TKT2 |
| 1158 | 5 | 2.961772661 | 0.256337155 | ADHEr, FRD and/or SUCD4, LDH_D, ME2, TKT2 |
| 1159 | 5 | 3.106778446 | 0.151550201 | ADHEr, FRD and/or SUCD4, FUM, LDH_D, PGI |
| 1160 | 5 | 3.04583421 | 0.164881948 | ADHEr, FRD and/or SUCD4, LDH_D, PPCK, PYK |
| 1161 | 5 | 3.038870487 | 0.203147899 | ADHEr, FRD and/or SUCD4, LDH_D, PPCK, TKT2 |
| 1162 | 5 | 3.886386663 | 0.225053566 | ADHEr, ASPT, LDH_D, MDH, TAL |
| 1163 | 5 | 3.670328799 | 0.167566962 | ADHEr, LDH_D, NADH6, PFK and/or FBA and/or TPI, TAL |
| 1164 | 5 | 3.480501908 | 0.264053132 | ADHEr, LDH_D, MDH, NADH6, TAL |
| 1165 | 5 | 3.554829627 | 0.226273464 | ADHEr, LDH_D, NADH6, PPCK, TAL |
| 1166 | 5 | 2.942885577 | 0.238150528 | ADHEr, FRD and/or SUCD4, LDH_D, MDH, TAL |
| 1167 | 5 | 2.99710338 | 0.20508081 | ADHEr, FRD and/or SUCD4, LDH_D, PPCK, TAL |
| 1168 | 5 | 3.964901837 | 0.267840742 | ADHEr, HEX1, LDH_D, MDH, THD2 and/or GLUDy |
| 1169 | 5 | 3.00074032 | 0.229453637 | ADHEr, LDH_D, MDH, THD2 and/or GLUDy, TKT2 |
| 1170 | 5 | 4.557091208 | 0.201359081 | ADHEr, FRD and/or SUCD4, LDH_D, ME2, THD2 and/or GLUDy |
| 1171 | 5 | 2.935925119 | 0.227915263 | ADHEr, LDH_D, MDH, PGDH, THD2 and/or GLUDy |
| 1172 | 5 | 2.97971305 | 0.22895456 | ADHEr, LDH_D, MDH, RPE, THD2 and/or GLUDy |
| 1173 | 5 | 2.958777052 | 0.228457649 | ADHEr, LDH_D, MDH, TAL, THD2 and/or GLUDy |
| 1174 | 5 | 3.886386663 | 0.225053566 | ADHEr, ASPT, LDH_D, MDH, TKT1 |
| 1175 | 5 | 2.934359102 | 0.243351183 | ADHEr, FUM, LDH_D, PPCK, TKT1 |
| 1176 | 5 | 2.934359102 | 0.243351183 | ADHEr, LDH_D, MDH, PPCK, TKT1 |
| 1177 | 5 | 3.670328799 | 0.167566962 | ADHEr, LDH_D, NADH6, PFK and/or FBA and/or TPI, TKT1 |
| 1178 | 5 | 3.379584856 | 0.31534776 | ADHEr, FUM, LDH_D, NADH6, TKT1 |
| 1179 | 5 | 3.374609422 | 0.317876699 | ADHEr, HEX1, LDH_D, NADH6, TKT1 |
| 1180 | 5 | 3.480501908 | 0.264053132 | ADHEr, LDH_D, MDH, NADH6, TKT1 |
| 1181 | 5 | 3.554829627 | 0.226273464 | ADHEr, LDH_D, NADH6, PPCK, TKT1 |
| 1182 | 5 | 2.942885577 | 0.238150528 | ADHEr, FRD and/or SUCD4, LDH_D, MDH, TKT1 |

TABLE 14-continued

Knockout strain designs for increased production of 6-ACA, showing yields of 6-ACA and biomass.

| New Design ID | Num KO | 6ACA. Yield | Biomass | Rxnlist |
|---|---|---|---|---|
| 1183 | 5 | 2.99710338 | 0.20508081 | ADHEr, FRD and/or SUCD4, LDH_D, PPCK, TKT1 |
| 1184 | 5 | 2.958777052 | 0.228457649 | ADHEr, LDH_D, MDH, THD2 and/or GLUDy, TKT1 |

TABLE 15

Knockout strain designs for increased production of adipate, showing yields of adipate and biomass.

| New Design ID | Num KO | Adipate. Yield | Biomass | Rxnlist |
|---|---|---|---|---|
| 1 | 3 | 5.47908 | 0.34054 | ADHEr, LDH_D, NADH6 |
| 2 | 3 | 4.26684 | 0.28031 | ADHEr, LDH_D, PPCK |
| 3 | 3 | 2.76166 | 0.38773 | ADHEr, ATPS4r, LDH_D |
| 4 | 3 | 1.54669 | 0.25966 | ADHEr, LDH_D, PGI |
| 5 | 3 | 1.33726 | 0.37808 | ADHEr, FUM, LDH_D |
| 6 | 3 | 0.83242 | 0.38953 | ADHEr, HEX1, LDH_D |
| 7 | 4 | 7.52636 | 0.16586 | ADHEr, HEX1, LDH_D, PGI |
| 8 | 4 | 6.84269 | 0.27849 | ADHEr, LDH_D, NADH6, PFLi |
| 9 | 4 | 6.5702 | 0.20631 | ADHEr, ASPT, LDH_D, MDH |
| 10 | 4 | 6.16994 | 0.16614 | ADHEr, LDH_D, NADH6, PGI |
| 11 | 4 | 6.0882 | 0.30766 | ADHEr, LDH_D, MDH, THD2 and/or GLUDy |
| 12 | 4 | 5.87407 | 0.22728 | ADHEr, LDH_D, NADH6, PPCK |
| 13 | 4 | 5.68406 | 0.28176 | ADHEr, LDH_D, MDH, NADH6 |
| 14 | 4 | 5.62555 | 0.33704 | ADHEr, LDH_D, NADH6, RPE |
| 15 | 4 | 5.60596 | 0.30416 | ADHEr, LDH_D, NADH6, THD2 and/or GLUDy |
| 16 | 4 | 5.55606 | 0.3387 | ADHEr, LDH_D, NADH6, TAL |
| 17 | 4 | 5.54557 | 0.32148 | ADHEr, FUM, LDH_D, NADH6 |
| 18 | 4 | 5.16028 | 0.24175 | ADHEr, LDH_D, PFLi, PPCK |
| 19 | 4 | 4.91511 | 0.27067 | ADHEr, LDH_D, PPCK, THD2 and/or GLUDy |
| 20 | 4 | 4.3568 | 0.24592 | ADHEr, GLCpts, LDH_D, PPCK |
| 21 | 4 | 4.35358 | 0.27902 | ADHEr, LDH_D, PPCK, RPE |
| 22 | 4 | 4.34095 | 0.25198 | ADHEr, FUM, LDH_D, PPCK |
| 23 | 4 | 4.34095 | 0.25198 | ADHEr, LDH_D, MDH, PPCK |
| 24 | 4 | 4.28493 | 0.2734 | ADHEr, FUM, LDH_D, THD2 and/or GLUDy |
| 25 | 4 | 4.0889 | 0.34834 | ADHEr, FUM, HEX1, LDH_D |
| 26 | 4 | 3.25969 | 0.38161 | ADHEr, ATPS4r, LDH_D, RPE |
| 27 | 4 | 3.18007 | 0.37054 | ADHEr, HEX1, LDH_D, THD2 and/or GLUDy |
| 28 | 4 | 3.11658 | 0.34524 | ADHEr, ATPS4r, LDH_D, THD2 and/or GLUDy |
| 29 | 4 | 3.02411 | 0.3845 | ADHEr, ATPS4r, LDH_D, TAL |
| 30 | 4 | 1.1506 | 0.38695 | ADHEr, HEX1, LDH_D, RPE |
| 31 | 4 | 0.99936 | 0.38818 | ADHEr, HEX1, LDH_D, TAL |
| 32 | 5 | 7.63281 | 0.14897 | ADHEr, HEX1, LDH_D, PGI, THD2 and/or GLUDy |
| 33 | 5 | 7.60368 | 0.23979 | ADHEr, ATPS4r, LDH_D, MDH, NADH6 |
| 34 | 5 | 7.25714 | 0.17876 | ADHEr, LDH_D, MDH, PFLi, THD2 and/or GLUDy |
| 35 | 5 | 7.21061 | 0.18996 | ADHEr, LDH_D, MDH, PFLi, PPCK |
| 36 | 5 | 7.21061 | 0.18996 | ADHEr, FUM, LDH_D, PFLi, PPCK |
| 37 | 5 | 7.11676 | 0.21254 | ADHEr, LDH_D, MDH, NADH6, PFLi |
| 38 | 5 | 7.10568 | 0.21521 | ADHEr, FUM, LDH_D, PFLi, THD2 and/or GLUDy |
| 39 | 5 | 6.9706 | 0.24771 | ADHEr, LDH_D, NADH6, PFLi, THD2 and/or GLUDy |
| 40 | 5 | 6.90675 | 0.27577 | ADHEr, LDH_D, NADH6, PFLi, RPE |
| 41 | 5 | 6.83498 | 0.1681 | ADHEr, ASPT, GLCpts, LDH_D, MDH |
| 42 | 5 | 6.80758 | 0.29402 | ADHEr, ATPS4r, LDH_D, MDH, TAL |
| 43 | 5 | 6.79015 | 0.29114 | ADHEr, ATPS4r, LDH_D, MDH, PGDH |
| 44 | 5 | 6.76743 | 0.17785 | ADHEr, ASPT, LDH_D, MDH, THD2 and/or GLUDy |
| 45 | 5 | 6.76201 | 0.23293 | ADHEr, LDH_D, MDH, NADH6, THD2 and/or GLUDy |
| 46 | 5 | 6.66991 | 0.23493 | ADHEr, LDH_D, PFLi, PPCK, THD2 and/or GLUDy |
| 47 | 5 | 6.66754 | 0.2967 | ADHEr, ATPS4r, LDH_D, MDH, RPE |
| 48 | 5 | 6.57746 | 0.21333 | ADHEr, LDH_D, NADH6, PPCK, THD2 and/or GLUDy |
| 49 | 5 | 6.34963 | 0.21785 | ADHEr, ATPS4r, LDH_D, NADH6, PPCK |
| 50 | 5 | 6.225 | 0.14772 | ADHEr, LDH_D, NADH6, PGI, THD2 and/or GLUDy |
| 51 | 5 | 6.18982 | 0.20058 | ADHEr, GLUDy, LDH_D, MDH, THD2 and/or GLUDy |
| 52 | 5 | 6.18254 | 0.21218 | ADHEr, LDH_D, MDH, PPCK, THD2 and/or GLUDy |
| 53 | 5 | 6.18254 | 0.21218 | ADHEr, FUM, LDH_D, PPCK, THD2 and/or GLUDy |
| 54 | 5 | 5.99792 | 0.19177 | ADHEr, GLCpts, LDH_D, NADH6, PPCK |
| 55 | 5 | 5.97051 | 0.22537 | ADHEr, LDH_D, NADH6, PPCK, RPE |
| 56 | 5 | 5.92744 | 0.32733 | ADHEr, ATPS4r, HEX1, LDH_D, NADH6 |
| 57 | 5 | 5.92472 | 0.22627 | ADHEr, LDH_D, NADH6, PPCK, TAL |
| 58 | 5 | 5.81113 | 0.24533 | ADHEr, GLCpts, LDH_D, MDH, NADH6 |
| 59 | 5 | 5.80132 | 0.28014 | ADHEr, LDH_D, MDH, NADH6, RPE |
| 60 | 5 | 5.74556 | 0.28091 | ADHEr, LDH_D, MDH, NADH6, TAL |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 61 | 5 | 5.74235 | 0.20973 | ADHEr, ATPS4r, LDH_D, MDH, THD2 and/or GLUDy |
| 62 | 5 | 5.73575 | 0.30136 | ADHEr, LDH_D, NADH6, RPE, THD2 and/or GLUDy |
| 63 | 5 | 5.72421 | 0.22208 | ADHEr, ATPS4r, LDH_D, MDH, PPCK |
| 64 | 5 | 5.72421 | 0.22208 | ADHEr, ATPS4r, FUM, LDH_D, PPCK |
| 65 | 5 | 5.68542 | 0.31766 | ADHEr, FUM, LDH_D, NADH6, RPE |
| 66 | 5 | 5.67414 | 0.30269 | ADHEr, LDH_D, NADH6, TAL, THD2 and/or GLUDy |
| 67 | 5 | 5.62871 | 0.29764 | ADHEr, FUM, HEX1, LDH_D, NADH6 |
| 68 | 5 | 5.61913 | 0.31947 | ADHEr, FUM, LDH_D, NADH6, TAL |
| 69 | 5 | 5.56433 | 0.06187 | ADHEr, ATPS4r, EDA and/or PGDHY, LDH_D, PGI |
| 70 | 5 | 5.53618 | 0.32417 | ADHEr, HEX1, LDH_D, NADH6, THD2 and/or GLUDy |
| 71 | 5 | 5.36114 | 0.24084 | ADHEr, LDH_D, PFLi, PPCK, RPE |
| 72 | 5 | 5.35732 | 0.32317 | ADHEr, ATPS4r, FUM, HEX1, LDH_D |
| 73 | 5 | 5.29193 | 0.25262 | ADHEr, ATPS4r, FUM, LDH_D, THD2 and/or GLUDy |
| 74 | 5 | 5.26552 | 0.24127 | ADHEr, LDH_D, PFLi, PPCK, TAL |
| 75 | 5 | 5.23886 | 0.36027 | ADHEr, HEX1, LDH_D, PFLi, PPS |
| 76 | 5 | 5.2123 | 0.3202 | ADHEr, ATPS4r, HEX1, LDH_D, PFLi |
| 77 | 5 | 5.20628 | 0.31113 | ADHEr, FUM, HEX1, LDH_D, PFLi |
| 78 | 5 | 5.20628 | 0.31113 | ADHEr, HEX1, LDH_D, MDH, PFLi |
| 79 | 5 | 5.00885 | 0.16853 | ADHEr, ATPS4r, LDH_D, PFLi, PGI |
| 80 | 5 | 4.73325 | 0.11896 | ADHEr, LDH_D, PGI, PPCK, THD2 and/or GLUDy |
| 81 | 5 | 4.71871 | 0.12544 | ADHEr, LDH_D, MDH, PGI, THD2 and/or GLUDy |
| 82 | 5 | 4.71871 | 0.12544 | ADHEr, FUM, LDH_D, PGI, THD2 and/or GLUDy |
| 83 | 5 | 4.46543 | 0.20438 | ADHEr, GLCpts, LDH_D, MDH, THD2 and/or GLUDy |
| 84 | 5 | 4.45303 | 0.23609 | ADHEr, LDH_D, MDH, RPE, THD2 and/or GLUDy |
| 85 | 5 | 4.44799 | 0.21105 | ADHEr, LDH_D, MDH, PYK, THD2 and/or GLUDy |
| 86 | 5 | 4.43313 | 0.21674 | ADHEr, GLCpts, LDH_D, MDH, PPCK |
| 87 | 5 | 4.43313 | 0.21674 | ADHEr, FUM, GLCpts, LDH_D, PPCK |
| 88 | 5 | 4.43289 | 0.24479 | ADHEr, GLCpts, LDH_D, PPCK, RPE |
| 89 | 5 | 4.42239 | 0.22084 | ADHEr, GLCpts, LDH_D, PPCK, THD2 and/or GLUDy |
| 90 | 5 | 4.4202 | 0.25027 | ADHEr, FUM, LDH_D, PPCK, RPE |
| 91 | 5 | 4.4202 | 0.25027 | ADHEr, LDH_D, MDH, PPCK, RPE |
| 92 | 5 | 4.41922 | 0.25069 | ADHEr, LDH_D, PPCK, RPE, THD2 and/or GLUDy |
| 93 | 5 | 4.41348 | 0.22425 | ADHEr, LDH_D, MDH, PPCK, PYK |
| 94 | 5 | 4.41348 | 0.22425 | ADHEr, FUM, LDH_D, PPCK, PYK |
| 95 | 5 | 4.3742 | 0.27012 | ADHEr, FUM, LDH_D, RPE, THD2 and/or GLUDy |
| 96 | 5 | 4.34566 | 0.25018 | ADHEr, FUM, GLCpts, LDH_D, THD2 and/or GLUDy |
| 97 | 5 | 4.22695 | 0.31979 | ADHEr, ATPS4r, HEX1, LDH_D, MDH |
| 98 | 5 | 4.21297 | 0.36989 | ADHEr, ATPS4r, HEX1, LDH_D, THD2 and/or GLUDy |
| 99 | 5 | 4.19799 | 0.34618 | ADHEr, FUM, HEX1, LDH_D, RPE |
| 100 | 5 | 4.15986 | 0.32121 | ADHEr, FUM, HEX1, LDH_D, THD2 and/or GLUDy |
| 101 | 5 | 4.14613 | 0.34721 | ADHEr, FUM, HEX1, LDH_D, TAL |
| 102 | 5 | 4.14548 | 0.36885 | ADHEr, HEX1, LDH_D, RPE, THD2 and/or GLUDy |
| 103 | 5 | 4.09366 | 0.36854 | ADHEr, HEX1, LDH_D, TAL, THD2 and/or GLUDy |
| 104 | 5 | 4.03694 | 0.36821 | ADHEr, HEX1, LDH_D, PGL and/or G6PDHy, THD2 and/or GLUDy |
| 105 | 5 | 4.03694 | 0.36821 | ADHEr, HEX1, LDH_D, PGDH, THD2 and/or GLUDy |
| 106 | 5 | 3.55579 | 0.34037 | ADHEr, ATPS4r, LDH_D, RPE, THD2 and/or GLUDy |
| 107 | 5 | 3.35244 | 0.11579 | ADHEr, FRD and/or SUCD4, LDH_D, PPS, THD2 and/or GLUDy |
| 108 | 5 | 3.34785 | 0.34268 | ADHEr, ATPS4r, LDH_D, TAL, THD2 and/or GLUDy |
| 109 | 5 | 2.86477 | 0.08801 | ADHEr, EDA and/or PGDHY, FUM, LDH_D, PGI |
| 110 | 5 | 1.41816 | 0.36252 | ADHEr, FUM, LDH_D, PGL and/or G6PDHy, TAL |
| 111 | 5 | 1.41816 | 0.36252 | ADHEr, FUM, LDH_D, PGDH, TAL |
| 112 | 6 | 8.40974 | 0.12863 | ADHEr, GLUDy, LDH_D, MDH, PFLi, THD2 and/or GLUDy |
| 113 | 6 | 8.3656 | 0.13555 | ADHEr, LDH_D, MDH, PFLi, PPCK, THD2 and/or GLUDy |
| 114 | 6 | 8.3656 | 0.13555 | ADHEr, FUM, LDH_D, PFLi, PPCK, THD2 and/or GLUDy |
| 115 | 6 | 8.30583 | 0.11621 | ACKr and/or PTAr, ADHEr, LDH_D, MDH, NADH6, THD2 and/or GLUDy |
| 116 | 6 | 8.24494 | 0.15445 | ADHEr, LDH_D, MDH, NADH6, PFLi, THD2 and/or GLUDy |
| 117 | 6 | 7.99084 | 0.19426 | ADHEr, ATPS4r, LDH_D, MDH, PFLi, THD2 and/or GLUDy |
| 118 | 6 | 7.9508 | 0.20053 | ADHEr, HEX1, LDH_D, MDH, PFLi, THD2 and/or GLUDy |
| 119 | 6 | 7.92831 | 0.12763 | ADHEr, ATPS4r, LDH_D, MDH, NADH6, THD2 and/or GLUDy |
| 120 | 6 | 7.91305 | 0.13531 | ADHEr, ATPS4r, LDH_D, MDH, NADH6, PPCK |
| 121 | 6 | 7.91305 | 0.13531 | ADHEr, ATPS4r, FUM, LDH_D, NADH6, PPCK |
| 122 | 6 | 7.87012 | 0.02274 | ACKr and/or PTAr, ADHEr, LDH_D, MDH, PPCK, THD2 and/or GLUDy |
| 123 | 6 | 7.7587 | 0.21695 | ADHEr, LDH_D, MDH, NADH12, NADH6, THD2 and/or GLUDy |
| 124 | 6 | 7.75003 | 0.03607 | ADHEr, ASPT, LDH_D, MDH, PGI, THD2 and/or GLUDy |
| 125 | 6 | 7.74149 | 0.21948 | ADHEr, ATPS4r, EDA and/or PGDHY, LDH_D, MDH, NADH6 |
| 126 | 6 | 7.7368 | 0.0672 | ADHEr, LDH_D, PFLi, PGI, PPCK, THD2 and/or GLUDy |
| 127 | 6 | 7.72197 | 0.07098 | ADHEr, LDH_D, MDH, PFLi, PGI, THD2 and/or GLUDy |
| 128 | 6 | 7.72197 | 0.07098 | ADHEr, FUM, LDH_D, PFLi, PGI, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 129 | 6 | 7.67273 | 0.08355 | ADHEr, LDH_D, NADH6, PFLi, PGI, THD2 and/or GLUDy |
| 130 | 6 | 7.64843 | 0.19881 | ADHEr, GLCpts, LDH_D, MDH, NADH6, THD2 and/or GLUDy |
| 131 | 6 | 7.61824 | 0.14232 | ADHEr, LDH_D, NADH6, PFLi, PPCK, THD2 and/or GLUDy |
| 132 | 6 | 7.60825 | 0.2542 | ADHEr, FUM, HEX1, LDH_D, PFLi, THD2 and/or GLUDy |
| 133 | 6 | 7.5467 | 0.16899 | ADHEr, ATPS4r, LDH_D, PFLi, PPCK, THD2 and/or GLUDy |
| 134 | 6 | 7.48349 | 0.12429 | ADHEr, FUM, LDH_D, NADH6, PFLi, THD2 and/or GLUDy |
| 135 | 6 | 7.4685 | 0.07894 | ADHEr, ASPT, LDH_D, MDH, PGL and/or G6PDHy, PYK |
| 136 | 6 | 7.4685 | 0.07894 | ADHEr, ASPT, EDA and/or PGDHY, LDH_D, MDH, PYK |
| 137 | 6 | 7.44298 | 0.08037 | ACKr and/or PTAr, ADHEr, ASPT, LDH_D, MDH, THD2 and/or GLUDy |
| 138 | 6 | 7.40415 | 0.13677 | ADHEr, LDH_D, NADH6, PFLi, PPCK, PYK |
| 139 | 6 | 7.4 | 0.14438 | ADHEr, GLCpts, LDH_D, MDH, PFLi, THD2 and/or GLUDy |
| 140 | 6 | 7.36241 | 0.15343 | ADHEr, GLCpts, LDH_D, MDH, PFLi, PPCK |
| 141 | 6 | 7.36241 | 0.15343 | ADHEr, FUM, GLCpts, LDH_D, PFLi, PPCK |
| 142 | 6 | 7.27527 | 0.1744 | ADHEr, ATPS4r, FUM, LDH_D, NADH6, THD2 and/or GLUDy |
| 143 | 6 | 7.27448 | 0.17459 | ADHEr, GLCpts, LDH_D, MDH, NADH6, PFLi |
| 144 | 6 | 7.24864 | 0.17893 | ADHEr, ATPS4r, LDH_D, MDH, PGL and/or G6PDHy, THD2 and/or GLUDy |
| 145 | 6 | 7.24278 | 0.26146 | ADHEr, HEX1, LDH_D, NADH6, PFLi, THD2 and/or GLUDy |
| 146 | 6 | 7.20895 | 0.28496 | ADHEr, ATPS4r, HEX1, LDH_D, PFLi, THD2 and/or GLUDy |
| 147 | 6 | 7.18819 | 0.12101 | ADHEr, ASPT, LDH_D, MDH, PYK, THD2 and/or GLUDy |
| 148 | 6 | 7.17088 | 0.20914 | ADHEr, LDH_D, MDH, PFLi, RPE, THD2 and/or GLUDy |
| 149 | 6 | 7.15564 | 0.2082 | ADHEr, LDH_D, MDH, PFLi, TAL, THD2 and/or GLUDy |
| 150 | 6 | 7.1458 | 0.12325 | ADHEr, ASPT, LDH_D, MDH, PPCK, THD2 and/or GLUDy |
| 151 | 6 | 7.13909 | 0.20717 | ADHEr, LDH_D, MDH, PFLi, PGDH, THD2 and/or GLUDy |
| 152 | 6 | 7.12504 | 0.22071 | ADHEr, LDH_D, PFLi, PPCK, RPE, THD2 and/or GLUDy |
| 153 | 6 | 7.10894 | 0.21971 | ADHEr, LDH_D, PFLi, PPCK, TAL, THD2 and/or GLUDy |
| 154 | 6 | 7.09146 | 0.21863 | ADHEr, LDH_D, PFLi, PGL and/or G6PDHy, PPCK, THD2 and/or GLUDy |
| 155 | 6 | 7.09146 | 0.21863 | ADHEr, LDH_D, PFLi, PGDH, PPCK, THD2 and/or GLUDy |
| 156 | 6 | 7.0863 | 0.31638 | ADHEr, HEX1, LDH_D, PFLi, PPS, THD2 and/or GLUDy |
| 157 | 6 | 7.06893 | 0.22405 | ADHEr, LDH_D, NADH12, NADH6, PFLi, THD2 and/or GLUDy |
| 158 | 6 | 7.054 | 0.1365 | ADHEr, ASPT, LDH_D, MDH, NADH6, THD2 and/or GLUDy |
| 159 | 6 | 7.02653 | 0.24555 | ADHEr, LDH_D, NADH6, PFLi, RPE, THD2 and/or GLUDy |
| 160 | 6 | 6.99568 | 0.14491 | ADHEr, ASPT, GLCpts, LDH_D, MDH, THD2 and/or GLUDy |
| 161 | 6 | 6.92353 | 0.16046 | ADHEr, ASPT, GLUDy, LDH_D, MDH, THD2 and/or GLUDy |
| 162 | 6 | 6.90243 | 0.27063 | ADHEr, HEX1, LDH_D, NADH6, PFLi, TAL |
| 163 | 6 | 6.8314 | 0.18819 | ADHEr, ATPS4r, LDH_D, MDH, PGL and/or G6PDHy, PPCK |
| 164 | 6 | 6.79251 | 0.30763 | ADHEr, ATPS4r, FUM, HEX1, LDH_D, PFLi |
| 165 | 6 | 6.70257 | 0.21085 | ADHEr, ATPS4r, LDH_D, NADH6, PGL and/or G6PDHy, PPCK |
| 166 | 6 | 6.70257 | 0.21085 | ADHEr, ATPS4r, LDH_D, NADH6, PGDH, PPCK |
| 167 | 6 | 6.66743 | 0.21154 | ADHEr, ATPS4r, LDH_D, NADH6, PPCK, TAL |
| 168 | 6 | 6.63518 | 0.21218 | ADHEr, ATPS4r, LDH_D, NADH6, PPCK, RPE |
| 169 | 6 | 6.48093 | 0.19172 | ADHEr, ATPS4r, FUM, LDH_D, PGL and/or G6PDHy, PPCK |
| 170 | 6 | 6.48093 | 0.19172 | ADHEr, ATPS4r, FUM, LDH_D, PGDH, PPCK |
| 171 | 6 | 6.44865 | 0.19659 | ADHEr, ATPS4r, GLCpts, LDH_D, PFLi, PPCK |
| 172 | 6 | 6.44275 | 0.19249 | ADHEr, ATPS4r, FUM, LDH_D, PPCK, TAL |
| 173 | 6 | 6.40767 | 0.1932 | ADHEr, ATPS4r, FUM, LDH_D, PPCK, RPE |
| 174 | 6 | 6.33204 | 0.06396 | ACKr and/or PTAr, ADHEr, LDH_D, NADH6, PPCK, THD2 and/or GLUDy |
| 175 | 6 | 6.28774 | 0.02127 | ADHEr, ATPS4r, EDA and/or PGDHY, LDH_D, PGI, THD2 and/or GLUDy |
| 176 | 6 | 6.27764 | 0.32432 | ADHEr, ATPS4r, HEX1, LDH_D, NADH6, PGL and/or G6PDHy |
| 177 | 6 | 6.27764 | 0.32432 | ADHEr, ATPS4r, HEX1, LDH_D, NADH6, PGDH |
| 178 | 6 | 6.21873 | 0.32483 | ADHEr, ATPS4r, HEX1, LDH_D, NADH6, TAL |
| 179 | 6 | 6.16484 | 0.32529 | ADHEr, ATPS4r, HEX1, LDH_D, NADH6, RPE |
| 180 | 6 | 6.12301 | 0.15589 | ADHEr, LDH_D, MDH, NADH6, PYK, THD2 and/or GLUDy |
| 181 | 6 | 6.09151 | 0.3086 | ADHEr, FUM, HEX1, LDH_D, PPS, THD2 and/or GLUDy |
| 182 | 6 | 6.08785 | 0.16598 | ADHEr, FUM, LDH_D, NADH6, PPCK, PYK |
| 183 | 6 | 6.08785 | 0.16598 | ADHEr, LDH_D, MDH, NADH6, PPCK, PYK |
| 184 | 6 | 6.07929 | 0.19015 | ADHEr, GLCpts, LDH_D, NADH6, PPCK, RPE |
| 185 | 6 | 6.0681 | 0.17164 | ADHEr, GLCpts, LDH_D, NADH6, PPCK, THD2 and/or GLUDy |
| 186 | 6 | 6.04302 | 0.20189 | ADHEr, LDH_D, NADH6, PPCK, RPE, THD2 and/or GLUDy |
| 187 | 6 | 6.01911 | 0.18569 | ADHEr, FUM, LDH_D, NADH12, NADH6, PPCK |
| 188 | 6 | 6.01911 | 0.18569 | ADHEr, LDH_D, MDH, NADH12, NADH6, PPCK |
| 189 | 6 | 5.98595 | 0.1952 | ADHEr, FUM, GLCpts, LDH_D, NADH6, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 190 | 6 | 5.93003 | 0.21123 | ADHEr, FUM, LDH_D, NADH12, NADH6, THD2 and/or GLUDy |
| 191 | 6 | 5.91322 | 0.24391 | ADHEr, GLCpts, LDH_D, MDH, NADH6, RPE |
| 192 | 6 | 5.89537 | 0.30664 | ADHEr, ATPS4r, HEX1, LDH_D, MDH, PFLi |
| 193 | 6 | 5.86467 | 0.24459 | ADHEr, GLCpts, LDH_D, MDH, NADH6, TAL |
| 194 | 6 | 5.8616 | 0.12855 | ADHEr, ATPS4r, LDH_D, MDH, PPCK, THD2 and/or GLUDy |
| 195 | 6 | 5.8616 | 0.12855 | ADHEr, ATPS4r, FUM, LDH_D, PPCK, THD2 and/or GLUDy |
| 196 | 6 | 5.75652 | 0.29464 | ADHEr, FUM, HEX1, LDH_D, NADH6, RPE |
| 197 | 6 | 5.71417 | 0.25845 | ADHEr, ATPS4r, LDH_D, MDH, PGL and/or G6PDHy, PPS |
| 198 | 6 | 5.69588 | 0.29606 | ADHEr, FUM, HEX1, LDH_D, NADH6, TAL |
| 199 | 6 | 5.53662 | 0.35787 | ADHEr, HEX1, LDH_D, PFLi, PPS, RPE |
| 200 | 6 | 5.4724 | 0.31504 | ADHEr, ATPS4r, HEX1, LDH_D, PFLi, RPE |
| 201 | 6 | 5.46402 | 0.30945 | ADHEr, FUM, HEX1, LDH_D, PFLi, RPE |
| 202 | 6 | 5.46402 | 0.30945 | ADHEr, HEX1, LDH_D, MDH, PFLi, RPE |
| 203 | 6 | 5.39509 | 0.35901 | ADHEr, HEX1, LDH_D, PFLi, PPS, TAL |
| 204 | 6 | 5.34939 | 0.31748 | ADHEr, ATPS4r, HEX1, LDH_D, PFLi, TAL |
| 205 | 6 | 5.34143 | 0.31025 | ADHEr, HEX1, LDH_D, MDH, PFLi, TAL |
| 206 | 6 | 5.34143 | 0.31025 | ADHEr, FUM, HEX1, LDH_D, PFLi, TAL |
| 207 | 6 | 5.07203 | 0.20521 | ADHEr, LDH_D, MDH, PFLi, PGDH, PGI |
| 208 | 6 | 5.07203 | 0.20521 | ADHEr, FUM, LDH_D, PFLi, PGDH, PGI |
| 209 | 6 | 5.04668 | 0.20656 | ADHEr, FUM, LDH_D, PFLi, PGI, TAL |
| 210 | 6 | 5.04668 | 0.20656 | ADHEr, LDH_D, MDH, PFLi, PGI, TAL |
| 211 | 6 | 5.02327 | 0.2078 | ADHEr, LDH_D, MDH, PFLi, PGI, RPE |
| 212 | 6 | 5.02327 | 0.2078 | ADHEr, FUM, LDH_D, PFLi, PGI, RPE |
| 213 | 6 | 4.96889 | 0.09918 | ACKr and/or PTAr, ADHEr, ATPS4r, LDH_D, PPCK, THD2 and/or GLUDy |
| 214 | 6 | 4.92469 | 0.33322 | ADHEr, HEX1, LDH_D, PGL and/or G6PDHy, PPS, THD2 and/or GLUDy |
| 215 | 6 | 4.92469 | 0.33322 | ADHEr, HEX1, LDH_D, PGDH, PPS, THD2 and/or GLUDy |
| 216 | 6 | 4.8531 | 0.05616 | ADHEr, LDH_D, MDH, PGI, PPCK, THD2 and/or GLUDy |
| 217 | 6 | 4.8531 | 0.05616 | ADHEr, FUM, LDH_D, PGI, PPCK, THD2 and/or GLUDy |
| 218 | 6 | 4.80931 | 0.34014 | ADHEr, HEX1, LDH_D, PPS, TAL, THD2 and/or GLUDy |
| 219 | 6 | 4.69982 | 0.3467 | ADHEr, HEX1, LDH_D, PPS, RPE, THD2 and/or GLUDy |
| 220 | 6 | 4.69121 | 0.11806 | ACKr and/or PTAr, ADHEr, FUM, HEX1, LDH_D, THD2 and/or GLUDy |
| 221 | 6 | 4.64152 | 0.13706 | ADHEr, FUM, GLCpts, LDH_D, PPCK, THD2 and/or GLUDy |
| 222 | 6 | 4.64152 | 0.13706 | ADHEr, GLCpts, LDH_D, MDH, PPCK, THD2 and/or GLUDy |
| 223 | 6 | 4.6299 | 0.1415 | ADHEr, LDH_D, MDH, PPCK, PYK, THD2 and/or GLUDy |
| 224 | 6 | 4.6299 | 0.1415 | ADHEr, FUM, LDH_D, PPCK, PYK, THD2 and/or GLUDy |
| 225 | 6 | 4.60999 | 0.16834 | ADHEr, LDH_D, MDH, PPCK, RPE, THD2 and/or GLUDy |
| 226 | 6 | 4.60999 | 0.16834 | ADHEr, FUM, LDH_D, PPCK, RPE, THD2 and/or GLUDy |
| 227 | 6 | 4.52953 | 0.20307 | ADHEr, GLCpts, LDH_D, MDH, RPE, THD2 and/or GLUDy |
| 228 | 6 | 4.5125 | 0.21043 | ADHEr, LDH_D, MDH, PYK, RPE, THD2 and/or GLUDy |
| 229 | 6 | 4.50129 | 0.21526 | ADHEr, GLCpts, LDH_D, MDH, PPCK, RPE |
| 230 | 6 | 4.50129 | 0.21526 | ADHEr, FUM, GLCpts, LDH_D, PPCK, RPE |
| 231 | 6 | 4.49048 | 0.21993 | ADHEr, GLCpts, LDH_D, PPCK, RPE, THD2 and/or GLUDy |
| 232 | 6 | 4.48211 | 0.22354 | ADHEr, FUM, LDH_D, PPCK, PYK, RPE |
| 233 | 6 | 4.48211 | 0.22354 | ADHEr, LDH_D, MDH, PPCK, PYK, RPE |
| 234 | 6 | 4.42882 | 0.24654 | ADHEr, FUM, GLCpts, LDH_D, RPE, THD2 and/or GLUDy |
| 235 | 6 | 4.36373 | 0.24327 | ADHEr, FUM, GLUDy, HEX1, LDH_D, THD2 and/or GLUDy |
| 236 | 6 | 4.35757 | 0.26123 | ADHEr, FUM, HEX1, LDH_D, TAL, THD2 and/or GLUDy |
| 237 | 6 | 4.31718 | 0.27765 | ADHEr, ASNS2, GLU5K, LDH_D, PPCK, TAL |
| 238 | 6 | 4.31718 | 0.27765 | ADHEr, ASNS2, G5SD, LDH_D, PPCK, TAL |
| 239 | 6 | 4.2573 | 0.32058 | ADHEr, FUM, HEX1, LDH_D, RPE, THD2 and/or GLUDy |
| 240 | 6 | 4.22017 | 0.33524 | ADHEr, GLUDy, HEX1, LDH_D, RPE, THD2 and/or GLUDy |
| 241 | 6 | 4.17617 | 0.33499 | ADHEr, GLUDy, HEX1, LDH_D, TAL, THD2 and/or GLUDy |
| 242 | 6 | 4.12454 | 0.33472 | ADHEr, GLUDy, HEX1, LDH_D, PGDH, THD2 and/or GLUDy |
| 243 | 6 | 4.12454 | 0.33472 | ADHEr, GLUDy, HEX1, LDH_D, PGL and/or G6PDHy, THD2 and/or GLUDy |
| 244 | 6 | 3.51205 | 0.21436 | ADHEr, LDH_D, PFLi, PGI, PPS, THD2 and/or GLUDy |
| 245 | 6 | 3.23372 | 0.26787 | ACKr and/or PTAr, ADHEr, ATPS4r, FUM, LDH_D, THD2 and/or GLUDy |
| 246 | 6 | 2.95584 | 0.24016 | ADHEr, FUM, LDH_D, PFLi, PGI, PPS |
| 247 | 6 | 2.95584 | 0.24016 | ADHEr, LDH_D, MDH, PFLi, PGI, PPS |
| 248 | 7 | 9.10608 | 0.01953 | ADHEr, GLUDy, LDH_D, MDH, PFLi, PPCK, THD2 and/or GLUDy |
| 249 | 7 | 9.10608 | 0.01953 | ADHEr, FUM, GLUDy, LDH_D, PFLi, PPCK, THD2 and/or GLUDy |
| 250 | 7 | 9.00855 | 0.03482 | ADHEr, GLUDy, LDH_D, MDH, NADH6, PFLi, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 251 | 7 | 8.9957 | 0.03683 | ADHEr, FUM, LDH_D, NADH6, PFLi, PPCK, THD2 and/or GLUDy |
| 252 | 7 | 8.9957 | 0.03683 | ADHEr, LDH_D, MDH, NADH6, PFLi, PPCK, THD2 and/or GLUDy |
| 253 | 7 | 8.98751 | 0.03811 | ADHEr, ATPS4r, HEX1, LDH_D, PFLi, PGI, THD2 and/or GLUDy |
| 254 | 7 | 8.98549 | 0.03843 | ADHEr, LDH_D, MDH, NADH12, NADH6, PFLi, THD2 and/or GLUDy |
| 255 | 7 | 8.78817 | 0.06934 | ADHEr, ATPS4r, GLUDy, LDH_D, MDH, PFLi, THD2 and/or GLUDy |
| 256 | 7 | 8.78695 | 0.06953 | ADHEr, ATPS4r, LDH_D, MDH, NADH6, PGDH, THD2 and/or GLUDy |
| 257 | 7 | 8.78371 | 0.07004 | ADHEr, ATPS4r, LDH_D, MDH, NADH6, TAL, THD2 and/or GLUDy |
| 258 | 7 | 8.78071 | 0.07051 | ADHEr, ATPS4r, LDH_D, MDH, NADH6, RPE, THD2 and/or GLUDy |
| 259 | 7 | 8.7615 | 0.07352 | ADHEr, ATPS4r, LDH_D, MDH, PFLi, PPCK, THD2 and/or GLUDy |
| 260 | 7 | 8.7615 | 0.07352 | ADHEr, ATPS4r, FUM, LDH_D, PFLi, PPCK, THD2 and/or GLUDy |
| 261 | 7 | 8.5647 | 0.10435 | ADHEr, GLUDy, HEX1, LDH_D, MDH, PFLi, THD2 and/or GLUDy |
| 262 | 7 | 8.54703 | 0.10712 | ADHEr, GLCpts, GLUDy, LDH_D, MDH, PFLi, THD2 and/or GLUDy |
| 263 | 7 | 8.53424 | 0.10913 | ADHEr, HEX1, LDH_D, MDH, PFLi, PPCK, THD2 and/or GLUDy |
| 264 | 7 | 8.53424 | 0.10913 | ADHEr, FUM, HEX1, LDH_D, PFLi, PPCK, THD2 and/or GLUDy |
| 265 | 7 | 8.50919 | 0.10634 | ACKr and/or PTAr, ADHEr, LDH_D, MDH, NADH12, NADH6, THD2 and/or GLUDy |
| 266 | 7 | 8.50798 | 0.11324 | ADHEr, FUM, GLCpts, LDH_D, PFLi, PPCK, THD2 and/or GLUDy |
| 267 | 7 | 8.50798 | 0.11324 | ADHEr, GLCpts, LDH_D, MDH, PFLi, PPCK, THD2 and/or GLUDy |
| 268 | 7 | 8.43629 | 0.12447 | ADHEr, HEX1, LDH_D, MDH, NADH6, PFLi, THD2 and/or GLUDy |
| 269 | 7 | 8.38405 | 0.13266 | ADHEr, GLCpts, LDH_D, MDH, NADH6, PFLi, THD2 and/or GLUDy |
| 270 | 7 | 8.37888 | 0.03978 | ADHEr, LDH_D, NADH12, NADH6, PFLi, PPCK, THD2 and/or GLUDy |
| 271 | 7 | 8.29239 | 0.14702 | ADHEr, ATPS4r, HEX1, LDH_D, MDH, PFLi, THD2 and/or GLUDy |
| 272 | 7 | 8.27109 | 0.10802 | ADHEr, ATPS4r, GLUDy, LDH_D, MDH, NADH6, THD2 and/or GLUDy |
| 273 | 7 | 8.25238 | 0.15328 | ADHEr, ATPS4r, LDH_D, MDH, NADH12, PFLi, THD2 and/or GLUDy |
| 274 | 7 | 8.24277 | 0.01559 | ACKr and/or PTAr, ADHEr, ATPS4r, LDH_D, NADH6, PGI, THD2 and/or GLUDy |
| 275 | 7 | 8.13676 | 0.03579 | ADHEr, ATPS4r, GLCpts, LDH_D, MDH, NADH6, THD2 and/or GLUDy |
| 276 | 7 | 8.112 | 0.11376 | ADHEr, ATPS4r, FUM, LDH_D, NADH6, PPCK, THD2 and/or GLUDy |
| 277 | 7 | 8.112 | 0.11376 | ADHEr, ATPS4r, LDH_D, MDH, NADH6, PPCK, THD2 and/or GLUDy |
| 278 | 7 | 8.02815 | 0.13154 | ADHEr, ATPS4r, GLCpts, LDH_D, MDH, PFLi, THD2 and/or GLUDy |
| 279 | 7 | 8.00984 | 0.13929 | ADHEr, ATPS4r, LDH_D, NADH12, PFLi, PPCK, THD2 and/or GLUDy |
| 280 | 7 | 8.0064 | 0.13951 | ADHEr, ATPS4r, FUM, GLCpts, LDH_D, PFLi, PPCK |
| 281 | 7 | 8.0064 | 0.13951 | ADHEr, ATPS4r, GLCpts, LDH_D, MDH, PFLi, PPCK |
| 282 | 7 | 7.98007 | 0.18432 | ADHEr, HEX1, LDH_D, MDH, NADH12, NADH6, THD2 and/or GLUDy |
| 283 | 7 | 7.97463 | 0.15783 | ADHEr, ATPS4r, EDA and/or PGDHY, LDH_D, MDH, NADH6, THD2 and/or GLUDy |
| 284 | 7 | 7.90344 | 0.19562 | ADHEr, GLCpts, LDH_D, MDH, NADH12, NADH6, THD2 and/or GLUDy |
| 285 | 7 | 7.89808 | 0.01471 | ADHEr, ASPT, GLCpts, LDH_D, MDH, PGI, THD2 and/or GLUDy |
| 286 | 7 | 7.89024 | 0.02802 | ADHEr, ATPS4r, LDH_D, PFLi, PGI, PPCK, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 287 | 7 | 7.88378 | 0.02967 | ADHEr, ATPS4r, LDH_D, MDH, PFLi, PGI, THD2 and/or GLUDy |
| 288 | 7 | 7.88242 | 0.11605 | ADHEr, GLUDy, LDH_D, MDH, NADH12, NADH6, THD2 and/or GLUDy |
| 289 | 7 | 7.87634 | 0.01837 | ADHEr, ASPT, LDH_D, MDH, NADH6, PGL and/or G6PDHy, PYK |
| 290 | 7 | 7.87634 | 0.01837 | ADHEr, ASPT, EDA and/or PGDHY, LDH_D, MDH, NADH6, PYK |
| 291 | 7 | 7.84906 | 0.21647 | ADHEr, ATPS4r, HEX1, LDH_D, NADH12, PFLi, THD2 and/or GLUDy |
| 292 | 7 | 7.84582 | 0.02225 | ACKr and/or PTAr, ADHEr, ASPT, LDH_D, MDH, PPCK, THD2 and/or GLUDy |
| 293 | 7 | 7.81872 | 0.2081 | ADHEr, ATPS4r, EDA and/or PGDHY, LDH_D, MDH, NADH6, PPS |
| 294 | 7 | 7.7627 | 0.0571 | ADHEr, LDH_D, MDH, PFLi, PPCK, PYK, THD2 and/or GLUDy |
| 295 | 7 | 7.7627 | 0.0571 | ADHEr, FUM, LDH_D, PFLi, PPCK, PYK, THD2 and/or GLUDy |
| 296 | 7 | 7.76232 | 0.02662 | ADHEr, ATPS4r, LDH_D, NADH6, PGI, PPCK, THD2 and/or GLUDy |
| 297 | 7 | 7.74907 | 0.0281 | ADHEr, ATPS4r, FUM, LDH_D, NADH6, PGI, THD2 and/or GLUDy |
| 298 | 7 | 7.74444 | 0.06699 | ACKr and/or PTAr, ADHEr, ATPS4r, GLCpts, LDH_D, MDH, NADH6 |
| 299 | 7 | 7.71368 | 0.10674 | ADHEr, GLCpts, LDH_D, NADH6, PFLi, PPCK, THD2 and/or GLUDy |
| 300 | 7 | 7.69617 | 0.04384 | ACKr and/or PTAr, ADHEr, ASPT, GLCpts, LDH_D, MDH, THD2 and/or GLUDy |
| 301 | 7 | 7.69209 | 0.0741 | ADHEr, LDH_D, MDH, NADH6, PFLi, PYK, THD2 and/or GLUDy |
| 302 | 7 | 7.61698 | 0.05527 | ADHEr, ASPT, LDH_D, MDH, PPCK, PYK, THD2 and/or GLUDy |
| 303 | 7 | 7.58851 | 0.09902 | ADHEr, FUM, HEX1, LDH_D, NADH6, PFLi, THD2 and/or GLUDy |
| 304 | 7 | 7.55893 | 0.07788 | ACKr and/or PTAr, ADHEr, GLUDy, LDH_D, MDH, RPE, THD2 and/or GLUDy |
| 305 | 7 | 7.55773 | 0.07778 | ACKr and/or PTAr, ADHEr, GLUDy, LDH_D, MDH, TAL, THD2 and/or GLUDy |
| 306 | 7 | 7.55641 | 0.07767 | ACKr and/or PTAr, ADHEr, GLUDy, LDH_D, MDH, PGDH, THD2 and/or GLUDy |
| 307 | 7 | 7.55604 | 0.07774 | ADHEr, GLUDy, LDH_D, MDH, NADH6, PPCK, THD2 and/or GLUDy |
| 308 | 7 | 7.52827 | 0.18666 | ADHEr, ATPS4r, FUM, HEX1, LDH_D, NADH6, PPS |
| 309 | 7 | 7.5043 | 0.12303 | ACKr and/or PTAr, ADHEr, HEX1, LDH_D, MDH, PGDH, THD2 and/or GLUDy |
| 310 | 7 | 7.50321 | 0.07168 | ACKr and/or PTAr, ADHEr, ASPT, GLUDy, LDH_D, MDH, THD2 and/or GLUDy |
| 311 | 7 | 7.50183 | 0.1239 | ACKr and/or PTAr, ADHEr, HEX1, LDH_D, MDH, TAL, THD2 and/or GLUDy |
| 312 | 7 | 7.49954 | 0.12472 | ACKr and/or PTAr, ADHEr, HEX1, LDH_D, MDH, RPE, THD2 and/or GLUDy |
| 313 | 7 | 7.44132 | 0.08061 | ADHEr, ASPT, LDH_D, MDH, NADH6, PPCK, THD2 and/or GLUDy |
| 314 | 7 | 7.43036 | 0.11712 | ADHEr, EDA and/or PGDHY, GLUDy, LDH_D, MDH, PPCK, THD2 and/or GLUDy |
| 315 | 7 | 7.38132 | 0.14888 | ADHEr, LDH_D, NADH12, NADH6, PFLi, PRO1z, THD2 and/or GLUDy |
| 316 | 7 | 7.37291 | 0.17014 | ACKr and/or PTAr, ADHEr, ATPS4r, FUM, HEX1, LDH_D, THD2 and/or GLUDy |
| 317 | 7 | 7.37059 | 0.09082 | ADHEr, ASPT, GLCpts, LDH_D, MDH, PPCK, THD2 and/or GLUDy |
| 318 | 7 | 7.3166 | 0.16445 | ADHEr, HEX1, LDH_D, NADH12, NADH6, PFLi, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 319 | 7 | 7.2905 | 0.10237 | ADHEr, ASPT, GLCpts, LDH_D, MDH, NADH6, THD2 and/or GLUDy |
| 320 | 7 | 7.24864 | 0.17893 | ADHEr, ATPS4r, EDA and/or PGDHY, LDH_D, MDH, PGDH, THD2 and/or GLUDy |
| 321 | 7 | 7.2288 | 0.11128 | ADHEr, ASPT, GLUDy, LDH_D, MDH, PPCK, THD2 and/or GLUDy |
| 322 | 7 | 7.22725 | 0.1115 | ADHEr, ASPT, LDH_D, MDH, NADH12, NADH6, THD2 and/or GLUDy |
| 323 | 7 | 7.21589 | 0.1796 | ADHEr, ATPS4r, EDA and/or PGDHY, LDH_D, MDH, TAL, THD2 and/or GLUDy |
| 324 | 7 | 7.21263 | 0.18991 | ADHEr, ATPS4r, EDA and/or PGDHY, LDH_D, MDH, PPCK, TAL |
| 325 | 7 | 7.20753 | 0.1999 | ADHEr, GLUDy, LDH_D, PFLi, PPCK, RPE, THD2 and/or GLUDy |
| 326 | 7 | 7.20507 | 0.13919 | ADHEr, FUM, HEX1, LDH_D, PGDH, PPS, THD2 and/or GLUDy |
| 327 | 7 | 7.20507 | 0.13919 | ADHEr, FUM, HEX1, LDH_D, PGL and/or G6PDHy, PPS, THD2 and/or GLUDy |
| 328 | 7 | 7.20053 | 0.0557 | ADHEr, ATPS4r, FUM, GLCpts, LDH_D, PPCK, THD2 and/or GLUDy |
| 329 | 7 | 7.20053 | 0.0557 | ADHEr, ATPS4r, GLCpts, LDH_D, MDH, PPCK, THD2 and/or GLUDy |
| 330 | 7 | 7.19596 | 0.14141 | ADHEr, FUM, HEX1, LDH_D, PPS, TAL, THD2 and/or GLUDy |
| 331 | 7 | 7.19261 | 0.19908 | ADHEr, GLUDy, LDH_D, PFLi, PPCK, TAL, THD2 and/or GLUDy |
| 332 | 7 | 7.18739 | 0.14349 | ADHEr, FUM, HEX1, LDH_D, PPS, RPE, THD2 and/or GLUDy |
| 333 | 7 | 7.18582 | 0.18022 | ADHEr, ATPS4r, EDA and/or PGDHY, LDH_D, MDH, RPE, THD2 and/or GLUDy |
| 334 | 7 | 7.18081 | 0.1906 | ADHEr, ATPS4r, EDA and/or PGDHY, LDH_D, MDH, PPCK, RPE |
| 335 | 7 | 7.17639 | 0.19819 | ADHEr, GLUDy, LDH_D, PFLi, PGDH, PPCK, THD2 and/or GLUDy |
| 336 | 7 | 7.17639 | 0.19819 | ADHEr, GLUDy, LDH_D, PFLi, PGL and/or G6PDHy, PPCK, THD2 and/or GLUDy |
| 337 | 7 | 7.15844 | 0.21228 | ADHEr, FUM, GLU5K, LDH_D, PFLi, RPE, THD2 and/or GLUDy |
| 338 | 7 | 7.15844 | 0.21228 | ADHEr, FUM, G5SD, LDH_D, PFLi, RPE, THD2 and/or GLUDy |
| 339 | 7 | 7.15832 | 0.21231 | ADHEr, ASNS2, FUM, LDH_D, PFLi, RPE, THD2 and/or GLUDy |
| 340 | 7 | 7.15023 | 0.12261 | ADHEr, ASPT, GLUDy, LDH_D, MDH, NADH6, THD2 and/or GLUDy |
| 341 | 7 | 7.14754 | 0.30973 | ADHEr, GLUDy, HEX1, LDH_D, PFLi, PPS, THD2 and/or GLUDy |
| 342 | 7 | 7.12499 | 0.05298 | ACKr and/or PTAr, ADHEr, ATPS4r, LDH_D, MDH, PPCK, THD2 and/or GLUDy |
| 343 | 7 | 7.12287 | 0.13074 | ADHEr, ASPT, GLCpts, GLUDy, LDH_D, MDH, THD2 and/or GLUDy |
| 344 | 7 | 7.12019 | 0.22193 | ADHEr, LDH_D, NADH12, NADH6, PFLi, RPE, THD2 and/or GLUDy |
| 345 | 7 | 7.11351 | 0.16642 | ACKr and/or PTAr, ADHEr, ATPS4r, HEX1, LDH_D, MDH, THD2 and/or GLUDy |
| 346 | 7 | 6.91657 | 0.2887 | ADHEr, ATPS4r, HEX1, LDH_D, MDH, PGDH, PPS |
| 347 | 7 | 6.89939 | 0.23701 | ADHEr, ATPS4r, FUM, LDH_D, MDH, PGL and/or G6PDHy, PPS |
| 348 | 7 | 6.89939 | 0.23701 | ADHEr, ATPS4r, LDH_D, MALS, MDH, PGL and/or G6PDHy, PPS |
| 349 | 7 | 6.89939 | 0.23701 | ADHEr, ATPS4r, ICL, LDH_D, MDH, PGL and/or G6PDHy, PPS |
| 350 | 7 | 6.84379 | 0.18963 | ADHEr, ATPS4r, EDA and/or PGDHY, GLUDy, LDH_D, MDH, THD2 and/or GLUDy |
| 351 | 7 | 6.75658 | 0.30629 | ADHEr, ATPS4r, FUM, HEX1, LDH_D, PPS, RPE |
| 352 | 7 | 6.62545 | 0.08375 | ACKr and/or PTAr, ADHEr, ATPS4r, GLUDy, LDH_D, MDH, THD2 and/or GLUDy |
| 353 | 7 | 6.61503 | 0.30219 | ADHEr, ATPS4r, FUM, HEX1, LDH_D, PPS, TAL |
| 354 | 7 | 6.5251 | 0.02706 | ACKr and/or PTAr, ADHEr, GLCpts, LDH_D, NADH6, PPCK, THD2 and/or GLUDy |
| 355 | 7 | 6.50064 | 0.04761 | ADHEr, GLCpts, LDH_D, NADH6, PGI, PPCK, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 356 | 7 | 6.49117 | 0.05032 | ADHEr, FUM, GLCpts, LDH_D, NADH6, PGI, THD2 and/or GLUDy |
| 357 | 7 | 6.49117 | 0.05032 | ADHEr, GLCpts, LDH_D, MDH, NADH6, PGI, THD2 and/or GLUDy |
| 358 | 7 | 6.46411 | 0.29781 | ADHEr, ATPS4r, FUM, HEX1, LDH_D, PGL and/or G6PDHy, PPS |
| 359 | 7 | 6.46411 | 0.29781 | ADHEr, ATPS4r, FUM, HEX1, LDH_D, PGDH, PPS |
| 360 | 7 | 6.37646 | 0.08322 | ADHEr, FUM, LDH_D, NADH12, NADH6, PPCK, THD2 and/or GLUDy |
| 361 | 7 | 6.37646 | 0.08322 | ADHEr, LDH_D, MDH, NADH12, NADH6, PPCK, THD2 and/or GLUDy |
| 362 | 7 | 6.33505 | 0.15513 | ADHEr, ATPS4r, FUM, LDH_D, NADH6, PGDH, PGI |
| 363 | 7 | 6.30836 | 0.31643 | ADHEr, HEX1, LDH_D, MALS, PGL and/or G6PDHy, PPS, THD2 and/or GLUDy |
| 364 | 7 | 6.30836 | 0.31643 | ADHEr, HEX1, ICL, LDH_D, PGL and/or G6PDHy, PPS, THD2 and/or GLUDy |
| 365 | 7 | 6.30836 | 0.31643 | ADHEr, HEX1, LDH_D, MALS, PGDH, PPS, THD2 and/or GLUDy |
| 366 | 7 | 6.30836 | 0.31643 | ADHEr, HEX1, ICL, LDH_D, PGDH, PPS, THD2 and/or GLUDy |
| 367 | 7 | 6.29139 | 0.03885 | ACKr and/or PTAr, ADHEr, ATPS4r, FUM, LDH_D, PPCK, THD2 and/or GLUDy |
| 368 | 7 | 6.27848 | 0.32143 | ADHEr, HEX1, LDH_D, NADH12, NADH6, PPS, THD2 and/or GLUDy |
| 369 | 7 | 6.27504 | 0.1561 | ADHEr, ATPS4r, FUM, LDH_D, NADH6, PGI, TAL |
| 370 | 7 | 6.19234 | 0.13601 | ADHEr, EDA and/or PGDHY, LDH_D, MDH, NADH6, PYK, THD2 and/or GLUDy |
| 371 | 7 | 6.19234 | 0.13601 | ADHEr, LDH_D, MDH, NADH6, PGL and/or G6PDHy, PYK, THD2 and/or GLUDy |
| 372 | 7 | 6.18835 | 0.15484 | ADHEr, LDH_D, MDH, NADH6, PYK, RPE, THD2 and/or GLUDy |
| 373 | 7 | 6.16073 | 0.14508 | ADHEr, EDA and/or PGDHY, LDH_D, MDH, NADH6, PPCK, PYK |
| 374 | 7 | 6.16073 | 0.14508 | ADHEr, LDH_D, MDH, NADH6, PGL and/or G6PDHy, PPCK, PYK |
| 375 | 7 | 6.15763 | 0.16479 | ADHEr, FUM, LDH_D, NADH6, PPCK, PYK, RPE |
| 376 | 7 | 6.15763 | 0.16479 | ADHEr, LDH_D, MDH, NADH6, PPCK, PYK, RPE |
| 377 | 7 | 6.14691 | 0.14904 | ADHEr, GLCpts, LDH_D, MDH, NADH12, NADH6, PPCK |
| 378 | 7 | 6.14691 | 0.14904 | ADHEr, FUM, GLCpts, LDH_D, NADH12, NADH6, PPCK |
| 379 | 7 | 6.14046 | 0.17035 | ADHEr, GLCpts, LDH_D, NADH6, PPCK, RPE, THD2 and/or GLUDy |
| 380 | 7 | 6.13285 | 0.17281 | ADHEr, LDH_D, MDH, NADH12, NADH6, RPE, THD2 and/or GLUDy |
| 381 | 7 | 6.09969 | 0.18355 | ADHEr, FUM, LDH_D, NADH12, NADH6, PPCK, RPE |
| 382 | 7 | 6.09969 | 0.18355 | ADHEr, LDH_D, MDH, NADH12, NADH6, PPCK, RPE |
| 383 | 7 | 6.07495 | 0.19156 | ADHEr, FUM, GLCpts, LDH_D, NADH6, RPE, THD2 and/or GLUDy |
| 384 | 7 | 6.02503 | 0.20772 | ADHEr, FUM, LDH_D, NADH12, NADH6, RPE, THD2 and/or GLUDy |
| 385 | 7 | 5.9952 | 0.19254 | ADHEr, FUM, HEX1, LDH_D, NADH12, NADH6, THD2 and/or GLUDy |
| 386 | 7 | 5.9868 | 0.32178 | ADHEr, ATPS4r, HEX1, LDH_D, NADH6, PPS, THD2 and/or GLUDy |
| 387 | 7 | 5.98012 | 0.20938 | ADHEr, FUM, LDH_D, NADH12, NADH6, TAL, THD2 and/or GLUDy |
| 388 | 7 | 5.94711 | 0.3261 | ADHEr, HEX1, ICL, LDH_D, PPS, TAL, THD2 and/or GLUDy |
| 389 | 7 | 5.94711 | 0.3261 | ADHEr, HEX1, LDH_D, MALS, PPS, TAL, THD2 and/or GLUDy |
| 390 | 7 | 5.93766 | 0.22464 | ACKr and/or PTAr, ADHEr, ATPS4r, HEX1, LDH_D, NADH12, THD2 and/or GLUDy |
| 391 | 7 | 5.84213 | 0.21172 | ACKr and/or PTAr, ADHEr, HEX1, LDH_D, NADH12, NADH6, THD2 and/or GLUDy |
| 392 | 7 | 5.77732 | 0.09217 | ACKr and/or PTAr, ADHEr, ATPS4r, LDH_D, PGDH, PPCK, THD2 and/or GLUDy |
| 393 | 7 | 5.77732 | 0.09217 | ACKr and/or PTAr, ADHEr, ATPS4r, LDH_D, PGL and/or G6PDHy, PPCK, THD2 and/or GLUDy |
| 394 | 7 | 5.7407 | 0.18622 | ACKr and/or PTAr, ADHEr, GLUDy, HEX1, LDH_D, NADH6, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 395 | 7 | 5.72608 | 0.09261 | ACKr and/or PTAr, ADHEr, ATPS4r, LDH_D, PPCK, TAL, THD2 and/or GLUDy |
| 396 | 7 | 5.67891 | 0.09302 | ACKr and/or PTAr, ADHEr, ATPS4r, LDH_D, PPCK, RPE, THD2 and/or GLUDy |
| 397 | 7 | 5.62569 | 0.20722 | ACKr and/or PTAr, ADHEr, HEX1, LDH_D, NADH6, TAL, THD2 and/or GLUDy |
| 398 | 7 | 5.60804 | 0.32285 | ADHEr, GLU5K, HEX1, LDH_D, NADH6, TAL, THD2 and/or GLUDy |
| 399 | 7 | 5.60804 | 0.32285 | ADHEr, G5SD, HEX1, LDH_D, NADH6, TAL, THD2 and/or GLUDy |
| 400 | 7 | 5.60791 | 0.32289 | ADHEr, ASNS2, HEX1, LDH_D, NADH6, TAL, THD2 and/or GLUDy |
| 401 | 7 | 5.59783 | 0.33545 | ADHEr, HEX1, ICL, LDH_D, PPS, RPE, THD2 and/or GLUDy |
| 402 | 7 | 5.59783 | 0.33545 | ADHEr, HEX1, LDH_D, MALS, PPS, RPE, THD2 and/or GLUDy |
| 403 | 7 | 5.58104 | 0.23062 | ACKr and/or PTAr, ADHEr, ATPS4r, HEX1, LDH_D, PGL and/or G6PDHy, THD2 and/or GLUDy |
| 404 | 7 | 5.58104 | 0.23062 | ACKr and/or PTAr, ADHEr, ATPS4r, HEX1, LDH_D, PGDH, THD2 and/or GLUDy |
| 405 | 7 | 5.35846 | 0.23124 | ACKr and/or PTAr, ADHEr, ATPS4r, HEX1, LDH_D, TAL, THD2 and/or GLUDy |
| 406 | 7 | 5.27565 | 0.07793 | ADHEr, EDA and/or PGDHY, LDH_D, MDH, PPCK, PYK, THD2 and/or GLUDy |
| 407 | 7 | 5.19178 | 0.1965 | ADHEr, FUM, LDH_D, PFLi, PGDH, PGI, TAL |
| 408 | 7 | 5.19178 | 0.1965 | ADHEr, LDH_D, MDH, PFLi, PGDH, PGI, TAL |
| 409 | 7 | 5.16412 | 0.3061 | ADHEr, HEX1, LDH_D, PGL and/or G6PDHy, PPS, TAL, THD2 and/or GLUDy |
| 410 | 7 | 5.16412 | 0.3061 | ADHEr, HEX1, LDH_D, PGDH, PPS, TAL, THD2 and/or GLUDy |
| 411 | 7 | 5.15646 | 0.16031 | ADHEr, ATPS4r, LDH_D, PFLi, PGDH, PGI, TAL |
| 412 | 7 | 5.14711 | 0.23182 | ACKr and/or PTAr, ADHEr, ATPS4r, HEX1, LDH_D, RPE, THD2 and/or GLUDy |
| 413 | 7 | 5.06593 | 0.18784 | ADHEr, LDH_D, PFLi, PGDH, PGI, PPS, THD2 and/or GLUDy |
| 414 | 7 | 5.06354 | 0.16677 | ADHEr, ATPS4r, GLYCL, LDH_D, PFLi, PGDH, PGI |
| 415 | 7 | 5.04267 | 0.18882 | ADHEr, LDH_D, PFLi, PGI, PPS, TAL, THD2 and/or GLUDy |
| 416 | 7 | 5.02125 | 0.18972 | ADHEr, LDH_D, PFLi, PGI, PPS, RPE, THD2 and/or GLUDy |
| 417 | 7 | 4.56087 | 0.18955 | ACKr and/or PTAr, ADHEr, FUM, HEX1, LDH_D, RPE, THD2 and/or GLUDy |
| 418 | 7 | 4.53442 | 0.18932 | ACKr and/or PTAr, ADHEr, FUM, HEX1, LDH_D, TAL, THD2 and/or GLUDy |
| 419 | 7 | 4.50549 | 0.18907 | ACKr and/or PTAr, ADHEr, FUM, HEX1, LDH_D, PGL and/or G6PDHy, THD2 and/or GLUDy |
| 420 | 7 | 4.50549 | 0.18907 | ACKr and/or PTAr, ADHEr, FUM, HEX1, LDH_D, PGDH, THD2 and/or GLUDy |
| 421 | 7 | 4.43945 | 0.24195 | ADHEr, FUM, GLUDy, HEX1, LDH_D, RPE, THD2 and/or GLUDy |
| 422 | 7 | 4.33649 | 0.2698 | ADHEr, ASNS2, FUM, G5SD, LDH_D, TAL, THD2 and/or GLUDy |
| 423 | 7 | 4.33649 | 0.2698 | ADHEr, ASNS2, FUM, GLU5K, LDH_D, TAL, THD2 and/or GLUDy |
| 424 | 7 | 3.82299 | 0.23376 | ACKr and/or PTAr, ADHEr, CITL, HEX1, LDH_D, PPS, THD2 and/or GLUDy |
| 425 | 7 | 3.40957 | 0.10927 | ADHEr, FRD and/or SUCD4, LDH_D, PGDH, PPS, TAL, THD2 and/or GLUDy |
| 426 | 7 | 3.40957 | 0.10927 | ADHEr, FRD and/or SUCD4, LDH_D, PGL and/or G6PDHy, PPS, TAL, THD2 and/or GLUDy |
| 427 | 7 | 3.30702 | 0.26731 | ACKr and/or PTAr, ADHEr, ATPS4r, FUM, LDH_D, TAL, THD2 and/or GLUDy |
| 428 | 7 | 1.7546 | 0.28013 | ACKr and/or PTAr, ADHEr, CITL, FUM, LDH_D, PPS, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 429 | 7 | 0.1401 | 0.25687 | ACKr and/or PTAr, ADHEr, GLCpts, LDH_D, MDH, RPE, SUCOAS |
| 430 | 7 | 0.13962 | 0.25599 | ACKr and/or PTAr, ADHEr, GLCpts, LDH_D, MDH, SUCOAS, TAL |
| 431 | 7 | 0.13909 | 0.25503 | ACKr and/or PTAr, ADHEr, GLCpts, LDH_D, MDH, PGDH, SUCOAS |
| 432 | 7 | 0.13909 | 0.25503 | ACKr and/or PTAr, ADHEr, GLCpts, LDH_D, MDH, PGL and/or G6PDHy, SUCOAS |
| 433 | 3 | 0.331362284 | 0.248770484 | ADHEr, LDH_D, PFK and/or FBA and/or TPI |
| 434 | 3 | 4.1886916 | 0.310192487 | ADHEr, FRD and/or SUCD4, LDH_D |
| 435 | 4 | 2.773932742 | 0.386261 | ADHEr, ASNS2, ATPS4r, LDH_D |
| 436 | 4 | 2.792658751 | 0.384018912 | ADHEr, ATPS4r, CBMK2, LDH_D |
| 437 | 4 | 5.490131382 | 0.33737393 | ADHEr, CBMK2, LDH_D, NADH6 |
| 438 | 4 | 6.078666008 | 0.168610416 | ADHEr, LDH_D, NADH6, PFK and/or FBA and/or TPI |
| 439 | 4 | 0.474685279 | 0.246014656 | ADHEr, LDH_D, PFK and/or FBA and/or TPI, RPE |
| 440 | 4 | 0.406720198 | 0.247321495 | ADHEr, LDH_D, PFK and/or FBA and/or TPI, TAL |
| 441 | 4 | 0.406720198 | 0.247321495 | ADHEr, LDH_D, PFK and/or FBA and/or TPI, TKT1 |
| 442 | 4 | 0.541935885 | 0.244721556 | ADHEr, LDH_D, PFK and/or FBA and/or TPI, TKT2 |
| 443 | 4 | 4.227003016 | 0.295544651 | ADHEr, FRD and/or SUCD4, FUM, LDH_D |
| 444 | 4 | 2.774411941 | 0.386203624 | ADHEr, ATPS4r, G5SD, LDH_D |
| 445 | 4 | 2.774411941 | 0.386203624 | ADHEr, ATPS4r, GLU5K, LDH_D |
| 446 | 4 | 2.552977098 | 0.152232967 | ADHEr, HEX1, LDH_D, PFK and/or FBA and/or TPI |
| 447 | 4 | 5.500068328 | 0.33452449 | ADHEr, HEX1, LDH_D, NADH6 |
| 448 | 4 | 4.226362219 | 0.295789651 | ADHEr, FRD and/or SUCD4, HEX1, LDH_D |
| 449 | 4 | 0.999358709 | 0.388175844 | ADHEr, HEX1, LDH_D, TKT1 |
| 450 | 4 | 1.300899111 | 0.38573732 | ADHEr, HEX1, LDH_D, TKT2 |
| 451 | 4 | 4.374206544 | 0.239263432 | ADHEr, FRD and/or SUCD4, LDH_D, MDH |
| 452 | 4 | 4.29486095 | 0.269600115 | ADHEr, FRD and/or SUCD4, LDH_D, ME2 |
| 453 | 4 | 4.488943189 | 0.195395474 | ADHEr, FRD and/or SUCD4, LDH_D, PPCK |
| 454 | 4 | 4.312306765 | 0.279635371 | ADHEr, LDH_D, PPCK, TAL |
| 455 | 4 | 4.312306765 | 0.279635371 | ADHEr, LDH_D, PPCK, TKT1 |
| 456 | 4 | 4.394666553 | 0.278410255 | ADHEr, LDH_D, PPCK, TKT2 |
| 457 | 4 | 4.290442023 | 0.306273023 | ADHEr, FRD and/or SUCD4, LDH_D, RPE |
| 458 | 4 | 4.242231032 | 0.308130129 | ADHEr, FRD and/or SUCD4, LDH_D, TAL |
| 459 | 4 | 3.02411229 | 0.384504476 | ADHEr, ATPS4r, LDH_D, TKT1 |
| 460 | 4 | 5.556064858 | 0.338701395 | ADHEr, LDH_D, NADH6, TKT1 |
| 461 | 4 | 4.242231032 | 0.308130129 | ADHEr, FRD and/or SUCD4, LDH_D, TKT1 |
| 462 | 4 | 3.491738883 | 0.378757536 | ADHEr, ATPS4r, LDH_D, TKT2 |
| 463 | 4 | 5.694356782 | 0.335394947 | ADHEr, LDH_D, NADH6, TKT2 |
| 464 | 4 | 4.338075359 | 0.30443817 | ADHEr, FRD and/or SUCD4, LDH_D, TKT2 |
| 465 | 5 | 3.269904021 | 0.380186443 | ADHEr, ASNS2, ATPS4r, LDH_D, RPE |
| 466 | 5 | 3.035292503 | 0.383059918 | ADHEr, ASNS2, ATPS4r, LDH_D, TAL |
| 467 | 5 | 2.786583612 | 0.384746295 | ADHEr, ASNS2, ATPS4r, GLU5K, LDH_D |
| 468 | 5 | 3.035292503 | 0.383059918 | ADHEr, ASNS2, ATPS4r, LDH_D, TKT1 |
| 469 | 5 | 4.891772757 | 0.345085032 | ADHEr, ATPS4r, LDH_D, ME2, THD2 and/or GLUDy |
| 470 | 5 | 4.906959994 | 0.170872463 | ADHEr, ATPS4r, LDH_D, PFK and/or FBA and/or TPI, PFLi |
| 471 | 5 | 2.80469336 | 0.382577993 | ADHEr, ASNS2, ATPS4r, CBMK2, LDH_D |
| 472 | 5 | 4.199370617 | 0.306109514 | ADHEr, ASNS2, CBMK2, FRD and/or SUCD4, LDH_D |
| 473 | 5 | 3.285503322 | 0.378014123 | ADHEr, ATPS4r, CBMK2, LDH_D, RPE |
| 474 | 5 | 3.052359629 | 0.380854732 | ADHEr, ATPS4r, CBMK2, LDH_D, TAL |
| 475 | 5 | 2.805163465 | 0.382521707 | ADHEr, ATPS4r, CBMK2, G5SD, LDH_D |
| 476 | 5 | 4.199487305 | 0.3060649 | ADHEr, CBMK2, FRD and/or SUCD4, G5SD, LDH_D |
| 477 | 5 | 2.805163465 | 0.382521707 | ADHEr, ATPS4r, CBMK2, GLU5K, LDH_D |
| 478 | 5 | 4.199487305 | 0.3060649 | ADHEr, CBMK2, FRD and/or SUCD4, GLU5K, LDH_D |
| 479 | 5 | 5.566341358 | 0.335567361 | ADHEr, CBMK2, LDH_D, NADH6, TAL |
| 480 | 5 | 6.853869476 | 0.27580388 | ADHEr, CBMK2, LDH_D, NADH6, PFLi |
| 481 | 5 | 3.052359629 | 0.380854732 | ADHEr, ATPS4r, CBMK2, LDH_D, TKT1 |
| 482 | 5 | 5.566341358 | 0.335567361 | ADHEr, CBMK2, LDH_D, NADH6, TKT1 |
| 483 | 5 | 3.515194954 | 0.375215574 | ADHEr, ATPS4r, CBMK2, LDH_D, TKT2 |
| 484 | 5 | 4.886253722 | 0.208900511 | ADHEr, LDH_D, MDH, PFK and/or FBA and/or TPI, PFLi |
| 485 | 5 | 4.621960711 | 0.144538077 | ADHEr, FRD and/or SUCD4, LDH_D, MDH, PFK and/or FBA and/or TPI |
| 486 | 5 | 6.151957387 | 0.166626529 | ADHEr, LDH_D, NADH6, PFK and/or FBA and/or TPI, RPE |
| 487 | 5 | 6.117214665 | 0.167566962 | ADHEr, LDH_D, NADH6, PFK and/or FBA and/or TPI, TAL |
| 488 | 5 | 0.436376298 | 0.238196669 | ADHEr, LDH_D, PFK and/or FBA and/or TPI, PGDH, TAL |
| 489 | 5 | 6.117214665 | 0.167566962 | ADHEr, LDH_D, NADH6, PFK and/or FBA and/or TPI, TKT1 |
| 490 | 5 | 0.436376298 | 0.238196669 | ADHEr, LDH_D, PFK and/or FBA and/or TPI, PGDH, TKT1 |
| 491 | 5 | 6.186312313 | 0.165696592 | ADHEr, LDH_D, NADH6, PFK and/or FBA and/or TPI, TKT2 |
| 492 | 5 | 5.556162772 | 0.318439293 | ADHEr, CBMK2, FUM, LDH_D, NADH6 |
| 493 | 5 | 4.886253722 | 0.208900511 | ADHEr, FUM, LDH_D, PFK and/or FBA and/or TPI, PFLi |
| 494 | 5 | 4.613740943 | 0.14768079 | ADHEr, FRD and/or SUCD4, FUM, LDH_D, PFK and/or FBA and/or TPI |
| 495 | 5 | 6.088195155 | 0.307660476 | ADHEr, FUM, LDH_D, ME2, THD2 and/or GLUDy |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 496 | 5 | 5.684064939 | 0.281763084 | ADHEr, FUM, LDH_D, ME2, NADH6 |
| 497 | 5 | 4.673184878 | 0.145745102 | ADHEr, FRD and/or SUCD4, FUM, LDH_D, PGI |
| 498 | 5 | 4.572772914 | 0.163344346 | ADHEr, FRD and/or SUCD4, FUM, LDH_D, PPCK |
| 499 | 5 | 4.382533025 | 0.251079405 | ADHEr, FUM, LDH_D, PPCK, TAL |
| 500 | 5 | 4.382533025 | 0.251079405 | ADHEr, FUM, LDH_D, PPCK, TKT1 |
| 501 | 5 | 4.457618973 | 0.24945663 | ADHEr, FUM, LDH_D, PPCK, TKT2 |
| 502 | 5 | 4.374206544 | 0.239263432 | ADHEr, FRD and/or SUCD4, FUM, LDH_D, ME2 |
| 503 | 5 | 4.324805294 | 0.29144049 | ADHEr, FRD and/or SUCD4, FUM, LDH_D, RPE |
| 504 | 5 | 4.278495915 | 0.29338381 | ADHEr, FRD and/or SUCD4, FUM, LDH_D, TAL |
| 505 | 5 | 5.619129051 | 0.319468644 | ADHEr, FUM, LDH_D, NADH6, TKT1 |
| 506 | 5 | 1.418161594 | 0.362515745 | ADHEr, FUM, LDH_D, PGDH, TKT1 |
| 507 | 5 | 1.418161594 | 0.362515745 | ADHEr, FUM, LDH_D, PGL and/or G6PDHy, TKT1 |
| 508 | 5 | 4.278495915 | 0.29338381 | ADHEr, FRD and/or SUCD4, FUM, LDH_D, TKT1 |
| 509 | 5 | 5.750964716 | 0.315868237 | ADHEr, FUM, LDH_D, NADH6, TKT2 |
| 510 | 5 | 4.370505222 | 0.289522745 | ADHEr, FRD and/or SUCD4, FUM, LDH_D, TKT2 |
| 511 | 5 | 2.786583612 | 0.384746295 | ADHEr, ASNS2, ATPS4r, G5SD, LDH_D |
| 512 | 5 | 3.270303172 | 0.380130859 | ADHEr, ATPS4r, G5SD, LDH_D, RPE |
| 513 | 5 | 3.035729231 | 0.38300349 | ADHEr, ATPS4r, G5SD, LDH_D, TAL |
| 514 | 5 | 3.035729231 | 0.38300349 | ADHEr, ATPS4r, G5SD, LDH_D, TKT1 |
| 515 | 5 | 3.270303172 | 0.380130859 | ADHEr, ATPS4r, GLU5K, LDH_D, RPE |
| 516 | 5 | 3.035729231 | 0.38300349 | ADHEr, ATPS4r, GLU5K, LDH_D, TAL |
| 517 | 5 | 4.101998016 | 0.149473222 | ADHEr, ATPS4r, HEX1, LDH_D, PFK and/or FBA and/or TPI |
| 518 | 5 | 5.510369128 | 0.331570715 | ADHEr, CBMK2, HEX1, LDH_D, NADH6 |
| 519 | 5 | 3.359019108 | 0.150796918 | ADHEr, HEX1, LDH_D, MDH, PFK and/or FBA and/or TPI |
| 520 | 5 | 4.301255739 | 0.267155156 | ADHEr, FRD and/or SUCD4, FUM, HEX1, LDH_D |
| 521 | 5 | 4.146125845 | 0.347209192 | ADHEr, FUM, HEX1, LDH_D, TKT1 |
| 522 | 5 | 4.24954345 | 0.345156537 | ADHEr, FUM, HEX1, LDH_D, TKT2 |
| 523 | 5 | 5.64062493 | 0.332159859 | ADHEr, HEX1, LDH_D, NADH6, RPE |
| 524 | 5 | 5.573829893 | 0.333283574 | ADHEr, HEX1, LDH_D, NADH6, TAL |
| 525 | 5 | 6.871954799 | 0.271451843 | ADHEr, HEX1, LDH_D, NADH6, PFLi |
| 526 | 5 | 1.026318237 | 0.371585169 | ADHEr, HEX1, LDH_D, PGDH, TAL |
| 527 | 5 | 1.026318237 | 0.371585169 | ADHEr, HEX1, LDH_D, PGL and/or G6PDHy, TAL |
| 528 | 5 | 4.321580803 | 0.292832307 | ADHEr, FRD and/or SUCD4, HEX1, LDH_D, RPE |
| 529 | 5 | 4.27640137 | 0.294235511 | ADHEr, FRD and/or SUCD4, HEX1, LDH_D, TAL |
| 530 | 5 | 4.292100506 | 0.270655532 | ADHEr, FRD and/or SUCD4, HEX1, LDH_D, THD2 and/or GLUDy |
| 531 | 5 | 5.573829893 | 0.333283574 | ADHEr, HEX1, LDH_D, NADH6, TKT1 |
| 532 | 5 | 1.026318237 | 0.371585169 | ADHEr, HEX1, LDH_D, PGDH, TKT1 |
| 533 | 5 | 1.026318237 | 0.371585169 | ADHEr, HEX1, LDH_D, PGL and/or G6PDHy, TKT1 |
| 534 | 5 | 4.27640137 | 0.294235511 | ADHEr, FRD and/or SUCD4, HEX1, LDH_D, TKT1 |
| 535 | 5 | 4.093661719 | 0.368542577 | ADHEr, HEX1, LDH_D, THD2 and/or GLUDy, TKT1 |
| 536 | 5 | 5.706971061 | 0.331043695 | ADHEr, HEX1, LDH_D, NADH6, TKT2 |
| 537 | 5 | 4.366331362 | 0.291442423 | ADHEr, FRD and/or SUCD4, HEX1, LDH_D, TKT2 |
| 538 | 5 | 4.197378033 | 0.36914891 | ADHEr, HEX1, LDH_D, THD2 and/or GLUDy, TKT2 |
| 539 | 5 | 6.584217406 | 0.204283888 | ADHEr, ASPT, CBMK2, LDH_D, MDH |
| 540 | 5 | 4.679174494 | 0.143073998 | ADHEr, FRD and/or SUCD4, LDH_D, MDH, PGI |
| 541 | 5 | 4.572772914 | 0.163344346 | ADHEr, FRD and/or SUCD4, LDH_D, MDH, PPCK |
| 542 | 5 | 4.382533025 | 0.251079405 | ADHEr, LDH_D, MDH, PPCK, TAL |
| 543 | 5 | 4.382533025 | 0.251079405 | ADHEr, LDH_D, MDH, PPCK, TKT1 |
| 544 | 5 | 4.457618973 | 0.24945663 | ADHEr, LDH_D, MDH, PPCK, TKT2 |
| 545 | 5 | 4.450595421 | 0.237144547 | ADHEr, FRD and/or SUCD4, LDH_D, MDH, RPE |
| 546 | 5 | 4.414328365 | 0.238150528 | ADHEr, FRD and/or SUCD4, LDH_D, MDH, TAL |
| 547 | 5 | 6.807575806 | 0.294019202 | ADHEr, ATPS4r, LDH_D, MDH, TKT1 |
| 548 | 5 | 5.745562276 | 0.280910173 | ADHEr, LDH_D, MDH, NADH6, TKT1 |
| 549 | 5 | 4.414328365 | 0.238150528 | ADHEr, FRD and/or SUCD4, LDH_D, MDH, TKT1 |
| 550 | 5 | 6.455745341 | 0.299423269 | ADHEr, ATPS4r, LDH_D, MDH, TKT2 |
| 551 | 5 | 5.856779801 | 0.27936769 | ADHEr, LDH_D, MDH, NADH6, TKT2 |
| 552 | 5 | 4.486557371 | 0.23614703 | ADHEr, FRD and/or SUCD4, LDH_D, MDH, TKT2 |
| 553 | 5 | 6.254106519 | 0.315300181 | ADHEr, LDH_D, ME2, NADH6, THD2 and/or GLUDy |
| 554 | 5 | 4.339242812 | 0.268682419 | ADHEr, FRD and/or SUCD4, LDH_D, ME2, TAL |
| 555 | 5 | 6.224794308 | 0.229694348 | ADHEr, FRD and/or SUCD4, LDH_D, ME2, THD2 and/or GLUDy |
| 556 | 5 | 6.876353164 | 0.277060587 | ADHEr, LDH_D, NADH6, PFLi, TAL |
| 557 | 5 | 7.122630133 | 0.211129547 | ADHEr, FRD and/or SUCD4, LDH_D, ME2, PFLi |
| 558 | 5 | 4.216706856 | 0.262624991 | ADHEr, FRD and/or SUCD4, LDH_D, PFLi, THD2 and/or GLUDy |
| 559 | 5 | 5.563197905 | 0.034931763 | ADHEr, EDA and/or PGDHY, FRD and/or SUCD4, LDH_D, PGI |
| 560 | 5 | 5.66839105 | 0.263566425 | ADHEr, LDH_D, ME2, PGL and/or G6PDHy, THD2 and/or GLUDy |
| 561 | 5 | 4.552158784 | 0.193305823 | ADHEr, FRD and/or SUCD4, LDH_D, PPCK, RPE |
| 562 | 5 | 4.522175259 | 0.194296957 | ADHEr, FRD and/or SUCD4, LDH_D, PPCK, TAL |
| 563 | 5 | 5.924716044 | 0.226273464 | ADHEr, LDH_D, NADH6, PPCK, TKT1 |
| 564 | 5 | 5.265518204 | 0.241270472 | ADHEr, LDH_D, PFLi, PPCK, TKT1 |

TABLE 15-continued

Knockout strain designs for increased production of adipate, showing yields of adipate and biomass.

| New Design ID | Num KO | Adipate. Yield | Biomass | Rxnlist |
|---|---|---|---|---|
| 565 | 5 | 4.522175259 | 0.194296957 | ADHEr, FRD and/or SUCD4, LDH_D, PPCK, TKT1 |
| 566 | 5 | 6.01594542 | 0.224464061 | ADHEr, LDH_D, NADH6, PPCK, TKT2 |
| 567 | 5 | 5.456414614 | 0.240407987 | ADHEr, LDH_D, PFLi, PPCK, TKT2 |
| 568 | 5 | 4.581837961 | 0.192324751 | ADHEr, FRD and/or SUCD4, LDH_D, PPCK, TKT2 |
| 569 | 5 | 3.352437372 | 0.115790546 | ADHEr, FADH4, LDH_D, PPS, THD2 and/or GLUDy |
| 570 | 5 | 4.568751314 | 0.164881948 | ADHEr, FRD and/or SUCD4, LDH_D, PPCK, PYK |
| 571 | 5 | 4.379456454 | 0.26785091 | ADHEr, FRD and/or SUCD4, LDH_D, ME2, RPE |
| 572 | 5 | 3.035729231 | 0.38300349 | ADHEr, ATPS4r, GLU5K, LDH_D, TKT1 |
| 573 | 5 | 6.876353164 | 0.277060587 | ADHEr, LDH_D, NADH6, PFLi, TKT1 |
| 574 | 5 | 4.339242812 | 0.268682419 | ADHEr, FRD and/or SUCD4, LDH_D, ME2, TKT1 |
| 575 | 5 | 4.419421961 | 0.267024532 | ADHEr, FRD and/or SUCD4, LDH_D, ME2, TKT2 |
| 576 | 5 | 6.185324416 | 0.166037364 | ADHEr, LDH_D, NADH6, PGI, TKT2 |
| 577 | 5 | 6.936871903 | 0.274483161 | ADHEr, LDH_D, NADH6, PFLi, TKT2 |
| 578 | 6 | 7.614634412 | 0.238178822 | ADHEr, ATPS4r, CBMK2, LDH_D, MDH, NADH6 |
| 579 | 6 | 7.603679301 | 0.239793337 | ADHEr, ATPS4r, FUM, LDH_D, ME2, NADH6 |
| 580 | 6 | 7.269154045 | 0.188693079 | ADHEr, FUM, LDH_D, PFLi, PPCK, TKT2 |
| 581 | 6 | 7.539172655 | 0.163831584 | ADHEr, ASNS2, CBMK2, HEX1, LDH_D, PGI |
| 582 | 6 | 7.539312732 | 0.163809352 | ADHEr, CBMK2, G5SD, HEX1, LDH_D, PGI |
| 583 | 6 | 7.539312732 | 0.163809352 | ADHEr, CBMK2, GLU5K, HEX1, LDH_D, PGI |
| 584 | 6 | 7.497875069 | 0.097945448 | ADHEr, FRD and/or SUCD4, HEX1, LDH_D, MDH, THD2 and/or GLUDy |
| 585 | 6 | 7.316598461 | 0.164453176 | ADHEr, FRD and/or SUCD4, HEX1, LDH_D, PFLi, THD2 and/or GLUDy |
| 586 | 6 | 7.269154045 | 0.188693079 | ADHEr, LDH_D, MDH, PFLi, PPCK, TKT2 |
| 587 | 6 | 7.389036066 | 0.088156259 | ADHEr, ASPT, FRD and/or SUCD4, LDH_D, MDH, THD2 and/or GLUDy |
| 588 | 6 | 8.258765764 | 0.152284822 | ADHEr, FRD and/or SUCD4, LDH_D, ME2, PFLi, THD2 and/or GLUDy |
| 589 | 6 | 8.999143093 | 0.036289126 | ADHEr, FRD and/or SUCD4, LDH_D, PFLi, PPCK, THD2 and/or GLUDy |

TABLE 16

Knockout strain designs for increased production of HMDA, showing yields of HMDA and biomass.

| New Design ID | Num KO | HMDA. Yield | Biomass | Rxnlist |
|---|---|---|---|---|
| 1 | 3 | 2.32302 | 0.35737 | ADHEr, LDH_D, NADH6 |
| 2 | 3 | 2.12864 | 0.28397 | ADHEr, LDH_D, PPCK |
| 3 | 3 | 1.2553 | 0.38773 | ADHEr, ATPS4r, LDH_D |
| 4 | 3 | 1.11254 | 0.26898 | ADHEr, FRD and/or SUCD4, LDH_D |
| 5 | 3 | 0.67068 | 0.37924 | ADHEr, FUM, LDH_D |
| 6 | 3 | 0.57155 | 0.26988 | ADHEr, LDH_D, PGI |
| 7 | 3 | 0.27747 | 0.38953 | ADHEr, HEX1, LDH_D |
| 8 | 4 | 4.46145 | 0.20591 | ADHEr, FRD and/or SUCD4, LDH_D, MDH |
| 9 | 4 | 4.38802 | 0.23398 | ADHEr, FRD and/or SUCD4, HEX1, LDH_D |
| 10 | 4 | 4.03852 | 0.23697 | ADHEr, HEX1, LDH_D, PGI |
| 11 | 4 | 3.73656 | 0.30662 | ADHEr, LDH_D, NADH6, PFLi |
| 12 | 4 | 3.05653 | 0.20692 | ACKr and/or PTAr, ADHEr, LDH_D, PPCK |
| 13 | 4 | 2.59406 | 0.20532 | ADHEr, LDH_D, NADH6, PGI |
| 14 | 4 | 2.58406 | 0.27187 | ADHEr, ASPT, LDH_D, MDH |
| 15 | 4 | 2.46512 | 0.26229 | ADHEr, LDH_D, NADH6, PPCK |
| 16 | 4 | 2.41847 | 0.29351 | ADHEr, LDH_D, MDH, NADH6 |
| 17 | 4 | 2.38828 | 0.35417 | ADHEr, LDH_D, NADH6, RPE |
| 18 | 4 | 2.29878 | 0.17947 | ADHEr, LDH_D, PGI, PPCK |
| 19 | 4 | 2.17588 | 0.24785 | ADHEr, FUM, LDH_D, THD2 and/or GLUDy |
| 20 | 4 | 2.14745 | 0.26084 | ADHEr, EDA and/or PGDHY, LDH_D, PGI |
| 21 | 4 | 2.03987 | 0.35185 | ADHEr, FUM, HEX1, LDH_D |
| 22 | 4 | 1.48168 | 0.38161 | ADHEr, ATPS4r, LDH_D, RPE |
| 23 | 4 | 1.47082 | 0.28924 | ADHEr, LDH_D, MDH, THD2 and/or GLUDy |
| 24 | 4 | 1.3746 | 0.3845 | ADHEr, ATPS4r, LDH_D, TAL |
| 25 | 4 | 1.26025 | 0.2616 | ADHEr, FRD and/or SUCD4, LDH_D, SUCOAS |
| 26 | 4 | 0.939 | 0.26603 | ADHEr, LDH_D, PFLi, PGI |
| 27 | 4 | 0.76149 | 0.2867 | ADHEr, ASPT, FUM, LDH_D |
| 28 | 4 | 0.38353 | 0.38695 | ADHEr, HEX1, LDH_D, RPE |
| 29 | 4 | 0.33312 | 0.38818 | ADHEr, HEX1, LDH_D, TAL |
| 30 | 5 | 5.53962 | 0.16718 | ADHEr, ATPS4r, FRD and/or SUCD4, LDH_D, MDH |
| 31 | 5 | 5.40224 | 0.22385 | ADHEr, HEX1, LDH_D, PFLi, PGI |
| 32 | 5 | 5.13405 | 0.1802 | ADHEr, ASPT, LDH_D, MDH, PFLi |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 33 | 5 | 5.0304 | 0.08351 | ADHEr, ATPS4r, FRD and/or SUCD4, LDH_D, PPCK |
| 34 | 5 | 4.96585 | 0.07704 | ADHEr, ATPS4r, FRD and/or SUCD4, LDH_D, THD2 and/or GLUDy |
| 35 | 5 | 4.88127 | 0.20295 | ADHEr, EDA and/or PGDHY, LDH_D, NADH6, PGI |
| 36 | 5 | 4.78114 | 0.2037 | ADHEr, HEX1, LDH_D, NADH6, PGI |
| 37 | 5 | 4.75518 | 0.09361 | ADHEr, FRD and/or SUCD4, LDH_D, PPCK, PYK |
| 38 | 5 | 4.61203 | 0.20383 | ACKr and/or PTAr, ADHEr, LDH_D, NADH6, PGI |
| 39 | 5 | 4.60391 | 0.15144 | ADHEr, FRD and/or SUCD4, LDH_D, MDH, THD2 and/or GLUDy |
| 40 | 5 | 4.56119 | 0.16777 | ADHEr, FRD and/or SUCD4, GLCpts, LDH_D, MDH |
| 41 | 5 | 4.52834 | 0.20359 | ADHEr, FRD and/or SUCD4, LDH_D, MDH, RPE |
| 42 | 5 | 4.51845 | 0.20259 | ADHEr, FRD and/or SUCD4, LDH_D, MDH, SUCOAS |
| 43 | 5 | 4.46585 | 0.23056 | ADHEr, FRD and/or SUCD4, HEX1, LDH_D, RPE |
| 44 | 5 | 4.45522 | 0.22919 | ADHEr, FRD and/or SUCD4, HEX1, LDH_D, SUCOAS |
| 45 | 5 | 4.44183 | 0.21341 | ADHEr, FRD and/or SUCD4, HEX1, LDH_D, THD2 and/or GLUDy |
| 46 | 5 | 4.44155 | 0.21352 | ADHEr, ATPS4r, FRD and/or SUCD4, HEX1, LDH_D |
| 47 | 5 | 4.42059 | 0.20565 | ADHEr, ASPT, LDH_D, MDH, SUCOAS |
| 48 | 5 | 4.36907 | 0.15859 | ADHEr, EDA and/or PGDHY, LDH_D, PGI, PPCK |
| 49 | 5 | 4.36067 | 0.16481 | ADHEr, ATPS4r, EDA and/or PGDHY, LDH_D, PGI |
| 50 | 5 | 4.33827 | 0.24026 | ADHEr, LDH_D, MDH, NADH6, THD2 and/or GLUDy |
| 51 | 5 | 4.24585 | 0.21569 | ADHEr, ASPT, FUM, LDH_D, MDH |
| 52 | 5 | 4.24585 | 0.21569 | ADHEr, ASPT, ICL, LDH_D, MDH |
| 53 | 5 | 4.24585 | 0.21569 | ADHEr, ASPT, LDH_D, MALS, MDH |
| 54 | 5 | 4.21843 | 0.08488 | ADHEr, FRD and/or SUCD4, LDH_D, PPCK, THD2 and/or GLUDy |
| 55 | 5 | 4.18265 | 0.21782 | ACKr and/or PTAr, ADHEr, ASPT, LDH_D, MDH |
| 56 | 5 | 4.13301 | 0.24796 | ADHEr, ASPT, FUM, HEX1, LDH_D |
| 57 | 5 | 4.03737 | 0.23515 | ACKr and/or PTAr, ADHEr, EDA and/or PGDHY, LDH_D, PGI |
| 58 | 5 | 4.02056 | 0.22023 | ADHEr, ASPT, LDH_D, MDH, THD2 and/or GLUDy |
| 59 | 5 | 4.0188 | 0.18437 | ADHEr, LDH_D, NADH6, PFLi, PPCK |
| 60 | 5 | 3.96576 | 0.20734 | ADHEr, FUM, LDH_D, PFLi, PPCK |
| 61 | 5 | 3.96576 | 0.20734 | ADHEr, LDH_D, MDH, PFLi, PPCK |
| 62 | 5 | 3.96266 | 0.23773 | ACKr and/or PTAr, ADHEr, LDH_D, MDH, NADH6 |
| 63 | 5 | 3.92623 | 0.22446 | ADHEr, LDH_D, MDH, NADH6, PFLi |
| 64 | 5 | 3.81332 | 0.27196 | ACKr and/or PTAr, ADHEr, FUM, HEX1, LDH_D |
| 65 | 5 | 3.81332 | 0.27196 | ACKr and/or PTAr, ADHEr, HEX1, LDH_D, MDH |
| 66 | 5 | 3.79273 | 0.28229 | ADHEr, HEX1, LDH_D, NADH6, PFLi |
| 67 | 5 | 3.77686 | 0.28031 | ACKr and/or PTAr, ADHEr, HEX1, LDH_D, NADH6 |
| 68 | 5 | 3.74717 | 0.3358 | ADHEr, FUM, LDH_D, PFLi, THD2 and/or GLUDy |
| 69 | 5 | 3.69789 | 0.22154 | ADHEr, LDH_D, NADH6, PPCK, THD2 and/or GLUDy |
| 70 | 5 | 3.69693 | 0.23186 | ADHEr, ASPT, ATPS4r, LDH_D, MDH |
| 71 | 5 | 3.57925 | 0.1851 | ACKr and/or PTAr, ADHEr, LDH_D, NADH6, PPCK |
| 72 | 5 | 3.55622 | 0.22164 | ADHEr, FUM, LDH_D, PPCK, THD2 and/or GLUDy |
| 73 | 5 | 3.55622 | 0.22164 | ADHEr, LDH_D, MDH, PPCK, THD2 and/or GLUDy |
| 74 | 5 | 3.51036 | 0.26322 | ADHEr, ATPS4r, LDH_D, MDH, NADH6 |
| 75 | 5 | 3.44912 | 0.18587 | ACKr and/or PTAr, ADHEr, LDH_D, MDH, PPCK |
| 76 | 5 | 3.44912 | 0.18587 | ACKr and/or PTAr, ADHEr, FUM, LDH_D, PPCK |
| 77 | 5 | 3.23914 | 0.31877 | ADHEr, ATPS4r, FDH2, LDH_D, NADH6 |
| 78 | 5 | 3.23669 | 0.2512 | ADHEr, EDA and/or PGDHY, LDH_D, PFLi, PGI |
| 79 | 5 | 3.22027 | 0.23733 | ADHEr, ATPS4r, LDH_D, NADH6, PPCK |
| 80 | 5 | 3.21813 | 0.22145 | ADHEr, ATPS4r, LDH_D, PFLi, PPCK |
| 81 | 5 | 3.20482 | 0.28717 | ACKr and/or PTAr, ADHEr, ATPS4r, LDH_D, SUCOAS |
| 82 | 5 | 3.19987 | 0.14763 | ADHEr, LDH_D, PFLi, PGI, PPCK |
| 83 | 5 | 3.04087 | 0.23963 | ADHEr, ATPS4r, FUM, LDH_D, PPCK |
| 84 | 5 | 3.04087 | 0.23963 | ADHEr, ATPS4r, LDH_D, MDH, PPCK |
| 85 | 5 | 3.01019 | 0.28849 | ADHEr, HEX1, LDH_D, MDH, THD2 and/or GLUDy |
| 86 | 5 | 2.94161 | 0.20506 | ADHEr, ATPS4r, LDH_D, NADH6, PGI |
| 87 | 5 | 2.88011 | 0.33864 | ADHEr, ATPS4r, FUM, LDH_D, NADH6 |
| 88 | 5 | 2.85293 | 0.25411 | ADHEr, ASPT, LDH_D, MDH, NADH6 |
| 89 | 5 | 2.75034 | 0.26847 | ADHEr, LDH_D, MDH, PFLi, THD2 and/or GLUDy |
| 90 | 5 | 2.74759 | 0.33105 | ADHEr, ATPS4r, HEX1, LDH_D, NADH6 |
| 91 | 5 | 2.67997 | 0.17637 | ADHEr, ATPS4r, LDH_D, PGI, PPCK |
| 92 | 5 | 2.67853 | 0.21976 | ADHEr, ASPT, LDH_D, MDH, PYK |
| 93 | 5 | 2.65374 | 0.15874 | ADHEr, LDH_D, NADH6, PGI, PPCK |
| 94 | 5 | 2.65207 | 0.23435 | ADHEr, ASPT, GLCpts, LDH_D, MDH |
| 95 | 5 | 2.64298 | 0.23937 | ADHEr, ASPT, LDH_D, MDH, PPCK |
| 96 | 5 | 2.63715 | 0.26997 | ADHEr, ASPT, LDH_D, MDH, RPE |
| 97 | 5 | 2.60095 | 0.33049 | ADHEr, ATPS4r, FUM, HEX1, LDH_D |
| 98 | 5 | 2.52584 | 0.22167 | ADHEr, LDH_D, NADH6, PPCK, PYK |
| 99 | 5 | 2.5171 | 0.22752 | ADHEr, GLCpts, LDH_D, NADH6, PPCK |
| 100 | 5 | 2.48801 | 0.24981 | ADHEr, ATPS4r, LDH_D, MDH, THD2 and/or GLUDy |
| 101 | 5 | 2.47253 | 0.25734 | ADHEr, GLCpts, LDH_D, MDH, NADH6 |
| 102 | 5 | 2.47049 | 0.29207 | ADHEr, LDH_D, MDH, NADH6, RPE |
| 103 | 5 | 2.38845 | 0.0995 | ADHEr, LDH_D, PGI, PPCK, THD2 and/or GLUDy |
| 104 | 5 | 2.3823 | 0.10498 | ADHEr, FUM, LDH_D, PGI, THD2 and/or GLUDy |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 105 | 5 | 2.3823 | 0.10498 | ADHEr, LDH_D, MDH, PGI, THD2 and/or GLUDy |
| 106 | 5 | 2.37356 | 0.34412 | ADHEr, HEX1, LDH_D, NADH6, TAL |
| 107 | 5 | 2.36643 | 0.29114 | ADHEr, ATPS4r, LDH_D, MDH, PGDH |
| 108 | 5 | 2.33103 | 0.23832 | ADHEr, ATPS4r, LDH_D, PPCK, THD2 and/or GLUDy |
| 109 | 5 | 2.32447 | 0.13422 | ADHEr, GLUDy, LDH_D, MDH, THD2 and/or GLUDy |
| 110 | 5 | 2.29184 | 0.29402 | ADHEr, ATPS4r, LDH_D, MDH, TAL |
| 111 | 5 | 2.282 | 0.28884 | ACKr and/or PTAr, ADHEr, LDH_D, MDH, THD2 and/or GLUDy |
| 112 | 5 | 2.22251 | 0.2967 | ADHEr, ATPS4r, LDH_D, MDH, RPE |
| 113 | 5 | 2.22197 | 0.24001 | ADHEr, LDH_D, MDH, RPE, THD2 and/or GLUDy |
| 114 | 5 | 2.21206 | 0.24857 | ADHEr, GLCpts, LDH_D, PPCK, RPE |
| 115 | 5 | 2.20561 | 0.23941 | ADHEr, LDH_D, MDH, TAL, THD2 and/or GLUDy |
| 116 | 5 | 2.20149 | 0.22826 | ADHEr, FUM, LDH_D, PPCK, PYK |
| 117 | 5 | 2.20149 | 0.22826 | ADHEr, LDH_D, MDH, PPCK, PYK |
| 118 | 5 | 2.19372 | 0.24909 | ADHEr, GLCpts, LDH_D, PPCK, TAL |
| 119 | 5 | 2.19132 | 0.23604 | ADHEr, GLCpts, LDH_D, MDH, PPCK |
| 120 | 5 | 2.19132 | 0.23604 | ADHEr, FUM, GLCpts, LDH_D, PPCK |
| 121 | 5 | 2.18792 | 0.26941 | ADHEr, FUM, LDH_D, PPCK, RPE |
| 122 | 5 | 2.18792 | 0.26941 | ADHEr, LDH_D, MDH, PPCK, RPE |
| 123 | 5 | 2.18777 | 0.23875 | ADHEr, LDH_D, MDH, PGDH, THD2 and/or GLUDy |
| 124 | 5 | 2.09486 | 0.34975 | ADHEr, FUM, HEX1, LDH_D, RPE |
| 125 | 5 | 1.89618 | 0.34765 | ADHEr, ATPS4r, HEX1, LDH_D, THD2 and/or GLUDy |
| 126 | 5 | 1.74629 | 0.36027 | ADHEr, HEX1, LDH_D, PFLi, PPS |
| 127 | 5 | 1.73743 | 0.3202 | ADHEr, ATPS4r, HEX1, LDH_D, PFLi |
| 128 | 5 | 1.73543 | 0.31113 | ADHEr, HEX1, LDH_D, MDH, PFLi |
| 129 | 5 | 1.69405 | 0.23402 | ADHEr, LDH_D, PFLi, PGDH, PGI |
| 130 | 5 | 1.68439 | 0.23524 | ADHEr, LDH_D, PFLi, PGI, TAL |
| 131 | 5 | 1.67549 | 0.23637 | ADHEr, LDH_D, PFLi, PGI, RPE |
| 132 | 5 | 1.66962 | 0.16853 | ADHEr, ATPS4r, LDH_D, PFLi, PGI |
| 133 | 5 | 1.66579 | 0.35584 | ADHEr, HEX1, LDH_D, PPS, THD2 and/or GLUDy |
| 134 | 5 | 1.44831 | 0.25358 | ACKr and/or PTAr, ADHEr, FRD and/or SUCD4, LDH_D, SUCOAS |
| 135 | 5 | 1.40898 | 0.31979 | ADHEr, ATPS4r, HEX1, LDH_D, MDH |
| 136 | 5 | 1.33078 | 0.25859 | ADHEr, ATPS4r, FRD and/or SUCD4, LDH_D, SUCOAS |
| 137 | 5 | 1.28594 | 0.26157 | ACKr and/or PTAr, ADHEr, FRD and/or SUCD4, ICL, LDH_D |
| 138 | 5 | 1.28594 | 0.26157 | ACKr and/or PTAr, ADHEr, FRD and/or SUCD4, LDH_D, MALS |
| 139 | 5 | 1.15083 | 0.26676 | ADHEr, ASPT, FUM, LDH_D, SUCOAS |
| 140 | 5 | 1.08556 | 0.26021 | ACKr and/or PTAr, ADHEr, LDH_D, PFLi, PGI |
| 141 | 5 | 1.08281 | 0.26394 | ADHEr, FUM, LDH_D, PFLi, PGI |
| 142 | 5 | 0.81325 | 0.32358 | ACKr and/or PTAr, ADHEr, HEX1, LDH_D, PPS |
| 143 | 5 | 0.73764 | 0.26814 | ADHEr, LDH_D, MDH, PGI, THD5 |
| 144 | 5 | 0.73764 | 0.26814 | ADHEr, FUM, LDH_D, PGI, THD5 |
| 145 | 6 | 6.49204 | 0.11612 | ADHEr, ASPT, LDH_D, MDH, PFLi, THD2 and/or GLUDy |
| 146 | 6 | 6.18999 | 0.07445 | ADHEr, ATPS4r, FRD and/or SUCD4, GLCpts, LDH_D, MDH |
| 147 | 6 | 6.1414 | 0.1578 | ADHEr, ATPS4r, LDH_D, MDH, NADH6, PGL and/or G6PDHy |
| 148 | 6 | 5.80857 | 0.1099 | ADHEr, ASPT, EDA and/or PGDHY, LDH_D, MDH, PYK |
| 149 | 6 | 5.62948 | 0.09192 | ADHEr, ATPS4r, HEX1, LDH_D, PFLi, PGI |
| 150 | 6 | 5.60131 | 0.13875 | ADHEr, EDA and/or PGDHY, LDH_D, PFLi, PGI, PPCK |
| 151 | 6 | 5.59693 | 0.15008 | ADHEr, FRD and/or SUCD4, HEX1, LDH_D, MDH, THD2 and/or GLUDy |
| 152 | 6 | 5.56181 | 0.13846 | ADHEr, EDA and/or PGDHY, FRD and/or SUCD4, LDH_D, MDH, THD2 and/or GLUDy |
| 153 | 6 | 5.52668 | 0.15619 | ADHEr, EDA and/or PGDHY, LDH_D, NADH6, PFLi, PGI |
| 154 | 6 | 5.52416 | 0.10076 | ADHEr, ASPT, LDH_D, MDH, PFLi, PGI |
| 155 | 6 | 5.44943 | 0.16764 | ADHEr, ASPT, ATPS4r, LDH_D, MDH, SUCOAS |
| 156 | 6 | 5.43906 | 0.17387 | ADHEr, ASPT, ATPS4r, FUM, LDH_D, MDH |
| 157 | 6 | 5.43906 | 0.17387 | ADHEr, ASPT, ATPS4r, ICL, LDH_D, MDH |
| 158 | 6 | 5.43906 | 0.17387 | ADHEr, ASPT, ATPS4r, LDH_D, MALS, MDH |
| 159 | 6 | 5.4269 | 0.11474 | ADHEr, ASPT, EDA and/or PGDHY, LDH_D, MDH, PGI |
| 160 | 6 | 5.39974 | 0.15728 | ADHEr, LDH_D, MDH, PFLi, PPCK, THD2 and/or GLUDy |
| 161 | 6 | 5.39974 | 0.15728 | ADHEr, FUM, LDH_D, PFLi, PPCK, THD2 and/or GLUDy |
| 162 | 6 | 5.36516 | 0.17457 | ADHEr, LDH_D, MDH, NADH6, PFLi, THD2 and/or GLUDy |
| 163 | 6 | 5.29594 | 0.12992 | ADHEr, ASPT, LDH_D, MDH, PFLi, PYK |
| 164 | 6 | 5.28218 | 0.07163 | ADHEr, ATPS4r, FRD and/or SUCD4, LDH_D, PGL and/or G6PDHy, PPCK |
| 165 | 6 | 5.28218 | 0.07163 | ADHEr, ATPS4r, FRD and/or SUCD4, LDH_D, PGDH, PPCK |
| 166 | 6 | 5.27982 | 0.10569 | ADHEr, ASPT, LDH_D, MDH, PGL and/or G6PDHy, PYK |
| 167 | 6 | 5.27077 | 0.07217 | ADHEr, ATPS4r, FRD and/or SUCD4, LDH_D, PPCK, TAL |
| 168 | 6 | 5.26177 | 0.14053 | ADHEr, ASPT, GLCpts, LDH_D, MDH, PFLi |
| 169 | 6 | 5.26021 | 0.07267 | ADHEr, ATPS4r, FRD and/or SUCD4, LDH_D, PPCK, RPE |
| 170 | 6 | 5.22996 | 0.24218 | ADHEr, HEX1, LDH_D, MDH, PFLi, THD2 and/or GLUDy |
| 171 | 6 | 5.22996 | 0.24218 | ADHEr, FUM, HEX1, LDH_D, PFLi, THD2 and/or GLUDy |
| 172 | 6 | 5.10795 | 0.18114 | ADHEr, ASPT, ATPS4r, LDH_D, MDH, PGL and/or G6PDHy |
| 173 | 6 | 5.07418 | 0.20379 | ADHEr, ATPS4r, FRD and/or SUCD4, HEX1, LDH_D, PPS |
| 174 | 6 | 5.05205 | 0.12049 | ADHEr, EDA and/or PGDHY, LDH_D, NADH6, PGI, PPCK |
| 175 | 6 | 5.02318 | 0.17043 | ACKr and/or PTAr, ADHEr, FUM, LDH_D, PFLi, PPCK |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 176 | 6 | 5.02318 | 0.17043 | ACKr and/or PTAr, ADHEr, LDH_D, MDH, PFLi, PPCK |
| 177 | 6 | 4.96023 | 0.0152 | ADHEr, FRD and/or SUCD4, LDH_D, MDH, PYK, THD2 and/or GLUDy |
| 178 | 6 | 4.96019 | 0.14703 | ADHEr, LDH_D, NADH6, PFLi, PPCK, THD2 and/or GLUDy |
| 179 | 6 | 4.95227 | 0.18511 | ACKr and/or PTAr, ADHEr, EDA and/or PGDHY, LDH_D, NADH6, PGI |
| 180 | 6 | 4.94767 | 0.18905 | ACKr and/or PTAr, ADHEr, LDH_D, MDH, NADH6, PFLi |
| 181 | 6 | 4.94078 | 0.08876 | ADHEr, ASPT, ATPS4r, FUM, LDH_D, PPCK |
| 182 | 6 | 4.88378 | 0.08315 | ADHEr, ASPT, ATPS4r, FUM, LDH_D, THD2 and/or GLUDy |
| 183 | 6 | 4.88138 | 0.0499 | ADHEr, FRD and/or SUCD4, LDH_D, MDH, SUCOAS, THD2 and/or GLUDy |
| 184 | 6 | 4.8705 | 0.04951 | ADHEr, FRD and/or SUCD4, GLCpts, LDH_D, PPCK, THD2 and/or GLUDy |
| 185 | 6 | 4.86653 | 0.05103 | ADHEr, FRD and/or SUCD4, LDH_D, MALS, MDH, THD2 and/or GLUDy |
| 186 | 6 | 4.86653 | 0.05103 | ADHEr, FRD and/or SUCD4, ICL, LDH_D, MDH, THD2 and/or GLUDy |
| 187 | 6 | 4.85555 | 0.05127 | ADHEr, ASPT, LDH_D, MDH, SUCOAS, THD2 and/or GLUDy |
| 188 | 6 | 4.81179 | 0.07918 | ADHEr, FRD and/or SUCD4, LDH_D, PPCK, SUCOAS, THD2 and/or GLUDy |
| 189 | 6 | 4.80834 | 0.05481 | ADHEr, ASPT, ICL, LDH_D, MDH, THD2 and/or GLUDy |
| 190 | 6 | 4.80834 | 0.05481 | ADHEr, ASPT, LDH_D, MALS, MDH, THD2 and/or GLUDy |
| 191 | 6 | 4.80546 | 0.08184 | ADHEr, FRD and/or SUCD4, HEX1, LDH_D, SUCOAS, THD2 and/or GLUDy |
| 192 | 6 | 4.79254 | 0.05156 | ACKr and/or PTAr, ADHEr, FRD and/or SUCD4, LDH_D, MDH, THD2 and/or GLUDy |
| 193 | 6 | 4.7879 | 0.08109 | ADHEr, FRD and/or SUCD4, LDH_D, MALS, PPCK, THD2 and/or GLUDy |
| 194 | 6 | 4.7879 | 0.08109 | ADHEr, FRD and/or SUCD4, ICL, LDH_D, PPCK, THD2 and/or GLUDy |
| 195 | 6 | 4.7863 | 0.15759 | ADHEr, LDH_D, NADH12, NADH6, PFLi, PGI |
| 196 | 6 | 4.78022 | 0.08403 | ADHEr, FRD and/or SUCD4, HEX1, LDH_D, MALS, THD2 and/or GLUDy |
| 197 | 6 | 4.78022 | 0.08403 | ADHEr, FRD and/or SUCD4, HEX1, ICL, LDH_D, THD2 and/or GLUDy |
| 198 | 6 | 4.75362 | 0.1717 | ADHEr, ATPS4r, LDH_D, MDH, NADH6, SUCOAS |
| 199 | 6 | 4.74482 | 0.14204 | ADHEr, FUM, LDH_D, PFLi, PGI, PPCK |
| 200 | 6 | 4.74482 | 0.14204 | ADHEr, LDH_D, MDH, PFLi, PGI, PPCK |
| 201 | 6 | 4.71665 | 0.15772 | ADHEr, FUM, LDH_D, NADH6, PFLi, PGI |
| 202 | 6 | 4.71665 | 0.15772 | ADHEr, LDH_D, MDH, NADH6, PFLi, PGI |
| 203 | 6 | 4.67938 | 0.12258 | ADHEr, FRD and/or SUCD4, GLCpts, LDH_D, MDH, THD2 and/or GLUDy |
| 204 | 6 | 4.67056 | 0.08187 | ACKr and/or PTAr, ADHEr, FRD and/or SUCD4, LDH_D, PPCK, THD2 and/or GLUDy |
| 205 | 6 | 4.65509 | 0.08572 | ACKr and/or PTAr, ADHEr, FRD and/or SUCD4, HEX1, LDH_D, THD2 and/or GLUDy |
| 206 | 6 | 4.65177 | 0.09959 | ADHEr, ASPT, FUM, LDH_D, PPCK, PYK |
| 207 | 6 | 4.64856 | 0.19942 | ADHEr, ATPS4r, LDH_D, MDH, NADH6, PFLi |
| 208 | 6 | 4.64527 | 0.14923 | ADHEr, LDH_D, MDH, NADH6, SUCOAS, THD2 and/or GLUDy |
| 209 | 6 | 4.62501 | 0.24401 | ADHEr, HEX1, LDH_D, NADH6, PFLi, THD2 and/or GLUDy |
| 210 | 6 | 4.61569 | 0.16588 | ADHEr, FRD and/or SUCD4, GLCpts, LDH_D, MDH, RPE |
| 211 | 6 | 4.58364 | 0.20034 | ADHEr, FRD and/or SUCD4, LDH_D, MDH, RPE, SUCOAS |
| 212 | 6 | 4.54149 | 0.17531 | ADHEr, ASPT, FRD and/or SUCD4, LDH_D, MDH, PYK |
| 213 | 6 | 4.53277 | 0.1423 | ACKr and/or PTAr, ADHEr, ATPS4r, LDH_D, PPCK, THD2 and/or GLUDy |
| 214 | 6 | 4.53052 | 0.2259 | ADHEr, FRD and/or SUCD4, HEX1, LDH_D, RPE, SUCOAS |
| 215 | 6 | 4.52789 | 0.16756 | ADHEr, ASPT, GLCpts, LDH_D, MDH, SUCOAS |
| 216 | 6 | 4.52733 | 0.16694 | ADHEr, ASPT, ATPS4r, GLCpts, LDH_D, MDH |
| 217 | 6 | 4.50564 | 0.17546 | ADHEr, ASPT, LDH_D, MDH, PYK, SUCOAS |
| 218 | 6 | 4.48785 | 0.20333 | ADHEr, ASPT, LDH_D, MDH, RPE, SUCOAS |
| 219 | 6 | 4.45673 | 0.0937 | ADHEr, ATPS4r, EDA and/or PGDHY, LDH_D, PGI, PPCK |
| 220 | 6 | 4.44964 | 0.1574 | ADHEr, ASPT, FUM, LDH_D, MDH, THD2 and/or GLUDy |
| 221 | 6 | 4.38551 | 0.17574 | ADHEr, ASPT, GLCpts, LDH_D, MALS, MDH |
| 222 | 6 | 4.38551 | 0.17574 | ADHEr, ASPT, FUM, GLCpts, LDH_D, MDH |
| 223 | 6 | 4.38551 | 0.17574 | ADHEr, ASPT, GLCpts, ICL, LDH_D, MDH |
| 224 | 6 | 4.3659 | 0.18135 | ADHEr, ASPT, LDH_D, MALS, MDH, PYK |
| 225 | 6 | 4.3659 | 0.18135 | ADHEr, ASPT, FUM, LDH_D, MDH, PYK |
| 226 | 6 | 4.3659 | 0.18135 | ADHEr, ASPT, ICL, LDH_D, MDH, PYK |
| 227 | 6 | 4.35016 | 0.23064 | ADHEr, FUM, HEX1, LDH_D, NADH6, SUCOAS |
| 228 | 6 | 4.34833 | 0.1713 | ADHEr, ATPS4r, LDH_D, NADH6, PFLi, PPCK |
| 229 | 6 | 4.34286 | 0.23323 | ADHEr, ASPT, FUM, HEX1, LDH_D, SUCOAS |
| 230 | 6 | 4.33401 | 0.17749 | ACKr and/or PTAr, ADHEr, ASPT, GLCpts, LDH_D, MDH |
| 231 | 6 | 4.31842 | 0.21314 | ADHEr, ASPT, ICL, LDH_D, MDH, RPE |
| 232 | 6 | 4.31842 | 0.21314 | ADHEr, ASPT, LDH_D, MALS, MDH, RPE |
| 233 | 6 | 4.31842 | 0.21314 | ADHEr, ASPT, FUM, LDH_D, MDH, RPE |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 234 | 6 | 4.31517 | 0.18251 | ACKr and/or PTAr, ADHEr, ASPT, LDH_D, MDH, PYK |
| 235 | 6 | 4.27405 | 0.08431 | ADHEr, FRD and/or SUCD4, LDH_D, PPCK, RPE, THD2 and/or GLUDy |
| 236 | 6 | 4.25521 | 0.17069 | ACKr and/or PTAr, ADHEr, LDH_D, MDH, PPCK, PYK |
| 237 | 6 | 4.25521 | 0.17069 | ACKr and/or PTAr, ADHEr, FUM, LDH_D, PPCK, PYK |
| 238 | 6 | 4.23738 | 0.22036 | ADHEr, FUM, HEX1, LDH_D, PGI, THD5 |
| 239 | 6 | 4.23738 | 0.22036 | ADHEr, HEX1, LDH_D, MDH, PGI, THD5 |
| 240 | 6 | 4.21937 | 0.24412 | ADHEr, ASPT, FUM, HEX1, LDH_D, RPE |
| 241 | 6 | 4.20848 | 0.22638 | ADHEr, ASPT, FUM, HEX1, LDH_D, THD2 and/or GLUDy |
| 242 | 6 | 4.1949 | 0.21515 | ACKr and/or PTAr, ADHEr, FDH2, LDH_D, MDH, NADH6 |
| 243 | 6 | 4.193 | 0.22615 | ADHEr, ASPT, ATPS4r, FUM, HEX1, LDH_D |
| 244 | 6 | 4.18464 | 0.18833 | ADHEr, HEX1, LDH_D, PPS, SUCOAS, THD2 and/or GLUDy |
| 245 | 6 | 4.17022 | 0.12602 | ADHEr, GLCpts, LDH_D, PFLi, PGI, PPCK |
| 246 | 6 | 4.15452 | 0.23423 | ACKr and/or PTAr, ACS, ADHEr, EDA and/or PGDHY, LDH_D, PGI |
| 247 | 6 | 4.13958 | 0.1401 | ADHEr, GLCpts, LDH_D, NADH6, PFLi, PGI |
| 248 | 6 | 4.12806 | 0.09037 | ADHEr, ASPT, FUM, LDH_D, PPCK, THD2 and/or GLUDy |
| 249 | 6 | 4.10281 | 0.14798 | ADHEr, GLCpts, LDH_D, NADH6, PFLi, PPCK |
| 250 | 6 | 4.09944 | 0.14944 | ADHEr, LDH_D, NADH6, PFLi, PPCK, PYK |
| 251 | 6 | 4.09149 | 0.20644 | ADHEr, ASPT, ATPS4r, LDH_D, MDH, NADH6 |
| 252 | 6 | 4.08305 | 0.24974 | ACKr and/or PTAr, ADHEr, FUM, HEX1, LDH_D, NADH6 |
| 253 | 6 | 4.07707 | 0.21283 | ADHEr, ATPS4r, GLCpts, LDH_D, MDH, NADH6 |
| 254 | 6 | 4.07083 | 0.2483 | ACKr and/or PTAr, ADHEr, FDH2, HEX1, LDH_D, NADH6 |
| 255 | 6 | 4.0547 | 0.15755 | ADHEr, LDH_D, NADH6, PFLi, PGDH, PGI |
| 256 | 6 | 4.04976 | 0.14332 | ADHEr, LDH_D, PFLi, PGDH, PGI, PPCK |
| 257 | 6 | 4.04925 | 0.17118 | ADHEr, GLCpts, LDH_D, MDH, PFLi, PPCK |
| 258 | 6 | 4.04925 | 0.17118 | ADHEr, FUM, GLCpts, LDH_D, PFLi, PPCK |
| 259 | 6 | 4.04921 | 0.20443 | ADHEr, ATPS4r, FUM, LDH_D, PFLi, PPCK |
| 260 | 6 | 4.04921 | 0.20443 | ADHEr, ATPS4r, LDH_D, MDH, PFLi, PPCK |
| 261 | 6 | 4.04701 | 0.15816 | ADHEr, LDH_D, NADH6, PFLi, PGI, TAL |
| 262 | 6 | 4.04276 | 0.14386 | ADHEr, LDH_D, PFLi, PGI, PPCK, TAL |
| 263 | 6 | 4.03993 | 0.15872 | ADHEr, LDH_D, NADH6, PFLi, PGI, RPE |
| 264 | 6 | 4.03632 | 0.14436 | ADHEr, LDH_D, PFLi, PGI, PPCK, RPE |
| 265 | 6 | 4.01325 | 0.18677 | ADHEr, GLCpts, LDH_D, MDH, NADH6, PFLi |
| 266 | 6 | 3.99577 | 0.19434 | ADHEr, LDH_D, MDH, NADH12, NADH6, PFLi |
| 267 | 6 | 3.97712 | 0.21218 | ADHEr, ATPS4r, LDH_D, NADH6, PPCK, RPE |
| 268 | 6 | 3.96781 | 0.21154 | ADHEr, ATPS4r, LDH_D, NADH6, PPCK, TAL |
| 269 | 6 | 3.95767 | 0.21085 | ADHEr, ATPS4r, LDH_D, NADH6, PGL and/or G6PDHy, PPCK |
| 270 | 6 | 3.95767 | 0.21085 | ADHEr, ATPS4r, LDH_D, NADH6, PGDH, PPCK |
| 271 | 6 | 3.95117 | 0.22396 | ADHEr, ATPS4r, LDH_D, MDH, NADH6, RPE |
| 272 | 6 | 3.94143 | 0.22325 | ADHEr, ATPS4r, LDH_D, MDH, NADH6, TAL |
| 273 | 6 | 3.93082 | 0.22248 | ADHEr, ATPS4r, LDH_D, MDH, NADH6, PGDH |
| 274 | 6 | 3.92007 | 0.30764 | ADHEr, HEX1, LDH_D, PFLi, PPS, THD2 and/or GLUDy |
| 275 | 6 | 3.90761 | 0.02965 | ADHEr, EDA and/or PGDHY, LDH_D, MDH, PGI, THD2 and/or GLUDy |
| 276 | 6 | 3.90761 | 0.02965 | ADHEr, EDA and/or PGDHY, FUM, LDH_D, PGI, THD2 and/or GLUDy |
| 277 | 6 | 3.88276 | 0.27815 | ADHEr, ATPS4r, HEX1, LDH_D, NADH6, PFLi |
| 278 | 6 | 3.87622 | 0.18142 | ADHEr, ATPS4r, FDH2, LDH_D, NADH6, PGI |
| 279 | 6 | 3.85591 | 0.25493 | ADHEr, HEX1, LDH_D, NADH12, NADH6, PFLi |
| 280 | 6 | 3.85214 | 0.25656 | ADHEr, FUM, HEX1, LDH_D, NADH6, PFLi |
| 281 | 6 | 3.80756 | 0.28917 | ADHEr, LDH_D, NADH12, NADH6, PFLi, RPE |
| 282 | 6 | 3.80403 | 0.29078 | ADHEr, GLCpts, LDH_D, NADH6, PFLi, RPE |
| 283 | 6 | 3.80376 | 0.2909 | ADHEr, FUM, LDH_D, NADH6, PFLi, RPE |
| 284 | 6 | 3.79095 | 0.29004 | ADHEr, LDH_D, NADH12, NADH6, PFLi, TAL |
| 285 | 6 | 3.78678 | 0.29189 | ADHEr, FUM, LDH_D, NADH6, PFLi, TAL |
| 286 | 6 | 3.74504 | 0.18693 | ADHEr, ATPS4r, GLCpts, LDH_D, NADH6, PPCK |
| 287 | 6 | 3.66618 | 0.23348 | ADHEr, ATPS4r, FDH2, LDH_D, MDH, NADH6 |
| 288 | 6 | 3.65047 | 0.29574 | ADHEr, ATPS4r, FDH2, LDH_D, NADH12, NADH6 |
| 289 | 6 | 3.64636 | 0.29624 | ADHEr, ATPS4r, FDH2, GLCpts, LDH_D, NADH6 |
| 290 | 6 | 3.61821 | 0.2978 | ADHEr, ATPS4r, FDH2, FUM, LDH_D, NADH6 |
| 291 | 6 | 3.59369 | 0.11801 | ADHEr, EDA and/or PGDHY, GLUDy, LDH_D, MDH, THD2 and/or GLUDy |
| 292 | 6 | 3.56749 | 0.21671 | ADHEr, HEX1, LDH_D, PFLi, PPCK, THD2 and/or GLUDy |
| 293 | 6 | 3.56467 | 0.20357 | ADHEr, ATPS4r, LDH_D, MDH, NADH6, PPCK |
| 294 | 6 | 3.56467 | 0.20357 | ADHEr, ATPS4r, FUM, LDH_D, NADH6, PPCK |
| 295 | 6 | 3.54915 | 0.24121 | ADHEr, ATPS4r, EDA and/or PGDHY, LDH_D, MDH, THD2 and/or GLUDy |
| 296 | 6 | 3.54182 | 0.17698 | ADHEr, ASPT, EDA and/or PGDHY, LDH_D, PGI, THD5 |
| 297 | 6 | 3.52871 | 0.18935 | ADHEr, ATPS4r, GLCpts, LDH_D, MDH, PPCK |
| 298 | 6 | 3.52871 | 0.18935 | ADHEr, ATPS4r, FUM, GLCpts, LDH_D, PPCK |
| 299 | 6 | 3.48585 | 0.20551 | ADHEr, ATPS4r, FDH2, LDH_D, NADH6, PPCK |
| 300 | 6 | 3.46875 | 0.14666 | ACKr and/or PTAr, ADHEr, LDH_D, PFLi, PGI, PPCK |
| 301 | 6 | 3.39774 | 0.24244 | ADHEr, ATPS4r, GLCpts, LDH_D, MDH, THD2 and/or GLUDy |
| 302 | 6 | 3.34501 | 0.09944 | ACKr and/or PTAr, ADHEr, ATPS4r, FRD and/or |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| | | | | SUCD4, LDH_D, PGI |
| 303 | 6 | 3.21571 | 0.21219 | ADHEr, LDH_D, MDH, NADH12, NADH6, SUCOAS |
| 304 | 6 | 3.13882 | 0.32432 | ADHEr, ATPS4r, HEX1, LDH_D, NADH6, PGL and/or G6PDHy |
| 305 | 6 | 3.13882 | 0.32432 | ADHEr, ATPS4r, HEX1, LDH_D, NADH6, PGDH |
| 306 | 6 | 3.10937 | 0.32483 | ADHEr, ATPS4r, HEX1, LDH_D, NADH6, TAL |
| 307 | 6 | 3.08568 | 0.30099 | ADHEr, ATPS4r, FUM, HEX1, LDH_D, NADH6 |
| 308 | 6 | 3.08242 | 0.32529 | ADHEr, ATPS4r, HEX1, LDH_D, NADH6, RPE |
| 309 | 6 | 3.05396 | 0.31324 | ADHEr, FUM, HEX1, LDH_D, PPS, THD2 and/or GLUDy |
| 310 | 6 | 3.04084 | 0.1442 | ADHEr, ATPS4r, GLCpts, LDH_D, PGI, PPCK |
| 311 | 6 | 3.0331 | 0.26033 | ACKr and/or PTAr, ADHEr, ATPS4r, LDH_D, MDH, PGDH |
| 312 | 6 | 2.95572 | 0.06686 | ADHEr, ASPT, LDH_D, MDH, PGI, THD2 and/or GLUDy |
| 313 | 6 | 2.95209 | 0.20166 | ADHEr, ASPT, LDH_D, MDH, NADH6, PYK |
| 314 | 6 | 2.93749 | 0.26369 | ACKr and/or PTAr, ADHEr, ATPS4r, LDH_D, MDH, TAL |
| 315 | 6 | 2.93137 | 0.23554 | ADHEr, EDA and/or PGDHY, FUM, LDH_D, PGI, THD5 |
| 316 | 6 | 2.93119 | 0.19434 | ADHEr, ATPS4r, FUM, LDH_D, NADH6, THD2 and/or GLUDy |
| 317 | 6 | 2.92428 | 0.21637 | ADHEr, ASPT, GLCpts, LDH_D, MDH, NADH6 |
| 318 | 6 | 2.90707 | 0.25203 | ADHEr, ASPT, LDH_D, MDH, NADH6, RPE |
| 319 | 6 | 2.88032 | 0.10845 | ADHEr, ASPT, LDH_D, MDH, PYK, THD2 and/or GLUDy |
| 320 | 6 | 2.85872 | 0.13782 | ADHEr, ASPT, GLCpts, LDH_D, MDH, PGI |
| 321 | 6 | 2.83622 | 0.13278 | ADHEr, ASPT, GLCpts, LDH_D, MDH, THD2 and/or GLUDy |
| 322 | 6 | 2.83037 | 0.25344 | ACKr and/or PTAr, ADHEr, ATPS4r, HEX1, LDH_D, THD2 and/or GLUDy |
| 323 | 6 | 2.73678 | 0.18763 | ADHEr, ASPT, LDH_D, MDH, PPCK, PYK |
| 324 | 6 | 2.73413 | 0.26033 | ACKr and/or PTAr, ADHEr, ATPS4r, LDH_D, MDH, PGL and/or G6PDHy |
| 325 | 6 | 2.70842 | 0.20327 | ADHEr, ASPT, GLCpts, LDH_D, MDH, PPCK |
| 326 | 6 | 2.68773 | 0.20429 | ADHEr, FUM, LDH_D, NADH6, PGI, THD5 |
| 327 | 6 | 2.68773 | 0.20429 | ADHEr, LDH_D, MDH, NADH6, PGI, THD5 |
| 328 | 6 | 2.6871 | 0.26683 | ACKr and/or PTAr, ADHEr, ATPS4r, LDH_D, MDH, RPE |
| 329 | 6 | 2.64071 | 0.07956 | ACKr and/or PTAr, ADHEr, GLUDy, LDH_D, MDH, THD2 and/or GLUDy |
| 330 | 6 | 2.61399 | 0.16269 | ADHEr, LDH_D, MDH, NADH12, NADH6, THD2 and/or GLUDy |
| 331 | 6 | 2.60256 | 0.17034 | ADHEr, LDH_D, NADH12, NADH6, PPCK, THD2 and/or GLUDy |
| 332 | 6 | 2.56541 | 0.1952 | ADHEr, FUM, GLCpts, LDH_D, NADH6, THD2 and/or GLUDy |
| 333 | 6 | 2.53808 | 0.13335 | ADHEr, ATPS4r, GLUDy, LDH_D, MDH, THD2 and/or GLUDy |
| 334 | 6 | 2.53559 | 0.33664 | ADHEr, ATPS4r, HEX1, LDH_D, PPS, THD2 and/or GLUDy |
| 335 | 6 | 2.53316 | 0.24472 | ADHEr, LDH_D, MDH, NADH6, PPCK, RPE |
| 336 | 6 | 2.53316 | 0.24472 | ADHEr, FUM, LDH_D, NADH6, PPCK, RPE |
| 337 | 6 | 2.53266 | 0.21711 | ADHEr, FUM, LDH_D, NADH12, NADH6, THD2 and/or GLUDy |
| 338 | 6 | 2.50897 | 0.31991 | ADHEr, HEX1, LDH_D, NADH6, PPS, THD2 and/or GLUDy |
| 339 | 6 | 2.47564 | 0.27754 | ADHEr, ATPS4r, LDH_D, MDH, PGDH, TAL |
| 340 | 6 | 2.37424 | 0.3231 | ADHEr, GLU5K, HEX1, LDH_D, NADH6, THD2 and/or GLUDy |
| 341 | 6 | 2.37424 | 0.3231 | ADHEr, G5SD, HEX1, LDH_D, NADH6, THD2 and/or GLUDy |
| 342 | 6 | 2.37418 | 0.32314 | ADHEr, ASNS2, HEX1, LDH_D, NADH6, THD2 and/or GLUDy |
| 343 | 6 | 2.35165 | 0.11344 | ADHEr, FUM, LDH_D, PPCK, PYK, THD2 and/or GLUDy |
| 344 | 6 | 2.35165 | 0.11344 | ADHEr, LDH_D, MDH, PPCK, PYK, THD2 and/or GLUDy |
| 345 | 6 | 2.28934 | 0.18186 | ADHEr, HEX1, LDH_D, PPS, RPE, THD2 and/or GLUDy |
| 346 | 6 | 2.28203 | 0.17727 | ADHEr, HEX1, LDH_D, PPS, TAL, THD2 and/or GLUDy |
| 347 | 6 | 2.27443 | 0.17249 | ADHEr, HEX1, LDH_D, PGDH, PPS, THD2 and/or GLUDy |
| 348 | 6 | 2.27443 | 0.17249 | ADHEr, HEX1, LDH_D, PGL and/or G6PDHy, PPS, THD2 and/or GLUDy |
| 349 | 6 | 2.23539 | 0.22843 | ADHEr, HEX1, LDH_D, PPCK, RPE, THD2 and/or GLUDy |
| 350 | 6 | 2.2276 | 0.23515 | ADHEr, FUM, HEX1, LDH_D, RPE, THD2 and/or GLUDy |
| 351 | 6 | 2.22058 | 0.22724 | ADHEr, HEX1, LDH_D, PPCK, TAL, THD2 and/or GLUDy |
| 352 | 6 | 2.20452 | 0.22594 | ADHEr, HEX1, LDH_D, PGDH, PPCK, THD2 and/or GLUDy |
| 353 | 6 | 2.20452 | 0.22594 | ADHEr, HEX1, LDH_D, PGL and/or G6PDHy, PPCK, THD2 and/or GLUDy |
| 354 | 6 | 2.10135 | 0.3242 | ADHEr, FUM, HEX1, LDH_D, TAL, THD2 and/or GLUDy |
| 355 | 6 | 2.02123 | 0.34714 | ADHEr, ATPS4r, HEX1, LDH_D, RPE, THD2 and/or GLUDy |
| 356 | 6 | 1.98114 | 0.30095 | ACKr and/or PTAr, ADHEr, ATPS4r, FUM, LDH_D, THD2 and/or GLUDy |
| 357 | 6 | 1.96512 | 0.30664 | ADHEr, ATPS4r, HEX1, LDH_D, MDH, PFLi |
| 358 | 6 | 1.96163 | 0.34738 | ADHEr, ATPS4r, HEX1, LDH_D, TAL, THD2 and/or GLUDy |
| 359 | 6 | 1.94766 | 0.26881 | ADHEr, ATPS4r, LDH_D, MDH, PGL and/or G6PDHy, PPS |
| 360 | 6 | 1.84554 | 0.35787 | ADHEr, HEX1, LDH_D, PFLi, PPS, RPE |
| 361 | 6 | 1.84094 | 0.27637 | ACKr and/or PTAr, ADHEr, ASPT, ATPS4r, FUM, LDH_D |
| 362 | 6 | 1.82413 | 0.31504 | ADHEr, ATPS4r, HEX1, LDH_D, PFLi, RPE |
| 363 | 6 | 1.82134 | 0.30945 | ADHEr, HEX1, LDH_D, MDH, PFLi, RPE |
| 364 | 6 | 1.79836 | 0.35901 | ADHEr, HEX1, LDH_D, PFLi, PPS, TAL |
| 365 | 6 | 1.74423 | 0.2066 | ADHEr, ASPT, ATPS4r, LDH_D, PGI, THD5 |
| 366 | 6 | 1.63108 | 0.27824 | ACKr and/or PTAr, ADHEr, LDH_D, MDH, PGDH, SUCOAS |
| 367 | 6 | 1.63108 | 0.27824 | ACKr and/or PTAr, ADHEr, LDH_D, MDH, PGL and/or G6PDHy, SUCOAS |
| 368 | 6 | 1.59283 | 0.279 | ACKr and/or PTAr, ADHEr, LDH_D, MDH, SUCOAS, TAL |
| 369 | 6 | 1.55776 | 0.2797 | ACKr and/or PTAr, ADHEr, LDH_D, MDH, RPE, SUCOAS |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 370 | 6 | 1.35784 | 0.33828 | ADHEr, FUM, LDH_D, PPS, SUCOAS, THD2 and/or GLUDy |
| 371 | 6 | 1.3281 | 0.25919 | ACKr and/or PTAr, ADHEr, ASPT, FUM, LDH_D, SUCOAS |
| 372 | 6 | 1.25004 | 0.31142 | ACKr and/or PTAr, ADHEr, FUM, LDH_D, SUCOAS, THD2 and/or GLUDy |
| 373 | 6 | 1.16323 | 0.25946 | ADHEr, FRD and/or SUCD4, GLYCL, LDH_D, PGL and/or G6PDHy, TAL |
| 374 | 6 | 1.16323 | 0.25946 | ADHEr, FRD and/or SUCD4, GLYCL, LDH_D, PGDH, TAL |
| 375 | 6 | 0.94735 | 0.32316 | ACKr and/or PTAr, ADHEr, HEX1, LDH_D, PPS, RPE |
| 376 | 6 | 0.88343 | 0.32336 | ACKr and/or PTAr, ADHEr, HEX1, LDH_D, PPS, TAL |
| 377 | 6 | 0.83542 | 0.27562 | ADHEr, ASPT, FUM, LDH_D, PGDH, TAL |
| 378 | 6 | 0.83542 | 0.27562 | ADHEr, ASPT, FUM, LDH_D, PGL and/or G6PDHy, TAL |
| 379 | 6 | 0.81371 | 0.28445 | ACKr and/or PTAr, ADHEr, ASPT, FUM, ICL, LDH_D |
| 380 | 6 | 0.81371 | 0.28445 | ACKr and/or PTAr, ADHEr, ASPT, FUM, LDH_D, MALS |
| 381 | 6 | 0.40293 | 0.37998 | ACKr and/or PTAr, ADHEr, CITL, ICL, LDH_D, SUCOAS |
| 382 | 6 | 0.40293 | 0.37998 | ACKr and/or PTAr, ADHEr, CITL, LDH_D, MALS, SUCOAS |
| 383 | 7 | 6.87929 | 0.03662 | ADHEr, ASPT, LDH_D, MDH, PFLi, PGL and/or G6PDHy, PYK |
| 384 | 7 | 6.87929 | 0.03662 | ADHEr, ASPT, EDA and/or PGDHY, LDH_D, MDH, PFLi, PYK |
| 385 | 7 | 6.82182 | 0.04856 | ADHEr, ASPT, EDA and/or PGDHY, LDH_D, MDH, PFLi, THD2 and/or GLUDy |
| 386 | 7 | 6.7498 | 0.06331 | ADHEr, ASPT, LDH_D, MDH, PFLi, PPCK, THD2 and/or GLUDy |
| 387 | 7 | 6.70416 | 0.07266 | ADHEr, ASPT, LDH_D, MDH, NADH6, PFLi, THD2 and/or GLUDy |
| 388 | 7 | 6.67113 | 0.07943 | ADHEr, ASPT, GLCpts, LDH_D, MDH, PFLi, THD2 and/or GLUDy |
| 389 | 7 | 6.65401 | 0.08294 | ADHEr, ATPS4r, FDH2, LDH_D, MDH, NADH6, PGL and/or G6PDHy |
| 390 | 7 | 6.45147 | 0.12443 | ADHEr, ATPS4r, LDH_D, MDH, NADH6, PFLi, PGL and/or G6PDHy |
| 391 | 7 | 6.44861 | 0.08805 | ADHEr, ASPT, ATPS4r, LDH_D, MALS, MDH, PGL and/or G6PDHy |
| 392 | 7 | 6.44861 | 0.08805 | ADHEr, ASPT, ATPS4r, ICL, LDH_D, MDH, PGL and/or G6PDHy |
| 393 | 7 | 6.44861 | 0.08805 | ADHEr, ASPT, ATPS4r, FUM, LDH_D, MDH, PGL and/or G6PDHy |
| 394 | 7 | 6.15823 | 0.07915 | ADHEr, ASPT, ATPS4r, GLCpts, LDH_D, MALS, MDH |
| 395 | 7 | 6.15823 | 0.07915 | ADHEr, ASPT, ATPS4r, GLCpts, ICL, LDH_D, MDH |
| 396 | 7 | 6.15823 | 0.07915 | ADHEr, ASPT, ATPS4r, FUM, GLCpts, LDH_D, MDH |
| 397 | 7 | 6.14605 | 0.07491 | ADHEr, ASPT, ATPS4r, GLCpts, LDH_D, MDH, SUCOAS |
| 398 | 7 | 6.1414 | 0.1578 | ADHEr, ATPS4r, EDA and/or PGDHY, LDH_D, MDH, NADH6, PGDH |
| 399 | 7 | 6.09037 | 0.16006 | ADHEr, ATPS4r, EDA and/or PGDHY, LDH_D, MDH, NADH6, TAL |
| 400 | 7 | 6.08683 | 0.10358 | ADHEr, LDH_D, MDH, NADH12, NADH6, PFLi, THD2 and/or GLUDy |
| 401 | 7 | 6.0464 | 0.06183 | ADHEr, ASPT, GLCpts, LDH_D, MDH, PFLi, PGI |
| 402 | 7 | 6.04253 | 0.16218 | ADHEr, ATPS4r, EDA and/or PGDHY, LDH_D, MDH, NADH6, RPE |
| 403 | 7 | 5.86291 | 0.1062 | ADHEr, ASPT, EDA and/or PGDHY, ICL, LDH_D, MDH, THD2 and/or GLUDy |
| 404 | 7 | 5.86291 | 0.1062 | ADHEr, ASPT, EDA and/or PGDHY, LDH_D, MALS, MDH, THD2 and/or GLUDy |
| 405 | 7 | 5.79637 | 0.08575 | ADHEr, ASPT, EDA and/or PGDHY, LDH_D, MDH, NADH6, PGI |
| 406 | 7 | 5.74642 | 0.10456 | ADHEr, EDA and/or PGDHY, FRD and/or SUCD4, GLCpts, LDH_D, MDH, THD2 and/or GLUDy |
| 407 | 7 | 5.71711 | 0.12348 | ADHEr, ASPT, ATPS4r, LDH_D, MDH, NADH6, PFLi |
| 408 | 7 | 5.71588 | 0.18172 | ADHEr, ATPS4r, FRD and/or SUCD4, HEX1, LDH_D, PGL and/or G6PDHy, PPS |
| 409 | 7 | 5.71588 | 0.18172 | ADHEr, ATPS4r, FRD and/or SUCD4, HEX1, LDH_D, PGDH, PPS |
| 410 | 7 | 5.70575 | 0.12457 | ADHEr, ASPT, ATPS4r, GLCpts, LDH_D, MDH, PFLi |
| 411 | 7 | 5.69395 | 0.07981 | ADHEr, ATPS4r, EDA and/or PGDHY, FRD and/or SUCD4, LDH_D, MDH, PPCK |
| 412 | 7 | 5.68826 | 0.10159 | ADHEr, EDA and/or PGDHY, GLCpts, LDH_D, PFLi, PGI, PPCK |
| 413 | 7 | 5.6857 | 0.18276 | ADHEr, ATPS4r, FRD and/or SUCD4, HEX1, LDH_D, PPS, TAL |
| 414 | 7 | 5.67373 | 0.1078 | ACKr and/or PTAr, ADHEr, EDA and/or PGDHY, LDH_D, PFLi, PGI, PPCK |
| 415 | 7 | 5.67231 | 0.09516 | ACKr and/or PTAr, ADHEr, ATPS4r, EDA and/or PGDHY, FRD and/or SUCD4, LDH_D, MDH |
| 416 | 7 | 5.65788 | 0.18372 | ADHEr, ATPS4r, FRD and/or SUCD4, HEX1, LDH_D, PPS, RPE |
| 417 | 7 | 5.65108 | 0.11748 | ADHEr, EDA and/or PGDHY, GLCpts, LDH_D, NADH6, PFLi, PGI |
| 418 | 7 | 5.64055 | 0.12198 | ACKr and/or PTAr, ADHEr, EDA and/or PGDHY, LDH_D, NADH6, PFLi, PGI |
| 419 | 7 | 5.63038 | 0.12633 | ADHEr, LDH_D, MDH, NADH12, NADH6, PFLi, PGI |
| 420 | 7 | 5.63037 | 0.14151 | ADHEr, FRD and/or SUCD4, HEX1, LDH_D, PPS, SUCOAS, THD2 and/or GLUDy |
| 421 | 7 | 5.61946 | 0.14377 | ADHEr, ATPS4r, EDA and/or PGDHY, FRD and/or SUCD4, LDH_D, MDH, SUCOAS |
| 422 | 7 | 5.61946 | 0.14377 | ADHEr, ATPS4r, EDA and/or PGDHY, LDH_D, MDH, NADH6, SUCOAS |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 423 | 7 | 5.60713 | 0.15264 | ADHEr, FRD and/or SUCD4, HEX1, LDH_D, MALS, PPS, THD2 and/or GLUDy |
| 424 | 7 | 5.60713 | 0.15264 | ADHEr, FRD and/or SUCD4, HEX1, ICL, LDH_D, PPS, THD2 and/or GLUDy |
| 425 | 7 | 5.60017 | 0.14365 | ADHEr, ATPS4r, FRD and/or SUCD4, LDH_D, MDH, PGDH, SUCOAS |
| 426 | 7 | 5.59518 | 0.14138 | ADHEr, FUM, LDH_D, NADH12, NADH6, PFLi, PGI |
| 427 | 7 | 5.59117 | 0.14212 | ADHEr, ATPS4r, FRD and/or SUCD4, FUM, LDH_D, MDH, PGDH |
| 428 | 7 | 5.58992 | 0.13977 | ADHEr, ATPS4r, FRD and/or SUCD4, LDH_D, MDH, PGDH, TAL |
| 429 | 7 | 5.57521 | 0.1433 | ADHEr, HEX1, LDH_D, MDH, PPS, SUCOAS, THD2 and/or GLUDy |
| 430 | 7 | 5.57521 | 0.1433 | ADHEr, FUM, HEX1, LDH_D, PPS, SUCOAS, THD2 and/or GLUDy |
| 431 | 7 | 5.56382 | 0.059 | ADHEr, HEX1, LDH_D, PFLi, PGI, PPS, THD2 and/or GLUDy |
| 432 | 7 | 5.55714 | 0.14423 | ADHEr, ASPT, EDA and/or PGDHY, FUM, LDH_D, MDH, THD2 and/or GLUDy |
| 433 | 7 | 5.5551 | 0.14719 | ADHEr, HEX1, LDH_D, MDH, NADH6, SUCOAS, THD2 and/or GLUDy |
| 434 | 7 | 5.54832 | 0.1485 | ADHEr, ASPT, HEX1, LDH_D, MDH, SUCOAS, THD2 and/or GLUDy |
| 435 | 7 | 5.54749 | 0.08705 | ADHEr, LDH_D, NADH12, NADH6, PFLi, PPCK, THD2 and/or GLUDy |
| 436 | 7 | 5.54 | 0.14449 | ADHEr, ATPS4r, LDH_D, MDH, NADH6, PGDH, SUCOAS |
| 437 | 7 | 5.53962 | 0.15019 | ADHEr, ASPT, ATPS4r, EDA and/or PGDHY, LDH_D, MDH, SUCOAS |
| 438 | 7 | 5.53831 | 0.08799 | ADHEr, LDH_D, MDH, NADH6, PFLi, PPCK, THD2 and/or GLUDy |
| 439 | 7 | 5.53831 | 0.08799 | ADHEr, FUM, LDH_D, NADH6, PFLi, PPCK, THD2 and/or GLUDy |
| 440 | 7 | 5.53405 | 0.05732 | ACKr and/or PTAr, ADHEr, ASPT, EDA and/or PGDHY, LDH_D, MDH, PGI |
| 441 | 7 | 5.52463 | 0.06237 | ADHEr, ASPT, ATPS4r, EDA and/or PGDHY, LDH_D, MDH, PGI |
| 442 | 7 | 5.51713 | 0.16489 | ADHEr, ATPS4r, FDH2, LDH_D, MDH, NADH6, SUCOAS |
| 443 | 7 | 5.51587 | 0.14532 | ADHEr, ATPS4r, LDH_D, MDH, NADH6, SUCOAS, TAL |
| 444 | 7 | 5.51034 | 0.14586 | ADHEr, ATPS4r, LDH_D, MDH, NADH6, PFLi, PGDH |
| 445 | 7 | 5.51034 | 0.14586 | ADHEr, ATPS4r, FDH2, LDH_D, MDH, NADH6, PGDH |
| 446 | 7 | 5.5014 | 0.07482 | ADHEr, ASPT, EDA and/or PGDHY, GLCpts, LDH_D, MDH, PGI |
| 447 | 7 | 5.49363 | 0.14609 | ADHEr, ATPS4r, LDH_D, MDH, NADH6, RPE, SUCOAS |
| 448 | 7 | 5.49315 | 0.18499 | ACKr and/or PTAr, ADHEr, EDA and/or PGDHY, HEX1, LDH_D, PFLi, PGI |
| 449 | 7 | 5.48581 | 0.14671 | ADHEr, ATPS4r, LDH_D, MDH, NADH6, PFLi, TAL |
| 450 | 7 | 5.48581 | 0.14671 | ADHEr, ATPS4r, FDH2, LDH_D, MDH, NADH6, TAL |
| 451 | 7 | 5.47686 | 0.19195 | ADHEr, EDA and/or PGDHY, LDH_D, MDH, NADH6, PGI, THD5 |
| 452 | 7 | 5.47123 | 0.12153 | ADHEr, GLCpts, LDH_D, MDH, PFLi, PPCK, THD2 and/or GLUDy |
| 453 | 7 | 5.47123 | 0.12153 | ADHEr, FUM, GLCpts, LDH_D, PFLi, PPCK, THD2 and/or GLUDy |
| 454 | 7 | 5.46318 | 0.14749 | ADHEr, ATPS4r, FDH2, LDH_D, MDH, NADH6, RPE |
| 455 | 7 | 5.46318 | 0.14749 | ADHEr, ATPS4r, LDH_D, MDH, NADH6, PFLi, RPE |
| 456 | 7 | 5.43967 | 0.13732 | ADHEr, GLCpts, LDH_D, MDH, NADH6, PFLi, THD2 and/or GLUDy |
| 457 | 7 | 5.41442 | 0.15603 | ADHEr, ASPT, FUM, HEX1, LDH_D, MDH, THD2 and/or GLUDy |
| 458 | 7 | 5.41442 | 0.15603 | ADHEr, ASPT, HEX1, LDH_D, MALS, MDH, THD2 and/or GLUDy |
| 459 | 7 | 5.41442 | 0.15603 | ADHEr, ASPT, HEX1, ICL, LDH_D, MDH, THD2 and/or GLUDy |
| 460 | 7 | 5.32088 | 0.07204 | ADHEr, FRD and/or SUCD4, HEX1, LDH_D, PPCK, SUCOAS, THD2 and/or GLUDy |
| 461 | 7 | 5.29376 | 0.07385 | ADHEr, FRD and/or SUCD4, HEX1, LDH_D, MALS, PPCK, THD2 and/or GLUDy |
| 462 | 7 | 5.29376 | 0.07385 | ADHEr, FRD and/or SUCD4, HEX1, ICL, LDH_D, PPCK, THD2 and/or GLUDy |
| 463 | 7 | 5.29342 | 0.0731 | ADHEr, HEX1, LDH_D, MDH, PPCK, SUCOAS, THD2 and/or GLUDy |
| 464 | 7 | 5.29342 | 0.0731 | ADHEr, FUM, HEX1, LDH_D, PPCK, SUCOAS, THD2 and/or GLUDy |
| 465 | 7 | 5.20741 | 0.07603 | ADHEr, ASPT, ATPS4r, FUM, LDH_D, PGDH, PPCK |
| 466 | 7 | 5.20741 | 0.07603 | ADHEr, ASPT, ATPS4r, FUM, LDH_D, PGL and/or G6PDHy, PPCK |
| 467 | 7 | 5.20289 | 0.16585 | ACKr and/or PTAr, ADHEr, ASPT, LDH_D, MDH, PFLi, RPE |
| 468 | 7 | 5.19469 | 0.07664 | ADHEr, ASPT, ATPS4r, FUM, LDH_D, PPCK, TAL |
| 469 | 7 | 5.18818 | 0.16709 | ACKr and/or PTAr, ADHEr, ASPT, LDH_D, MDH, PFLi, TAL |
| 470 | 7 | 5.18292 | 0.0772 | ADHEr, ASPT, ATPS4r, FUM, LDH_D, PPCK, RPE |
| 471 | 7 | 5.18092 | 0.10975 | ADHEr, FUM, GLCpts, LDH_D, PFLi, PGI, PPCK |
| 472 | 7 | 5.18092 | 0.10975 | ADHEr, GLCpts, LDH_D, MDH, PFLi, PGI, PPCK |
| 473 | 7 | 5.18025 | 0.13169 | ACKr and/or PTAr, ADHEr, GLCpts, LDH_D, MDH, PFLi, PPCK |
| 474 | 7 | 5.18025 | 0.13169 | ACKr and/or PTAr, ADHEr, FUM, GLCpts, LDH_D, PFLi, PPCK |
| 475 | 7 | 5.17526 | 0.14527 | ADHEr, ATPS4r, LDH_D, MDH, NADH12, NADH6, PFLi |
| 476 | 7 | 5.15999 | 0.12483 | ADHEr, GLCpts, LDH_D, MDH, NADH6, PFLi, PGI |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 477 | 7 | 5.15742 | 0.1471 | ADHEr, ATPS4r, GLCpts, LDH_D, MDH, NADH6, PFLi |
| 478 | 7 | 5.13283 | 0.14064 | ACKr and/or PTAr, ADHEr, LDH_D, MDH, PFLi, PGI, PPCK |
| 479 | 7 | 5.13283 | 0.14064 | ACKr and/or PTAr, ADHEr, FUM, LDH_D, PFLi, PGI, PPCK |
| 480 | 7 | 5.11128 | 0.1487 | ACKr and/or PTAr, ADHEr, GLCpts, LDH_D, MDH, NADH6, PFLi |
| 481 | 7 | 5.10917 | 0.0835 | ADHEr, EDA and/or PGDHY, GLCpts, LDH_D, NADH6, PGI, PPCK |
| 482 | 7 | 5.10795 | 0.18114 | ADHEr, ASPT, ATPS4r, EDA and/or PGDHY, LDH_D, MDH, PGDH |
| 483 | 7 | 5.08422 | 0.18199 | ADHEr, ASPT, ATPS4r, EDA and/or PGDHY, LDH_D, MDH, TAL |
| 484 | 7 | 5.08162 | 0.15602 | ACKr and/or PTAr, ADHEr, LDH_D, NADH12, NADH6, PFLi, PGI |
| 485 | 7 | 5.08154 | 0.15604 | ACKr and/or PTAr, ADHEr, LDH_D, MDH, NADH6, PFLi, PGI |
| 486 | 7 | 5.07957 | 0.15652 | ACKr and/or PTAr, ADHEr, FUM, LDH_D, MDH, NADH6, PFLi, PGI |
| 487 | 7 | 5.06238 | 0.18278 | ADHEr, ASPT, ATPS4r, EDA and/or PGDHY, LDH_D, MDH, RPE |
| 488 | 7 | 5.04933 | 0.08188 | ADHEr, ATPS4r, FDH2, LDH_D, NADH6, PPCK, SUCOAS |
| 489 | 7 | 5.04086 | 0.10883 | ACKr and/or PTAr, ADHEr, LDH_D, MDH, NADH6, PGDH, PGI |
| 490 | 7 | 5.03782 | 0.10979 | ACKr and/or PTAr, ADHEr, LDH_D, MDH, NADH6, PGI, TAL |
| 491 | 7 | 5.03499 | 0.11069 | ACKr and/or PTAr, ADHEr, LDH_D, MDH, NADH6, PGI, RPE |
| 492 | 7 | 5.0347 | 0.123 | ACKr and/or PTAr, ADHEr, ATPS4r, LDH_D, MDH, NADH6, SUCOAS |
| 493 | 7 | 5.02325 | 0.08242 | ADHEr, ATPS4r, LDH_D, MDH, PPCK, SUCOAS |
| 494 | 7 | 5.02325 | 0.08242 | ADHEr, ATPS4r, FUM, LDH_D, NADH6, PPCK, SUCOAS |
| 495 | 7 | 5.02233 | 0.1115 | ADHEr, GLCpts, LDH_D, NADH6, PFLi, PPCK, THD2 and/or GLUDy |
| 496 | 7 | 5.00367 | 0.01301 | ADHEr, ATPS4r, LDH_D, MDH, NADH6, SUCOAS, THD2 and/or GLUDy |
| 497 | 7 | 5.00099 | 0.08371 | ADHEr, ASPT, ATPS4r, FUM, LDH_D, PPCK, SUCOAS |
| 498 | 7 | 4.9785 | 0.07565 | ADHEr, ATPS4r, FDH2, LDH_D, NADH6, SUCOAS, THD2 and/or GLUDy |
| 499 | 7 | 4.97218 | 0.04755 | ADHEr, EDA and/or PGDHY, HEX1, LDH_D, NADH6, PGI, THD2 and/or GLUDy |
| 500 | 7 | 4.96921 | 0.01295 | ADHEr, FRD and/or SUCD4, GLUDy, LDH_D, MDH, SUCOAS, THD2 and/or GLUDy |
| 501 | 7 | 4.96716 | 0.01165 | ADHEr, GLUDy, HEX1, LDH_D, MDH, SUCOAS, THD2 and/or GLUDy |
| 502 | 7 | 4.96611 | 0.01426 | ADHEr, FRD and/or SUCD4, GLCpts, LDH_D, MDH, SUCOAS, THD2 and/or GLUDy |
| 503 | 7 | 4.96543 | 0.01322 | ADHEr, FRD and/or SUCD4, GLUDy, ICL, LDH_D, MDH, THD2 and/or GLUDy |
| 504 | 7 | 4.96543 | 0.01322 | ADHEr, FRD and/or SUCD4, GLUDy, LDH_D, MALS, MDH, THD2 and/or GLUDy |
| 505 | 7 | 4.96335 | 0.01401 | ADHEr, AKGD, FRD and/or SUCD4, ICL, LDH_D, PPCK, THD2 and/or GLUDy |
| 506 | 7 | 4.96335 | 0.01401 | ADHEr, AKGD, FRD and/or SUCD4, LDH_D, MALS, PPCK, THD2 and/or GLUDy |
| 507 | 7 | 4.96309 | 0.0131 | ADHEr, GLUDy, LDH_D, MDH, NADH6, SUCOAS, THD2 and/or GLUDy |
| 508 | 7 | 4.96271 | 0.01323 | ADHEr, ASPT, GLUDy, LDH_D, MDH, SUCOAS, THD2 and/or GLUDy |
| 509 | 7 | 4.96187 | 0.01458 | ADHEr, FRD and/or SUCD4, GLCpts, LDH_D, MALS, MDH, THD2 and/or GLUDy |
| 510 | 7 | 4.96187 | 0.01458 | ADHEr, FRD and/or SUCD4, GLCpts, ICL, LDH_D, MDH, THD2 and/or GLUDy |
| 511 | 7 | 4.95873 | 0.01465 | ADHEr, ASPT, GLCpts, LDH_D, MDH, SUCOAS, THD2 and/or GLUDy |
| 512 | 7 | 4.95686 | 0.01531 | ADHEr, ASPT, LDH_D, MDH, PYK, SUCOAS, THD2 and/or GLUDy |
| 513 | 7 | 4.95085 | 0.01406 | ADHEr, ASPT, GLUDy, LDH_D, MALS, MDH, THD2 and/or GLUDy |
| 514 | 7 | 4.95085 | 0.01406 | ADHEr, ASPT, GLUDy, ICL, LDH_D, MDH, THD2 and/or GLUDy |
| 515 | 7 | 4.94529 | 0.0136 | ACKr and/or PTAr, ADHEr, FRD and/or SUCD4, GLUDy, LDH_D, MDH, THD2 and/or GLUDy |
| 516 | 7 | 4.94524 | 0.01566 | ADHEr, ASPT, GLCpts, LDH_D, MALS, MDH, THD2 and/or GLUDy |
| 517 | 7 | 4.94524 | 0.01566 | ADHEr, ASPT, GLCpts, ICL, LDH_D, MDH, THD2 and/or GLUDy |
| 518 | 7 | 4.94393 | 0.07737 | ADHEr, ATPS4r, FUM, LDH_D, NADH6, SUCOAS, THD2 and/or GLUDy |
| 519 | 7 | 4.94353 | 0.01615 | ADHEr, ASPT, FUM, LDH_D, MDH, PYK, THD2 and/or GLUDy |
| 520 | 7 | 4.94353 | 0.01615 | ADHEr, ASPT, ICL, LDH_D, MDH, PYK, THD2 and/or GLUDy |
| 521 | 7 | 4.94353 | 0.01615 | ADHEr, ASPT, LDH_D, MALS, MDH, PYK, THD2 and/or GLUDy |
| 522 | 7 | 4.94073 | 0.01473 | ACKr and/or PTAr, ADHEr, FRD and/or SUCD4, GLCpts, LDH_D, MDH, THD2 and/or GLUDy |
| 523 | 7 | 4.9406 | 0.01618 | ACKr and/or PTAr, ADHEr, LDH_D, MDH, NADH6, PYK, THD2 and/or GLUDy |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 524 | 7 | 4.93746 | 0.13888 | ADHEr, ASPT, ATPS4r, GLCpts, LDH_D, MDH, NADH6 |
| 525 | 7 | 4.93038 | 0.19331 | ACKr and/or PTAr, ADHEr, ATPS4r, LDH_D, MDH, NADH6, PGDH |
| 526 | 7 | 4.92604 | 0.19438 | ACKr and/or PTAr, ADHEr, ATPS4r, LDH_D, MDH, NADH6, TAL |
| 527 | 7 | 4.92485 | 0.04913 | ACKr and/or PTAr, ADHEr, HEX1, LDH_D, NADH6, PGI, THD2 and/or GLUDy |
| 528 | 7 | 4.92203 | 0.19537 | ACKr and/or PTAr, ADHEr, ATPS4r, LDH_D, MDH, NADH6, RPE |
| 529 | 7 | 4.89572 | 0.18301 | ACKr and/or PTAr, ADHEr, ASPT, ATPS4r, LDH_D, MDH, PGDH |
| 530 | 7 | 4.88586 | 0.18375 | ACKr and/or PTAr, ADHEr, ASPT, ATPS4r, LDH_D, MDH, TAL |
| 531 | 7 | 4.8768 | 0.18443 | ACKr and/or PTAr, ADHEr, ASPT, ATPS4r, LDH_D, MDH, RPE |
| 532 | 7 | 4.87463 | 0.19612 | ACKr and/or PTAr, ADHEr, LDH_D, MDH, NADH6, PGI, THD5 |
| 533 | 7 | 4.87463 | 0.19612 | ACKr and/or PTAr, ADHEr, FUM, LDH_D, NADH6, PGI, THD5 |
| 534 | 7 | 4.85806 | 0.05038 | ADHEr, LDH_D, MDH, NADH12, NADH6, SUCOAS, THD2 and/or GLUDy |
| 535 | 7 | 4.85603 | 0.21579 | ADHEr, ASPT, ATPS4r, FUM, HEX1, LDH_D, PPS |
| 536 | 7 | 4.84975 | 0.05712 | ADHEr, FRD and/or SUCD4, LDH_D, MDH, PGL and/or G6PDHy, PPCK, PYK |
| 537 | 7 | 4.84975 | 0.05712 | ADHEr, EDA and/or PGDHY, FRD and/or SUCD4, LDH_D, MDH, PPCK, PYK |
| 538 | 7 | 4.81569 | 0.05271 | ADHEr, ASPT, FUM, GLCpts, LDH_D, PPCK, THD2 and/or GLUDy |
| 539 | 7 | 4.81323 | 0.1198 | ADHEr, ATPS4r, GLCpts, LDH_D, NADH6, PFLi, PPCK |
| 540 | 7 | 4.81194 | 0.09049 | ADHEr, FRD and/or SUCD4, LDH_D, PPCK, PYK, RPE, SUCOAS |
| 541 | 7 | 4.81179 | 0.07918 | ADHEr, LDH_D, NADH12, NADH6, PPCK, SUCOAS, THD2 and/or GLUDy |
| 542 | 7 | 4.79812 | 0.05498 | ACKr and/or PTAr, ADHEr, FUM, LDH_D, MDH, NADH6, THD2 and/or GLUDy |
| 543 | 7 | 4.79812 | 0.05498 | ACKr and/or PTAr, ADHEr, LDH_D, MALS, MDH, NADH6, THD2 and/or GLUDy |
| 544 | 7 | 4.79812 | 0.05498 | ACKr and/or PTAr, ADHEr, ICL, LDH_D, MDH, NADH6, THD2 and/or GLUDy |
| 545 | 7 | 4.79409 | 0.12192 | ADHEr, ATPS4r, LDH_D, NADH12, NADH6, PFLi, PPCK |
| 546 | 7 | 4.79101 | 0.05495 | ACKr and/or PTAr, ADHEr, ASPT, FUM, LDH_D, MDH, THD2 and/or GLUDy |
| 547 | 7 | 4.78296 | 0.12315 | ADHEr, ATPS4r, LDH_D, MDH, NADH6, PFLi, PPCK |
| 548 | 7 | 4.78296 | 0.12315 | ADHEr, ATPS4r, FUM, LDH_D, NADH6, PFLi, PPCK |
| 549 | 7 | 4.77588 | 0.08569 | ADHEr, AKGD, FRD and/or SUCD4, LDH_D, MALS, MDH, THD2 and/or GLUDy |
| 550 | 7 | 4.77588 | 0.08569 | ADHEr, AKGD, FRD and/or SUCD4, ICL, LDH_D, MDH, THD2 and/or GLUDy |
| 551 | 7 | 4.77561 | 0.07964 | ADHEr, FUM, LDH_D, NADH6, PPCK, SUCOAS, THD2 and/or GLUDy |
| 552 | 7 | 4.77561 | 0.07964 | ADHEr, LDH_D, MDH, NADH6, PPCK, SUCOAS, THD2 and/or GLUDy |
| 553 | 7 | 4.77329 | 0.08047 | ADHEr, ASPT, LDH_D, MDH, PPCK, SUCOAS, THD2 and/or GLUDy |
| 554 | 7 | 4.77329 | 0.08047 | ADHEr, ASPT, FUM, LDH_D, PPCK, SUCOAS, THD2 and/or GLUDy |
| 555 | 7 | 4.7705 | 0.16052 | ADHEr, ATPS4r, FDH2, GLCpts, LDH_D, MDH, NADH6 |
| 556 | 7 | 4.76518 | 0.08334 | ADHEr, FUM, HEX1, LDH_D, NADH6, SUCOAS, THD2 and/or GLUDy |
| 557 | 7 | 4.76374 | 0.0222 | ADHEr, ASPT, ATPS4r, GLCpts, LDH_D, MDH, THD2 and/or GLUDy |
| 558 | 7 | 4.76264 | 0.08425 | ADHEr, ASPT, FUM, HEX1, LDH_D, SUCOAS, THD2 and/or GLUDy |
| 559 | 7 | 4.74028 | 0.09218 | ADHEr, FUM, LDH_D, NADH6, PPCK, PYK, SUCOAS |
| 560 | 7 | 4.74028 | 0.09218 | ADHEr, LDH_D, MDH, NADH6, PPCK, PYK, SUCOAS |
| 561 | 7 | 4.73717 | 0.09329 | ADHEr, ASPT, LDH_D, MDH, PPCK, PYK, SUCOAS |
| 562 | 7 | 4.73717 | 0.09329 | ADHEr, ASPT, FUM, LDH_D, PPCK, PYK, SUCOAS |
| 563 | 7 | 4.71257 | 0.12092 | ADHEr, GLCpts, LDH_D, MDH, NADH6, SUCOAS, THD2 and/or GLUDy |
| 564 | 7 | 4.69803 | 0.08636 | ADHEr, ASPT, FUM, LDH_D, MALS, PPCK, THD2 and/or GLUDy |
| 565 | 7 | 4.69803 | 0.08636 | ADHEr, ASPT, FUM, ICL, LDH_D, PPCK, THD2 and/or GLUDy |
| 566 | 7 | 4.69803 | 0.08636 | ADHEr, ASPT, LDH_D, MALS, MDH, PPCK, THD2 and/or GLUDy |
| 567 | 7 | 4.69803 | 0.08636 | ADHEr, ASPT, ICL, LDH_D, MDH, PPCK, THD2 and/or GLUDy |
| 568 | 7 | 4.68998 | 0.14917 | ADHEr, FRD and/or SUCD4, LDH_D, MDH, RPE, SUCOAS, THD2 and/or GLUDy |
| 569 | 7 | 4.68111 | 0.0912 | ADHEr, ASPT, FUM, HEX1, LDH_D, MALS, THD2 and/or GLUDy |
| 570 | 7 | 4.68111 | 0.0912 | ADHEr, ASPT, FUM, HEX1, ICL, LDH_D, THD2 and/or GLUDy |
| 571 | 7 | 4.68063 | 0.05195 | ACKr and/or PTAr, ADHEr, LDH_D, MDH, NADH6, SUCOAS, THD2 and/or GLUDy |
| 572 | 7 | 4.67974 | 0.09159 | ADHEr, AKGD, ASPT, LDH_D, MALS, MDH, THD2 and/or GLUDy |
| 573 | 7 | 4.67974 | 0.09159 | ADHEr, AKGD, ASPT, ICL, LDH_D, MDH, THD2 and/or GLUDy |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 574 | 7 | 4.6782 | 0.13538 | ACKr and/or PTAr, ADHEr, FRD and/or SUCD4, LDH_D, MDH, SUCOAS, THD2 and/or GLUDy |
| 575 | 7 | 4.67079 | 0.08656 | ACKr and/or PTAr, ADHEr, ASPT, FUM, LDH_D, PPCK, THD2 and/or GLUDy |
| 576 | 7 | 4.66866 | 0.1492 | ADHEr, FRD and/or SUCD4, LDH_D, MDH, SUCOAS, TAL, THD2 and/or GLUDy |
| 577 | 7 | 4.66526 | 0.1329 | ADHEr, HEX1, LDH_D, MDH, RPE, SUCOAS, THD2 and/or GLUDy |
| 578 | 7 | 4.65177 | 0.09959 | ADHEr, ASPT, LDH_D, MALS, MDH, PPCK, PYK |
| 579 | 7 | 4.65177 | 0.09959 | ADHEr, ASPT, ICL, LDH_D, MDH, PPCK, PYK |
| 580 | 7 | 4.65148 | 0.09163 | ACKr and/or PTAr, ADHEr, ASPT, FUM, HEX1, LDH_D, THD2 and/or GLUDy |
| 581 | 7 | 4.64795 | 0.13132 | ADHEr, ATPS4r, HEX1, LDH_D, MDH, SUCOAS, THD2 and/or GLUDy |
| 582 | 7 | 4.64717 | 0.13258 | ADHEr, HEX1, LDH_D, MDH, SUCOAS, TAL, THD2 and/or GLUDy |
| 583 | 7 | 4.63555 | 0.16411 | ADHEr, FRD and/or SUCD4, GLCpts, LDH_D, MDH, SUCOAS, TAL |
| 584 | 7 | 4.62743 | 0.13223 | ADHEr, HEX1, LDH_D, MDH, PGDH, SUCOAS, THD2 and/or GLUDy |
| 585 | 7 | 4.62722 | 0.10661 | ADHEr, AKGD, ASPT, ICL, LDH_D, MDH, PYK |
| 586 | 7 | 4.62722 | 0.10661 | ADHEr, AKGD, ASPT, LDH_D, MALS, MDH, PYK |
| 587 | 7 | 4.61442 | 0.12597 | ACKr and/or PTAr, ADHEr, ATPS4r, FUM, LDH_D, PPCK, THD2 and/or GLUDy |
| 588 | 7 | 4.60692 | 0.10476 | ACKr and/or PTAr, ADHEr, ASPT, ATPS4r, LDH_D, MDH, PGI |
| 589 | 7 | 4.60239 | 0.15202 | ADHEr, AKGD, FRD and/or SUCD4, HEX1, LDH_D, MALS, THD2 and/or GLUDy |
| 590 | 7 | 4.60239 | 0.15202 | ADHEr, AKGD, FRD and/or SUCD4, HEX1, ICL, LDH_D, THD2 and/or GLUDy |
| 591 | 7 | 4.59777 | 0.03574 | ACKr and/or PTAr, ADHEr, GLUDy, LDH_D, MDH, NADH6, THD2 and/or GLUDy |
| 592 | 7 | 4.59693 | 0.17398 | ADHEr, ASPT, FRD and/or SUCD4, LDH_D, MDH, PYK, RPE |
| 593 | 7 | 4.59408 | 0.12607 | ADHEr, ASPT, ATPS4r, GLCpts, LDH_D, MDH, PPCK |
| 594 | 7 | 4.588 | 0.17333 | ADHEr, ASPT, LDH_D, MDH, NADH6, PYK, SUCOAS |
| 595 | 7 | 4.58269 | 0.16568 | ADHEr, ASPT, GLCpts, LDH_D, MDH, RPE, SUCOAS |
| 596 | 7 | 4.5614 | 0.17413 | ADHEr, ASPT, LDH_D, MDH, PYK, RPE, SUCOAS |
| 597 | 7 | 4.55514 | 0.12723 | ADHEr, ASPT, FUM, GLCpts, LDH_D, MDH, THD2 and/or GLUDy |
| 598 | 7 | 4.54823 | 0.19006 | ACKr and/or PTAr, ADHEr, FRD and/or SUCD4, HEX1, LDH_D, SUCOAS, THD2 and/or GLUDy |
| 599 | 7 | 4.54674 | 0.19069 | ACKr and/or PTAr, ADHEr, ATPS4r, FRD and/or SUCD4, HEX1, LDH_D, SUCOAS |
| 600 | 7 | 4.53866 | 0.20774 | ADHEr, FRD and/or SUCD4, HEX1, LDH_D, SUCOAS, TAL, THD2 and/or GLUDy |
| 601 | 7 | 4.53699 | 0.1728 | ADHEr, FRD and/or SUCD4, FUM, LDH_D, MDH, PYK, TAL |
| 602 | 7 | 4.53586 | 0.209 | ADHEr, ATPS4r, FRD and/or SUCD4, HEX1, LDH_D, SUCOAS, TAL |
| 603 | 7 | 4.51849 | 0.13149 | ADHEr, ATPS4r, FDH2, GLCpts, LDH_D, NADH6, PPCK |
| 604 | 7 | 4.51845 | 0.20259 | ADHEr, FDH2, LDH_D, MDH, NADH12, NADH6, SUCOAS |
| 605 | 7 | 4.50909 | 0.20652 | ADHEr, ATPS4r, FRD and/or SUCD4, HEX1, LDH_D, SUCOAS, THD2 and/or GLUDy |
| 606 | 7 | 4.50549 | 0.20804 | ADHEr, FRD and/or SUCD4, GLU5K, HEX1, LDH_D, SUCOAS, THD2 and/or GLUDy |
| 607 | 7 | 4.50549 | 0.20804 | ADHEr, FRD and/or SUCD4, G5SD, HEX1, LDH_D, SUCOAS, THD2 and/or GLUDy |
| 608 | 7 | 4.50543 | 0.20807 | ADHEr, ASNS2, FRD and/or SUCD4, HEX1, LDH_D, SUCOAS, THD2 and/or GLUDy |
| 609 | 7 | 4.50378 | 0.20876 | ADHEr, HEX1, LDH_D, NADH12, NADH6, SUCOAS, THD2 and/or GLUDy |
| 610 | 7 | 4.50198 | 0.20952 | ADHEr, ATPS4r, FDH2, HEX1, LDH_D, NADH6, SUCOAS |
| 611 | 3 | 0.669528208 | 0.263200019 | ADHEr, FADH4, LDH_D |
| 612 | 3 | 0.110808857 | 0.249569497 | ADHEr, LDH_D, PFK and/or FBA and/or TPI |
| 613 | 4 | 0.93088625 | 0.384018912 | ADHEr, ATPS4r, CBMK2, LDH_D |
| 614 | 4 | 1.163912961 | 0.378757536 | ADHEr, ATPS4r, LDH_D, TKT2 |
| 615 | 4 | 4.552254757 | 0.171189177 | ADHEr, FADH4, LDH_D, MDH |
| 616 | 4 | 0.710935568 | 0.257359864 | ADHEr, FADH4, LDH_D, RPE |
| 617 | 4 | 0.702400877 | 0.260125701 | ADHEr, FADH4, LDH_D, TAL |
| 618 | 4 | 0.719290675 | 0.254652225 | ADHEr, FADH4, LDH_D, TKT2 |
| 619 | 4 | 2.283994469 | 0.165173433 | ADHEr, LDH_D, PFK and/or FBA and/or TPI, PPCK |
| 620 | 4 | 0.18159615 | 0.246009686 | ADHEr, LDH_D, PFK and/or FBA and/or TPI, TKT2 |
| 621 | 4 | 4.555303308 | 0.170023606 | ADHEr, FRD and/or SUCD4, LDH_D, ME2 |
| 622 | 4 | 0.710935568 | 0.257359864 | ADHEr, FRD and/or SUCD4, LDH_D, RPE |
| 623 | 4 | 0.702400877 | 0.260125701 | ADHEr, FRD and/or SUCD4, LDH_D, TAL |
| 624 | 4 | 0.753832099 | 0.262897433 | ADHEr, FRD and/or SUCD4, LDH_D, THD2 and/or GLUDy |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 625 | 4 | 0.719290675 | 0.254652225 | ADHEr, FRD and/or SUCD4, LDH_D, TKT2 |
| 626 | 4 | 2.165485624 | 0.255793845 | ADHEr, FUM, LDH_D, PPCK |
| 627 | 4 | 2.279039418 | 0.168962421 | ADHEr, HEX1, LDH_D, PFK and/or FBA and/or TPI |
| 628 | 4 | 0.24281895 | 0.340878264 | ADHEr, HEX1, LDH_D, MDH |
| 629 | 4 | 2.165485624 | 0.255793845 | ADHEr, LDH_D, MDH, PPCK |
| 630 | 4 | 4.555303308 | 0.170023606 | ADHEr, FADH4, LDH_D, ME2 |
| 631 | 4 | 2.575639756 | 0.188350402 | ADHEr, LDH_D, NADH6, PFK and/or FBA and/or TPI |
| 632 | 4 | 2.359364668 | 0.333057496 | ADHEr, FUM, LDH_D, NADH6 |
| 633 | 4 | 2.365271913 | 0.329105029 | ADHEr, HEX1, LDH_D, NADH6 |
| 634 | 4 | 2.381170653 | 0.338701395 | ADHEr, LDH_D, NADH6, TAL |
| 635 | 4 | 2.440438621 | 0.335394947 | ADHEr, LDH_D, NADH6, TKT2 |
| 636 | 4 | 0.303924042 | 0.270354967 | ADHEr, LDH_D, PPCK, TKT2 |
| 637 | 4 | 0.276184314 | 0.387717801 | ADHEr, HEX1, LDH_D, PPS |
| 638 | 4 | 0.158957458 | 0.24714816 | ADHEr, LDH_D, PFK and/or FBA and/or TPI, RPE |
| 639 | 4 | 0.268683115 | 0.271077634 | ADHEr, LDH_D, PPCK, RPE |
| 640 | 4 | 2.268133298 | 0.177302028 | ADHEr, FRD and/or SUCD4, LDH_D, PFK and/or FBA and/or TPI |
| 641 | 4 | 2.303972218 | 0.174839451 | ADHEr, FRD and/or SUCD4, LDH_D, PGI |
| 642 | 4 | 2.202777355 | 0.227277897 | ADHEr, FRD and/or SUCD4, LDH_D, PPCK |
| 643 | 4 | 0.136108259 | 0.248297219 | ADHEr, LDH_D, PFK and/or FBA and/or TPI, TAL |
| 644 | 4 | 0.233253283 | 0.271804175 | ADHEr, LDH_D, PPCK, TAL |
| 645 | 4 | 0.753832099 | 0.262897433 | ADHEr, FADH4, LDH_D, THD2 and/or GLUDy |
| 646 | 4 | 1.00803743 | 0.384504476 | ADHEr, ATPS4r, LDH_D, TKT1 |
| 647 | 4 | 0.702400877 | 0.260125701 | ADHEr, FADH4, LDH_D, TKT1 |
| 648 | 4 | 0.136108259 | 0.248297219 | ADHEr, LDH_D, PFK and/or FBA and/or TPI, TKT1 |
| 649 | 4 | 0.702400877 | 0.260125701 | ADHEr, FRD and/or SUCD4, LDH_D, TKT1 |
| 650 | 4 | 2.381170653 | 0.338701395 | ADHEr, LDH_D, NADH6, TKT1 |
| 651 | 4 | 0.233253283 | 0.271804175 | ADHEr, LDH_D, PPCK, TKT1 |
| 652 | 5 | 0.506864978 | 0.275350379 | ADHEr, ASPT, FUM, LDH_D, TKT2 |
| 653 | 5 | 2.69303784 | 0.249064654 | ADHEr, ASPT, LDH_D, MDH, TKT2 |
| 654 | 5 | 4.367851715 | 0.180794605 | ADHEr, ASPT, FUM, LDH_D, ME2 |
| 655 | 5 | 0.41729748 | 0.278421057 | ADHEr, ASPT, FUM, LDH_D, RPE |
| 656 | 5 | 0.325709758 | 0.281560994 | ADHEr, ASPT, FUM, LDH_D, TAL |
| 657 | 5 | 2.645877173 | 0.251090969 | ADHEr, ASPT, LDH_D, MDH, TAL |
| 658 | 5 | 0.746129455 | 0.280922235 | ADHEr, ASPT, FUM, LDH_D, THD2 and/or GLUDy |
| 659 | 5 | 1.038232852 | 0.250484522 | ADHEr, ATPS4r, FADH4, LDH_D, SUCOAS |
| 660 | 5 | 1.091156432 | 0.260562519 | ADHEr, ATPS4r, FADH4, LDH_D, THD2 and/or GLUDy |
| 661 | 5 | 3.468709118 | 0.171072336 | ADHEr, ATPS4r, FRD and/or SUCD4, LDH_D, ME2 |
| 662 | 5 | 1.635653331 | 0.170872463 | ADHEr, ATPS4r, LDH_D, PFK and/or FBA and/or TPI, PFLi |
| 663 | 5 | 0.971889592 | 0.254878539 | ADHEr, ATPS4r, LDH_D, PPCK, PYK |
| 664 | 5 | 2.773151559 | 0.15594541 | ADHEr, ATPS4r, FRD and/or SUCD4, LDH_D, PGI |
| 665 | 5 | 0.794188757 | 0.220436537 | ADHEr, FADH4, HEX1, LDH_D, TKT2 |
| 666 | 5 | 4.635305085 | 0.167733685 | ADHEr, FADH4, LDH_D, MDH, TKT2 |
| 667 | 5 | 0.726213349 | 0.222710178 | ADHEr, FADH4, HEX1, LDH_D, RPE |
| 668 | 5 | 4.60885325 | 0.168834272 | ADHEr, FADH4, LDH_D, MDH, RPE |
| 669 | 5 | 4.600497528 | 0.168070055 | ADHEr, FADH4, LDH_D, MDH, SUCOAS |
| 670 | 5 | 4.582051994 | 0.169949398 | ADHEr, FADH4, LDH_D, MDH, TAL |
| 671 | 5 | 1.218736747 | 0.252980412 | ADHEr, FADH4, LDH_D, SUCOAS, THD2 and/or GLUDy |
| 672 | 5 | 2.323324205 | 0.162516565 | ADHEr, LDH_D, PFK and/or FBA and/or TPI, PPCK, TKT2 |
| 673 | 5 | 0.794188757 | 0.220436537 | ADHEr, FRD and/or SUCD4, HEX1, LDH_D, TKT2 |
| 674 | 5 | 1.080064187 | 0.261131964 | ADHEr, FRD and/or SUCD4, ICL, LDH_D, THD2 and/or GLUDy |
| 675 | 5 | 1.080064187 | 0.261131964 | ADHEr, FRD and/or SUCD4, LDH_D, MALS, THD2 and/or GLUDy |
| 676 | 5 | 4.635305085 | 0.167733685 | ADHEr, FRD and/or SUCD4, LDH_D, MDH, TKT2 |
| 677 | 5 | 4.611480051 | 0.167700442 | ADHEr, FRD and/or SUCD4, LDH_D, ME2, RPE |
| 678 | 5 | 4.603168381 | 0.166946432 | ADHEr, FRD and/or SUCD4, LDH_D, ME2, SUCOAS |
| 679 | 5 | 4.584877196 | 0.168800591 | ADHEr, FRD and/or SUCD4, LDH_D, ME2, TAL |
| 680 | 5 | 4.692124349 | 0.117711987 | ADHEr, FRD and/or SUCD4, LDH_D, ME2, THD2 and/or GLUDy |
| 681 | 5 | 4.637738386 | 0.16661454 | ADHEr, FRD and/or SUCD4, LDH_D, ME2, TKT2 |
| 682 | 5 | 4.582051994 | 0.169949398 | ADHEr, FRD and/or SUCD4, LDH_D, MDH, TAL |
| 683 | 5 | 1.218736747 | 0.252980412 | ADHEr, FRD and/or SUCD4, LDH_D, SUCOAS, THD2 and/or GLUDy |
| 684 | 5 | 2.22459069 | 0.253337321 | ADHEr, FUM, LDH_D, PPCK, TKT2 |
| 685 | 5 | 2.084553651 | 0.317680271 | ADHEr, FRD and/or SUCD4, FUM, GLU5K, LDH_D |
| 686 | 5 | 2.319043241 | 0.166454441 | ADHEr, HEX1, LDH_D, PFK and/or FBA and/or TPI, TKT2 |
| 687 | 5 | 0.379133409 | 0.337257295 | ADHEr, FUM, HEX1, LDH_D, TKT2 |
| 688 | 5 | 0.379133409 | 0.337257295 | ADHEr, HEX1, LDH_D, MDH, TKT2 |
| 689 | 5 | 1.080064187 | 0.261131964 | ADHEr, FADH4, ICL, LDH_D, THD2 and/or GLUDy |
| 690 | 5 | 1.080064187 | 0.261131964 | ADHEr, FADH4, LDH_D, MALS, THD2 and/or GLUDy |
| 691 | 5 | 2.22459069 | 0.253337321 | ADHEr, LDH_D, MDH, PPCK, TKT2 |
| 692 | 5 | 4.611480051 | 0.167700442 | ADHEr, FADH4, LDH_D, ME2, RPE |
| 693 | 5 | 4.603168381 | 0.166946432 | ADHEr, FADH4, LDH_D, ME2, SUCOAS |
| 694 | 5 | 4.584877196 | 0.168800591 | ADHEr, FADH4, LDH_D, ME2, TAL |
| 695 | 5 | 4.692124349 | 0.117711987 | ADHEr, FADH4, LDH_D, ME2, THD2 and/or GLUDy |
| 696 | 5 | 4.637738386 | 0.16661454 | ADHEr, FADH4, LDH_D, ME2, TKT2 |
| 697 | 5 | 2.871064894 | 0.268281645 | ACKr and/or PTAr, ADHEr, LDH_D, ME2, NADH6 |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 698 | 5 | 2.165924808 | 0.255458013 | ADHEr, FRD and/or SUCD4, FUM, LDH_D, ME2 |
| 699 | 5 | 4.328684855 | 0.179395311 | ACKr and/or PTAr, ADHEr, FRD and/or SUCD4, LDH_D, ME2 |
| 700 | 5 | 1.421860815 | 0.279607649 | ADHEr, FUM, LDH_D, ME2, THD2 and/or GLUDy |
| 701 | 5 | 2.626697246 | 0.185479991 | ADHEr, LDH_D, NADH6, PFK and/or FBA and/or TPI, TKT2 |
| 702 | 5 | 2.515320971 | 0.228708985 | ADHEr, FUM, LDH_D, NADH6, PPCK |
| 703 | 5 | 2.3870222 | 0.31455217 | ADHEr, FUM, HEX1, LDH_D, NADH6 |
| 704 | 5 | 2.452754421 | 0.325482265 | ADHEr, HEX1, LDH_D, NADH6, TKT2 |
| 705 | 5 | 2.515320971 | 0.228708985 | ADHEr, LDH_D, MDH, NADH6, PPCK |
| 706 | 5 | 2.517581576 | 0.273304492 | ADHEr, LDH_D, MDH, NADH6, TKT2 |
| 707 | 5 | 2.44490357 | 0.275824433 | ADHEr, FUM, LDH_D, ME2, NADH6 |
| 708 | 5 | 2.6103794 | 0.186397367 | ADHEr, LDH_D, NADH6, PFK and/or FBA and/or TPI, RPE |
| 709 | 5 | 2.555986853 | 0.242393036 | ADHEr, LDH_D, NADH6, PPCK, TKT2 |
| 710 | 5 | 2.421064631 | 0.329399782 | ADHEr, FUM, LDH_D, NADH6, RPE |
| 711 | 5 | 2.424713593 | 0.326643472 | ADHEr, HEX1, LDH_D, NADH6, RPE |
| 712 | 5 | 2.535155189 | 0.243219368 | ADHEr, LDH_D, NADH6, PPCK, RPE |
| 713 | 5 | 2.593899337 | 0.187323863 | ADHEr, LDH_D, NADH6, PFK and/or FBA and/or TPI, TAL |
| 714 | 5 | 2.391804455 | 0.331134392 | ADHEr, FUM, LDH_D, NADH6, TAL |
| 715 | 5 | 2.470792173 | 0.274926806 | ADHEr, LDH_D, MDH, NADH6, TAL |
| 716 | 5 | 2.514181006 | 0.244051353 | ADHEr, LDH_D, NADH6, PPCK, TAL |
| 717 | 5 | 0.318612958 | 0.180159999 | ACKr and/or PTAr, ADHEr, LDH_D, MDH, PFK and/or FBA and/or TPI |
| 718 | 5 | 2.298067641 | 0.164222738 | ADHEr, LDH_D, PFK and/or FBA and/or TPI, PPCK, TAL |
| 719 | 5 | 1.630847318 | 0.197351873 | ADHEr, LDH_D, MDH, PFK and/or FBA and/or TPI, PFLi |
| 720 | 5 | 4.068156517 | 0.116307981 | ADHEr, LDH_D, PFK and/or FBA and/or TPI, PFLi, PPCK |
| 721 | 5 | 1.630847318 | 0.197351873 | ADHEr, FUM, LDH_D, PFK and/or FBA and/or TPI, PFLi |
| 722 | 5 | 1.732749142 | 0.29901565 | ADHEr, FUM, HEX1, LDH_D, PFLi |
| 723 | 5 | 1.717432965 | 0.229711682 | ADHEr, HEX1, LDH_D, PFLi, PPCK |
| 724 | 5 | 3.998783556 | 0.193038233 | ADHEr, FRD and/or SUCD4, LDH_D, ME2, PFLi |
| 725 | 5 | 4.075902556 | 0.129526478 | ADHEr, LDH_D, NADH6, PFK and/or FBA and/or TPI, PFLi |
| 726 | 5 | 3.837085522 | 0.275765851 | ADHEr, LDH_D, NADH6, PFLi, RPE |
| 727 | 5 | 3.820196202 | 0.277060587 | ADHEr, LDH_D, NADH6, PFLi, TAL |
| 728 | 5 | 3.853817724 | 0.274483161 | ADHEr, LDH_D, NADH6, PFLi, TKT2 |
| 729 | 5 | 3.839632897 | 0.261974412 | ADHEr, FRD and/or SUCD4, LDH_D, PFLi, THD2 and/or GLUDy |
| 730 | 5 | 4.393030474 | 0.140852085 | ADHEr, EDA and/or PGDHY, FRD and/or SUCD4, LDH_D, PGI |
| 731 | 5 | 0.430495607 | 0.382946425 | ADHEr, HEX1, LDH_D, PPS, TKT2 |
| 732 | 5 | 0.381078242 | 0.384474433 | ADHEr, HEX1, LDH_D, PPS, RPE |
| 733 | 5 | 0.331264934 | 0.386014683 | ADHEr, HEX1, LDH_D, PPS, TAL |
| 734 | 5 | 0.331264934 | 0.386014683 | ADHEr, HEX1, LDH_D, PPS, TKT1 |
| 735 | 5 | 0.318612958 | 0.180159999 | ACKr and/or PTAr, ADHEr, FUM, LDH_D, PFK and/or FBA and/or TPI |
| 736 | 5 | 2.310761865 | 0.163365197 | ADHEr, LDH_D, PFK and/or FBA and/or TPI, PPCK, RPE |
| 737 | 5 | 2.306254619 | 0.167256205 | ADHEr, HEX1, LDH_D, PFK and/or FBA and/or TPI, RPE |
| 738 | 5 | 0.335428873 | 0.338418234 | ADHEr, HEX1, LDH_D, MDH, RPE |
| 739 | 5 | 2.674115155 | 0.222196435 | ADHEr, ASPT, FRD and/or SUCD4, LDH_D, MDH |
| 740 | 5 | 2.310408468 | 0.174397201 | ADHEr, FRD and/or SUCD4, LDH_D, PFK and/or FBA and/or TPI, TKT2 |
| 741 | 5 | 2.084492611 | 0.317726946 | ADHEr, ASNS2, FRD and/or SUCD4, FUM, LDH_D |
| 742 | 5 | 2.086878053 | 0.315902866 | ADHEr, CBMK2, FRD and/or SUCD4, FUM, LDH_D |
| 743 | 5 | 2.084553651 | 0.317680271 | ADHEr, FRD and/or SUCD4, FUM, G5SD, LDH_D |
| 744 | 5 | 2.221671127 | 0.212830356 | ADHEr, FRD and/or SUCD4, FUM, LDH_D, PPCK |
| 745 | 5 | 2.110766092 | 0.297636347 | ADHEr, FRD and/or SUCD4, FUM, HEX1, LDH_D |
| 746 | 5 | 2.221671127 | 0.212830356 | ADHEr, FRD and/or SUCD4, LDH_D, MDH, PPCK |
| 747 | 5 | 2.29690811 | 0.175324843 | ADHEr, FRD and/or SUCD4, LDH_D, PFK and/or FBA and/or TPI, RPE |
| 748 | 5 | 2.283263365 | 0.176262405 | ADHEr, FRD and/or SUCD4, LDH_D, PFK and/or FBA and/or TPI, TAL |
| 749 | 5 | 2.799273371 | 0.150483141 | ACKr and/or PTAr, ADHEr, FRD and/or SUCD4, LDH_D, PGI |
| 750 | 5 | 2.255979533 | 0.224464061 | ADHEr, FRD and/or SUCD4, LDH_D, PPCK, TKT2 |
| 751 | 5 | 4.330026614 | 0.179036754 | ACKr and/or PTAr, ADHEr, FRD and/or SUCD4, LDH_D, MDH |
| 752 | 5 | 2.238942691 | 0.225365131 | ADHEr, FRD and/or SUCD4, LDH_D, PPCK, RPE |
| 753 | 5 | 2.119938959 | 0.309086971 | ADHEr, FRD and/or SUCD4, HEX1, LDH_D, TAL |
| 754 | 5 | 2.221768517 | 0.226273464 | ADHEr, FRD and/or SUCD4, LDH_D, PPCK, TAL |
| 755 | 5 | 2.186545813 | 0.254918542 | ADHEr, FUM, LDH_D, PPCK, TAL |
| 756 | 5 | 2.293342202 | 0.16806573 | ADHEr, HEX1, LDH_D, PFK and/or FBA and/or TPI, TAL |
| 757 | 5 | 0.29142241 | 0.339587193 | ADHEr, FUM, HEX1, LDH_D, TAL |
| 758 | 5 | 0.29142241 | 0.339587193 | ADHEr, HEX1, LDH_D, MDH, TAL |
| 759 | 5 | 2.186545813 | 0.254918542 | ADHEr, LDH_D, MDH, PPCK, TAL |
| 760 | 5 | 3.603753429 | 0.189374217 | ADHEr, FADH4, HEX1, LDH_D, THD2 and/or GLUDy |
| 761 | 5 | 4.688321717 | 0.11916587 | ADHEr, FADH4, LDH_D, MDH, THD2 and/or GLUDy |
| 762 | 5 | 3.879826068 | 0.057433556 | ADHEr, FADH4, LDH_D, PPCK, THD2 and/or GLUDy |
| 763 | 5 | 2.092923946 | 0.31127974 | ADHEr, FUM, HEX1, LDH_D, THD2 and/or GLUDy |
| 764 | 5 | 1.181362879 | 0.252361787 | ADHEr, HEX1, LDH_D, PPCK, THD2 and/or GLUDy |
| 765 | 5 | 0.325709758 | 0.281560994 | ADHEr, ASPT, FUM, LDH_D, TKT1 |
| 766 | 5 | 2.645877173 | 0.251090969 | ADHEr, ASPT, LDH_D, MDH, TKT1 |
| 767 | 5 | 4.582051994 | 0.169949398 | ADHEr, FADH4, LDH_D, MDH, TKT1 |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 768 | 5 | 2.298067641 | 0.164222738 | ADHEr, LDH_D, PFK and/or FBA and/or TPI, PPCK, TKT1 |
| 769 | 5 | 4.582051994 | 0.169949398 | ADHEr, FRD and/or SUCD4, LDH_D, MDH, TKT1 |
| 770 | 5 | 4.584877196 | 0.168800591 | ADHEr, FRD and/or SUCD4, LDH_D, ME2, TKT1 |
| 771 | 5 | 2.186545813 | 0.254918542 | ADHEr, FUM, LDH_D, PPCK, TKT1 |
| 772 | 5 | 2.293342202 | 0.16806573 | ADHEr, HEX1, LDH_D, PFK and/or FBA and/or TPI, TKT1 |
| 773 | 5 | 0.29142241 | 0.339587193 | ADHEr, FUM, HEX1, LDH_D, TKT1 |
| 774 | 5 | 0.29142241 | 0.339587193 | ADHEr, HEX1, LDH_D, MDH, TKT1 |
| 775 | 5 | 2.186545813 | 0.254918542 | ADHEr, LDH_D, MDH, PPCK, TKT1 |
| 776 | 5 | 4.584877196 | 0.168800591 | ADHEr, FADH4, LDH_D, ME2, TKT1 |
| 777 | 5 | 2.593899337 | 0.187323863 | ADHEr, LDH_D, NADH6, PFK and/or FBA and/or TPI, TKT1 |
| 778 | 5 | 2.391804455 | 0.331134392 | ADHEr, FUM, LDH_D, NADH6, TKT1 |
| 779 | 5 | 2.396471968 | 0.327812994 | ADHEr, HEX1, LDH_D, NADH6, TKT1 |
| 780 | 5 | 2.470792173 | 0.274926806 | ADHEr, LDH_D, MDH, NADH6, TKT1 |
| 781 | 5 | 2.514181006 | 0.244051353 | ADHEr, LDH_D, NADH6, PPCK, TKT1 |
| 782 | 5 | 3.820196202 | 0.277060587 | ADHEr, LDH_D, NADH6, PFLi, TKT1 |
| 783 | 5 | 2.283263365 | 0.176262405 | ADHEr, FRD and/or SUCD4, LDH D, PFK and/or FBA and/or TPI, TKT1 |
| 784 | 5 | 2.119938959 | 0.309086971 | ADHEr, FRD and/or SUCD4, HEX1, LDH_D, TKT1 |
| 785 | 5 | 2.221768517 | 0.226273464 | ADHEr, FRD and/or SUCD4, LDH_D, PPCK, TKT1 |
| 786 | 6 | 4.63815309 | 0.138347146 | ADHEr, ASPT, FADH4, LDH_D, MDH, PYK |
| 787 | 6 | 4.459389393 | 0.176944819 | ADHEr, ASPT, FUM, LDH_D, MDH, TKT2 |
| 788 | 6 | 4.380192095 | 0.177265253 | ADHEr, ASPT, FRD and/or SUCD4, LDH_D, MALS, MDH |
| 789 | 6 | 4.40071793 | 0.179412355 | ADHEr, ASPT, LDH_D, MALS, MDH, TAL |
| 790 | 6 | 4.60130813 | 0.167781976 | ADHEr, ASPT, LDH_D, MDH, SUCOAS, TKT2 |
| 791 | 6 | 4.459389393 | 0.176944819 | ADHEr, ASPT, FUM, LDH_D, ME2, TKT2 |
| 792 | 6 | 4.430256792 | 0.178170044 | ADHEr, ASPT, FUM, LDH_D, ME2, RPE |
| 793 | 6 | 4.40071793 | 0.179412355 | ADHEr, ASPT, FUM, LDH_D, ME2, TAL |
| 794 | 6 | 4.563806878 | 0.124751372 | ADHEr, ASPT, FUM, LDH_D, ME2, THD2 and/or GLUDy |
| 795 | 6 | 4.380192095 | 0.177265253 | ADHEr, ASPT, FRD and/or SUCD4, FUM, LDH_D, MDH |
| 796 | 6 | 4.380192095 | 0.177265253 | ADHEr, ASPT, FRD and/or SUCD4, FUM, LDH_D, ME2 |
| 797 | 6 | 4.40071793 | 0.179412355 | ADHEr, ASPT, FUM, LDH_D, MDH, TAL |
| 798 | 6 | 4.547590285 | 0.169998972 | ADHEr, ASPT, LDH_D, MDH, SUCOAS, TAL |
| 799 | 6 | 4.32598859 | 0.179624623 | ACKr and/or PTAr, ADHEr, ASPT, LDH_D, MDH, THD2 and/or GLUDy |
| 800 | 6 | 4.503409516 | 0.124027245 | ADHEr, ASPT, ATPS4r, LDH_D, MDH, TKT2 |
| 801 | 6 | 4.55209485 | 0.121669936 | ADHEr, ASPT, ATPS4r, LDH_D, MDH, PGDH |
| 802 | 6 | 4.519337222 | 0.123256037 | ADHEr, ASPT, ATPS4r, LDH_D, MDH, RPE |
| 803 | 6 | 4.535068073 | 0.12249436 | ADHEr, ASPT, ATPS4r, LDH_D, MDH, TAL |
| 804 | 6 | 5.189612621 | 0.143792027 | ADHEr, ATPS4r, FRD and/or SUCD4, LDH_D, ME2, PFLi |
| 805 | 6 | 4.321178853 | 0.120168187 | ADHEr, ATPS4r, FRD and/or SUCD4, LDH_D, MDH, PGI |
| 806 | 6 | 4.555303308 | 0.170023606 | ADHEr, DAAD, FRD and/or SUCD4, LDH_D, ME2, PRO1z |
| 807 | 6 | 4.552254757 | 0.171189177 | ADHEr, DAAD, FRD and/or SUCD4, LDH_D, MDH, PRO1z |
| 808 | 6 | 4.611166872 | 0.137118286 | ADHEr, FADH4, FUM, LDH_D, MDH, PYK |
| 809 | 6 | 4.681108251 | 0.164738111 | ADHEr, FADH4, LDH_D, MDH, SUCOAS, TKT2 |
| 810 | 6 | 4.655427003 | 0.165799614 | ADHEr, FADH4, LDH_D, MDH, RPE, SUCOAS |
| 811 | 6 | 4.62941265 | 0.166874885 | ADHEr, FADH4, LDH_D, MDH, SUCOAS, TAL |
| 812 | 6 | 4.57471951 | 0.178914826 | ADHEr, FADH4, HEX1, LDH_D, SUCOAS, THD2 and/or GLUDy |
| 813 | 6 | 4.72140048 | 0.117206382 | ADHEr, FADH4, LDH_D, MDH, SUCOAS, THD2 and/or GLUDy |
| 814 | 6 | 5.77503303 | 0.099302315 | ADHEr, EDA and/or PGDHY, FADH4, LDH_D, MDH, THD2 and/or GLUDy |
| 815 | 6 | 4.802404267 | 0.049107371 | ACKr and/or PTAr, ADHEr, FADH4, LDH_D, PPCK, THD2 and/or GLUDy |
| 816 | 6 | 4.611166872 | 0.137118286 | ADHEr, FRD and/or SUCD4, FUM, LDH_D, MDH, PYK |
| 817 | 6 | 4.681108251 | 0.164738111 | ADHEr, FRD and/or SUCD4, LDH_D, MDH, SUCOAS, TKT2 |
| 818 | 6 | 4.640728933 | 0.137362308 | ADHEr, FRD and/or SUCD4, LDH_D, MDH, ME2, PYK |
| 819 | 6 | 4.657699713 | 0.164706045 | ADHEr, FRD and/or SUCD4, LDH_D, ME2, RPE, SUCOAS |
| 820 | 6 | 4.683198197 | 0.163658455 | ADHEr, FRD and/or SUCD4, LDH_D, ME2, SUCOAS, TKT2 |
| 821 | 6 | 4.63187269 | 0.165767133 | ADHEr, FRD and/or SUCD4, LDH_D, ME2, SUCOAS, TAL |
| 822 | 6 | 5.443882794 | 0.111598427 | ADHEr, FRD and/or SUCD4, HEX1, LDH_D, ME2, THD2 and/or GLUDy |
| 823 | 6 | 4.714403301 | 0.10919394 | ACKr and/or PTAr, ADHEr, FRD and/or SUCD4, LDH_D, ME2, THD2 and/or GLUDy |
| 824 | 6 | 4.727966085 | 0.117420509 | ADHEr, FRD and/or SUCD4, LDH_D, ME2, RPE, THD2 and/or GLUDy |
| 825 | 6 | 4.724744313 | 0.115799637 | ADHEr, FRD and/or SUCD4, LDH_D, ME2, SUCOAS, THD2 and/or GLUDy |
| 826 | 6 | 4.710892193 | 0.11755936 | ADHEr, FRD and/or SUCD4, LDH_D, ME2, TAL, THD2 and/or GLUDy |
| 827 | 6 | 4.744999691 | 0.117281986 | ADHEr, FRD and/or SUCD4, LDH_D, ME2, THD2 and/or GLUDy, TKT2 |
| 828 | 6 | 4.62941265 | 0.166874885 | ADHEr, FRD and/or SUCD4, LDH_D, MDH, SUCOAS, TAL |
| 829 | 6 | 4.74186178 | 0.118725202 | ADHEr, FRD and/or SUCD4, LDH_D, MDH, THD2 and/or GLUDy, TKT2 |
| 830 | 6 | 4.512318137 | 0.052959973 | ADHEr, FRD and/or SUCD4, LDH_D, PPCK, PYK, THD2 and/or GLUDy |

TABLE 16-continued

Knockout strain designs for increased production of HMDA, showing yields of HMDA and biomass.

| New Design ID | Num KO | HMDA. Yield | Biomass | Rxnlist |
|---|---|---|---|---|
| 831 | 6 | 4.724614564 | 0.118867157 | ADHEr, FRD and/or SUCD4, LDH_D, MDH, RPE, THD2 and/or GLUDy |
| 832 | 6 | 4.707326054 | 0.119009453 | ADHEr, FRD and/or SUCD4, LDH_D, MDH, TAL, THD2 and/or GLUDy |
| 833 | 6 | 4.459389393 | 0.176944819 | ADHEr, ASPT, ICL, LDH_D, MDH, TKT2 |
| 834 | 6 | 4.380192095 | 0.177265253 | ADHEr, ASPT, FRD and/or SUCD4, ICL, LDH_D, MDH |
| 835 | 6 | 4.40071793 | 0.179412355 | ADHEr, ASPT, ICL, LDH_D, MDH, TAL |
| 836 | 6 | 4.874048363 | 0.048155873 | ADHEr, FADH4, ICL, LDH_D, PPCK, THD2 and/or GLUDy |
| 837 | 6 | 4.520685593 | 0.183259208 | ADHEr, FADH4, HEX1, ICL, LDH_D, THD2 and/or GLUDy |
| 838 | 6 | 4.459389393 | 0.176944819 | ADHEr, ASPT, LDH_D, MALS, MDH, TKT2 |
| 839 | 6 | 4.520685593 | 0.183259208 | ADHEr, FADH4, HEX1, LDH_D, MALS, THD2 and/or GLUDy |
| 840 | 6 | 4.874048363 | 0.048155873 | ADHEr, FADH4, LDH_D, MALS, PPCK, THD2 and/or GLUDy |
| 841 | 6 | 4.517532821 | 0.171239478 | ADHEr, ASPT, FUM, LDH_D, ME2, SUCOAS |
| 842 | 6 | 4.640728933 | 0.137362308 | ADHEr, FADH4, LDH_D, MDH, ME2, PYK |
| 843 | 6 | 4.657699713 | 0.164706045 | ADHEr, FADH4, LDH_D, ME2, RPE, SUCOAS |
| 844 | 6 | 4.683198197 | 0.163658455 | ADHEr, FADH4, LDH_D, ME2, SUCOAS, TKT2 |
| 845 | 6 | 4.63187269 | 0.165767133 | ADHEr, FADH4, LDH_D, ME2, SUCOAS, TAL |
| 846 | 6 | 4.724744313 | 0.115799637 | ADHEr, FADH4, LDH_D, ME2, SUCOAS, THD2 and/or GLUDy |
| 847 | 6 | 4.744999691 | 0.117281986 | ADHEr, FADH4, LDH_D, ME2, THD2 and/or GLUDy, TKT2 |
| 848 | 6 | 4.526462669 | 0.168070055 | ADHEr, FRD and/or SUCD4, FUM, LDH_D, ME2, SUCOAS |
| 849 | 6 | 5.443882794 | 0.111598427 | ADHEr, FADH4, HEX1, LDH_D, ME2, THD2 and/or GLUDy |
| 850 | 6 | 4.714403301 | 0.10919394 | ACKr and/or PTAr, ADHEr, FADH4, LDH_D, ME2, THD2 and/or GLUDy |
| 851 | 6 | 4.727966085 | 0.117420509 | ADHEr, FADH4, LDH_D, ME2, RPE, THD2 and/or GLUDy |
| 852 | 6 | 4.710892193 | 0.11755936 | ADHEr, FADH4, LDH_D, ME2, TAL, THD2 and/or GLUDy |
| 853 | 6 | 4.33071542 | 0.180983121 | ACKr and/or PTAr, ADHEr, ASPT, LDH_D, MDH, NADH6 |
| 854 | 6 | 4.313819364 | 0.203396482 | ACKr and/or PTAr, ADHEr, LDH_D, MDH, NADH6, THD2 and/or GLUDy |
| 855 | 6 | 4.836109146 | 0.120863498 | ADHEr, FRD and/or SUCD4, LDH_D, ME2, PFLi, PGI |
| 856 | 6 | 5.044438059 | 0.165184738 | ACKr and/or PTAr, ADHEr, HEX1, LDH_D, PFLi, PGI |
| 857 | 6 | 5.168015107 | 0.134224131 | ADHEr, FRD and/or SUCD4, LDH_D, ME2, PFLi, THD2 and/or GLUDy |
| 858 | 6 | 5.320455827 | 0.059323173 | ADHEr, FRD and/or SUCD4, LDH_D, MDH, PFLi, THD2 and/or GLUDy |
| 859 | 6 | 4.74186178 | 0.118725202 | ADHEr, FADH4, LDH_D, MDH, THD2 and/or GLUDy, TKT2 |
| 860 | 6 | 4.512318137 | 0.052959973 | ADHEr, FADH4, LDH_D, PPCK, PYK, THD2 and/or GLUDy |
| 861 | 6 | 4.724614564 | 0.118867157 | ADHEr, FADH4, LDH_D, MDH, RPE, THD2 and/or GLUDy |
| 862 | 6 | 4.888461627 | 0.046924032 | ADHEr, FADH4, LDH_D, PPCK, SUCOAS, THD2 and/or GLUDy |
| 863 | 6 | 4.707326054 | 0.119009453 | ADHEr, FADH4, LDH_D, MDH, TAL, THD2 and/or GLUDy |
| 864 | 6 | 4.40071793 | 0.179412355 | ADHEr, ASPT, FUM, LDH_D, MDH, TKT1 |
| 865 | 6 | 4.547590285 | 0.169998972 | ADHEr, ASPT, LDH_D, MDH, SUCOAS, TKT1 |
| 866 | 6 | 4.535068073 | 0.12249436 | ADHEr, ASPT, ATPS4r, LDH_D, MDH, TKT1 |
| 867 | 6 | 4.62941265 | 0.166874885 | ADHEr, FADH4, LDH_D, MDH, SUCOAS, TKT1 |
| 868 | 6 | 4.63187269 | 0.165767133 | ADHEr, FRD and/or SUCD4, LDH_D, ME2, SUCOAS, TKT1 |
| 869 | 6 | 4.710892193 | 0.11755936 | ADHEr, FRD and/or SUCD4, LDH_D, ME2, THD2 and/or GLUDy, TKT1 |
| 870 | 6 | 4.62941265 | 0.166874885 | ADHEr, FRD and/or SUCD4, LDH_D, MDH, SUCOAS, TKT1 |
| 871 | 6 | 4.707326054 | 0.119009453 | ADHEr, FRD and/or SUCD4, LDH_D, MDH, THD2 and/or GLUDy, TKT1 |
| 872 | 6 | 4.40071793 | 0.179412355 | ADHEr, ASPT, ICL, LDH_D, MDH, TKT1 |
| 873 | 6 | 4.40071793 | 0.179412355 | ADHEr, ASPT, LDH_D, MALS, MDH, TKT1 |
| 874 | 6 | 4.40071793 | 0.179412355 | ADHEr, ASPT, FUM, LDH_D, ME2, TKT1 |
| 875 | 6 | 4.63187269 | 0.165767133 | ADHEr, FADH4, LDH_D, ME2, SUCOAS, TKT1 |
| 876 | 6 | 4.710892193 | 0.11755936 | ADHEr, FADH4, LDH_D, ME2, THD2 and/or GLUDy, TKT1 |
| 877 | 6 | 4.707326054 | 0.119009453 | ADHEr, FADH4, LDH_D, MDH, THD2 and/or GLUDy, TKT1 |

Minimal Gene Deletion Sets for Enhanced Production of 6-ACA.

Described above are strain design strategies for improving 6-aminocaproate (6-ACA) production in microorganisms that possess the 6-ACA pathway via acetyl-CoA and succinyl-CoA. Based on an extensive analysis of the strain designs for 6-ACA production described in Table 14, a minimum set of deletions that is required for growth-coupled 6-ACA production has been identified. Note that phosphoenolpyruvate carboxykinase (PPCK) was assumed to be reversible.

Figure 28:
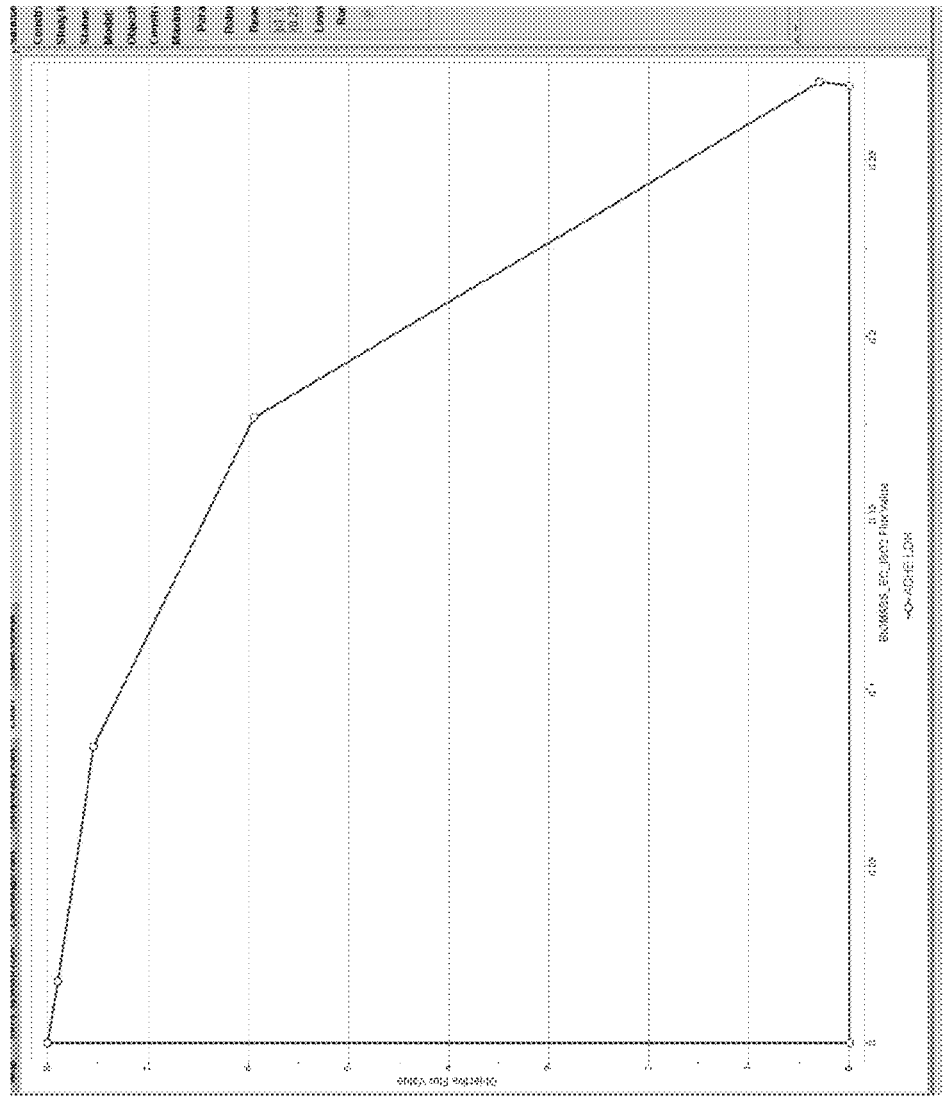
FIG. 28 shows the 6-ACA versus growth yields for an ADHEr, LDH_D mutant.
Figure 29:
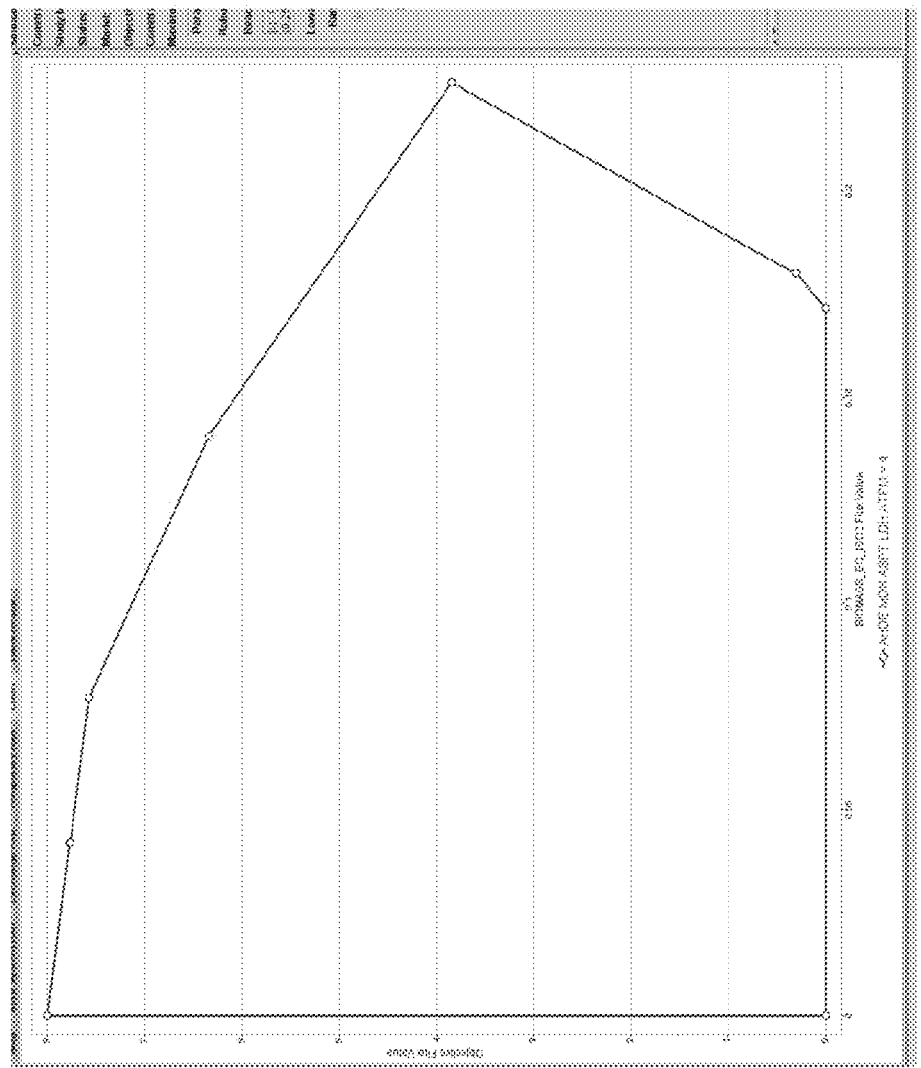
FIG. 29 shows the 6-ACA versus growth yields for an ADHEr, MDH, ASPT, LDH_D mutant.
Figure 30:
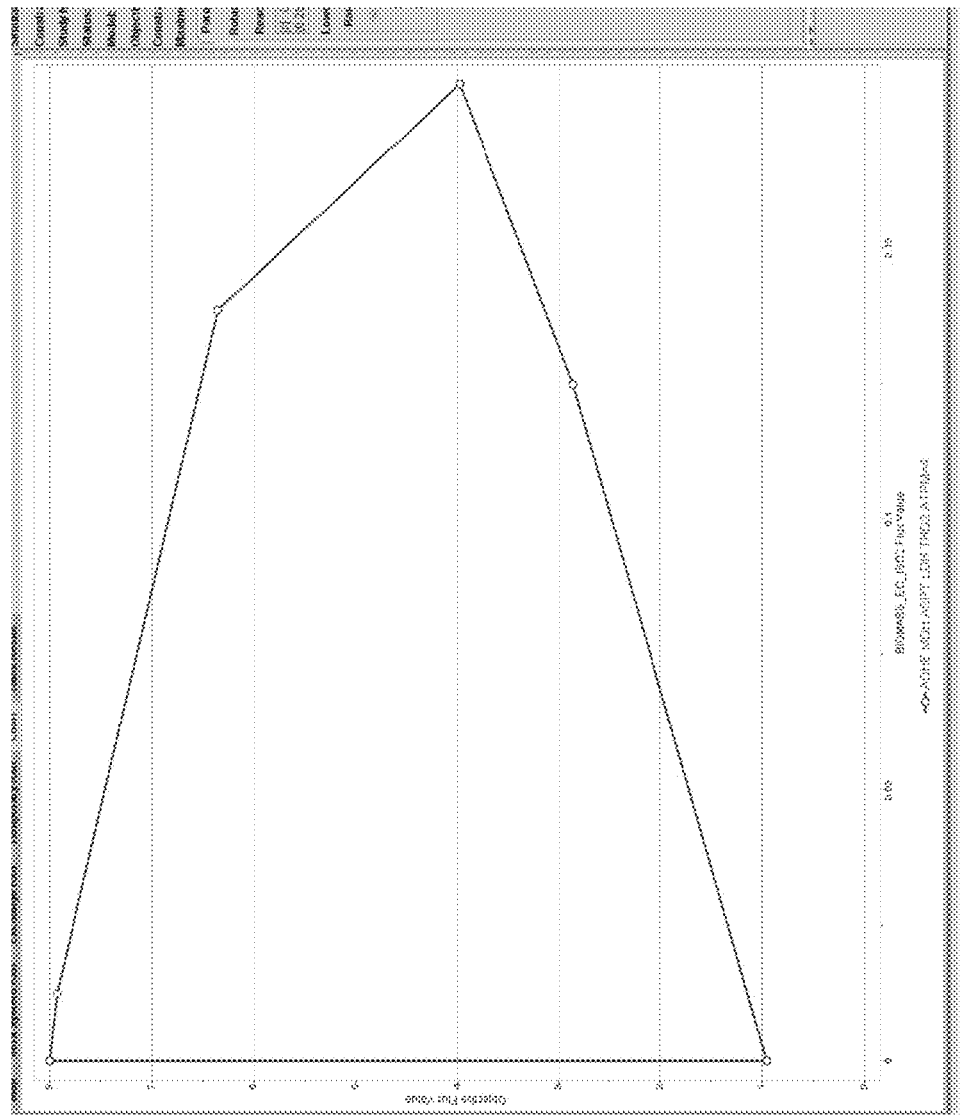
FIG. 30 shows the 6-ACA versus growth yields for an ADHEr, MDH, ASPT, LDH_D, THD2 mutant.
Figure 31:
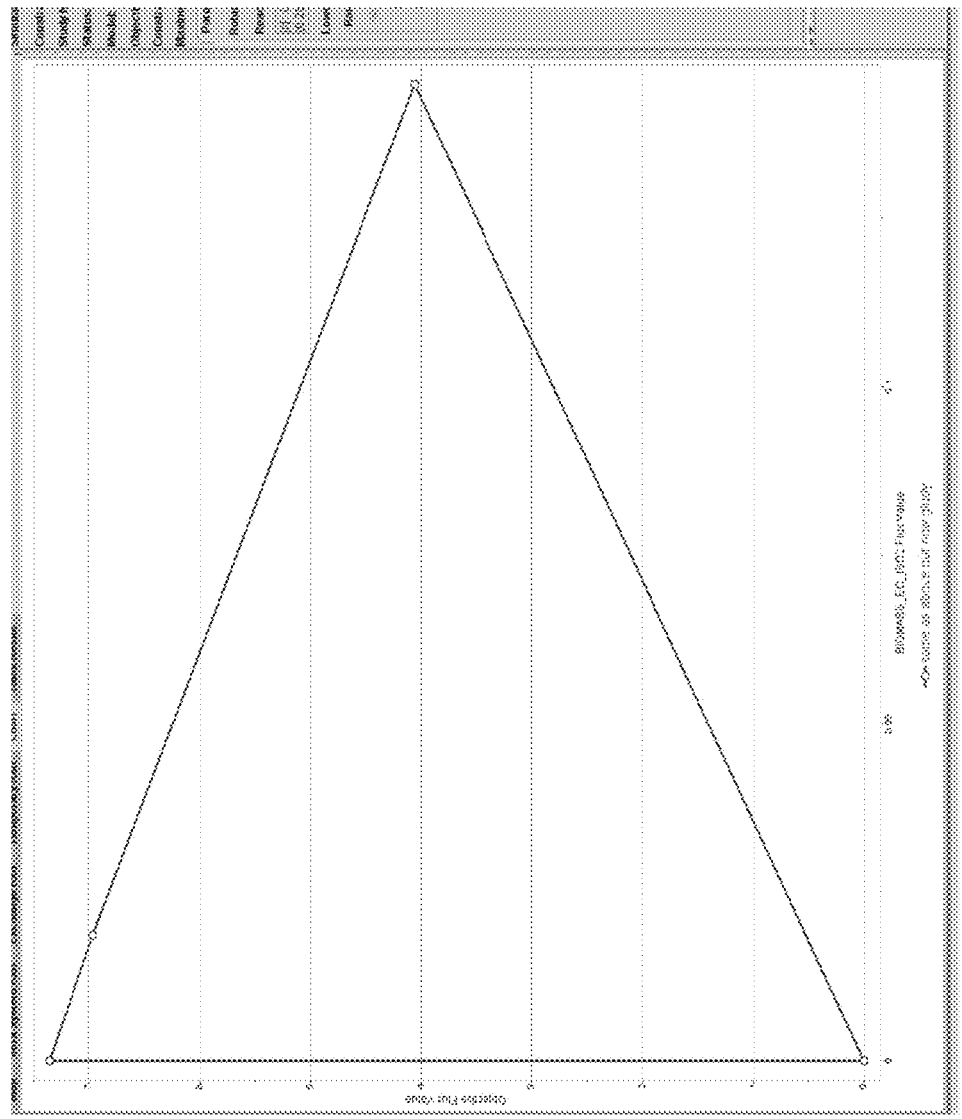
FIG. 31 shows the 6-ACA versus growth yields for an ADHEr, MDH, ASPT, LDH_D, GLUDy mutant.

Briefly, deletions in acetaldehyde dehydrogenase (ADHEr) and lactate dehydrogenase (LDH_D) are required for preventing the formation of competing byproducts, ethanol and lactate. Therefore, the minimal deletion set comprises deletion of acetaldehyde dehydrogenase (ADHEr) and lactate dehydrogenase (LDH_D). Additional deletion strains include strains lacking at least one of the following activities in addition to ADHEr and LDH_D: malate dehydrogenase (MDH), aspartase (ASPT), NAD(P) transhydrogenase (THD2), and glutamate dehydrogenase (GLUDy). Such additional deletions result in a much tighter coupling of production with cell growth. FIGS. 28-31 show calculated 6-ACA versus growth yields for deletion mutants having at least deletion of ADHEr and LDH_D (FIG. 28). Calculated yields for strains with additional deletions are shown in FIGS. 29-31.

An additional minimal set of deletions includes phosphoglucoisomerase (PGI). This design focuses on generating reducing equivalents via the pentose phosphate pathway.

Figure 32:
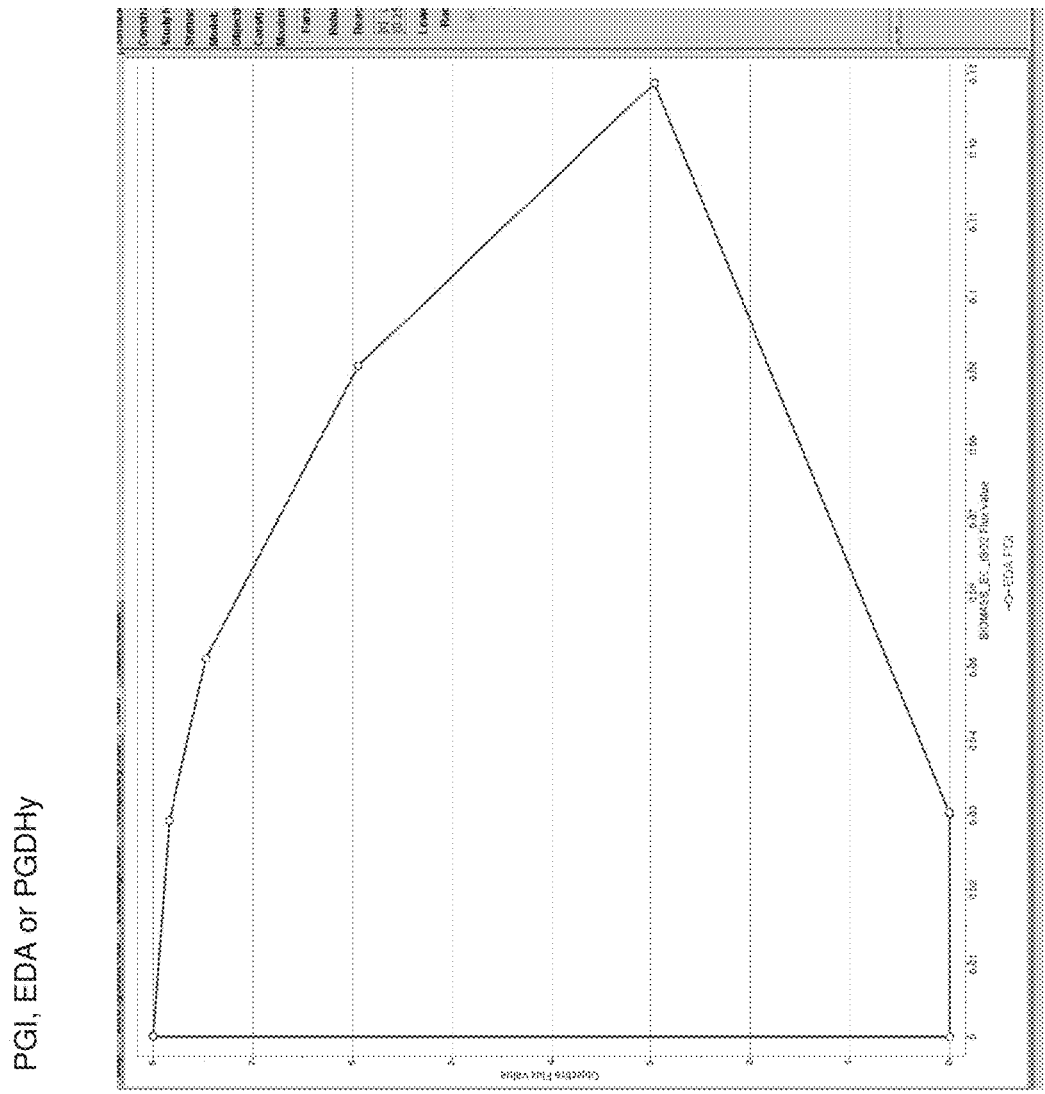
FIG. 32 shows the 6-ACA versus growth yields for a PGI, EDA mutant or a PGI, PGDHy mutant.
Figure 33:
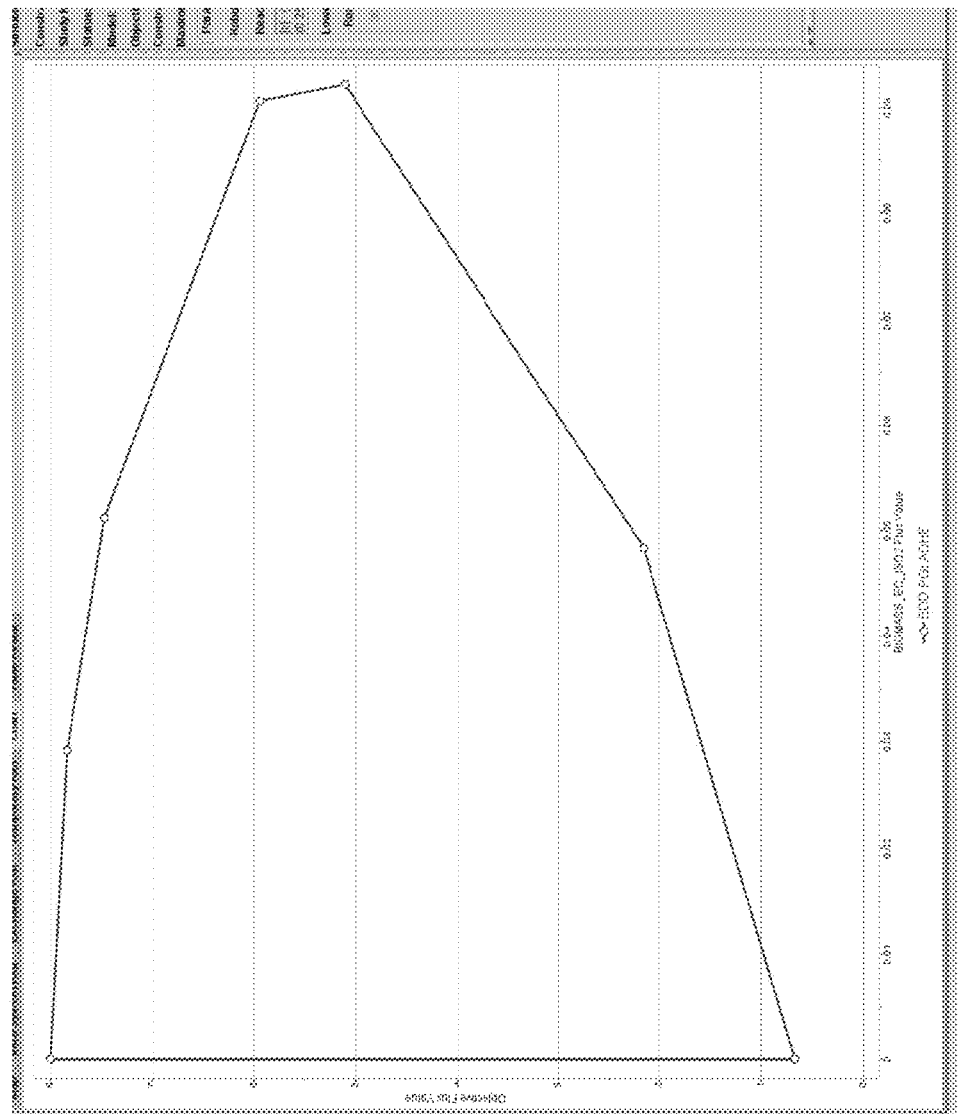
FIG. 33 shows the 6-ACA versus growth yields for a PGI, EDA, ADHEr mutant or a PGI, PGDHy, ADHEr mutant.
Figure 34:
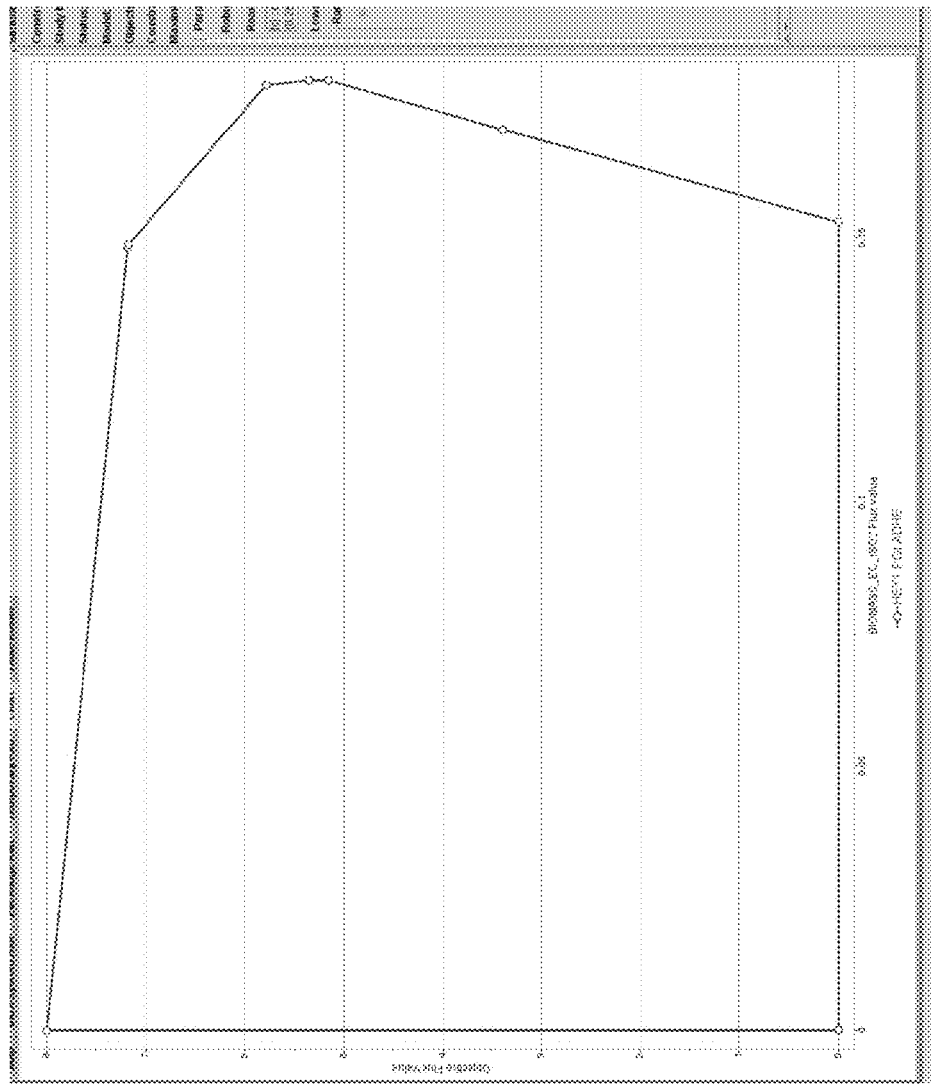
FIG. 34 shows the 6-ACA versus growth yields for an ADHEr, PGI, HEX1 mutant.

Additional beneficial deletions include any of: acetaldehyde dehydrogenase (ADHEr), hexokinase (HEX1), 2-dehydro-3-deoxy-phosphogluconate aldolase (EDA) and phosphogluconate dehydratase (PGDHy). FIGS. 32-34 show calculated 6-ACA versus growth yields for deletion mutants having at least deletion of PGI, with additional exemplary mutants shown FIGS. 32-34.

Each of these strains can be supplemented with additional deletions if it is determined that the predicted strain designs do not sufficiently couple the formation of the product with biomass formation or for increased efficiency of coupling the formation of the product with biomass formation. Alternatively, some other enzymes not known to possess significant activity under the growth conditions can become active due to adaptive evolution or random mutagenesis. Such enzyme activities can also be knocked out. For example, succinate dehydrogenase that oxidizes succinate to fumarate and is known to be active only under aerobic conditions can assume significant activity even under anaerobic conditions, and therefore such activity can be knocked out. However, the list of gene deletion sets provided herein serves as a good starting point for construction of high-yielding growth-coupled 6-ACA production strains.

Minimal Gene Deletion Sets for Enhanced Production of Adipate.

Described above are strain design strategies for improving adipate production in microorganisms that possess the adipate pathway via acetyl-CoA and succinyl-CoA. Based on an extensive analysis of the strain designs for adipate production described in Table 15, a minimum set of deletions that is required for growth-coupled adipate production in the network has been identified. Note that phosphoenolpyruvate carboxykinase (PPCK) was assumed to be reversible in the network.

Briefly, deletions in acetaldehyde dehydrogenase (ADHEr) and lactate dehydrogenase (LDH_D) are required for preventing the formation of competing byproducts, ethanol and lactate. Therefore, the minimal deletion set comprises deletion of acetaldehyde dehydrogenase (ADHEr) and lactate dehydrogenase (LDH_D). Additional deletion strains include a strain lacking at least one of the following activities in addition to acetaldehyde dehydrogenase (ADHEr) and lactate dehydrogenase (LDH_D): fumarase (FUM), phosphoglucose isomerase (PGI), PEP carboxykinase (PPCK), hexokinase (HEX1), malate dehydrogenase (MDH), and NADH dehydrogenase (NADH6).

Additional deletions have been identified by the OptKnock framework for improving the growth-coupled formation of adipate. These include one or more of the following: malic enzyme (ME2), aspartate transaminase (ASPT), acetate kinase (ACKr), phosphotransacetylase (PTAr), pyruvate formate lyase (PFL), transhydrogenase (THD2), and glutamate dehydrogenase (GLUDy), and PTS system of glucose uptake (GLCpts). Further improvements in yields can be achieved by additional deletions in any of the following enzymes: ATP synthase (ATPS4r), phosphogluconate dehydratase (PGDHY), 2-dehydro-3-deoxy-phosphogluconate aldolase (EDA), 6-phosphogluconolactonase (PGL), glucose 6-phosphate dehydrogenase (G6PDHY), and phosphogluconate dehydrogenase (PGDH).

Each of these strains can be supplemented with additional deletions if it is determined that the predicted strain designs do not sufficiently couple the formation of the product with biomass formation or for increased efficiency of coupling the formation of the product with biomass formation. Alternatively, some other enzymes not known to possess significant activity under the growth conditions can become active due to adaptive evolution or random mutagenesis. Such enzyme activities can also be knocked out. However, the list of gene deletion sets provided herein serves as a good starting point for construction of high-yielding growth-coupled adipate production strains.

Minimal Gene Deletion Sets for Enhanced Production of HMDA.

Described above are strain design strategies for improving hexamethylene diamine (HMDA) production in microorganisms that possess the HMDA pathway via acetyl-CoA and succinyl-CoA. Based on an extensive analysis of the strain designs for HMDA production described in Table 16, a minimum set of deletions that is required for growth-coupled HMDA production in the network has been identified. Note that phosphoenolpyruvate carboxykinase (PPCK) was assumed to be reversible in the network.

Briefly, deletions in acetaldehyde dehydrogenase (ADHEr) and lactate dehydrogenase (LDH_D) are required for preventing the formation of competing byproducts, ethanol and lactate. Therefore, the minimal deletion set comprises deletion of acetaldehyde dehydrogenase (ADHEr) and lactate dehydrogenase (LDH_D). Additional deletion strains include a strain lacking at least one of the following activities in addition to acetaldehyde dehydrogenase (ADHEr) and lactate dehydrogenase (LDH_D): fumarate reductase (FRD2), fumarase (FUM), phosphoglucose isomerase (PGI), or PEP carboxykinase (PPCK).

Additional deletions have been identified by the OptKnock framework for improving the growth-coupled formation of HMDA. These include one or more of the following: hexokinase (HEX1), malic enzyme (ME2), malate dehydrogenase (MDH), aspartate transaminase (ASPT), acetate kinase (ACKr), phosphotransacetylase (PTAr), pyruvate formate lyase (PFL), and pyruvate kinase (PYK). The HMDA yields can be further improved by further deleting one or more of the following enzymes: transhydrogenase (THD2), glutamate dehydrogenase (GLUDy), ATP synthase (ATPS4r), GLCpts (PTS system of glucose uptake), PGDHY (phosphogluconate dehydratase) and EDA (2-dehydro-3-deoxy-phosphogluconate aldolase).

Each of these strains can be supplemented with additional deletions if it is determined that the predicted strain designs do not sufficiently couple the formation of the product with biomass formation or for increased efficiency of coupling the formation of the product with biomass formation. Alternatively, some other enzymes not known to possess significant activity under the growth conditions can become active due to adaptive evolution or random mutagenesis. Such enzyme activities can also be knocked out. For example, succinate dehydrogenase that oxidizes succinate to fumarate and is known to be active only under aerobic conditions can assume significant activity even under anaerobic conditions, and therefore such activity can be knocked out. However, the list of gene deletion sets provided herein serves as a good starting point for construction of high-yielding growth-coupled HMDA production strains.

Optknock Strain Design for Growth-Coupled Production of Adipic Acid.

Figure 35:
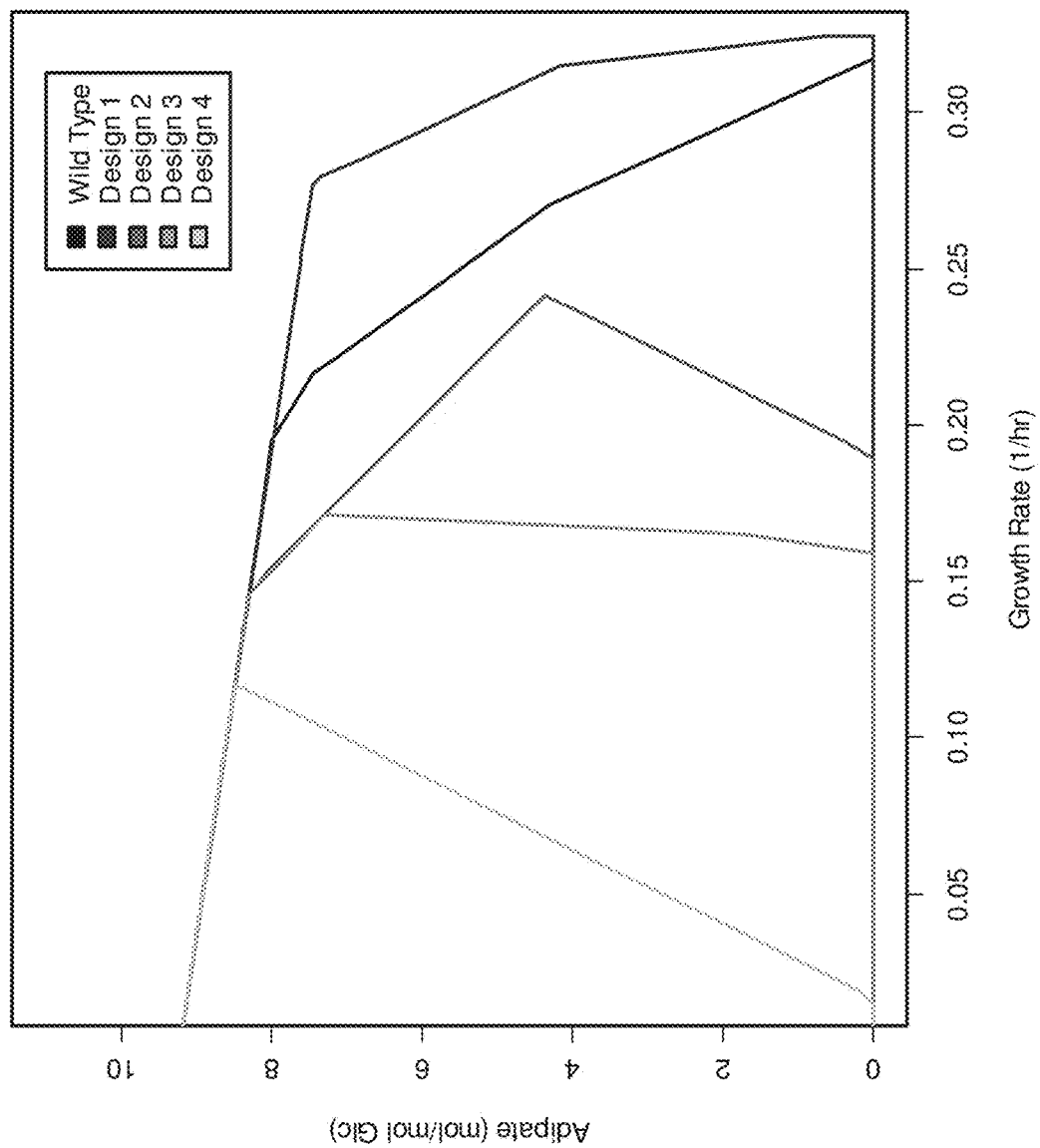
FIG. 35 shows growth-coupled adipate production characteristics of high priority strain designs (grey) compared with that of wild-type E. coli (black). A glucose uptake rate of 10 mmol/gDW/hr is assumed.

Described below is a further exemplification of a deletion strategy for engineering a strain to synthesize adipate using a succinyl-CoA pathway. All high-priority growth-coupled designs for adipate synthesis build upon a strain lacking acetylaldehyde-CoA dehydrogenase (ADHEr) and lactate dehydrogenase (LDH_D) activities to prevent the formation of fermentation byprouducts, as discussed above. The further deletion of malate dehydrogenase (MDH) also reduces byproduct production. FIG. 35 shows growth-coupled adipate production characteristics of high priority strain designs (grey) compared with that of wild-type *E. coli* (black). A glucose uptake rate of 10 mmol/gDW/hr is assumed. A strain deficient in ADHEr, LDH_D and MDH activities (Design 1 in FIG. 35) is predicted to achieve an adipate yield of 0.51 grams adipate per gram of glucose utilized (g/g) at the maximum biomass yield.

Designs 2-4 build on Design 1 as a base design. Design 2 entails the removal of phosphoenolpyruvate carboxykinase (PPCK). This design improves the adipate yield to 3.6 g/g at the maximum biomass yield. The additional deletion of pyruvate formate lyase (PFLi) activity in Design 3 further improves yield by preventing secretion of formate as a byproduct. The predicted adipate yield of this design is 5.8 g/g. Design 4 features the deletion of NAD(P) transhydrogenase (THD2) in addition to ADHEr, LDH_D, MDH, PPCK and PFLi. This results in an adipate yield of 6.8 g/g at a growth rate of 0.117 l/hr. Design 4 serves to tightly couple adipate production to cell growth while achieving 91% of the theoretical maximum yield.

Example XXXI

Biosynthesis of Adipate Semialdehyde from Adipate and 6-Aminocaproate Semialdehyde from 6-Aminocaproate This Example describes the biosynthetic production of adipate semialdehyde from adipate and of 6-aminocaproate semialdehyde from 6-aminocaproate.

The transformation from adipate to adipate semialdehyde (FIG. 25, step X) can by catalyzed by the carboxylic acid reductases (CAR). This is demonstrated by the following results. Chemically competent cells of *E. coli* strain ECKh-422 (ΔadhE, ΔldhA, ΔpflB, ΔlpdA, integrated lpdA from *Klebsiella pneumonia*::E354K, Δmdh, ΔarcA, gltA-R163L) with f'pKLJ33s were transformed with pZs*13s plasmids harboring various CAR gene (Table 17) or a control plasmid without any CAR gene. Single colonies of the transformations were selected and grown overnight in LB at 37° C. with 100 µg/ml carbenicillin and 10 µg/ml chloramphenicol. The cells were subcultured at a ratio of 1:50 and induced with 200 µM IPTG at an OD600 of 0.6. Cells were incubated for 5 hours at 37° C. before harvesting. Cell cultures were aliquoted into 15 ml samples and pelleted. The cell pellets were stored at −80° C. until used for the assay.

TABLE 17

| CAR genes used this example | | | |
|---|---|---|---|
| Protein | GenBank ID | GI Number | Organism |
| 720 | AAR91681.1 | 40796035 | *Nocardia iowensis* |
| 889 | YP_887275.1 | 118473501 | *Mycobacterium smegmatis* str. MC2 155 |

TABLE 17-continued

| CAR genes used this example | | | |
|---|---|---|---|
| Protein | GenBank ID | GI Number | Organism |
| 890 | YP_889972.1 | 118469671 | *Mycobacterium smegmatis* str. MC2 155 |
| 891 | NP_959974.1 | 41407138 | *Mycobacterium avium* subsp. *paratuberculosis* K-10 |
| 892 | YP_001850422.1 | 183982131 | *Mycobacterium marinum* M |

Cell pellets were lysed by addition of 500 µl B-PER with 0.5 µl lysozyme and benzonase. CAR activity was measured by addition of 2 µl of crude lysate to the assay solution of 50 mM Tris (pH 7.2), 1 mM EDTA, 10 mM $MgCl_2$, 1 mM DTT, 10% (v/v) glycerol, 1 mM ATP, 0.5 mM NADPH and 20 mM Adipate or 50 mM 6-Aminocaproate in a 96 well format microplate with a total volume of 250 µl. The oxidation of NADPH to $NADP^+$ was monitored at an absorbance of 340 nm for 30 minutes at room temperature. The rate of NADPH depletion was used to calculate activity of the various CAR proteins. Total protein concentration of each lysate was determined by Bradford, and the activity was normalized to the total protein concentration (Units/mg).

Transformation from Adipate to Adipate Semialdehyde (FIG. 24, Step).

Figure 36:
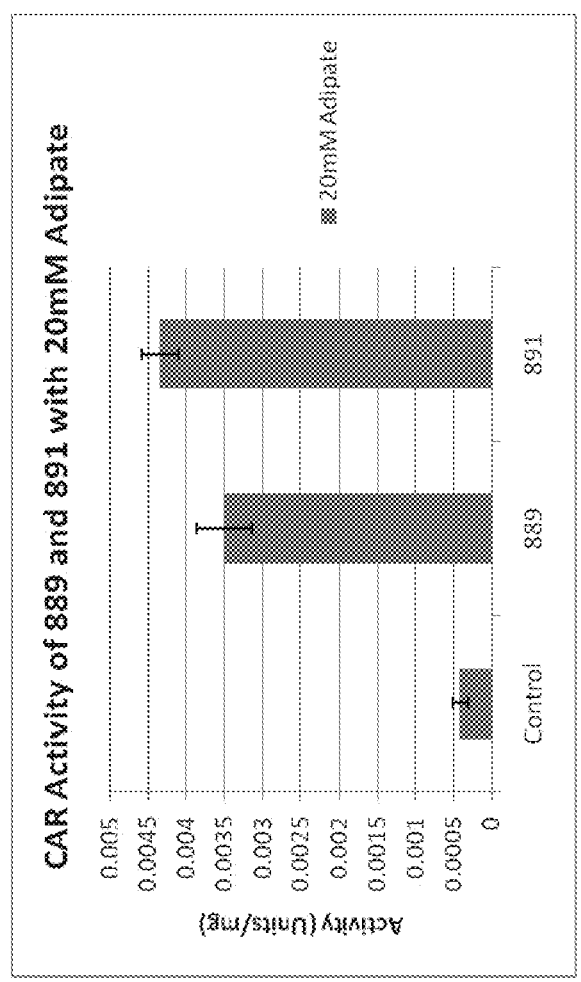
FIG. 36 shows the activity of CAR 889 and 891 using 20 mM Adipate. Activity is shown as units per mg of total protein in the crude lysate.

As shown in FIG. 36, significant CAR activities using adipate as a substrate was observed with both CAR genes 889 and 891, whereas the control lysate did not show CAR activity.

Furthermore, a reaction was setup consisting of 500 µl of 50 mM Tris (pH 7.2), 1 mM EDTA, 10 mM $MgCl_2$, 1 mM DTT, 10% (v/v) glycerol, 5 mM ATP, 3 mM NADPH and 20 mM Adipate. The reaction was incubated at room temperature for 30 minutes and stopped by addition of 1% formic acid. The sample was then centrifuged and the supernatant was analyzed by LC-MS. Low mM level of adipate semialdehyde was detected that confirmed the transformation from adipate to adipate semialdehyde.

Transformation from 6-aminocaproate to 6-aminocaproate Semialdehyde.

Figure 37:
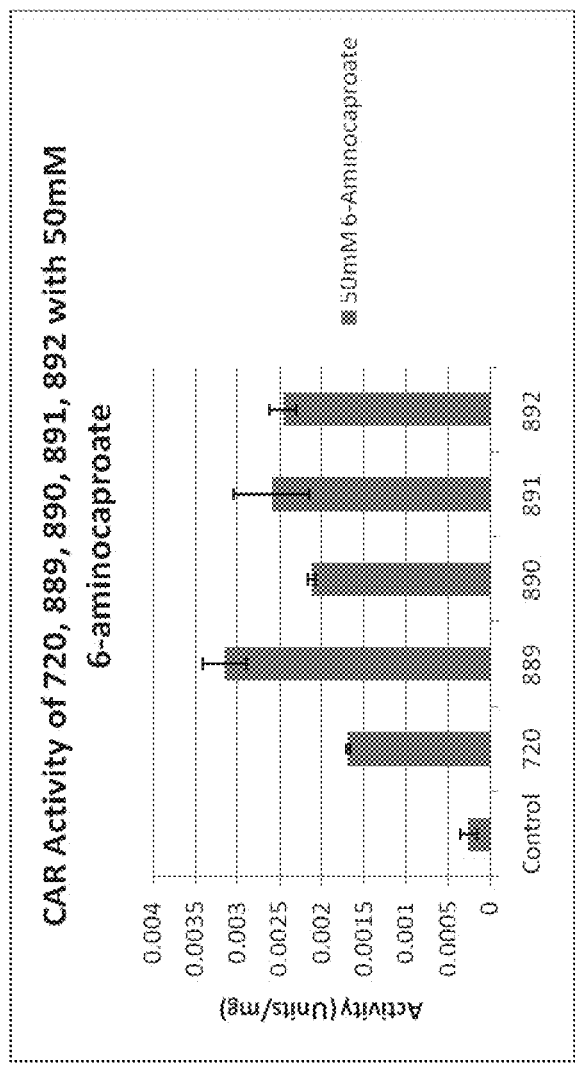
FIG. 37 shows the activity of CAR 720, 889, 890, 891 using 50 mM 6-aminocaproate. Activity is shown as units per mg of total protein in the crude lysate.

As shown in FIG. 37, significant CAR activities using 6-aminocaproate as a substrate was observed with several CAR genes 720, 889, 890, 891 and 892, whereas the control lysate did not show CAR activity. These results indicate the transformation from 6-aminocaproate to 6-aminocaproate semialdehyde.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A non-naturally occurring microbial organism, comprising a microbial organism having a 6-aminocaproic acid (6-ACA) pathway comprising at least two exogenous nucleic acids encoding 6-ACA pathway enzymes expressed in a sufficient amount to produce 6-ACA from glutamate, said 6-ACA pathway enzymes comprising: a glutamyl-CoA transferase or a glutamyl-CoA ligase; a beta-ketothiolase; an 3-oxo-6-aminopimeloyl-CoA oxidoreductase; a 3-hydroxy-6-aminopimeloyl-CoA dehydratase; a 6-amino-7-carboxy-hept-2-enoyl-CoA reductase; 6-aminopimeloyl-CoA hydrolase, transferase and/or ligase; and a 2-aminopimelate decarboxylase.

2. The non-naturally occurring microbial organism of claim 1, wherein said microbial organism comprises a set of exogenous nucleic acids encoding 6-ACA pathway enzymes expressed in a sufficient amount to produce 6-ACA, said set of exogenous nucleic acids comprising: a glutamyl-CoA transferase or a glutamyl-CoA ligase; a beta-ketothiolase; a 3-oxo-6-aminopimeloyl-CoA oxidoreductase; a 3-hydroxy-6-aminopimeloyl-CoA dehydratase; a 6-amino-7-carboxy-hept-2-enoyl-CoA reductase; 6-aminopimeloyl-CoA hydrolase, transferase and/or ligase; and a 2-aminopimelate decarboxylase.

3. The non-naturally occurring microbial organism of claim 1, wherein said 6-ACA pathway comprises at least three exogenous nucleic acids.

4. The non-naturally occurring microbial organism of claim 1, wherein said exogenous nucleic acid is a heterologous nucleic acid.

5. The non-naturally occurring microbial organism of claim 1, wherein said non-naturally occurring microbial organism is in culture medium, wherein said culture medium is in an atmosphere of less than 1% oxygen or comprises dissolved oxygen in an amount that is less than 10% of saturation.

6. The non-naturally occurring microbial organism of claim 1, wherein said 6-ACA pathway comprises at least four exogenous nucleic acids.

7. The non-naturally occurring microbial organism of claim 1, wherein said 6-ACA pathway comprises at least five exogenous nucleic acids.

8. The non-naturally occurring microbial organism of claim 1, wherein said 6-ACA pathway comprises at least six exogenous nucleic acids.

9. The non-naturally occurring microbial organism of claim 1, wherein said 6-ACA pathway comprises at least seven exogenous nucleic acids.

10. The non-naturally occurring microbial organism of claim 1, wherein said 6-ACA pathway comprises at least eight exogenous nucleic acids.

11. A method for producing 6-aminocaproic acid (6-ACA), comprising culturing a non-naturally occurring microbial organism of claim 5 under conditions and for a sufficient period of time to produce 6-ACA.

12. The non-naturally occurring microbial organism of claim 1, part (iv), further comprising a 2-amino-7-oxosubarate pathway comprising at least one exogenous nucleic acid encoding a 2-amino-7-oxosubarate pathway enzyme expressed in a sufficient amount to produce 2-amino-7-oxosubarate, said 2-amino-7-oxosubarate pathway comprising a 2-amino-5-hydroxy-7-oxosubarate aldolase, a 2-amino-5-hydroxy-7-oxosubarate dehydratase, or a 2-amino-5-ene-7-oxosubarate reductase.

13. The non-naturally occurring microbial organism of claim 2, part (v), further comprising a 2-amino-7-oxosubarate pathway comprising a second set of exogenous nucleic acids encoding 2-amino-7-oxosubarate pathway enzymes expressed in a sufficient amount to produce 2-amino-7-oxosubarate, said second set of exogenous nucleic acids encoding a 2-amino-5-hydroxy-7-oxosubarate aldolase; a 2-amino-5-hydroxy-7-oxosubarate dehydratase; and a 2-amino-5-ene-7-oxosubarate reductase.

14. A method for producing 6-aminocaproic acid (6-ACA), comprising culturing a non-naturally occurring microbial organism of claim 1 under conditions and for a sufficient period of time to produce 6-ACA.

* * * * *

SEQUENCE LISTING

```
<160> NUMBER OF SEQ ID NOS: 50

<210> SEQ ID NO 1
<211> LENGTH: 20
<212> TYPE: PRT
<213> ORGANISM: Euglena gracilis

<400> SEQUENCE: 1
```

```
Met Thr Tyr Lys Ala Pro Val Lys Asp Val Lys Phe Leu Leu Asp Lys
1               5                   10                  15
Val Phe Lys Val
            20

<210> SEQ ID NO 2
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 2

His His His His His His
1               5

<210> SEQ ID NO 3
<211> LENGTH: 26
<212> TYPE: DNA
<213> ORGANISM: Artificial Sequence
<220> FEATURE:
<223> OTHER INFORMATION: Synthetic primer

<400> SEQUENCE: 3
atgacgcgtg aagtggtagt ggtaag                                    26

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
gatacgctcg aagatggcgg                                           20

<210> SEQ ID NO 5
<211> LENGTH: 1185
<212> TYPE: DNA
<213> ORGANISM: Ralstonia eutropha

<400> SEQUENCE: 5
atgacgcgtg aagtggtagt ggtaagcggt gtccgtaccg cgatcgggac ctttggcggc    60
agcctgaagg atgtggcacc ggcggagctg ggcgcactgg tggtgcgcga ggcgctggcg   120
cgcgcgcagg tgtcgggcga cgatgtcggc cacgtggtat tcggcaacgt gatccagacc   180
gagccgcgcg acatgtatct gggccgcgtc gcggccgtca acggcggggt gacgatcaac   240
gcccccgcgc tgaccgtgaa ccgcctgtgc ggctcgggcc tgcaggccat tgtcagcgcc   300
gcgcagacca tcctgctggg cgataccgac gtcgccatcg gcggcggcgc ggaaagcatg   360
agccgcgcac cgtacctggc gccggcagcg cgctggggcg cacgcatggg cgacgccggc   420
ctggtcgaca tgatgctggg tgcgctgcac gatcccttcc atcgcatcca catgggcgtg   480
accgccgaga atgtcgccaa ggaatacgac atctcgcgcg cgcagcagga cgaggccgcg   540
ctggaatcgc accgccgcgc ttcggcagcg atcaaggccg gctacttcaa ggaccagatc   600
gtcccggtgg tgagcaaggg ccgcaagggc gacgtgacct cgacaccga cgagcacgtg   660 cgccatgacg ccaccatcga cgacatgacc aagctcaggc cggtcttcgt caaggaaaac   720
ggcacggtca cggccggcaa tgcctcgggc ctgaacgacg ccgccgccgc ggtggtgatg   780
atggagcgcg ccgaagccga cgccgcggc ctgaagccgc tggcccgcct ggtgtcgtac   840
```

```
ggccatgccg gcgtggaccc gaaggccatg ggcatcggcc cggtgccggc gacgaagatc    900
gcgctggagc gcgccggcct gcaggtgtcg gacctggacg tgatcgaagc caacgaagcc    960
tttgccgcac aggcgtgcgc cgtgaccaag gcgctcggtc tggacccggc caaggttaac   1020
ccgaacggct cgggcatctc gctgggccac ccgatcggcg ccaccggtgc cctgatcacg   1080
gtgaaggcgc tgcatgagct gaaccgcgtg cagggccgct acgcgctggt gacgatgtgc   1140
atcggcggcg gcagggcat tgccgccatc ttcgagcgta tctga                    1185
```

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6

```
atggaagtaa gatgcctgga acgaag                                          26
```

<210> SEQ ID NO 7
<211> LENGTH: 21
<212> TYPE: DNA
<213> ORGANISM: Artificial Sequence
<220> FEATURE:
<223> OTHER INFORMATION: Synthetic primer

<400> SEQUENCE: 7

```
cagcttctca atcagcaggg c                                               21
```

<210> SEQ ID NO 8
<211> LENGTH: 1215
<212> TYPE: DNA
<213> ORGANISM: Mus musculus

<400> SEQUENCE: 8

```
atggaagtaa gatgcctgga acgaagttat gcatccaaac ccactttgaa tgaagtggtt     60
atagtaagtg ctataagaac tcccattgga tccttcctgg gcagccttgc ctctcagccg    120
gccactaaac ttggtactgc tgcaattcag ggagccattg agaaggcagg gattccaaaa    180
gaagaagtga aggaagtcta catgggcaat gtcatccaag ggggtgaagg acaggcccct    240
accaggcaag caacactggg cgcaggttta cctatttcca ctccatgcac acagtaaac    300 aaggtttgtg cttcaggaat gaaagccatc atgatggcct ctcaaagtct tatgtgtgga    360
catcaggatg tgatggtggc aggcgggatg gagagcatgt ccaatgtccc atacgtaatg    420
agcagaggag caacaccata tggtgggta aaacttgaag acctgattgt aaaagacggg    480
ctaactgatg tctacaataa aattcatatg ggtaactgtg ctgagaatac tgcaaagaag    540
atgaatatct cacggcagga acaggatacg tacgctctca gctcttacac cagaagtaaa    600
gaagcgtggg acgcagggaa gtttgccagt gagattactc ccatcaccat ctcagtgaaa    660
ggtaaaccag atgtggtggt gaaagaagat gaagaataca gcgtgttga ctttagtaaa    720 gtgccaaagc tcaagaccgt gttccagaaa gaaatggca caataacagc tgccaatgcc    780
agcacactga acgatggagc agctgctctg gttctcatga ctgcagaggc agcccagagg    840
ctcaatgtta agccattggc acgaattgca gcatttgctg atgctgccgt agacccatt    900 gattttccac ttgcgcctgc atatgccgta cctaaggttc ttaaatatgc aggactgaaa    960
aaagaagaca ttgccatgtg ggaagtaaat gaagcattca gtgtggttgt gctagccaac   1020
```

```
attaaaatgc tggagattga cccccaaaaa gtaaatatcc acggaggagc tgtttctctg      1080
ggccatccaa ttgggatgtc tggagcccgg attgttgttc atatggctca tgccctgaag      1140
ccaggagagt tcggtctggc tagtatttgc aacggaggag gaggtgcttc cgccctgctg      1200
attgagaagc tgtag                                                       1215

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
atgaccctcg ccaatgaccc                                                    20

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
gtacaggcat tcaacagcca tgg                                                23

<210> SEQ ID NO 11
<211> LENGTH: 1194
<212> TYPE: DNA
<213> ORGANISM: Pseudomonas putida

<400> SEQUENCE: 11
atgaccctcg ccaatgaccc catcgttatc gtcagcgccg tgcgcacgcc catgggcggg       60
ttgcagggcg acctcaagag cctgactgcg ccgcaactgg gcagcgccgc cattcgtgct      120
gccgtggaac gggccggcat cgatgccgcc ggtgtcgagc aggtactgtt cggctgcgtg      180
ctgccggccg gccagggcca ggcaccggca cgccaggccg cgctgggcgc cgggctggac      240
aagcacacca cctgcaccac cctgaacaag atgtgcggct cgggtatgca agccgcgatc      300
atggcccatg acctgctgct ggccggcacc gcagacgtgg tagtggcggg tggcatggaa      360
agcatgacca acgcgccgta cctgctggac aaagcccgtg gcggctaccg catgggccac      420
ggcaagatca tcgaccacat gttcatggac ggtctcgaag acgcctacga caaaggccgc      480
ctgatgggta ccttttgccga ggactgtgcc caggccaatg ccttcagccg cgaggcccag      540
gaccagttcg ccatcgcctc gctgacccga gcgcaggaag ccatcagcag cggccgtttt      600
gccgccgaga tcgtgccggt ggaagtcacc gagggcaagg aaaagcgcgt catcaaggat      660
gacgagcagc cgcccaaggc gcgtctggac aagattgcgc agctcaaacc ggcgtttcgt      720
gaaggcggca ccgtgacggc ggccaacgcc agttcgattt ccgacggcgc tgcggcgctg      780
gtactgatgc gccgctccga ggccgacaaa cgtggcctca agccattggc cgtcatccac      840
ggccacgccg cctttgccga cacccgggcg ctgttcccga ccgccccgat cggcgcgatc      900
gacaaactga tgaaacgcac cggctggaac ctggccgaag tcgacctgtt cgagatcaac      960
gaggccttcg ccgtggtcac cctggcggcc atgaaacacc tcgacctgcc acacgacaag     1020
gtcaatatcc acggcggcgc ctgcgccctc ggtcacccga tcggcgcttc tggcgcacgt     1080
attctggtca ccctgttgtc ggccttgcgc cagaacaatc tgcgtcgggg tgtggcggcc     1140
atctgcatcg gcggtggcga ggccacggcc atggctgttg aatgcctgta ctga          1194
```

<210> SEQ ID NO 12
<211> LENGTH: 25
<212> TYPE: DNA
<213> ORGANISM: Artificial Sequence
<220> FEATURE:
<223> OTHER INFORMATION: Synthetic primer

<400> SEQUENCE: 12

```
atgaacaaac atgctttcat cgtcg                                     25
```

<210> SEQ ID NO 13
<211> LENGTH: 29
<212> TYPE: DNA
<213> ORGANISM: Artificial Sequence
<220> FEATURE:
<223> OTHER INFORMATION: Synthetic primer

<400> SEQUENCE: 13

```
taatttctgg ataaccattc cacttgagc                                 29
```

<210> SEQ ID NO 14
<211> LENGTH: 1167
<212> TYPE: DNA
<213> ORGANISM: Caenorhabditis elegans

<400> SEQUENCE: 14

```
atgaacaaac atgctttcat cgtcggagcc gcccgtacac ctattggatc atttcgttct    60
tctctctctt cggtaactgc tccagagctc gcctcggttg ccatcaaagc agcattggag   120
cgtggagcag tgaagccgag ttcaattcag gaggtgttcc ttggtcaagt ctgtcaagca   180
aatgctggtc aagctcccgc tcgtcaagca gctcttggag ccggactcga tctttcggtt   240
gctgttacca ccgtcaataa agtgtgctct tctgggctga agcaatcat tcttgctgcc    300
cagcaaattc aaaccggtca tcaagatttt gccattggcg gaggaatgga gagcatgtca   360
caagtaccat tttatgttca agaggagag atcccatatg gtggatttca gtgattgat     420
ggaatcgtca agacggact gaccgatgct tatgataaag ttcacatggg aaactgcgga   480
gagaagactt caaaagaaat gggaattaca cgtaaagacc aagacgaata tgctatcaac   540
agctacaaaa agtcagctaa agcatgggag aatggaaata tcggaccaga agtggtgcca   600
gtgaacgtca aatcaaagaa gggagtcacg attgttgata agatgaaga gttcacaaaa   660
gtcaatttcg acaagttcac ctcgctgaga actgttttcc agaaagacgg aactatcact   720
gctgctaatg cttcaacatt gaacgacggt gcagctgctg tcattgttgc ctcacaggaa   780
gcagtttccg agcaaagctt aaagcctctg gcccgaattt tggcttatgg agatgccgcc   840
acgcacccac tcgatttcgc tgtagcacca actttgatgt tcccaaaaat tcttgaaaga   900
gcaggagtga agcaatcaga tgttgctcaa tgggaagtta atgaagcctt ctcatgtgtt   960
cccctttgctt tcatcaaaaa actaggagtc gatccatccc ttgtgaaccc acatggagga  1020
gctgtttcaa ttggtcaccc catcggaatg tccggagccc gcctcatcac tcatcttgtg  1080
cacacactca aaagtggcca aatcggagtt gctgccattt gcaatggagg tggtggctca  1140
agtggaatgg ttatccagaa attataa                                     1167
```

<210> SEQ ID NO 15
<211> LENGTH: 25
<212> TYPE: DNA
<213> ORGANISM: Artificial Sequence
<220> FEATURE:

<223> OTHER INFORMATION: Synthetic primer

<400> SEQUENCE: 15
atgcgtgaag cctttatttg tgacg     25

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
aacacgctcc agaatcatgg cg     22

<210> SEQ ID NO 17
<211> LENGTH: 1206
<212> TYPE: DNA
<213> ORGANISM: Escherichia coli

<400> SEQUENCE: 17

| | | | | | |
|---|---|---|---|---|---|
| atgcgtgaag | cctttatttg | tgacggaatt | cgtacgccaa | ttggtcgcta | cggcggggca | 60 |
| ttatcaagtg | ttcgggctga | tgatctggct | gctatccctt | gcgggaact | gctggtgcga | 120 |
| aacccgcgtc | tcgatgcgga | gtgtatcgat | gatgtgatcc | tcggctgtgc | taatcaggcg | 180 |
| ggagaagata | accgtaacgt | agcccggatg | gcgactttac | tggcggggct | gccgcagagt | 240 |
| gtttccggca | caaccattaa | ccgcttgtgt | ggttccgggc | tggacgcact | ggggtttgcc | 300 |
| gcacgggcga | ttaaagcggg | cgatggcgat | ttgctgatcg | ccgtggcgt | ggagtcaatg | 360 |
| tcacgggcac | cgtttgttat | gggcaaggca | gccagtgcat | tttctcgtca | ggctgagatg | 420 |
| ttcgatacca | ctattggctg | gcgatttgtg | aacccgctca | tggctcagca | atttggaact | 480 |
| gacagcatgc | cggaaacggc | agagaatgta | gctgaactgt | taaaaatctc | acgagaagat | 540 |
| caagatagtt | tgcgctacg | cagtcagcaa | cgtacggcaa | aagcgcaatc | ctcaggcatt | 600 |
| ctggctgagg | agattgttcc | ggttgtgttg | aaaaacaaga | aggtgttgt | aacagaaata | 660 |
| caacatgatg | agcatctgcg | cccggaaacg | acgctggaac | agttacgtgg | gttaaaagca | 720 |
| ccatttcgtg | ccaatggggt | gattaccgca | ggcaatgctt | ccggggtgaa | tgacggagcc | 780 |
| gctgcgttga | ttattgccag | tgaacagatg | gcagcagcgc | aaggactgac | accgcgggcg | 840 |
| cgtatcgtag | ccatggcaac | cgccggggtg | gaaccgcgcc | tgatggggct | tggtccggtg | 900 |
| cctgcaactc | gccgggtgct | ggaacgcgca | gggctgagta | ttcacgatat | ggacgtgatt | 960 |
| gaactgaacg | aagcgttcgc | ggcccaggcg | ttgggtgtac | tacgcgaatt | ggggctgcct | 1020 |
| gatgatgccc | cacatgttaa | ccccaacgga | ggcgctatcg | ccttaggcca | tccgttggga | 1080 |
| atgagtggtg | cccgcctggc | actggctgcc | agccatgagc | tgcatcggcg | taacggtcgt | 1140 |
| tacgcattgt | gcaccatgtg | catcggtgtc | ggtcagggca | tcgccatgat | tctggagcgt | 1200 |
| gtttga | | | | | | 1206 |

<210> SEQ ID NO 18
<211> LENGTH: 21
<212> TYPE: DNA
<213> ORGANISM: Artificial Sequence
<220> FEATURE:
<223> OTHER INFORMATION: Synthetic primer

<400> SEQUENCE: 18
atgaatgaac cgacccacgc c     21

```
<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
gaggcgctcg atgatcatgg                                                  20

<210> SEQ ID NO 20
<211> LENGTH: 1221
<212> TYPE: DNA
<213> ORGANISM: Pseudomonas putida

<400> SEQUENCE: 20
atgaatgaac cgacccacgc cgatgccttg atcatcgacg ccgtgcgcac gcccattggc      60
cgctatgccg ggccctgag cagcgtgcgc gccgacgacc tggcggccat cccgctcaaa     120
gccttgatcc agcgtcaccc cgaactggac tggaaagcca ttgatgacgt tatcttcggc    180
tgtgccaacc aggctggcga agacaaccgc aacgtggccc acatggcgag cctgctggcc    240
gggctgccac tcgaagtacc agggaccacg atcaaccgcc tgtgcggttc cggtctggat    300
gccatcggta atgcggcacg tgccctgcgc tgcggtgaag cggggctcat gctgccggt    360 ggtgtggagt ccatgtcgcg tgcaccgttt gtgatgggta agtcggagca ggcattcggg    420
cgtgcggccg agctgttcga caccaccatc ggctggcgtt tcgtcaaccc gctgatgaag    480
gccgcctacg gcatcgattc gatgccggaa acggctgaaa acgtggccga acagttcggc    540
atctcgcgcg ccgaccagga tgcctttgcc ctgcgcagcc agcacaaagc cgcagcagct    600
caggcccgcg gccgcctggc gcgggaaatc gtgccggtcg aaatcccgca acgcaaaggc    660
ccagccaaag tggtcgagca tgacgagcac ccgcgcggcg acacgaccct ggagcagctg    720
gctcggctcg ggacgccgtt tcgtgaaggc ggcagcgtaa cggcgggtaa tgcctccggc    780
gtgaatgacg gcgcttgcgc cctgctgctg gccagcagcg ccgcggcccg ccgccatggg    840
ttgaaggccc gcgccgcat cgtcggcatg gcggtggccg gggttgagcc caggctgatg    900
ggcattggtc cggtgcctgc gacccgcaag gtgctggcgc tcaccggcct ggcactggct    960
gacctggatg tcatcgaact caatgaggcc tttgccgccc aagggctggc cgtgttgcgc   1020
gagctgggcc tggccgacga cgacccgcga gtcaaccgca acggcggcgc catcgccctg   1080
ggccatcccc tgggcatgag cggtgcccgg ttggtgacca ctgccttgca cgagcttgaa   1140
gaaacggccg gccgctacgc cctgtgcacc atgtgcatcg gcgtaggcca aggcattgcc   1200
atgatcatcg agcgcctctg a                                             1221

<210> SEQ ID NO 21
<211> LENGTH: 35
<212> TYPE: DNA
<213> ORGANISM: Artificial Sequence
<220> FEATURE:
<223> OTHER INFORMATION: Synthetic primer

<400> SEQUENCE: 21
atgaaagaag ttgtaatagc tagtgcagta agaac                                 35

<210> SEQ ID NO 22
<211> LENGTH: 27
<212> TYPE: DNA
```

<213> ORGANISM: Artificial Sequence
<220> FEATURE:
<223> OTHER INFORMATION: Synthetic primer

<400> SEQUENCE: 22

| gcactttctct agcaatattg ctgttcc | 27 |

<210> SEQ ID NO 23
<211> LENGTH: 1179
<212> TYPE: DNA
<213> ORGANISM: Clostridium acetobutylicum

<400> SEQUENCE: 23

| atgaaagaag ttgtaatagc tagtgcagta agaacagcga ttggatctta tggaaagtct | 60 |
| cttaaggatg taccagcagt agatttagga gctacagcta taaggaagc agttaaaaaa | 120 |
| gcaggaataa aaccagagga tgttaatgaa gtcattttag gaaatgttct tcaagcaggt | 180 |
| ttaggacaga atccagcaag acaggcatct tttaaagcag gattaccagt tgaaattcca | 240 |
| gctatgacta ttaataaggt ttgtggttca ggacttagaa cagttagctt agcagcacaa | 300 |
| attataaaag caggagatgc tgacgtaata atagcaggtg gtatggaaaa tatgtctaga | 360 |
| gctccttact tagcgaataa cgctagatgg ggatatagaa tgggaaacgc taaatttgtt | 420 |
| gatgaaatga tcactgacgg attgtgggat gcatttaatg attaccacat gggaataaca | 480 |
| gcagaaaaca tagctgagag atggaacatt tcaagagaag aacaagatga gtttgctctt | 540 |
| gcatcacaaa aaaagctga agaagctata aaatcaggtc aatttaaaga tgaaatagtt | 600 |
| cctgtagtaa ttaaaggcag aaaggggaaa actgtagttg atacagatga gcaccctaga | 660 |
| tttggatcaa ctatagaagg acttgcaaaa ttaaaacctg ccttcaaaaa agatggaaca | 720 |
| gttacagctg gtaatgcatc aggattaaat gactgtgcag cagtacttgt aatcatgagt | 780 |
| gcagaaaaag ctaaagagct tggagtaaaa ccacttgcta agatagtttc ttatggttca | 840 |
| gcaggagttg acccagcaat aatgggatat ggacctttct atgcaacaaa agcagctatt | 900 |
| gaaaaagcag gttggacagt tgatgaatta gatttaatag aatcaaatga agcttttgca | 960 |
| gctcaaagtt tagcagtagc aaaagattta aaatttgata tgaataaagt aaatgtaaat | 1020 |
| ggaggagcta ttgcccttgg tcatccaatt ggagcatcag gtgcaagaat actcgttact | 1080 |
| cttgtacacg caatgcaaaa aagagatgca aaaaaaggct tagcaacttt atgtataggt | 1140 |
| ggcggacaag gaacagcaat attgctagaa aagtgctag | 1179 |

<210> SEQ ID NO 24
<211> LENGTH: 37
<212> TYPE: DNA
<213> ORGANISM: Artificial Sequence
<220> FEATURE:
<223> OTHER INFORMATION: Synthetic primer

<400> SEQUENCE: 24

| atgagagatg tagtaatagt aagtgctgta agaactg | 37 |

<210> SEQ ID NO 25
<211> LENGTH: 28
<212> TYPE: DNA
<213> ORGANISM: Artificial Sequence
<220> FEATURE:
<223> OTHER INFORMATION: Synthetic primer

<400> SEQUENCE: 25

| gtctctttca actacgagag ctgttccc | 28 |

<210> SEQ ID NO 26
<211> LENGTH: 1179
<212> TYPE: DNA
<213> ORGANISM: Clostridium acetobutylicum

<400> SEQUENCE: 26

```
atgagagatg tagtaatagt aagtgctgta agaactgcaa taggagcata tggaaaaaca       60
ttaaaggatg tacctgcaac agagttagga gctatagtaa taaaggaagc tgtaagaaga      120
gctaatataa atccaaatga gattaatgaa gttatttttg gaaatgtact tcaagctgga      180
ttaggccaaa acccagcaag acaagcagca gtaaaagcag gattaccttt agaaacacct      240
gcgtttacaa tcaataaggt ttgtggttca ggtttaagat ctataagttt agcagctcaa      300
attataaaag ctggagatgc tgataccatt gtagtaggtg gtatggaaaa tatgtctaga      360
tcaccatatt tgattaacaa tcagagatgg ggtcaaagaa tgggagatag tgaattagtt      420
gatgaaatga taaggatgg tttgtgggat gcatttaatg gatatcatat gggagtaact      480
gcagaaaata ttgcagaaca atggaatata acaagagaag agcaagatga attttcactt      540
atgtcacaac aaaaagctga aaaagccatt aaaaatggag aatttaagga tgaaatagtt      600
cctgtattaa taaagactaa aaaaggtgaa atagtctttg atcaagatga atttcctaga      660
ttcggaaaca ctattgaagc attaagaaaa cttaaaccta ttttcaagga aaatggtact      720
gttacagcag gtaatgcatc cggattaaat gatggagctg cagcactagt aataatgagc      780
gctgataaag ctaacgctct cggaataaaa ccacttgcta agattacttc ttacggatca      840
tatgggtag atccatcaat aatgggatat ggagcttttt atgcaactaa agctgcctta      900
gataaaatta atttaaaacc tgaagactta gatttaattg aagctaacga ggcatatgct      960
tctcaaagta tagcagtaac tagagattta aatttagata tgagtaaagt taatgttaat     1020
ggtggagcta tagcacttgg acatccaata ggtgcatctg gtgcacgtat tttagtaaca     1080
ttactatacg ctatgcaaaa aagagattca aaaaaaggtc ttgctactct atgtattggt     1140
ggaggtcagg gaacagctct cgtagttgaa agagactaa                            1179
```

<210> SEQ ID NO 27
<211> LENGTH: 31
<212> TYPE: DNA
<213> ORGANISM: Artificial Sequence
<220> FEATURE:
<223> OTHER INFORMATION: Synthetic primer

<400> SEQUENCE: 27

```
atgttcaaga aatcagctaa tgatattgtt g                                      31
```

<210> SEQ ID NO 28
<211> LENGTH: 22
<212> TYPE: DNA
<213> ORGANISM: Artificial Sequence
<220> FEATURE:
<223> OTHER INFORMATION: Synthetic primer

<400> SEQUENCE: 28

```
ctcgttagca aacaaggcag cg                                                22
```

<210> SEQ ID NO 29
<211> LENGTH: 1182
<212> TYPE: DNA
<213> ORGANISM: Candida albicans

<400> SEQUENCE: 29

```
atgttcaaga atcagctaa tgatattgtt gttattgcag caaagagaac tccaatcacc      60
aagtcaatta aggtgggtt gagtagatta tttcctgagg aaatattata tcaagtggtt     120
aagggtactg tatcagattc acaagttgat ttaaacttga ttgatgatgt gttagtcggt    180
acggtcttgc aaactttagg gggacagaaa gctagtgcct tggccattaa aaagattgga    240
ttcccaatta agaccacggt taatacggtc aatcgtcaat gtgctagttc tgctcaagcg    300
attacttatc aagcaggtag tttgcgtagt ggggagaatc aatttgctat tgctgctgga    360
gtagaaagta tgactcatga ttattttcct catcgtggga ttcccacaag aatttctgaa    420
tcattttag ctgatgcatc cgatgaagct aaaaacgtct tgatgccaat ggggataacc      480
agtgaaaatg ttgccactaa atatggaatt tctcgtaaac aacaagatga gtttgcccct    540
aattctcatt tgaaagcaga caaggctaca aaactgggtc attttgcaaa agaaatcatt    600
cctattcaaa caacgatga aaacaaccaa cacgtttcaa taaccaaaga tgatggtata    660
aggggaagtt caacaattga aaagttgggt ggcttaaaac ctgtgttcaa ggatgatggg    720
actactactg ctggtaattc ctcgcaaatt tcagatggag ggtctgctgt gattttaact    780
actcgtcaaa atgctgagaa atcggagta aagccaatag ctagatttat tggttcgtca    840
gtagctggtg ttccttcggg acttatggga attggtccat cggctgctat tcctcaattg    900
ttgtcgagat taaatgttga cacgaaagac attgatattt ttgaattgaa cgaggcattt    960
gcatcccaac tgatttattg tattgaaaaa ttgggtcttg attatgataa agtcaatcca   1020
tatggtggag ctatagcctt gggacatcca ttaggagcca ctggcgcaag agttacggca   1080
acgttgctta atggattaaa agatcagaat aaagagttgg gtgtcatctc aatgtgcaca   1140
tccacaggtc aaggatacgc tgccttgttt gctaacgagt ag                      1182
```

<210> SEQ ID NO 30
<211> LENGTH: 38
<212> TYPE: DNA
<213> ORGANISM: Artificial Sequence
<220> FEATURE:
<223> OTHER INFORMATION: Synthetic primer

<400> SEQUENCE: 30

```
atggatagat taaatcaatt aagtggtcaa ttaaaacc                             38
```

<210> SEQ ID NO 31
<211> LENGTH: 26
<212> TYPE: DNA
<213> ORGANISM: Artificial Sequence
<220> FEATURE:
<223> OTHER INFORMATION: Synthetic primer

<400> SEQUENCE: 31

```
ttccttaatc aatatggagg cagcac                                          26
```

<210> SEQ ID NO 32
<211> LENGTH: 1227
<212> TYPE: DNA
<213> ORGANISM: Candida albicans

<400> SEQUENCE: 32

```
atggatagat taaatcaatt aagtggtcaa ttaaaaccaa cttcaaaaca atcccttact     60
caaaagaacc cagacgatgt tgtcatcgtt gcagcataca gaactgccat cggtaaaggt    120
ttcaaagggt cttttcaaatc tgtgcaatct gaattcatct tgactgaatt cttgaaagaa   180
```

```
tttattaaaa agactggagt cgatgcatct tgattgaag atgttgctat tggtaacgtt      240
ttgaaccaag ctgctggtgc caccgaacac agaggtgcta gtttggctgc aggtattcct      300
tacactgcag ctttccttgc catcaacaga ttgtgttcct cagggttaat ggccatttct      360
gacattgcca acaaaatcaa aaccggtgaa atcgaatgtg gtcttgctgg tggtattgaa      420
tccatgtcta aaaactatgg tagtccaaaa gttattccaa agattgaccc acacttggct      480
gatgacgaac aaatgagtaa atgtttgatt ccaatgggta tcaccaacga aaatgttgct      540
aatgaattca acattccaag agaaaaacaa gatgcctttg ctgctaaatc ttatagtaaa      600
gccgaaaaag ccatctcctc tggagctttc aaagatgaaa tcttaccaat cagatccatt      660
atcagatccc cagacggttc tgaaaagaa atcattgtcg ataccgacga aggtccaaga      720
aagggtgttg acgctgcttc cttgagcaaa ttgaaaccag catttggtgg tactaccact      780
gccggtaacg cttctcaaat ttcagatggt gctgctggtg ttttattgat gaagagaagt      840
ttggctgaag ccaaaggtta cccaattgtt gctaaataca ttgcttgttc aactgttggt      900
gttccgccag aaatcatggg tgttggtcca gcttacgcca ttccagaagt gttgaagaga      960
actggattga ctgtggatga cgttgatgtg tttgaaatca cgaagctttt tgctgctcaa     1020
tgtctttact cagctgaaca atgtaatgtt ccagaagaaa aattgaacat aaacggtggt     1080
gccatcgctt taggtcatcc tcttggttgt actggtgcca gacaatatgc cactatcttg     1140
agattgttga accaggtga aattggtttg acttctatgt gtatcggtag tggtatgggt     1200
gctgcctcca tattgattaa ggaatag                                         1227

<210> SEQ ID NO 33
<211> LENGTH: 30
<212> TYPE: DNA
<213> ORGANISM: Artificial Sequence
<220> FEATURE:
<223> OTHER INFORMATION: Synthetic primer

<400> SEQUENCE: 33
atgtcatcca aacaacaata cttgaagaag                                        30

<210> SEQ ID NO 34
<211> LENGTH: 27
<212> TYPE: DNA
<213> ORGANISM: Artificial Sequence
<220> FEATURE:
<223> OTHER INFORMATION: Synthetic primer

<400> SEQUENCE: 34
ttctctaacc aaaacagaag cagcacc                                           27

<210> SEQ ID NO 35
<211> LENGTH: 1233
<212> TYPE: DNA
<213> ORGANISM: Candida albicans

<400> SEQUENCE: 35
atgtcatcca aacaacaata cttgaagaag aatcctgacg atgtcgttgt cgttgcagca       60
tacagaactg ctttaaccaa aggtggaaga ggtggattca aagatgttgg atctgatttc      120
cttttgaaaa aattgactga agaatttgtt aaaaaaactg gtgttgaccc taaaatcatt      180
caagatgctg ccattggtaa tgtccttgaa cagaagagctg gtgatttcga acatagaggt      240
gcattattat ctgctggatt acctattcca gttccatttg ttgcccttaa cagacaatgt      300
```

```
tcatctgggt taatggccat ttctcaagtg gccaacaaga tcaagactgg tgaaattgaa      360
tgtggtttag ctggtggtgt tgaaagtatg acaaaaaact atggtccaga agcattgatt      420
gctattgacc ctgcttatga aaaagaccca gaatttgtta aaaacggtat tccaatgggt      480
attactaatg aaaatgtttg tgccaaattc aatatttcaa gagatgttca agatcaattt      540
gctgctgaat cttatcaaaa agctgaaaag gcacaaaaag aaggtaaatt tgatgatgaa      600
attttaccaa ttgaagtttt ccaagaagat gaagatgctg aagatgaaga cgaagatgaa      660
gatgaagatg ctgaaccaaa agaaaaattg gttgttatta gtaaagatga aggtattaga      720
ccaggtgtta ctaaagaaaa attggctaaa attaaaccag ctttcaaatc tgatggtgta      780
tcttcagctg gtaactcttc acaagtttcc gatggtgctg ccttggtgtt attgatgaaa      840
cgttcatttg ctgaaaagaa tggattcaaa ccattggcta atacatttc  ttgtggtgtt      900 gctggtgtcc caccagaaat tatgggtatt ggtccagctg ttgccattcc aaaagttttg      960
aaacaaactg gattatcagt cagtgatatt gatatttatg aaatcaatga agcatttgcc     1020
ggtcaatgtt tgtactcaat tgaaagttgt aatattccaa gagaaaaagt caatcttaat     1080
gggggtgcta ttgccttggg tcaccctctt ggttgtactg gtgctagaca atacgctact     1140
attttaagat tgttaaaacc aggtgaattt ggtgtgactt ctatgtgtat tggtactggt     1200
atgggtgctg cttctgtttt ggttagagaa taa                                 1233
```

<210> SEQ ID NO 36
<211> LENGTH: 23
<212> TYPE: DNA
<213> ORGANISM: Artificial Sequence
<220> FEATURE:
<223> OTHER INFORMATION: Synthetic primer

<400> SEQUENCE: 36

```
atgagccgcg aggtattcat ctg                                              23
```

<210> SEQ ID NO 37
<211> LENGTH: 18
<212> TYPE: DNA
<213> ORGANISM: Artificial Sequence
<220> FEATURE:
<223> OTHER INFORMATION: Synthetic primer

<400> SEQUENCE: 37

```
gacccgctcg atggccag                                                    18
```

<210> SEQ ID NO 38
<211> LENGTH: 1206
<212> TYPE: DNA
<213> ORGANISM: Pseudomonas aeruginosa

<400> SEQUENCE: 38

```
atgagccgcg aggtattcat ctgcgatgcc gtgcgcacgc cgatcggccg tttcggcggc       60
agtctttccg cggtgcgcgc cgacgacctc gcggcggtgc cgctgaaggc cctggtcgag      120
cgcaacccgg gggtcgactg gtcggcgttg gacgaggtgt tcctcggctg cgccaaccag      180
gccggcgagg acaaccgtaa cgtggcgcgc atggcgctgc tgctggccgg tttgccggag      240
agcgtgcccg gcgtcaccct caaccgcctc tgcgcctcgg ggatggacgc catcggcacg      300 gcgttccgg ccatcgcctg cggcgagatg gagctggcca tcgccggcgg cgtcgagtcg      360
atgtcgcgcg cgccgtacgt gatgggcaag gccgatagcg ccttcggtcg cggccagaag      420
atcgaggaca ccaccatcgg ctggcgcttc gtcaatccgc tgatgaagga gcagtacggc      480
```

```
atcgacccga tgccgcagac cgccgacaac gtcgccgacg actatcgcgt gtcgcgtgcc      540
gaccaggatg ccttcgccct gcgcagccag cagcgcgccg gcagggcgca ggaggccggt      600
ttcttcgccg aggaaatcgt cccggtgacg attcgcgggc gcaagggcga cacCctggtc      660
gagcacgacg agcatccgcg tcccgacacc accctggagg cgctggcccg gctcaagccg      720
gtcaacgggc cggagaagac cgtcaccgcc ggcaacgcgt ccggggtcaa cgacggcgcc      780
gccgcgctgt tcctggcctc cgccgaggca gtggagaagc acggcctgac tccgcgcgcg      840
cgggtgctgg gcatggccag cgccggcgtc gccccacgga tcatgggcat cggcccggtg      900
ccggcggtgc gcaagctgct gcggcgcctg gacctggcga tcgacgcctt cgacgtgatc      960
gaactcaacg aagccttcgc cagccagggc ctggcctgcc tgcgcgaact gggcgtggcc     1020
gacgacagtg agaaggtcaa cccgaacggc ggtgccatcg ccctcggcca cccgctgggg     1080
atgagcggtg cgcggctggt cctcaccgcg ctccatcaac ttgagaagag cggcggccgg     1140
cgcggcctgg cgaccatgtg cgtaggcgtc ggccaaggcc tggcgctggc catcgagcgg     1200
gtctga                                                                1206

<210> SEQ ID NO 39
<211> LENGTH: 24
<212> TYPE: DNA
<213> ORGANISM: Artificial Sequence
<220> FEATURE:
<223> OTHER INFORMATION: Synthetic primer

<400> SEQUENCE: 39
atgctcgatg cctatatcta cgcc                                              24

<210> SEQ ID NO 40
<211> LENGTH: 18
<212> TYPE: DNA
<213> ORGANISM: Artificial Sequence
<220> FEATURE:
<223> OTHER INFORMATION: Synthetic primer

<400> SEQUENCE: 40
tcggcagcgc tcgatcac                                                     18

<210> SEQ ID NO 41
<211> LENGTH: 1206
<212> TYPE: DNA
<213> ORGANISM: Pseudomonas aeruginosa

<400> SEQUENCE: 41
atgctcgatg cctatatcta cgccggcctg cgtacgcctt tcggccggca tgccggtgca       60
ctctcgacgg tgcgtccgga cgacctggcc ggcctgctgc tggcgcgtct cgcggaaacc      120
tccgggttcg ccgtcgacga cctggaggat gtgatcctcg gttgcaccaa ccaggccggc      180
gaagacagcc gcaacctggc gcgcaacgcg ctgctcgcag ccggcctgcc ggcgcggctg      240
cccgggcaga cggtcaaccg cttgtgtgcc agcggactgt cggcggtgat cgacgcggcg      300
cgcgcgatca gttgcggtga gggcggctg tacctggccg gcggcgccga aagcatgtcc      360
cgggcgccgt tcgtcatggg caaggcgag agcgccttca gccgcacgct ggaggtcttc      420
gacagcacca tcggcgcgcg cttcgccaac cccaggctgg tcgagcgcta tgcaacgac      480 agcatgccgg agaccggcga caacgtggcc cgcgccttcg gcatcgcccg cgaagacgcc      540
gaccgtttcg ccgcttcttc ccaggcgcgc taccaggctg cgctggagga gggcttttt      600
```

-continued

```
ctcggcgaga tccttccggt ggaggtgcgt gccggacgca agggcgagac gcggctggtg      660
gagcgcgacg agcatccgcg accgcaggcc gacctggcgg ccctggcgcg cttgccggcg      720
ttgttcgccg gtggggtagt gaccgccggt aatgcgtctg ggatcaacga cggggcggcg      780
gtagtgctgc tgggcgatcg cgcgatcggc gagcgcgagg gcatccggcc gttggcgcgg      840
atcctcgcca gcgccagcgt cggcgtcgag ccccggttga tgggcatcgg cccgcagcag      900
gcgatcctcc gcgcgctgca acgcgccggc atcgacctgg acgaggtcgg cctgatcgag      960
atcaacgaag ccttcgcgcc gcaggtcctg gcctgcctga agttgctcgg cctggactac     1020
gaggacccgc gggtcaatcc ccatggcggc gccattgccc tcggccatcc gctcggcgcc     1080
tccggtgcgc gcctggtgct caccgccgcc cgcgggctgc aacgcatcga gcggcgctac     1140
gcggtggtca gcctgtgcgt cgggctcggc cagggcgtgg cgatggtgat cgagcgctgc     1200
cgatga                                                                1206
```

<210> SEQ ID NO 42
<211> LENGTH: 25
<212> TYPE: DNA
<213> ORGANISM: Artificial Sequence
<220> FEATURE:
<223> OTHER INFORMATION: Synthetic primer

<400> SEQUENCE: 42

```
atgcacgacg tattcatctg tgacg                                             25
```

<210> SEQ ID NO 43
<211> LENGTH: 19
<212> TYPE: DNA
<213> ORGANISM: Artificial Sequence
<220> FEATURE:
<223> OTHER INFORMATION: Synthetic primer

<400> SEQUENCE: 43

```
aacccgctcg atggccaac                                                    19
```

<210> SEQ ID NO 44
<211> LENGTH: 1203
<212> TYPE: DNA
<213> ORGANISM: Pseudomonas putida

<400> SEQUENCE: 44

```
atgcacgacg tattcatctg tgacgccatc cgtaccccga tcggccgctt cggcggcgcc       60
ctggccagcg tgcgggccga cgacctggcc gccgtgccgc tgaaggcgct gatcgagcgc      120
aaccctggcg tgcagtggga ccaggtagac gaagtgttct tcggctgcgc caaccaggcc      180
ggtgaagaca accgcaacgt ggcccgcatg gcactgctgc tggccggcct gccggaaagc      240
atcccgggcg tcaccctgaa ccgtctgtgc gcgtcgggca tggatgccgt cggcaccgcg      300
ttccgcgcca tcgccagcgg cgagatggag ctggtgattg ccggtggcgt cgagtcgatg      360
tcgcgcgccc cgttcgtcat gggcaaggct gaaagcgcct attcgcgcaa catgaagctg      420
gaagacacca ccattggctg gcgtttcatc aacccgctga tgaagagcca gtacggtgtg      480
gattccatgc cggaaaccgc cgacaacgtg gccgacgact atcaggtttc gcgtgctgat      540
caggacgctt tcgccctgcg cagccagcag aaggctgccg ctgcgcaggc tgccggcttc      600
tttgccgaag aaatcgtgcc ggtgcgtatc gctcacaaga agggcgaaat catcgtcgaa      660
cgtgacgaac cctgcgcccc ggaaaccacg ctggaggcgc tgaccaagct caaaccggtc      720
aacggcccgg acaagacggt caccgccggc aacgcctcgg gcgtgaacga cggtgctgcg      780
```

```
gcgatgatcc tggcctcggc cgcagcggtg aagaaacacg gcctgactcc gcgtgcccgc      840
gttctgggca tggccagcgg cggcgttgcg ccacgtgtca tgggcattgg cccggtgccg      900
gcggtgcgca aactgaccga gcgtctgggg atagcggtaa gtgatttcga cgtgatcgag      960
cttaacgaag cgtttgccag ccaaggcctg gcggtgctgc gtgagctggg tgtggctgac     1020
gatgcgcccc aggtaaaccc taatggcggt gccattgccc tgggccaccc cctgggcatg     1080
agcggtgcac gcctggtact gactgcgttg caccagctgg agaagagtgg cggtcgcaag     1140
ggcctggcga ccatgtgtgt gggtgtcggc caaggtctgg cgttggccat cgagcgggtt     1200
tga                                                                   1203

<210> SEQ ID NO 45
<211> LENGTH: 22
<212> TYPE: DNA
<213> ORGANISM: Artificial Sequence
<220> FEATURE:
<223> OTHER INFORMATION: Synthetic primer

<400> SEQUENCE: 45
atgaccgacg cctacatctg cg                                               22

<210> SEQ ID NO 46
<211> LENGTH: 19
<212> TYPE: DNA
<213> ORGANISM: Artificial Sequence
<220> FEATURE:
<223> OTHER INFORMATION: Synthetic primer

<400> SEQUENCE: 46
cacgcgttcg atcgcgatc                                                   19

<210> SEQ ID NO 47
<211> LENGTH: 1203
<212> TYPE: DNA
<213> ORGANISM: Burkholderia ambifaria

<400> SEQUENCE: 47
atgaccgacg cctacatctg cgatgcgatt cgcacaccca tcggccgcta cggcggcgcc       60
ctgaaagacg ttcgtgccga cgatctcggc gcggtgccgc tcaaggcgct gatcgaacgc      120
aaccggaacc tcgactggtc ggcgatcgac gacgtgatct atggctgcgc gaaccaggcc      180
ggcgaagaca accgcaacgt cgcgcgcatg tccgcgctgc tcgcgggctt gccgaccgcc      240
gtgccgggca cgacgctgaa ccggttatgc ggctcgggca tggacgccgt cggcacggcc      300
gcgcgcgcga tcaaggcggg cgaggcacgc ttgatgatcg cgggcggcgt cgaaagcatg      360
acgcgcgcgc cgttcgtgat gggcaaggcc gccagcgcat cgcgcgcca ggctgcgatt      420 ttcgacacga cgatcggctg gcgtttcatt aatccgctga tgaaacagca atacggcgtc      480
gattcgatgc ccgagacggc cgagaacgtc gcggtcgact acaacatcag ccgcgccgac      540
caggatctat cgcgctgcg cagccagcag aaggccgcgc gtgcgcagca ggacggcacg      600
ctcgccgccg aaatcgtccc cgtcacgatt gcgcagaaaa aaggcgacgc gctcgtcgta      660
tcgctcgacg agcatccgcg cgaaacatcg ctcgaagcgc tcgcgaagct gaagggcgtc      720
gtgcgtcccg acggctcggt cacggccggc aacgcgtcag gcgtcaacga cggcgcatgc      780
gcactgctgc tcgccaacgc ggaagccgcc gatcaaatatg gctgcgccg ccgcgcgcgt      840 gtcgtcggca tggcgagcgc cggcgtcgag ccgcgcgtga tgggtatcgg cccggcgccg      900
```

```
gccacgcaga aactgttgcg ccagctcggc atgacgatcg accagttcga cgtgatcgag    960
ctgaacgaag cgttcgcgtc gcagggtctc gcggtgctgc gcatgctcgg tgtcgccgac   1020
gacgatccgc gcgtgaaccc caacggcggt gcgatcgcgc tcggccatcc gctcggcgca   1080
tcgggtgcgc ggctcgtgac cacggcgctt caccaactcg agcgtacggg cggccgcttt   1140
gcgctctgta cgatgtgcat cggcgtcggc cagggcatcg cgatcgcgat cgaacgcgtg   1200
taa                                                                 1203

<210> SEQ ID NO 48
<211> LENGTH: 24
<212> TYPE: DNA
<213> ORGANISM: Artificial Sequence
<220> FEATURE:
<223> OTHER INFORMATION: Synthetic primer

<400> SEQUENCE: 48
atggccacct caagacttgt ctgc                                            24

<210> SEQ ID NO 49
<211> LENGTH: 24
<212> TYPE: DNA
<213> ORGANISM: Artificial Sequence
<220> FEATURE:
<223> OTHER INFORMATION: Synthetic primer

<400> SEQUENCE: 49
caatttctcg atgaccattc cacc                                            24

<210> SEQ ID NO 50
<211> LENGTH: 1242
<212> TYPE: DNA
<213> ORGANISM: Ascaris suum

<400> SEQUENCE: 50
gtgatggcca cctcaagact tgtctgcagc aatttaacga agcaatgctt tacgatctcg     60
tcacgtgctg ctagccaatt taccgatgtg gtattcgtgg gtgccgcacg aacaccggtc    120
ggatcgtttc gctcttcgct ttccactgtt ccagccactg tcctcggagc tgaggctatt    180
aagggtgcac ttaaacatgc caatctaaaa ccctcacaag tgcaagaggt gttctttggc    240
tgtgtcgttc catccaactg tggacaagtt cctgcccgtc aagcgacact tggagctgga    300
tgcgatcctt cgacaatcgt tacaactctc aataaattgt gcgcctcggg aatgaagtcg    360
attgcttgtg ccgcctcact tttgcaactt ggtcttcaag aggttaccgt tggtggcggt    420
atggagagca tgagcttagt gccgtactat cttgaacgtg gtgaaactac ttatggtgga    480
atgaagctca tcgacggtat cccaagagat ggtccgactg atgcatatag taatcaactt    540
atgggtgcat gcgctgataa tgtggctaaa cgattcaaca tcacccgtga ggaacaggat    600
aaattcgcta ttgaaagcta taacgatct gctgctgcat gggagagtgg agcatgcaaa    660
gctgaagtag ttcctattga agtgacaaag ggcaagaaaa catacattgt caacaaggat    720
gaggaataca tcaaagtcaa cttcgagaag cttcccaaac tgaaacccgc cttcttgaaa    780
gacggaacca tcacggctgg caatgcttca acactgaacg atggtgctgc ggcagttgtg    840
atgacgactg tcgaaggagc gaaaaaatac ggtgtgaaac cattggcccg attgctctca    900
tatggtgatg cggcaacaaa tccagtcgat tttgctattg caccatcaat ggttatccca    960
aaggtactta aattggctaa tctcgagatc aaggatattg atttgtggga aatcaacgag   1020
gctttcgccg ttgttcccct tcattcaatg aagacactcg gtatcgatca ctcgaaagtg   1080
```

```
aacattcatg gtggtggcgt atctcttgga catcctattg gaatgtctgg agctcgaatt    1140
atcgttcatc tgattcatgc gttgaaacct ggccagaaag gctgcgctgc aatctgcaat    1200
ggtggcggtg gcgctggtgg aatggtcatc gagaaattgt aa                       1242
```